US012760128B2

(12) United States Patent
O'Connor et al.

(10) Patent No.: US 12,760,128 B2
(45) **Date of Patent: *Oct. 13, 2026**

(54) CYCLODEXTRIN DIMERS AND USES THEREOF

(71) Applicant: CYCLARITY THERAPEUTICS, INC., Novato, CA (US)

(72) Inventors: Matthew S. O'Connor, Richmond, CA (US); Maria de los Angeles Estiarte-Martinez, Barcelona (ES); Amelia M. Anderson, San Jose, CA (US); Daniel M. Clemens, Mountain View, CA (US); Christina A.T.M.B. Tom, Eugene, OR (US); Milo Malanga, Budapest (HU); Michael Kope, El Granada, CA (US); Keivan Sadrerafi, Los Angeles, CA (US)

(73) Assignee: CYCLARITY THERAPEUTICS, INC., Novato, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 17/369,791

(22) Filed: Jul. 7, 2021

(65) Prior Publication Data

US 2021/0403607 A1 Dec. 30, 2021

Related U.S. Application Data

(63) Continuation-in-part of application No. 16/733,945, filed on Jan. 3, 2020, now Pat. No. 11,279,774.

(60) Provisional application No. 63/048,824, filed on Jul. 7, 2020, provisional application No. 63/048,886, filed on Jul. 7, 2020, provisional application No. 63/048,941, filed on Jul. 7, 2020, provisional application No. 62/850,334, filed on May 20, 2019, provisional application No. 62/787,869, filed on Jan. 3, 2019.

(51) Int. Cl.

| | |
|---|---|
| ***C08B 37/16*** | (2006.01) |
| ***A61K 31/575*** | (2006.01) |
| ***A61K 47/40*** | (2006.01) |

(52) U.S. Cl.

CPC ........ *C08B 37/0012* (2013.01); *A61K 31/575* (2013.01); *A61K 47/40* (2013.01)

(58) Field of Classification Search

CPC ............ C08B 37/0012; C08B 37/0015; A61K 31/724; A61K 47/40; A61K 47/6951; A61K 31/575; C08L 5/16

See application file for complete search history.

(56) References Cited

U.S. PATENT DOCUMENTS

| | | | | |
|---|---|---|---|---|
| 5,324,750 | A | 6/1994 | Lincoln et al. | |
| 12,157,779 | B2 | 12/2024 | O'Connor et al. | |
| 2011/0312914 | A1 * | 12/2011 | Kano | A61P 39/02 514/58 |
| 2016/0002721 | A1 | 1/2016 | Liu et al. | |

FOREIGN PATENT DOCUMENTS

| | | |
|---|---|---|
| EP | 0104857 | 4/1984 |
| JP | 2016-512206 | 4/2016 |
| JP | 2024-112990 | 8/2024 |
| JP | 7607935 | 1/2025 |
| WO | 01/41757 | 6/2021 |

OTHER PUBLICATIONS

Aime, S. et al "New cyclodextrin dimers and trimers . . . " Org. Biomol. Chem., vol. 7 pp. 370-379. (Year: 2009).*

Breslow, R. et al "Cholesterol recognition and binding . . . " JACS, vol. 118, pp. 8495-8496. (Year: 1996).*

Chiu, S. et al "Novel ether-linked secondary face-to-face . . . " J. Org. Chem., vol. 65, pp. 2792-2796. (Year: 2000).*

Mao, Q. et al "Optimized synthesis of a per-O-methylated beta-cyclodextrin dimer . . . " J. Incl. Phen. Macro. Chem., vol. 93, pp. 67-76. (Year: 2019).*

Schwarz et al. (International Journal of Pharmaceutics, 2017, 531, 559-567) (Year: 2017).*

Haskard et al. J. Chem. Soc., Faraday Trans., 1997, 93, 279-282. (Year: 1997).*

Munteanu et al. (Journal of Inclusion Phenomena and Macrocyclic Chemistry, 2008, 62, 197-202) (Year: 2008).*

Casas-Solvas et al. (Langmuir, 2011, vol. 27, pp. 9729-9737) (Year: 2011).*

Margaretha (Science of Synthesis, 2009 , 40a, pp. 119-156) (Year: 2009).*

Aime (Organic & Biomolecular Chemistry, 2009, vol. 7, pp. 370-379) (Year: 2009).*

Yergey (Plos One, 2017, vol. 12, article 0175478). (Year: 2017).*

Pattarino et al. "Inclusion of methotrexate in alkyl-cyclodextrins: Effects of host substitutents on the stability of complexes." Journal of drug delivery science and technology. Jan. 1, 2005;15(6):465-8.

Loftsson et al. "Cyclodextrins in drug delivery." Expert opinion on drug delivery. Mar. 1, 2005;2(2):335-51.

de Jong et al. "Cyclodextrin dimers as receptor molecules for steroid sensors." Chemistry—A European Journal. Nov. 3, 2000;6(21):4034-40.

(Continued)

*Primary Examiner* — Dale R Miller

(74) *Attorney, Agent, or Firm* — Robin L. Teskin; Baker, Donelson, Bearman, Caldwell & Berkowitz PC

(57) ABSTRACT

CD dimers, CD compositions, and uses thereof are disclosed herein.

15 Claims, 134 Drawing Sheets

(56) References Cited

OTHER PUBLICATIONS

Michels et al. "Noncovalent binding of sensitizers for lanthanide (III) luminescence in an EDTA-bis (β-cyclodextrin) ligand." Journal of the American Chemical Society. Mar. 6, 2002;124(9):2056-64.
Casas-Solvas et al. "β-Cyclodextrin dimers linked through their secondary faces with rigid spacer arms as hosts for bile salts." Langmuir. Aug. 16, 2011;27(16):9729-37.
de Jong, Menno R., et al. "Complexation and sensing behavior of dansyl-appended cyclodextrins and cyclodextrin dimers with bile salts." Supramolecular Chemistry 14.2-3 (2002): 143-151.
Liu, Yu, et al. "Biquinolino-Modified β-Cyclodextrin Dimers and Their Metal Complexes as Efficient Fluorescent Sensors for the Molecular Recognition of Steroids." Chemistry—A European Journal 10.15 (2004): 3685-3696.
Liu, Yu, et al. "Molecular recognition thermodynamics and structural elucidation of interactions between steroids and bridged bis (β-cyclodextrin) s." The Journal of Organic Chemistry 69.20 (2004): 6590-6602.

* cited by examiner

C6DS4

C3DS4

C2DS4

FIG. 2A.
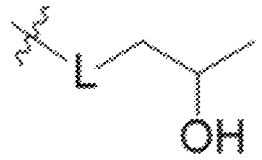
2-Hydroxypropyl (HP)
Methyl (Me)
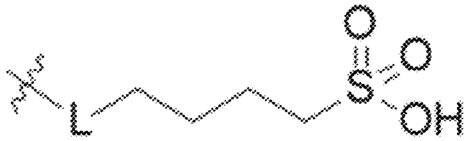
Sulfobutyl (SB)
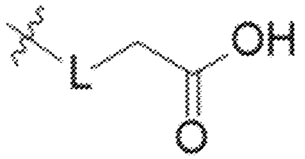
Carboxymethyl (CM)
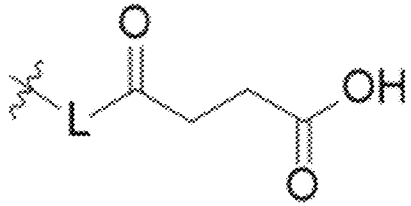
Succinyl (SUCC)
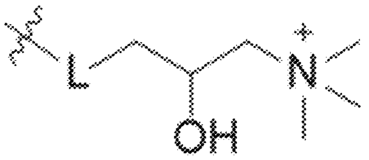
Quaternary Ammonium (QA)

A, B, C, D, E, F, G, H, I, J, K, L, M, N, O, P, Q, R, S, T, U, V, W

L-A-B-A'-L'

Where n, n1, n2 = 1, 2, 3, 4 or 5 carbons
and L or L' = L1, L1', L2 or L2'

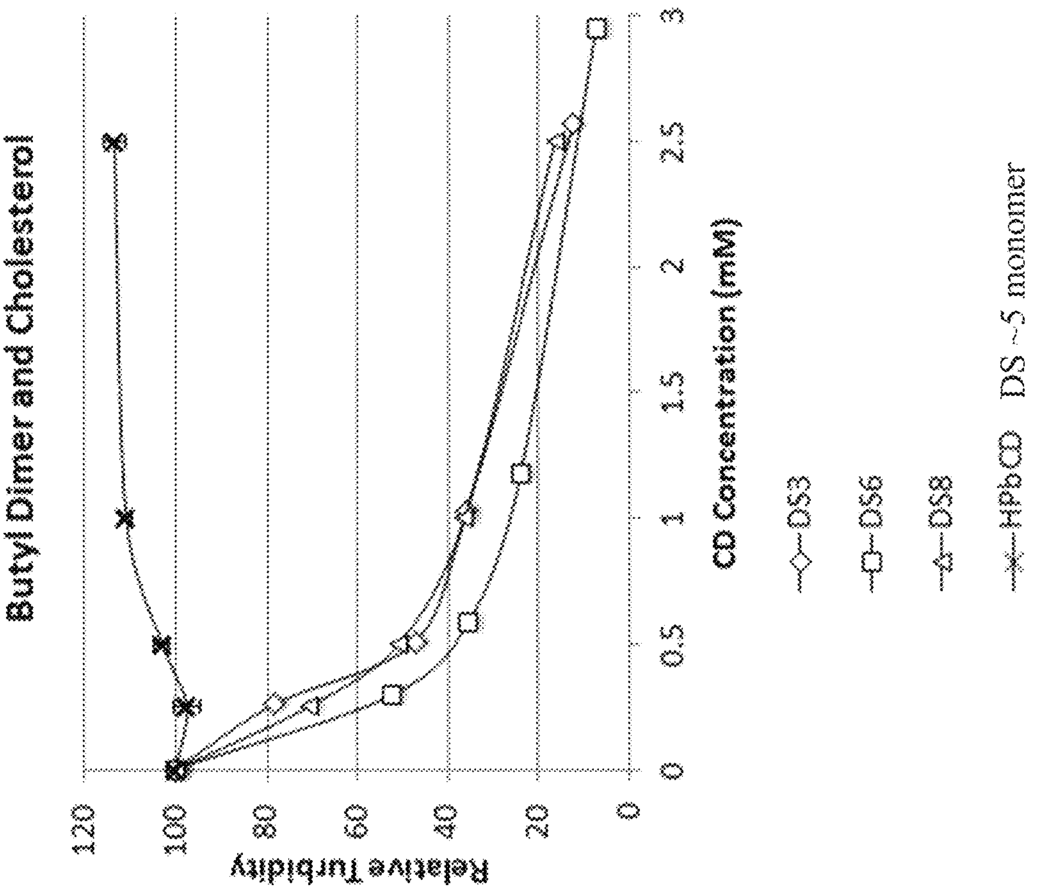
FIG. 5E.
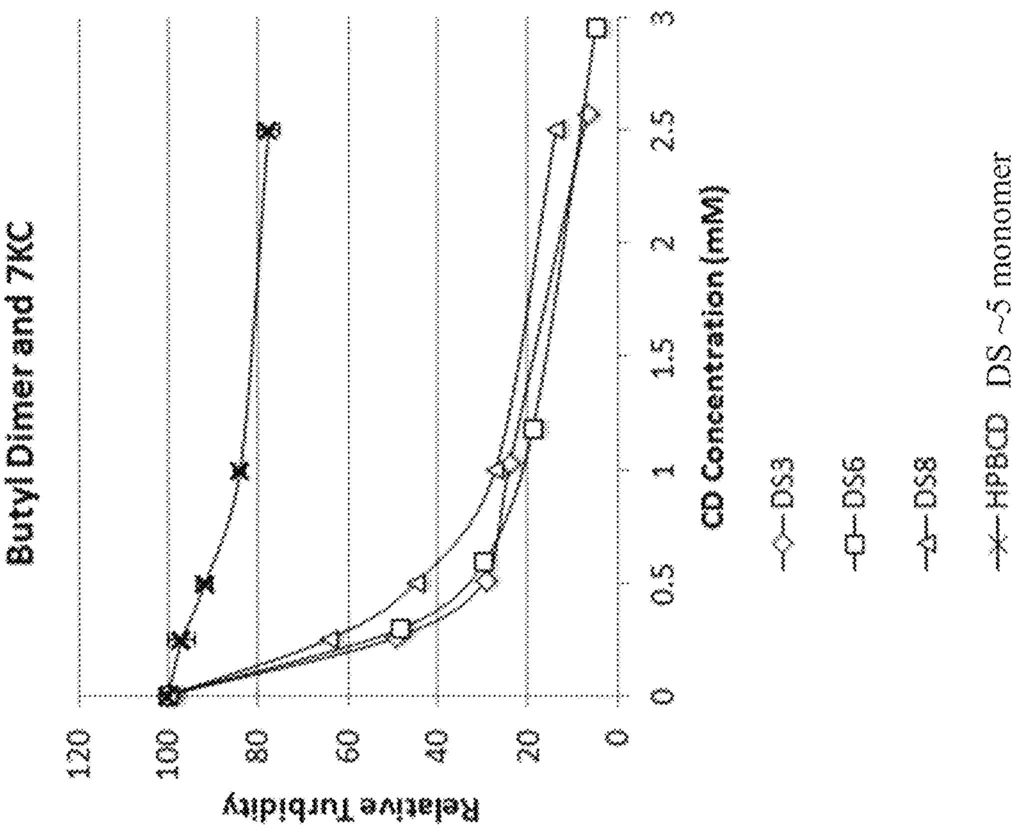

HPβCD Dimer DS~8

HPβCD Monomer DS~5

FIG. 8A.
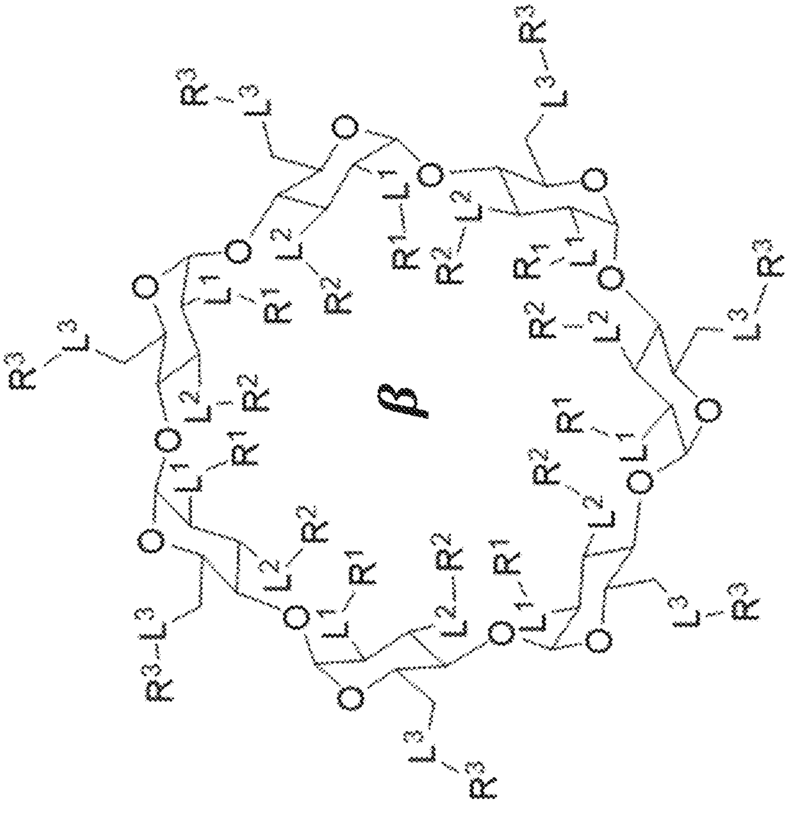
A-Xa
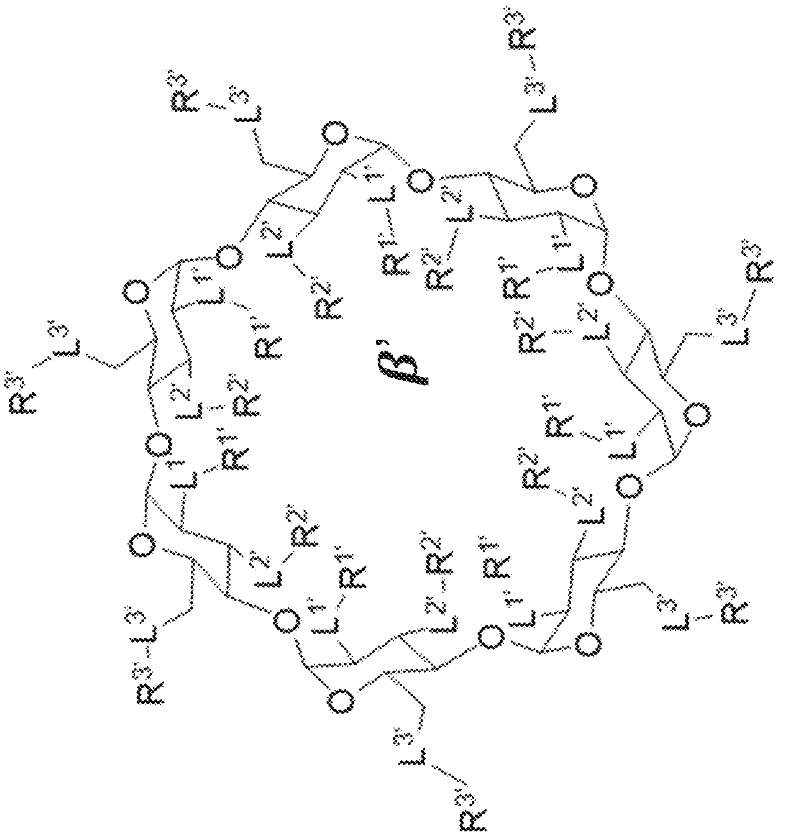
A-Xb

FIG. 12A. Synthesis of butyl-linked aCD Homodimers
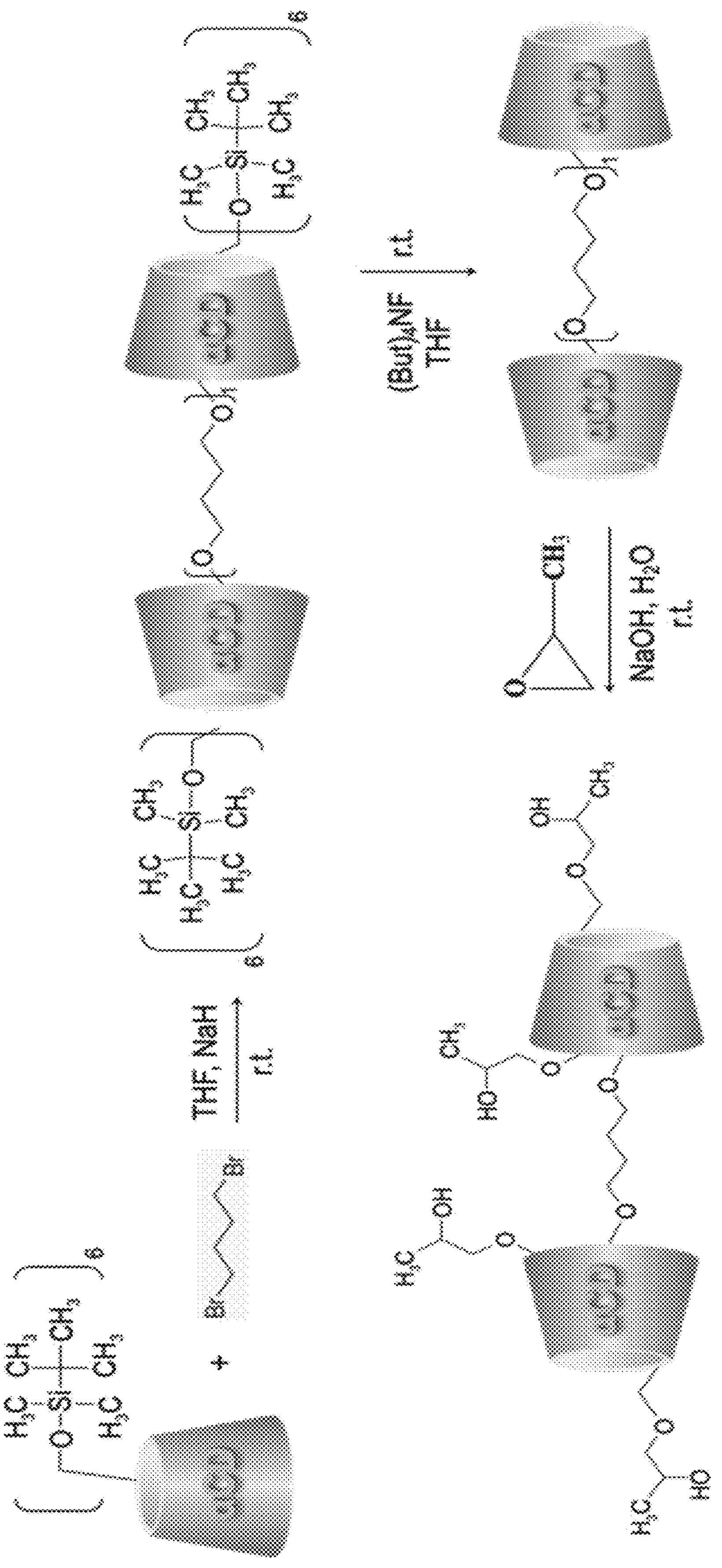

FIG. 12B. Synthesis of triazole-linked aCD homodimers .
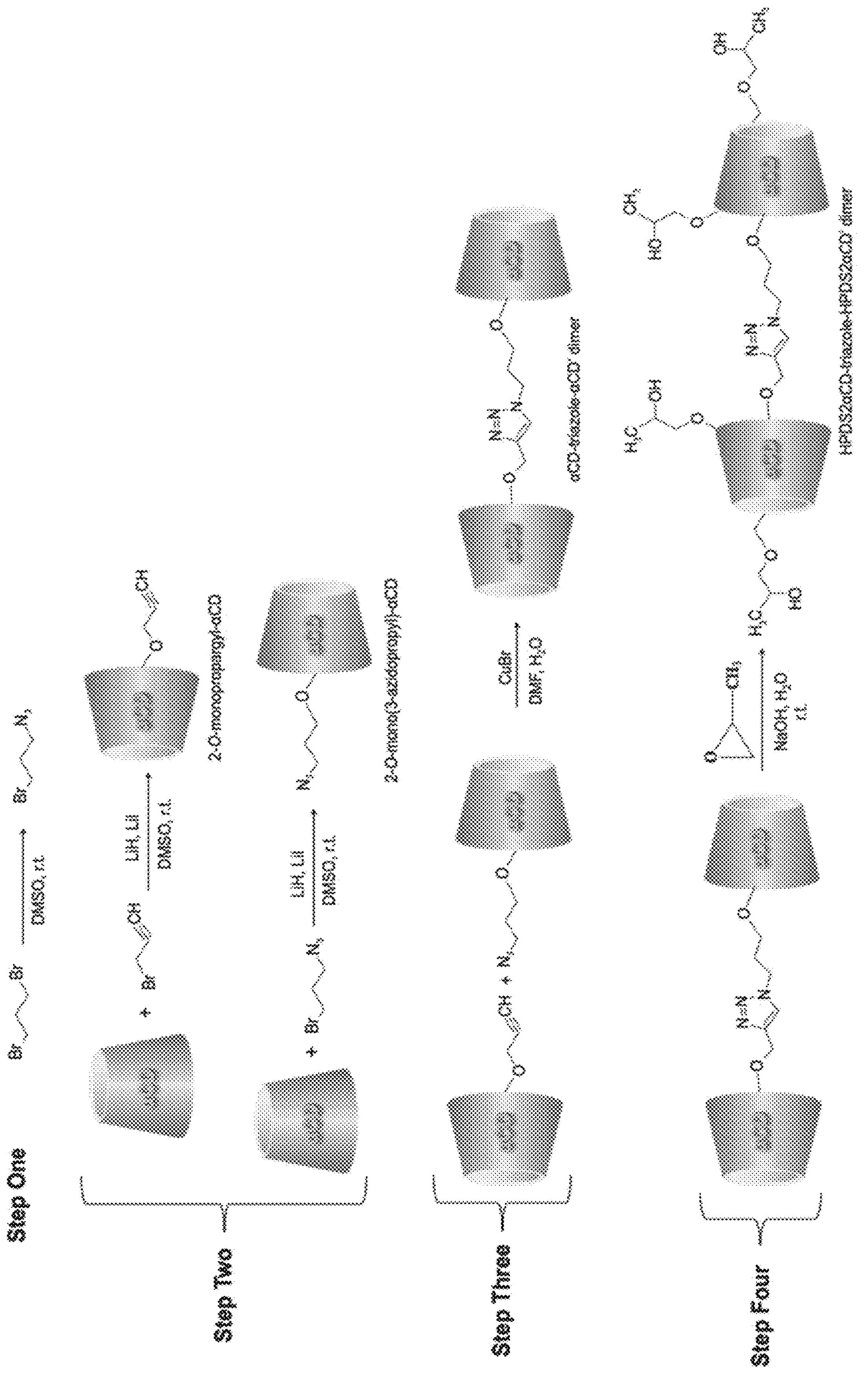

FIG. 13A.
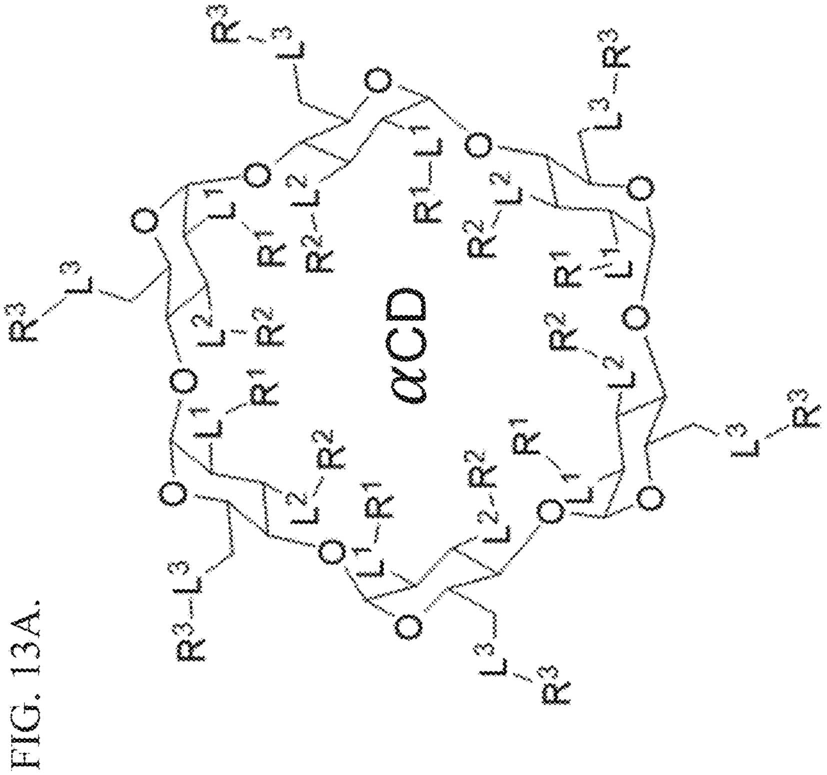
B-Xa
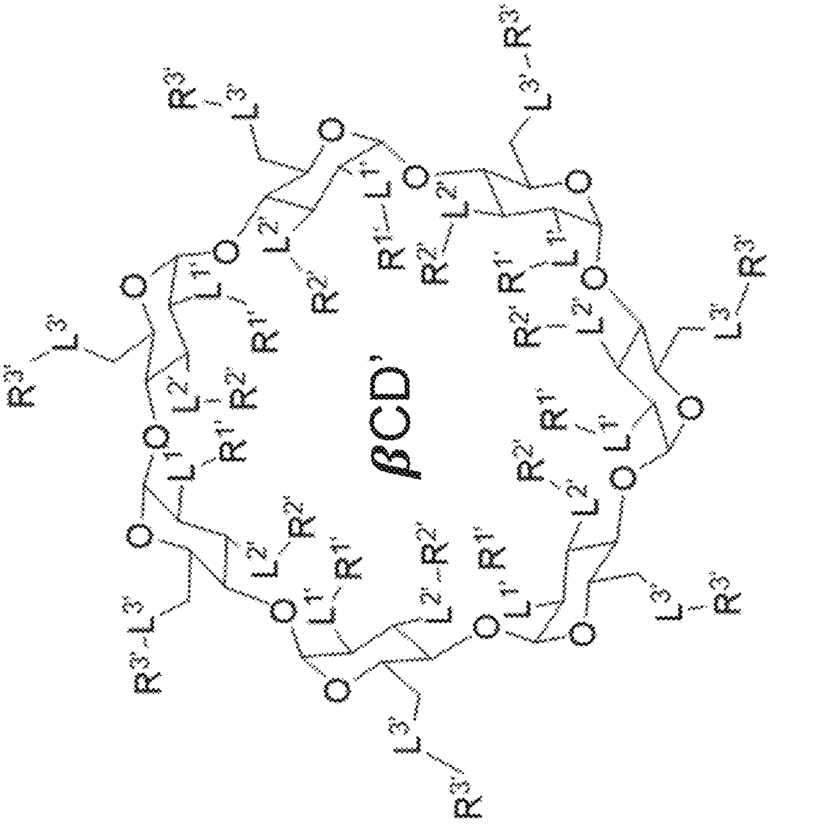
B-Xb

| | 7KC EC50 (mM) | | Cholesterol EC50 (mM) | |
|---|---|---|---|---|
| Cyclodextrin | Value | SEM | Value | SEM |
| HPβCD DS~5 | 4.742 | 0.532 | >10 | N/A |
| αCD DS0 | N/A | N/A | >10 | N/A |
| HPβCD DS~5 + αCD DS0 Mixed Monomer | 6.445 | 0.804 | >10 | N/A |

| | 7KC EC50 (mM) | | Cholesterol EC50 (mM) | |
|---|---|---|---|---|
| Cyclodextrin | Value | SEM | Value | SEM |
| HPβCD DS~5 | 4.742 | 0.532 | >10 | N/A |
| HPαCD DS~3.5 | >10 | N/A | >10 | N/A |
| HPβCD DS~5 + HPαCD DS~3.5 Mixed Monomer | 3.665 | 0.314 | >10 | N/A |

FIG. 16A. Synthesis of butyl-linked bCD-aCD heterodimers
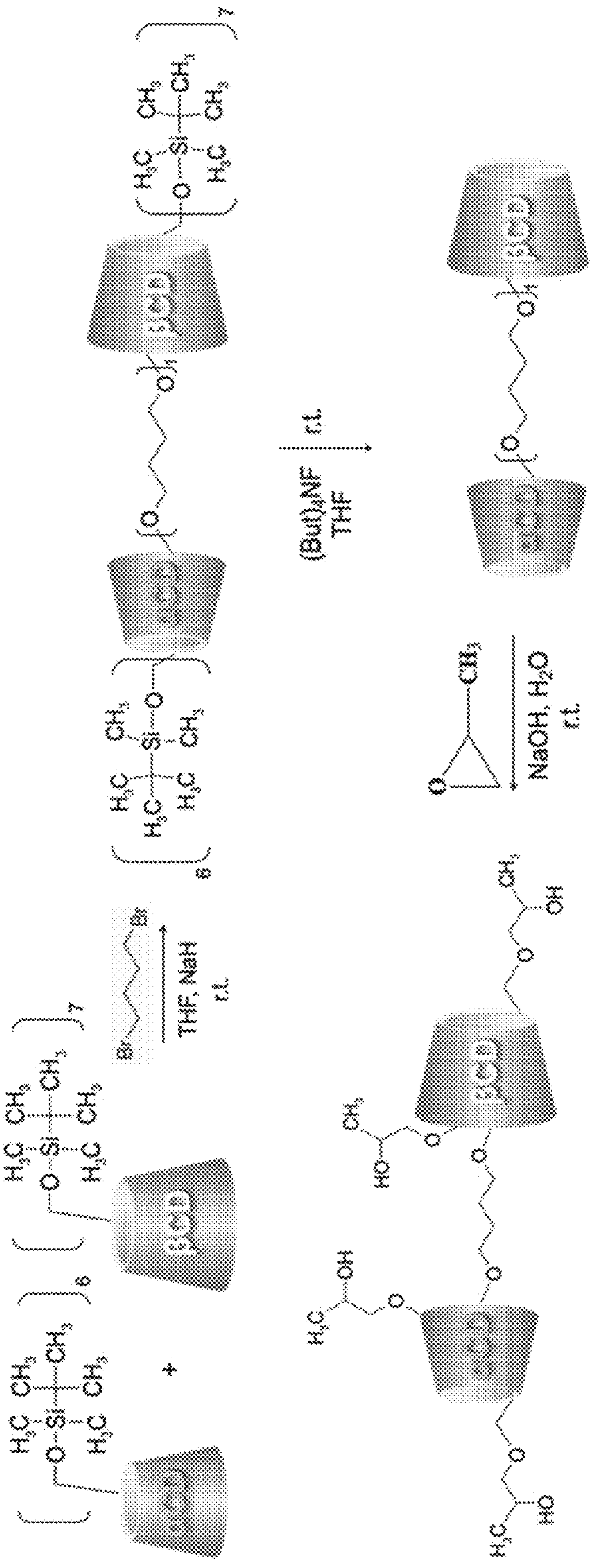

FIG. 16B. Synthesis of triazole-linked bCD-aCD heterodimers .
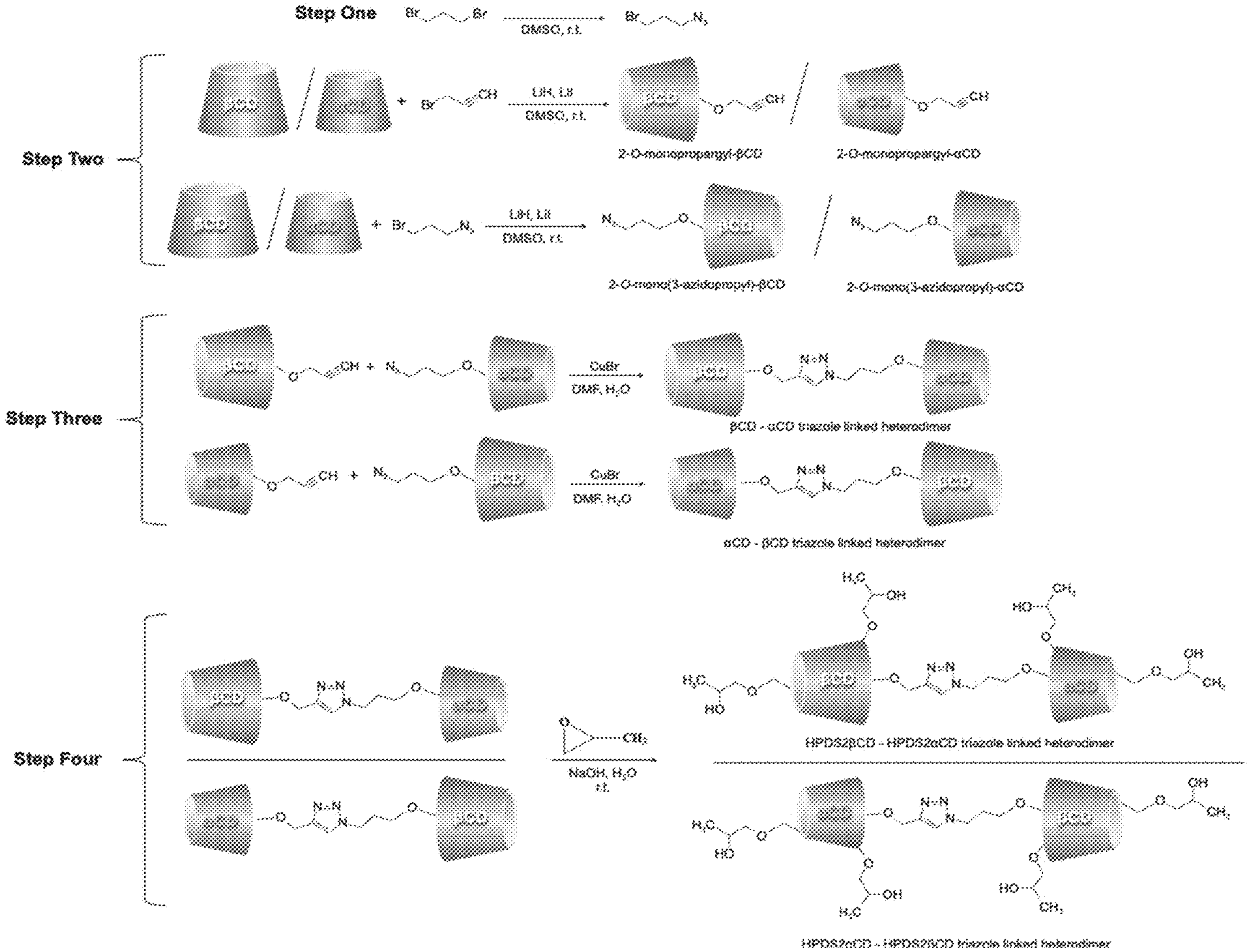

FIG. 16C. Synthesis of sulfobutylated triazole-linked bCD-aCD heterodimers.
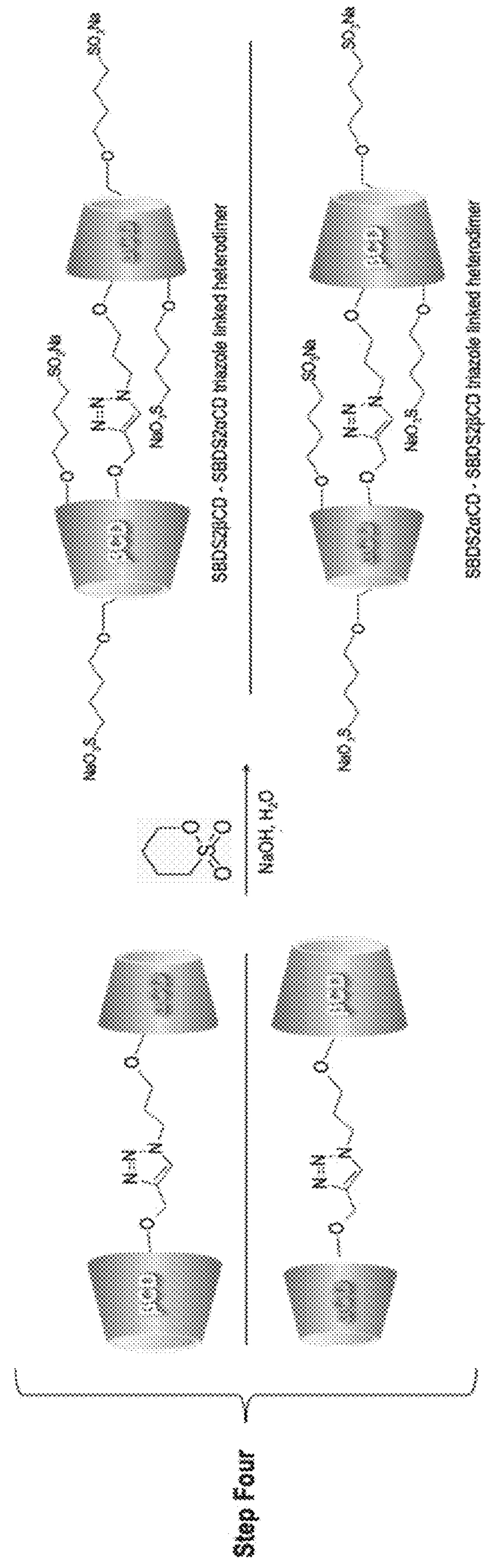

FIG. 17A.
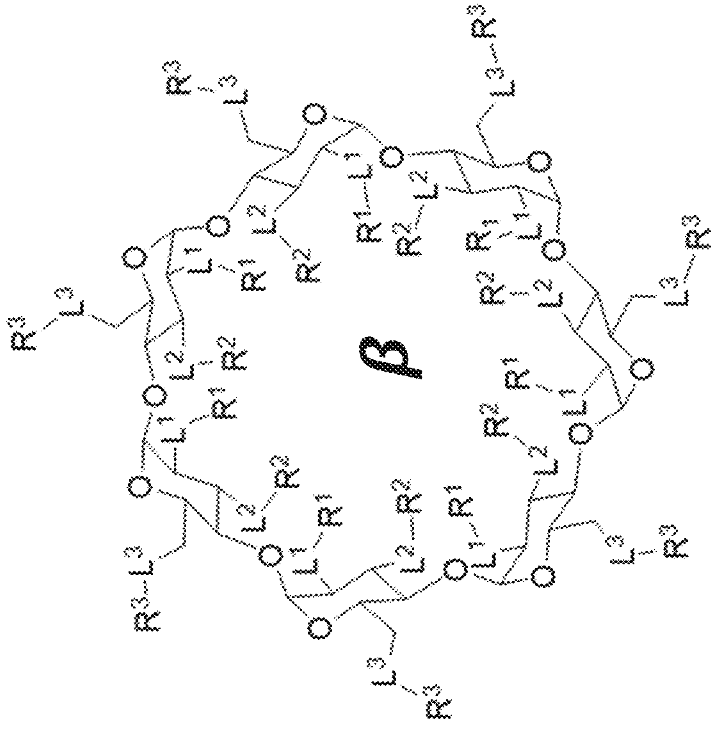
C-Xa
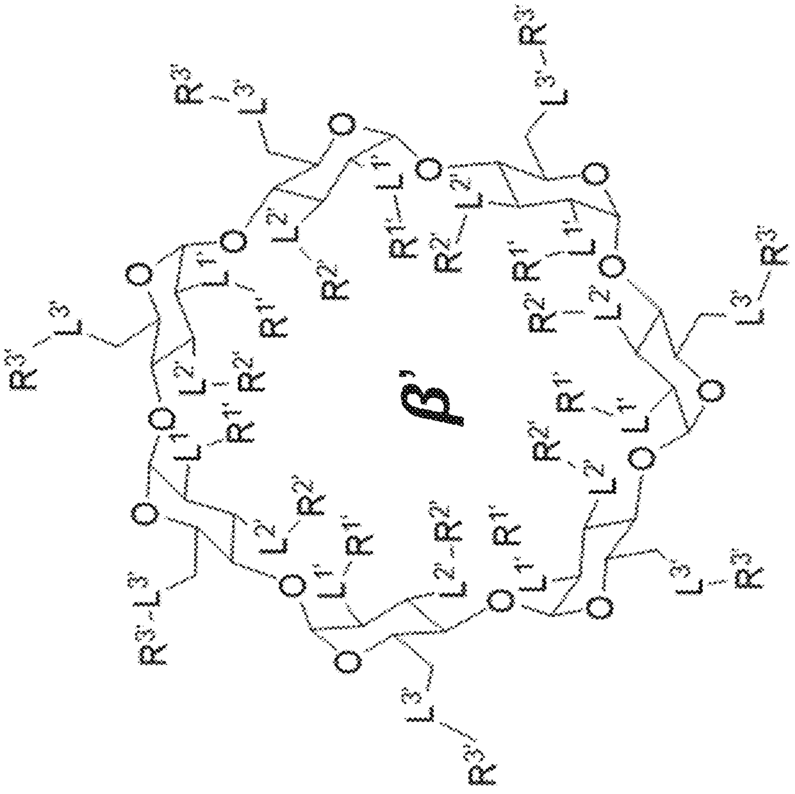
C-Xb

2-O-monopropargyl-βCD

2-O-monopropargyl-βCD

Random (2-hydroxypropyl)-2-O-monopropargyl-βCD

2-O-mono(3-azidopropyl)-βCD

Step Three

HPβCD-triazole-βCD DS3 (random substituted) asymmetric dimer

Step Two

2-O-monopropargyl-βCD

2-O-monopropargyl-βCD

Per-6-O-*tert*-butyldimethylsilyl-2-O-monopropargyl-βCD

Per-6-O-*tert*-butyldimethylsilyl-per-2,3-O-benzyl-2-O-monopropargyl-βCD

Per-2,3-O-benzyl-2-O-monopropargyl-βCD
(key-intermediate)

Step Two (Cont.)

Per-2,3-O-benzyl-2-O-monopropargyl-βCD (key-intermediate)

Tris(6-O-(2-O-benzyloxypropyl))-per-2,3-O-benzyl-2-O-monopropargyl-βCD

Tris-6-O-(2-O-hydroxypropyl)-2-O-monopropargyl-βCD

2-O-mono(3-azidopropyl)-βCD

Step Three

C6HPβCD-triazole-βCD DS3 asymmetric dimer

Step Two (cont.)

Per-2,3-*O*-benzyl-2-*O*-monopropargyl-βCD (key intermediate)

Per-6-(2-*O*-benzyloxypropyl)-per-2,3-*O*-benzyl-2-*O*-monopropargyl-βCD

Per-6-(2-*O*-benzyloxypropyl)-per-2,3-*O*-benzyl-2-*O*-monopropargyl-βCD

Per-6-(2-*O*-hydroxypropyl)-2-*O*-monopropargyl-βCD

2-*O*-mono(3-azidopropyl)-βCD

Step Three

C6HPβCD-triazole-βCD DS7 asymmetric dimer

Random (2-hydroxypropyl)-2-O-monopropargyl-βCD
($^1$H-NMR spectrum, $D_2O$, 298 K)

*Per-6-O-tert-butyldimethylsilyl-2-O-monopropargyl-βCD*

*Per-6-O-tert-butyldimethylsilyl-2-O-monopropargyl-βCD*

*MALDI Spectrum*

NOTES:

- The main peak is the product plus sodium

*Per-6-O-tert-butyldimethylsilyl-2-O-monopropargyl-βCD*
*$^1$H NMR Spectrum ($CDCl_3$, 298 K)*

*Per-6-O-tert-butyldimethylsilyl-2-O-monopropargyl-βCD*

*$^1H$ NMR Spectrum, enlargement on CD core ($CDCl_3$, 298 K)*

*Per-6-O-tert-butyldimethylsilyl-2-O-monopropargyl-βCD*

*IR Spectrum ($CDCl_3$, 298 K)*

CYCLODEXTRIN DIMERS AND USES THEREOF

CROSS-REFERENCE TO RELATED APPLICATIONS

This application claims the benefit of U.S. Ser. No. 63/048,824, filed Jul. 7, 2020, U.S. Ser. No. 63/048,886, filed Jul. 7, 2020, and U.S. Ser. No. 63/048,941, filed Jul. 7, 2020, and is a continuation-in-part of U.S. Ser. No. 16/733,945, filed Jan. 3, 2020, which claims the benefit of U.S. Ser. No. 62/787,869 filed Jan. 3, 2019 and 62/850,334 filed May 20, 2019, each of which is hereby incorporated by reference in its entirety.

BACKGROUND 7-ketocholesterol (7KC) is an oxysterol produced by the non-enzymatic reaction of oxygen radicals with cholesterol. 7KC can be formed in organisms or consumed in food, but it is potentially toxic and is thought to serve no useful purpose in humans and other eukaryotes. Like cholesterol, 7KC is found in atherosclerotic plaques. 7KC is the most abundant non-enzymatically produced oxysterol in atherosclerotic plaques and may contribute to the pathogenesis of atherosclerosis and other diseases of aging, lysosomal storage diseases such as Niemann-Pick Type C (NPC), heart diseases, cystic fibrosis, liver damage and failure, and complications of hypercholesterolemia. When someone is affected by hypercholesterolemia, 7KC can diffuse through the membranes of cells where it affects receptors and enzymatic function; the increased rates of dementia in hypercholesterolemia have been associated with 7KC accumulation. In the liver, 7KC affects fenestration and porosity in the tissue, which increases with age. 7KC also promotes translocation of cytosolic NADPH oxidase components to the membrane in neutrophils (white blood cells) and enhances rapid reactive oxygen species production. Pathogenesis of other diseases of aging such as Age-Related Macular Degeneration (AMD—dry form), Alzheimer's disease, as well as lysosomal storage diseases such as Niemann-Pick Type C (NPC) have also been tied to increased levels of 7KC. Oxysterols, including 7KC, are also involved in increasing free radical levels, which in turn affect lipid circulation in cystic fibrosis. The increase in free radicals caused by oxysterols like 7KC are believed to be involved in apoptosis, cytotoxicity, impairment of endothelial function, and regulation of enzymes involved in inflammation and in fatty acid metabolism.

7KC is formed from the non-enzymatic reaction of an oxygen radical with cholesterol, indicating that its formation may not be beneficial. Indeed, 7KC is believed to enhance the production of free radicals everywhere in the body, with the heart and vascular tissue being of particular concern. Free radicals affect cells and enzymatic reactions that are important for cholesterol mediated tissue damage, which is especially important in these tissues; this is believed to enhance inflammation in the vasculature. By disrupting the function of cell and organelle membranes, 7KC is believed to cause dysfunction of mitochondria and lysosomes and is thought to be involved in increasing the frequency of formation of foam cells from macrophages in atherosclerotic plaques. The scavenging functions of these macrophages would be expected to help ameliorate the plaque, but instead they can become part of the plaque when they are congested with cholesterol and oxysterols.

Cyclodextrins (CDs) are cyclic oligosaccharides composed of 6 (αCD), 7 (βCD), or 8 (γCD) sugar rings (FIG. 1A). Alpha, beta, and gamma CDs are the most common forms, having many medical, industrial, consumer, and food related uses. CDs have been used for a variety of applications, including as a food additive form of dietary fiber. CDs have also been used in pharmaceutical compositions as an aerosolizing agent and as excipients for small hydrophobic drugs, typically in combination with an active pharmaceutical ingredient.

Previously, we have shown that two βCDs can be covalently linked in a head-to-head fashion to significantly improve their ability to form inclusion complexes with target molecules such as 7KC. Also, αCDs have been shown to non-covalently dimerize in a head-to-head fashion when complexing 1,12-Diaminododecane. The structure of this guest molecule contains a long aliphatic chain.

BRIEF SUMMARY

In the present disclosure, we address additional CD dimers that may be useful for various purposes including the targeting of 7KC. The design and testing of CD dimers are described herein. Exemplary CD dimers include heterodimers (preferably containing αCD and βCD), homodimers (preferably containing two αCDs or two βCD having the same substituents on each monomer), or asymmetric dimers (e.g., having two CD monomers with different combinations of substituents on each).

With respect to CD heterodimers, we hypothesized that the smaller ring structure of αCD (relative to βCD and γCD) will favorably interact with the tail group of 7KC. Particularly, we propose that a linked CD dimer composed of one αCD and one βCD will selectively and asymmetrically target both parts of the guest molecule: βCD complexing with the headgroup while αCD encapsulates the tail. Other guest molecules having a similar structure may likewise be encapsulated. Neither, either, or both of these CD monomers may have substitution groups added to modify solubility.

Further, we propose uncommon and/or new substitution groups that can be added to CD dimers to increase the target specificity of these molecules. Exemplary CD dimers disclosed herein include substituents that can increase the affinity and/or specificity of these CD dimers for target molecules, e.g., 7KC, cholesterol, and other sterols. Certain of the substituted CDs described herein are predicted to interact strongly with the carbonyl group of 7KC. Because cholesterol does not have a carbonyl group, we hypothesize that such substitutions will create significant specificity for 7KC over cholesterol.

In one aspect the disclosure provides variously substituted alpha-beta heterodimers of CD, such as a combination of one αCD and one βCD monomer, which may exhibit enhanced binding properties.

In CD heterodimers having the structure αCD linked to βCD, the smaller cavity of αCD allows it to more effectively encapsulate the tail group of 7KC, making it less likely to bind other, bulkier hydrophobic molecules. The αCD and βCD may each be substituted with a variety of chemical groups to tune the affinity of that subunit to the intended head or tail group of the target molecule.

In another aspect, the disclosure provides CD heterodimers in which alkyl groups are used as substitution groups. Alkyl groups are more hydrophobic than the charged and polar substituents demonstrated thus far and will therefore extend the hydrophobic cavity of one or both of the subunits, thereby creating a better environment for the encapsulation of the tail group of 7KC, cholesterol, and other sterols with long aliphatic chains.

The present disclosure further describes the design and testing of various asymmetric dimers of CD including (2-hydroxypropyl)-βCD (HPβCD) dimers, methyl-βCD (MeβCD) dimers, succinyl-βCD (SUCCβCD) dimers, sulfobutyl-βCD (SBβCD) dimers, and quaternary ammonium-CD (QAβCD) dimers, among others. The asymmetric dimers comprise a combination of two different CD monomers. Exemplary asymmetric dimers of the disclosure exhibit enhanced binding properties.

Exemplary asymmetric dimers of the present disclosure may be useful for the targeting of 7KC. For example, the asymmetric dimers may comprise two differentially substituted monomers, e.g., a native βCD linked to a HPβCD, or a SBβCD linked to MeβCD, for example. Without intent to be limited by theory, it is believed that different substitution types can change the affinity and specificity of CD asymmetric dimers for guests, and asymmetric substitution of the dimer may render it more specific for the head or tail group of the target. In exemplary embodiments, substitution at a single location, e.g. the C6 position, can create a more homogenous product upon synthesis and further (without intent to be limited by theory) is expected to elongate the cavity of the CD, increasing its ability to solubilize hydrophobic molecules such as sterols, e.g., 7KC.

We further describe substitution groups that can be added to asymmetric CD dimers that may increase the target specificity of these molecules. Some of the substitutions and substitution patterns described herein are expected to promote the specific or preferential binding of 7KC. Without intent to be limited by theory, it is believed that because cholesterol does not have a carbonyl group, these substitutions will create significant specificity for 7KC over cholesterol.

We further describe substitutions of opposite charges on the two CD subunits of an asymmetric dimer, i.e. positively charged substitutions on one monomer and negatively charged substitutions on the other monomer. Without intent to be limited by theory, such substitutions are predicted to drive stability of the CD-target complexes by providing electrostatic attraction between the two CD subunits of the asymmetric dimer and/or provide specificity for target molecules containing highly polar regions that can interact with the charged moieties.

Embodiments of the invention provide compositions and methods for the treatment or prevention of atherosclerosis and other age-related diseases. 7KC is the most abundant non-enzymatically produced oxysterol in atherosclerotic plaques and is believed to contribute to the pathogenesis of atherosclerosis. Treatment with the asymmetric CD dimers of this invention is expected to be beneficial for the prevention and/or reversal of atherosclerotic plaque formation.

In another aspect, the disclosure provides a method of engineering asymmetric CD dimers with specificity for additional small molecules. Exemplary methods are carried out by first creating a CD dimer core of a certain, possibly asymmetric, structure specified in the synthesis. Then, any substitutions can be added to create specificity for said hydrophobic molecules while maintaining the high affinity conveyed by the CD dimer core. This specificity can further be modified with different linkers.

The present disclosure also describes the design and testing of various homodimers of CD (CD) including HPβCD dimers, methyl-βCD dimers, succinyl-βCD dimers, sulfobutyl-βCD dimers, and quaternary ammonium-CD dimers, among others. The present disclosure describes dimers consisting of a combination of two CD monomers. Exemplary homodimers show enhanced binding properties for target molecules including 7KC, cholesterol, and other sterols, including exemplary homodimers having increased specificity for 7KC over cholesterol.

Exemplary embodiments provide use of the CD dimers of the present disclosure (e.g., heterodimers, homodimers, or asymmetric dimers) in compositions and methods for the treatment of diseases associated with and/or exacerbated by 7KC accumulation, such as atherosclerosis, AMD, arteriosclerosis, coronary atherosclerosis due to calcified coronary lesion, heart failure (all stages), Alzheimer's disease, Amyotrophic lateral sclerosis, Parkinson's disease, Huntington's disease, vascular dementia, multiple sclerosis, Smith-Lemli-Opitz Syndrome, infantile neuronal ceroid Lipofuscinosis, Lysosomal acid lipase deficiency, Cerebrotendinous xanthomatosis, X-linked adrenoleukodystrophy, Sickle cell disease, Niemann-Pick Type A disease, Niemann-Pick Type B disease, Niemann-Pick Type C disease, Gaucher's disease, Stargardt's disease, idiopathic pulmonary fibrosis, chronic obstructive pulmonary disease, cystic fibrosis, liver damage, liver failure, non-alcoholic steatohepatitis, non alcoholic fatty liver disease, irritable bowel syndrome, Crohn's disease, ulcerative colitis, and/or hypercholesterolemia or dementia associated with hypercholesterolemia. Preferred CD dimers, i.e., heterodimers, homodimers, or asymmetric dimers are selective for 7KC (compared to cholesterol). Preferably, said CD dimer preferentially solubilizes 7KC, while minimizing or avoiding potentially deleterious or toxic effects that can result from excessive removal of cholesterol.

Exemplary embodiments of the invention provide for the use of CD (e.g., HPα-βCD, Meα-βCD, SUCCα-βCD, QAα-βCD, or SBα-βCD) dimers for the solubilization and/or removal of 7KC, which may be performed in vitro or in vivo.

In exemplary embodiments, said CD (e.g., HPα-βCD, MEα-βCD, SUCCα-βCD, QAα-βCD, or SBα-βCD) dimer, exhibits greater binding affinity and/or solubilization of 7KC than cholesterol. The specificity for 7KC over cholesterol is most evident at sub-saturating concentrations, whereas at higher concentrations the solubilization of both sterols can approach 100%. This specificity allows for use of such CD dimers in order to preferentially solubilize and remove 7KC.

The phrase "pharmaceutically acceptable" is used herein to refer to those compounds, materials, compositions, and/or dosage forms that are, within the scope of sound medical judgment, suitable for entering a living organism or living biological tissue, preferably without significant toxicity, irritation, or allergic response. The present invention includes methods which comprise administering a CD dimer to a patient, wherein the CD dimer is contained within a pharmaceutical composition. The pharmaceutical compositions of the invention are formulated with pharmaceutically acceptable carriers, excipients, and other agents that provide suitable transfer, delivery, tolerance, and the like. A multitude of appropriate formulations can be found in the formulary known to pharmaceutical chemists, such as Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also (Powell [et al.], J. Pharm. Sci. Technol., 52:238-311, (1998)).

The phrase "pharmaceutically acceptable carrier," as used herein, generally refers to a pharmaceutically acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body. Each carrier must be "acceptable" in the sense of being compatible with other ingredients of the formulation and not injurious to the patient. Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

Other examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition. Some examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Pharmaceutical formulations of the present invention may be prepared by any of the methods known in the pharmaceutical arts. The amount of active ingredient (i.e., CD dimer such as HPβCD dimer or another CD dimer of the present disclosure) that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. The amount of active compound may be in the range of about 0.1 to 99.9 percent, more typically, about 80 to 99.9 percent, and more typically, about 99 percent. The amount of active compound may be in the range of about 0.1 to 99 percent, more typically, about 5 to 70 percent, and more typically, about 10 to 30 percent. In an exemplary embodiment, the dosage form is provided for intravenous administration in an aqueous solution having a concentration of between 0.5% and 0.001%, such as between 0.12% and 0.0105%, e.g., about 0.01% (W/V). In an exemplary embodiment, the dosage form is provided for intravenous administration in an aqueous solution having a concentration of between 2.5% and 0.25%, such as between 2% and 0.5%, e.g., about 1% (W/V). In an exemplary embodiment, the dosage form provides for intravenous administration of up to 500 mLs of a 1% solution (W/V), resulting in a dosage of up to 5 grams. Further exemplary embodiments provide dosage forms containing one or more CDs in a total concentration up to about 60% (w/v) or about 50% (w/v), e.g., about 5% (w/v), about 10% (w/v), about 15% (w/v), about 20% (w/v), about 25% (w/v), about 30% (w/v), about 35% (w/v), about 40% (w/v), about 45% (w/v), about 50% (w/v), about 55% (w/v), or about 60% (w/v); or at least about 5% (w/v), at least about 10% (w/v), at least about 15% (w/v), at least about 20% (w/v), at least about 25% (w/v), at least about 30% (w/v), at least about 35% (w/v), at least about 40% (w/v), at least about 45% (w/v), at least about 50% (w/v), or at least about 55% (w/v), or between about 1% (w/v)-60% (w/v), 5% (w/v)-55% (w/v), 10% (w/v)-50% (w/v), 15% (w/v)-45% (w/v), 20% (w/v)-40% (w/v), 25% (w/v)-35% (w/v) or about 30% (w/v); or up to about 10% (w/v), up to about 15% (w/v), up to about 20% (w/v), up to about 25% (w/v), up to about 30% (w/v), up to about 35% (w/v), up to about 40% (w/v), up to about 45% (w/v), up to about 50% (w/v), up to about 55% (w/v), or up to about 60% (w/v). Said CD dosage form may be formulated for administration to a patient, e.g., parenteral administration, preferably intravenous administration, wherein said administration optionally includes dilution prior to said administration, e.g., to a concentration prior to administration of about 5% (w/v), about 10% (w/v), about 15% (w/v), about 20% (w/v), about 25% (w/v), about 30% (w/v), or about 35% (w/v).

In exemplary embodiments, the CD dimer may be administered to a patient in an amount of between 1 mg and 10 g, such as between 10 mg and 1 g, between 100 mg and 500 mg. In exemplary embodiments, about 400 mg of CD dimer may be administered. In exemplary embodiments, between 1 and 10 g of CD dimer may be administered, such as about 2 g, about 3 g, about 4 g, or about 5 g. In exemplary embodiments, between 50 mg and 5 g of CD dimer may be administered, such as between 100 mg and 2.5 g, between 100 mg and 2 g, between 250 mg and 2.5 g, e.g., about 1 g.

Exemplary embodiments provide a single dosage form, which may comprise the foregoing amount of CD dimer, which may be packaged for individual administration, optionally further comprising a pharmaceutically acceptable carrier or excipient. The total amount of said CD dimer in said single dosage form may be as provided above, e.g., between 1 mg and 10 g, such as between 10 mg and 1 g, between 100 mg and 500 mg, between 1 and 10 g of CD dimer, between 50 mg and 5 g, between 100 mg and 2.5 g, between 100 mg and 2 g, between 250 mg and 2.5 g, such as about 1 g, 2 g, about 3 g, about 4 g, or about 5 g.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. The active compound may also be administered as a bolus, electuary, or paste.

Methods of preparing these formulations or compositions generally include the step of admixing a compound of the present invention with the carrier, and optionally, one or more auxiliary agents. In the case of a solid dosage form (e.g., capsules, tablets, pills, powders, granules, trouches, and the like), the active compound can be admixed with a finely divided solid carrier, and typically, shaped, such as by pelletizing, tableting, granulating, powderizing, or coating. Generally, the solid carrier may include, for example, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more auxiliary ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent.

The tablets, and other solid dosage forms of the active agent, such as capsules, pills and granules, may optionally be scored or prepared with coatings and shells, such as enteric coatings and other coatings well known in the pharmaceutical-formulating art. The dosage form may also be formulated so as to provide slow or controlled release of the active ingredient therein using, for example, hydroxypropyl methyl cellulose in varying proportions to provide the desired release profile, other polymer matrices, liposomes and/or microspheres. The dosage form may alternatively be formulated for rapid release, e.g., freeze-dried.

Generally, the dosage form is required to be sterile. For this purpose, the dosage form may be sterilized by, for example, filtration through a bacteria-retaining filter, or by incorporating sterilizing agents in the form of sterile solid compositions which can be dissolved in sterile water, or some other sterile injectable medium immediately before use. The pharmaceutical compositions may also contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms are typically a pharmaceutically acceptable emulsion, microemulsion, solution, suspension, syrup, or elixir of the active agent. In addition to the active ingredient, the liquid dosage form may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Dosage forms specifically intended for topical or transdermal administration can be in the form of, for example, a powder, spray, ointment, paste, cream, lotion, gel, solution, or patch. Ophthalmic formulations, such as eye ointments, powders, solutions, and the like, are also contemplated herein. The active compound may be mixed under sterile conditions with a pharmaceutically acceptable carrier, and with any preservatives, buffers, or propellants that may be required. The topical or transdermal dosage form may contain, in addition to an active compound of this invention, one or more excipients, such as those selected from animal and vegetable fats, oils, waxes, paraffins, starch, tragacanth, cellulose derivatives, polyethylene glycols, silicones, bentonites, silicic acid, talc and zinc oxide, and mixtures thereof. Sprays may also contain customary propellants, such as chlorofluorohydrocarbons and volatile unsubstituted hydrocarbons, such as butane and propane.

For purposes of this invention, transdermal patches may provide the advantage of permitting controlled delivery of a compound of the present invention into the body. Such dosage forms can be made by dissolving or dispersing the compound in a suitable medium. Absorption enhancers can also be included to increase the flux of the compound across the skin. The rate of such flux can be controlled by either providing a rate-controlling membrane or dispersing the compound in a polymer matrix or gel.

Pharmaceutical compositions of this invention suitable for parenteral administration generally include one or more compounds of the invention in combination with one or more pharmaceutically acceptable sterile isotonic aqueous or nonaqueous solutions, dispersions, suspensions or emulsions, or sterile powders that may be reconstituted into sterile injectable solutions or dispersions prior to use, which may contain sugars, alcohols, antioxidants, buffers, bacteriostats, or solutes that render the formulation isotonic with the blood of the intended recipient.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms can be made by forming microencapsule matrices of the active compound in a biodegradable polymer, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissue.

The pharmaceutical composition may also be in the form of a microemulsion. In the form of a microemulsion, bioavailability of the active agent may be improved. Reference is made to (Dorunoo [et al.], Drug Development and Industrial Pharmacy, 17(12):1685-1713 (1991)) and (Sheen [et al.], J. Pharm. Sci., 80(7):712-714, (1991)), the contents of which are herein incorporated by reference in their entirety.

The pharmaceutical composition may also contain micelles formed from a compound of the present invention and at least one amphiphilic carrier, in which the micelles have an average diameter of less than about 100 nm. In some embodiments, the micelles have an average diameter less than about 50 nm, or an average diameter less than about 30 nm, or an average diameter less than about 20 nm.

While any suitable amphiphilic carrier is considered herein, the amphiphilic carrier is generally one that has been granted Inactive Pharmaceutical Ingredient status, and that can both solubilize the compound of the present invention and microemulsify it at a later stage when the solution comes into a contact with a complex water phase (such as one found in the living biological tissue). Usually, amphiphilic ingredients that satisfy these requirements have HLB (hydrophilic to lipophilic balance) values of 2-20, and their structures contain straight chain aliphatic radicals in the range of C-6 to C-20. Some examples of amphiphilic agents include polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series). Commercially available amphiphilic carriers are particularly contemplated, including the Gelucire®-series, Labrafil®, Labrasol®, or Lauroglycol®, PEG-mono-oleate, PEG-di-oleate, PEG-mono-laurate and di-laurate, Lecithin, Polysorbate 80.

The CD (such as HPβCD or another CD of the present disclosure) dimer may be administered by any suitable means. Preferred routes of administration include parenteral (e.g., subcutaneous, intramuscular, or intravenous), topical, transdermal, oral, sublingual, or buccal. Said administration may be ocular (e.g., in the form of an eyedrop), intravitreous, retro-orbital, subretinal, subscleral, which may be preferred in case of ocular disorders, such as AMD.

The CD (such as HPβCD or another CD of the present disclosure) dimer may be administered to a subject, or may be used in vitro, e.g., applied to a cell or tissue that have been removed from an animal. Said cell or tissue may then be introduced into a subject, whether the subject from which it was removed or another individual, preferably of the same species.

The subject (i.e., patient) receiving the treatment is typically an animal, generally a mammal, preferably a human. The subject may be a non-human animal, which includes all vertebrates, e.g., mammals and non-mammals, such as non-human primates, sheep, dogs, cats, cows, horses, chickens, amphibians, and reptiles. In some embodiments, the subject is livestock, such as cattle, swine, sheep, poultry, and horses, or companion animals, such as dogs and cats. The subject may be genetically male or female. The subject may be any age, such as elderly (generally, at least or above 60, 70, or 80 years of age), elderly-to-adult transition age subjects, adults, adult-to-pre-adult transition age subjects, and pre-adults, including adolescents (e.g., 13 and up to 16, 17, 18, or 19 years of age), children (generally, under 13 or before the onset of puberty), and infants. The subject can also be of any ethnic population or genotype. Some examples of human ethnic populations include Caucasians, Asians, Hispanics, Africans, African Americans, Native Americans, Semites, and Pacific Islanders. The methods of the invention may be more appropriate for some ethnic populations, such as Caucasians, especially northern European populations, and Asian populations.

The present disclosure includes further substitutions of the dimeric CDs (such as HPβCDs or another CD of the present disclosure) described herein. Chemical modification may be performed before or after dimerization. Chemical modification of CDs can be made directly on the native beta CD rings by reacting a chemical reagent (nucleophile or electrophile) with a properly functionalized CD (Adair-Kirk [et al.], Nat. Med., 14(10):1024-5, (2008)); (Khan, [et al.], Chem. Rev., 98(5):1977-1996, (1998)). To date, more than 1,500 CD derivatives have been made by chemical modification of native CDs. CDs can also be prepared by de novo synthesis, starting with glucopyranose-linked oligopyranosides. Such a synthesis can be accomplished by using various chemical reagents or biological enzymes, such as CD transglycosylase. An overview of chemically modified CDs as drug carriers in drug delivery systems is described, for example, in (Stella, [et al.], Toxicol. Pathol., 36(1):30-42, (2008)), the disclosure of which is herein incorporated by reference in its entirety. U.S. Pat. Nos. 3,453,259 and 3,459,731 describe electroneutral CDs, the disclosures of which are herein incorporated by reference in its entirety. Other derivatives include CDs with cationic properties, as disclosed in U.S. Pat. No. 3,453,257; insoluble crosslinked CDs, as disclosed in U.S. Pat. No. 3,420,788; and CDs with anionic properties, as disclosed in U.S. Pat. No. 3,426,011, the disclosures of which are all hereby incorporated by reference in their entirety. Among the CD derivatives with anionic properties, carboxylic acids, phosphorous acids, phosphinous acids, phosphonic acids, phosphoric acids, thiophosphonic acids, thiosulphinic acids, and sulfonic acids have been appended to the parent CD, as disclosed, for example, in U.S. Pat. No. 3,426,011. Sulfoalkyl ether CD derivatives have also been described, e.g., in U.S. Pat. No. 5,134,127, the disclosure of which is hereby incorporated by reference in its entirety. In some embodiments, the cyclic oligosaccharide can have two or more of the monosaccharide units replaced by triazole rings, which can be synthetized by the Azide-alkyne Huisgen cycloaddition reaction ((Bodine, [et al.], J. Am. Chem. Soc., 126(6):1638-9, (2004)).

The dimeric CDs of the disclosure are joined by a linker. Methods that may be used to join the CD subunits to a linker are described in the working examples. Additional methods of joining CD subunits to a linker are known in the art. (Georgeta [et al.], J. Bioact. Compat. Pol., 16:39-48. (2001)), (Uu [et al.], Acc. Chem. Res., 39:681-691. (2006)), (Ozmen [et al.], J. Mol. Catal. B-Enzym., 57:109-114. (2009)), (Trotta [et al.], Compos. Interface, 16:39-48. (2009)), each of which is hereby incorporated by reference in its entirety. For example, a linker group containing a portion reactive to a hydroxyl group (e.g., a carboxyl group, which may be activated by a carbodiimide) can be reacted with the CD to form a covalent bond thereto. In another example, one or more hydroxyl groups of the CD can be activated by known methods (e.g., tosylation) to react with a reactive group (e.g., amino group) on the linker.

In general, the linker initially contains two reactive portions that react with and bond to each CD monomer. In one embodiment, a linker is first attached to a CD to produce a linker-CD compound that is isolated, and then the remaining reactive portion of the linker in the linker-CD compound is subsequently reacted with a second CD. The second reactive portion of the linker may be protected during reaction of the first reactive group, though protection may not be employed where the first and second reactive portions of the linker react with the two molecules differently. A linker may be reacted with both molecules simultaneously to link them together. In other embodiments, the linker can have additional reactive groups in order to link to other molecules.

Numerous linkers are known in the art. Such linkers can be used for linking any of a variety of groups together when the groups possess, or have been functionalized to possess, groups that can react and link with the reactive linker. Some groups capable of reacting with double-reactive linkers include amino, thiol, hydroxyl, carboxyl, ester, and alkyl halide groups. For example, amino-amino coupling reagents can be employed to link a cyclic oligosaccharide with a polysaccharide when each of the groups to be linked possess at least one amino group. Some examples of amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. In other embodiments, amino-thiol coupling agents can be employed to link a thiol group of one molecule with an amino group of another molecule. Some examples of amino-thiol coupling reagents include succinimidyl 4-(N-maleimidomethyl)-cyclohexane-1-carboxylate (SMCC), and sulfosuccinimidyl 4-(N-maleimidomethyl)-cyclohexane-1-carboxylate (sulfo-SMCC). In yet other embodiments, thiol-thiol coupling agents can be employed to link groups bearing at least one thiol group.

In some embodiments, the linker is as small as a single atom (e.g., an —O—, —CH2-, or —NH— linkage), or two or three atoms in length (e.g., an amido, ureido, carbamate, ester, carbonate, sulfone, ethylene, or trimethylene linkage). In other embodiments, the linker provides more freedom of movement by being at least four, five, six, seven, or eight atom lengths, and up to, for example, 10, 12, 14, 16, 18, 20, 22, 24, 26, 28, or 30 atom lengths. Preferred linker lengths are between 2 and 12 atoms, or between 4 and 8 atoms. In exemplary embodiments, the linker is C4 alkyl, which may be unsubstituted. In exemplary embodiments, the linker comprises a triazole.

Atherosclerosis

Exemplary CD dimers described herein are useful to prevent or treat disease such as atherosclerosis. The combination of the CD dimer and one or more active agents, such as those described herein (e.g., antihyperlipidemic agents such as statins) are useful in treating any atherosclerosis, as well as the signs, symptoms or complications of atherosclerosis. Atherosclerosis (also known as arteriosclerotic vascular disease or ASVD and known as coronary artery disease or CAD) is a condition in which an artery wall thickens as a result of the accumulation of fatty materials such as cholesterol. Atherosclerosis is a chronic disease that can remain asymptomatic for decades. It is a syndrome affecting arterial blood vessels, a chronic inflammatory response in the walls of arteries, thought to be caused largely by the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

The pathobiology of atherosclerotic lesions is complicated but generally, stable atherosclerotic plaques, which tend to be asymptomatic, are rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap expose thrombogenic material, such as collagen to the circulation and eventually induce thrombus formation in the lumen. Upon formation, intraluminal thrombi can occlude arteries outright (e.g., coronary occlusion), but more often they detach, move into the circulation and can eventually occlude smaller downstream branches causing thromboembolism (e.g., stroke is often caused by thrombus formation in the carotid arteries). Apart from thromboembolism, chronically expanding atherosclerotic lesions can cause complete closure of the lumen. Chronically expanding lesions are often asymptomatic until lumen stenosis is so severe that blood supply to downstream tissue(s) is insufficient, resulting in ischemia.

These complications of advanced atherosclerosis are chronic, slowly progressive and cumulative. In some instances, soft plaques suddenly rupture, causing the formation of a thrombus that will rapidly slow or stop blood flow, leading to death of the tissues fed by the artery (infarction). Coronary thrombosis of a coronary artery is also a common complication which can lead to myocardial infarction. Blockage of an artery to the brain may result in stroke. In advanced atherosclerotic disease, claudication from insufficient blood supply to the legs, typically caused by a combination of both stenosis and aneurysmal segments narrowed with clots, may occur.

Atherosclerosis can affect the entire artery tree, but larger, high-pressure vessels such as the coronary, renal, femoral, cerebral, and carotid arteries are typically at greater risk.

Signs, symptoms and complications of atherosclerosis include, but are not limited to increased plasma total cholesterol, VLDL-C, LDL-C, free cholesterol, cholesterol ester, triglycerides, phospholipids and the presence of lesions (e.g., plaques) in arteries, as discussed above. In some instances, increased cholesterol (e.g., total cholesterol, free cholesterol and cholesterol esters) can be seen in one or more of plasma, aortic tissue and aortic plaques.

Certain individuals may be predisposed to atherosclerosis. Accordingly, the present disclosure relates to methods of administering the subject CD dimers alone, or in combination with one or more additional therapeutic agents (e.g., antihyperlipidemic agents, such as statins), to prevent atherosclerosis, or the signs, symptoms or complications thereof. In some embodiments a subject predisposed to atherosclerosis may exhibit one or more of the following characteristics: advanced age, a family history of heart disease, a biological condition, high blood cholesterol. In some embodiments, the biological condition comprises high levels of low-density lipoprotein cholesterol (LDL-C) in the blood, low levels of high-density lipoprotein cholesterol (HDL-C) in the blood, hypertension, insulin resistance, diabetes, excess body weight, obesity, sleep apnea, contributing lifestyle choice(s) and/or contributing behavioral habit (s). In some embodiments, the behavioral habit comprises smoking and/or alcohol use. In some embodiments, the lifestyle choice comprises an inactive lifestyle and/or a high stress level.

Exemplary embodiments provide for the administration of a CD dimer of the present disclosure, optionally in combination with one or more additional agents, to a patient having atherosclerosis. The patient may exhibit one or more signs or symptoms of atherosclerosis. Atherosclerosis may be diagnosed based on one or more of Doppler ultrasound, ankle-brachial index, electrocardiogram, stress test, angiogram (optionally with cardiac catheterization), computerized tomography (CT), magnetic resonance angiography (MRA), or other methods of imaging arteries or measuring blood flow.

Exemplary embodiments provide for the administration of a combination of therapies comprising a CD dimer of the present disclosure and one or more additional therapies. These combination therapies for treatment of atherosclerosis may include a CD dimer of the present disclosure and another therapy for the treatment or prevention of atherosclerosis, such as an anti-cholesterol drug, anti-hypertension drug, anti-platelet drug, dietary supplement, or surgical or behavioral intervention, including but not limited to those described below. Additional combination therapies include a CD dimer of the present disclosure and another therapy for the treatment of heart failure, such as one or more aldosterone antagonists, ACE inhibitors, ARBs (angiotensin II receptor blockers), ARNIs (angiotensin receptor-neprilysin inhibitors), beta-blockers, blood vessel dilators, calcium channel blockers, digoxin, diuretics, heart pump medications, potassium, magnesium, selective sinus node inhibitors, or combinations thereof. Combination therapies for the treatment of the dry form of age-related macular degeneration (AMD) or Stargardt's disease include a CD dimer of the present disclosure and another therapy for the treatment of AMD, such as, LBS-008 (Belite Bio) (a nonretinoid antagonist of retinol binding protein 4), AREDS supplement formula comprising vitamins C and E, beta-carotene, zinc, and copper, AREDS2 supplement formula comprising a supplement formula that has vitamins C and E, zinc, copper, lutein, zeaxanthin, and omega-3 fatty acids, or combinations thereof. Combination therapies for treatment of Alzheimer's disease include a CD dimer of the present disclosure and one or more cholinesterase inhibitors (ARICEPT®, EXELON®, RAZADYNE®) and memantine (NAMENDA®) or a combination thereof. Combination therapies for Niemann-Pick Disease include a CD dimer of the present disclosure and one or more of miglustat (ZAVESCA®), HPβCD (TRAPPSOL CYCLO, VTS-270), and physical therapy. The combination therapies may be administered simultaneously, essentially simultaneously, or sequentially, in either order. Combination therapies may be co-administered in a single formulation, or separately, optionally in a dosage kit or pack containing each medication in the combination, e.g., in a convenient pre-measured format in which one or more single doses of each drug in the combination is provided. The combination therapy may exhibit a synergistic effect, wherein the effects of the combined therapies exceed the effects of the individual treatments alone. While combination therapies in general include administration of an effective amount of the CD dimer and the combined therapy, the combination therapies may allow for effective treatment with a lower dosage of the CD and/or the combined therapy, which advantageously may decrease side-effects associated with the regular (non-combination) dosage.

Combination therapies may include therapies for the treatment or prevention of diseases or conditions related to atherosclerosis, such as coronary artery disease, angina pectoralis, heart attack, cerebrovascular disease, transient ischemic attack, and/or peripheral artery disease. Combination therapies may include therapies for the treatment or prevention of conditions that may contribute to atherosclerosis formation and/or a worse prognosis, such as hypertension, hypercholesterolemia, hyperglycemia, and diabetes.

In exemplary embodiments, a CD dimer of the present invention is co-administered with an anti-cholesterol drug, such as a fibrate or statin, e.g., ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and/or ZOCOR® (simvastatin). The anti-cholesterol drug may be administered in an amount effective to prevent or treat hypercholesterolemia.

In exemplary embodiments, a CD dimer of the present invention is co-administered with an anti-platelet drug, e.g., aspirin.

In exemplary embodiments, a CD dimer of the present invention is co-administered with an anti-hypertension drug. Exemplary anti-hypertension drugs include beta blockers, Angiotensin-converting enzyme (ACE) inhibitors, calcium channel blockers, and/or diuretics.

In exemplary embodiments, a CD dimer of the present invention is co-administered with a dietary supplement, such as one or more of alpha-linolenic acid (ALA), barley, beta-sitosterol, black tea, blond psyllium, calcium, cocoa, cod liver oil, coenzyme Q10, fish oil, folic acid, garlic, green tea, niacin, oat bran, omega-3 fatty acids (such as eicosapentaenoic acid (EPA) and/or docosahexaenoic acid (DHA)), sitostanol, and/or vitamin C.

Exemplary combination therapies also include intervention in patient behavior and/or lifestyle, including counseling and/or supporting smoking cessation, exercise, and a healthy diet, such as a diet low in low density lipoprotein (LDL) and optionally elevated in high density lipoprotein (HDL).

Exemplary combination therapies also include surgical intervention, such as angioplasty, stenting, or both.

The methods of the present invention are useful for treating or preventing atherosclerosis in human subjects. In some instances, the patient is otherwise healthy except for exhibiting atherosclerosis. For example, the patient may not exhibit any other risk factor of cardiovascular, thrombotic or other diseases or disorders at the time of treatment. In other instances, however, the patient is selected on the basis of being diagnosed with, or at risk of developing, a disease or disorder that is caused by or correlated with atherosclerosis. For example, at the time of, or prior to administration of the pharmaceutical composition of the present invention, the patient may be diagnosed with or identified as being at risk of developing a cardiovascular disease or disorder, such as, e.g., coronary artery disease, acute myocardial infarction, asymptomatic carotid atherosclerosis, stroke, peripheral artery occlusive disease, etc. The cardiovascular disease or disorder, in some instances, is hypercholesterolemia.

In other instances, at the time of, or prior to administration of the pharmaceutical composition of the present invention, the patient may be diagnosed with or identified as being at risk of developing atherosclerosis.

In yet other instances, the patient who is to be treated with the methods of the present invention is selected on the basis of one or more factors selected from the group consisting of age (e.g., older than 40, 45, 50, 55, 60, 65, 70, 75, or 80 years), race, gender (male or female), exercise habits (e.g., regular exerciser, non-exerciser), other preexisting medical conditions (e.g., type-II diabetes, high blood pressure, etc.), and current medication status (e.g., currently taking statins, such as e.g., cerivastatin, atorvastatin, simvastatin, pitavastatin, rosuvastatin, fluvastatin, lovastatin, pravastatin, etc., beta blockers, niacin, etc.).

BRIEF DESCRIPTION OF THE SEVERAL VIEWS OF THE DRAWINGS

FIG. 2A depicts examples of possible substitution groups.

FIG. 5E. Solubilization of cholesterol and 7KC by HPβCD butyl-linked dimers of various DS compared to HPβCD monomer.

FIG. 7AA. Synthetic scheme for QA-(CD-TRIAZOLE-βCD) dimer.

FIG. 7AB. MALDI spectrum for QA-(CD-TRIAZOLE-βCD) dimer.

FIG. 7AC. Structure of one possible QA-(CD-TRIAZOLE-βCD) dimer isomer (DS4) with atom numbering.

FIG. 7AD. $^1$H-NMR spectrum of QA(βCD-TRIAZOLE-βCD) ($D_2O$, 298K) with signals labeled and DS calculation.

FIG. 7AE. COSY spectrum of QA(βCD-TRIAZOLE-βCD) dimer with partial assignment ($D_2O$, 298K).

FIG. 7AF. DEPT-edited HSQC spectrum of QA(βCD-TRIAZOLE-βCD) dimer with full assignment ($D_2O$, 298K). Converted to black and white.

FIG. 7AG. Synthetic scheme for SUCC-(CD-TRIAZOLE-βCD) dimer.

FIG. 7AH. MALDI spectrum for SUCC-(CD-TRIAZOLE-βCD) dimer.

FIG. 7AI. Structure of one possible SUCC-(CD-TRIAZOLE-βCD) dimer isomer (DS4) with atom numbering (free acid form).

FIG. 7AJ. $^1$H-NMR spectrum of SUCC(βCD-TRIAZOLE-βCD) ($D_2O$, 298K) with signals labeled.

FIG. 7AK. COSY spectrum of SUCC(βCD-TRIAZOLE-βCD) dimer with partial assignment ($D_2O$, 298K).

FIG. 7AL. DEPT-edited HSQC spectrum of SUCC(βCD-TRIAZOLE-βCD) dimer with full assignment ($D_2O$, 298K). Converted to black and white.

FIG. 8A depicts chemical structures of βCD and β'CD, Structure A-Xa and Structure A-Xb, that are combined to form a homodimer by covalently linking at the L1, L2, L1', and L2' positions of the CD secondary face.

FIG. 12A depicts the synthetic route for butyl-linked αCD homodimers

FIG. 12B depicts the synthetic route for triazole-linked αCD homodimers

FIG. 131 depicts a schematic structure of an HPDS2αCD-HPDS2βCD triazole-linked heterodimer assessed in MD simulations.

FIG. 16A shows a synthetic route for creating butyl-linked βCD-αCD heterodimers.

FIG. 16B shows a synthetic route for creating triazole-linked βCD-αCD heterodimers.

FIG. 16C shows a synthetic route for creating sulfobutylated, triazole-linked βCD-αCD heterodimers.

FIG. 17B depicts the chemical structure of an asymmetric dimer consisting of βCD covalently bonded at the L1 and L1' positions on the secondary face of each CD with general linker A-B-A', wherein said A-B-A' are as defined herein.

FIG. 17C depicts the chemical structure of an asymmetric dimer consisting of two βCD covalently bonded at the L1 and L2' positions on the secondary face of each CD with general linker A-B-A', wherein said A-B-A' are as defined herein.

FIG. 17D depicts the chemical structure of an asymmetric dimer consisting of two βCD covalently bonded at the L2 and 12' positions on the secondary face of each CD with general linker A-B-A', wherein said A-B-A' are as defined herein.

FIG. 18A depicts a schematic structure of a native βCD-HPβCD (DS3—randomly substituted) asymmetric dimer assessed in MD simulations.

FIG. 18B depicts a schematic structure of a native βCD-C6HPβCD (DS3) asymmetric dimer assessed in MD simulations.

FIG. 18C depicts a schematic structure of a native βCD-C6HPβCD (DS7) asymmetric dimer assessed in MD simulations.

FIG. 19A depicts results from MD simulations of a native βCD-HPβCD (DS3—randomly substituted) asymmetric dimer complexed with 7KC or cholesterol in both orientations.

FIG. 19B depicts results from MD simulations of a native βCD-C6HPβCD (DS3) asymmetric dimer complexed with 7KC or cholesterol in both orientations.

FIG. 19C depicts results from MD simulations of a native βCD-C6HPβCD (DS7) asymmetric dimer complexed with 7KC or cholesterol in both orientations.

FIG. 20A shows the first two steps in a synthetic route for creating triazole-linked HPβCD-βCD asymmetric dimers.

FIG. 20B shows the third step in a synthetic route for creating triazole-linked HPβCD-βCD asymmetric dimers. DS3 is depicted.

FIG. 20C depicts the preparation of the azido-linker (3-azido-1-bromo-propane) (Step one A) and the protected 2-hydroxypropylating agent (Step one B).

Figure 20A:
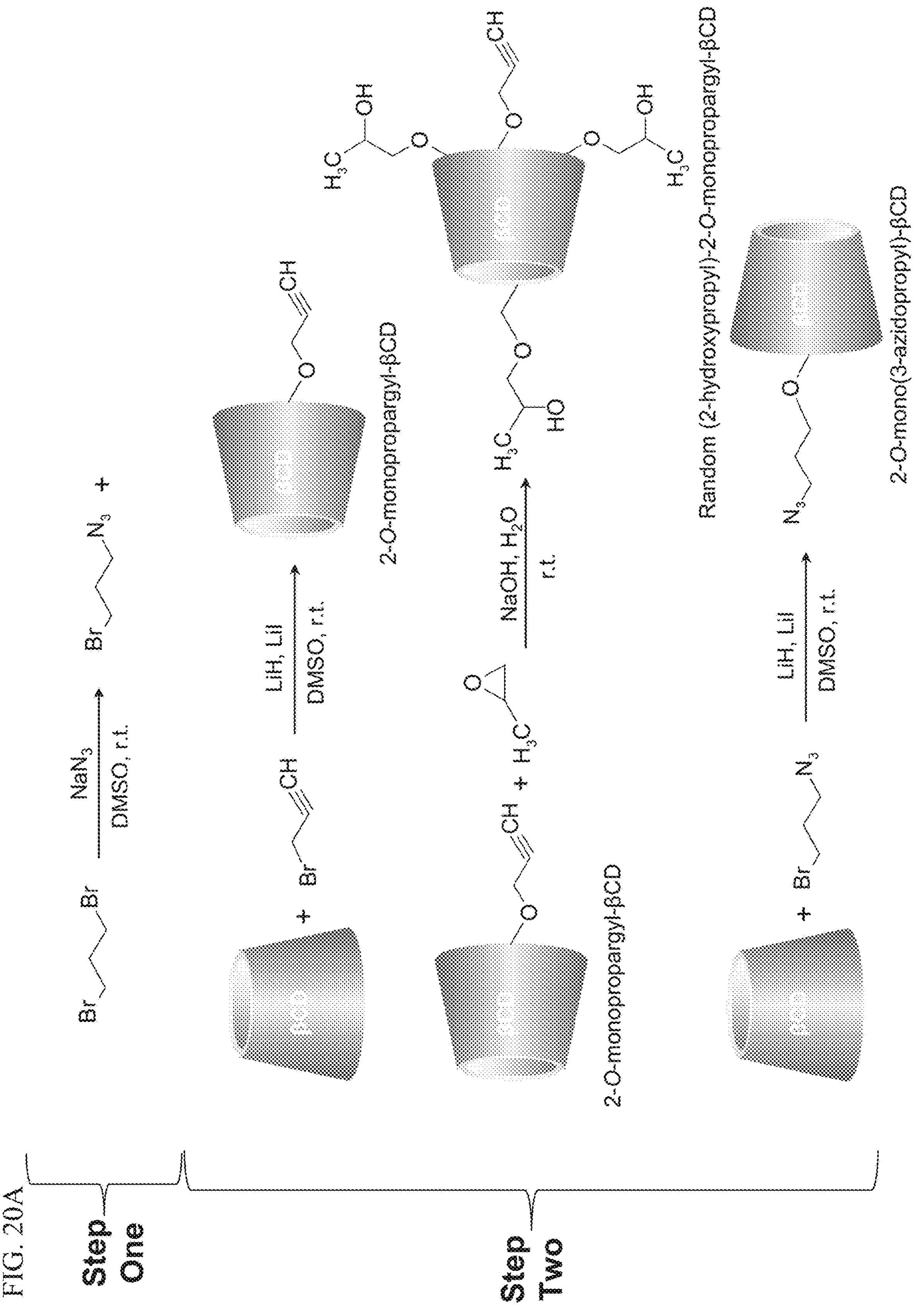
Figure 20B:
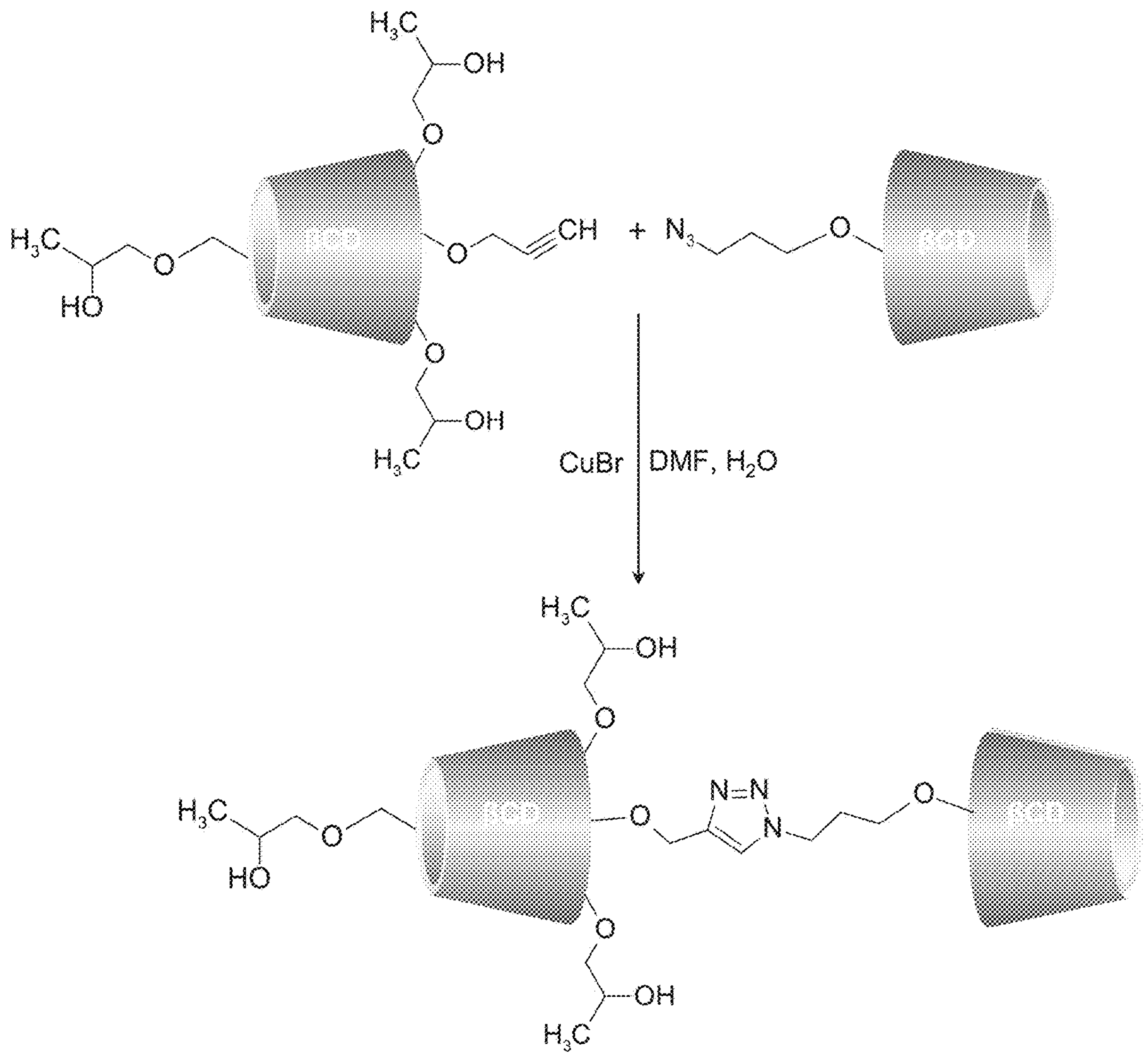
Figure 20C:
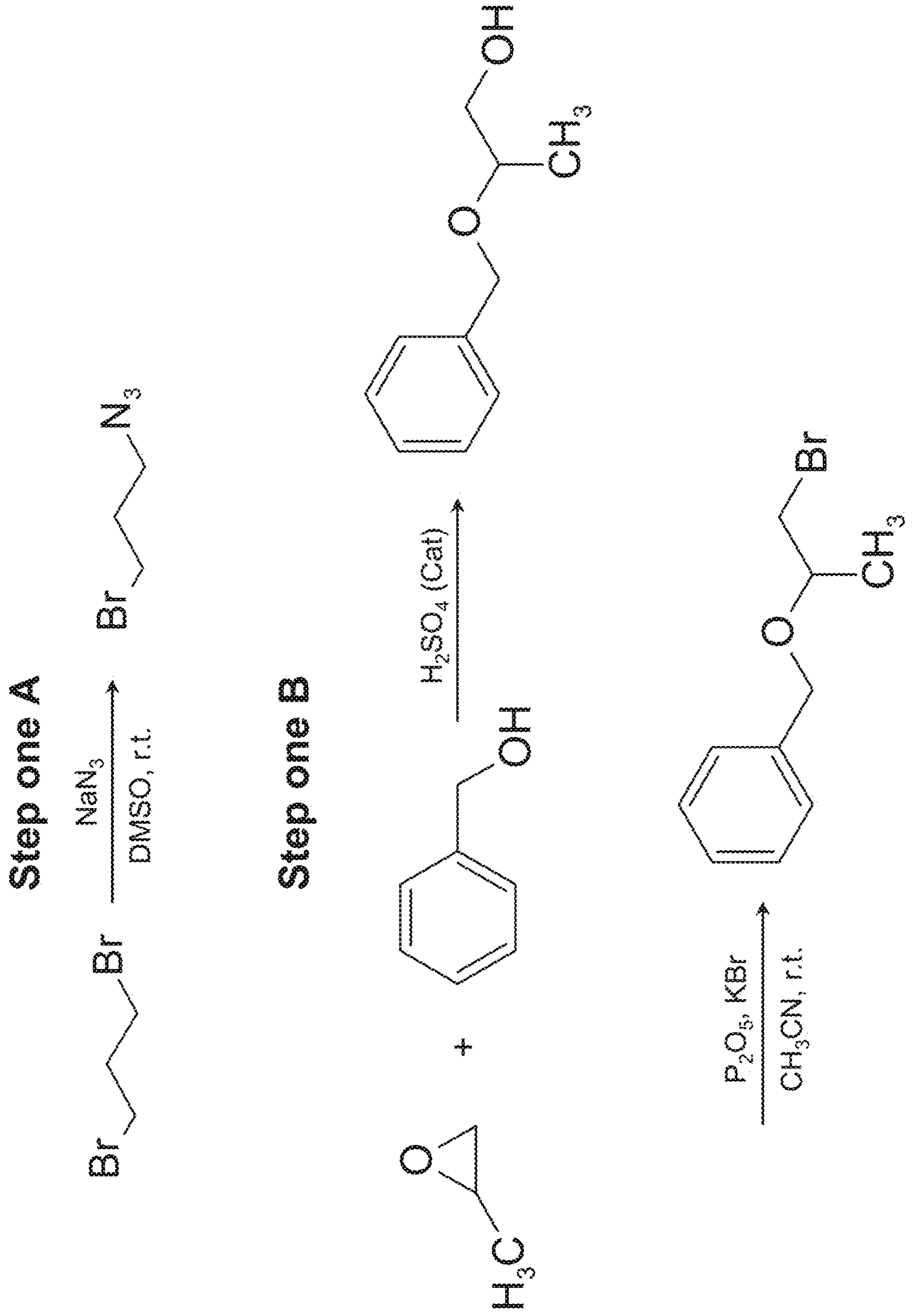
Figure 20D:
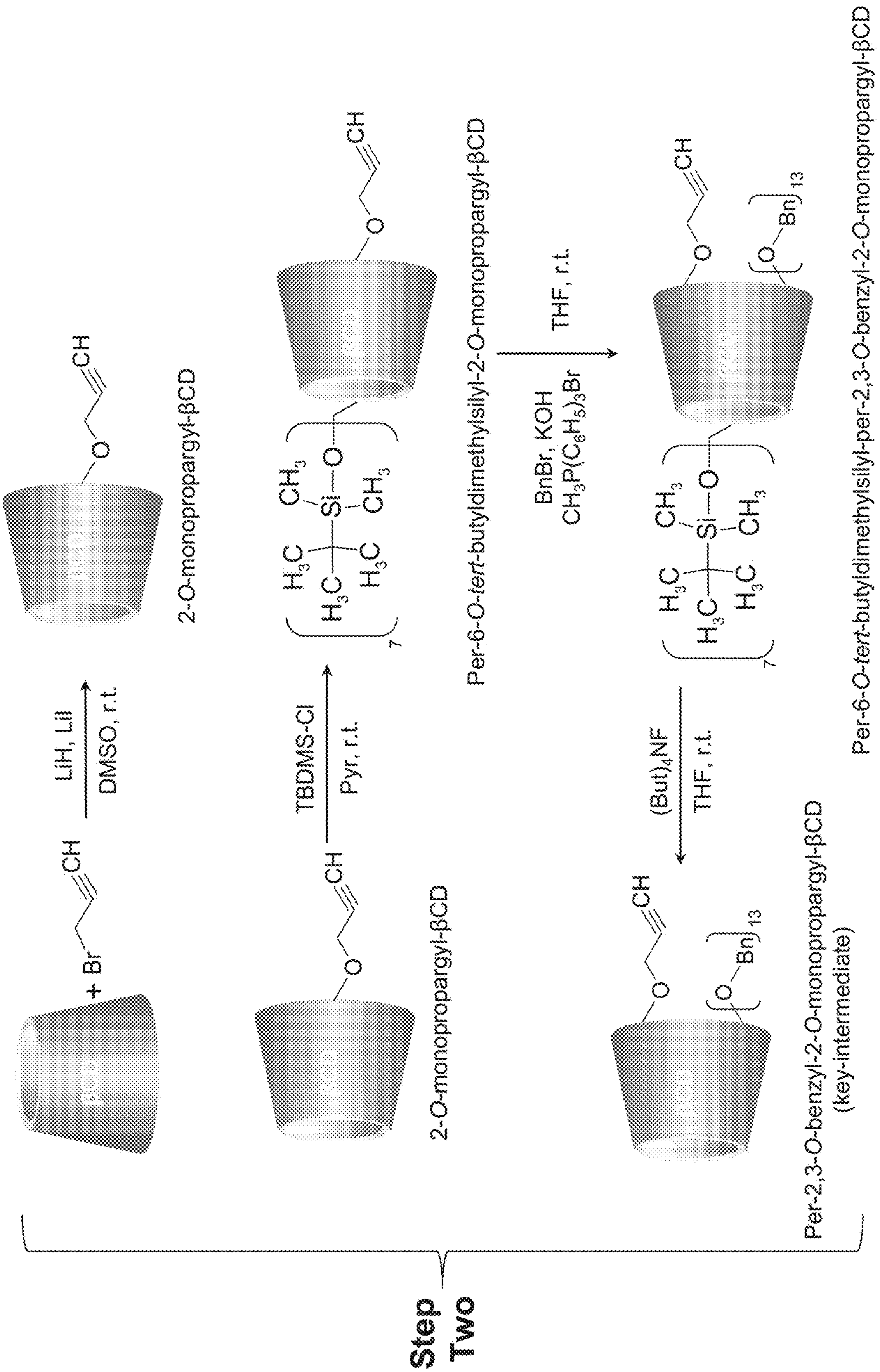

FIG. 20D depicts part of the construction of one of the βCD monomers, the tris-6-O-(2-O-hydroxypropyl)-2-O-monopropargyl-βCD.

Figure 20E:
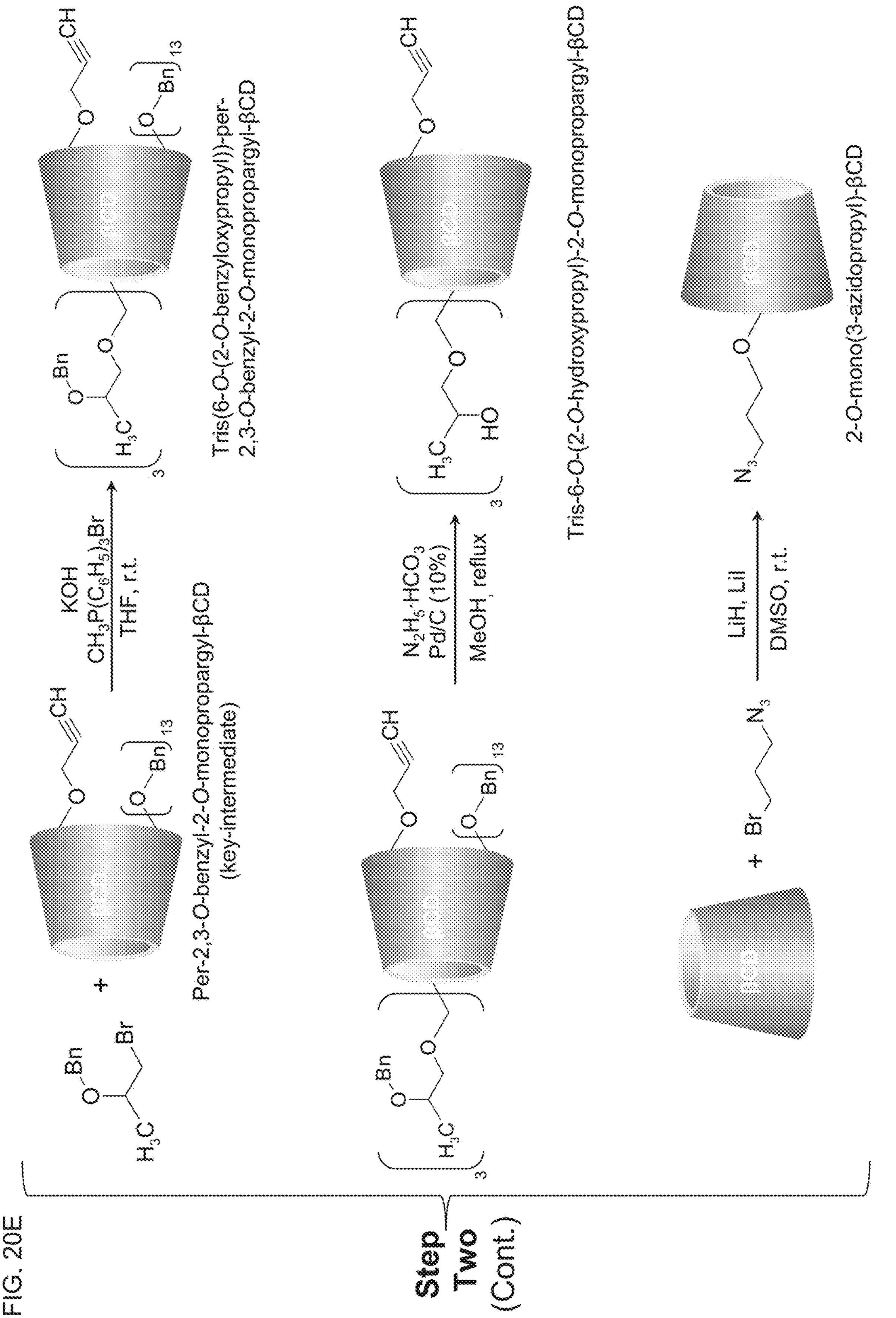

FIG. 20E depicts the completion of the construction of the tris-6-O-(2-O-hydroxypropyl)-2-O-monopropargyl-βCD and the 2-O-mono(3-azidopropyl)-βCD, respectively.

Figure 20F:
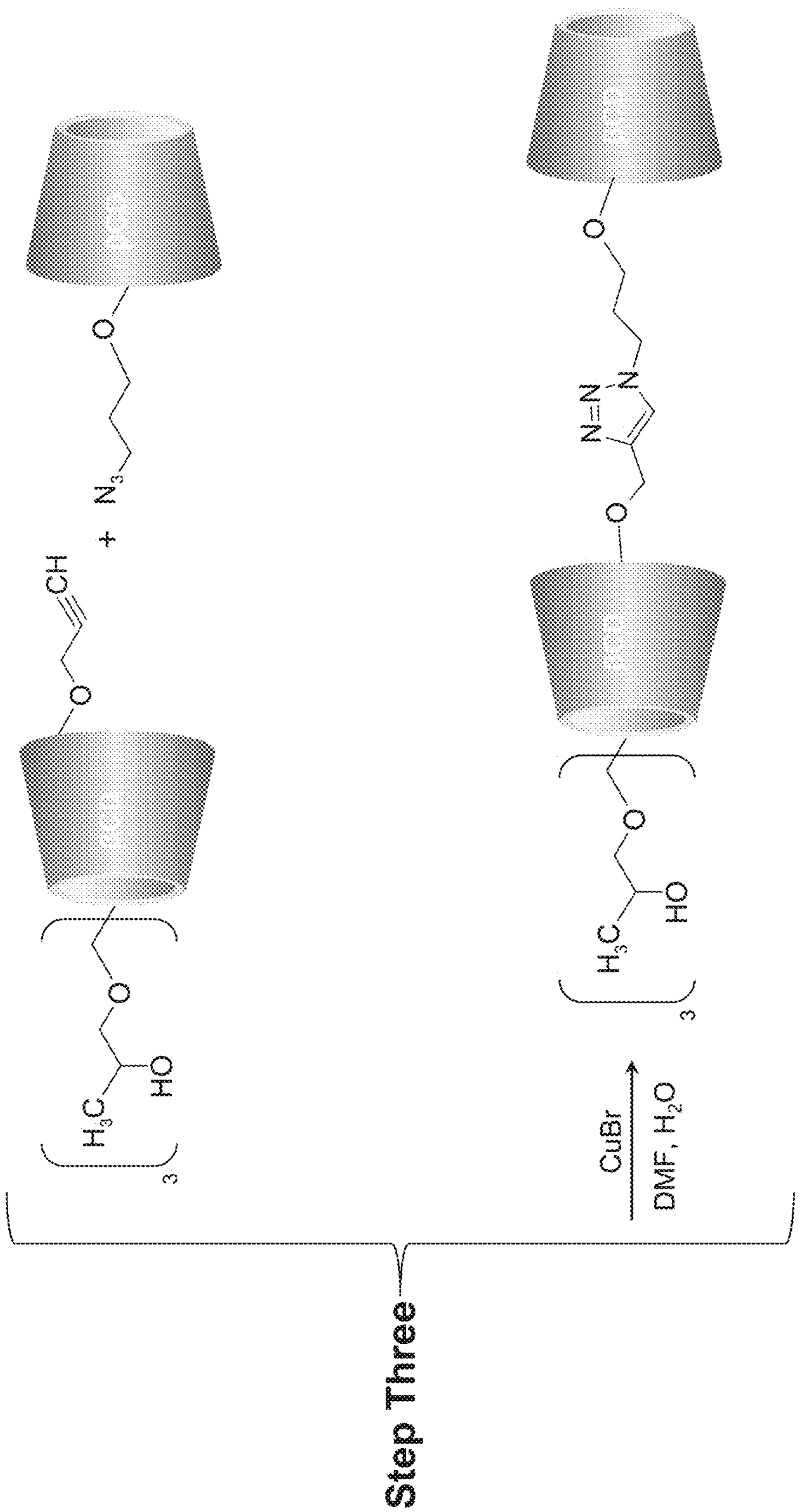

FIG. 20F depicts the cycloaddition reaction to create triazole-linked HPβCD-βCD asymmetric dimers. DS3 is depicted.

Figure 21A:
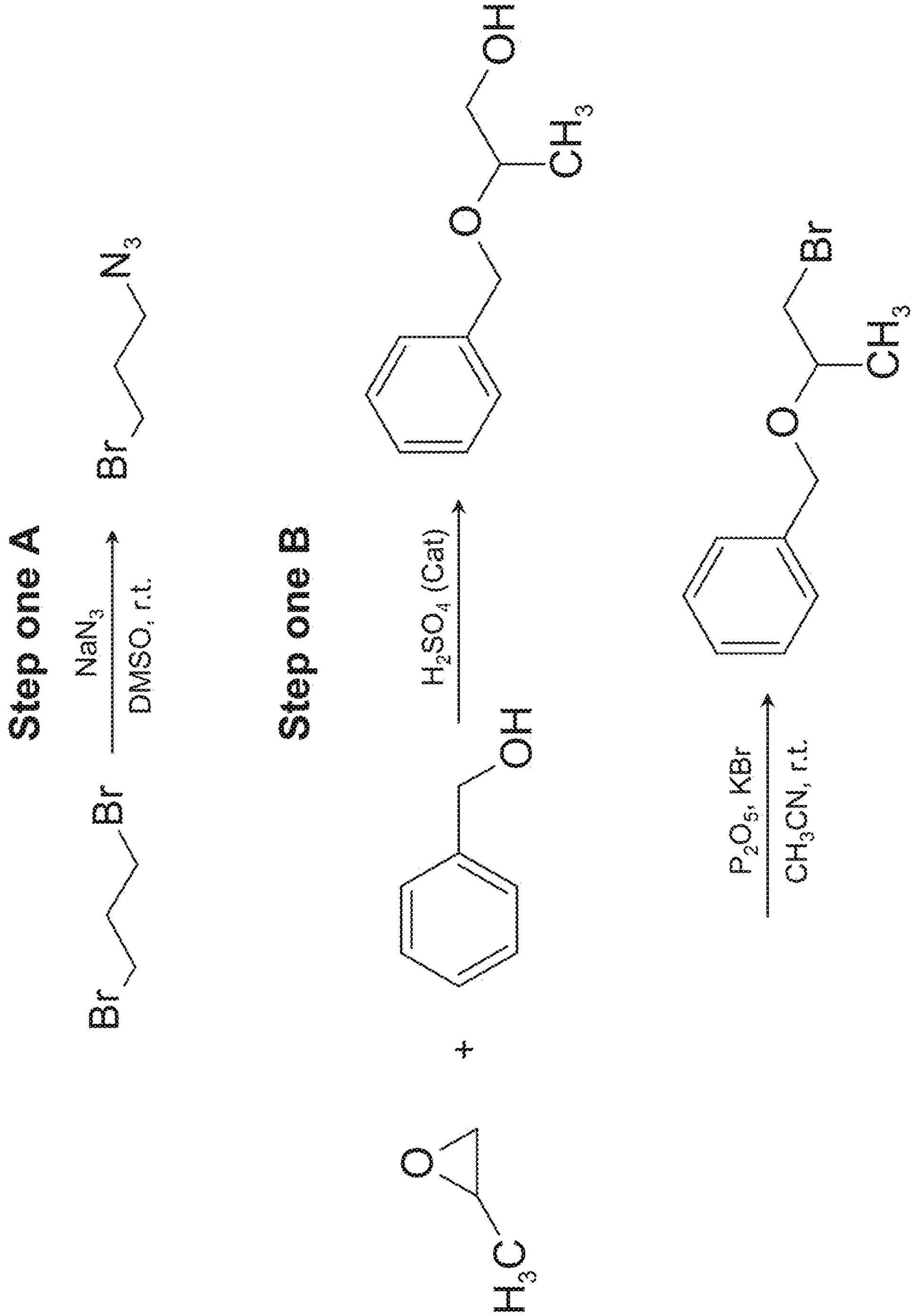

FIG. 21A. The preparation of the azido-linker (3-azido-1-bromo-propane) and the protected version of the 2-hydroxypropylating agent FIG. 21B. Step two: the construction of the two βCD monomers, the 2-O-mono(3-azidopropyl)-βCD and the asymmetric monomer per-6-O-(2-O-hydroxypropyl)-2-O-monopropargyl-βCD, respectively.

FIG. 21G. Step two (continued): the construction of the two βCD monomers, the 2-O-mono(3-azidopropyl)-βCD and the asymmetric monomer per-O-(2-O-hydroxypropyl)-2-O-monopropargyl-βCD, respectively.

Figure 21B:
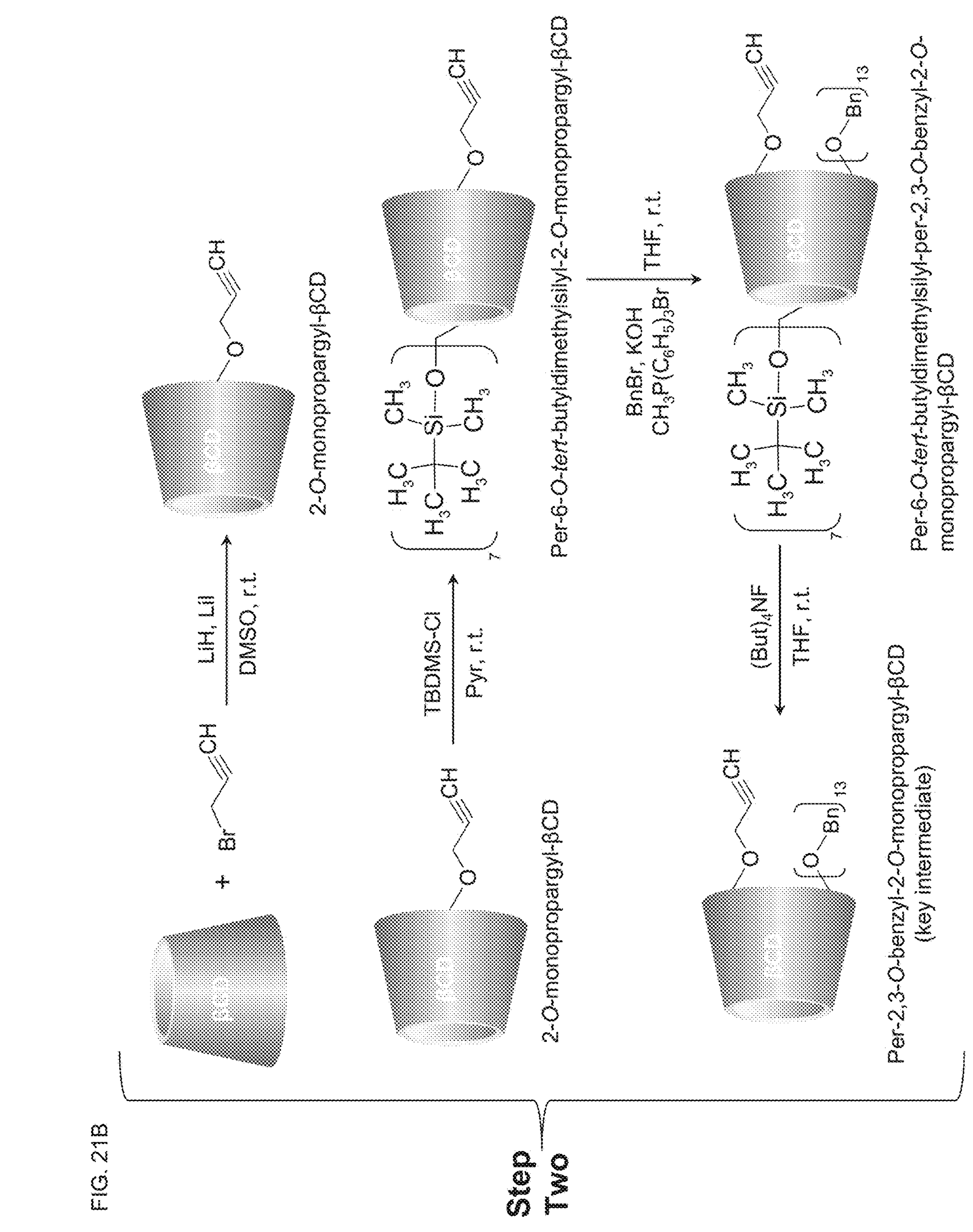
Figure 21C:
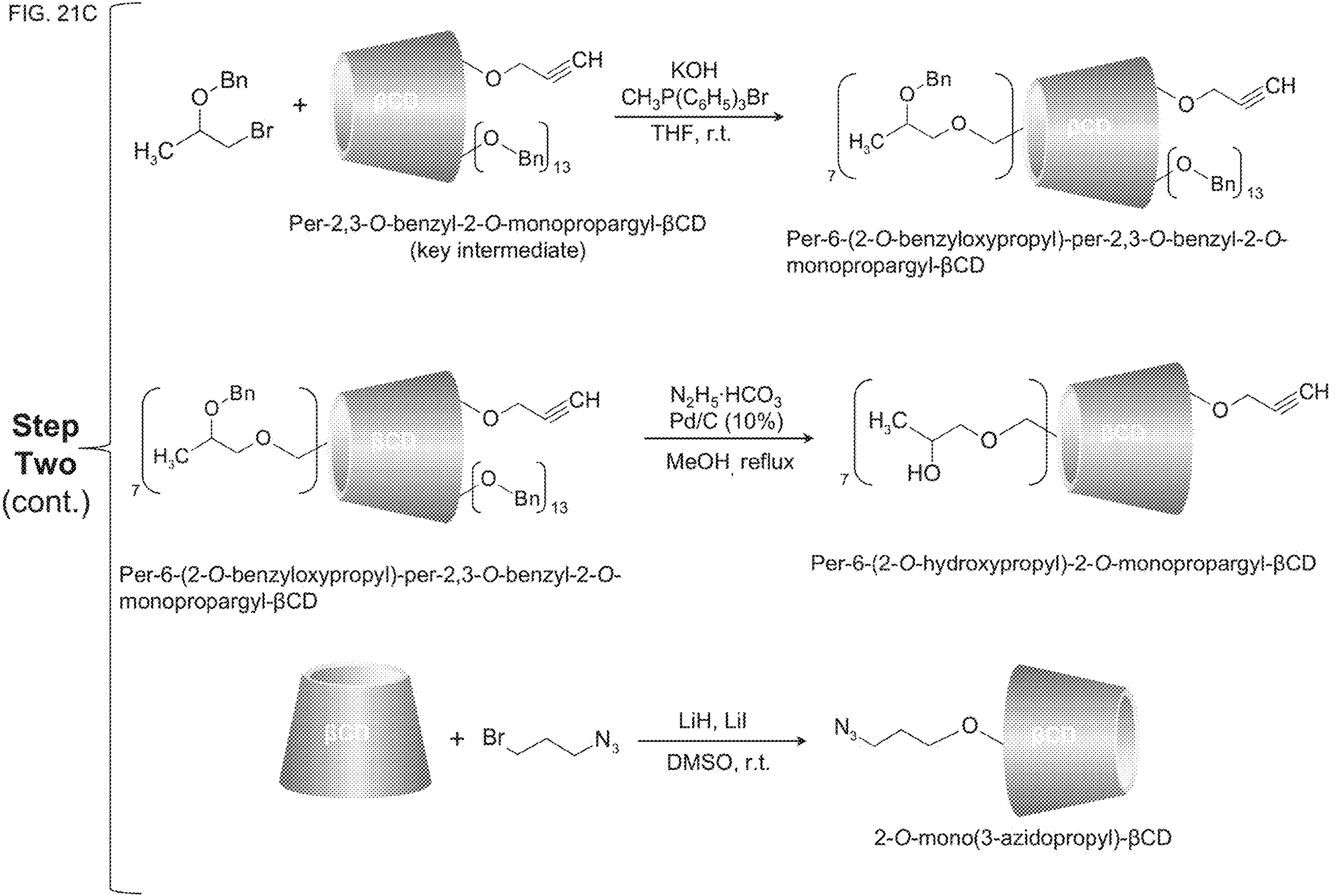
Figure 21D:
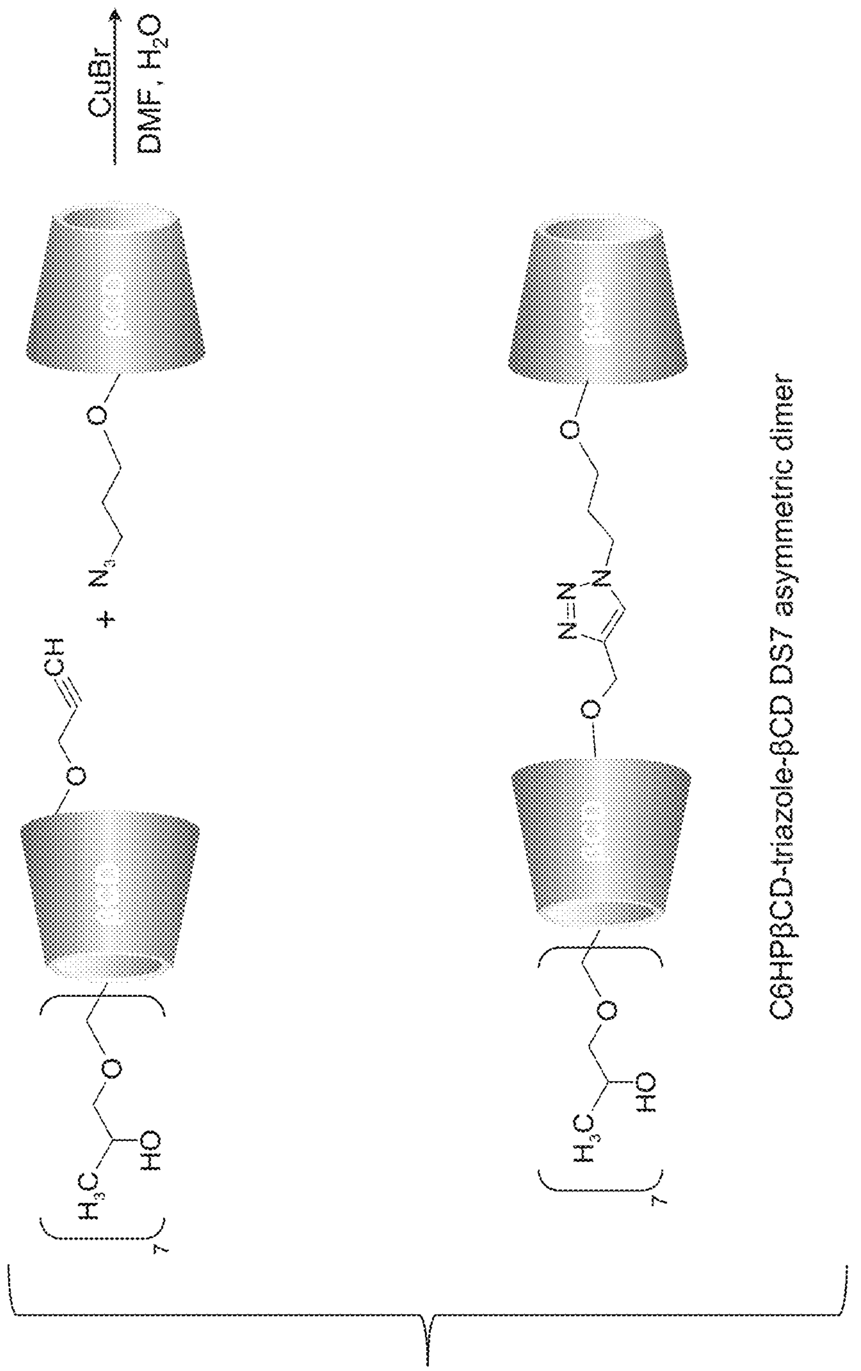

FIG. 21D depicts the cycloaddition reaction to create the C6HPβCD-triazole-βCD DS7 asymmetric dimer.

Figure 22A:
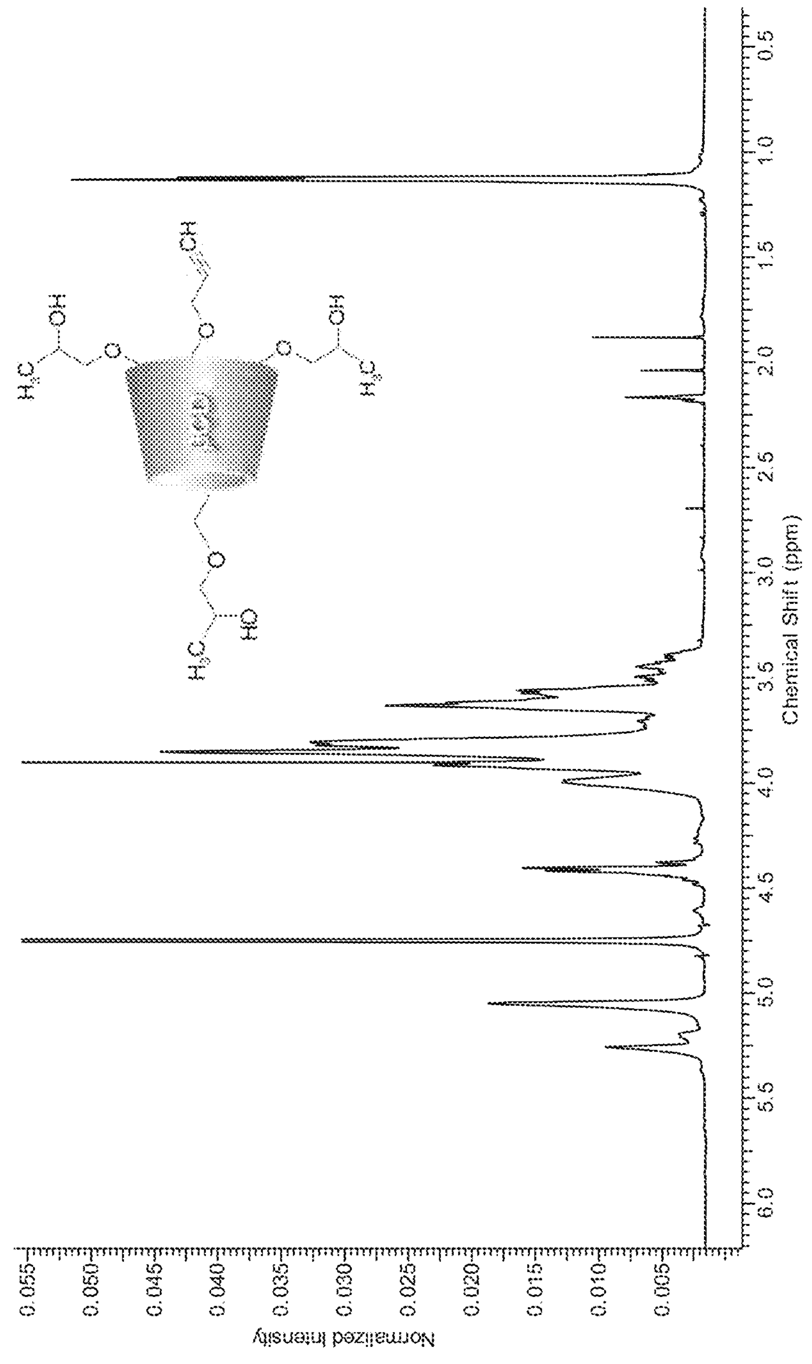

FIG. 22A. $^{1}$H-NMR spectrum, $D_2O$, 298 K of (2-hydroxypropyl)-2-O-monopropargyl-βCD.

Figure 22B:
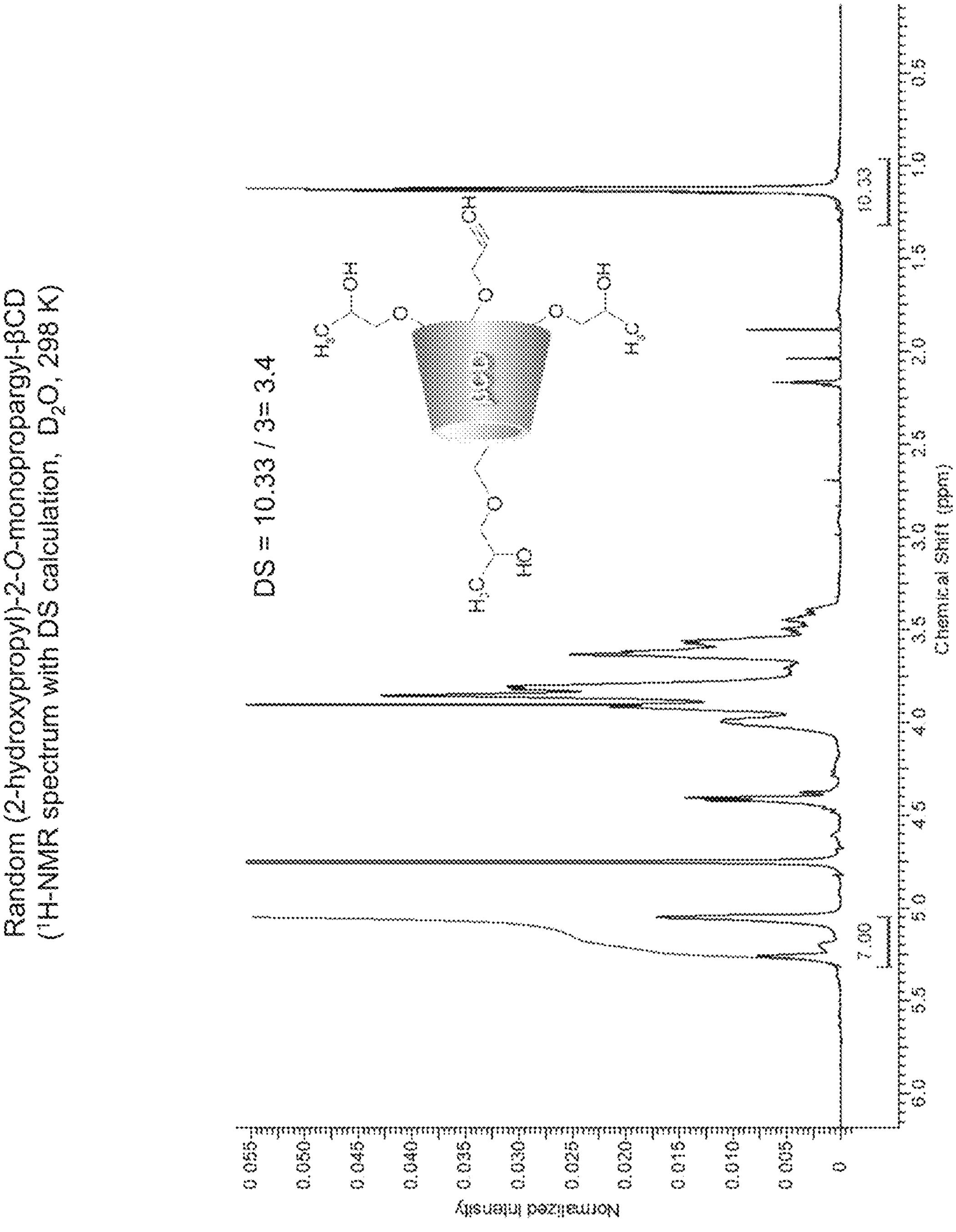

FIG. 22B. $^{1}$H-NMR spectrum, $D_2O$, 298 K of (2-hydroxypropyl)-2-O-monopropargyl-βCD with DS calculation.

Figure 22C:
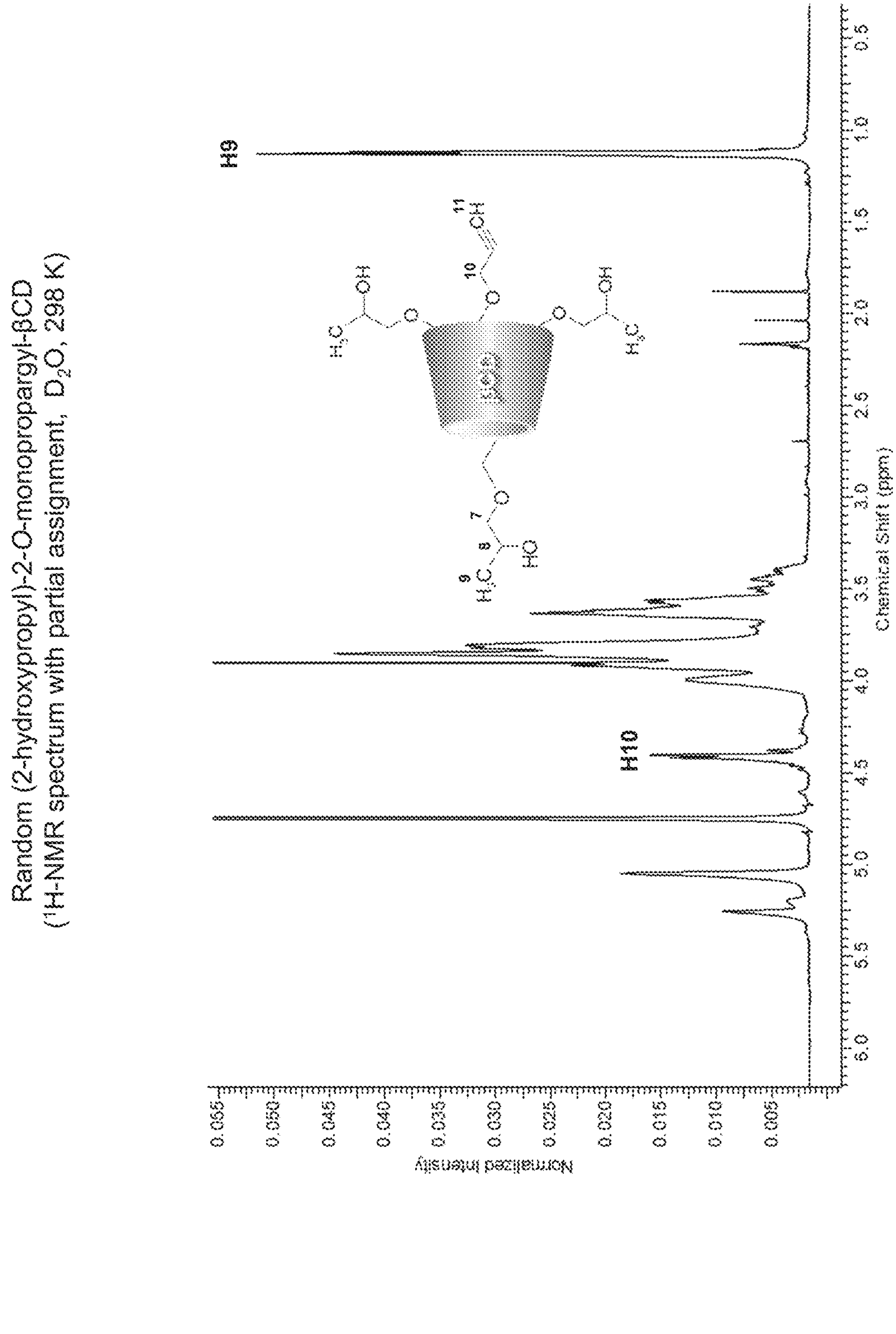

FIG. 22C. $^{1}$H-NMR spectrum, $D_2O$, 298 K of (2-hydroxypropyl)-2-O-monopropargyl-βCD with partial assignment.

Figure 22D:
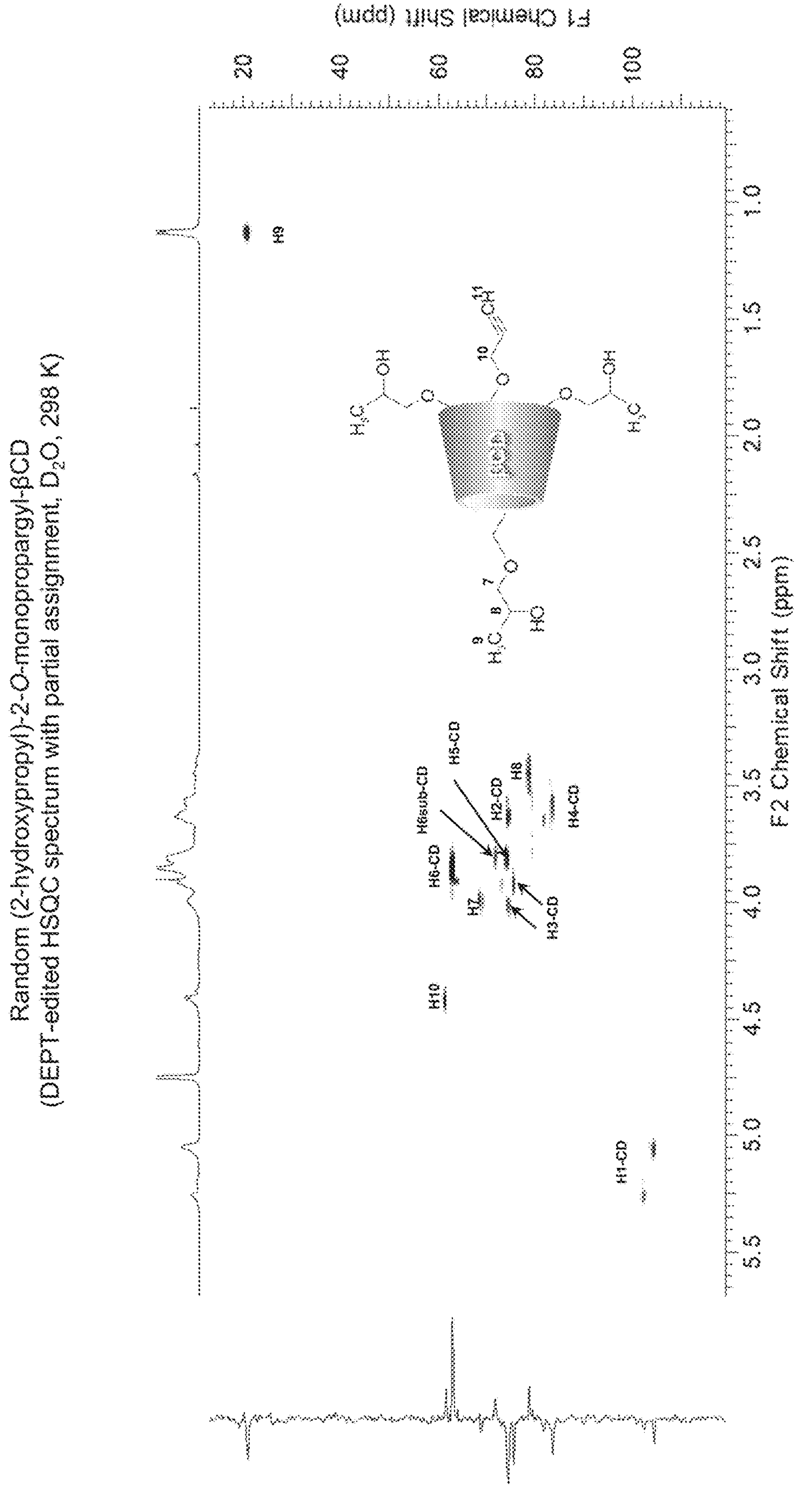

FIG. 22D. DEPT-edited HSQC spectrum with partial assignment, $D_2O$, 298 K of (2-hydroxypropyl)-2-O-monopropargyl-βCD.

Figure 23A:
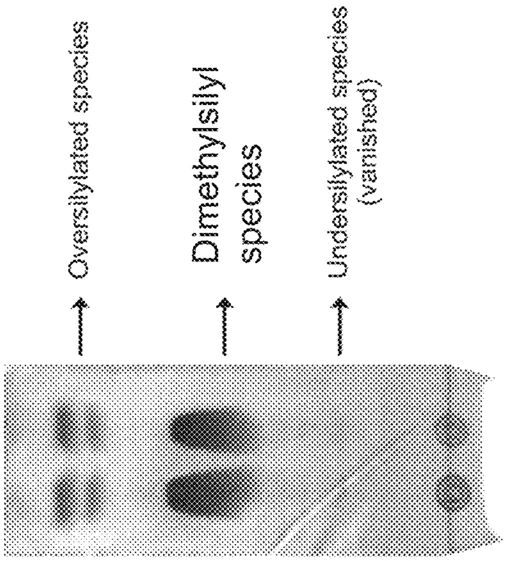

FIG. 23A. TLC of Per-6-O-tert-butyldmethylsilyl-2-O-monopropargyl-βCD.

Figure 23B:
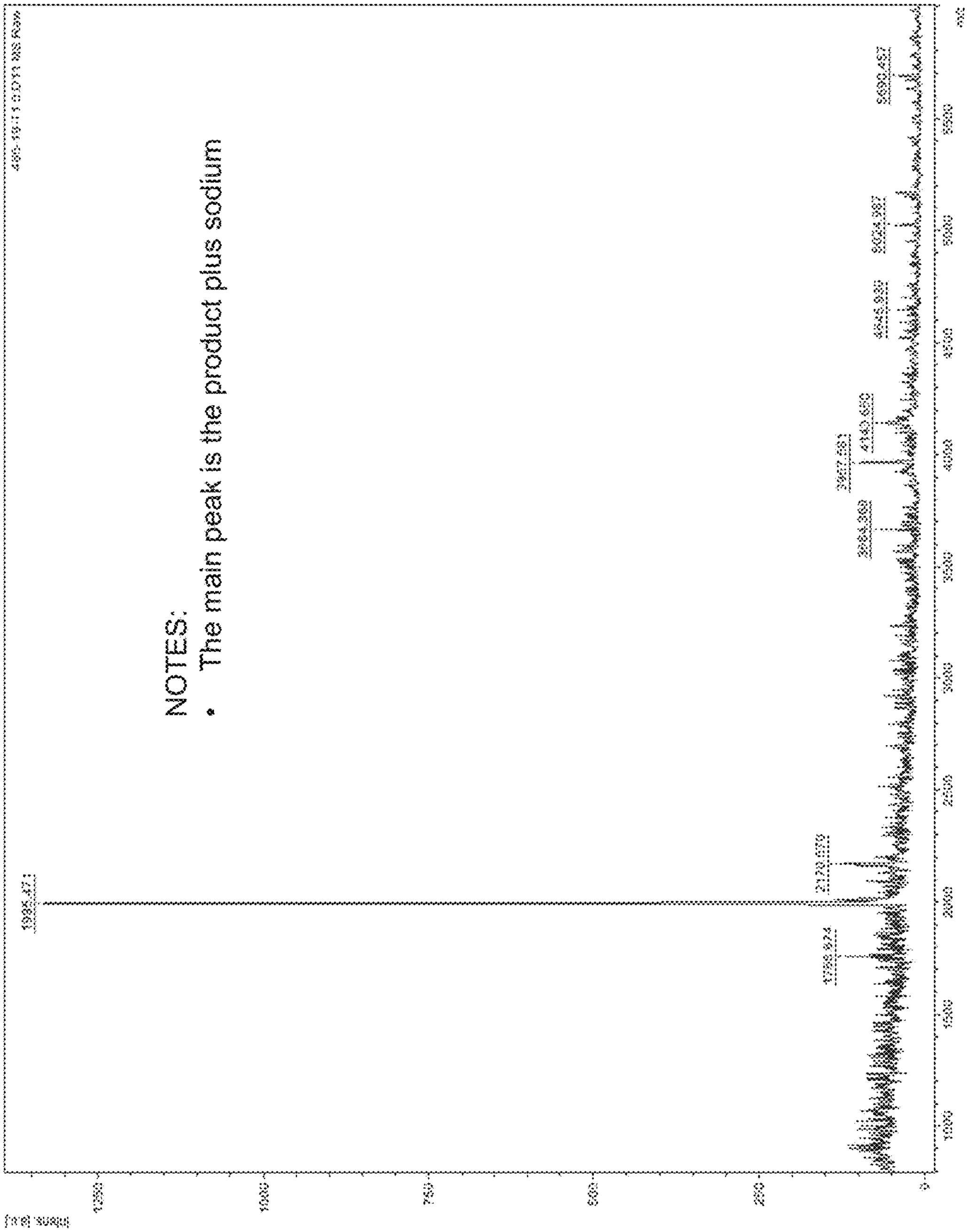

FIG. 23B. MALDI spectrum of Per-6-O-tert-butyldimethylsilyl-2-O-monopropargyl-βCD.

Figure 23C:
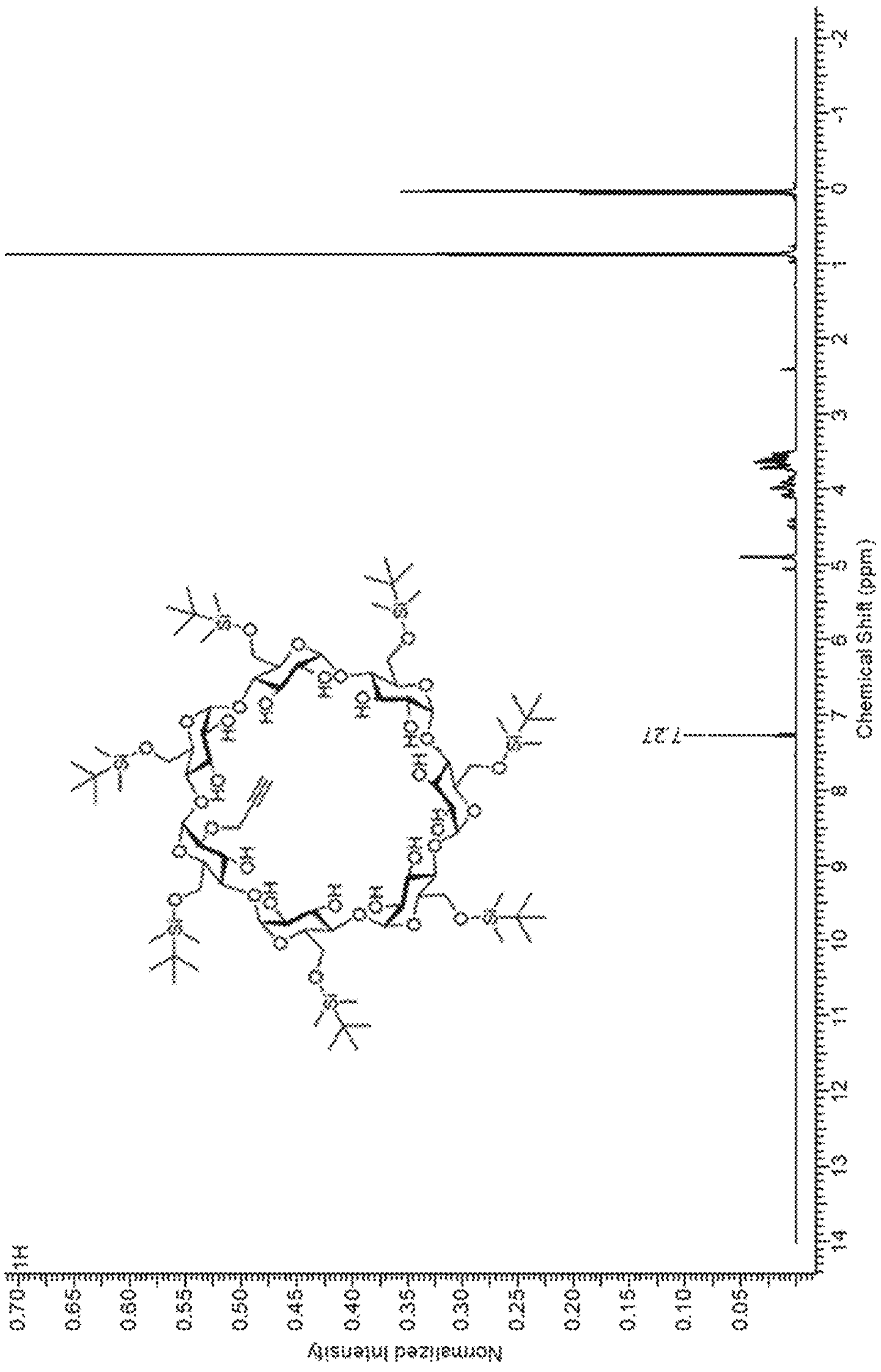

FIG. 23C. $^{1}$H NMR Spectrum of Per-6-O-tert-butyldimethylsilyl-2-O-monopropargyl-βCD.

Figure 23D:
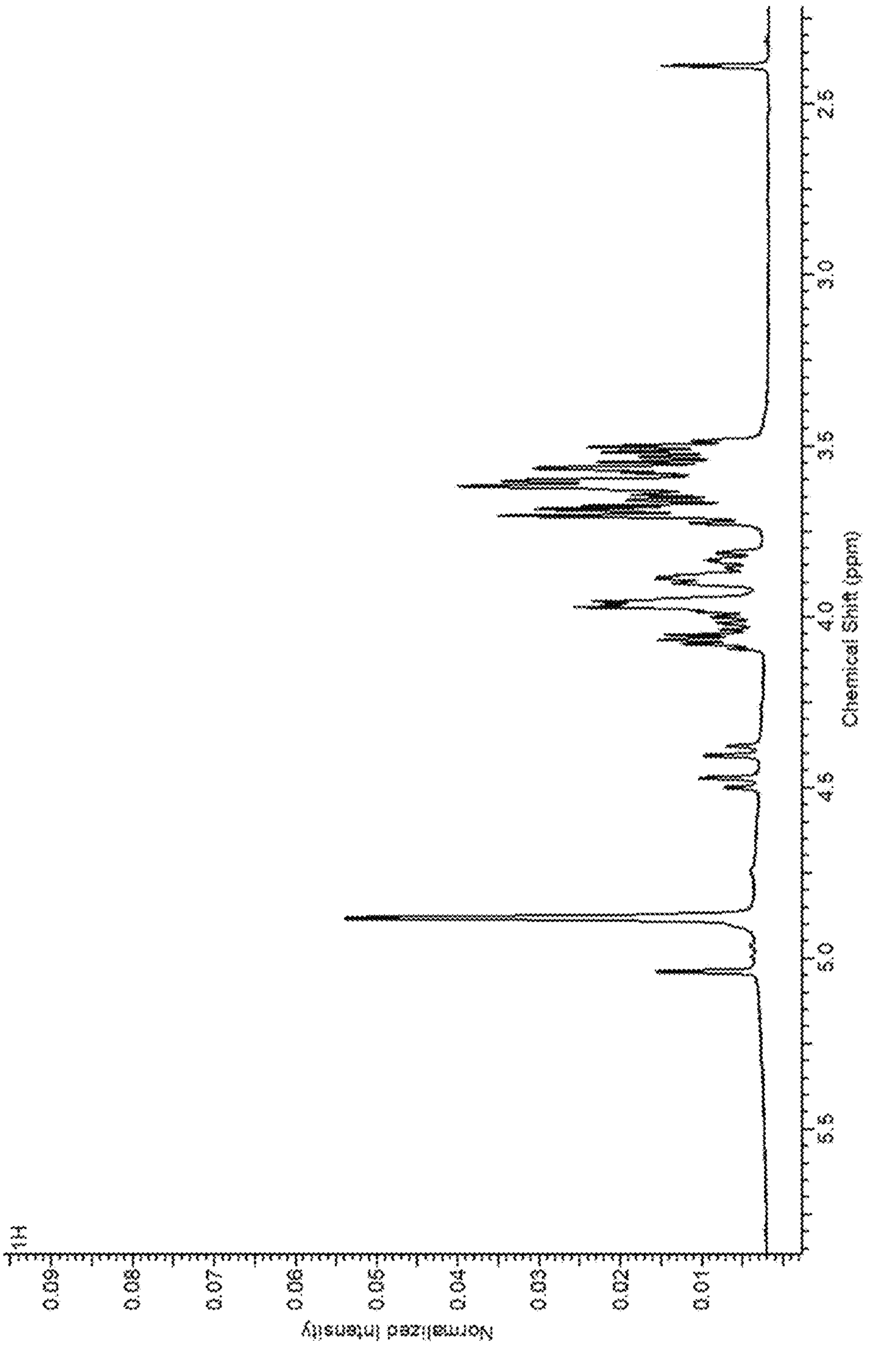

FIG. 23D. $^{1}$H NMR Spectrum (as in 23C), zoomed in on CD core for Per-6-O-tert-butyldimethylsilyl-2-O-monopropargyl-βCD.

Figure 23E:
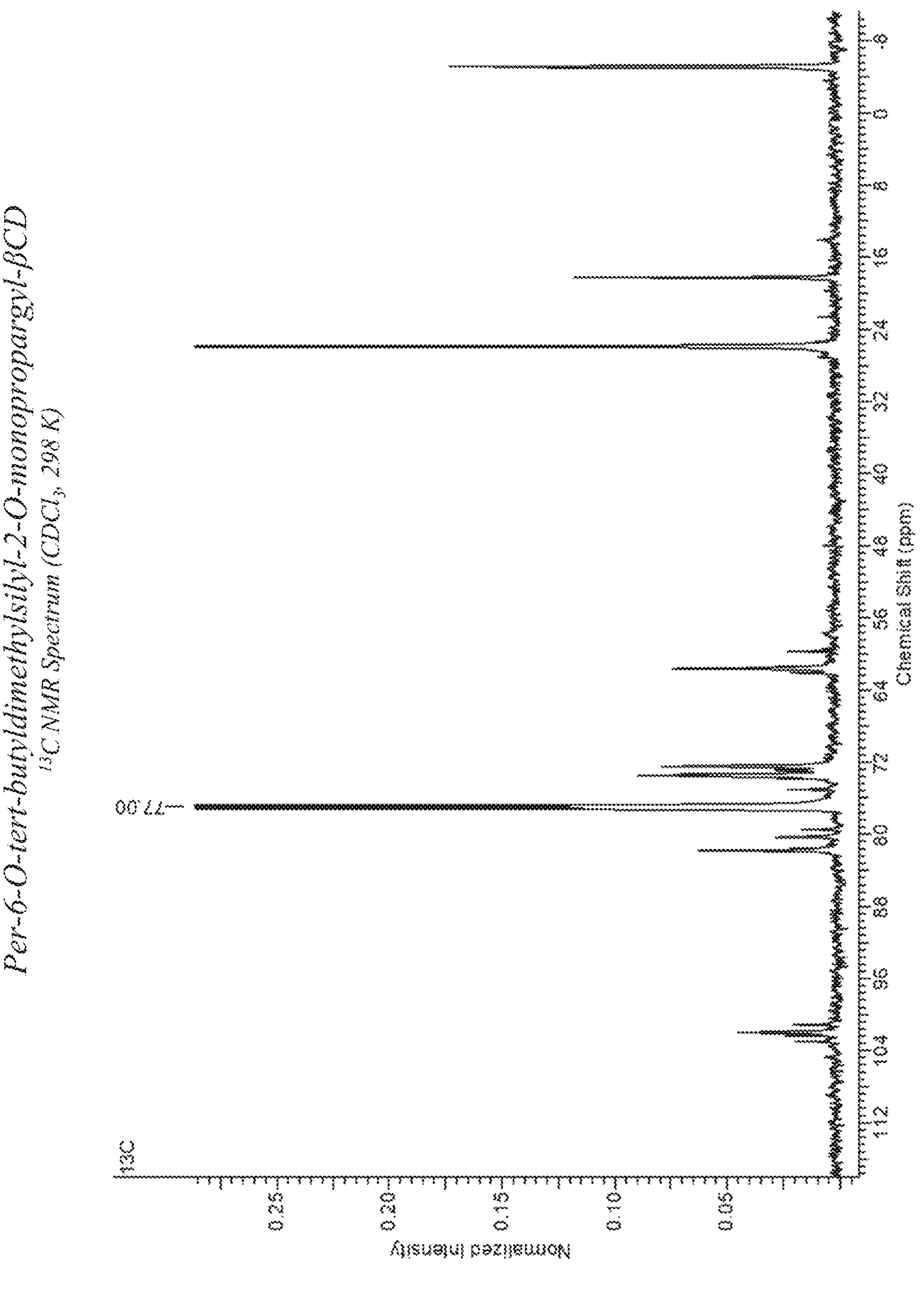

FIG. 23E. $^{13}$C NMR Spectrum ($CDCl_3$, 298 K) of Per-6-O-tert-butyldimethylsilyl-2-O-monopropargyl-βCD.

Figure 23F:
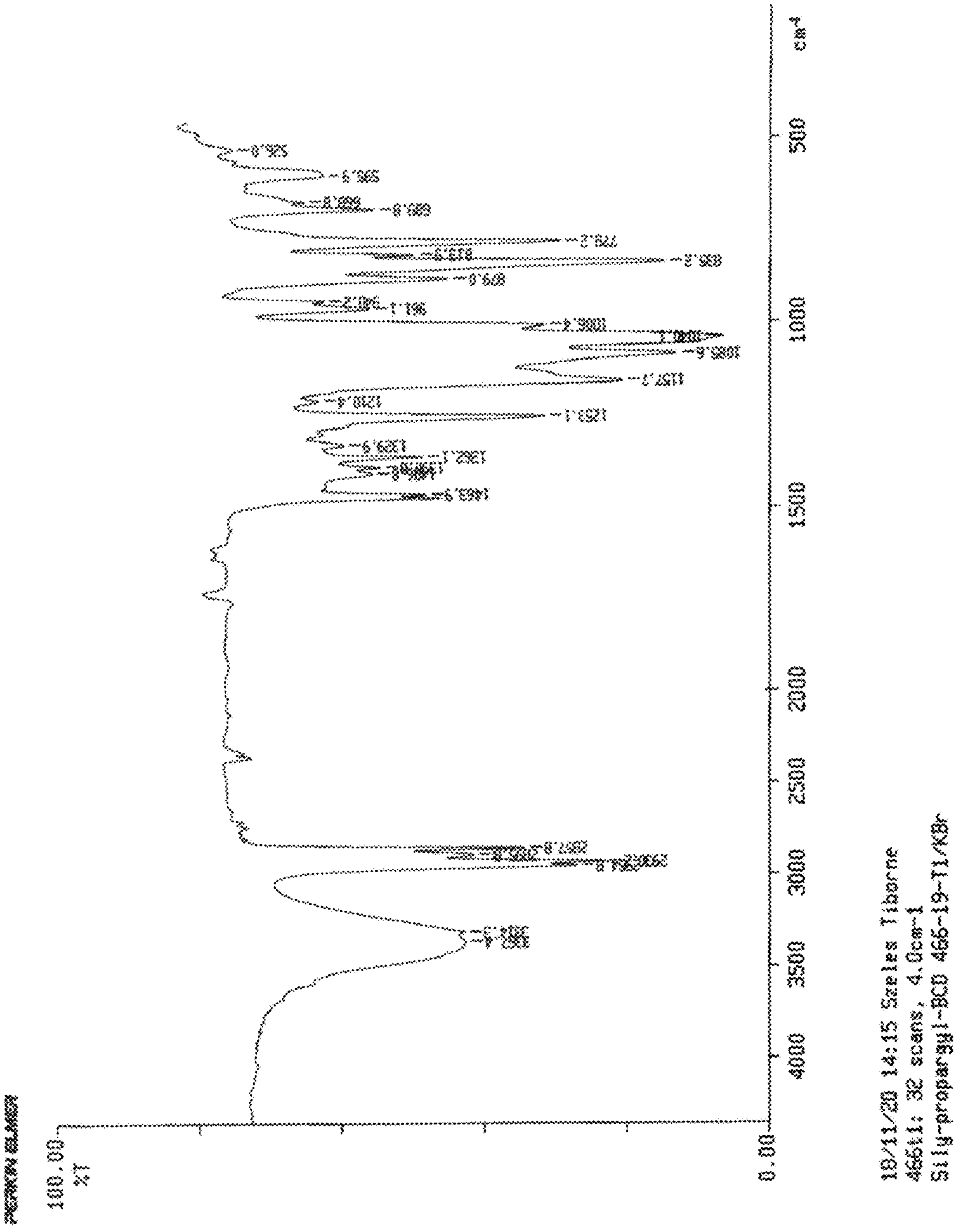

FIG. 23F. IR Spectrum ($CDCl_3$, 298 K) of Per-6-O-tert-butyldimethylsilyl-2-O-monopropargyl-βCD.

DETAILED DESCRIPTION

I. Definitions

Unless otherwise stated, the following terms used in this Application, including the specification and claims, have the definitions given herein.

As used in the specification and the appended claims, the singular forms “a”, “an”, and “the” include plural referents unless the context clearly dictates otherwise.

CDs (CDs) refer to cyclic oligosaccharides composed of 6 (αCD), 7 (βCD), or 8 (γCD) sugar rings.

“Hydroxypropyl (HP)” substituted CD (CD). As used herein, the term “hydroxypropyl substituted CD” or “HP substituted CD” or “HPβCD” or “HPαCD” refers to a CD that is linked to at least one 2-hydroxypropyl group, i.e., $—CH_2—CH(OH)—CH_3$. Typically, the HP groups are linked to the oxygen atoms linked to the C2, C3, and/or C6 carbons of the CD (most commonly having a mixture of those attachment sites).

Sulfobutyl (SB) beta CD, abbreviated as SBβCD, SBBCD, SB-BCD, SB-βCD, and similar terms, refers to a beta CD that is substituted with one or more sulfobutyl groups, i.e., —CH2-CH2-CH2-CH2-SO3H or —CH2-CH2-CH2-CH2-SO3Na or another salt thereof, typically linked to the oxygen atoms linked to the C2, C3, and/or C6 carbons of the CD (most commonly having a mixture of those attachment sites).

“Quaternary ammonium (QA) beta CD,” abbreviated as QAβCD, QABCD, QA-BCD, QA-βCD, and similar terms, refers to a beta CD that is substituted with one or more substituted or unsubstituted quaternary ammonium groups. One quaternary ammonium salt that may be substituted has the structure trimethylammonium propyl, which may be substituted, preferably 2-hyroxytrimethylaminopropyl—i.e. $—CH_2—CH(OH)—CH_2—N(CH_3)_3$. The quaternary ammonium salt is typically linked to the oxygen atoms linked to the C2, C3, and/or C6 carbons of the CD (most commonly having a mixture of those attachment sites).

Methylated (Me) beta CD, abbreviated as MeβCD, MeBCD, Me-BCD, Me-βCD, and similar terms, refers to a beta CD that is substituted with one or more methyl groups, i.e., —CH3, typically linked to the oxygen atoms linked to the C2, C3, and/or C6 carbons of the CD (most commonly having a mixture of those attachment sites).

Carboxymethylated (CM) beta CD, abbreviated as CMβCD, CMBCD, CM-BCD, CM-CD, and similar terms, refers to a beta CD that is substituted with one or more carboxymethyl groups, e.g., $—CH_2—CO_2H$ or —CH2-CO2Na or another salt thereof, typically linked to the oxygen atoms linked to the C2, C3, and/or C6 carbons of the CD (most commonly having a mixture of those attachment sites).

Succinylated (SUCC) beta CD, abbreviated as SUCCβCD, SUCCBCD, SUCC-BCD, SUCC-CD, and similar terms, refers to a beta CD that is substituted with one or more succinyl groups, which may be substituted or unsubstituted, preferably e.g., $—CO—CH_2—CH_2—COOH$ or —CO-CH2-CH2-COONa or another salt thereof, typically linked to the oxygen atoms linked to the C2, C3, and/or C6 carbons of the CD (most commonly having a mixture of those attachment sites).

“C2”, “C3”, and “C6” each refer to the carbon positions of the glucose subunits with hydroxyl functional groups that can be substituted with different substituents (e.g. methyl, hydroxypropyl, sulfobutyl, succinyl, carboxymethyl and quaternary ammonium functional groups) or a linker between CD monomers.

Large (secondary) face refers to the side of the CD monomer with the hydroxyl group from the C2 and C3 carbons of the glucose subunits.

Small (primary) face refers to the side of the CD monomer with the hydroxyl groups from the C6 carbons of the glucose subunits.

Headgroup refers to the cyclic region of the structure of a sterol such as cholesterol or 7KC. See FIG. 3B.

Tailgroup refers to the alkyl region of the structure of a sterol such as cholesterol or 7KC. See FIG. 3B.

A linker, synonymous with a linking group, is defined as a chemical unit, often represented as [A-B-A'] that connects to CDs of a CD dimer. Exemplary linkers can connect through C2 or C3 carbons of each CD subunit, e.g., through an L1, L1', L2, or L2' attached to said carbons, which may be oxygen or a bond.

Linker length. As used herein, the length of a linker or interchangeably “linker length” refers to the number atoms of the linker on the shortest path through the linker connecting the two CD subunits of a CD dimer. In many embodiments, the linker length is the shortest chain of atoms between the terminal atom of A that connects to a CD to the terminal atom of A' that connects to the other CD, wherein that chain of atoms passes through only atoms of A, B and A', i.e., referring to Structure A-X, B-X, or C-X, the linker length does not include counting the atoms of L1, L2, or L3, if present, through which A and A' connect to each CD subunit.

Head-to-head CD dimer refers to a CD dimer wherein two CD monomers linked through the large (secondary) face of the CD, typically attached via C2 and/or C3 carbons of each CD monomer.

Tail-to-tail CD dimer refers to a CD dimer wherein two CD monomers are attached on the small (primary) face of the CD molecule, typically attached via the C6 carbons of each CD monomer.

Head-to-tail CD dimer refers to a CD dimer wherein two CD monomers attached at opposite ends, i.e., one monomer attached from the small (primary) face, typically through a C6 carbon, and the other attached from the large (secondary) face, typically via a C2 and/or C3 carbon.

Degree of Substitution (DS), as used herein, the degree of substitution (DS) describes the quantity of substitution groups attached to a CD monomer or dimer. In general the DS refers to the total number of substitutions (i.e., number of positions substituted with atoms other than hydrogen) at all positions, e.g., linked to all of the C2, C3, and C6 carbons contained in the CD monomer or dimer. For clarity, in case of a dimer or multimer, DS does not include counting the attachment point(s) of the linker to each CD subunit, nor does DS include substituents attached only to the linker itself. For example, referring to Structure A-X (or likewise, structures B-X or C-X mutatis mutandis) comprising Structures A-Xa and A-Xb, the term refers to the total number of R1, R1', R2, R2', R3, and R3' atoms that are not H. In that example, DS is determined based on the aforementioned R groups, irrespective of the structure of the corresponding L1, L1', L2, L2', L3, or L3' (e.g., bond, O, S, etc.). The term DS can be used in conjunction with a specific substitution group name to describe that specific group's total count. The term DS can also be used in conjunction with a position for substitutions (e.g. the C6 position of a D-glucose monomer) to describe the total count of substitution groups in that analogous position around all the CD monomer. For example, a C6 2-hydroxypropyl DS4 βCD is intended to communicate that each CD monomer of the CD dimer has four 2-hydroxypropyl groups bound in the available C6 positions. For clarity, the term DS is used to refer to substituents of the CD subunit or subunits, which in general is independent from the number of substitutions that may be made elsewhere, e.g., in linker joining a CD dimer. Further, DS can refer to an average value, such as in the case of a preparation containing CD molecules having varying numbers of substituents, e.g., substituted CDs, and thus can also be a non-whole value such as DS~4.2.

The DS may be measured by known techniques including mass spectrometry (e.g., matrix assisted laser desorption/ionization, "MALDI") or by NMR. MALDI is preferred in for CD derivatives containing substituents that give a more typical Gaussian distribution of ions in the mass spectrum, e.g., as exhibited for methyl, hydroxypropyl, and sulfobutyl substituents (see, e.g., FIGS. 7B, 7G, 7R, 7W, 7AB, 7AH herein, and U.S. application Ser. No. 16/733,945, FIGS. 10G-101, 10P-10Q, 11C-11G, 11I, 12E, and 12K). Average DS as determined by MALDI is calculated by averaging the peak intensities of the signals corresponding to each DS species of the CD in question. In other instances a less regular pattern of ion peaks may be present, e.g., due to the formation of various adducts, fragmentation, elimination products, etc. Other mass spectrometric techniques may be utilized to potentially circumvent these issues. NMR also may be used to determine the DS value by identifying a peak that corresponds to protons from the core dimer and first scaling the measured values such that the peak area corresponds to the known number of such protons in the structure. A signal corresponding to protons in the substituent group is then examined and scaled appropriately in order to yield the average DS. In the simpler case, a dearly resolved peak corresponding to substituent protons is identified, and having already been scaled as described previously, is then divided by the number of protons represented in that peak in order to yield the average number of substituents. For example, in the case of hydroxypropyl substituents, a peak identified as corresponding to 14 protons in the core structure (the anomeric region of the glucopyranose) was identified and signalized normalized to 14, then the peak corresponding to the 3 protons of the methyl substituent was identified, and finally the area of that peak was divided by 3 in order to yield the average number of hydroxypropyl groups present per molecule. In other instances, substituent peaks and CD core peaks may be in close proximity or overlapping. In this case, the number of contributing protons from the CD core structure is identified and then subtracted from the peak area (the peak area having already been scaled to an integrated area of 1 per proton), and then the remaining area is divided by the number of contributing protons in order to yield the average DS. For example, in the case of a methyl substituent (illustrated in see, e.g., U.S. application Ser. No. 16/733,945, FIGS. 11K-11L; also see McTriDi NMR illustrated in FIGS. 7N-7P herein), a cluster of peaks was identified corresponding to the three methyl hydrogens of the substituent, and additionally a group of 86 protons of the core CD dimer structure. As in the hydroxypropyl substituent example, a peak identified as corresponding to 14 protons in the core structure (the anomeric region of the glucopyranose) was identified and the signalized normalized to 14; the area of the peak containing the methyl hydrogens and core CD hydrogens was determined to be 92.77, leaving 6.77 after subtracting the signal from the 86 protons of the core CD structure; and after dividing by the 3 protons of each methyl group, the average DS was estimated to be 2.26. For HP and ME substituted CDs integration is divided by 3, for QA the integration is divided by 9, for SB the integration is divided by 2, and for SUCC the integration is divided by 4. The foregoing calculation is straightforwardly adapted to other substituent types based on the identification of peaks corresponding to protons in the substituent structure. A CD composition, such as a CD dimer composition (defined below) may comprise a mixture of individual molecules substituted with differing numbers of substituents, in which case the DS value is expressed as the average (median) number of substitutions. Fractional DS values reflect the case where the median value may be between whole number substitutions. Unless indicated otherwise, a whole number DS value indicates a CD composition having that DS number when rounded to the nearest whole number. For example, DS4 refers to a DS value of at least 3.5 and less than 4.5.

CD dimer composition. As used herein, the term "CD dimer composition" or "CD dimer composition" refers to a mixture of CD dimers, e.g., CD dimers substituted with varying numbers of the same substituent. Typically, a CD dimer composition is characterized by having a specified DS with a specified substituent. A CD dimer composition can result from of a synthesis process wherein the substituent is added to the CD dimers in a stochastic manner due to the mostly symmetrical nature of the CD molecule, such that individual CD molecules will vary in the number and position of substituents. Additionally, a CD dimer composition may comprise a mixture of individual molecules having different sites of linker attachment (e.g., O2 to O2, O2 to O3, O3 to O2, or O3 to O3), or alternatively the site of linker attachment may be uniform (e.g., only O2 to O2, only O2 to O3, only O3 to O2, or only O3 to O3). The DS of the CD dimer composition may be determined by NMR and/or mass spectrometry, e.g., as described above.

The term "specifically binds," or the like, means that a molecule, e.g., a CD dimer of the present disclosure, forms a complex with a binding partner, e.g., a cholesterol (such as an oxysterol, e.g., 7KC) that is relatively stable under physiologic conditions. Methods for determining whether a molecule specifically binds to a binding partner are well known in the art and include, for example, equilibrium dialysis, surface plasmon resonance, and the like. In exemplary embodiments, a CD dimer of the present disclosure binds to a cholesterol, oxysterol, or 7KC with a KD of between about 5 μM and about 100 μM, between about 10 μM and about 90 μM, between about 20 μM and about 80 μM, between about 30 μM and about 70 μM, between about 40 μM and about 60 μM, between about 0.5 μM and about 50 μM, between about 1 μM and about 40 NM, between about 2 μM and about 30 NM, between about 3 μM and about 20 μM, between about 4 μM and about 10 μM, less than about 1000 μM, less than about 500 μM, less than about 300 μM, less than about 200 μM, less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 4 μM, less than about 3 μM, less than about 2 μM, less than about 1 μM or less than about 0.5 μM.

Greater affinity for 7KC than cholesterol. As used herein, the term "greater affinity for 7KC than cholesterol" refers to a compound (e.g., a CD) having a greater ability to solubilize 7KC than cholesterol. Greater affinity can be also be predicted by molecular docking, predicted by molecular dynamic simulation, or measured by calorimetry. In exemplary embodiments, the CD dimer has a binding affinity for 7KC that, compared to its binding affinity for cholesterol, is at least 1.5-fold, at least 2-fold, at least 3-fold, at least 4-fold, at least 5-fold, at least 8-fold, at least 10-fold, at least 15-fold, at least 20-fold, at least 30-fold, or at least 50-fold stronger, which optionally may be determined by comparing concentrations at which 50% of 7KC in a suspension becomes solubilized, e.g., using the procedures described in the working examples herein. In exemplary embodiments, the CD dimer has a binding affinity for 7-KC that, compared to its binding affinity for cholesterol, is at least 1.1-fold, 1.5-fold, 2-fold, 3-fold, 4-fold, 5-fold, or 10-fold stronger, which optionally may be determined by dividing the computed or measured binding affinity (KD) for cholesterol by the computed binding affinity for 7KC.

Greater affinity for one compound than another, e.g., greater affinity for 7KC than cholesterol, may be determined using a "turbidity test" performed on an aqueous suspension containing 3% ethanol, 300 uM sterol, in PBS and 1 mM of the CD to be tested. This single concentration of CD is used in order to standardize the test results. To perform the test, the samples are incubated for 30 mins at 37 C, and then absorbance at 350 nm is measured, e.g., using a spectrophotometer plate reader. Relative turbidity is determined by dividing the measured turbidity in the presence of the CD to the baseline turbidity without the CD. A given CD has greater affinity for 7KC than cholesterol if the relative turbidity of the 7KC suspension is lower than the relative turbidity of the cholesterol solution.

Hydrophobic drug. As used herein, the term "hydrophobic drug" refers to a drug that is not soluble in water absent some detergent or other solvent. Hydrophobic drugs include, but are not limited to, hormones such as estrogen, progesterone, and testosterone. The CD dimers of the present disclosure may be used as an excipient for hydrophobic drugs. Additional exemplary hydrophobic drugs include dexamethorphan (DXM), diphenhydramine (DPH), lidocaine (LDC), Bendroflumethiazide, acyclovir, Revaprazan, curcumin, and testosterone propionate (TP), to name a few. The CD dimer may be present in an amount sufficient to increase the solubility of the molecule and/or aid in better drug delivery. The molecular ratio of the drug to CD may be 1:1 ratio or more than 1:1.

Amount effective to solubilize said hydrophobic drug. As used herein, the phrase "amount effective to solubilize said hydrophobic drug" refers to the concentration of a substance (e.g., a CD dimer or dimers) that is able to solubilize a hydrophobic drug, typically in an aqueous composition such as phosphate buffered saline (PBS) or water. The solubilization can be determined by spectrophotometry or other means known in the art. Solubilization may be determined at room temperature, physiological temperature (37 degrees C.) or another appropriate temperature (e.g., between 0 and 4 degrees C.).

Heterodimer. As used herein, heterodimers refer to two different CD monomer forms, covalently linked with linker A-B-A' (i.e. αCD-A-B-A'-βCD).

Homodimer. As used herein, homodimers refer to two identical CD monomer forms, with the same functional groups, covalently linked with a linker such as [A-B-A'] (i.e. βCD-[A-B-A']-βCD').

Asymmetric dimer. As used herein, asymmetric dimers refer to two CD monomers with different combinations of substitutions on each CD monomer, covalently linked with a linker such as A-B-A'. Non-limiting examples of asymmetric dimers include dimers having two subunits that each contain different numbers of the same substituent, dimers that each contain different substituents, dimers wherein one substituent is contained at one position on one monomer and the same or a different substituent is contained at a different position on the other monomer (e.g., C2 or C3 substituents on one monomer) and C6 substituents on the other monomer, dimers wherein one monomer substituted and one is unsubstituted, etc. dimers having positively charged substituents on one monomer and negatively charged substituents on the other monomer, etc. Combinations of the foregoing are also envisioned, e.g., dimers containing differing numbers of substituents of different types on each monomer.

Molecular Dynamics (MD) refers to the computer simulation method using GROMACS (e.g., through GROMOS 54a7) software that is used to determine the intermolecular interactions of the CD-sterol complex.

"Up Orientation" refers to the position of the cholesterol and/or 7KC, relative to the CD where the head group of the sterol is associated with the small/primary and the tail group is associated with the large/secondary face. For heterodimers, the up orientation refers to that where the headgroup of the sterol is in the βCD sister monomer while the tail group is in the αCD sister monomer.

"Down Orientation" refers to the position of the cholesterol and/or 7KC, relative to the CD where the tail group of the sterol is associated with the small/primary and the head group is associated with the large/secondary face. For heterodimers, the down orientation refers to that where the headgroup of the sterol is in the αCD sister monomer while the tail group is in the βCD sister monomer.

O4 Plane (or O4 Axis) refers to the plane formed by the O4 oxygens of the glucose units comprising the CD molecule. O4 refers to the oxygen number 4 according to the standard nomenclature of glucose units. See FIG. 3.

The term "angle" used in conjunction with the O4 plane, e.g., "O4 Plane Angle" refers to the angle between the O4 plane of one CD monomer and the ligand axis, indicating how well nested the ligand is inside the CD cavity. The "angle" measurement can be useful to determine how well shielded the ligand is from surrounding water molecules: zero or 180 degrees indicates that the ligand is perpendicular to the O4 plane of the CD, and therefore the two molecules are most likely in a soluble complex while 90 degrees would indicate that the ligand is parallel to the CD plane and likely not complexed within the cavity. For our complexes, approximately 30 degrees corresponds to the complexed "up" orientation and about 150 degrees corresponds to the complexed "down" orientation.

Distance in regards to MD simulations refers to the distance between the center of mass of the sterol and the center of mass of the CD dimer.

Energy in regards to MD simulations refers to the energy of interaction between the sterol and CD dimer.

"Alkyl" means a linear or branched hydrocarbon moiety consisting solely of carbon and hydrogen atoms.

"Lower alkyl" refers to an alkyl group of one to six carbon atoms, i.e. C3 alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Heteroalkyl" means a linear or branched hydrocarbon moiety wherein at least one of the C atoms has been replaced by a heteroatom selected from the list consisting of O, N, or S, or optionally Si or P. Example include but are not limited to alkoxyalkyl, alkoxyalkoxyalkyl, alkylcarbonyloxyalkyl, alkylcarbonyl, alkylsulfonyl, alkylsulfonylalkyl, alkylamino, alkylsulfanyl, alkylaminoalkyl, aminoalkyl, dialkylaminoalkyl, aminoalkoxy, alkylsulfonylamido, aminocarbonyloxyalkyl, aminosulfonyl, alkylaminosulfonyl or dialkylaminosulfonyl.

"Alkenyl" means a linear monovalent hydrocarbon radical of two to twelve carbon atoms or a branched monovalent hydrocarbon radical of three to twelve carbon atoms, containing at least one double bond. Examples of alkenyl groups include, but are not limited to, ethenyl (vinyl, $—CH{=}CH_2$), 1-propenyl ($—CH{=}CH—CH_3$), 2-propenyl (allyl, —CH—

$CH{=}CH_2$) moieties include, but are not limited to, methoxy, ethoxy, iso-propoxy, and the like.

"Alkoxyalkyl" means a moiety of the formula Ra-O-Rb-, where Ra is alkyl and Rb is alkylene as defined herein. Exemplary alkoxyalkyl groups include, by way of example, 2-methoxyethyl, 3-methoxypropyl, 1-methyl-2-methoxy-ethyl, 1-(2-methoxyethyl)-3-methoxy-propyl, and 1-(2-methoxyethyl)-3-methoxypropyl.

"Alkoxyalkoxyalkyl" means a group of the formula —R—O—R'—O—R" wherein R and R' each are alkylene and R" is alkyl as defined herein.

"Alkylcarbonyloxyalkyl" means a group of the formula —R—O—C(O)—R' wherein R is alkylene and R' is alkyl as defined herein.

"Alkylcarbonyl" means a moiety of the formula —R'—R", where R' is —C(=O)— and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R'" where R' is alkyl, R" is —$SO_2$— and R'" is alkyl as defined herein.

"Alkylamino" means a moiety of the formula —NR—R' wherein R is hydrogen or alkyl and R' is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Alkylsulfanyl" means a moiety of the formula —SR wherein R is alkyl as defined herein.

"Alkali metal ion" means a monovalent ion of a group I metal such as lithium, sodium, potassium, rubidium or cesium, preferably sodium or potassium.

"Alkaline earth metal ion" means a divalent ion of a group II metal such as beryllium, magnesium, calcium, strontium or barium, preferably magnesium or calcium.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group —R—O—C(=O)—R' wherein R' is amino and R is alkylene as defined herein.

"Aminosulfonyl" means a group —$SO_2$—NR'R" wherein R' and R" each independently is hydrogen or alkyl. "Aminosulfonyl" as used herein thus encompasses "alkylaminosulfonyl" and "dialkylaminosulfonyl".

"Alkynylalkoxy" means a group of the formula —O—R—R' wherein R is alkylene and R' is alkynyl as defined herein.

"Cycloalkyl" means a saturated or partially unsaturated carbocyclic moiety consisting of one or more rings. Examples include but are not limited to cyclopropyl, cyclobutyl, cyclopentyl, cyclohexyl, cycloheptyl, and the like, including partially unsaturated derivatives thereof.

"Heterocycloalkyl" means a saturated or partially unsaturated carbocyclic moiety consisting of one or more rings wherein at least one C has been replaced by a heteroatom selected from the list consisting of O, N, or S, or optionally Si or P.

"Aryl" means a cyclic aromatic hydrocarbon moiety consisting of a mono-, bi-, or tricyclic system including fused ring systems. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Heteroaryl" means a cyclic aromatic moiety having at least one ring and wherein at least one ring contains at least one heteroatom selected from the list consisting of O, N, or S which the remaining ring atoms as C. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazole, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Amine" or "amino" means a group —NR'R" wherein R' and R" each independently is hydrogen or alkyl. "Amino" as used herein thus encompasses "alkylamino" and "dialkylamino".

"Alkoxyamine"" or "Alkoxyamino" means a group —OR—R' wherein R' is amino and R is alkylene as defined herein.

Multiple linkers refers to the multiple, preferably identical, linkages between two CD monomers that interact with the hydroxyl group at C2 or C3 of the glucose subunits on each CD monomer.

As used herein, the terms "halogen," "halo," and "halide refer to any of —F, —Cl, —Br, and —I. In certain embodiments, these groups are named specifically as fluoro-, chloro-, bromo-, and iodo-.

Any open valency appearing on a carbon, oxygen, sulfur or nitrogen atom in the structures herein indicates the presence of a hydrogen atom.

Unless otherwise specified, when any of the above groups are described herein as "substituted" it is to be understood that one or more hydrogens of the group is replaced by any group named herein the definitions section or elsewhere named herein, including without limitation thereto, alkyl, cycloalkyl, cycloalkylalkyl, heteroalkyl, hydroxyalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl), —(CR'R")n-COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")n-CONRaRb (where n is an integer from 0 to 5, R' and R" are independently hydrogen or alkyl, and Ra and Rb are, independently of each other, hydrogen, alkyl, cycloalkyl, cycloalkylalkyl, phenyl or phenylalkyl). These groups that replace hydrogens themselves can be substituted where applicable. However, any substituent group of a substituent group cannot be further substituted.

For all of the above defined chemicals groups, it should be understood that every group has at least the appropriate number of valencies to satisfy any connectivity demanded of it by a more general chemical structure regardless of whether the "-yl," "-ylene," or other endings are used. As a non-limiting example, if a variable B is depicted as having connectivity to variables A and A', any selection for variable B will have at least two valencies even if the recited selection ends with "-yl" or another ending that implies less than two available valencies for bonding. To continue this non-limiting example, if B is selected as heteroaryl, it should be understood that any selected "heteroaryl" group will have at least two valencies available for bonding with variables A and A'.

In certain embodiments, it can be useful to describe two variable groups of a chemical structure as a "respective pair". A respective pair can also be denoted by listing the two variables separated by a slash (e.g. L1/R1). By term respective pair, it is meant to be understood that the selection of each of the variables of the respective pair is to follow a subsequent listing of selections for each variable respectively. As a non-limiting example, a statement reading 'the respective pair of L1/R1 is a bond and a hydroxyl group' is defined here to communicate that L1 is a bond and R1 is a hydroxyl group.

In certain embodiments, the term "corresponding" is used to refer to elements that are shown connected to one another within a structural formula. For instance, in Structure A-Xa, B-Xa, and C-Xa, each instance of R1 is shown linked to an instance of L1, wherein the pair of L1 and R1 elements show linked are referred to as corresponding to one another. Likewise, each R2 and R3 has a corresponding L2 and L3, respectively in Structure A-Xa, B-Xa, and C-Xa, and each in Structure A-Xb, B-Xb, and C-Xb, each R1', R2', and R3' has a corresponding L1', L2', and L3' to which it is linked.

"Arylalkyl" and "Aralkyl", which may be used interchangeably, mean a radical-RaRb where Ra is an alkylene group and Rb is an aryl group as defined herein; e.g., phenylalkyls such as benzyl, phenylethyl, 3-(3-chlorophenyl)-2-methylpentyl, and the like are examples of arylalkyl.

"Arylsulfonyl" means a group of the formula —$SO_2$R wherein R is aryl as defined herein.

"Aryloxy" means a group of the formula —O—R wherein R is aryl as defined herein.

"Aralkyloxy" or "Arylalkyloxy" means a group of the formula —O—R—R" wherein R is alkylene and R' is aryl as defined herein.

"Cyanoalkyl" means a moiety of the formula —R'—R", where R' is alkylene as defined here-in and R" is cyano or nitrile.

"Cycloalkenyl" means a monovalent unsaturated carbocyclic moiety consisting of mono- or bicyclic rings containing at least one double bond. Cycloalkenyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkenyl moieties include, but are not limited to, cyclopropenyl, cyclobutenyl, cyclopentenyl, cyclohexenyl, cycloheptenyl.

"Cycloalkylalkyl" means a moiety of the formula —R'—R", where R' is alkylene and R" is cycloalkyl as defined herein.

"Cycloalkylene" means a divalent saturated carbocyclic radical consisting of mono- or bi-cyclic rings. Cycloalkylene can optionally be substituted with one or more substituents, wherein each substituent is independently hydroxy, alkyl, alkoxy, halo, haloalkyl, amino, monoalkylamino, or dialkylamino, unless otherwise specifically indicated.

"Cycloalkylalkylene" means a moiety of the formula —R'—R"—, where R' is alkylene and R" is cycloalkylene as defined herein.

"Heteroarylalkyl" or "heteroaralkyl" means a group of the formula —R—R' wherein R is alkylene and R' is heteroaryl as defined herein.

"Heteroarylsulfonyl" means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

"Heterocycloalkylene" means cycloalkylene as defined herein wherein one or more carbon atoms have been replaced by a heteroatom selected from N, O, or S.

"Heterocyclylalkoxy" means a group of the formula-O—R—R' wherein R is alkylene and R' is heterocyclyl as defined herein.

"Haloalkyl" means alkyl as defined herein in which one or more hydrogen has been replaced with same or different halogen. In some embodiments, haloalkyl is a fluoroalkyl; in some embodiments, the haloalkyl is a perfluoroalkyl. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. In some embodiments, haloalkoxy is a fluoroalkoxy; in some embodiments, the haloalkoxyl is a perfluoroalkoxy. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydroisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxy-propyl, 2-hydroxy-1-hydroxymethylethyl, 2,3-dihydroxybutyl, 3,4-dihydroxybutyl and 2-(hydroxymethyl)-3-hydroxypropyl.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxyl-5-methyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

"Hydroxycycloalkyl" means a cycloalkyl moiety as defined herein wherein one, two, or three hydrogen atoms in the cycloalkyl radical have been replaced with a hydroxy substituent. Representative examples include, but are not limited to, 2-, 3-, or 4-hydroxy-cyclohexyl, and the like.

"Urea" or "ureido" means a group of the formula —NR'—C(O)—NR"R" wherein R, R" and R"' each independently is hydrogen or alkyl.

"Carbamate" means a group of the formula —O—C(O)—NR'R" wherein R' and R" each independently is hydrogen or alkyl.

"Carboxy" means a group of the formula —C(O)OH.

"Sulfonamido" means a group of the formula —$SO_2$—NR'R" wherein R', R" and R" each independently is hydrogen or alkyl.

"Nitro" means —$NO_2$.

"Cyan" means —CN.

"Phenoxy" means a phenyl ring that is substituted with at least one —OH group.

"Acetyl" means —C(═O)—$CH_3$.

"Cn-m-" is used as a prefix before a functional group wherein 'n' and 'm' are recited as integer values (i.e., 0, 1, 2, 12), for example C1-12-alkyl or C5-12-heteroaryl. The prefix denotes the number, or range of numbers, of carbon atoms present in the functional group. In the case of ring systems, the prefix denotes the number of ring atoms, or range of the number of ring atoms, whether the ring atoms are carbon atoms or heteroatoms. In the case of functional groups made up a ring portion and a non-ring portion (i.e. "arylalkyl" is made up of an aryl portion and an alkyl portion) the prefix is used to denote how many carbon atoms and ring atoms are present in total. For example, with arylalkyl, "C7-arylalkyl" may be used to denote "phenyl-$CH_2$—". In the case of some functional groups zero carbon atoms may be present, for example CO-aminosulfonyl (i.e. —$SO_2$—$NH_2$, with both potential R groups as hydrogen) the '0' indicates that no carbon atoms are present.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, trifluoromethanesulfonyloxy, thiomethyl, benzenesulfonyloxy, tosyloxy, and thienyloxy, dihalophosphinoyloxy, quaternized ammonium, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including, e.g., benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present disclosure are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalene-sulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, trimethylamine, tromethamine, and the like. Acceptable inorganic bases include aluminum hydroxide, calcium hydroxide, potassium hydroxide, sodium carbonate and sodium hydroxide. The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium. All references to pharmaceutically acceptable salts include solvent addition forms (solvates) or crystal forms (polymorphs) as defined herein, of the same acid addition salt. In general, when a particular salt is included in a structure or formula herein, it is understood that other pharmaceutically acceptable salts may be substituted within the scope of the present disclosure, e.g., in the case of the quaternary ammonium salt of formula VIII, chloride or another negative ion or combination of ions may be included, and similarly in the carboxymethyl sodium salt of formula IX another positive ion may be substituted for the depicted sodium.

The phrase "pharmaceutically acceptable carrier," as used herein, generally refers to a pharmaceutically acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body. Each carrier must be "acceptable" in the sense of being compatible with other ingredients of the formulation and not injurious to the patient Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

Other examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition. Some examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of the present disclosure rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The person skilled in the art will know how to choose a group for the ease of removal and for the ability to withstand the following reactions.

"Subject" means mammals and non-mammals. Mammals means any member of the Mammalia class including, but not limited to, humans; non-human primates such as chimpanzees and other apes and monkey species; farm animals such as cows, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to affect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes: (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

As used herein, the phrase "can be the same or different in each instance," (or similar variations thereof) means that each depiction (i.e. an "instance") of a singular group variable (e.g. "L1" or "R3") within a general formula be either the same as or different from other instances of that variable, e.g., each instance can be independently selected from among a set or list of available options for that group. Consequently, in certain embodiments of a general formula in which two positions both labeled with the same variable have different selections or values. As a non-limiting example, embodiments of general Structure A-X can include an embodiment in which three of the R3 groups of CD are hydrogen and four of the R3 groups of CD are 2-hydroxypropyl.

II. Compounds

Figure 1A:
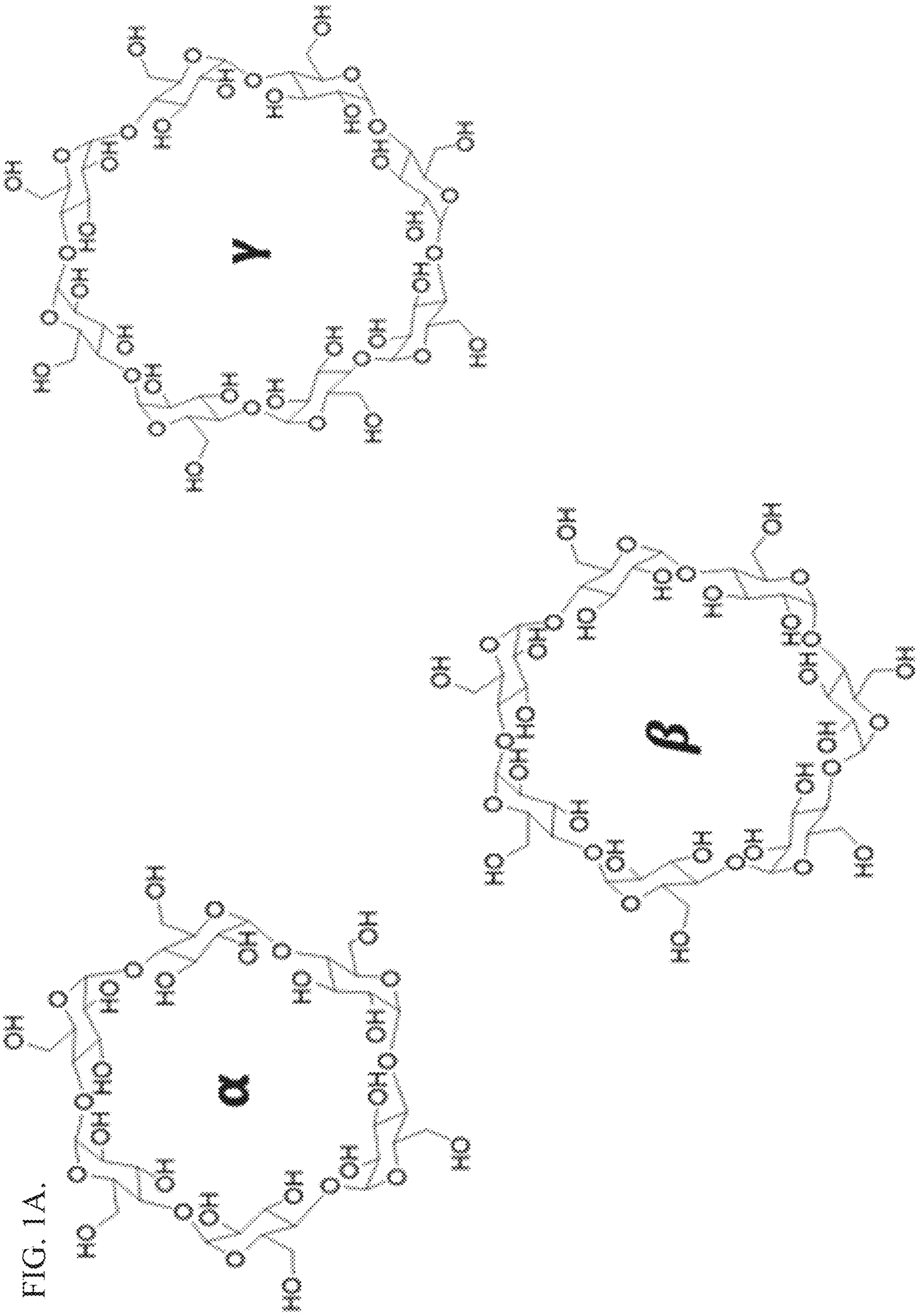
FIG. 1A depicts chemical structures of unsubstituted cyclic oligosaccharides composed of 6 (αCD) or, 7 (CD), or 8 (γCD) sugar rings (left to right). All the sugar rings in all CDs are D-glucose molecules.
Figure 1B:
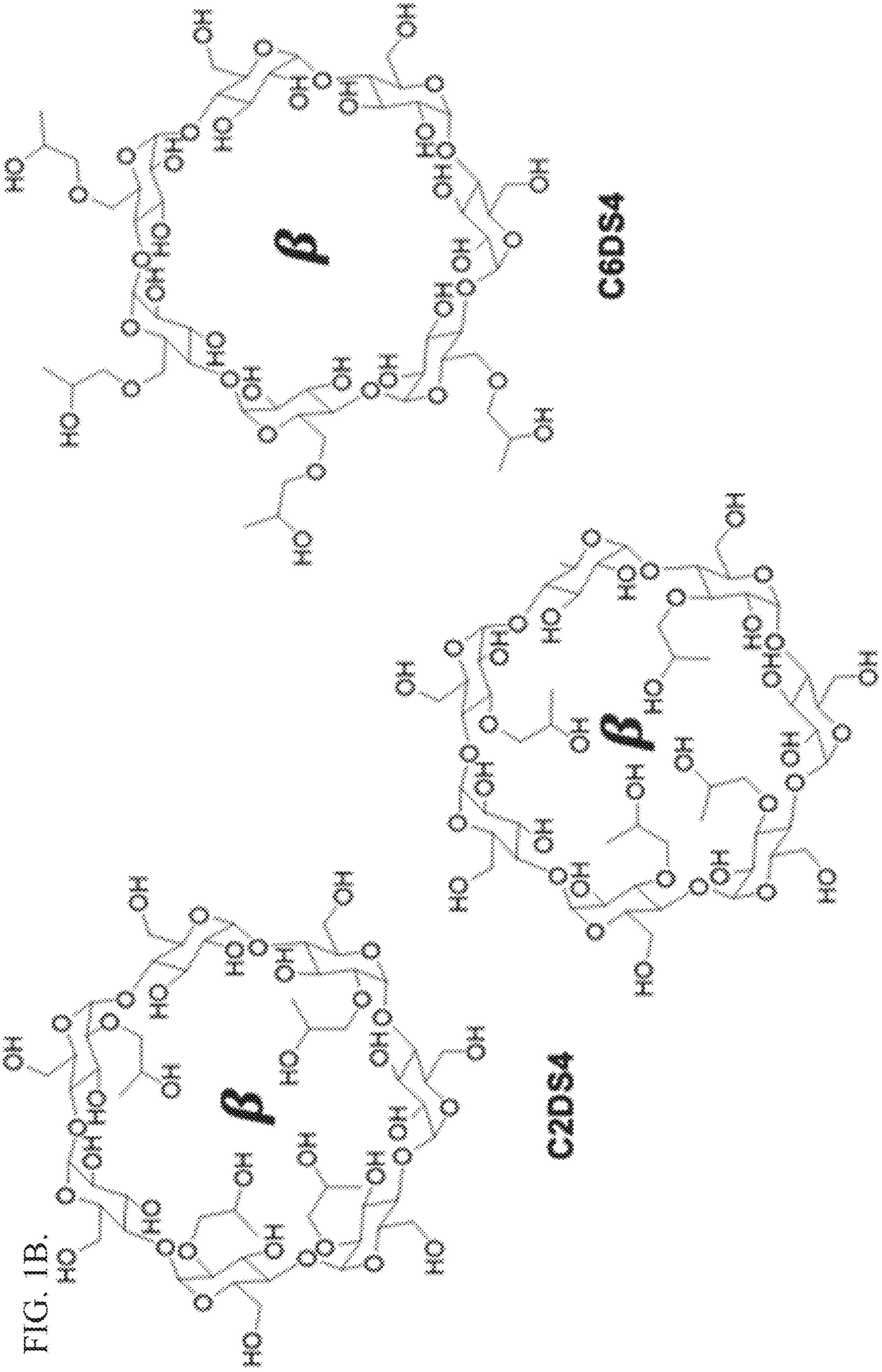
FIG. 1B. Chemical structures of HPβCD C2DS4, C3DS4, C6DS4.
Figure 1D:
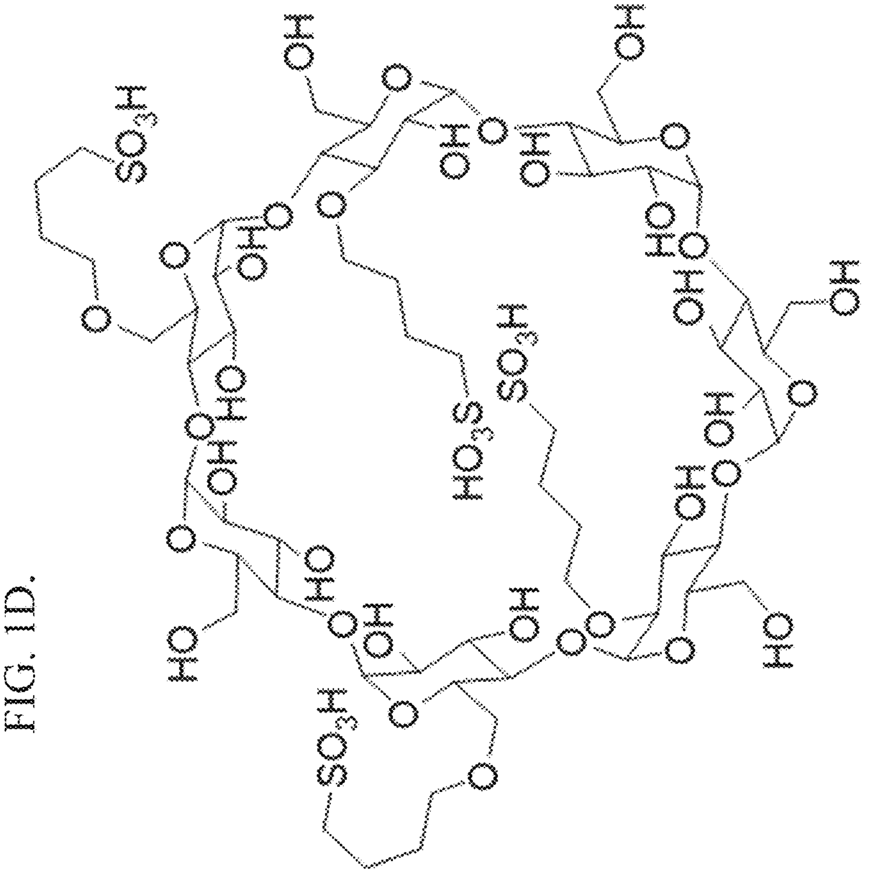
FIG. 1D. Chemical structures of randomly substituted SBβCD DS4 (free acid form).
Figure 1C:
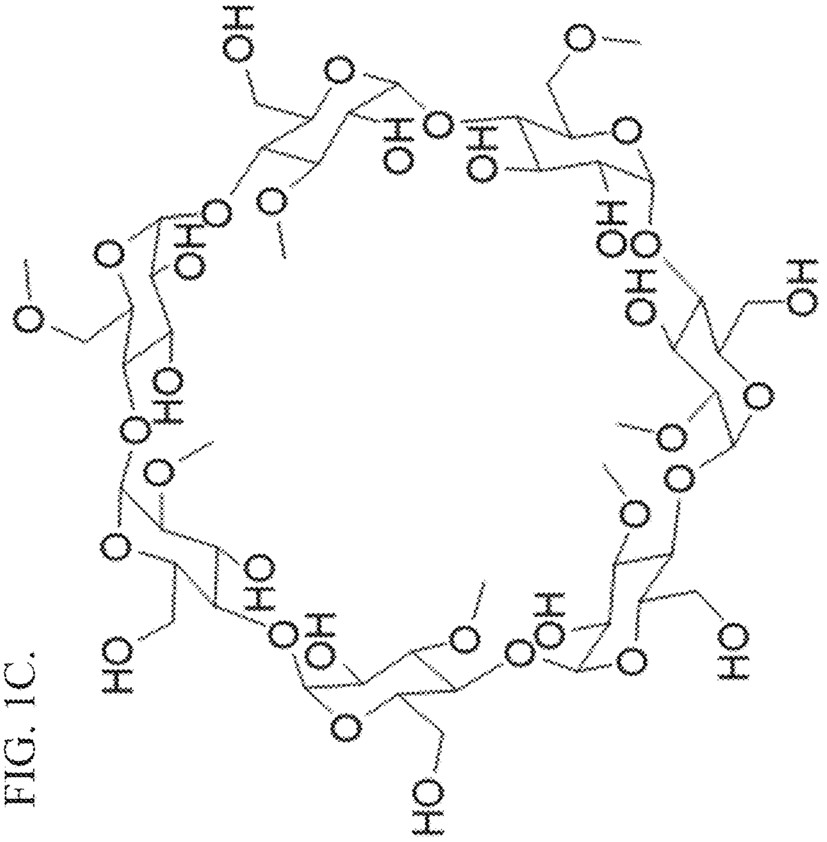
FIG. 1C. Chemical structures of randomly substituted MeβCD DS7.
Figure 1E:
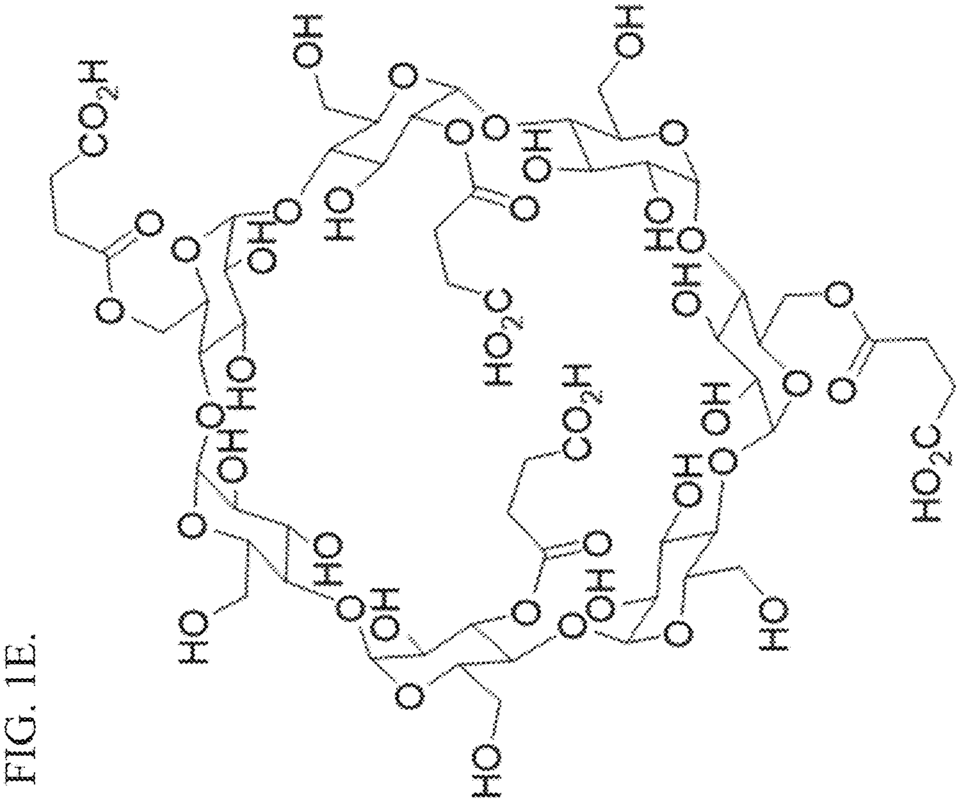
FIG. 1E. Chemical structures of randomly substituted SUCCβCD DS4 (free acid form).
Figure 1F:
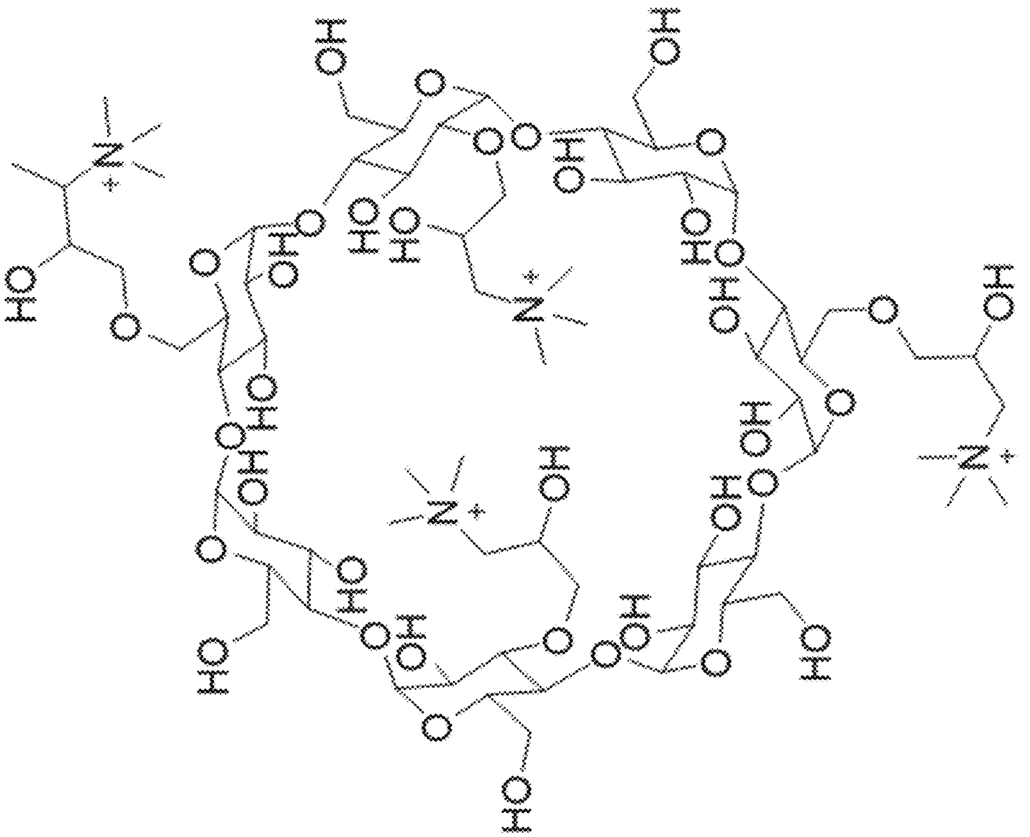
FIG. 1F. Chemical structures of randomly substituted QAβCD DS4.
Figure 1G:
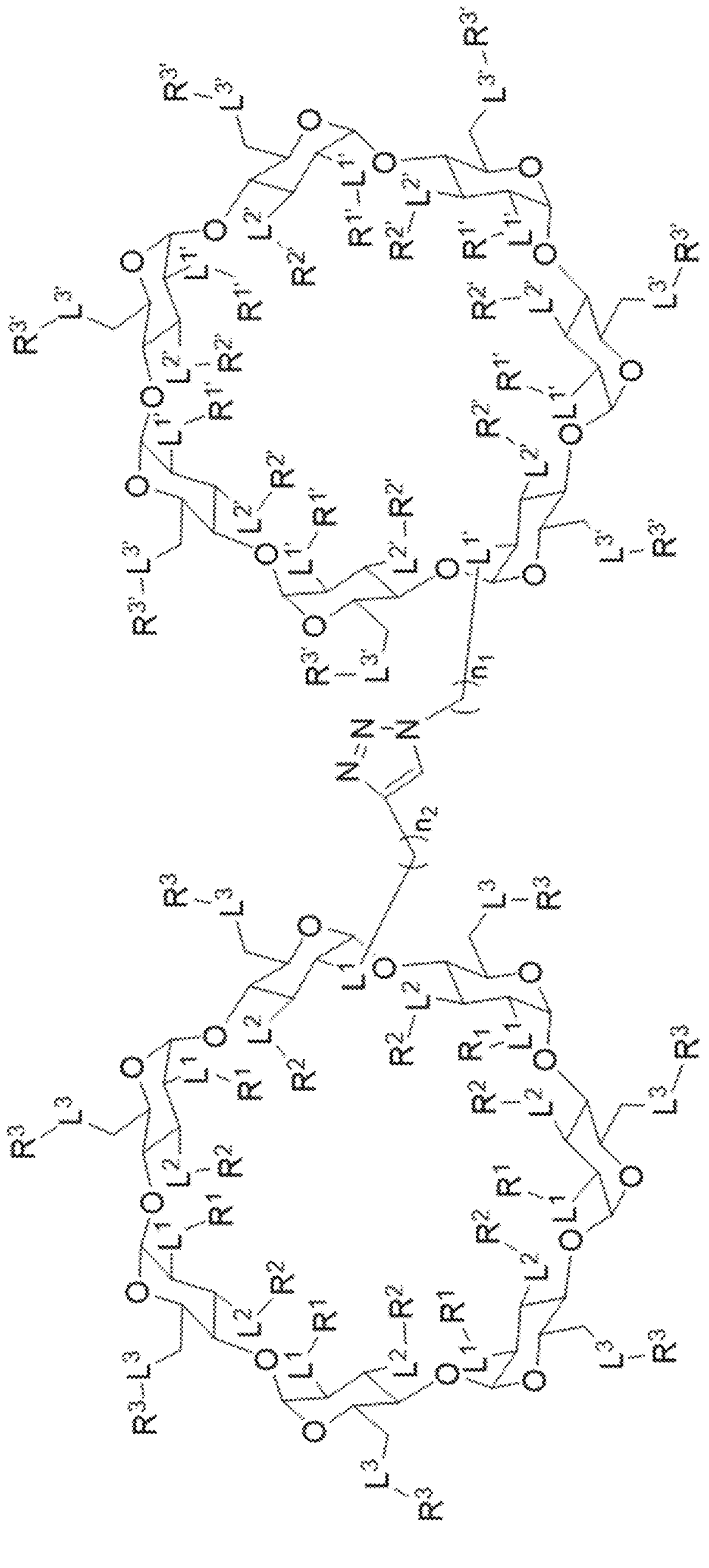
FIG. 1G. Dimer structures. Formula I. C2-C2 βCD dimer linked through the secondary face with a triazole linker FIG. 1H. Dimer structures. Formula II. C3-C2 βCD dimer linked through the secondary face with a triazole linker.
Figure 1H:
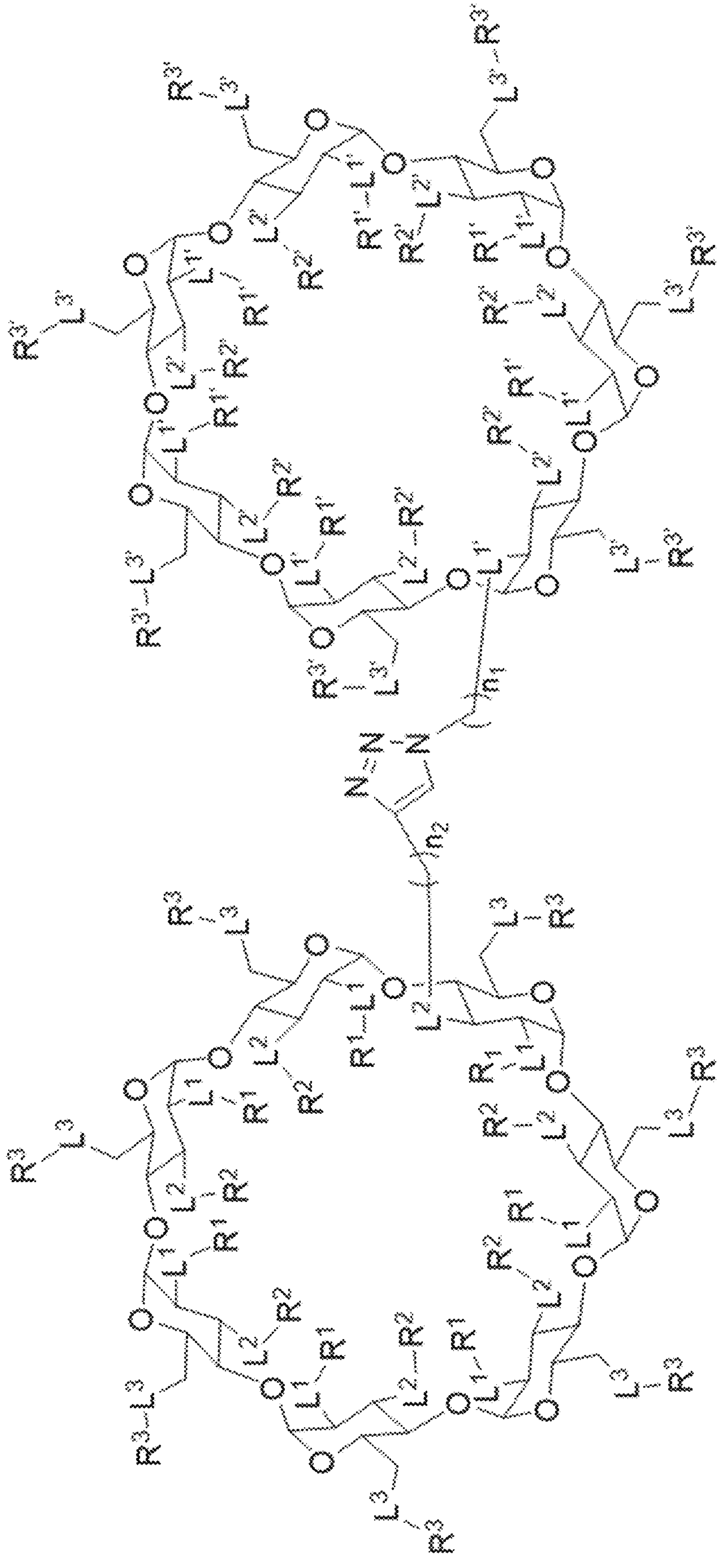
FIG. 1I. Dimer structures. Formula III. C3-C3 βCD dimer linked through the secondary face with a triazole linker.
FIG. 1J. Dimer structures. Hydroxypropyl βCD dimer linked through the secondary face with a variable linker.
FIG. 1K. Dimer structures. Methyl βCD dimer linked through the secondary face with a variable linker.
Figure 1I:
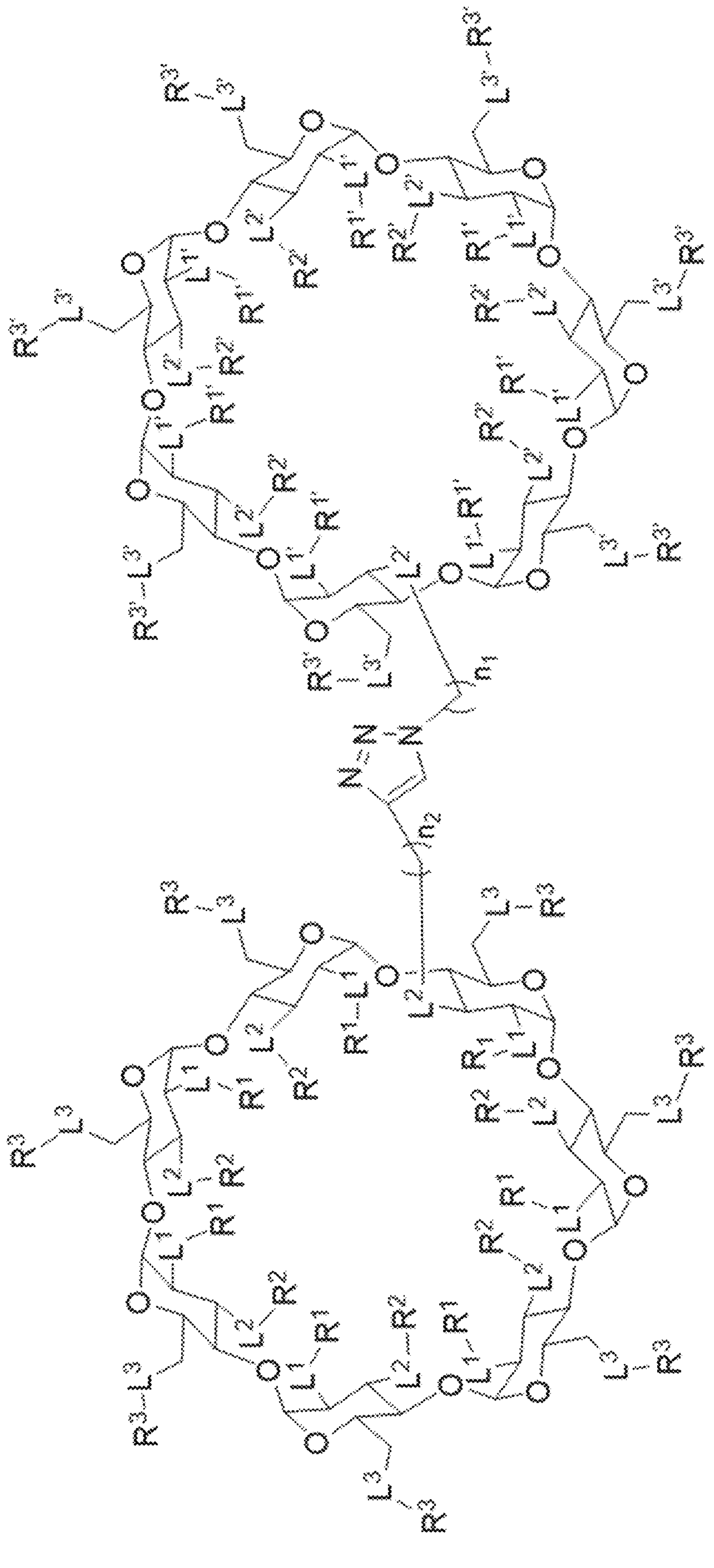
Figure 1J:
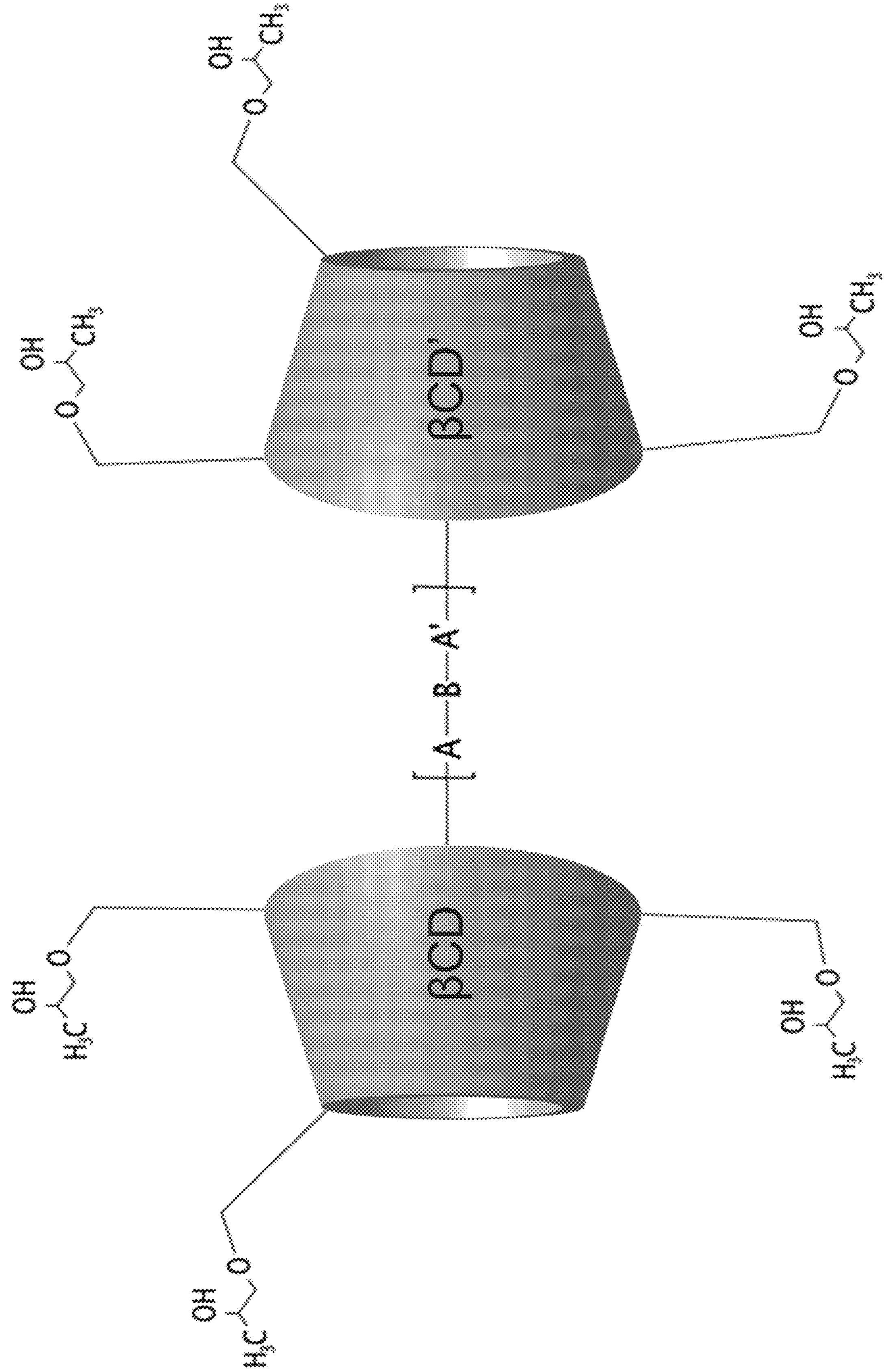
Figure 1K:
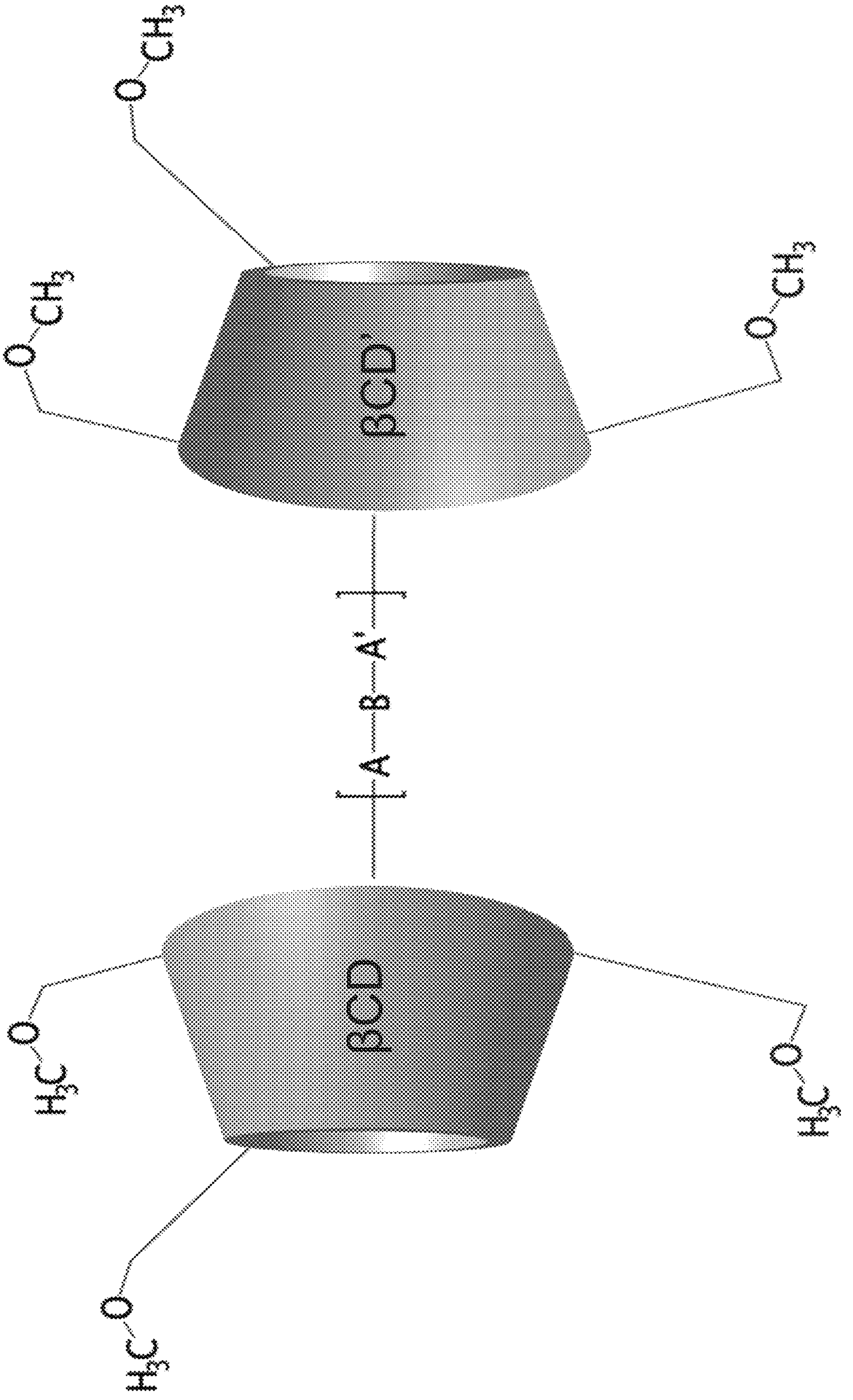

The present disclosure describes the design and testing of various dimers of CD. As shown in FIG. 1A, CDs are cyclic oligosaccharides composed of 6 (αCD), 7 (βCD), or 8 (γCD) D-glucose molecules in their native (i.e., unsubstituted) states. These CDs can be substituted in a variety of ways, including but not limited to the functionalization the hydroxyl groups at the C2, C3, and C6 position of the glucose rings with methyl, succinyl, sulfobutyl, or hydroxypropyl groups, as is shown in FIG. 1B which depicts the chemical structure of an exemplary HPβCD with substitutions in various positions around the CD ring.

Figure 3A:
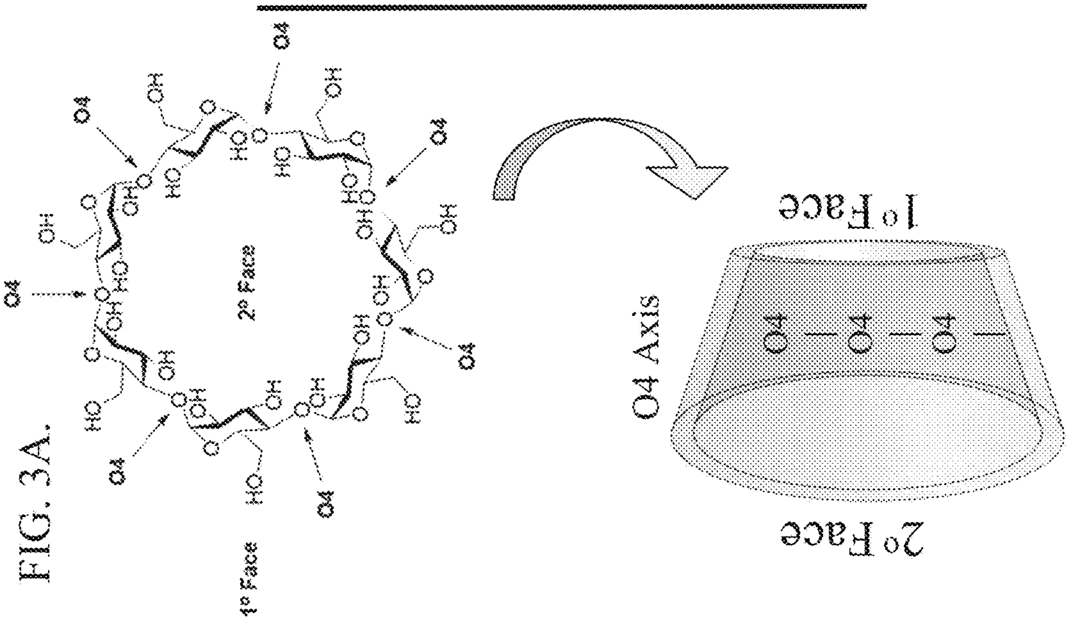
FIG. 3A depicts a schematic representation of βCD as a "truncated cone" shape having a primary (1°) and secondary (2°) face.

As shown in FIG. 3A, it can be convenient to describe CDs as a "truncated cone" shape having a primary (1°) and secondary (2°) face. The primary and secondary faces of a CD monomer can be described as the "smaller" and "larger" faces, respectively, due to the difference in number and orientations of hydroxyl groups available on each face while in an unsubstituted state. The oxygens at the four position of each D-glucose monomer (i.e., the "O4" oxygen) can be considered to form a ring around the perimeter of the truncated cone shape between the primary and secondary faces.

Figure 3B:
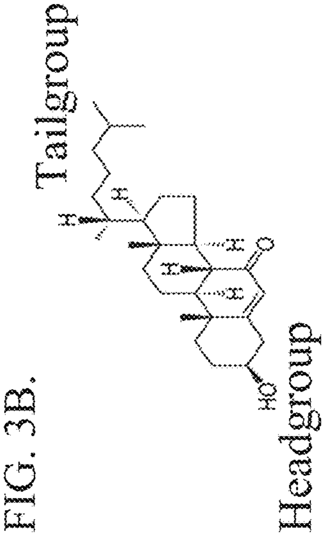
FIG. 3B depicts the structure of the 7KC oxysterol having a "headgroup" and a "tailgroup."
Figure 3C:
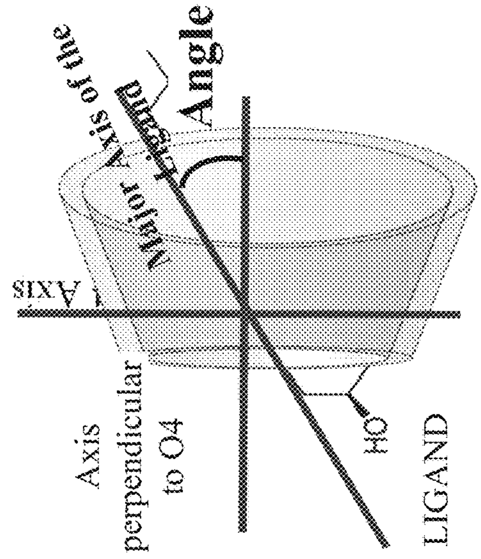
FIG. 3C depicts a diagram of angle measurements between the βCD O4 plane and ligand axis.
Figure 3D:
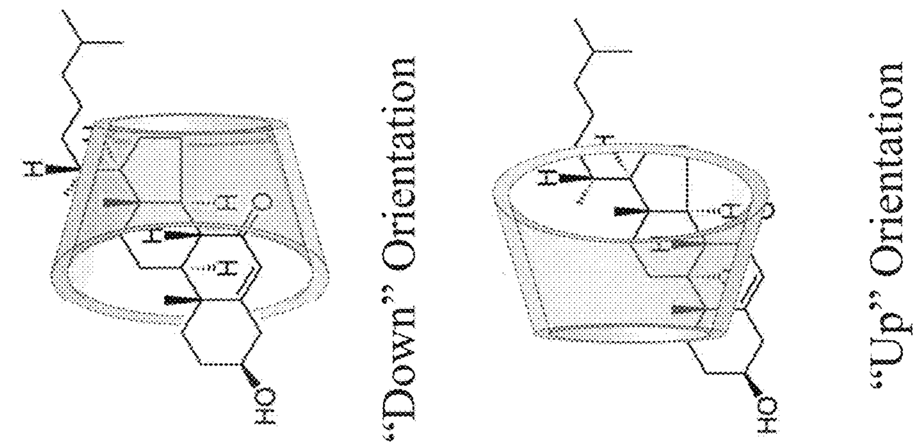
FIG. 3D depicts a diagram of the βCD monomer-ligand complex in the "up" and "down" orientations. 7KC is shown as an example, but the same applies to cholesterol, which differs only by the carbonyl group at the 7 position.
Figure 3E:
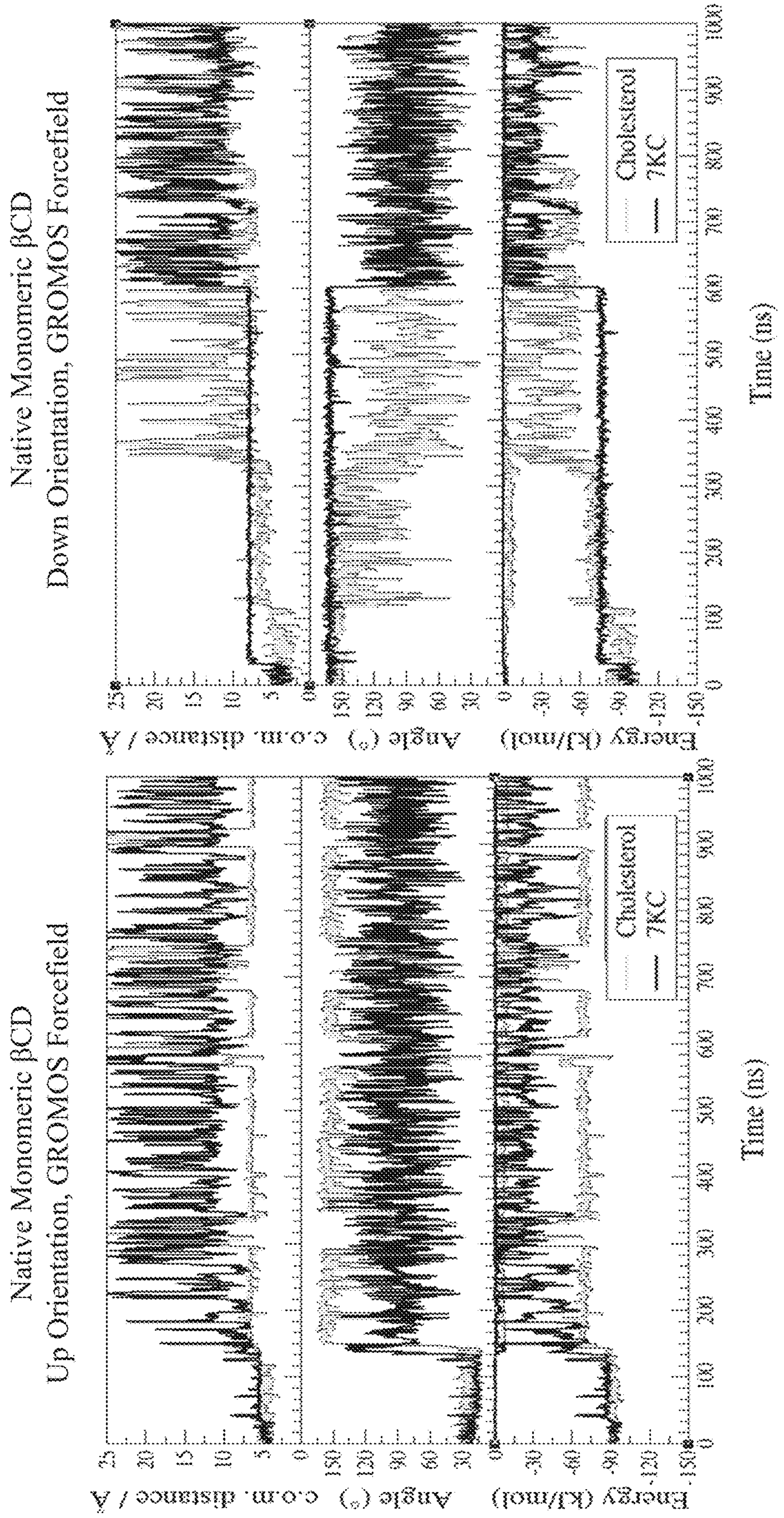
FIG. 3E depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for monomeric, native (DSO) βCD, up and down ligand orientations, in the GROMOS forcefield.
Figure 3F:
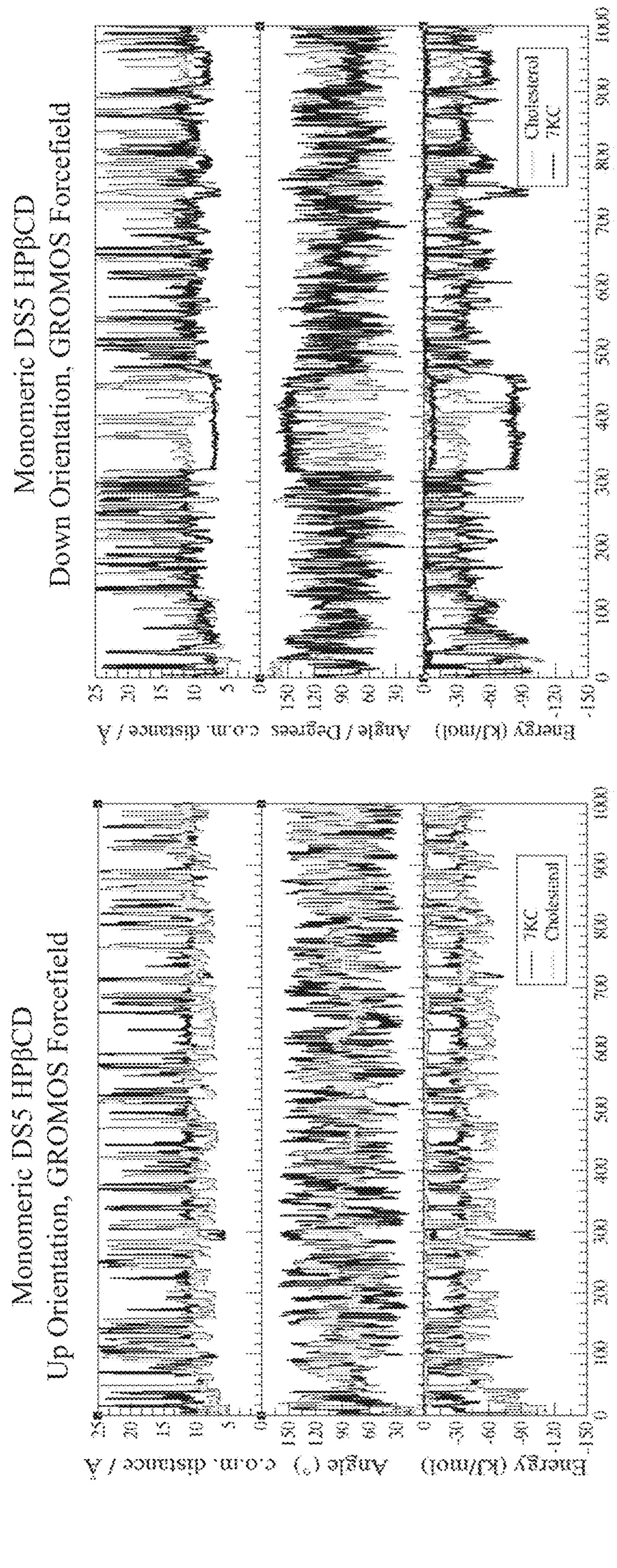
FIG. 3F depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for monomeric, HPβCD DS5, up and down ligand orientations, in the GROMOS forcefield.

CD monomers engage in host-guest chemistry with biomolecules such as 7-ketocholesterol (7KC), as shown in FIG. 3B with its depicted head- and tailgroups, thereby forming a 7KC-CD complex. As shown in FIG. 3C, when 7KC is complexed with a CD, the major axis of 7KC forms an angle against an axis that is perpendicular to the plane of the ring of O4 atoms. Furthermore, the 7KC can complex with the CD with either its headgroup or tailgroup associated with the primary face. If the tailgroup is associated with the primary face, as shown in FIG. 3D (top), the 7KC is said to be in a down orientation. If the headgroup is associated with the primary face, as shown in FIG. 3D (bottom), the 7KC is said to be in an up orientation.

Two CDs can be joined by one or more linking groups to generate CD dimers. CD dimers composed of the CD monomers of different ring sizes can be considered "heterodimers." CD dimers composed of the CD monomers of the same ring sizes can be considered "homodimers" or "asymmetric dimers" depending on whether their substituents are the same or different. These dimers can include but are not limited to HPα-βCD dimers, methyl-α-βCD dimers, succinyl-α-βCD dimers, sulfobutyl-α-βCD dimers, HPβCD dimers, methyl-βCD dimers, succinyl-CD dimers, sulfobutyl-βCD dimers, and quaternary ammonium dimers (e.g. 2-hydroxy trimethylammonium propyl). FIGS. 7C, 7H, 7M, 7S, 7AC, 7AI depict various functionalized CD dimers as disclosed herein. We have previously demonstrated that certain dimers' affinity for 7KC and cholesterol are increased dramatically compared to monomeric CDs. FIG. 3A shows an exemplary CD dimer empty and complexed with a sterol in contrast to the empty and complexed CD monomer of FIG. 3D. The present disclosure describes dimers comprising particular combinations of CD monomers, which in exemplary embodiments possess enhanced binding properties.

In certain embodiments each instance of a variable can be the "same" selection of another variable or another instance of the same variable so that the two or more chemical formula variables or respective pairs can be considered as "fused." By the term "fused" when applied to chemical formula variables and variable instances, it is to be understood that the two or more variables and/or respective pairs are connected such that there is a continuous chain of atoms between any two atoms of the "fused" variables without passing through any atom not represented by the "fused" variables or respective pairs. As a non-limiting example, one of skill in the art will appreciate that a divalent substitution group that connects to a CD of a structure (e.g., Structure A-Xa, A-Xb, B-Xa, B-Xb, C-Xa, C-Xb, etc.) to two instances of R1 can be considered a "same" selection for each instance of R1 such that they are "fused." As another non-limiting example, one of skill in the art will appreciate that a divalent substitution group that connects to a CD of a structure (e.g., Structure A-Xa, A-Xb, B-Xa, B-Xb, C-Xa, C-Xb, etc.) to one instance of R1 and one instance of R2 can be considered a "same" selection for the instance of R1 and the instance of R2 such that they are "fused."

Due to the sets of available selections for variables named above as part of certain embodiments for general formula I, specific selections from adjacent variables can result in redundant selections and embodiments. For example, one of skill in the art will appreciate that a selection for the respective pair of L1/R1 of a bond and a hydroxyl group is identical to a selection of —O— and hydrogen, respectively, for the pair. One of skill in the art will then also appreciate that recitation of all possible redundant selections across each variable is not required for the presentation of any specific embodiment. Moreover, when a particular structure is stated to be absent with reference to a particular combination of variable values, it means that other combinations variable values that produce said structure are likewise prohibited. For example, stated that an L1/R1 pair may not be oxygen and hydrogen, respectively, it also means that said L1 and R1 may not be a bond and hydroxyl, respectively, because the assignments of those values would result in the very same structure that is specified to be absent.

Compounds disclosed herein are intended to include for any combination of isotopomers made possible the selection of the groups herein. Furthermore, where stereochemistry is present or where one or more stereoisomers can be generated by the selection of various groups, it should be understood that the disclosure herein includes both racemic mixtures and isolated stereoisomeric products unless otherwise specified. In a preferred embodiment, each CD monomer comprises all D-glucose.

In one aspect, the disclosure provides CD dimers of the general structure CD-L CD' in which one or both of CD and CD' are specifically and fully substituted on the C6 position (i.e. having a selection for L3/R3 and L3'/R3' that are not a bond and hydroxyl, respectively). Such a position may also be referred to as being "saturated". By placing substitutions only at the C6 position, without intent to be limited by theory it is believed that the hydrophobic cavity of one or both of CD and CD' can be effectively extended, thereby creating a better environment for the encapsulation of the tail group of 7KC and other sterols with long aliphatic chains. By substituting only on the primary face of the CDs, the native hydroxyl groups on the secondary face are all available for hydrogen bonding with target molecule headgroups and the hydroxyl groups of the opposing CD, increasing complex stability by both mechanisms. An additional potential benefit of C6 substitutions is that they can be made as single isomer molecule in some instances. This can reduce the complexity and improve the batch-to-batch reproducibility of the final product.

In another aspect, the disclosure provides CD dimers in which alkyl groups are used as substitution groups. Without intent to be limited by theory, it is believed that since alkyl groups are more hydrophobic than charged and polar substitutions, they are better able to and will therefore extend the hydrophobic cavity of one or both of the subunits, thereby creating a better environment for the encapsulation of the tail group of 7KC and other sterols with long aliphatic chains.

The present disclosure includes further substitutions of the dimeric CDs (such as HPβCDs or another CD of the present disclosure) described herein. Chemical modification may be performed before or after dimerization. Chemical modification of CDs can be made directly on the native beta CD rings by reacting it with a chemical reagent (nucleophile or electrophile) or on a properly functionalized CD (Adair-Kirk [et al.], Nat Med., 14(10):1024-5, (2008)); (Khan, [et al.], Chem. Rev., 98(5):1977-1996, (1998)). To date, more than 1,500 CD derivatives have been made by chemical modification of native CDs. CDs can also be prepared by de novo synthesis, starting with glucopyranose-linked oligopyranosides. Such a synthesis can be accomplished by using various chemical reagents or biological enzymes, such as CD transglycosylase. An overview of chemically modified CDs as drug carriers in drug delivery systems is described, for example, in (Stella, [et al.], Toxicol. Pathol., 36(1):30-42, (2008)), the disclosure of which is herein incorporated by reference in its entirety. U.S. Pat. Nos. 3,453,259 and 3,459,731 describe electroneutral CDs, the disclosures of which are herein incorporated by reference in its entirety. Other derivatives include CDs with cationic properties, as disclosed in U.S. Pat. No. 3,453,257; insoluble crosslinked CDs, as disclosed in U.S. Pat. No. 3,420,788; and CDs with anionic properties, as disclosed in U.S. Pat. No. 3,426,011, the disclosures of which are all hereby incorporated by reference in their entirety. Among the CD derivatives with anionic properties, carboxylic acids, phosphorous acids, phosphinous acids, phosphonic acids, phosphoric acids, thiophosphonic acids, thiosulphinic acids, and sulfonic acids have been appended to the parent CD, as disclosed, for example, in U.S. Pat. No. 3,426,011. Sulfoalkyl ether CD derivatives have also been described, e.g., in U.S. Pat. No. 5,134,127, the disclosure of which is hereby incorporated by reference in its entirety. In some embodiments, the cyclic oligosaccharide can have two or more of the monosaccharide units replaced by triazole rings, which can be synthetized by the azide-alkyne Huisgen cycloaddition reaction (Bodine [et al.], J. Am. Chem. Soc., 126(6):1638-9, (2004)).

The two CDs monomers of the CD dimers of the disclosure are joined by a linker (also referred to herein as a linking group). Methods that may be used to join the CD subunits to a linker are described below. Additional methods of joining CD subunits to a linker are known in the art. (Georgeta [et al.], J. Bioact Compat. Pol., 16:39-48. (2001)), (Uu [et al.], Acc. Chem. Res., 39:681-691. (2006)), (Ozmen [et al.], J. Mol. Catal. B-Enzym., 57:109-114. (2009)), (Trotta [et al.], Compos. Interface, 16:39-48. (2009)), each of which is hereby incorporated by reference in its entirety. For example, a linker group containing a portion reactive to a hydroxyl group (e.g., a carboxyl group, which may be activated by a carbodiimide) can be reacted with the CD to form a covalent bond thereto. In another example, one or more hydroxyl groups of the CD can be activated by known methods (e.g., tosylation) to react with a reactive group (e.g., amino group) on the linker.

In general, the linker initially contains two reactive portions that react with and bond to each CD monomer. In one embodiment, a linker is first attached to a CD to produce a linker-CD compound that is isolated, and then the remaining reactive portion of the linker in the linker-CD compound is subsequently reacted with a second CD. The linker-cyclodextrin compound can be further modified with protecting groups and/or with ad-hoc designed functional moieties in order to introduce additional interacting functionalities and/or to achieve the desired regiochemistry in the target key-intermediate. The second reactive portion of the linker may be protected during reaction of the first reactive group, though protection may not be employed where the first and second reactive portions of the linker react with the two molecules differently. A linker may be reacted with both molecules simultaneously to link them together. In other embodiments, the linker can have additional reactive groups in order to link to other molecules.

Numerous linkers are known in the art. Such linkers can be used for linking any of a variety of groups together when the groups possess, or have been functionalized to possess, groups that can react and link with the reactive linker. Some groups capable of reacting with double-reactive linkers include amino, thiol, hydroxyl, carboxyl, ester, and alkyl halide groups. For example, amino-amino coupling reagents can be employed to link a cyclic oligosaccharide with a polysaccharide when each of the groups to be linked possess at least one amino group. Some examples of amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. In other embodiments, amino-thiol coupling agents can be employed to link a thiol group of one molecule with an amino group of another molecule. Some examples of amino-thiol coupling reagents include succinimidyl 4-(N-maleimidomethyl)-cyclohexane-1-carboxylate (SMCC), and sulfosuccinimidyl 4-(N-maleimidomethyl)-cyclohexane-1-carboxylate (sulfo-SMCC). In yet other embodiments, thiol-thiol coupling agents can be employed to link groups bearing at least one thiol group.

In some embodiments, the linker is as small as a single atom (e.g., an —O—, —$CH_2$—, or —NH— linkage), or two or three atoms in length (e.g., an amido, ureido, carbamate, ester, carbonate, sulfone, ethylene, or trimethylene linkage). In other embodiments, the linker provides more freedom of movement by being at least four, five, six, seven, or eight atom lengths, and up to, for example, 10, 12, 14, 16, 18, 20, 22, 24, 26, 28, or 30 atom lengths. Preferred linker lengths are between 2 and 12 atoms, or between 4 and 8 atoms. In exemplary embodiments, the linker is C4 alkyl, which may be unsubstituted. In some embodiments, the linker comprises a triazole (e.g. B is triazole). In further embodiments, the linker comprises a triazole connected to each CD monomer by alkyl chains of equal or different lengths (e.g. A and A are alkyl chains of various lengths and B is triazole.)

In another aspect, the disclosure provides a method of engineering CD dimers with specificity for other small hydrophobic molecules. Exemplary methods are carried out by first creating a CD dimer core of a certain structure specified in the synthesis. Then, any substitutions can be added to create specificity for the selected hydrophobic molecule(s) while maintaining the high affinity conveyed by the CD dimer core. This specificity can further be modified with different linkers.

III. Pharmaceutical Compositions

In another aspect, the disclosure provides a pharmaceutical composition comprising a CD dimer composition as disclosed herein and a pharmaceutically acceptable carrier. Said pharmaceutical composition may be suitable for administration to a subject, e.g., parenteral (e.g., subcutaneous, intramuscular, or intravenous), topical, transdermal, oral, sublingual, or buccal administration, preferably intravenous or subcutaneous administration, more preferably intravenous administration. Said CD dimer composition may be the only active ingredient in said composition. Said pharmaceutical composition may consist of or consist essentially of said CD dimer and said pharmaceutically acceptable carrier.

In another aspect, the disclosure provides pharmaceutical compositions comprising a CD dimer or dimers as disclosed herein and a hydrophobic drug. Said hydrophobic drug may comprise a hormone or sterol, such as estrogen, an estrogen analog, etc. Said CD dimer or dimers may be present in an amount effective to solubilize said hydrophobic drug.

The phrase "pharmaceutically acceptable" is used herein to refer to those compounds, materials, compositions, and/or dosage forms that are, within the scope of sound medical judgment, suitable for entering a living organism or living biological tissue, preferably without significant toxicity, irritation, or allergic response. The present invention includes methods which comprise administering a CD dimer to a patient, wherein the CD dimer is contained within a pharmaceutical composition. The pharmaceutical compositions of the invention are formulated with pharmaceutically acceptable carriers, excipients, and other agents that provide suitable transfer, delivery, tolerance, and the like. A multitude of appropriate formulations can be found in the formulary known to pharmaceutical chemists, such as Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also (Powell [et al.], J. Pharm. Sci. Technol., 52:238-311, (1998)).

The phrase "pharmaceutically acceptable carrier," as used herein, generally refers to a pharmaceutically acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body. Each carrier must be "acceptable" in the sense of being compatible with other ingredients of the formulation and not injurious to the patient Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

Other examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition. Some examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Pharmaceutical formulations of the present invention may be prepared by any of the methods known in the pharmaceutical arts. The amount of active ingredient (i.e., CD dimer such as HPβCD dimer or another CD dimer of the present disclosure) that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. The amount of active compound may be in the range of about 0.1 to 99.9 percent, more typically, about 80 to 99.9 percent, and more typically, about 99 percent. The amount of active compound may be in the range of about 0.1 to 99 percent, more typically, about 5 to 70 percent, and more typically, about 10 to 30 percent. In an exemplary embodiment, the dosage form is provided for intravenous administration in an aqueous solution having a concentration of between 0.5% and 0.001%, such as between 0.12% and 0.0105%, e.g., about 0.01% (W/V). In an exemplary embodiment, the dosage form is provided for intravenous administration in an aqueous solution having a concentration of between 2.5% and 0.25%, such as between 2% and 0.5%, e.g., about 1% (W/V). In an exemplary embodiment, the dosage form provides for intravenous administration of up to 500 mLs of a 1% solution (W/V), resulting in a dosage of up to 5 grams.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. The active compound may also be administered as a bolus, electuary, or paste.

Methods of preparing these formulations or compositions generally include the step of admixing a compound of the present invention with the carrier, and optionally, one or more auxiliary agents. In the case of a solid dosage form (e.g., capsules, tablets, pills, powders, granules, trouches, and the like), the active compound can be admixed with a finely divided solid carrier, and typically, shaped, such as by pelletizing, tableting, granulating, powderizing, or coating. Generally, the solid carrier may include, for example, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more auxiliary ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent.

The tablets, and other solid dosage forms of the active agent, such as capsules, pills and granules, may optionally be scored or prepared with coatings and shells, such as enteric coatings and other coatings well known in the pharmaceutical-formulating art. The dosage form may also be formulated so as to provide slow or controlled release of the active ingredient therein using, for example, hydroxypropyl methyl cellulose in varying proportions to provide the desired release profile, other polymer matrices, liposomes and/or microspheres. The dosage form may alternatively be formulated for rapid release, e.g., freeze-dried.

Generally, the dosage form is required to be sterile. For this purpose, the dosage form may be sterilized by, for example, filtration through a bacteria-retaining filter, or by incorporating sterilizing agents in the form of sterile solid compositions which can be dissolved in sterile water, or some other sterile injectable medium immediately before use. The pharmaceutical compositions may also contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms are typically a pharmaceutically acceptable emulsion, microemulsion, solution, suspension, syrup, or elixir of the active agent. In addition to the active ingredient, the liquid dosage form may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Dosage forms specifically intended for topical or transdermal administration can be in the form of, for example, a powder, spray, ointment, paste, cream, lotion, gel, solution, or patch. Ophthalmic formulations, such as eye ointments, powders, solutions, and the like, are also contemplated herein. The active compound may be mixed under sterile conditions with a pharmaceutically acceptable carrier, and with any preservatives, buffers, or propellants that may be required. The topical or transdermal dosage form may contain, in addition to an active compound of this invention, one or more excipients, such as those selected from animal and vegetable fats, oils, waxes, paraffins, starch, tragacanth, cellulose derivatives, polyethylene glycols, silicones, bentonites, silicic acid, talc and zinc oxide, and mixtures thereof. Sprays may also contain customary propellants, such as chlorofluorohydrocarbons and volatile unsubstituted hydrocarbons, such as butane and propane.

For purposes of this invention, transdermal patches may provide the advantage of permitting controlled delivery of a compound of the present invention into the body. Such dosage forms can be made by dissolving or dispersing the compound in a suitable medium. Absorption enhancers can also be included to increase the flux of the compound across the skin. The rate of such flux can be controlled by either providing a rate-controlling membrane or dispersing the compound in a polymer matrix or gel.

Pharmaceutical compositions of this invention suitable for parenteral administration generally include one or more compounds of the invention in combination with one or more pharmaceutically acceptable sterile isotonic aqueous or nonaqueous solutions, dispersions, suspensions or emulsions, or sterile powders that may be reconstituted into sterile injectable solutions or dispersions prior to use, which may contain sugars, alcohols, antioxidants, buffers, bacteriostats, or solutes that render the formulation isotonic with the blood of the intended recipient.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms can be made by forming microencapsule matrices of the active compound in a biodegradable polymer, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissue.

The pharmaceutical composition may also be in the form of a microemulsion. In the form of a microemulsion, bioavailability of the active agent may be improved. Reference is made to (Dorunoo [et al.], Drug Development and Industrial Pharmacy, 17(12):1685-1713 (1991)) and (Sheen [et al.], J. Pharm. Sci., 80(7):712-714, (1991)), the contents of which are herein incorporated by reference in their entirety.

The pharmaceutical composition may also contain micelles formed from a compound of the present invention and at least one amphiphilic carrier, in which the micelles have an average diameter of less than about 100 nm. In some embodiments, the micelles have an average diameter less than about 50 nm, or an average diameter less than about 30 nm, or an average diameter less than about 20 nm.

While any suitable amphiphilic carrier is considered herein, the amphiphilic carrier is generally one that has been granted Inactive Pharmaceutical Ingredient status, and that can both solubilize the compound of the present invention and microemulsify it at a later stage when the solution comes into a contact with a complex water phase (such as one found in the living biological tissue). Usually, amphiphilic ingredients that satisfy these requirements have HLB (hydrophilic to lipophilic balance) values of 2-20, and their structures contain straight chain aliphatic radicals in the range of C-6 to C-20. Some examples of amphiphilic agents include polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series). Commercially available amphiphilic carriers are particularly contemplated, including the Gelucire®-series, Labrafil®, Labrasol®, or Lauroglycol®, PEG-mono-oleate, PEG-di-oleate, PEG-mono-laurate and di-laurate, Lecithin, Polysorbate 80.

IV. Disease Indications and Methods of Treatment and Prevention

Exemplary embodiments of the invention provide for the use of CD dimers, as disclosed herein, for the solubilization and/or removal of 7KC, which may be performed in vitro or in vivo.

In exemplary embodiments, said CD dimer, as disclosed herein, exhibits greater binding affinity and/or solubilization of 7KC than cholesterol. The specificity for 7KC over cholesterol is most evident at sub-saturating concentrations, whereas at higher concentrations the solubilization of both sterols can approach 100%. This specificity allows for use of such CD dimers in order to preferentially solubilize and remove 7KC.

7KC is believed to be involved in heart diseases, cystic fibrosis, liver damage and failure, and complications of hypercholesterolemia. When someone is affected by hypercholesterolemia, 7KC can diffuse through the membranes of cells where it affects receptors and enzymatic function; the increased rates of dementia in hypercholesterolemia have been associated with 7KC accumulation. In the liver, 7KC affects fenestration and porosity in the tissue, which increases with age. 7KC also promotes translocation of cytosolic NADPH oxidase components to the membrane in neutrophils (white blood cells) and enhances rapid reactive oxygen species production. Pathogenesis of other diseases of aging such as Age-Related Macular Degeneration (AMD—dry form), Alzheimer's disease, as well as lysosomal storage diseases such as Niemann-Pick Type C (NPC) have also been tied to increased levels of 7KC. Oxysterols, including 7KC, are also involved in increasing free radical levels, which in turn affect lipid circulation in cystic fibrosis. The increase in free radicals caused by oxysterols like 7KC are believed to be involved in apoptosis, cytotoxicity, impairment of endothelial function, and regulation of enzymes involved in inflammation and in fatty acid metabolism.

7KC is formed from the non-enzymatic reaction of an oxygen radical with cholesterol, indicating that its formation may not be beneficial. Indeed, 7KC is believed to enhance the production of free radicals everywhere in the body, but heart and vascular tissue is of particular concern. Free radicals affect cells and enzymatic reactions that are important for cholesterol mediated tissue damage, which is especially important in these tissues; this is believed to enhance inflammation in the vasculature. By disrupting the function of cell and organelle membranes, 7KC is believed to cause dysfunction of mitochondria and lysosomes and is thought to be involved in increasing the frequency of formation of foam cells from macrophages in atherosclerotic plaques. The scavenging functions of these macrophages would be expected to help ameliorate the plaque, but instead they can become part of the plaque when they are congested with cholesterol and oxysterols.

Exemplary embodiments provide for the treatment of diseases associated with and/or exacerbated by 7KC accumulation, such as atherosclerosis, AMD, arteriosclerosis, coronary atherosclerosis due to calcified coronary lesion, heart failure (all stages), Alzheimer's disease, Amyotrophic lateral sclerosis, Parkinson's disease, Huntington's disease, vascular dementia, multiple sclerosis, Smith-Lemli-Opitz Syndrome, infantile neuronal ceroid Lipofuscinosis, Lysosomal acid lipase deficiency, Cerebrotendinous xanthomatosis, X-linked adrenoleukodystrophy, Sickle cell disease, Niemann-Pick Type A disease, Niemann-Pick Type B disease, Niemann-Pick Type C disease, Gaucher's disease, Stargardt's disease, idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia or dementia associated with hypercholesterolemia. Preferred CD dimers are selective for 7KC (compared to cholesterol). Preferably, said CD dimer preferentially solubilizes 7KC, while minimizing or avoiding potentially deleterious or toxic effects that can result from excessive removal of cholesterol.

In another aspect, the disclosure provides a therapeutic method comprising administration of an effective amount of a CD dimer composition as disclosed herein to a subject in need thereof. Said subject may be suffering from harmful or toxic effects of 7KC or a condition associated with harmful or toxic effects of 7KC.

In another aspect, the disclosure provides a method for reducing the amount of 7KC in a subject in need thereof comprising administration of an effective amount of a CD dimer composition as disclosed herein or pharmaceutical composition comprising a CD dimer composition as disclosed herein to said subject.

Said CD dimer composition may be administered to said subject via parenteral (e.g., subcutaneous, intramuscular, or intravenous), topical, transdermal, oral, sublingual, or buccal administration, preferably intravenous administration.

Said method may comprise administering to said subject (a) between about 1 mg and 20 g, such as between 10 mg and 1 g, between 50 mg and 200 mg, or 100 mg of said CD dimer composition to said subject, or (b) between 1 and 10 g of said CD dimer composition, such as about 2 g, about 3 g, about 4 g, or about 5 g, or (c) between 50 mg and 5 g of said CD dimer composition, such as between 100 mg and 2.5 g, between 100 mg and 2 g, between 250 mg and 2.5 g.

Said method may be used to prevent, treat, or ameliorate the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy. Said method may comprise administering a second therapy to said subject, wherein said second therapy is administered concurrently or sequentially in either order.

Said method may be for the prevention, treatment, or ameliorating the symptoms of atherosclerosis. Said CD dimer composition may be administered in combination with another therapy for the treatment or prevention of atherosclerosis, such as an anti-cholesterol drug, anti-hypertension drug, anti-platelet drug, dietary supplement, or surgical or behavioral intervention, including but not limited to those described herein. Said anti-cholesterol drug, may comprise a fibrate or statin, anti-platelet drug, anti-hypertension drug, or dietary supplement. Said statin may comprise ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), or ZOCOR® (simvastatin).

Said method may be for the prevention, treatment, or ameliorating the symptoms of dry age-related macular degeneration. Said method may be for the prevention, treatment, or ameliorating the symptoms of Stargardt's disease. Said CD dimer composition may be administered in combination with another therapy for the treatment or prevention of dry AMD or Stargardt's Disease, such as LBS-008 (Belite Bio) (a nonretinoid antagonist of retinol binding protein 4), AREDS supplement formula comprising vitamins C and E, beta-carotene, zinc, and copper, AREDS2 supplement formula comprising a supplement formula that has vitamins C and E, zinc, copper, lutein, zeaxanthin, and omega-3 fatty acids, or combinations thereof.

Said method may be for the prevention, treatment, or ameliorating the symptoms of Niemann-Pick Disease. Said CD dimer composition may be administered in combination with another therapy for the treatment or prevention of Niemann-Pick Disease, such as one or more of miglustat (ZAVESCA®), HPβCD (TRAPPSOL CYCLO, VTS-270), and physical therapy.

Said method may be for the prevention, treatment, or ameliorating the symptoms of Alzheimer's Disease. Said CD dimer composition may be administered in combination with another therapy for the treatment or prevention of Alzheimer's Disease, such as cholinesterase inhibitors (ARICEPT®, EXELON®, RAZADYNE®) and memantine (NAMENDA®) or a combination thereof.

Said method may be for the prevention, treatment, or ameliorating the symptoms of heart failure. Said CD dimer composition may be administered in combination with another therapy for the treatment or prevention of heart failure, such as one or more aldosterone antagonists, ACE inhibitors, ARBs (angiotensin II receptor blockers), ARNIs (angiotensin receptor-neprilysin inhibitors), beta-blockers, blood vessel dilators, calcium channel blockers, digoxin, diuretics, heart pump medications, potassium, magnesium, selective sinus node inhibitors, or combinations thereof.

In exemplary embodiments, the CD dimer may be administered to a patient in an amount of between 1 mg and 10 g, such as between 10 mg and 1 g, between 100 mg and 500 mg. In exemplary embodiments, about 400 mg of CD dimer may be administered. In exemplary embodiments, between 1 and 10 g of CD dimer may be administered, such as about 2 g, about 3 g, about 4 g, or about 5 g. In exemplary embodiments, between 50 mg and 5 g of CD dimer may be administered, such as between 100 mg and 2.5 g, between 100 mg and 2 g, between 250 mg and 2.5 g, e.g., about 1 g.

Exemplary embodiments provide a single dosage form, which may comprise the foregoing amount of CD dimer, which may be packaged for individual administration, optionally further comprising a pharmaceutically acceptable carrier or excipient. The total amount of said CD dimer in said single dosage form may be as provided above, e.g., between 1 mg and 10 g, such as between 10 mg and 1 g, between 100 mg and 500 mg, between 1 and 10 g of CD dimer, between 50 mg and 5 g, between 100 mg and 2.5 g, between 100 mg and 2 g, between 250 mg and 2.5 g, such as about 1 g, 2 g, about 3 g, about 4 g, or about 5 g.

The CD (such as HPβCD or another CD of the present disclosure) dimer may be administered by any suitable means. Preferred routes of administration include parenteral (e.g., subcutaneous, intramuscular, or intravenous), topical, transdermal, oral, sublingual, or buccal. Said administration may be ocular (e.g., in the form of an eyedrop), intravitreous, retro-orbital, subretinal, subscleral, which may be preferred in case of ocular disorders, such as AMD.

The CD (such as HPβCD or another CD of the present disclosure) dimer may be administered to a subject, or may be used in vitro, e.g., applied to a cell or tissue that have been removed from an animal. Said cell or tissue may then be introduced into a subject, whether the subject from which it was removed or another individual, preferably of the same species.

The subject (i.e., patient) receiving the treatment is typically an animal, generally a mammal, preferably a human. The subject may be a non-human animal, which includes all vertebrates, e.g., mammals and non-mammals, such as non-human primates, sheep, dogs, cats, cows, horses, chickens, amphibians, and reptiles. In some embodiments, the subject is livestock, such as cattle, swine, sheep, poultry, and horses, or companion animals, such as dogs and cats. The subject may be genetically male or female. The subject may be any age, such as elderly (generally, at least or above 60, 70, or 80 years of age), elderly-to-adult transition age subjects, adults, adult-to-pre-adult transition age subjects, and pre-adults, including adolescents (e.g., 13 and up to 16, 17, 18, or 19 years of age), children (generally, under 13 or before the onset of puberty), and infants. The subject can also be of any ethnic population or genotype. Some examples of human ethnic populations include Caucasians, Asians, Hispanics, Africans, African Americans, Native Americans, Semites, and Pacific Islanders. The methods of the invention may be more appropriate for some ethnic populations, such as Caucasians, especially northern European populations, and Asian populations.

Atherosclerosis

Exemplary CD dimers described herein are useful to prevent or treat disease such as atherosclerosis. The combination of the CD dimer and one or more active agents, such as those described herein (e.g., antihyperlipidemic agents such as statins) are useful in treating any atherosclerosis, as well as the signs, symptoms or complications of atherosclerosis. Atherosclerosis (also known as arteriosclerotic vascular disease or ASVD and known as coronary artery disease or CAD) is a condition in which an artery wall thickens as a result of the accumulation of fatty materials such as cholesterol. Atherosclerosis is a chronic disease that can remain asymptomatic for decades. It is a syndrome affecting arterial blood vessels, a chronic inflammatory response in the walls of arteries, thought to be caused largely by the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

The pathobiology of atherosclerotic lesions is complicated but generally, stable atherosclerotic plaques, which tend to be asymptomatic, are rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap expose thrombogenic material, such as collagen to the circulation and eventually induce thrombus formation in the lumen. Upon formation, intraluminal thrombi can occlude arteries outright (e.g., coronary occlusion), but more often they detach, move into the circulation and can eventually occlude smaller downstream branches causing thromboembolism (e.g., stroke is often caused by thrombus formation in the carotid arteries). Apart from thromboembolism, chronically expanding atherosclerotic lesions can cause complete closure of the lumen. Chronically expanding lesions are often asymptomatic until lumen stenosis is so severe that blood supply to downstream tissue(s) is insufficient, resulting in ischemia.

These complications of advanced atherosclerosis are chronic, slowly progressive and cumulative. In some instances, soft plaques suddenly rupture, causing the formation of a thrombus that will rapidly slow or stop blood flow, leading to death of the tissues fed by the artery (infarction). Coronary thrombosis of a coronary artery is also a common complication which can lead to myocardial infarction. Blockage of an artery to the brain may result in stroke. In advanced atherosclerotic disease, claudication from insufficient blood supply to the legs, typically caused by a combination of both stenosis and aneurysmal segments narrowed with dots, may occur.

Atherosclerosis can affect the entire artery tree, but larger, high-pressure vessels such as the coronary, renal, femoral, cerebral, and carotid arteries are typically at greater risk.

Signs, symptoms and complications of atherosclerosis include, but are not limited to increased plasma total cholesterol, VLDL-C, LDL-C, free cholesterol, cholesterol ester, triglycerides, phospholipids and the presence of lesions (e.g., plaques) in arteries, as discussed above. In some instances, increased cholesterol (e.g., total cholesterol, free cholesterol and cholesterol esters) can be seen in one or more of plasma, aortic tissue and aortic plaques.

Certain individuals may be predisposed to atherosclerosis. Accordingly, the present disclosure relates to methods of administering the subject CD dimers alone, or in combination with one or more additional therapeutic agents (e.g., antihyperlipidemic agents, such as statins), to prevent atherosclerosis, or the signs, symptoms or complications thereof. In some embodiments a subject predisposed to atherosclerosis may exhibit one or more of the following characteristics: advanced age, a family history of heart disease, a biological condition, high blood cholesterol. In some embodiments, the biological condition comprises high levels of low-density lipoprotein cholesterol (LDL-C) in the blood, low levels of high-density lipoprotein cholesterol (HDL-C) in the blood, hypertension, insulin resistance, diabetes, excess body weight, obesity, sleep apnea, contributing lifestyle choice(s) and/or contributing behavioral habit(s). In some embodiments, the behavioral habit comprises smoking and/or alcohol use. In some embodiments, the lifestyle choice comprises an inactive lifestyle and/or a high stress level.

Exemplary embodiments provide for the administration of a CD dimer of the present disclosure, optionally in combination with one or more additional agents, to a patient having atherosclerosis. The patient may exhibit one or more signs or symptoms of atherosclerosis. Atherosclerosis may be diagnosed based on one or more of Doppler ultrasound, ankle-brachial index, electrocardiogram, stress test, angiogram (optionally with cardiac catheterization), computerized tomography (CT), magnetic resonance angiography (MRA), or other methods of imaging arteries or measuring blood flow.

Exemplary embodiments provide for the administration of a combination of therapies comprising a CD dimer of the present disclosure and one or more additional therapies. These combination therapies for treatment of atherosclerosis may include a CD dimer of the present disclosure and another therapy for the treatment or prevention of atherosclerosis, such as an anti-cholesterol drug, anti-hypertension drug, anti-platelet drug, dietary supplement, or surgical or behavioral intervention, including but not limited to those described below. Additional combination therapies include a CD dimer of the present disclosure and another therapy for the treatment of heart failure, such as one or more aldosterone antagonists, ACE inhibitors, ARBs (angiotensin II receptor blockers), ARNIs (angiotensin receptor-neprilysin inhibitors), beta-blockers, blood vessel dilators, calcium channel blockers, digoxin, diuretics, heart pump medications, potassium, magnesium, selective sinus node inhibitors, or combinations thereof. Combination therapies for the treatment of the dry form of age-related macular degeneration (AMD) or Stargardt's disease include a CD dimer of the present disclosure and another therapy for the treatment of AMD, such as, LBS-008 (Belite Bio) (a nonretinoid antagonist of retinol binding protein 4), AREDS supplement formula comprising vitamins C and E, beta-carotene, zinc, and copper, AREDS2 supplement formula comprising a supplement formula that has vitamins C and E, zinc, copper, lutein, zeaxanthin, and omega-3 fatty acids, or combinations thereof. Combination therapies for treatment of Alzheimer's disease include a CD dimer of the present disclosure and one or more cholinesterase inhibitors (ARICEPT®, EXELON®, RAZADYNE®) and memantine (NAMENDA®) or a combination thereof. Combination therapies for Niemann-Pick Disease include a CD dimer of the present disclosure and one or more of miglustat (ZAVESCA®), HPβCD (TRAPPSOL CYCLO, VTS-270), and physical therapy. The combination therapies may be administered simultaneously, essentially simultaneously, or sequentially, in either order. Combination therapies may be co-administered in a single formulation, or separately, optionally in a dosage kit or pack containing each medication in the combination, e.g., in a convenient pre-measured format in which one or more single doses of each drug in the combination is provided. The combination therapy may exhibit a synergistic effect, wherein the effects of the combined therapies exceed the effects of the individual treatments alone. While combination therapies in general include administration of an effective amount of the CD dimer and the combined therapy, the combination therapies may allow for effective treatment with a lower dosage of the CD and/or the combined therapy, which advantageously may decrease side-effects associated with the regular (non-combination) dosage.

Combination therapies may include therapies for the treatment or prevention of diseases or conditions related to atherosclerosis, such as coronary artery disease, angina pectoralis, heart attack, cerebrovascular disease, transient ischemic attack, and/or peripheral artery disease. Combination therapies may include therapies for the treatment or prevention of conditions that may contribute to atherosclerosis formation and/or a worse prognosis, such as hypertension, hypercholesterolemia, hyperglycemia, and diabetes.

In exemplary embodiments, a CD dimer of the present invention is co-administered with an anti-cholesterol drug, such as a fibrate or statin, e.g., ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and/or ZOCOR® (simvastatin). The anti-cholesterol drug may be administered in an amount effective to prevent or treat hypercholesterolemia.

In exemplary embodiments, a CD dimer of the present invention is co-administered with an anti-platelet drug, e.g., aspirin.

In exemplary embodiments, a CD dimer of the present invention is co-administered with an anti-hypertension drug. Exemplary anti-hypertension drugs include beta blockers, Angiotensin-converting enzyme (ACE) inhibitors, calcium channel blockers, and/or diuretics.

In exemplary embodiments, a CD dimer of the present invention is co-administered with a dietary supplement, such as one or more of alpha-linolenic acid (ALA), barley, beta-sitosterol, black tea, blond psyllium, calcium, cocoa, cod liver oil, coenzyme Q10, fish oil, folic acid, garlic, green tea, niacin, oat bran, omega-3 fatty acids (such as eicosapentaenoic acid (EPA) and/or docosahexaenoic acid (DHA)), sitostanol, and/or vitamin C.

Exemplary combination therapies also include intervention in patient behavior and/or lifestyle, including counseling and/or supporting smoking cessation, exercise, and a healthy diet, such as a diet low in low density lipoprotein (LDL) and optionally elevated in high density lipoprotein (HDL).

Exemplary combination therapies also include surgical intervention, such as angioplasty, stenting, or both.

The methods of the present invention are useful for treating or preventing atherosclerosis in human subjects. In some instances, the patient is otherwise healthy except for exhibiting atherosclerosis. For example, the patient may not exhibit any other risk factor of cardiovascular, thrombotic or other diseases or disorders at the time of treatment. In other instances, however, the patient is selected on the basis of being diagnosed with, or at risk of developing, a disease or disorder that is caused by or correlated with atherosclerosis. For example, at the time of, or prior to administration of the pharmaceutical composition of the present invention, the patient may be diagnosed with or identified as being at risk of developing a cardiovascular disease or disorder, such as, e.g., coronary artery disease, acute myocardial infarction, asymptomatic carotid atherosclerosis, stroke, peripheral artery occlusive disease, etc. The cardiovascular disease or disorder, in some instances, is hypercholesterolemia.

In other instances, at the time of, or prior to administration of the pharmaceutical composition of the present invention, the patient may be diagnosed with or identified as being at risk of developing atherosclerosis.

In yet other instances, the patient who is to be treated with the methods of the present invention is selected on the basis of one or more factors selected from the group consisting of age (e.g., older than 40, 45, 50, 55, 60, 65, 70, 75, or 80 years), race, gender (male or female), exercise habits (e.g., regular exerciser, non-exerciser), other preexisting medical conditions (e.g., type-II diabetes, high blood pressure, etc.), and current medication status (e.g., currently taking statins, such as e.g., cerivastatin, atorvastatin, simvastatin, pitavastatin, rosuvastatin, fluvastatin, lovastatin, pravastatin, etc., beta blockers, niacin, etc.).

Embodiments of the invention provide compositions and methods for the treatment or prevention of atherosclerosis and other age-related diseases. 7KC is the most abundant non-enzymatically produced oxysterol in atherosclerotic plaques and is believed to contribute to the pathogenesis of atherosclerosis. Treatment with the CD dimers of this invention is expected to be beneficial for the prevention and/or reversal of atherosclerotic plaque formation.

Embodiments of the invention provide compositions and methods for the treatment or prevention of diseases and conditions in which 7KC has been implicated. These include, but are not limited to, diseases of aging such as Age-Related Macular Degeneration (AMD), Alzheimer's disease, as well as lysosomal storage disease such as Niemann-Pick Type C (NPC). 7KC has also been implicated in the pathogenesis of cystic fibrosis, liver damage and failure and hypercholesterolemia. The increased rates of dementia in hypercholesterolemia have been implicated with 7KC accumulation.

V. Examples

Example 1. Previous MD Simulations of βCDs and βCD Dimers

Previously, we have conducted various simulations of monomeric (FIGS. 3E-F) and dimerized (FIGS. 4A-H) βCD molecules complexing 7KC and cholesterol. After these studies conclusively showed that dimerization significantly improves complexation with these ligands, as supported by wet-lab and NMR data shown in FIGS. 5-6, we have extended these types of simulations to include other types of dimers. Computational analysis before chemical synthesis and wet lab studies allows us to test these molecules in theory before investing in physically synthesizing and testing them. A brief summary of previous studies follows:

Compared to monomers (FIGS. 3E-3F), our novel, butyl-linked DS5 hydroxypropyl β-CD dimer (FIG. 4A) was significantly better at forming a stable complex with 7KC and cholesterol in the GROMOS forcefield. The contrast between the plots of these trajectories and those for monomeric HPβCD (DS 5) and native βCD provide clear evidence that the dimerized version consistently binds sterols significantly more reliably than its monomeric counterpart, hydroxypropylated or not. This is consistent with our experimental data comparing monomers and dimers (FIGS. 5A-5Q, 6A-6D). The angle, distance, and energy are all much more stable and in a presumably more solubilized orientation than in the monomeric simulations. We can see less than five angstroms between the center of mass of the ligand and the CD when the complex was fully formed in the down orientation, while monomers in the GROMOS forcefield consistently showed upwards of 5-10 angstroms between the molecules when the complex was formed. This indicates that the dimer forms a very strong, stable complex with both ligands, especially in the down orientation and particularly when compared to monomeric βCD. The data indicate that the dimerized HPβCD has much greater sterol affinity overall than the monomer and that it has preference for 7KC as 7KC is associated with at least one CD for significantly longer than cholesterol.

Figure 4A:
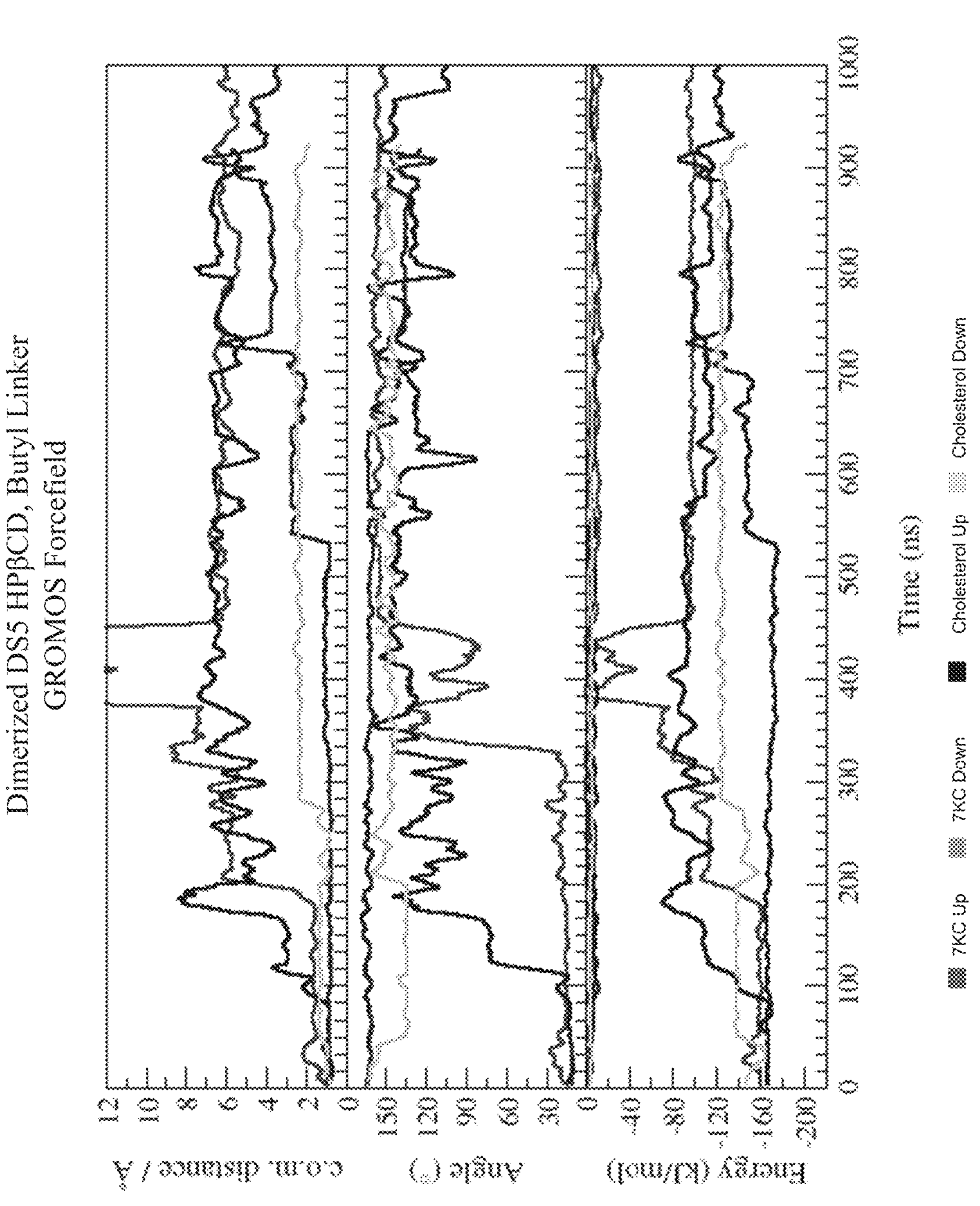
FIG. 4A depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a butyl-linked HPβCD DS5 dimer, up and down ligand orientations, in the GROMOS forcefield.
Figure 4B:
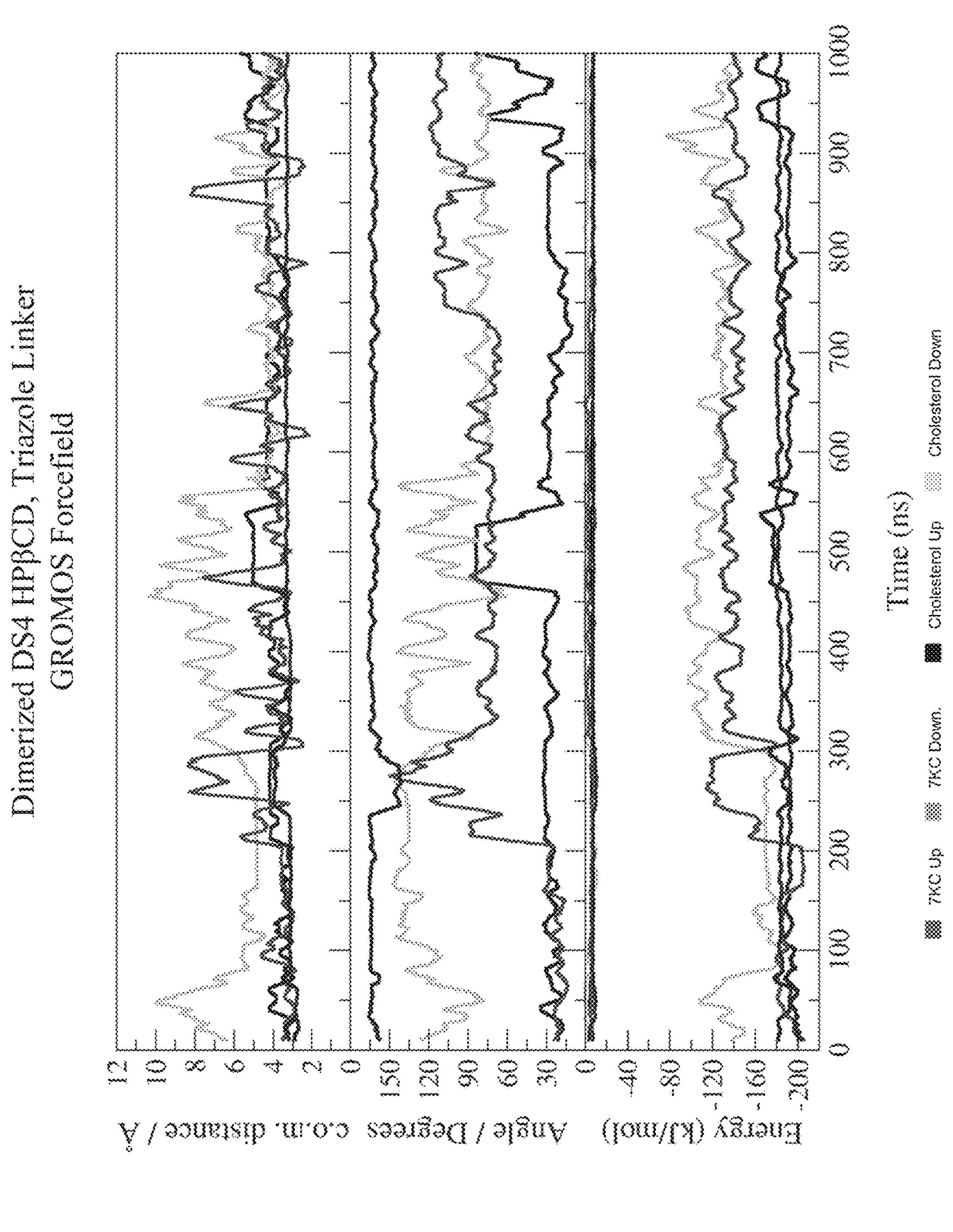
FIG. 4B depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a triazole linked HPβCD DS4 dimer up and down ligand orientations, in the GROMOS forcefield.
Figure 4C:
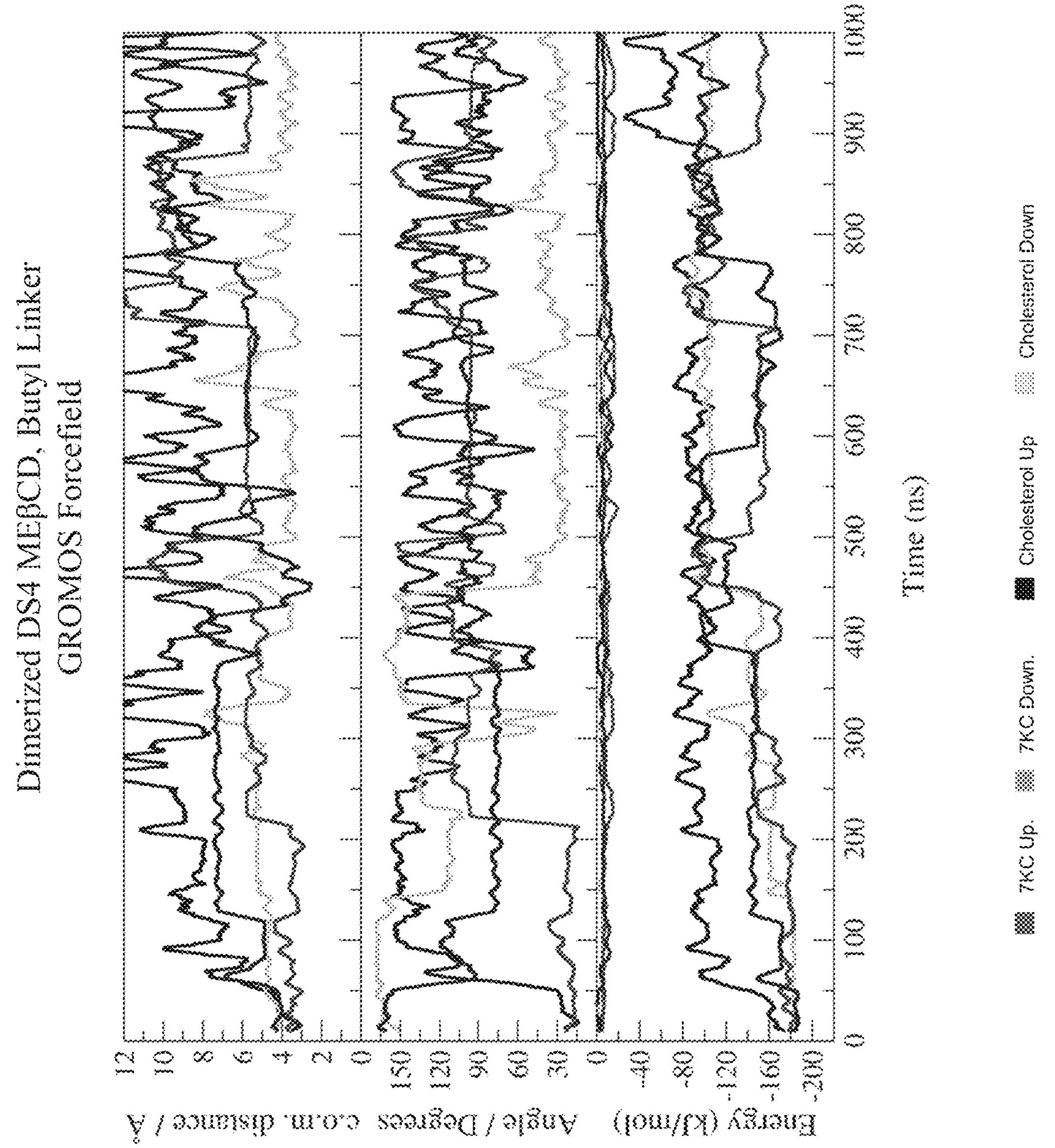
FIG. 4C depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a butyl linked MeβCD DS4 dimer, up and down ligand orientations, in the GROMOS forcefield.
Figure 4D:
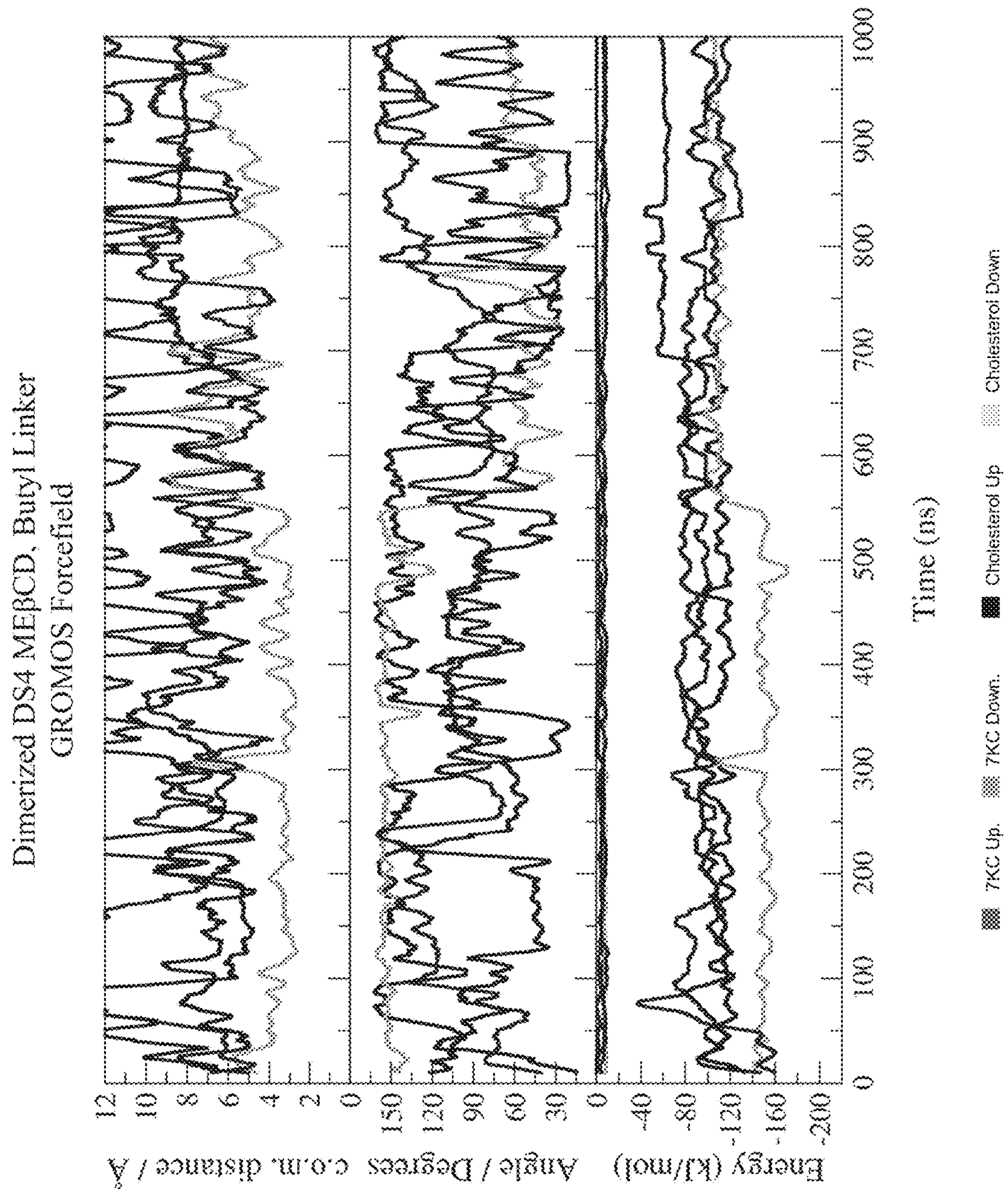
FIG. 4D depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a triazole linked MeβCD DS4 dimer, up and down ligand orientations, in the GROMOS forcefield.
Figure 4E:
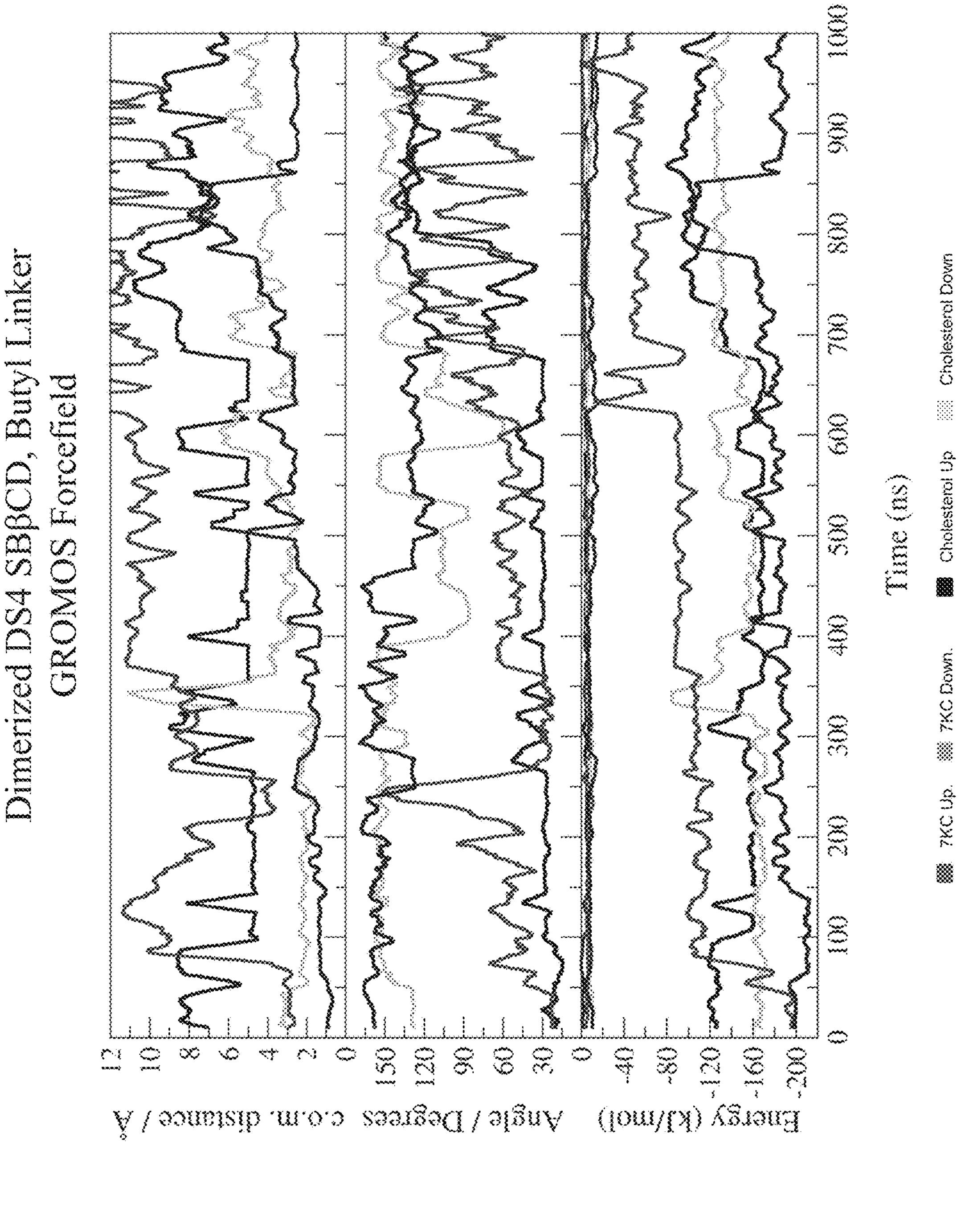
FIG. 4E depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a butyl linked SBβCD DS4 dimer, up and down ligand orientations, in the GROMOS forcefield.
Figure 4F:
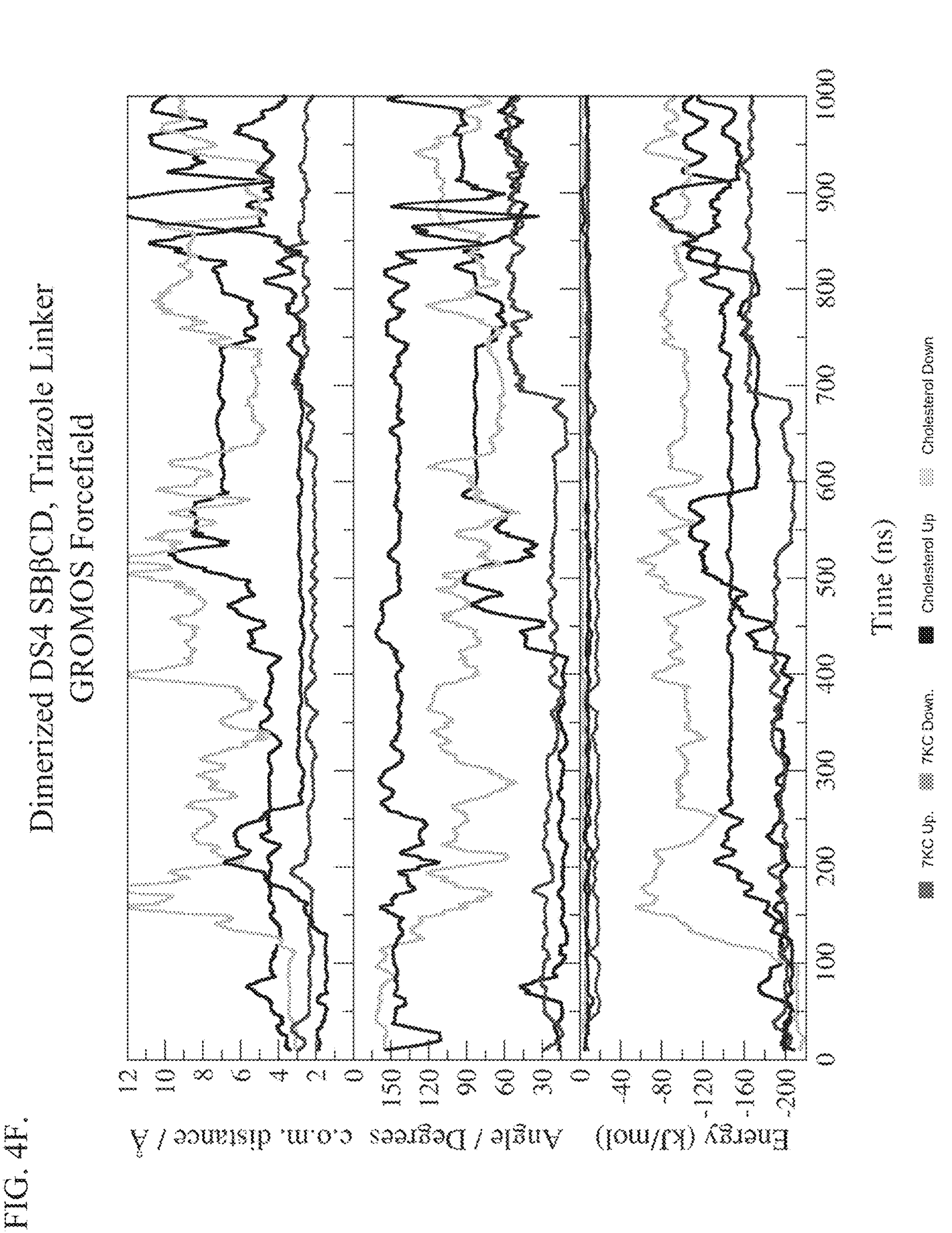
FIG. 4F depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a triazole linked SBβCD DS4 dimer, up and down ligand orientations, in the GROMOS forcefield.
Figure 4G:
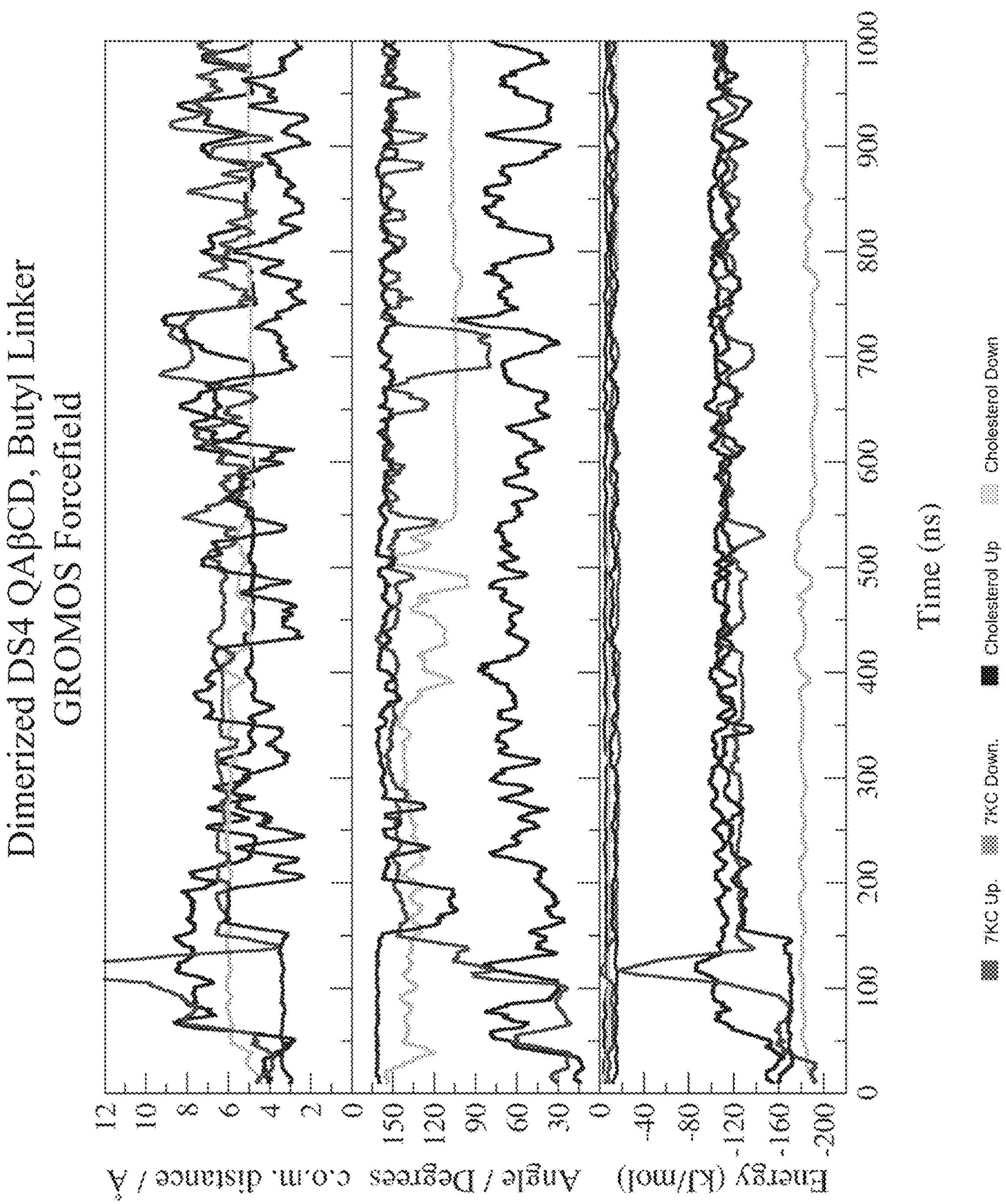
FIG. 4G depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a butyl linked QAβCD DS4dimer, up and down ligand orientations, in the GROMOS forcefield.
Figure 4H:
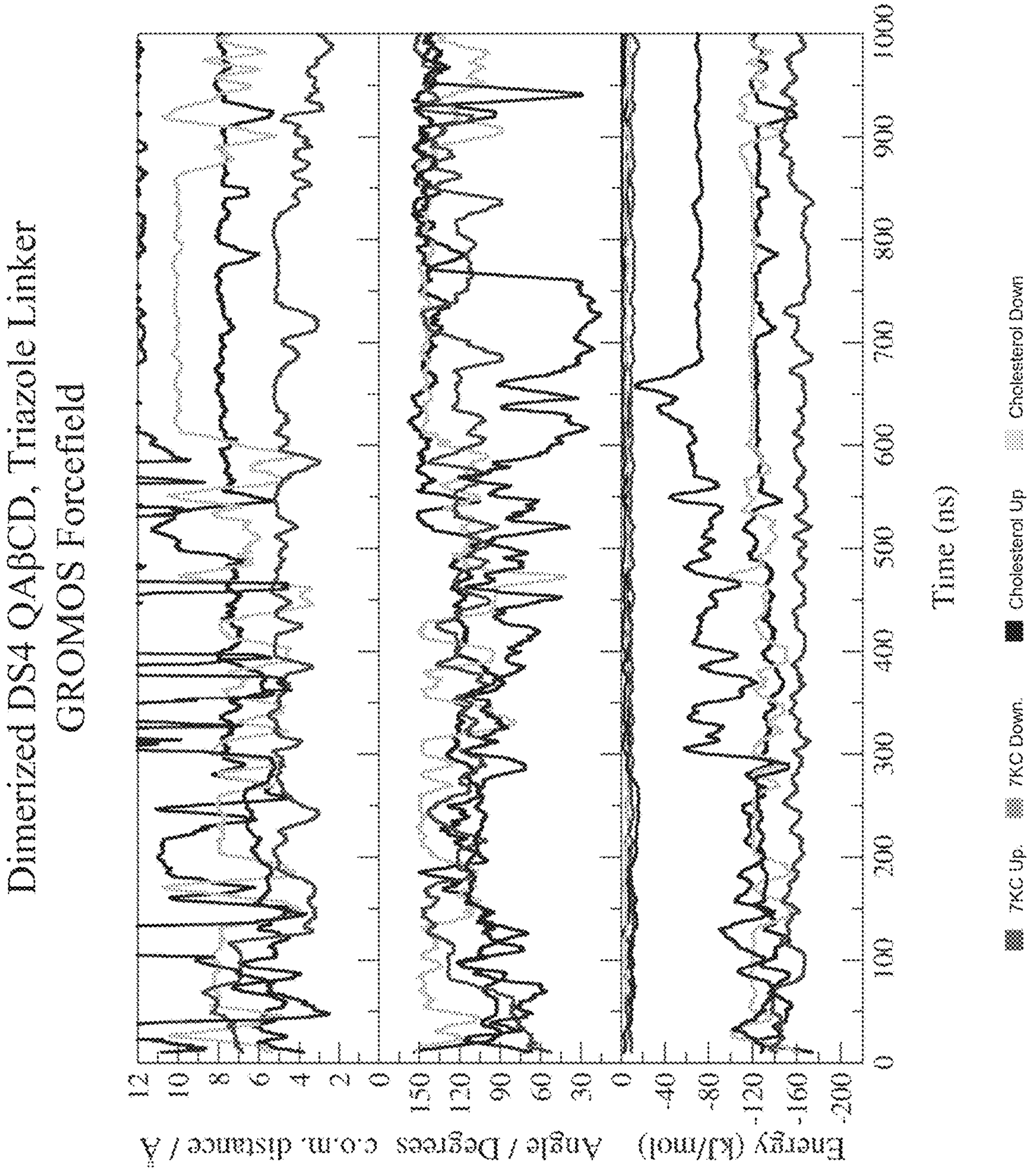
FIG. 4H depicts MD analysis of the distance between the center of mass of all O4 oxygens and the center of mass of the ligand; the angle between a vector perpendicular to the plane formed by the O4 atoms of CD and the main axis of the ligand; Lennard-Jones and Coulombic energy of interaction between the CD and the ligand for a triazole linked QAβCD DS4 dimer, up and down ligand orientations, in the GROMOS forcefield.

Based on these and other initial HPβCD simulations, it was concluded that the GROMOS forcefield in the ideal inclusion complex starting position (both orientations) produced the best and most dynamic results for these complexes. This long, initial analysis was important for establishing a precedent for modeling these novel molecules so that shorter, more targeted simulations could be conducted for other types of dimers. Thus, an extension of the molecular dynamics analysis was conducted with various types of linkers and substitutions which showed promise, including triazole and butyl-linked methyl βCD, sulfobutyl βCD, and quaternary ammonium βCD, all DS4 (FIGS. 4A-4H). Use of a triazole linker for the HPβCD dimer appeared to create less stable complexes, but these complexes were more specific for 7KC over cholesterol (FIG. 4B). The methyl dimers (FIGS. 4C-D) showed the most stable complexes with the butyl linker and appeared to favor the up orientation in both linker cases, however the interactions are quite similar for the two methyl dimers tested. It is difficult to distinguish which is more practically effective, but both types of linker easily form complexes with both ligands for methyl substitutions. The trajectory revealed that the headgroup of 7KC was not entirely within the cavity of the dimer but remained stably between the two sister monomers.

The negatively-charged sulfobutyl dimers (FIGS. 4E-4F) show a similar pattern to the methyl and hydroxypropyl dimers, where the triazole linker creates a slightly less stable complex which then allows for 7KC specificity. The charged, bulky sulfobutyl groups appear to interact quite favorably with both 7KC and cholesterol, but in both linker cases the only complex which breaks is that of cholesterol. This indicates that sulfobutyl dimers likely have very good specificity for 7KC as compared to methyl and hydroxypropyl.

To further explore the possibility of charged substitution groups, an MD analysis of DS4 positively-charged quaternary ammonium βCD (FIGS. 4G-4H) was conducted. QA dimers show similar properties to the SB dimers, with better 7KC specificity seen with the triazole linker but overall good complexation with both ligands. A particularly strong complex is formed between butyl-linked QAβCD and cholesterol in the down orientation, while triazole-linked QAβCD forms the most stable complex with 7KC in the down orientation.

Based on the predictive nature of these simulations, we have expanded this type of analysis to include the CD dimers described presently.

Figures 11A, 11B:
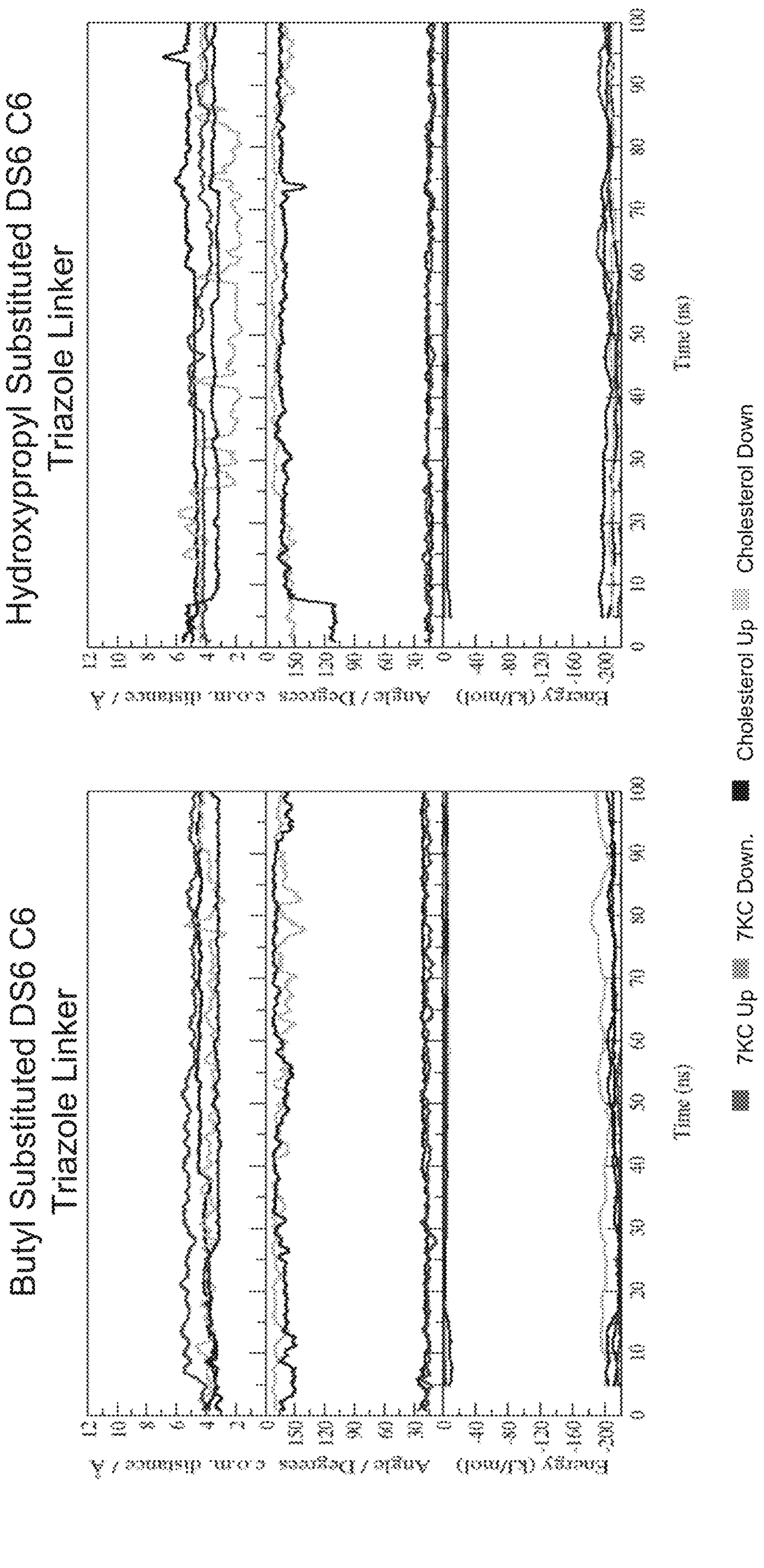
FIG. 11A depicts results from MD simulations of a triazole-linked βCD homodimer substituted with butyl moieties on the primary side DS6 complexed with 7KC or cholesterol in both orientations.
FIG. 11B depicts results from MD simulations of a triazole-linked βCD homodimer substituted with (2-hydroxypropyl) moieties on the primary side DS6 complexed with 7KC or cholesterol in both orientations.
Figure 13B:
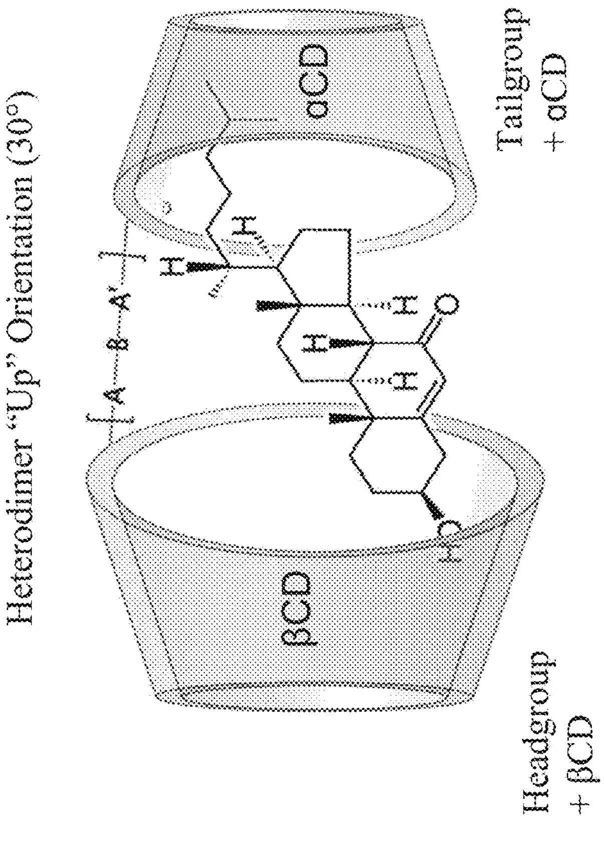
FIG. 13B depicts an “up” orientation for a complex of 7KC with a heterodimer CD.
Figure 13C:
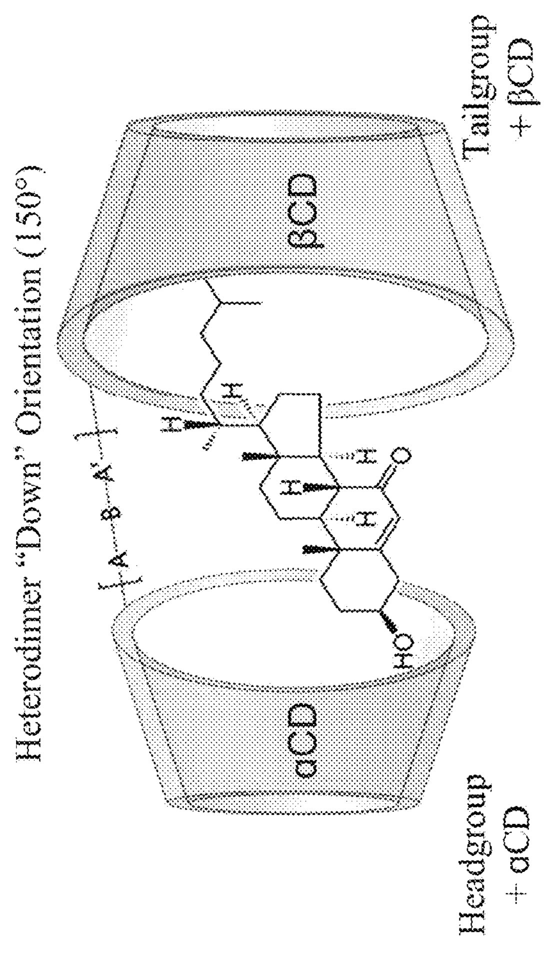
FIG. 13C depicts an “down” orientation for a complex of 7KC with a heterodimer CD.
Figure 13D:
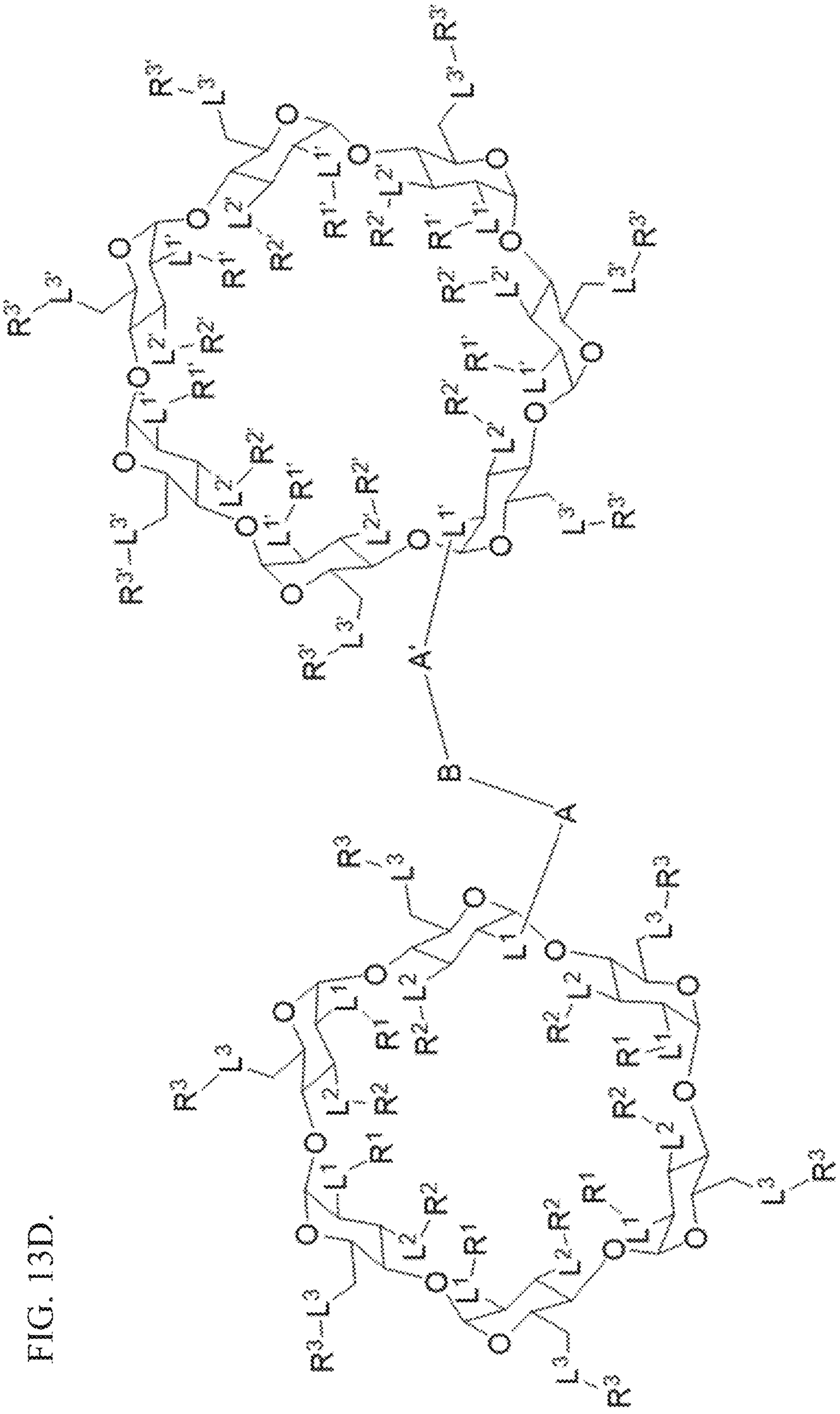
FIG. 13D depicts the chemical structure of a heterodimer consisting of an αCD and a βCD covalently bonded at the L1 and L1' positions on the secondary face of each CD with general linker A-B-A', wherein said A-B-A' are as defined herein.
Figure 13E:
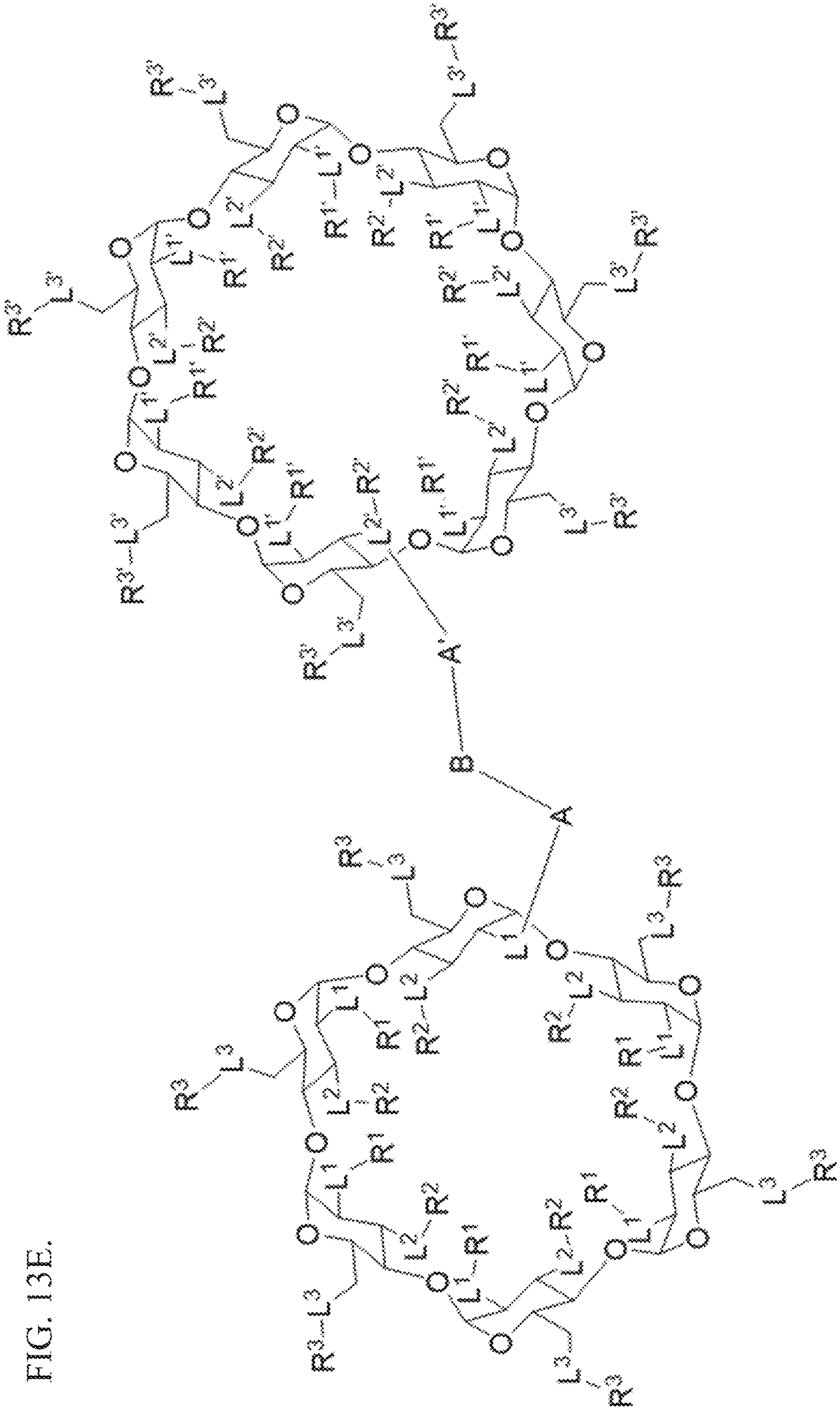
FIG. 13E depicts the chemical structure of a heterodimer consisting of an αCD and a βCD covalently bonded at the L1 and L2' positions on the secondary face of each CD with general linker A-B-A', wherein said A-B-A' are as defined herein.
Figure 13F:
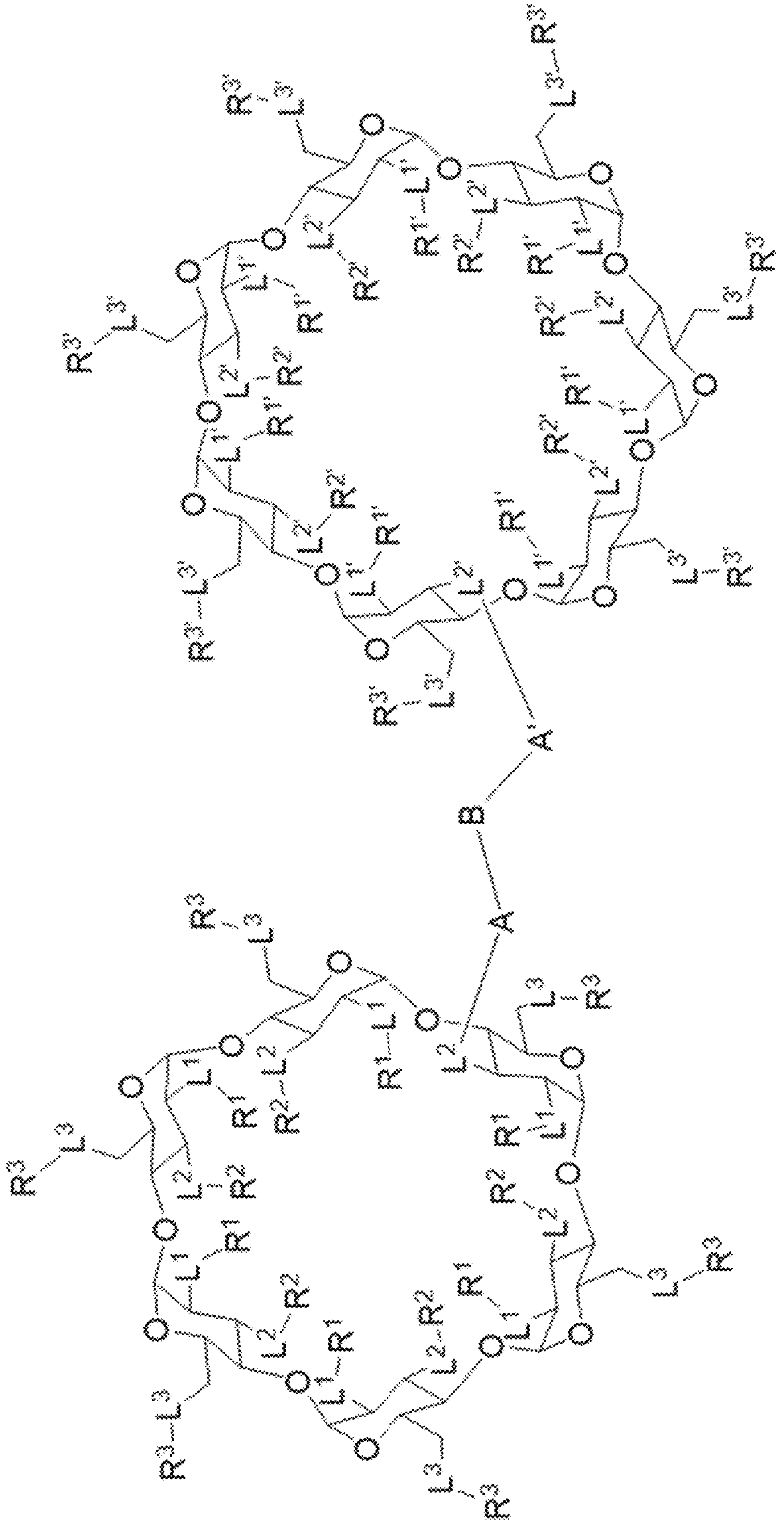
FIG. 13F depicts the chemical structure of a heterodimer consisting of an αCD and a βCD covalently bonded at the L2 and L2' positions on the secondary face of each CD with general linker A-B-A', wherein said A-B-A' are as defined herein.
Figure 13G:
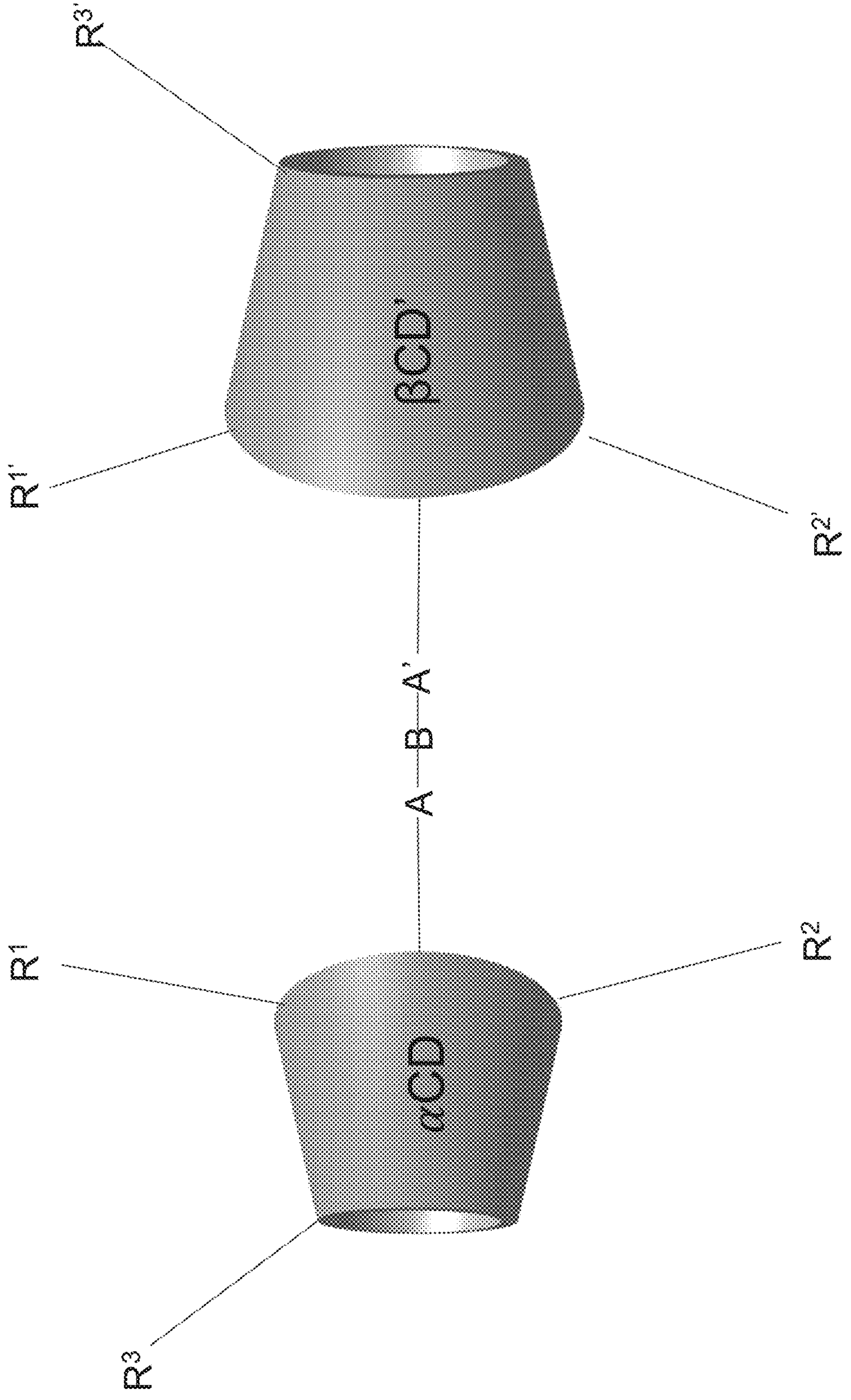
FIG. 13G depicts a schematic structure of an αCD-CD' heterodimer with a general linker denoted by A-B-A', wherein said A-B-A' are as defined herein. Both monomers are randomly substituted with the same functional group at the primary and secondary faces.
Figure 13H:
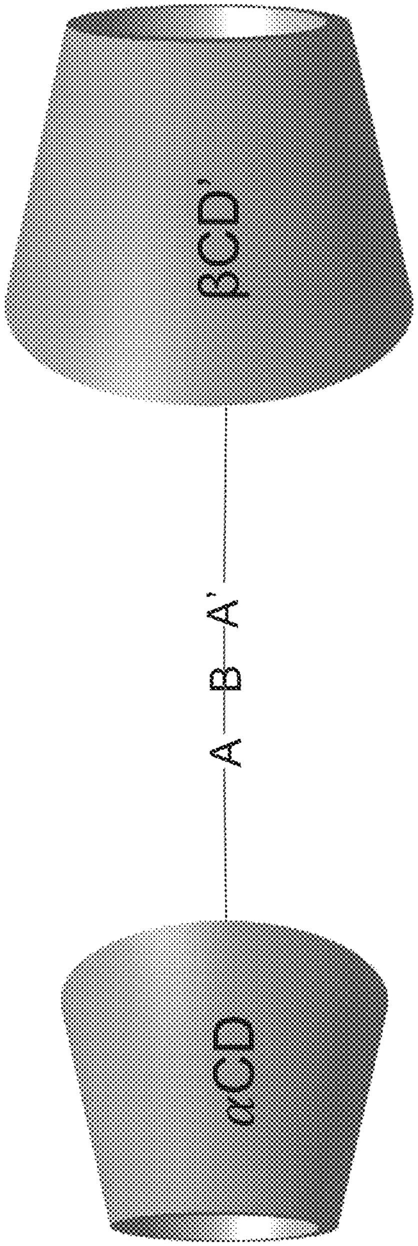
FIG. 13H depicts a schematic structure of a native αCD-native βCD triazole-linked heterodimer assessed in MD simulations.
Figure 13L:
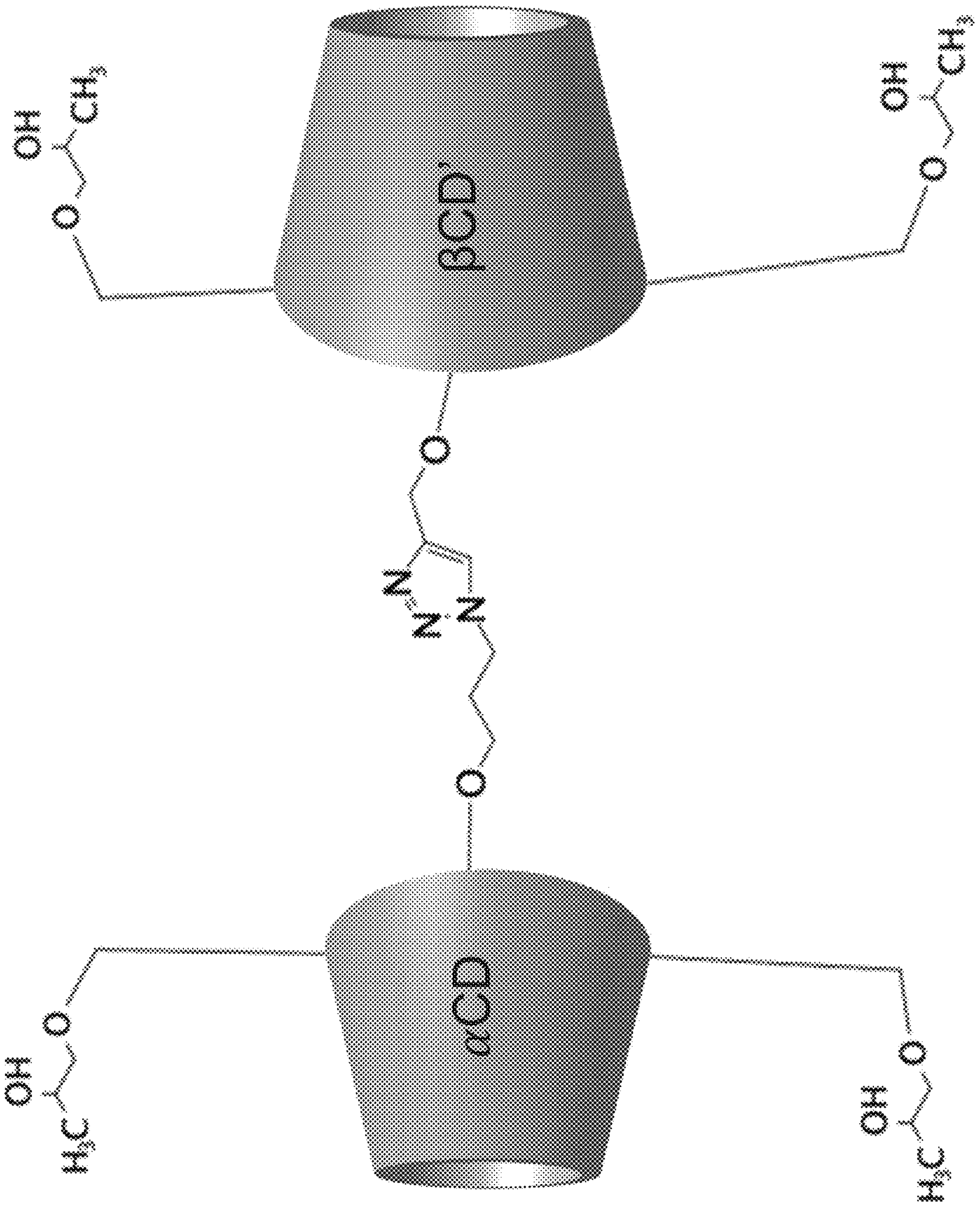
FIG. 13A depicts chemical structures of an αCD and a βCD, Structure B-Xa and Structure B-Xb, respectively, that are combined to form a heterodimer by covalently linking at the L1, L2, L1', and L2' positions of the CD secondary face.
FIG. 13J depicts a schematic structure of a SBDS2αCD-SBDS2βCD triazole linked heterodimer assessed in MD simulations.
Figure 13J:
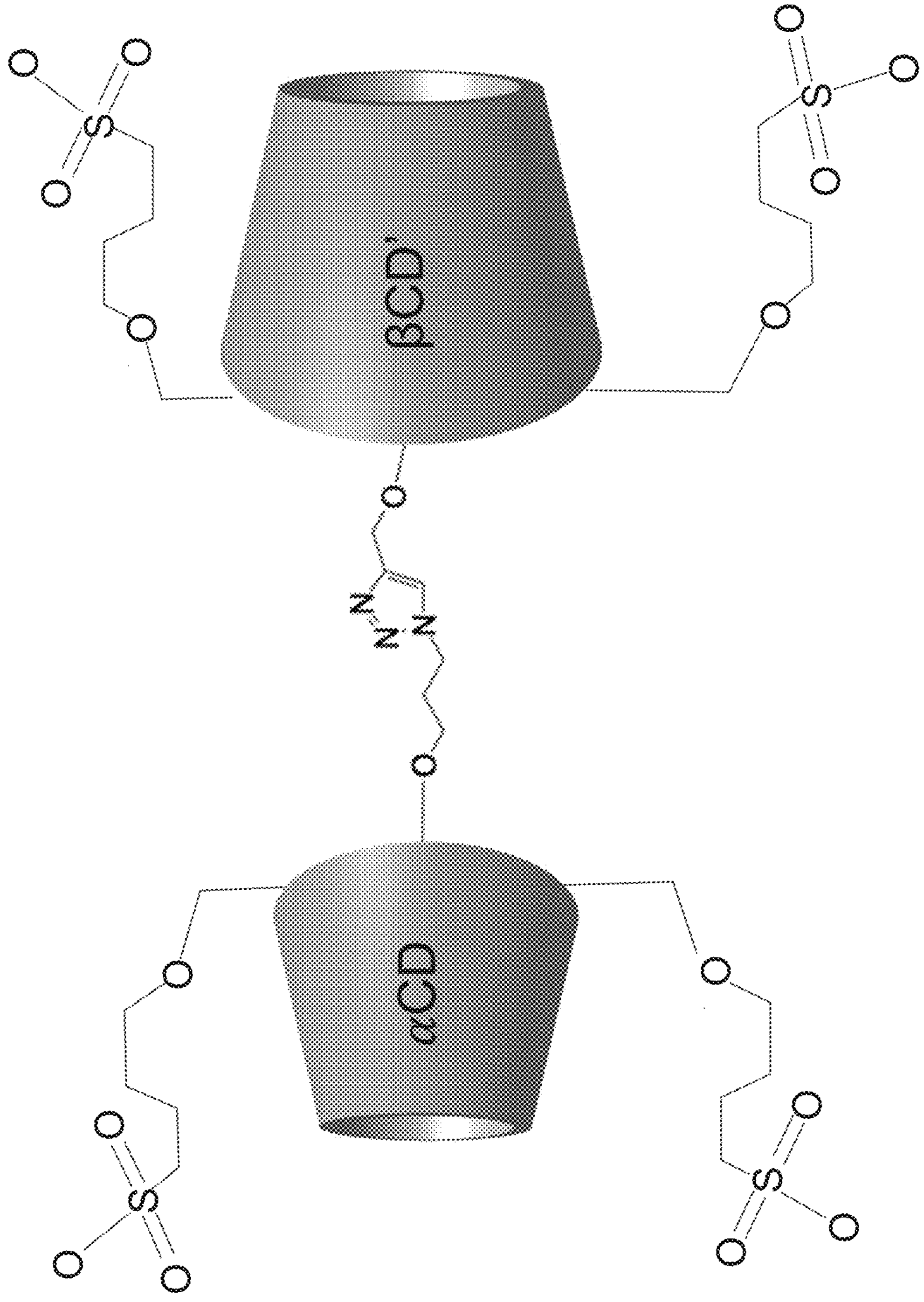

Example 2. MD Simulations of C6 Butyl-Substituted DS6 Triazole-Linked βCD Dimers Complexes with Sterols FIG. 11A shows trajectory results from MD simulations of a C6 butyl-substituted DS6 βCD dimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns. The sterols and their orientations are represented by the following colors: 7KC-up (red), 7KC-down (blue), cholesterol-up (black) and cholesterol-down (orange).

The data indicate that the dimer forms comparatively stable host-guest interactions with both 7KC and cholesterol regardless of an up or down orientation as there is little variance across each run of the simulation for a given complex, and shows that this dimer is an effective encapsulator of sterol-like molecules.

Example 3. MD Simulations of C6 2-hydroxypropyl DS6 Triazole-linked βCD Dimers Complexes with Sterols FIG. 11B shows trajectory results from MD simulations of a C6 2-hydroxypropyl DS6 βCD dimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns.

The data indicate that the dimer forms comparatively stable host-guest interactions with both 7KC and cholesterol regardless of an up or down orientation as there is little variance across each run of the simulation for a given complex, and shows that this dimer is an effective encapsulator of sterol-like molecules.

Methods for Molecular Dynamics

For a more comprehensive view of CD-sterol complexation and the role of dimerization for these molecules, we conducted various MD simulations using GROMACS software. These simulations also provide a clear view of the behavior of the water molecules around the structures as well as of the internal dynamics of the different molecular groups within the complex. Both issues were recently reported to be extremely specific in these types of structures. GROMOS parameters were obtained by combining our own topology for native CDs [J. Phys. Chem B, 118, 2014, 699958] with the parametrization for the different groups obtained from the ATB server and sequentially validated taking as a reference building blocks of known molecules as well as the intrinsic parameters of the force field. Two inclusion complex structures, named "up" and "down", were prepared for each force field and ligand, with opposite orientations of the sterol molecule inside the CD cavity, i.e. parallel and antiparallel to the symmetry axis of the CD aligned with their principal axes (FIG. 3A). The obtained structures were solvated with approximately 3000 water molecules. Upon minimization, the resulting systems were employed as initial structures for the MD simulations. Unrestrained production trajectories were generated for 100 ns using an integration time step of 2 fs. In all the simulations, the pressure and temperature were controlled at 1 bar and 298 K using an isotropic Parrinello-Rahman barostat [J. Appl. Phys. 52, 1981, 7182] and a V-rescale thermostat [J. Phys. Chem. 126, 2007, 014101], respectively. The LINCS algorithm [J. Comput. Chem. 18, 1997, 1463] was employed to remove the bond vibrations. The particle mesh Ewald method coupled to periodic boundary conditions with a direct space cutoff of 1.2 nm together with a grid-spacing of 0.15 nm in all cases, was used to treat the long-range electrostatics. The van der Waals interactions were computed using a spherical cutoff of 1.2 nm. The analysis of the simulations was performed using standard GROMACS tools and processed using Python scripts.

FIG. 3C indicates how the "angle" measurement is useful to determine how well shielded the ligand is from surrounding water molecules: zero or 180 degrees indicates that the ligand is perpendicular to the plane of the CD, and therefore the two molecules are most likely in a soluble complex while 90 degrees would indicate that the ligand is parallel to the CD plane and likely not complexed within the cavity. For our complexes, approximately 30 degrees corresponds to the complexed "up" orientation (head of sterol associated with the secondary face of CD, tail with primary, the entire ligand inserted into the cavity of CD) and about 150 degrees corresponds to the complexed "down" orientation (tail of sterol associated with the secondary face of CD, head with the primary face, the entire ligand inserted into the cavity of the CD).

Example 4. Solubilization of Compounds by βCD Monomers

Figure 5B:
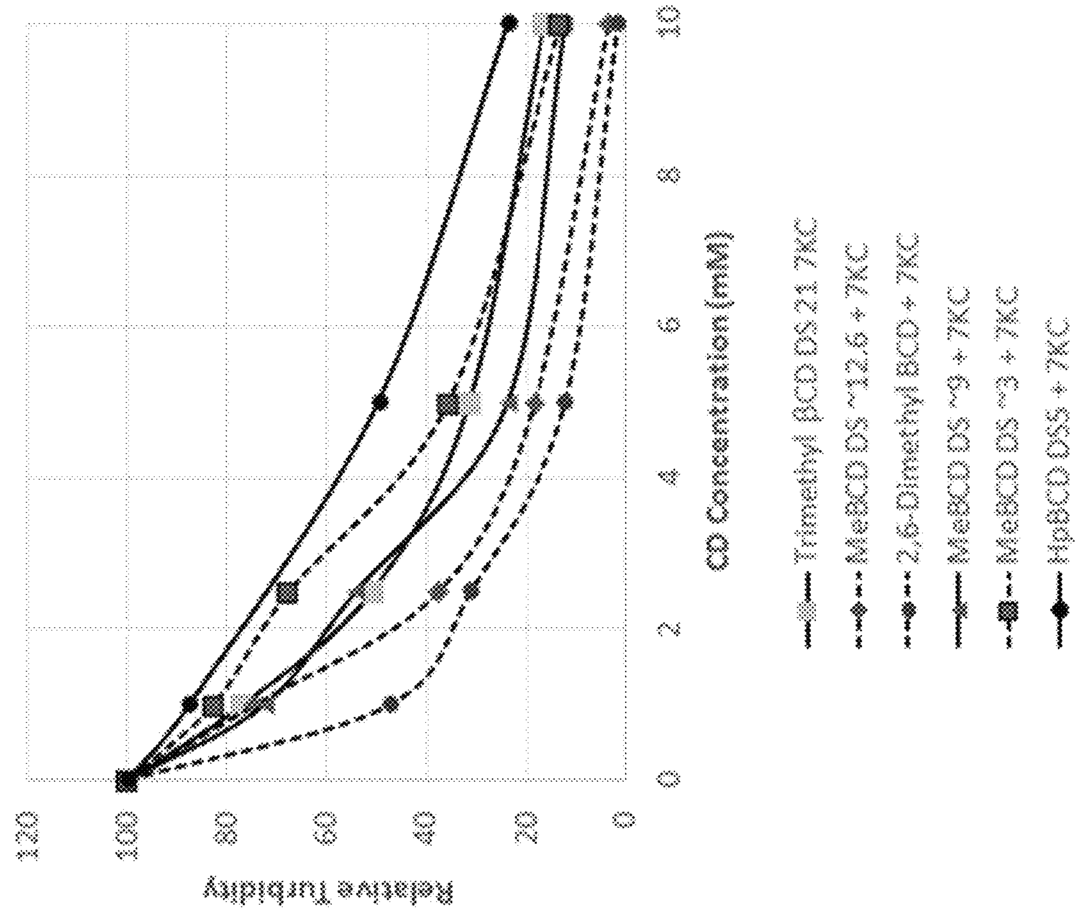
FIG. 5B. Solubilization of 7KC by HPβCD DS~5 and MEβCD monomers of various DS.
Figure 5A:
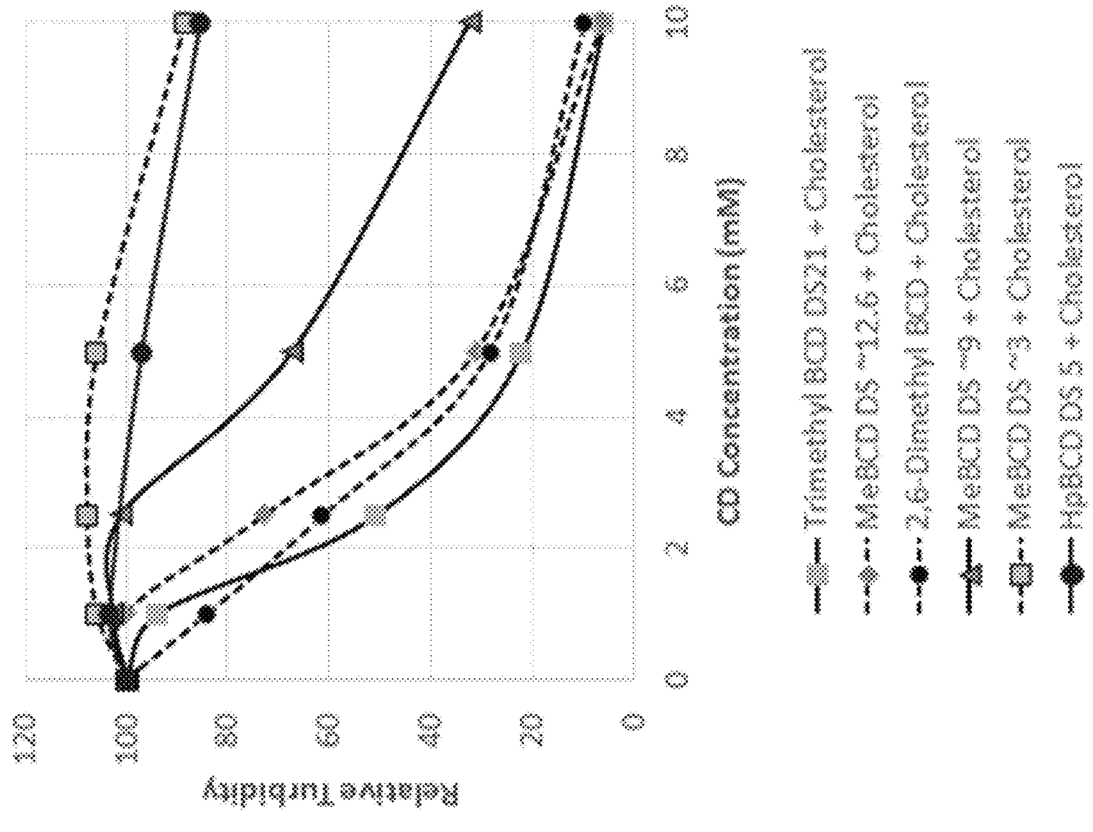
FIG. 5A. Solubilization of cholesterol by HP and Me βCD monomers of various DS.
Figure 5C:
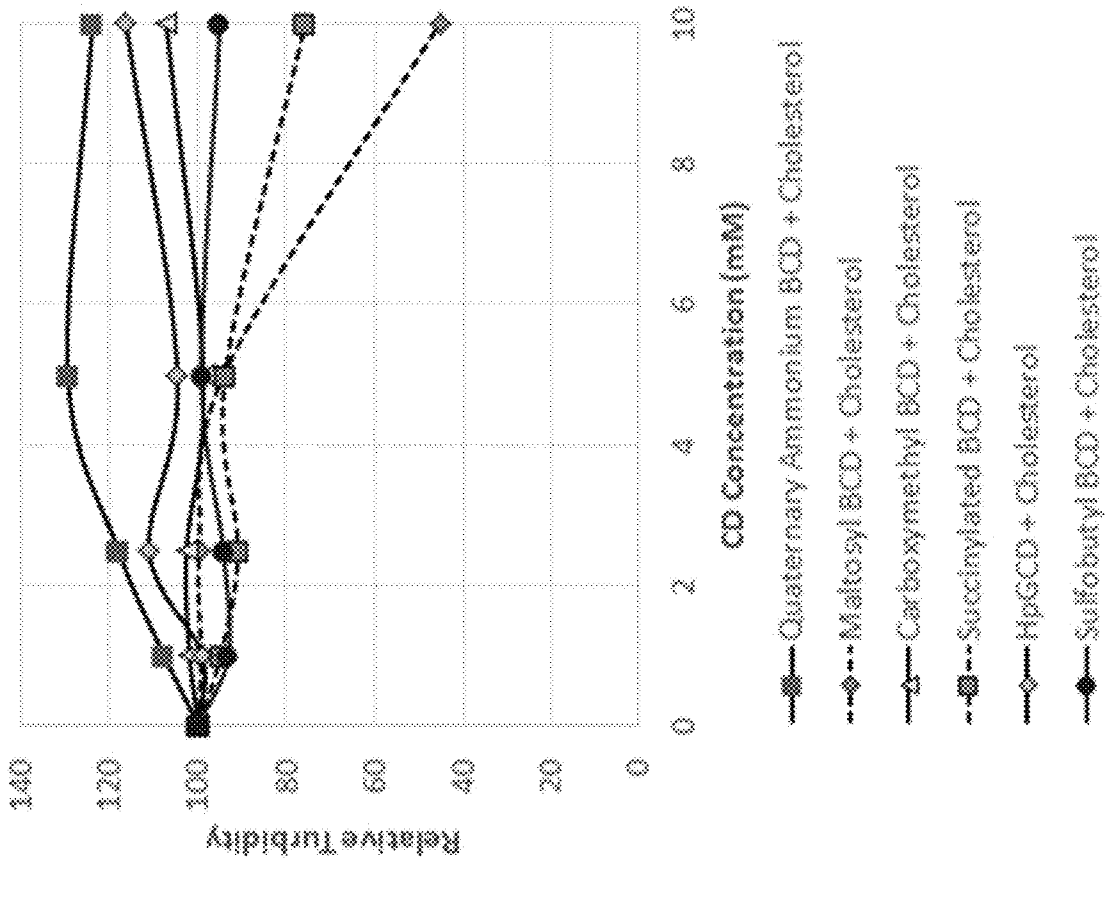
FIG. 5C. Solubilization of cholesterol by QA, maltosyl, carboxymethyl, succinylated, SB βCD and HP γCD monomers of various DS.
Figure 5D:
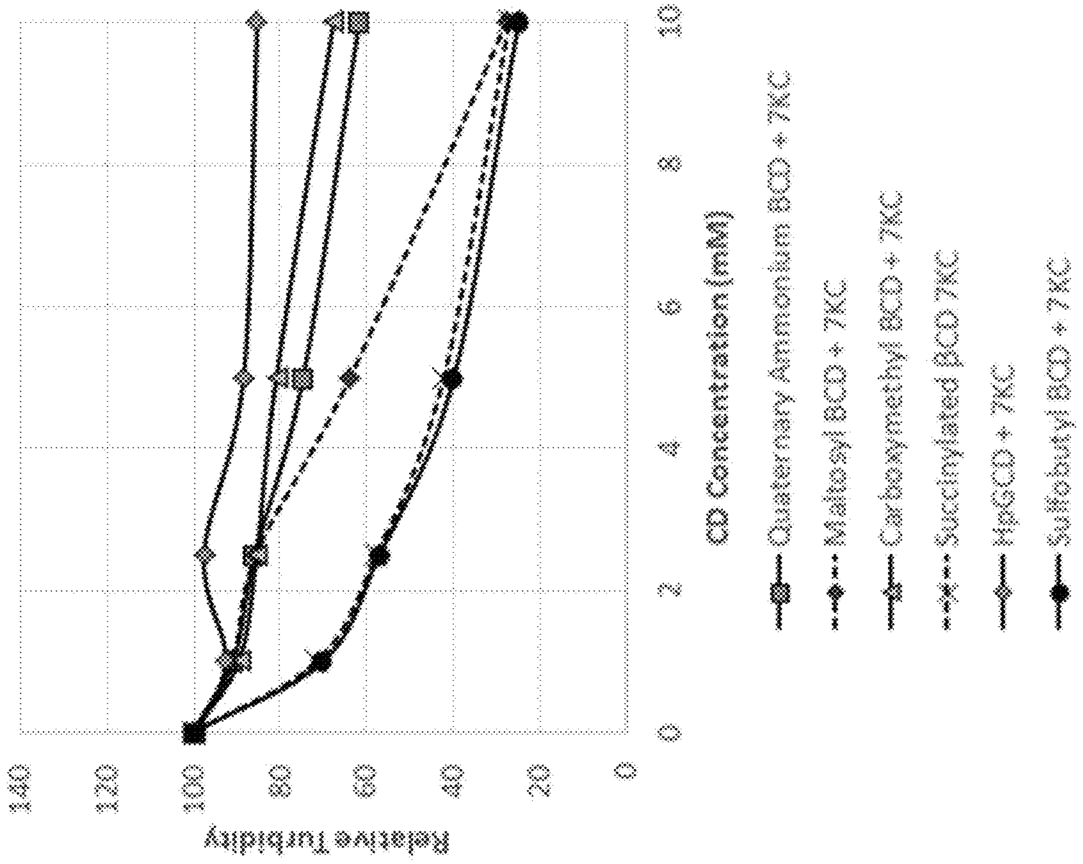
FIG. 5D. Solubilization of 7KC by QA maltosyl, carboxymethyl, succinylated, SB βCD and HPγCD monomers of various DS. In some instances in the figures βCD is labeled BCD and γCD is labeled GCD.

Example 4 is a demonstration of the ability of various substituted βCD monomers to solubilize cholesterol and 7KC (FIGS. 5A-5D). Lower turbidity indicates greater ability to solubilize a given sterol. The ability to solubilize 7KC and cholesterol decreased with greater degrees of substitution (FIGS. 5A-5B). Lower DS HPβCDs showed a preference for solubilizing 7KC over cholesterol suggesting that they have specificity for 7KC. Without intent to be limited by theory, a potential explanation is the availability of the maximum number of hydroxyl groups for hydrogen bonding with the keto group at the 7 position on 7KC, however, this theory is not required in order to practice the invention.

Example 5. Synthesis of HPβCD Substituted CD Dimers

Figure 7A:
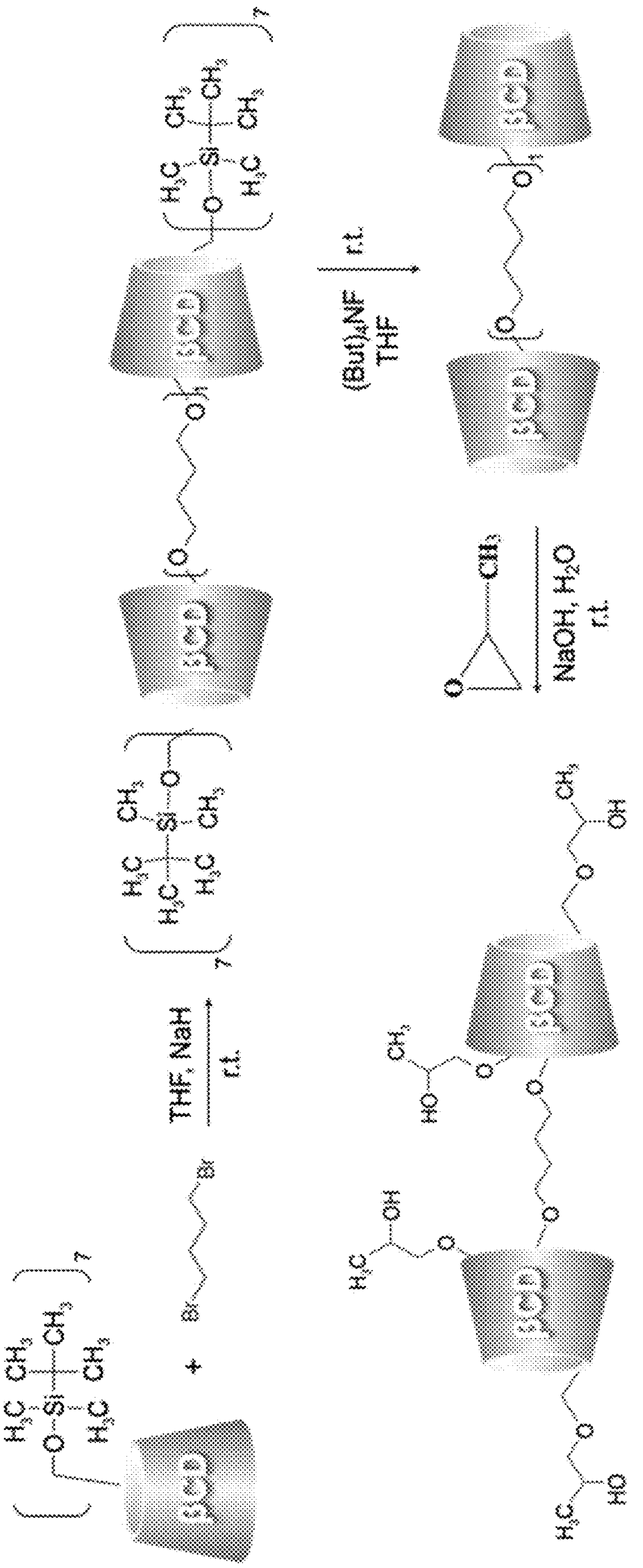
FIG. 7A. Synthetic strategy for hydroxypropylated-dimer connected with one linker unit based on 1,4-dibromobutane (resulting in a butyl linked HPβCD dimer HP-(CD-BUTYL-CD)).
Figure 7B:
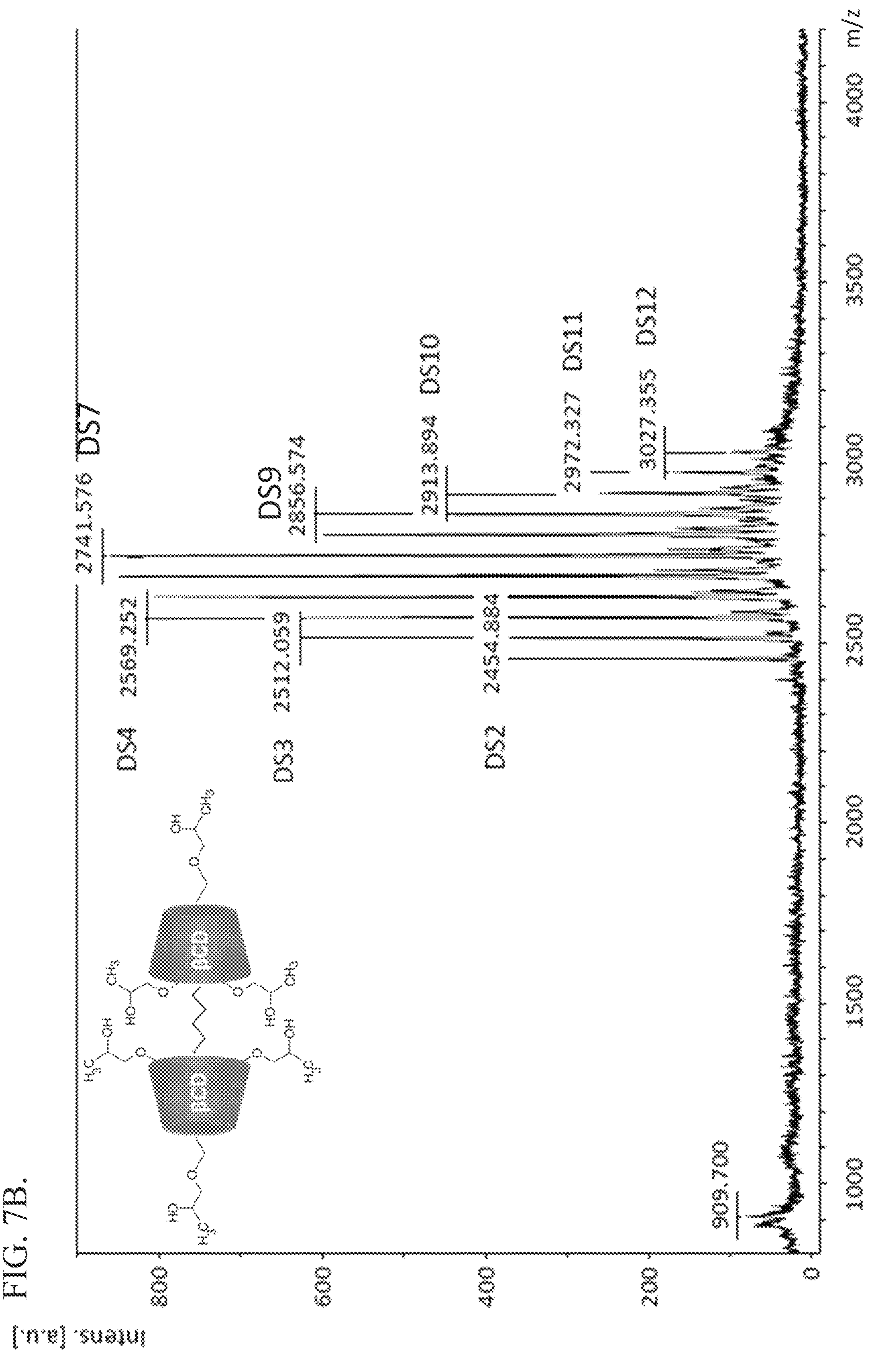
FIG. 7B. MALDI spectrum for HP-(CD-BUTYL-CD) dimer.
Figure 7C:
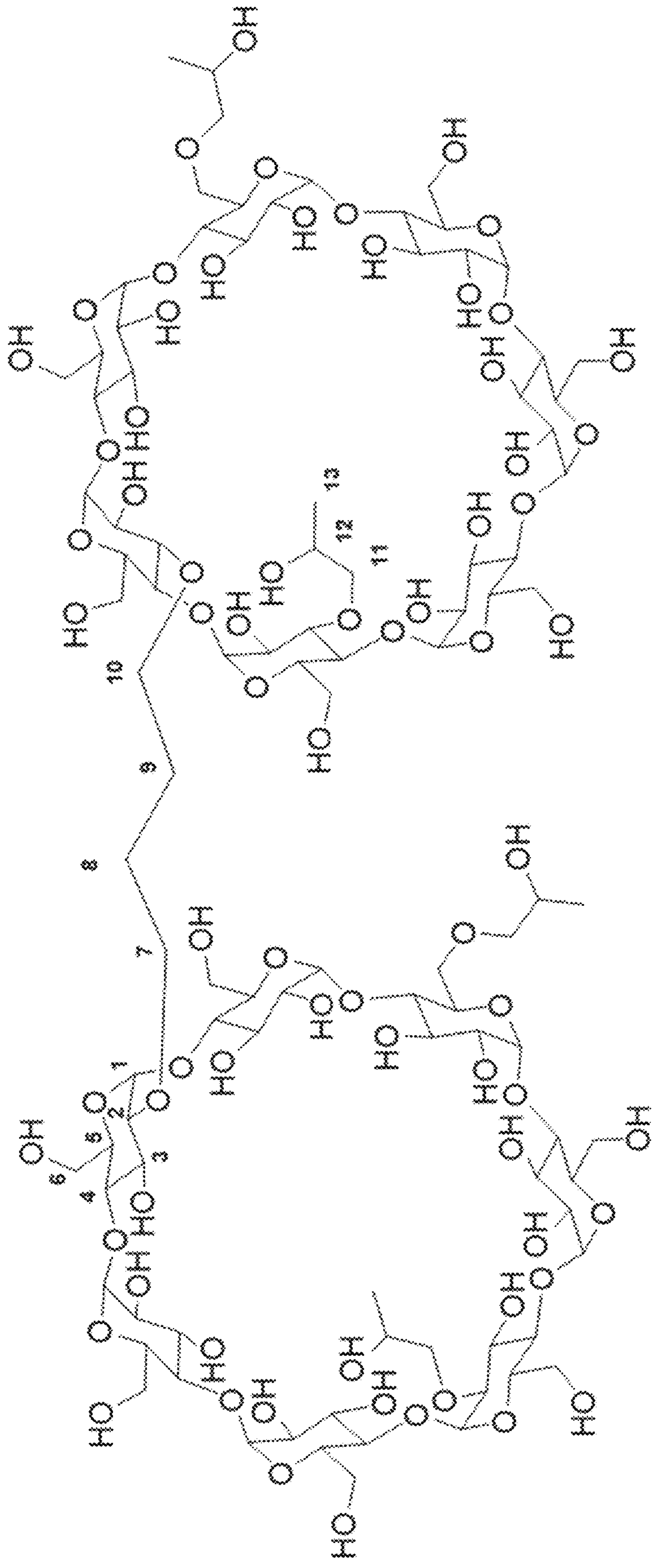
FIG. 7C. Structure of one possible isomer of HP-(CD-BUTYL-CD) dimer with atom numbering.
Figure 7D:
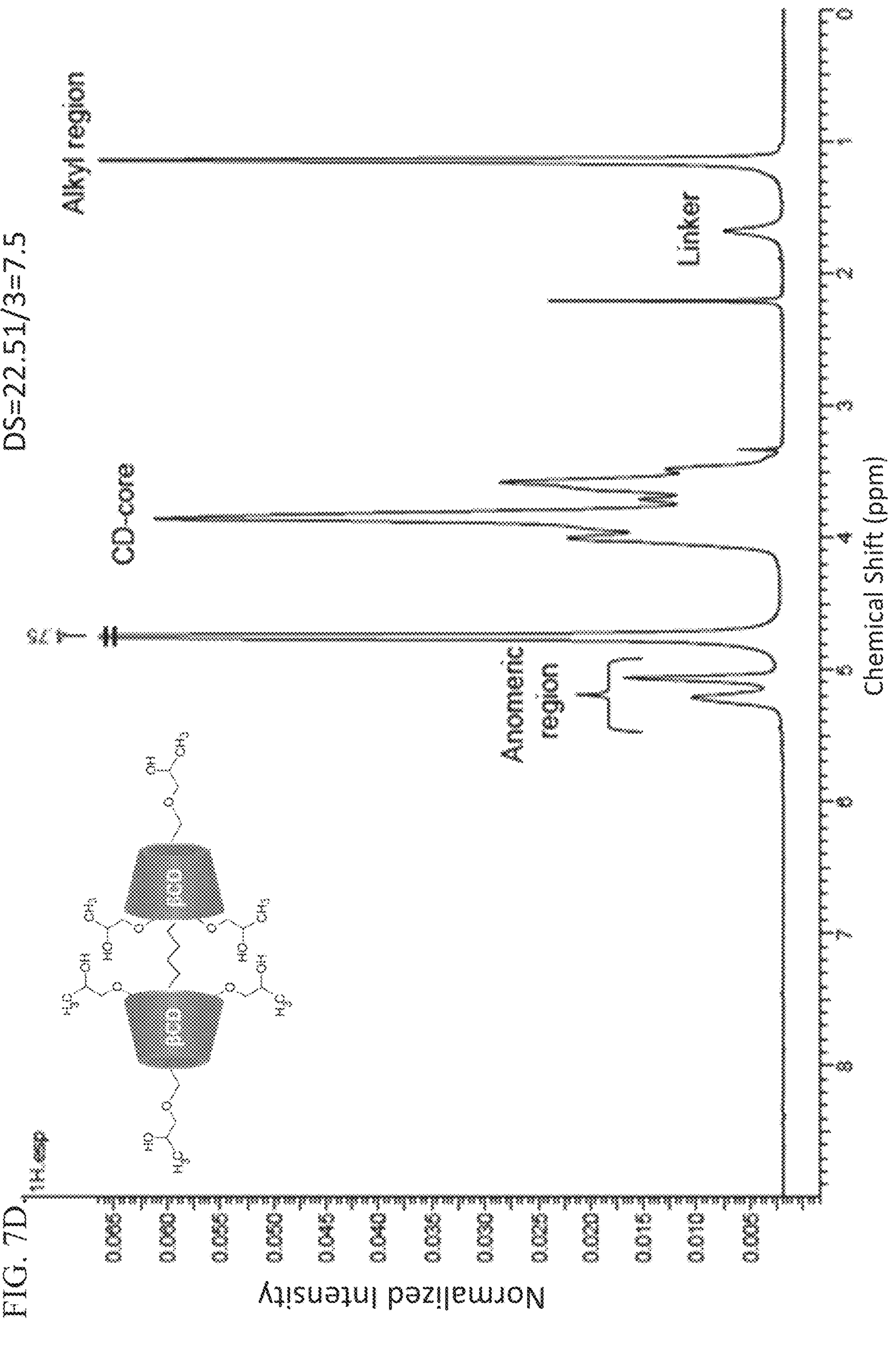
FIG. 7D. $^1$H-NMR spectrum of HP(βCD-BUT-βCD) ($D_2O$, 298 K) with signals labeled and DS calculation.
Figure 7E:
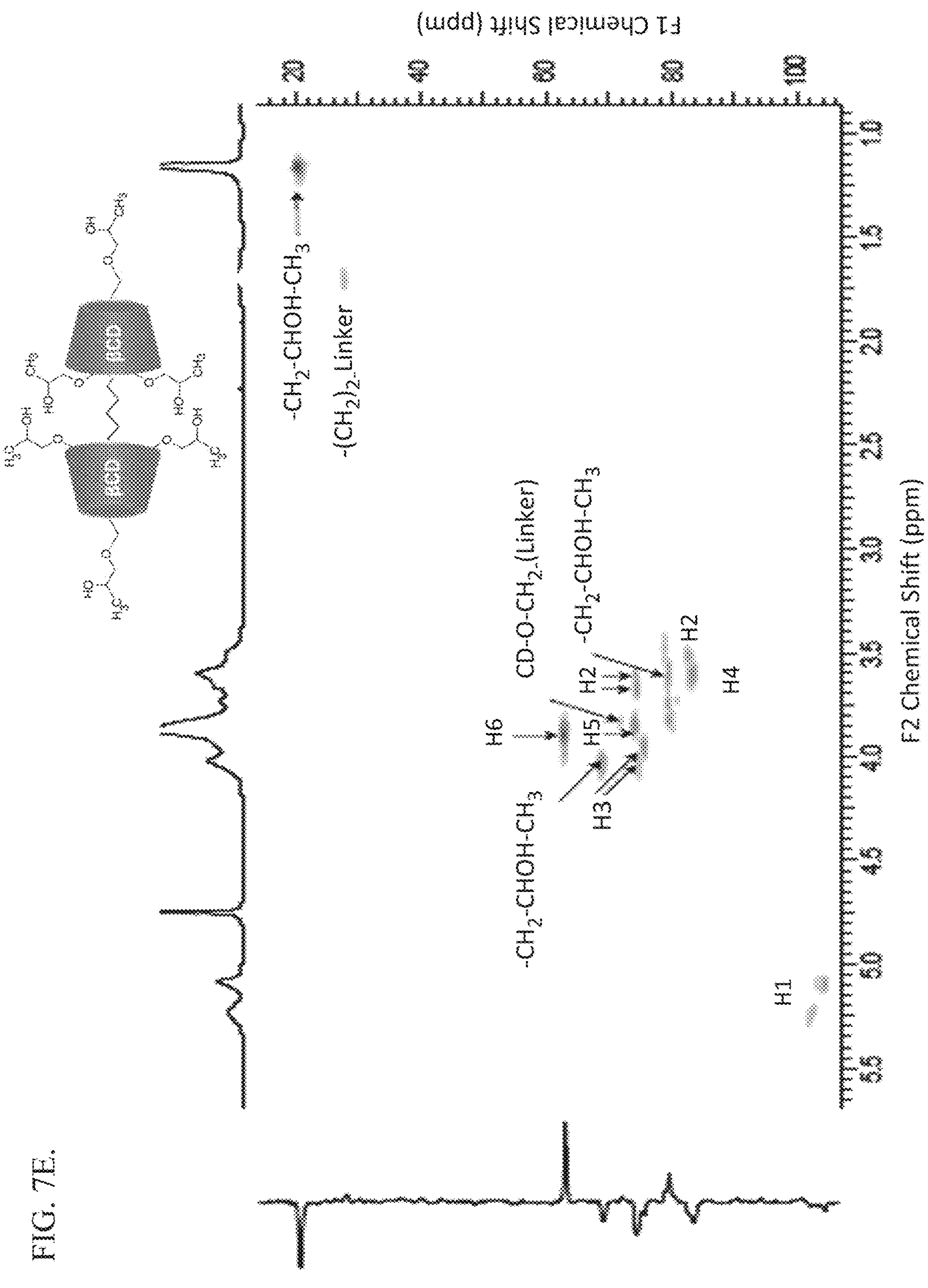
FIG. 7E. DEPT-edited HSQC spectrum of HP(βCD-BUT-βCD) with full assignment ($D_2O$, 298 K). Converted to black and white.
Figure 7F:
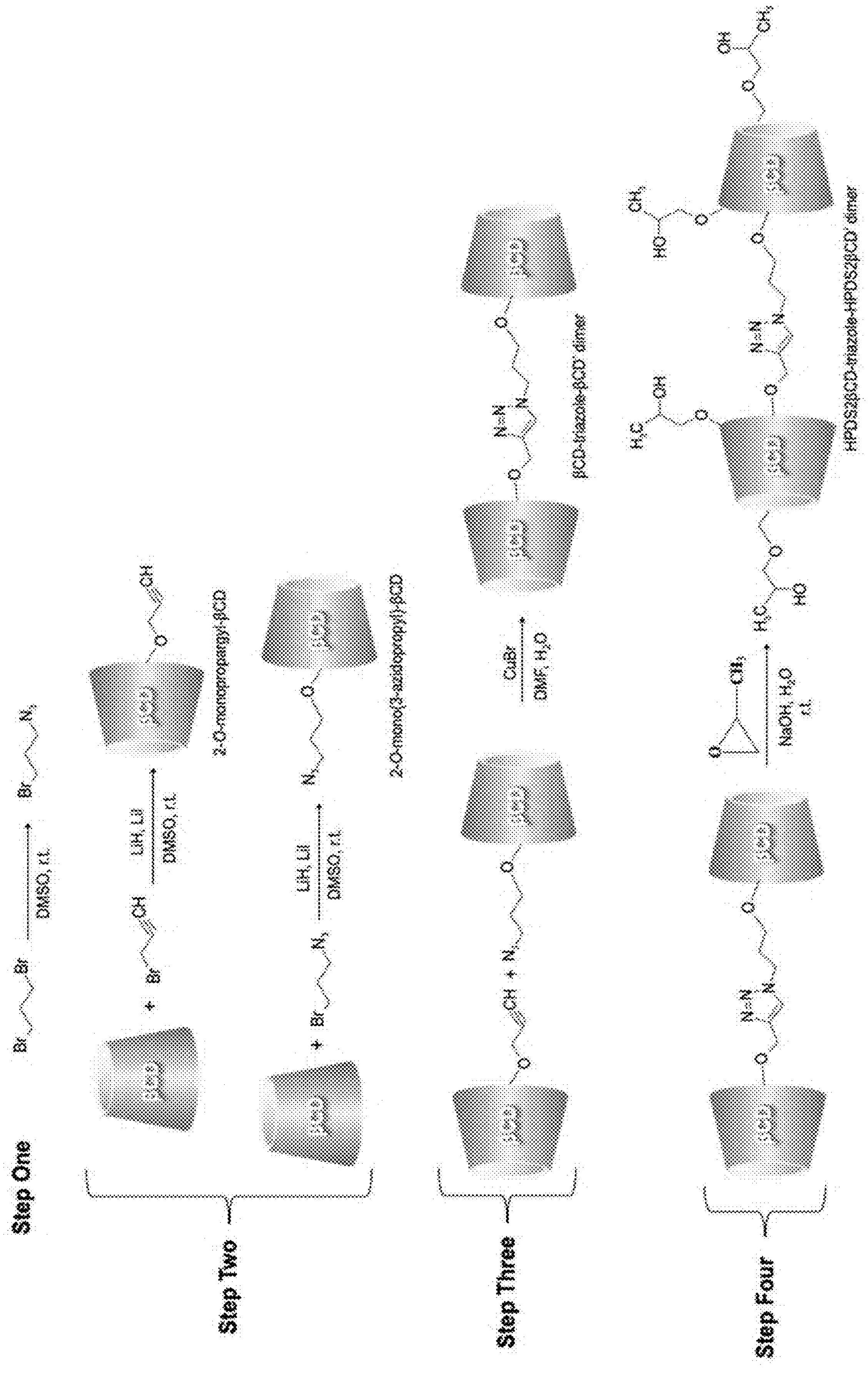
FIG. 7F. Synthetic strategy for 2-hydroxypropylated dimers connected with one linker unit based on 3-azido-1-bromo-propane (resulting in a triazole linked HPβCD dimer HP-(βCD-TRIAZOLE-βCD)).
Figure 7G:
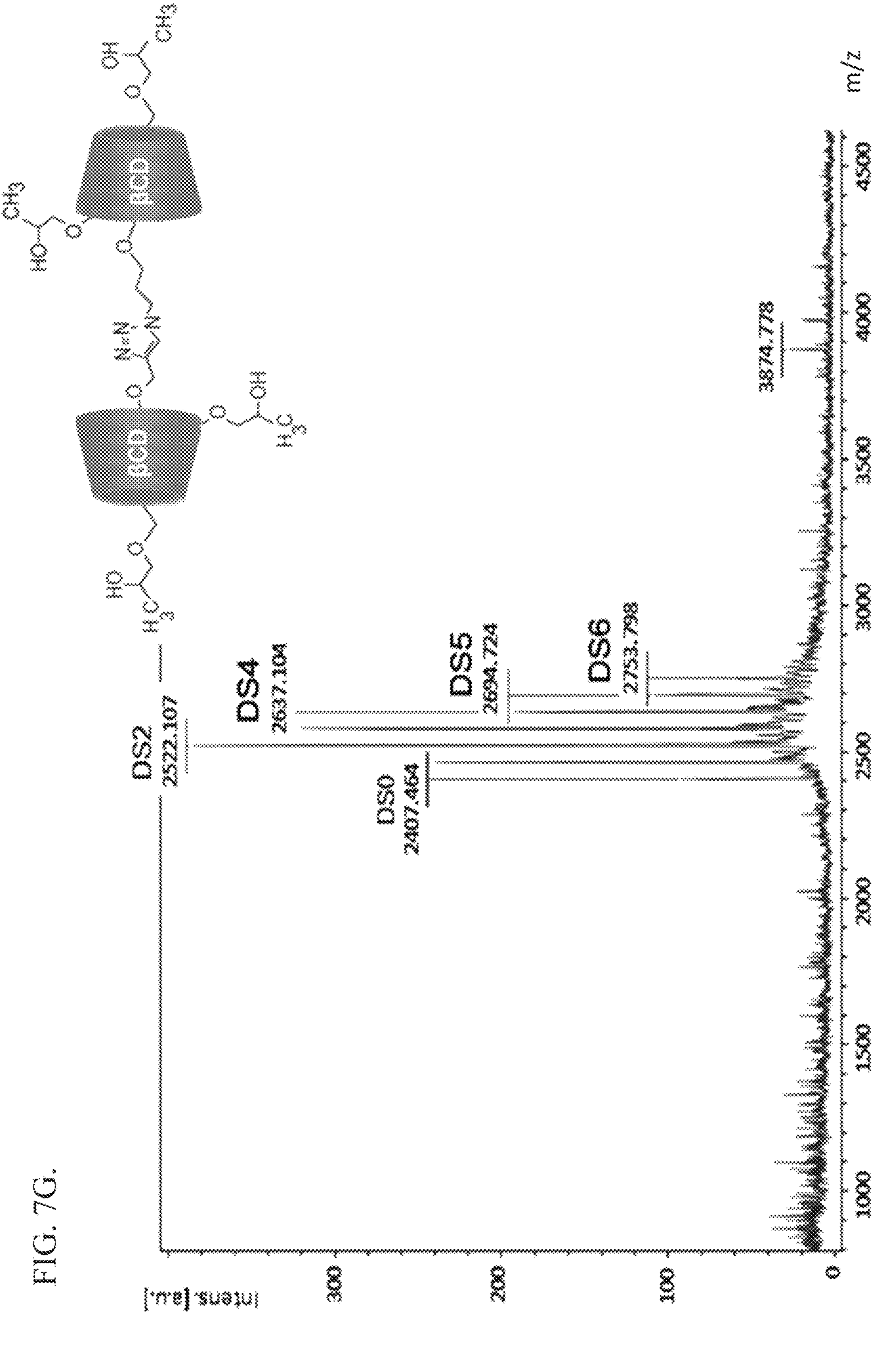
FIG. 7G. MALDI spectrum for HP-(CD-TRIAZOLE-βCD) dimer.
Figure 7H:
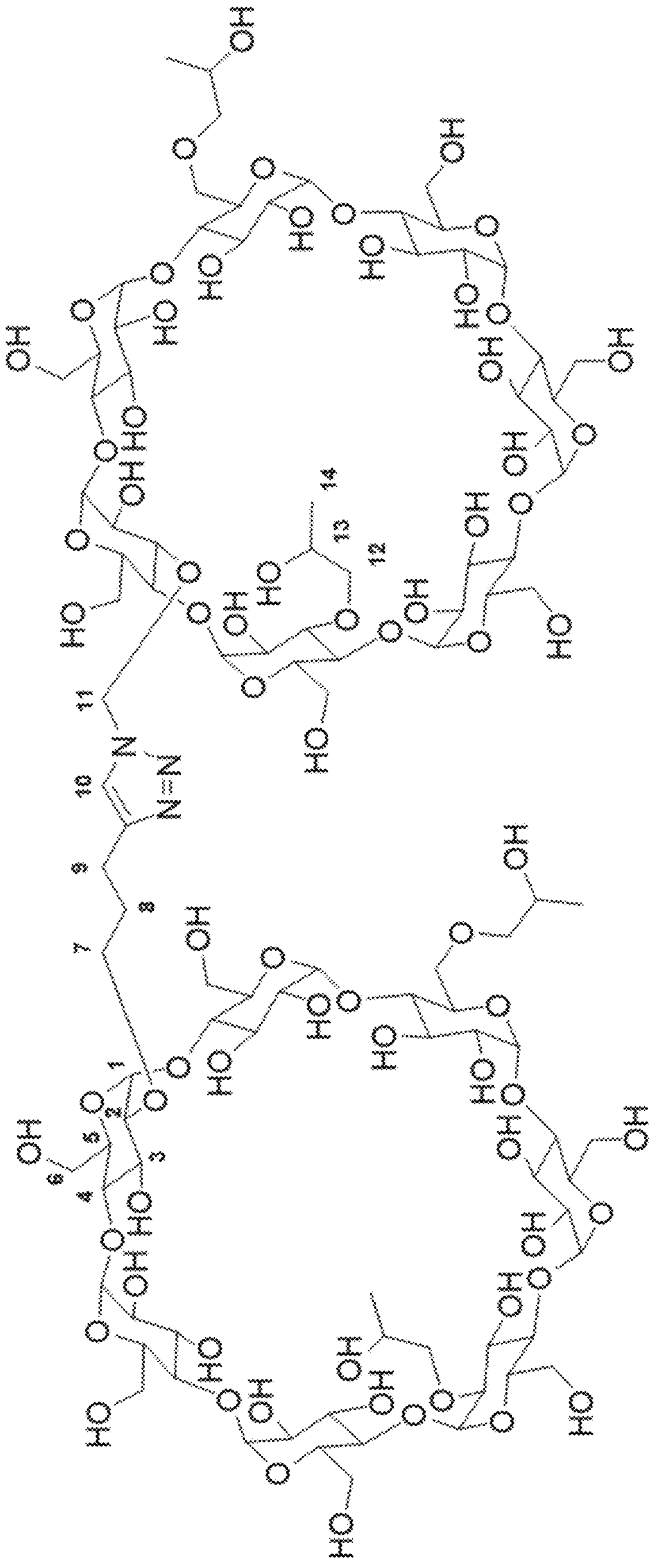
FIG. 7H. Structure of one possible isomer of HP-(CD-TRIAZOLE-βCD) dimer with atom numbering.

FIGS. 7C and 7H illustrate certain molecules to be synthesized in the current example.

This example describes the synthesis of substituted CD dimers, first linked by a butyl linker and then a triazole-containing linker.

For DS measurement, 1H and 2D NMR spectra are recorded on Varian VXR-600 at 600 MHz, using residual solvent signal as an internal reference. The sample is dissolved in DMSO-$d_6$/$D_2O$ for the structure elucidation. The FID signals are recorded with at least 16 scans so as to obtain a spectral window comprised, at least, between 0 ppm and +10 ppm. The calculation of the average DS can be accomplished by setting to fourteen the integral of the anomeric region (fourteen being the number of the anomeric protons for a beta-CD dimer) and by dividing by three the integral of the alkyl region (see FIG. 7D).

General Description of Synthesis and Characterization Hp(βCd-Butyl-βCd) Homodimer The synthesis of HPβCD butyl-linked dimers was accomplished through a three-step synthesis (see FIG. 7A). The starting material is monomeric β-CD protected on the primary side with tert-butyldimethylsilyl groups (TBDMS-βCD, CycloLab, Budapest, Hungary).

The secondary face dimerization was achieved by using TBDMS-βCD, anhydrous conditions, and sodium hydride as base. The dialkylating agent was added dropwise to the heterogeneous reaction mixture and exhaustively reacted at room temperature.

The primary side protected βCD dimer (TBDMS-βCD-BUTYL-βCD-TBDMS) was purified by chromatography with isocratic elution (chloroform:methanol:water=50:8:0.8

(v/v/v) as eluent). The MALDI and NMR analysis of the compound confirmed the identity of the product.

The desilylation (deprotection) was performed in THE with tetrabutylammonium fluoride at room temperature. The βCD dimer (CD-BUTYL-βCD) was purified by chromatography with isocratic elution (1,4-dioxane:25% $NH_{3(aq)}$=10:7 (v/v) as eluent). The MALDI and TLC analysis of the compound confirmed the identity of the product.

The hydroxypropylation of the βCD dimer was achieved in aqueous conditions by using sodium hydroxide as base at room temperature. The purification of the hydroxypropylated βCD dimer (HP(βCD-BUTYL-βCD)) dimer was based on ion exchange resins treatment, charcoal clarification and extensive dialysis. The MALDI and NMR analyses of the compound confirmed the identity and the structure of the product (FIGS. 7B, 7D, and 7E). Edited HSQC is an HSQC in which one can distinguish CH2 correlations (which wee visualize as blue cross-peaks, as in the C6 signals of the cydodextrin unit) from CH3 (methyl)/CH (methine) correlations (which we visualize as red cross-peaks, as in C1, C2, C3, C4 and C5 of the cyclodextrin unit, or, alternatively, for example, methyl groups in the case of methyl-substituted CDs), because they are oppositely phased. Though these colors may not be distinguishable in a black and white reproduction, the analysis of the original color HSQC figures showed the expected features including red and blue cross-peaks.

Hp(αCd-Butyl-αCd) Homodimer

The synthesis of butyl-linked HPαCD dimers is accomplished through a three-step synthesis (see FIG. 12A). The starting material is monomeric αCD protected on the primary side with tert-butyldimethylsilyl groups (TBDMS-αCD, CycloLab, Budapest, Hungary).

The secondary face dimerization was achieved by using TBDMS-αCD, anhydrous conditions, and sodium hydride as base. The dialkylating agent is added dropwise to the heterogeneous reaction mixture and exhaustively reacted at room temperature.

The primary side protected αCD dimer (TBDMS-αCD-BUTYL-αCD-TBDMS) is purified by chromatography with isocratic elution (chloroform:methanol:water=50:8:0.8 (v/v/v) as eluent).

The desilylation (deprotection) is performed in THE with tetrabutylammonium fluoride at room temperature. The αCD dimer (αCD-BUTYL-αCD) is purified by chromatography with isocratic elution (1,4-dioxane:25% NH3 aq=10:7 (v/v) as eluent).

The hydroxypropylation of the αCD-BUTYL-αCD dimer is achieved in aqueous conditions by using sodium hydroxide as base at room temperature. The purification of the hydroxypropylated αCD dimer, HP(αCD-BUTYL-αCD) is based on ion exchange resins treatment, charcoal clarification and extensive dialysis.

Hp(βCd-Triazole-βCd) Homodimer

The synthesis of hydroxypropylated n-CD dimers connected through the secondary face with one triazole moiety is performed in a four-part procedure (FIG. 7F). The first part is the preparation of the azido-linker (3-azido-1-bromopropane) as this reagent is not commercially available. The second part is the construction of the two βCD monomers, 2-O-monopropargyl-β-CD and 2-O-mono(3-azidopropyl)-βCD, respectively. The third synthetic step is the build-up of the βCD-TRIAZOLE-βCD dimer core by copper-assisted azide-alkyne cycloaddition, and the final part is the preparation of a series of 2-hydroxypropylated triazole-linked dimer according to the classical alkylation approach.

In particular, the preparation of the azido-linker can be achieved by strictly limiting the amount of sodium azide and by elongating the addition time of the limiting reagent. The azido-linker is characterized by NMR spectroscopy and TLC.

The syntheses of the two monomers are accomplished by using lithium hydride as a base for the selective deprotonation of the secondary hydroxyl groups. In particular, according to this approach only the hydroxyl groups located on C2 are mostly reacted. As a consequence, monomers prepared by this method are preferentially substituted on the O2 (they are single isomers). The two monomers are characterized by NMR spectroscopy, MALDI and TLC.

The preparation of the dimer core is then achieved by reacting the two monomers in aqueous DMF with copper bromide as catalyst. The resulting compound, a single isomer, (BCD-TRIAZOLE-BCD DS=0) is characterized by NMR spectroscopy and MALDI.

Figure 7I:
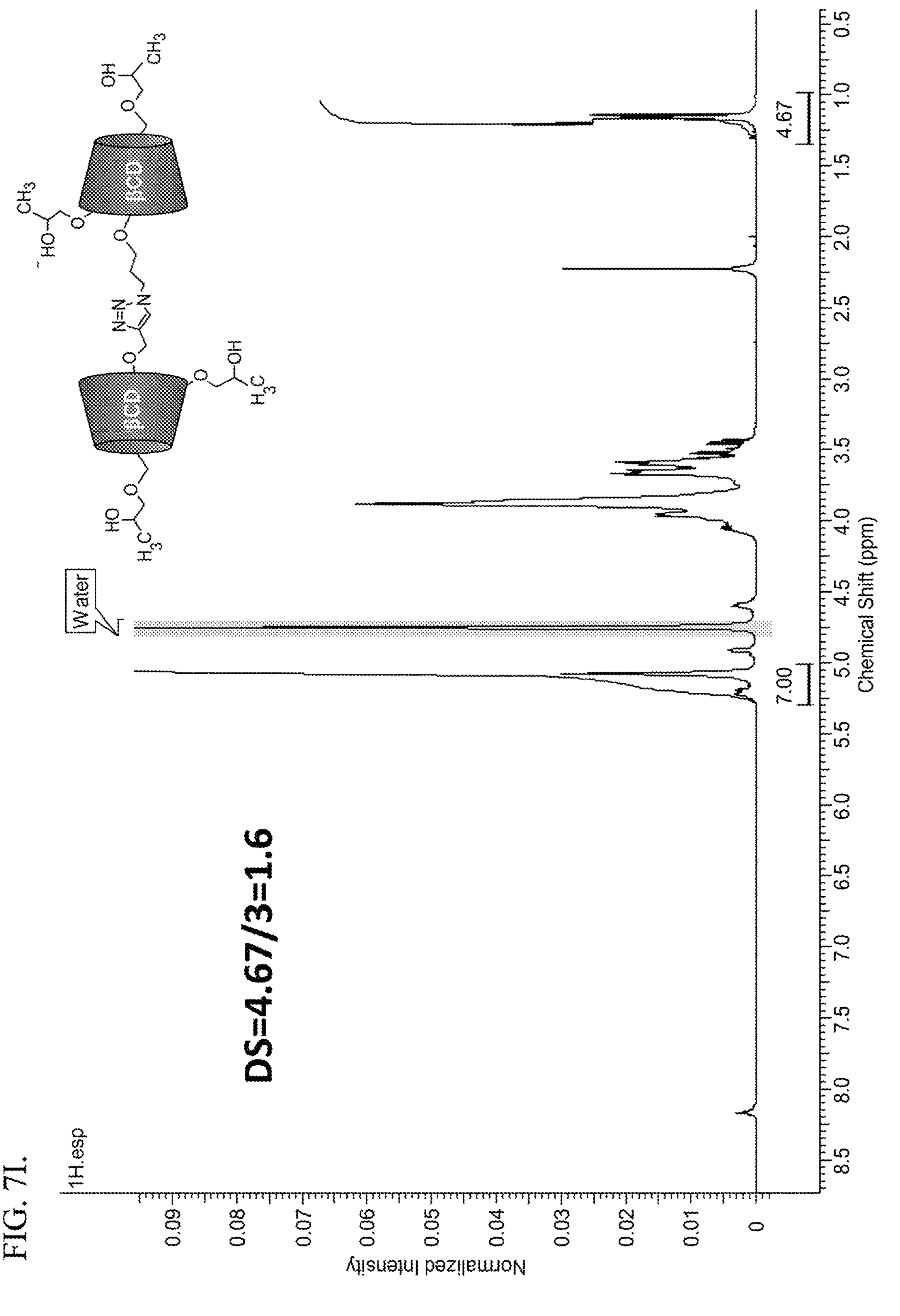
FIG. 7I. $^1$H-NMR spectrum of HP(βCD-TRIAZOLE-βCD) ($D_2O$, 298K) with DS calculation.
Figure 7J:
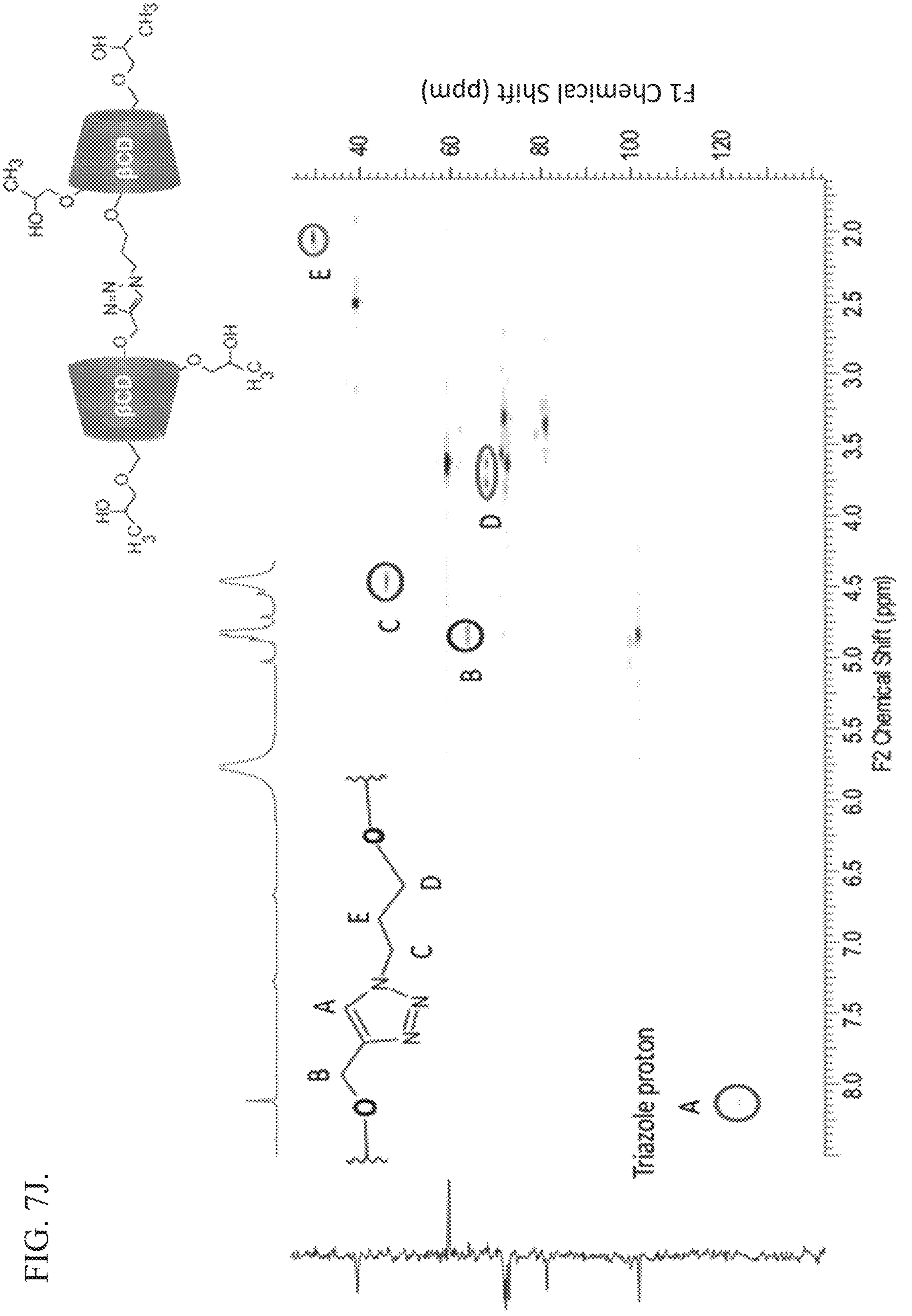
FIG. 7J. DEPT-edited HSQC spectrum of HP(βCD-TRIAZOLE-βCD) with linker assignment ($D_2O$, 298 K). Converted to black and white.

Hydroxypropylation of BCD-TRIAZOLE-BCD was accomplished using propylene oxide and alkaline aqueous conditions. The series of hydroxypropylated compounds was characterized by NMR spectroscopy (FIG. 7I-7J), and MALDI (FIG. 7G).

HpβCd-Triazole-βCd (Random Substituted) Asymmetric Dimer

The synthesis of the 2-hydroxypropylated βCD asymmetric dimers randomly substituted and connected through the secondary face with one triazole moiety is performed in a three-part procedure (FIG. 20A-20F). The first part is the preparation of the azido-linker (3-azido-1-bromo-propane) as this reagent is not commercially available. The second part is the construction of the two βCD monomers, the 2-O-mono(3-azidopropyl)-βCD and the asymmetric monomer randomly substituted, (2-hydroxypropylated)-2-O-monopropargyl-βCD, respectively. The third synthetic part is the build-up of the final dimer by copper-assisted azide-alkyne cycloaddition. For the preparation of an asymmetric dimer it is mandatory to customize the asymmetric monomers before the cycloaddition as the "asymmetry" in the final dimer can be only introduced at this stage of the development.

In particular, the preparation of the azido-linker can be achieved by strictly limiting the amount of sodium azide and by elongating the addition time of the limiting reagent. The azido-linker is characterized by NMR spectroscopy and TLC.

The syntheses of the monomers are accomplished by using lithium hydride as a base for the selective deprotonation of the secondary side. In particular, according to this approach the hydroxyl groups located on C2 are mostly reacted. As a consequence, monomers prepared by this method are dominantly substituted on the O2. 2-O-Mono (3-azidopropyl)-βCD is prepared according to the aforementioned method in one step and it is obtained as single isomer. In order to introduce "asymmetry" in the second monomer, 2-O-monopropargyl-βCD is 2-hydroxypropylated by using propylene oxide and alkaline aqueous conditions. The two monomers are characterized by NMR spectroscopy, MALDI and TLC.

The preparation of the asymmetric dimer is then achieved by reacting the two monomers in aqueous DMF with copper bromide as catalyst. The resulting compound, HPβCD'-TRIAZOLE-βCD DS3 (random substituted) asymmetric dimer, will be characterized by NMR spectroscopy and MALDI.

C6HpβCd-Triazole-βCd Ds3 Asymmetric Dimer

The synthesis of the C6-primary-side (2-hydroxypropylated)-βCD asymmetric dimers DS3, connected through the secondary face with one triazole moiety, is performed in a three-part procedure (FIGS. 20B-F). The first part is the preparation of the azido-linker (3-azido-1-bromo-propane) and the protected 2-hydroxypropylating agent as these reagents are not commercially available (FIG. 20C).

The second part is the construction of the two βCD monomers, the 2-O-mono(3-azidopropyl)-βCD and the asymmetric monomer tris-6-O-(2-O-hydroxypropyl)-2-O-monopropargyl-βCD, respectively (FIGS. 20D-E).

The third synthetic part is the build-up of the final dimer by copper-assisted azide-alkyne cycloaddition (FIG. 20F).

For the preparation of an asymmetric dimer it is mandatory to customize the asymmetric monomers before the cycloaddition as the "asymmetry" in the final dimer can be only introduce at this stage of the development.

In particular, the preparation of the azido-linker can be achieved by strictly limiting the amount of sodium azide and by elongating the addition time of the limiting reagent. The azido-linker is characterized by NMR spectroscopy and TLC. The synthesis of the protected 2-hydroxypropylating agent (1-bromo-2-benzyloxy-propane) is achieved in two-step. Propylene oxide is reacted in acidic conditions with benzyl alcohol as solvent resulting in 2-benzyloxy-1-propanol; the obtained alcohol is then converted to the bromo-analogue with potassium bromide in acetonitrile under acidic conditions.

The syntheses of the monomers are accomplished by using lithium hydride as a base for the selective deprotonation of the secondary side. In particular, according to this approach the hydroxyl groups located on C2 are mostly reacted. As a consequence, monomers prepared by this method are dominantly substituted on the O2. 2-O-Mono (3-azidopropyl)-βCD is prepared according to the aforementioned method in one step and it is obtained as single isomer. In order to introduce "asymmetry" exclusively on the primary-side of the second monomer, 2-O-monopropargyl-βCD is modified according to a multiple-step synthetic procedure (FIG. 20C). 2-O-Monopropargyl-βCD is selectively protected on the primary-side with tert-butyldimethylsilyl moieties and subsequently modified exhaustively on the secondary-side with benzyl bromide under phase-transfer catalysis (PTC) conditions thus generating the asymmetrically protected monomer, per-6-O-tert-butyldimethylsilyl-per-2,3-O-benzyl-2-O-monopropargyl-βCD. Selective removal of the tert-butyldimethylsilyl moieties is easily achieved with tetrabutylammonium fluoride in THF. The key-intermediate, per-2,3-O-benzyl-2-O-monopropargyl-βCD, is reacted with the protected 2-hydroxypropylating agent (1-bromo-2-benzyloxy-propane) under PTC conditions. The desired DS3 is achieved by strictly limiting the amount of base (KOH). Finally, exhaustive deprotection of the benzyl groups by hydrazine-mediated transfer-hydrogenation yields the asymmetric monomer, tris-6-O-(2-O-hydroxypropyl)-2-O-monopropargyl-βCD. The two monomers are characterized by NMR spectroscopy, MALDI and TLC.

The preparation of the asymmetric dimer is then achieved by reacting the two monomers in aqueous DMF with copper bromide as catalyst. The resulting compound, C6HPβCD'-triazole-βCD DS3 asymmetric dimer, is characterized by NMR spectroscopy and MALDI.

C6HPβCD-TRIAZOLE-βCD DS7 Asymmetric Dimer

The synthesis of the fully substituted C6-primary-side (2-hydroxypropylated)-βCD asymmetric dimers DS7, connected through the secondary face with one triazole moiety, is performed in a three-part procedure (FIGS. 21A-D). The first part is the preparation of the azido-linker (3-azido-1-bromo-propane) and the protected version of the 2-hydroxypropylating agent as these reagents are not commercially available (FIG. 21A).

The second part is the construction of the two βCD monomers, the 2-O-mono(3-azidopropyl)-βCD and the asymmetric monomer per-6-O-(2-O-hydroxypropyl)-2-O-monopropargyl-βCD, respectively (FIG. 21B-C).

The third synthetic part is the build-up of the final dimer by copper-assisted azide-alkyne cycloaddition (FIG. 21D).

For the preparation of an asymmetric dimer it is mandatory to customize the asymmetric monomers before the cycloaddition as the "asymmetry" in the final dimer can be only introduce at this stage of the development.

In particular, the preparation of the azido-linker can be achieved by strictly limiting the amount of sodium azide and by elongating the addition time of the limiting reagent. The azido-linker is characterized by NMR spectroscopy and TLC. The synthesis of the protected 2-hydroxypropylating agent (1-bromo-2-benzyloxy-propane) is achieved in two-step. Propylene oxide is reacted in acidic conditions with benzyl alcohol as solvent resulting in 2-benzyloxy-1-propanol; the obtained alcohol is then converted to the bromo-analogue with potassium bromide in acetonitrile under acidic conditions.

The syntheses of the monomers are accomplished by using lithium hydride as a base for the selective deprotonation of the secondary side. In particular, according to this approach the hydroxyl groups located on C2 are mostly reacted. As a consequence, monomers prepared by this method are dominantly substituted on the O2. 2-O-Mono (3-azidopropyl)-βCD is prepared according to the aforementioned method in one step and it is obtained as single isomer. In order to introduce "asymmetry" exclusively on the primary-side of the second monomer, 2-O-monopropargyl-βCD is modified according to a multiple-step synthetic procedure (FIG. 21B). 2-O-Monopropargyl-βCD is selectively protected on the primary-side with tert-butyldimethylsilyl moieties and subsequently modified exhaustively on the secondary-side with benzyl bromide under phase-transfer catalysis (PTC) conditions thus generating the asymmetrically protected monomer, per-6-O-tert-butyldimethylsilyl-per-2,3-O-benzyl-2-O-monopropargyl-βCD. Selective removal of the tert-butyldimethylsilyl moieties is easily achieved with tetrabutylammonium fluoride in THF. The key-intermediate, per-2,3-O-benzyl-2-O-monopropargyl-βCD, is reacted with an excess of the protected 2-hydroxypropylating agent (1-bromo-2-benzyloxy-propane) under PTC conditions. The fully substitution of the primary side, the desired DS7, is achieved by using simultaneous excess of the base (KOH) and of the protected 2-hydroxypropylating agent. Finally, exhaustive deprotection of the benzyl groups by hydrazine-mediated transfer-hydrogenation yields the asymmetric monomer, per-6-O-(2-O-hydroxypropyl)-2-O-monopropargyl-βCD. The two monomers are characterized by NMR spectroscopy, MALDI and TLC.

The preparation of the asymmetric dimer is then achieved by reacting the two monomers in aqueous DMF with copper bromide as catalyst. The resulting compound, C6HPβCD'-triazole-βCD DS7 asymmetric dimer, is characterized by NMR spectroscopy and MALDI.

Hp(αCd-Triazole-αCd) Homodimer

The preparation of hydroxypropylated αCD dimers connected through the secondary face with one triazole moiety is performed in a four-part procedure (FIG. 12B). The first part is the preparation of the azido-linker (3-azido-1-bromo-propane) as this reagent is not commercially available. The second part is the preparation of the two αCD monomers, 2-O-monopropargyl-αCD and 2-O-mono(3-azidopropyl)-αCD, respectively. The third synthetic part is the build-up of the αCD-TRIAZOLE-αCD dimer by copper-assisted azide-alkyne cycloaddition, and the final part is preparation of a series of 2-hydroxypropylated triazole-linked dimers according to the classical alkylation approach.

In particular, the preparation of the azido-linker can be achieved by strictly limiting the amount of sodium azide and by elongating the addition time of the limiting reagent. The azido-linker is then characterized by NMR spectroscopy and TLC.

The syntheses of the two monomers are accomplished by using lithium hydride as base for the selective deprotonation of the secondary side. In particular, according to this approach the hydroxyl groups located on C2 are mostly reacted. As a consequence, monomers prepared by this method are predominantly substituted on the O2 (they are single isomers).

The preparation of the αCD-TRIAZOLE-αCD dimer is then achieved by reacting the two monomers.

Hydroxypropylation of αCD-TRIAZOLE-αCD dimer is accomplished using propylene oxide and alkaline aqueous conditions.

Hp(αCd-Butyl-βCd) Heterodimer

The preparation of butyl-linked HPαCD-βCD dimers was accomplished through a three-step synthesis (see FIG. 16A). The starting materials are monomeric αCD and βCD protected on the primary side with tert-butyldimethylsilyl groups (TBDMS-αCD and TBDMS-βCD, CycloLab, Budapest, Hungary).

The secondary face dimerization was achieved by using equimolar amounts of TBDMS-αCD and TBDMS-βCD, anhydrous conditions, and sodium hydride as base. The dialkylating agent was added dropwise to the heterogeneous reaction mixture and exhaustively reacted at room temperature.

The primary side protected αCD-βCD dimer (TBDMS-αCD-BUTYL-βCD-TBDMS) was purified by chromatography with isocratic elution (chloroform:methanol:water=50:8:0.8 (v/v/v) as eluent).

The desilylation (deprotection) was performed in THF with tetrabutylammonium fluoride at room temperature. The αCD-βCD dimer (αCD-BUTYL-βCD) was purified by chromatography with isocratic elution (1,4-dioxane:25% $NH_3$ aq=10:7 (v/v) as eluent).

The hydroxypropylation of the αCD-BUTYL-βCD dimer was achieved in aqueous conditions by using sodium hydroxide as base at room temperature. The purification of the hydroxypropylated αCD-βCD dimer, HP(αCD-BUTYL-βCD) was based on ion exchange resins treatment, charcoal clarification and extensive dialysis.

Hp(αCd-Triazole-βCd) and Hp(βCd-Triazole-αCd) Heterodimers

The preparation of hydroxypropylated αCD-βCD and βCD-αCD dimers connected through the secondary face with one triazole moiety is performed in a four-part procedure (FIG. 16B). The first part is the preparation of the azido-linker (3-azido-1-bromo-propane) as this reagent is not commercially available. The second part is the preparation of the four monomers, 2-O-monopropargyl-αCD, 2-O-monopropargyl-βCD and 2-O-mono(3-azidopropyl)-αCD, 2-O-mono(3-azidopropyl)-βCD. The third synthetic part is the build-up of the two dimers core, αCD-TRIAZOLE-βCD dimer and βCD-TRIAZOLE-αCD dimer, by copper-assisted azide-alkyne cycloaddition, and the final part is preparation of a series of 2-hydroxypropylated triazole-linked dimers according to the classical alkylation approach.

In particular, the preparation of the azido-linker can be achieved by strictly limiting the amount of sodium azide and by elongating the addition time of the limiting reagent. The azido-linker is then characterized by NMR spectroscopy and TLC.

The syntheses of the four monomers are accomplished by using lithium hydride as base for the selective deprotonation of the secondary side. In particular, according to this approach the hydroxyl groups located on C2 are mostly reacted. As a consequence, monomers prepared by this method are predominantly substituted on the O2 (they are single isomers).

The preparation of the two dimers core, αCD-TRIAZOLE-βCD and βCD-TRIAZOLE-αCD dimers, is then achieved by reacting the monomer 2-O-monopropargyl-αCD with monomer 2-O-mono(3-azidopropyl)-βCD and the monomer 2-O-monopropargyl-βCD with monomer 2-O-mono(3-azidopropyl)-αCD, respectively.

Hydroxypropylation of αCD-TRIAZOLE-βCD and βCD-TRIAZOLE-αCD dimers is accomplished using propylene oxide and alkaline aqueous conditions.

Detailed Description of Synthesis (Hp(βCd-Butyl-βCd) Homodimer)

Step 1: Secondary Face Dimerization of TBDMS-βCD

Anhydrous TBDMS-βCD (10 g, 5.17 mmol) was solubilized in THF (400 mL) under inert atmosphere and sodium hydride (2.5 g, 50 mmol) was carefully added portion wise (in 30 min). The addition of sodium hydride caused hydrogen formation and intense bubbling of the suspension. After 15 min stirring, the reaction mixture gelified (became viscous), and stirring became difficult. In order to destroy the gel, the reaction mixture was heated until a gentle reflux occurred, and kept at reflux for 30 min. The yellowish, heterogeneous suspension became easier to stir, and the gel-like material disappeared. The reaction mixture was cooled down to room temperature with a water bath. The alkylating agent, 1,4-dibromobutane (1.25 mL, 2.25 g, 10.5 mmol), was added dropwise (15 min) and the color of the reaction mixture turned to dark orange.

The brownish suspension was stirred overnight under inert atmosphere. The conversion rate was estimated by TLC between 10-15% (eluent: chloroform:methanol:water=50:10:1, v/v/v) and considered acceptable for work-up.

The reaction mixture was quenched with methanol (30 mL), concentrated under reduced pressure (~20 mL) and precipitated with water (200 mL). The reaction crude was filtered on a sintered glass filter and extensively washed with water (3×300 mL). The crude material was dried until constant weight in a drying box in the presence of KOH and P2O5 (material recovered: 12.1 g).

The reaction crude was purified by chromatography, fractions containing the products were collected and evaporated until dryness under reduced pressure based on TLC analysis, yielding a white material that was dried until constant weight in a drying box in the presence of KOH and P2O5 (TBDMS-βCD-BUT-βCD-TBDMS, 3.5 g).

Step 2: Deprotection of TBDMS-βCD Butyl-Linked Dimer

Anhydrous TBDMS-βCD-BUT-βCD-TBDMS (3.5 g, 0.89 mmol) was solubilized in THE (250 mL) under inert atmosphere and tetrabutylammonium fluoride (8.75 g, 33.47 mmol) was added in one portion to the yellowish solution. After 30 min stirring at room temperature, the color of the reaction mixture turned to dark green. The reaction mixture was stirred at room temperature overnight TLC analysis (1,4-dioxane:25% $NH_3$=10:7 (v/v)) revealed that the reaction was not completed and a second portion of tetrabutylammonium fluoride (4 g, 13.3 mmol) was added to the vessel. The reaction mixture was warmed to a gentle reflux and refluxed for two hours. The reaction conversion at this stage was exhaustive as no starting material could be detected by TLC. The reaction mixture was cooled-down to room temperature, concentrated under reduced pressure (to ~10 mL) and addition of methanol (200 mL) yielded a white precipitate. The solid was filtered-out, analyzed by TLC and dried until constant weight in a drying box in the presence of KOH and P2O5 (1.2 g). According to TLC analysis the material contained a negligible (s 3%) amount of tetrabutylammonium fluoride. The mother liquor was concentrated under reduced pressure (to ~10 mL) and purified by chromatography (eluent 1,4-dioxane:$NH_3$=10:7 v/v), fractions containing the products were collected and evaporated until dryness under reduced pressure, yielding a white material that was dried until constant weight in a drying box in the presence of KOH and $P_2O_5$ (CD-BUT-CD, 0.55 g).

Step 3: Hydroxypropylation of βCd-Butyl-βCD Homodimer

βCD-BUTYL-βCD DSO (0.5 g, 0.21 mmol) was suspended in water (10 mL), sodium hydroxide (0.1 g, 2.5 mmol) was added to the reaction vessel and the color of the mixture turned to a slight yellow solution. The reaction mixture was cooled with a water bath (10° C.) and propylene oxide (0.5 mL, 0.415 g, 7.14 mmol) was added in one portion. The reaction vessel was flushed with argon, sealed and stirred for two days at room temperature. The reaction mixture was concentrated under reduced pressure until obtaining a viscous syrup that was precipitated with acetone (50 mL). The white solid was filtered on a sintered glass filter and extensively washed with acetone (3×15 mL). The material was solubilized with water (50 mL), treated with ion exchange resins (in order to remove the salts), clarified with charcoal, membrane filtered and dialyzed for one day against purified water. The retentate was evaporated under reduced pressure until dryness yielding a white solid (0.8 g).

Detailed Description of Synthesis for (HP(αCD-BUTYL-αCD) Homodimer)

Step 1: Secondary Face Dimerization of TBDMS-αCD

Anhydrous TBDMS-αCD (10 g, 6.03 mmol) is solubilized in THF (400 mL) under inert atmosphere and sodium hydride (2.9 g, 58 mmol) is carefully added portion wise (in 30 min). The addition of sodium hydride caused hydrogen formation and intense bubbling of the suspension. After 15 min stirring, the reaction mixture gelifies (becomes viscous), and stirring becomes difficult. In order to destroy the gel, the reaction mixture is heated until a gentle reflux occurred, and kept at reflux for 30 min. The yellowish, heterogeneous suspension becomes easier to stir, and the gel-like architecture disappears. The reaction mixture is cooled down to room temperature with a water bath. The alkylating agent, 1,4-dibromobutane (1.45 mL, 2.61 g, 12.2 mmol), is added dropwise (15 min) and the color of the reaction mixture turns to dark orange.

The brownish suspension is stirred overnight under inert atmosphere. The conversion rate is estimated by TLC between 10-15% (eluent: chloroform:methanol:water=50:10:1, v/v/v) and considered acceptable for work-up.

The reaction mixture is quenched with methanol (30 mL), concentrated under reduced pressure (~20 mL) and precipitated with water (200 mL). The reaction crude is filtered on a sintered glass filter and extensively washed with water (3×300 mL). The crude material is dried until constant weight in a drying box in the presence of KOH and P2O5 (recovered material: 11.2 g).

The reaction crude is purified by chromatography, fractions containing the products are collected based on TLC analysis and evaporated until dryness under reduced pressure yielding a white material that is dried until constant weight in a drying box in the presence of KOH and P2O5 (TBDMS-αCD-BUTYL-αCD-TBDMS, 3.3 g).

Step 2: Deprotection of Butyl-Linked TBDMS-αCD Dimer

Anhydrous TBDMS-αCD-BUTYL-αCD-TBDMS dimer (3.3 g, 0.98 mmol) is solubilized in THF (250 mL) under inert atmosphere and tetrabutylammonium fluoride (9.63 g, 36.85 mmol) is added in one portion to the yellowish solution. After 30 min stirring at room temperature, the color of the reaction mixture turns to dark green. The reaction mixture is stirred at room temperature overnight TLC analysis (1,4-dioxane:25% NH3 aq=10:7 (v/v)) revealed that the reaction is not completed and a second portion of tetrabutylammonium fluoride (4 g, 13.3 mmol) is added to the vessel. The reaction mixture is warmed to a gentle reflux and refluxed for two hours. The reaction conversion at this stage is exhaustive as no starting material could be detected by TLC. The reaction mixture is cooled-down to room temperature, concentrated under reduced pressure (to ~10 mL) and addition of methanol (200 mL) yielded a white precipitate. The solid is filtered-out, analyzed by TLC and dried until constant weight in a drying box in the presence of KOH and P2O5 (1.1 g). The mother liquor is concentrated under reduced pressure (to ~10 mL) and purified by chromatography (eluent 1,4-dioxane:25% NH3 aq=10:7 v/v), fractions containing the products are collected based on TLC analysis and evaporated until dryness under reduced pressure, yielding a white material that is dried until constant weight in a drying box in the presence of KOH and P2O5 (αCD-BUTYL-αCD dimer, 0.52 g).

Step 3: Hydroxypropylation of αCd-Butyl-αCD Homodimer

αCD-BUTYL-αCD dimer (0.52 g, 0.26 mmol) is suspended in water (10 mL), sodium hydroxide (0.1 g, 2.5 mmol) is added to the reaction vessel and the color of the mixture turns to a slight yellow solution. The reaction mixture is cooled with a water bath (10° C.) and propylene oxide (0.5 mL, 0.415 g, 7.14 mmol) is added in one portion. The reaction vessel is flushed with argon, sealed and stirred for two days at room temperature. The reaction mixture is concentrated under reduced pressure until obtaining a viscous syrup that is precipitated with acetone (50 mL). The white solid is filtered on a sintered glass filter and extensively washed with acetone (3×15 mL). The material is solubilized with water (50 mL), treated with ion exchange resins (in order to remove the salts), clarified with charcoal, membrane filtered and dialyzed for one day against purified water. The retentate is evaporated under reduced pressure until dryness yielding a white solid (0.6 g).

Detailed Description of Synthesis (HP(βCD-Triazole-βCD) Homodimer)

Step 1: Preparation of the Azido-Linker 1,3-Dibromopropane (10 mL, 20.18 g, 0.1 mol) was solubilized in 40 mL DMSO under vigorous stirring. A solution of sodium azide (6.7 g, 0.1 mol) in DMSO (240 mL) was prepared and added dropwise (2 hours addition) to the solution of 1,2-dihalopropane. The solution was stirred at room temperature overnight. The reaction crude was then extracted with n-hexane (3×100 mL), the collected organic phases are retro-extracted with water (3×50 mL), and the organic phases are carefully evaporated under reduced pressure (at 40° C., 400 mbar strictly, otherwise the target compound may distillate out). The residue, an oil, is purified by chromatography (n-hexane-EtOAc=98:2 as eluent, isocratic elution). The appropriate fractions are collected based on TLC analysis, and concentrated under reduced pressure and the target compound is obtained as a viscous oil (which may be stored under inert atmosphere in a dark, refrigerated container). The compound is visualized by dipping the TLC plate in a triphenylphosphine solution in dichloromethane (10%) for ~15 s, drying the TLC plate below 60° C., dipping the TLC in a ninhydrin ethanol solution (2%) for ~15 s and final drying of the TLC plate below 60° C. The target compound appears as a violet spot on the TLC plate.

Step 2.1: Preparation of 2-O-Monopropargyl-βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h). Propargyl bromide (1.97 mL, 17.62 mmol) and a catalytic amount of lithium iodide (~20 mg) are then added and the mixture is stirred at 55° C. in the absence of light for 5 h. TLC (10:5:2 $CH_3CN$—$H_2O$-25% v/v aqueous $NH_3$(aq)) is used to characterize the products and it shows spots corresponding to 2-O-monopropargylated and nonpropargylated βCD, respectively. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and chromatography (10:5:2 $CH_3CN$—$H_2O$-25% aqueous $NH_3$) to yield, after freeze-drying, 2-O-monopropargyl-β-CD as a solid. The 2-O-propargyl-β-CD was analyzed by MALDI and NMR.

Step 2.2: Synthesis of 2-O-Mono(3-Azidopropyl)-βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h). 3-Azido-1-bromo-propane (3 mL) and a catalytic amount of lithium iodide (~20 mg) are then added and the mixture is stirred at 55° C. in the absence of light for 5 h. TLC (10:5:2 CH3CN—H2O-25% v/v aqueous NH3) is used to characterize the products and it shows spots corresponding to 2-O-mono(3-azidopropyl)-βCD and βCD. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue was obtained. This crude mixture is applied on top of a column of silica and chromatography (10:5:2 $CH_3CN$—$H_2O$-25% aqueous $NH_3$) to yield, after drying, 2-O-mono(3-azidopropyl)-β-CD as a white solid.

Step 3: Synthesis of βCd-Triazole-βCD Homodimer

2-O-Monopropargyl-β-CD and 2-O-mono(3-azidopropyl)-β-CD are suspended in water (300 mL) under vigorous stirring (each at a concentration of between about 8-12 mM). N,N-Dimethylformamide (DMF) (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent $CH_3CN$:$H_2O$:25% $NH_3$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% v/v aqueous $NH_3$) to yield, after drying, BCD-TRIAZOLE-BCD DIMER. A preparation of BCD-TRIAZOLE-BCD DIMER was extensively characterized by NMR.

Step 4: Hp(βCd-Triazole-βCd)

βCD-TRIAZOLE-βCD DIMER, which may be obtained according to steps 1-3 above or by other methods, (1 g, 0.418 mmol) was suspended in water (50 mL), sodium hydroxide (DS3=0.32 g, 8 mmol; DS6=0.74 g, 18.5 mmol; DS7=0.87 g, 21.75 mmol) was added to the reaction vessel and the mixture turned to a slight yellow solution. The reaction mixture was cooled by water bath (10° C.) and propylene oxide (DS3=0.49 mL, 0.42 g, 7.25 mmol; DS6=1.21 mL, 1.04 g, 17.9 mmol; DS7=1.46 mL, 1.7 g, 29.3 mmol) was added in one portion. The reaction vessel was flushed with argon, sealed and stirred for two days at room temperature. The solution was concentrated under reduced pressure until obtaining a viscous syrup that was precipitated with acetone (50 mL). The white solid was filtered on a sintered glass filter and extensively washed with acetone (3×15 mL). The material was solubilized with water (50 mL), treated with ion exchange resins (in order to remove the salts), clarified with charcoal, membrane filtered and dialyzed for one day against purified water. The retentate was evaporated under reduced pressure until dryness yielded a white solid (0.8 g). HP(βCD-TRIAZOLE-βCD) dimers were analyzed by NMR (FIGS. 7G, 7I, and 7J) and the DS thereof was calculated for each as shown in the figures.

Detailed Description of Synthesis (Hp(αCd-Triazole-αCd) Homodimer)

Step 2.1: Preparation of 2-O-Monopropargyl-αCD

Lithium hydride (212 mg, 26.432 mmol) is added to a solution of αCD (17.14 g, 17.62 mmol) in dry DMSO (400 mL). The resulting suspension is stirred under N2 at room temperature until it becomes clear (12-24 h). Propargyl bromide (1.964 mL, 17.62 mmol) and a catalytic amount of lithium iodide (~20 mg) are then added and the mixture is stirred at 55° C. in the absence of light for 5 h. TLC (10:5:2 CH3CN—H2O-25% aqueous NH3) is used to characterize the products and it shows spots corresponding to monopropargylated and nonpropargylated αCD, respectively. The solution is poured into acetone (3.5 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and purified by chromatography (10:5:2 CH3CN—H2O-25% v/v aqueous NH3) to yield, after drying, 2-O-monopropargyl-αCD as a solid.

Step 2.2: Synthesis of 2-O-Mono(3-Azidopropyl)-αCD

Lithium hydride (212 mg, 26.432 mmol) is added to a solution of βCD (17.14 g, 17.62 mmol) in dry DMSO (400 mL). The resulting suspension is stirred under N2 at room temperature until it becomes clear (12-24 h). 3-Azido-1-bromo-propane (3 mL) and a catalytic amount of lithium iodide (~20 mg) are then added and the mixture is stirred at 55° C. in the absence of light for 5 h. TLC (10:5:2 CH3CN—H2O-25% v/v aqueous NH3) is used to characterize the products and it shows spots corresponding to 2-O-mono(3-azidopropyl)-αCD and αCD. The solution is poured into acetone (3.5 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica and chromatography (10:5:2 CH3CN—H2O-25% v/v aqueous NH3) to yield, after drying, 2-O-mono(3-azidopropyl)-αCD as a white solid.

Step 3: Synthesis of αCd-Triazole-αCD Dimer

2-O-monopropargyl-αCD and 2-O-mono(3-azidopropyl)-αCD are suspended in water (300 mL) under vigorous stirring (each at a concentration of between about 8-12 mM). N, N-Dimethylformamide (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN$:$H_2O$:$NH_3$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% v/v aqueous $NH_3$) to yield, after drying, αCD-TRIAZOLE-αCD dimer.

Step 4: Hp(αCd-Triazole-αCd) Homodimer

αCD-TRIAZOLE-αCD dimer, which is obtained according to steps 1-3 above or by other methods, (1 g, 0.418 mmol) is suspended in water (50 mL), sodium hydroxide (DS3=0.32 g, 8 mmol; DS6=0.74 g, 18.5 mmol; DS7=0.87 g, 21.75 mmol) is added to the reaction vessel and the mixture turned to a slight yellow solution. The reaction mixture is cooled by water bath (10° C.) and propylene oxide (DS3=0.49 mL, 0.42 g, 7.25 mmol; DS6=1.21 mL, 1.04 g, 17.9 mmol; DS7=1.46 mL, 1.7 g, 29.3 mmol) is added in one portion. The reaction vessel is flushed with argon, sealed and stirred for two days at room temperature. The solution is concentrated under reduced pressure until obtaining a viscous syrup that is precipitated with acetone (50 mL). The white solid is filtered on a sintered glass filter and extensively washed with acetone (3×15 mL). The material is solubilized with water (50 mL), treated with ion exchange resins (in order to remove the salts), clarified with charcoal, membrane filtered and dialyzed for one day against purified water. The retentate is evaporated under reduced pressure until dryness yielded a white solid (0.6 g).

Detailed Description of Synthesis of Hp(αCd-Butyl-βCd) Heterodimer

Step 1: Secondary Face Dimerization of TBDMS-αCD and TBDMS-βCD

Anhydrous TBDMS-αCD (5 g, 3.01 mmol) and TBDMS-βCD (5.8 g, 3.01 mmol) are solubilized in THF (400 mL) under inert atmosphere and sodium hydride (2.9 g, 58 mmol) is carefully added portion wise (in 30 min). The addition of sodium hydride caused hydrogen formation and intense bubbling of the suspension. After 15 min stirring, the reaction mixture becomes viscous, and agitation becomes difficult. In order to destroy the gel, the reaction mixture is heated until a gentle reflux occurred, and kept at reflux for 30 min. The yellowish, heterogeneous suspension becomes easier to stir, and the gel-like architecture disappears. The reaction mixture is cooled down to room temperature with a water bath. The alkylating agent, 1,4-dibromobutane (1.45 mL, 2.61 g, 12.2 mmol), is added dropwise (15 min) and the color of the reaction mixture turns to dark orange.

The brownish suspension is stirred overnight under inert atmosphere. The conversion rate is estimated by TLC between 10-15% (eluent: chloroform:methanol:water=50:10:1, v/v/v) and considered acceptable for work-up.

The reaction mixture is quenched with methanol (30 mL), concentrated under reduced pressure (~20 mL) and precipitated with water (200 mL). The reaction crude is filtered on a sintered glass filter and extensively washed with water (3×300 mL). The crude material is dried until constant weight in a drying box in the presence of KOH and P2O5 (recovered material: 10.1 g).

The reaction crude is purified by chromatography, fractions containing the products are collected based on TLC analysis and evaporated until dryness under reduced pressure yielding a white material that is dried until constant weight in a drying box in the presence of KOH and P2O5 (TBDMS-αCD-BUTYL-βCD-TBDMS dimer, 3.6 g).

Step 2: Deprotection of Butyl-Linked TBDMS-αCD-βCD Dimer

Anhydrous TBDMS-αCD-BUTYL-βCD-TBDMS dimer (3.6 g, 0.98 mmol) is solubilized in THF (250 mL) under inert atmosphere and tetrabutylammonium fluoride (9.63 g, 36.85 mmol) is added in one portion to the yellowish solution. After 30 min stirring at room temperature, the color of the reaction mixture turns to dark green. The reaction mixture is stirred at room temperature overnight TLC analysis (1,4-dioxane:25% $NH3_{(aq)}$=10:7 (v/v)) revealed that the reaction is not completed and a second portion of tetrabutylammonium fluoride (4 g, 13.3 mmol) is added to the vessel. The reaction mixture is warmed to a gentle reflux and refluxed for two hours. The reaction conversion at this stage is exhaustive as no starting material could be detected by TLC. The reaction mixture is cooled-down to room temperature, concentrated under reduced pressure (to ~10 mL) and addition of methanol (200 mL) yielded a white precipitate. The solid is filtered-out, analyzed by TLC and dried until constant weight in a drying box in the presence of KOH and $P_2O_5$ (1.1 g). The mother liquor is concentrated under reduced pressure (to ~10 mL) and purified by chromatography (eluent: 1,4-dioxane:25% $NH3_{(aq)}$=10:7 v/v), fractions containing the products are collected based on TLC analysis and evaporated until dryness under reduced pressure, yielding a white material that is dried until constant weight in a drying box in the presence of KOH and $P_2O_5$ (αCD-BUTYL-βCD dimer, 0.55 g).

Step 3: Hydroxypropylation of αCd-Butyl-βCd Heterodimer

αCD-BUTYL-βCD dimer (0.55 g, 0.25 mmol) is suspended in water (10 mL), sodium hydroxide (0.1 g, 2.5 mmol) is added to the reaction vessel and the color of the mixture turns to a slight yellow solution. The reaction mixture is cooled with a water bath (10° C.) and propylene oxide (0.5 mL, 0.415 g, 7.14 mmol) is added in one portion. The reaction vessel is flushed with argon, sealed and stirred for two days at room temperature. The reaction mixture is concentrated under reduced pressure until obtaining a viscous syrup that is precipitated with acetone (50 mL). The white solid is filtered on a sintered glass filter and extensively washed with acetone (3×15 mL). The material is solubilized with water (50 mL), treated with ion exchange resins (in order to remove the salts), clarified with charcoal, membrane filtered and dialyzed for one day against purified water. The retentate is evaporated under reduced pressure until dryness yielding a white solid (0.63 g).

Detailed Description of Synthesis (Hp(αCd-Triazole-βCd) and Hp(βCd-Triazole-αCd) Heterodimers)

Step 3a: Synthesis of αCd-Triazole-βCd Dimer

2-O-monopropargyl-αCD and 2-O-mono(3-azidopropyl)-βCD are suspended in water (300 mL) under vigorous stirring (each at a concentration of between about 8-12 mM). N, N-Dimethylformamide (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN$:$H_2O$:$NH_3$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% v/v aqueous $NH_3$) to yield, after drying, αCD-TRIAZOLE-βCD dimer.

Step 3b: Synthesis of βCd-Triazole-αCd Dimer

2-O-monopropargyl-βCD and 2-O-mono(3-azidopropyl)-αCD are suspended in water (300 mL) under vigorous stirring (each at a concentration of between about 8-12 mM). N, N-Dimethylformamide (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN$:$H_2O$:NH3=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% v/v aqueous $NH_3$) to yield, after drying, βCD-TRIAZOLE-αCD dimer.

Step 4a: Hp(αCd-Triazole-βCd) Dimer

αCD-TRIAZOLE-βCD dimer, which may be obtained according to steps 1-3 above or by other methods, (1 g, 0.418 mmol) is suspended in water (50 mL), sodium hydroxide (DS3=0.32 g, 8 mmol; DS6=0.74 g, 18.5 mmol; DS7=0.87 g, 21.75 mmol) is added to the reaction vessel and the mixture turns to a slight yellow solution. The reaction mixture is cooled by water bath (10° C.) and propylene oxide (DS3=0.49 mL, 0.42 g, 7.25 mmol; DS6=1.21 mL, 1.04 g, 17.9 mmol; DS7=1.46 mL, 1.7 g, 29.3 mmol) is added in one portion. The reaction vessel is flushed with argon, sealed and stirred for two days at room temperature. The solution is concentrated under reduced pressure until obtaining a viscous syrup that is precipitated with acetone (50 mL). The white solid is filtered on a sintered glass filter and extensively washed with acetone (3×15 mL). The material is solubilized in water (50 mL), treated with ion exchange resins (in order to remove the salts), clarified with charcoal, membrane filtered and dialyzed for one day against purified water. The retentate is evaporated under reduced pressure until dryness yielded a white solid (0.7 g).

Step 4b: Hp(βCd-Triazole-αCd) Dimer

βCD-TRIAZOLE-αCD dimer, which may be obtained according to steps 1-3 above or by other methods, (1 g, 0.418 mmol) is suspended in water (50 mL), sodium hydroxide (DS3=0.32 g, 8 mmol; DS6=0.74 g, 18.5 mmol; DS7=0.87 g, 21.75 mmol) is added to the reaction vessel and the mixture turns to a slight yellow solution. The reaction mixture is cooled by water bath (10° C.) and propylene oxide (DS3=0.49 mL, 0.42 g, 7.25 mmol; DS6=1.21 mL, 1.04 g, 17.9 mmol; DS7=1.46 mL, 1.7 g, 29.3 mmol) is added in one portion. The reaction vessel is flushed with argon, sealed and stirred for two days at room temperature. The solution is concentrated under reduced pressure until obtaining a viscous syrup that is precipitated with acetone (50 mL). The white solid is filtered on a sintered glass filter and extensively washed with acetone (3×15 mL). The material is solubilized in water (50 mL), treated with ion exchange resins (in order to remove the salts), clarified with charcoal, membrane filtered and dialyzed for one day against purified water. The retentate is evaporated under reduced pressure until dryness yielded a white solid (0.6 g).

Example 6. Synthesis of Methyl Substituted CD Dimers

Figure 7K:
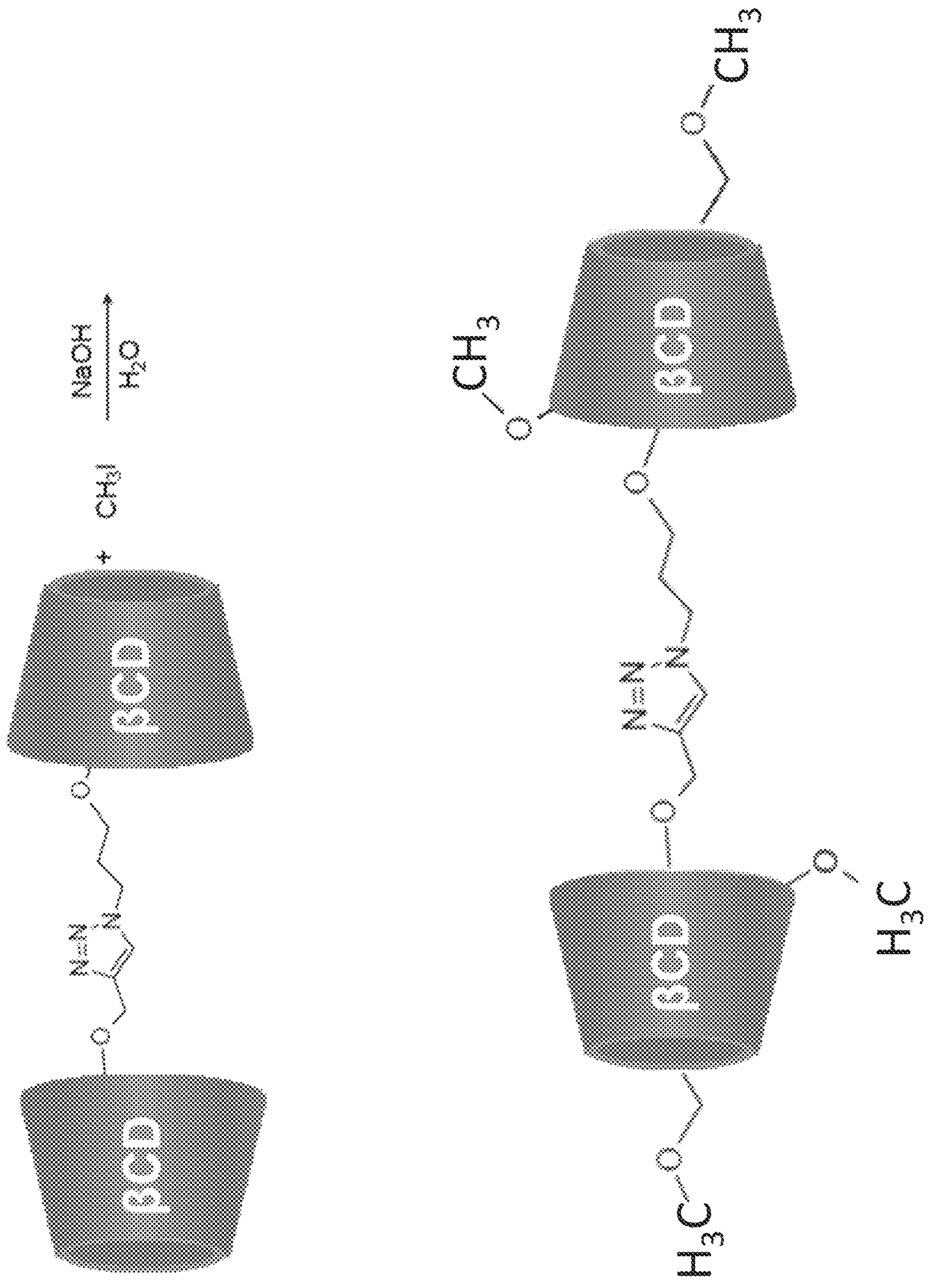
FIG. 7K. Synthetic scheme for Me-(CD-TRIAZOLE-βCD) dimer.
Figure 7L:
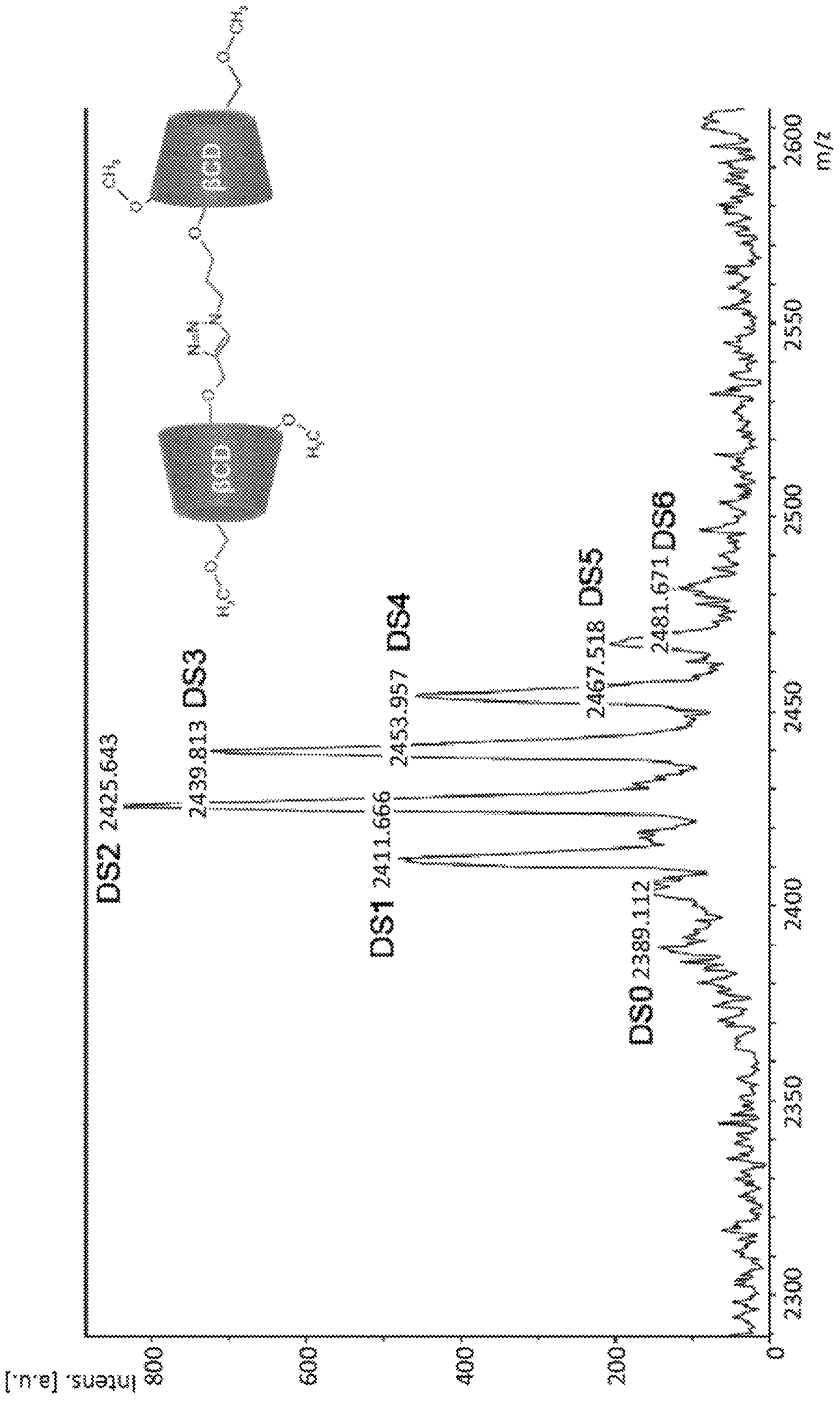
FIG. 7L. MALDI spectrum for Me-(CD-TRIAZOLE-βCD) dimer.
Figure 7M:
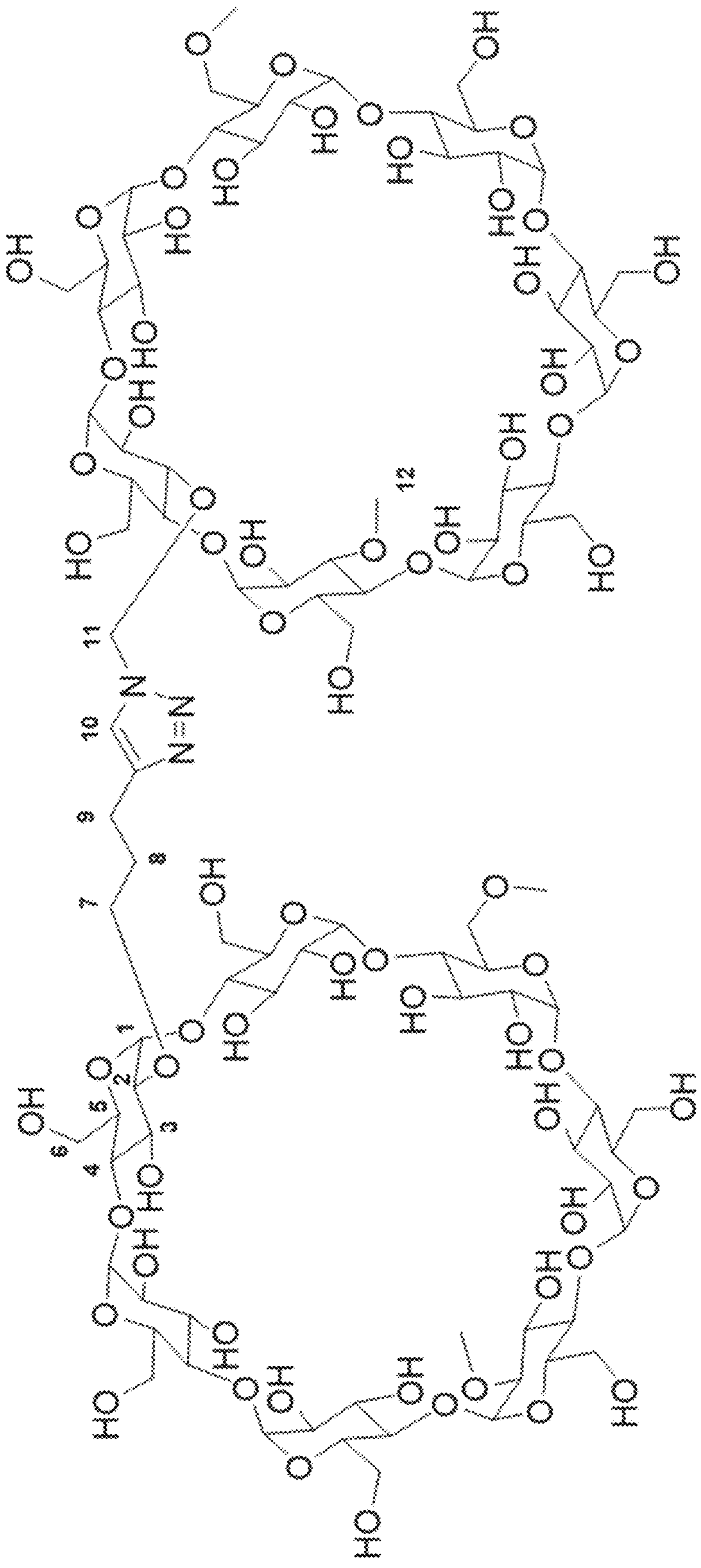
FIG. 7M. Structure of one possible isomer of Me-(CD-TRIAZOLE-βCD) dimer with atom numbering.

FIG. 7M illustrates the molecule to be synthesized.

This example describes the synthesis of methyl substituted CD dimers with a triazole-containing linker.

Methyl(βCd-Triazole-βCd) Dimer (Exemplary Synthesis)

The preparation of the methylated n-CD dimer was accomplished in a one-step reaction (see FIG. 7K). The βCD-TRIAZOLE-βCD DIM ER core is prepared according to the synthetic strategy described in Example 5 above.

Synthesis

βCD-TRIAZOLE-βCD dimer core (1.1 g, 0.46 mmol) was suspended in deionized $H_2O$ (100 mL) under vigorous stirring and sodium hydroxide (0.35 g, 8.8 mmol) was added. The resulting slightly yellow suspension was stirred for 30 min until complete solubilization. When the temperature of the yellowish, transparent solution was stabilized at ~20° C., methyl iodide (0.5 mL, 1.14 g, 8.03 mmol) was added in one portion under vigorous stirring (NOTE: methyl iodide is not miscible with the reaction mixture and, as a consequence, vigorous stirring was used to achieve a more efficient conversion). The reaction mixture was stirred for 24 h at room temperature, then it was treated with ion exchange resins: $H^+$ resin (6 g) and $OH^-$ (6 g) resin were added to the solution, stirred for 15 min and filtered-off (the resins were washed with deionized water 3×15 mL). The resulting filtrate (final pH=7) was clarified with activated charcoal: under vigorous stirring, activated charcoal (0.2 g) was added to the solution, stirred for 30 min and filtered-off (the charcoal pad was washed with deionized water 3×15 mL). Evaporation of the colorless solution under reduced pressure (40° C.) yielded the title compound as white powder (~1 g).

Characterization

Figure 7N:
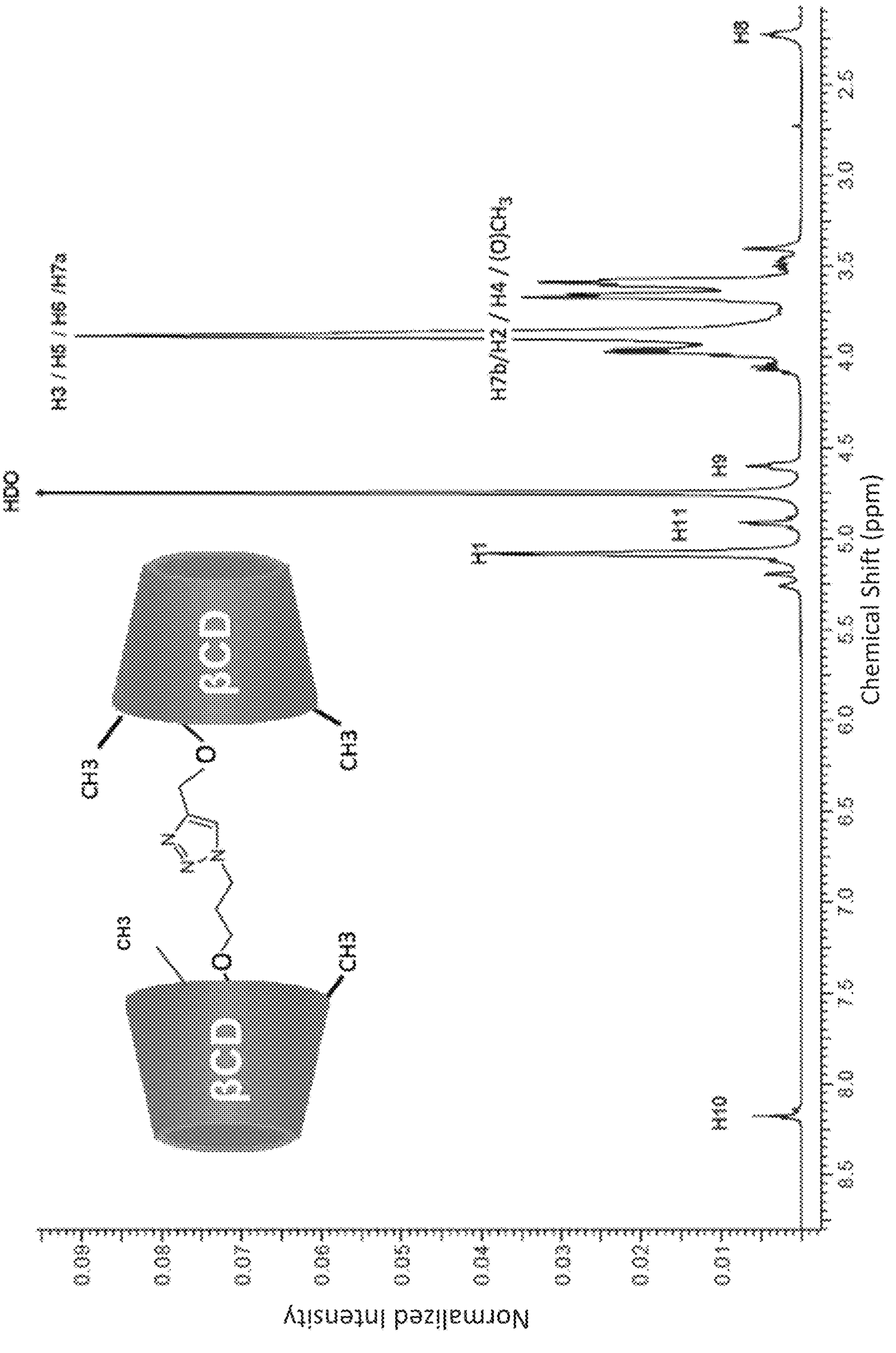
FIG. 7N. $^1$H-NMR spectrum of Me(βCD-TRIAZOLE-βCD) ($D_2O$, 298 K) with signals labeled.
Figure 7O:
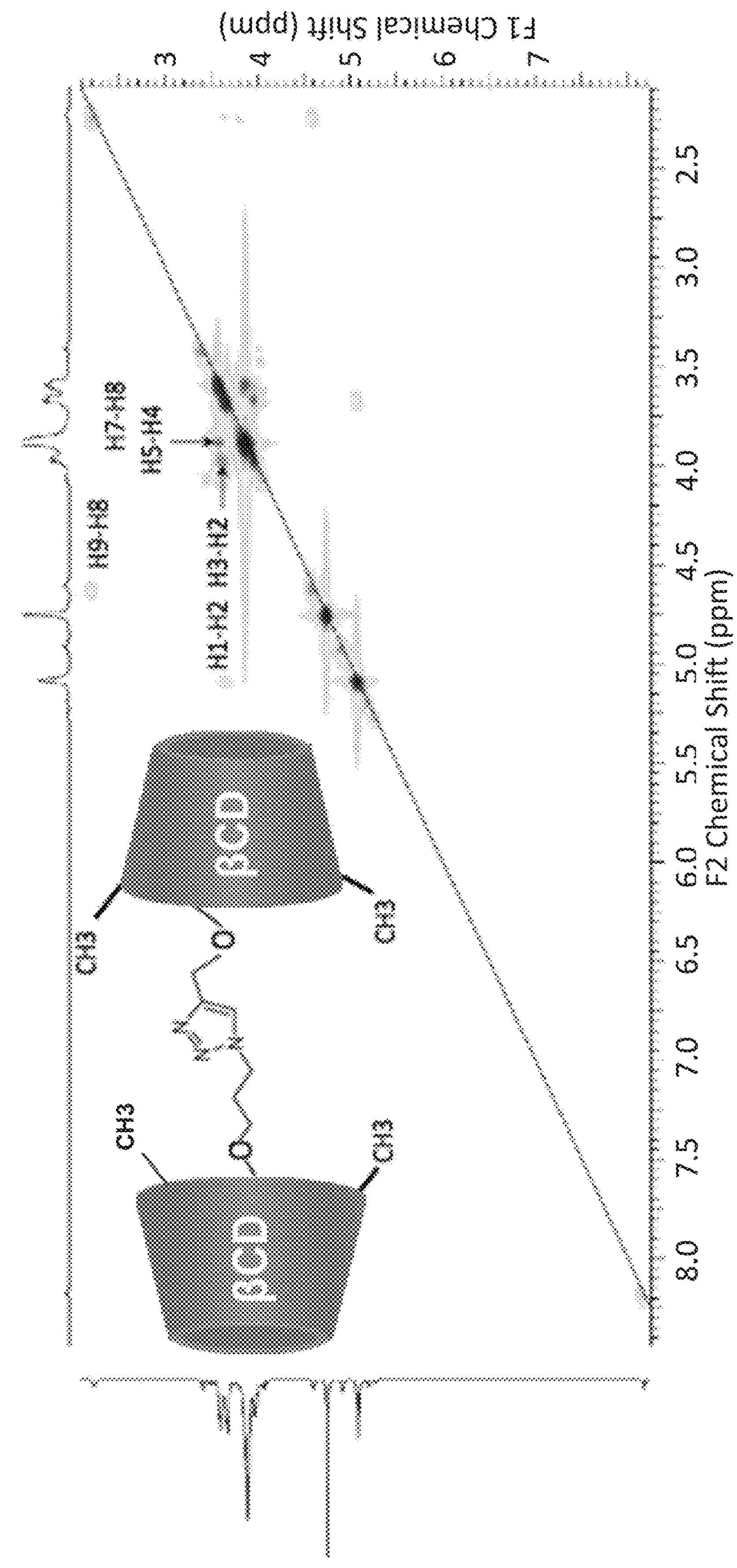
FIG. 7O. COSY-NMR spectrum of Me-(CD-TRIAZOLE-βCD) dimer with partial assignment.
Figure 7P:
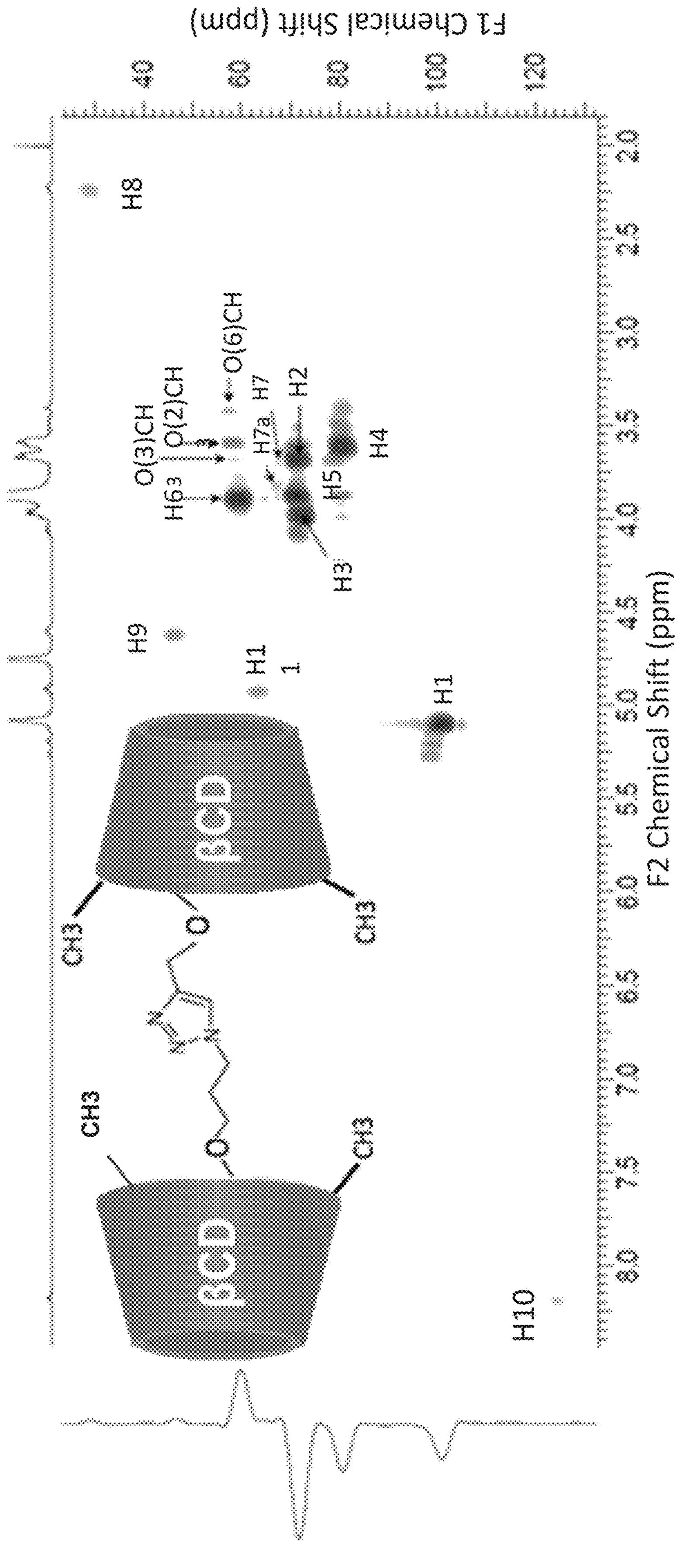
FIG. 7P. DEPT-edited HSQC spectrum of Me-(CD-TRIAZOLE-βCD) dimer with full assignment. Converted to black and white.

The reaction process was monitored by TLC and the resulting material was characterized by MALDI-TOF (FIG. 7L) and NMR analysis as in FIGS. 7N, 7O, and 7P.

Example 7. Synthesis of Sulfobutyl Substituted CD Dimers

Figure 7Q:
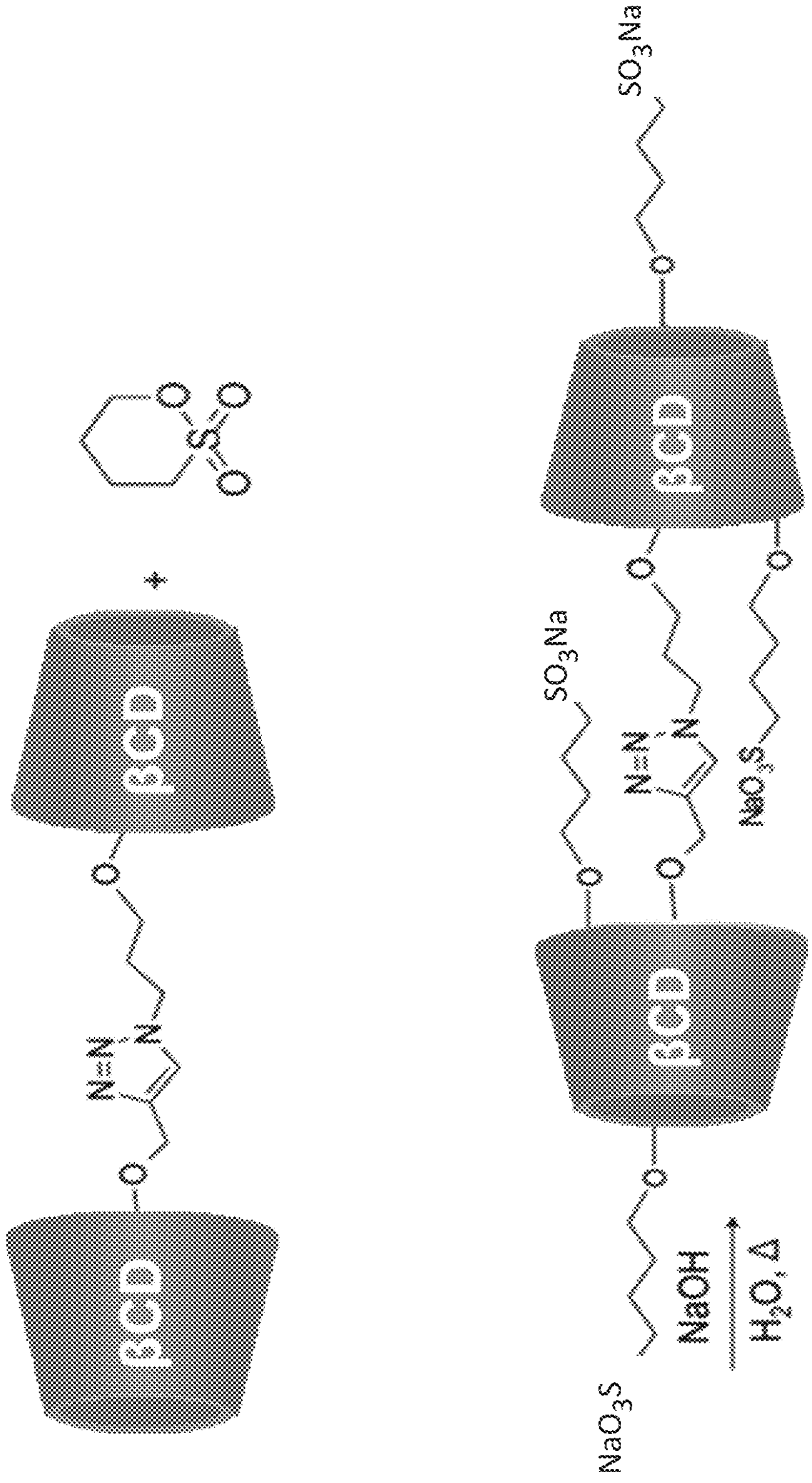
FIG. 7Q. Synthetic scheme for SB-(CD-TRIAZOLE-βCD) dimer.
Figure 7R:
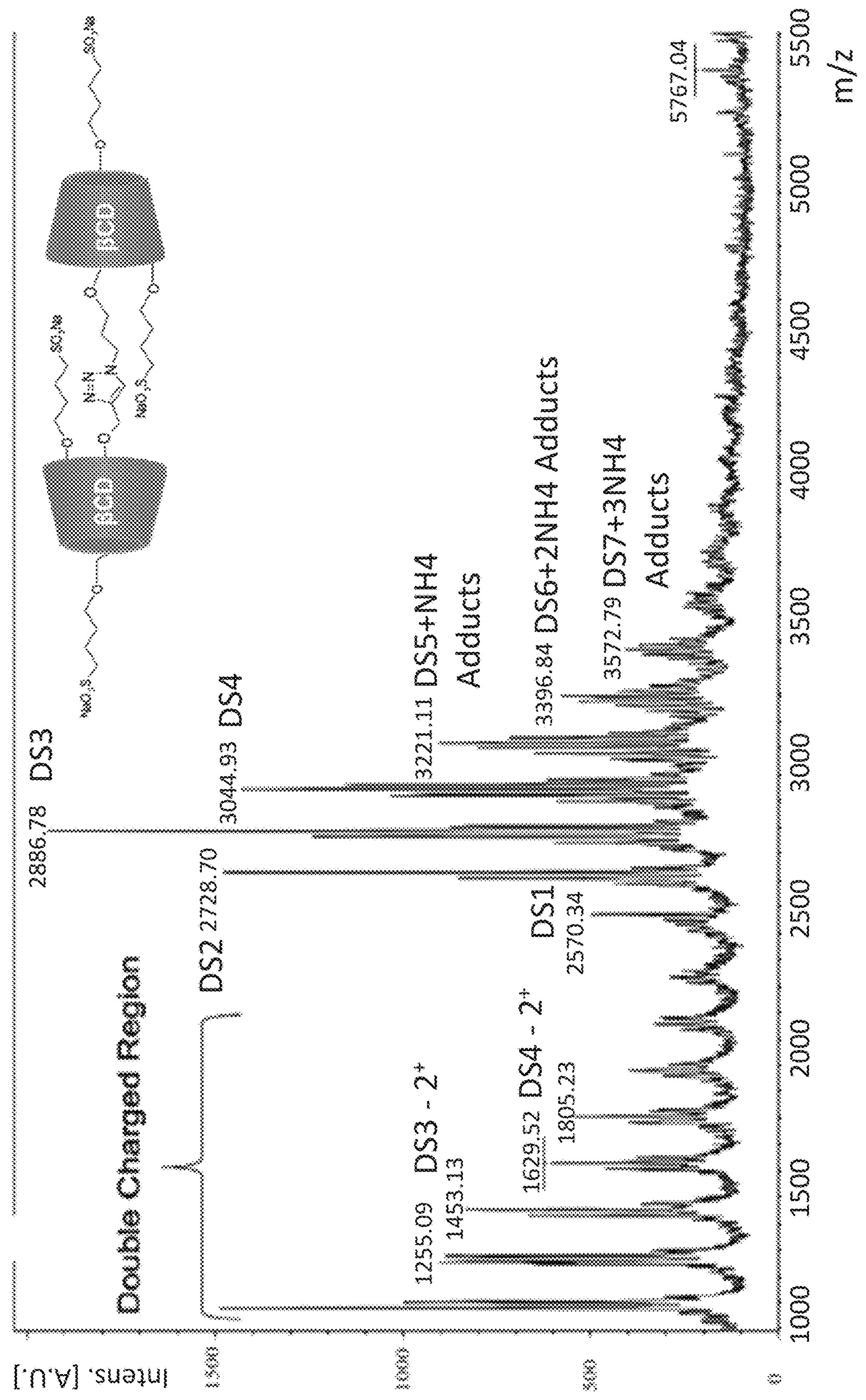
FIG. 7R. MALDI spectrum for SB-(CD-TRIAZOLE-βCD) dimer Low DS.
Figure 7S:
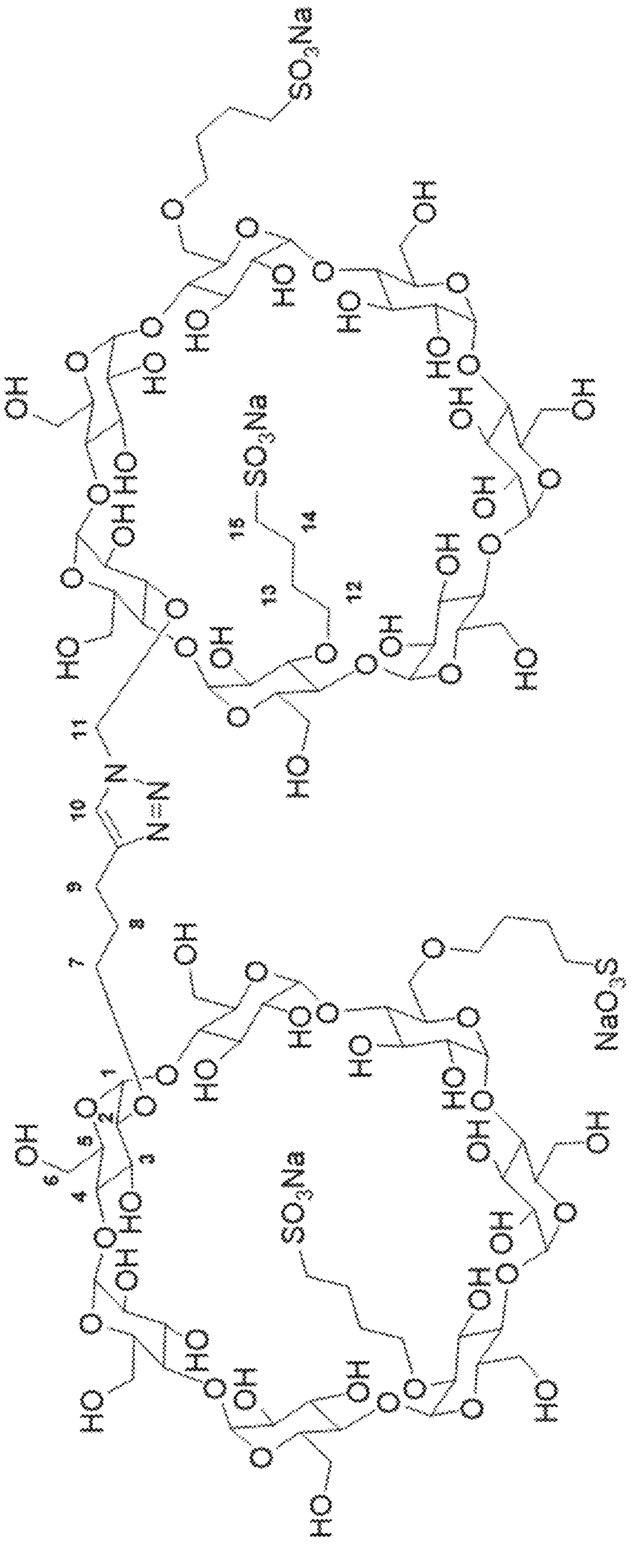
FIG. 7S. One possible isomer of SB-(CD-TRIAZOLE-βCD) dimer with atom numbering (sodium salt form).
Figure 7T:
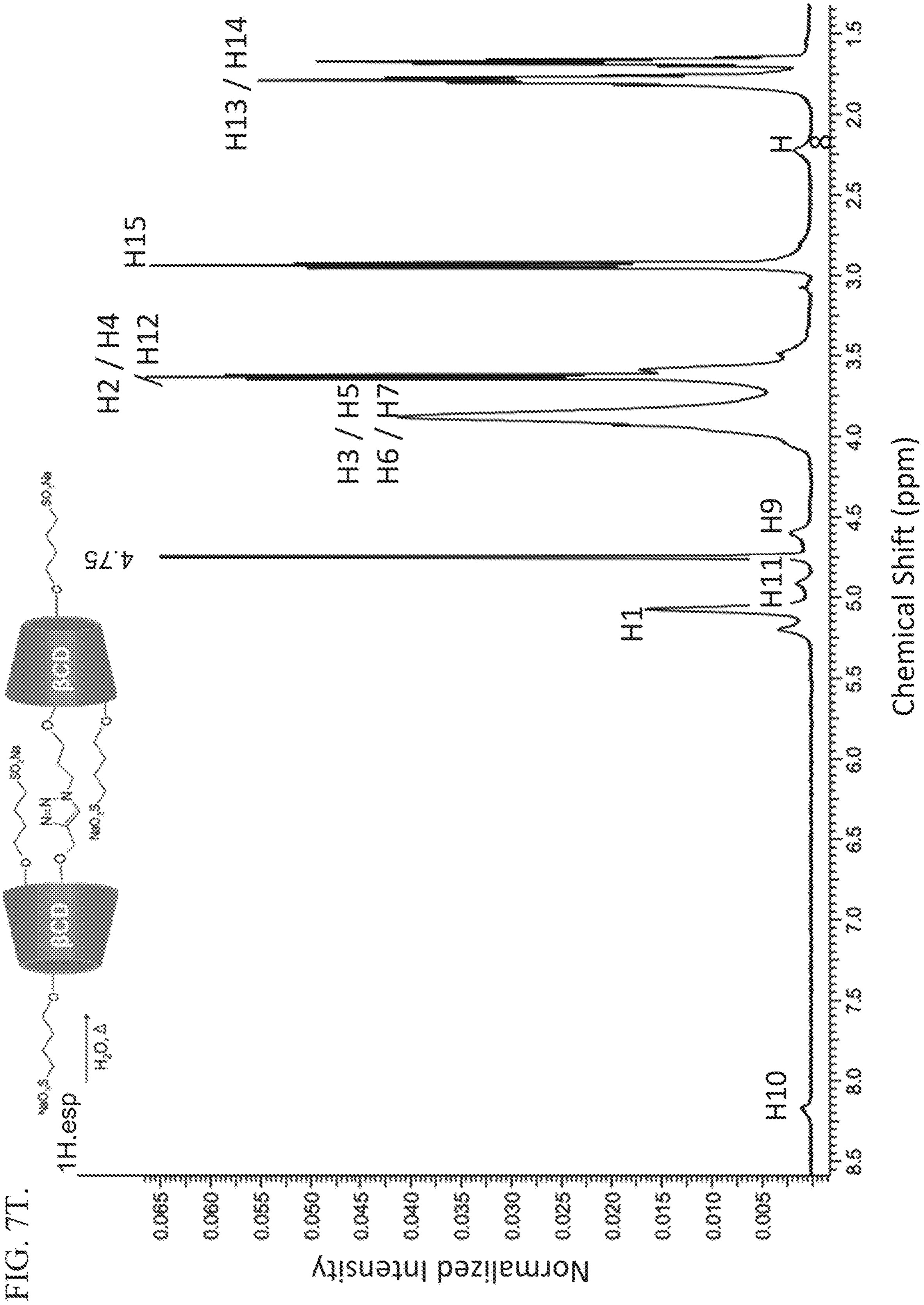
FIG. 7T. $^1$H-NMR spectrum of SB(βCD-TRIAZOLE-βCD) Low DS ($D_2O$, 298K) with signals labeled.
Figure 7U:
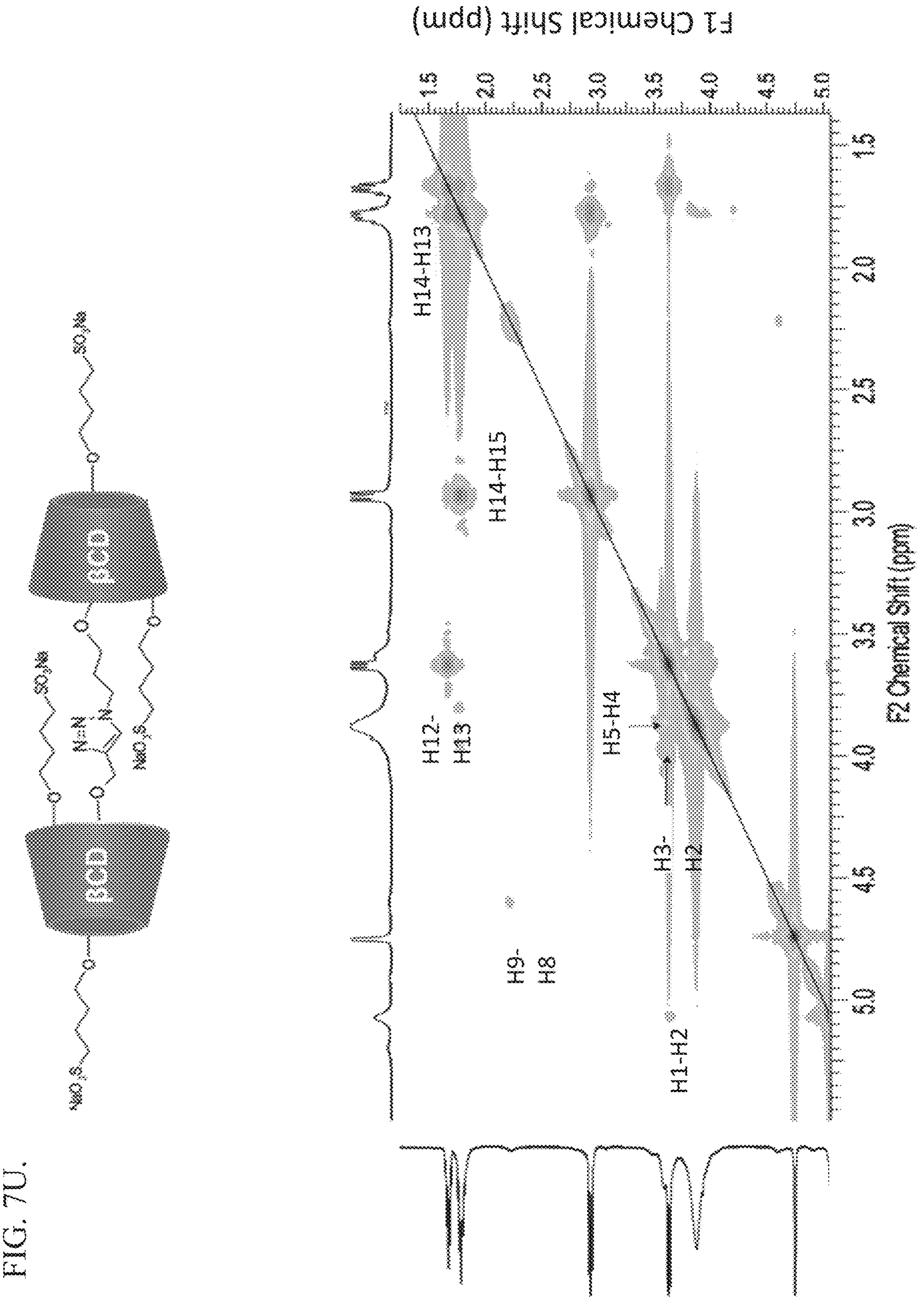
FIG. 7U. COSY spectrum of SB(βCD-TRIAZOLE-βCD) dimer Low DS with partial assignment ($D_2O$, 298K).
Figure 7V:
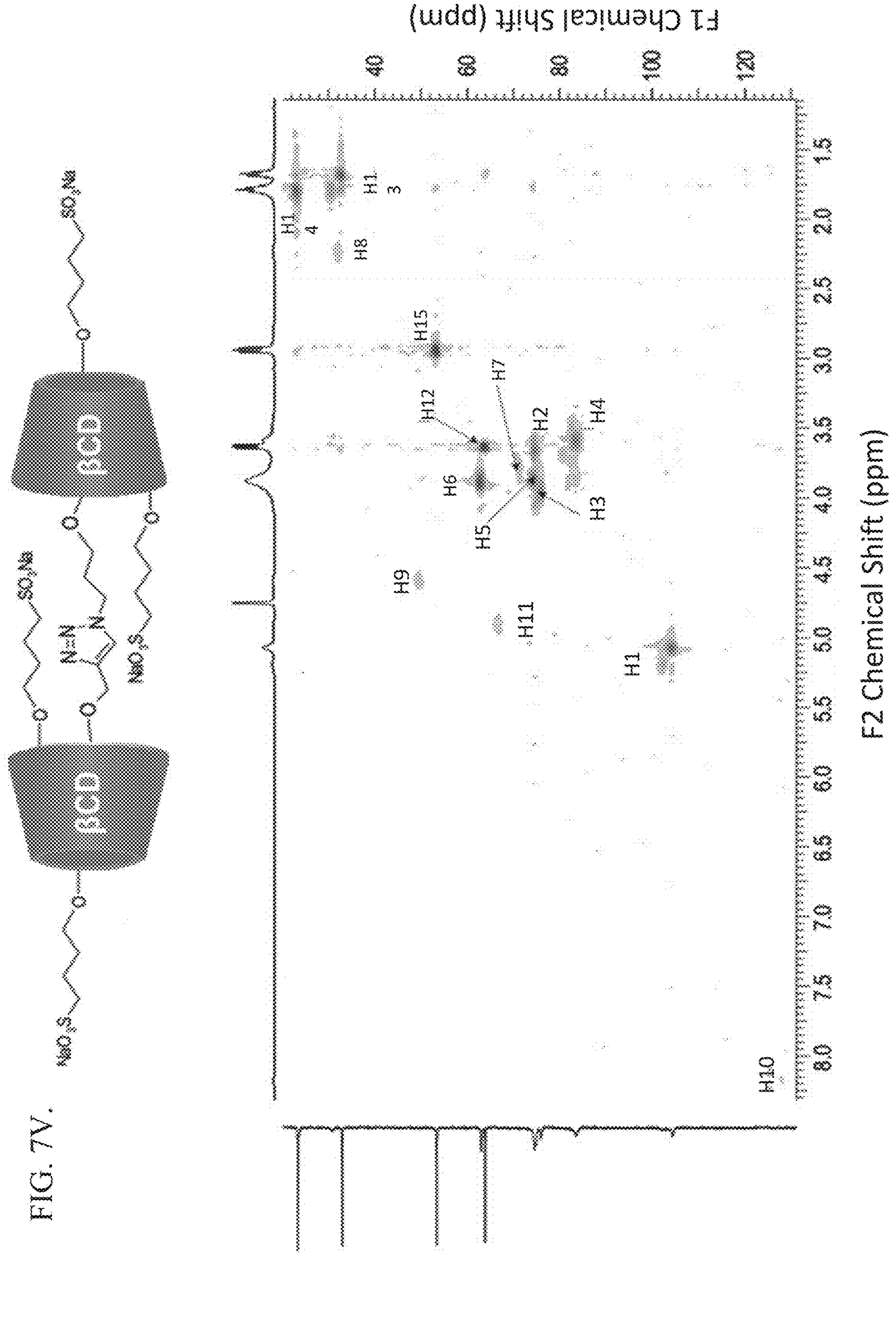
FIG. 7V. DEPT-edited HSQC spectrum of SB-(CD-TRIAZOLE-βCD) dimer Low DS with full assignment ($D_2O$, 298K). Converted to black and white.
Figure 7W:
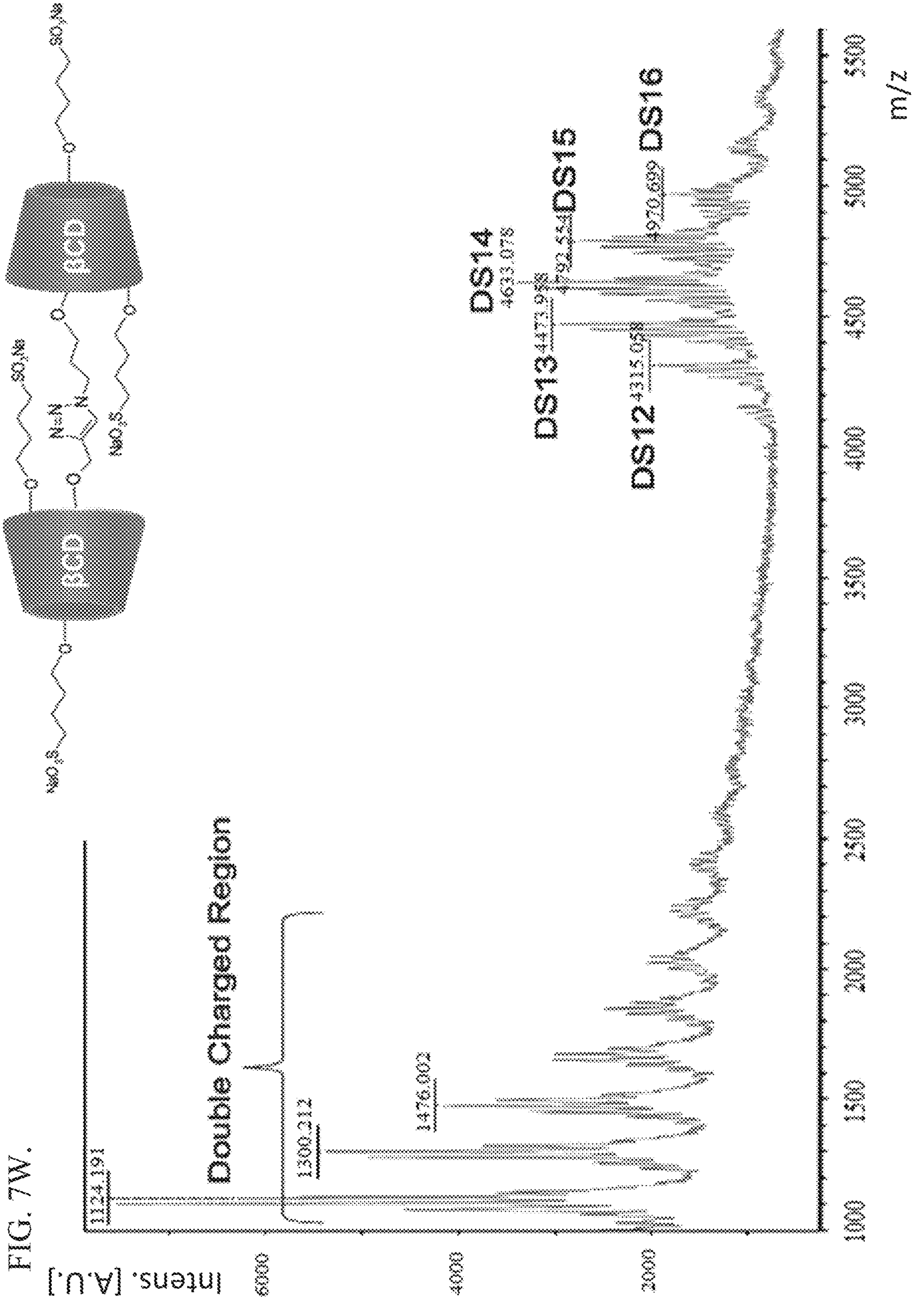
FIG. 7W. MALDI spectrum of SB-(CD-TRIAZOLE-βCD) High DS.

FIG. 7S illustrates the molecule to be synthesized.

This example describes the synthesis of sulfobutyl substituted CD dimers with a triazole-containing linker.

The preparation of the SB-DIM ERs was achieved in one-step reaction (FIG. 7Q).

Synthesis of Sb(βCd-Triazole-βCd) Dimer Low DS

βCD-TRIAZOLE-βCD dimer core (1.2 g, 0.5 mmol) was suspended in deionized H2O (60 mL) under vigorous stirring. Sodium hydroxide (0.39 g, 9.75 mmol) was added to the mixture and the obtained solution was heated at 60° C. 14-Butane sultone (0.88 mL, 1.17 g, 8.6 mmol) was added dropwise at 60° C. and the solution was heated at the same temperature for 3 h. The reaction was then heated to 90° C. for 1 additional hour in order to destroy the unreacted 1,4-butane sultone. The reaction mixture was cooled down and treated with ion exchange resins. Cationic exchange resin (H resin, 2 g) and anionic exchange resin ($OH^-$ resin, 2 g) were added to the solution, stirred for 15 min and filtered-off (the resins were washed with deionized water 3×15 mL). The resulting filtrate (final pH=7) was clarified with activated charcoal: under vigorous stirring, activated charcoal (0.3 g) was added to the solution, stirred for 30 min and filtered-off (the charcoal pad was washed with deionized water 3×15 mL).

Evaporation of the colorless solution under reduced pressure (40° C.) yielded a white powder (1.47 g).

Characterization

The reactions were monitored by TLC analysis and the resulting material was characterized by MALDI-TOF (FIG. 7R) and NMR analysis as in FIGS. 7T-7Z.

Synthesis of Sb(βCd-Triazole-βCd) Dimer High DS (CD-TRIAZOLE-βCD) dimer core (1.2 g, 0.5 mmol) was suspended in deionized H2O (60 mL) under vigorous stirring. Sodium hydroxide (1.22 g, 30.5 mmol) was added to the mixture and the obtained solution was heated at 60° C. 14-Butane sultone (2.8 mL, 3.72 g, 27.35 mmol) was added dropwise at 60° C. and the solution was heated at the same temperature for 3 h. The reaction was then heated at 90° C. for 1 additional hour in order to destroy the residual 1,4-butane sultone. The reaction mixture was cooled and treated with ion exchange resins. Cationic exchange resin ($H^+$ resin, 4 g) and anionic exchange resin ($OH^-$ resin, 4 g) were added to the solution, stirred for 15 min and filtered-off (the resins were washed with deionized water 3×15 mL). The resulting filtrate (final pH=7) was clarified with activated charcoal: under vigorous stirring, activated charcoal (0.5 g) was added to the solution, stirred for 30 min and filtered (the charcoal pad was washed with deionized water 3×15 mL). Evaporation of the colorless solution under reduced pressure (40° C.) yielded a white powder (1.51 g).

Characterization

Figure 7X:
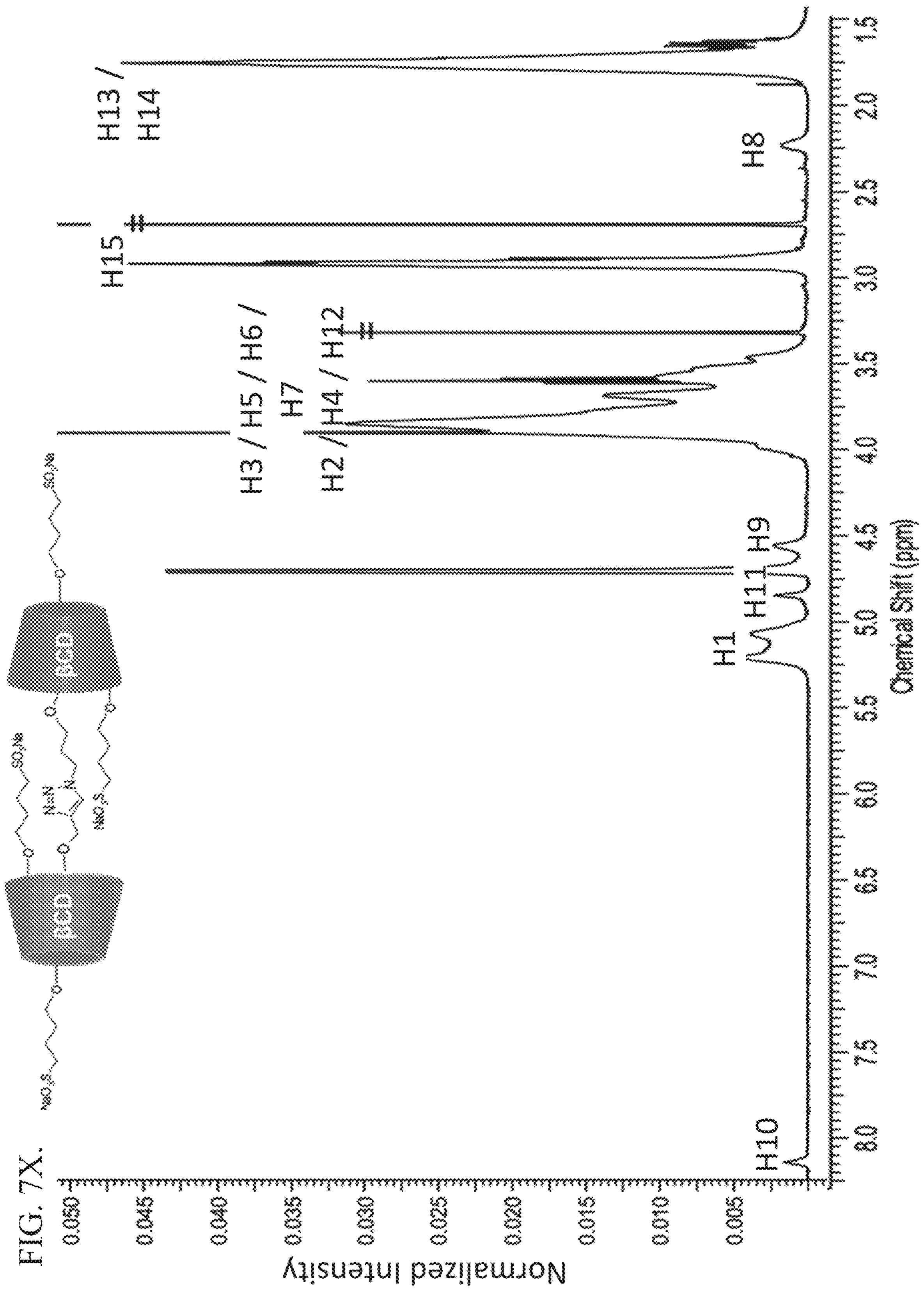
FIG. 7X. $^1$H-NMR spectrum of SB(βCD-TRIAZOLE-βCD) High DS ($D_2O$, 298 K).
Figure 7Y:
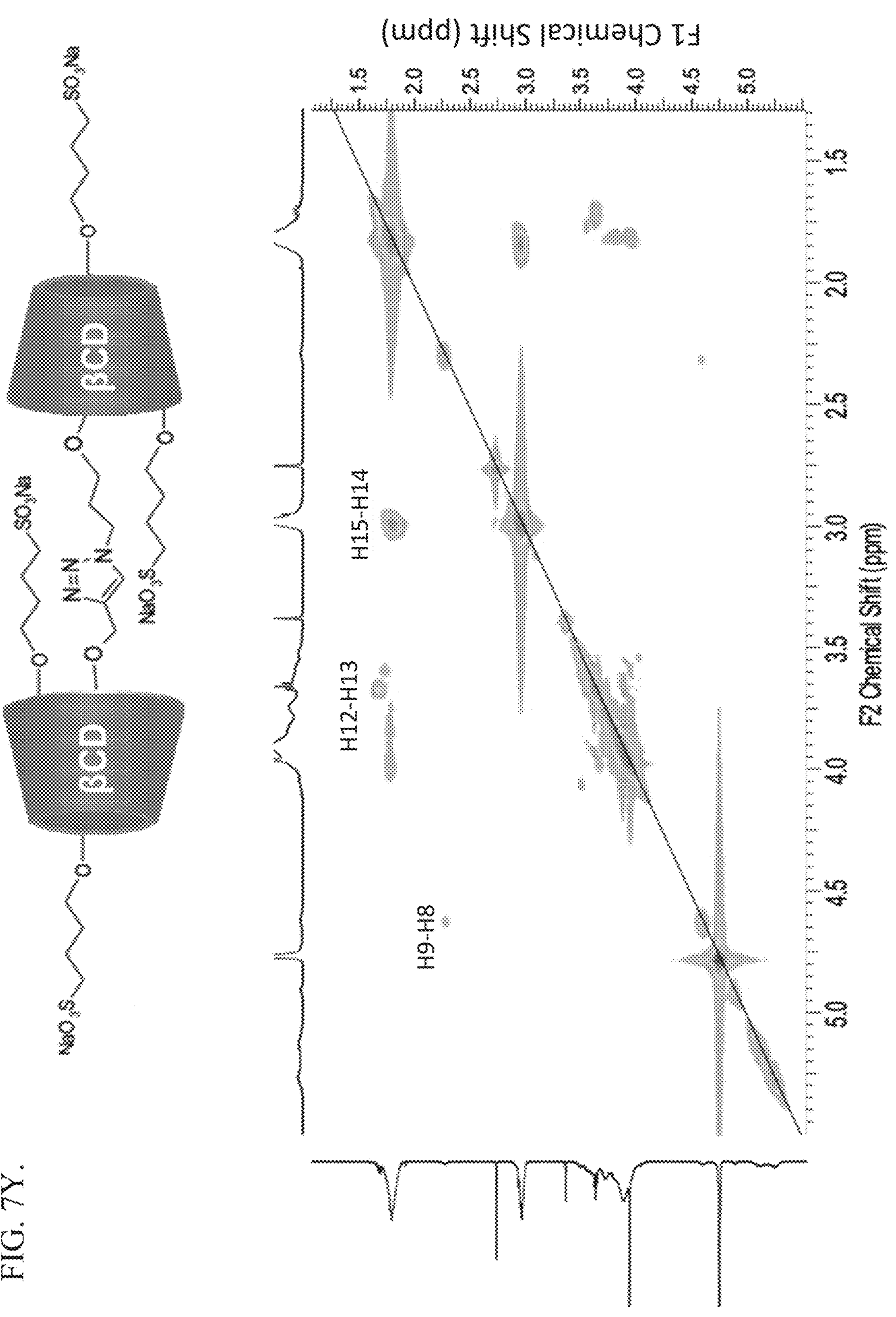
FIG. 7Y. COSY spectrum of SB(βCD-TRIAZOLE-βCD) dimer High DS with partial assignment ($D_2O$, 298K).
Figure 7Z:
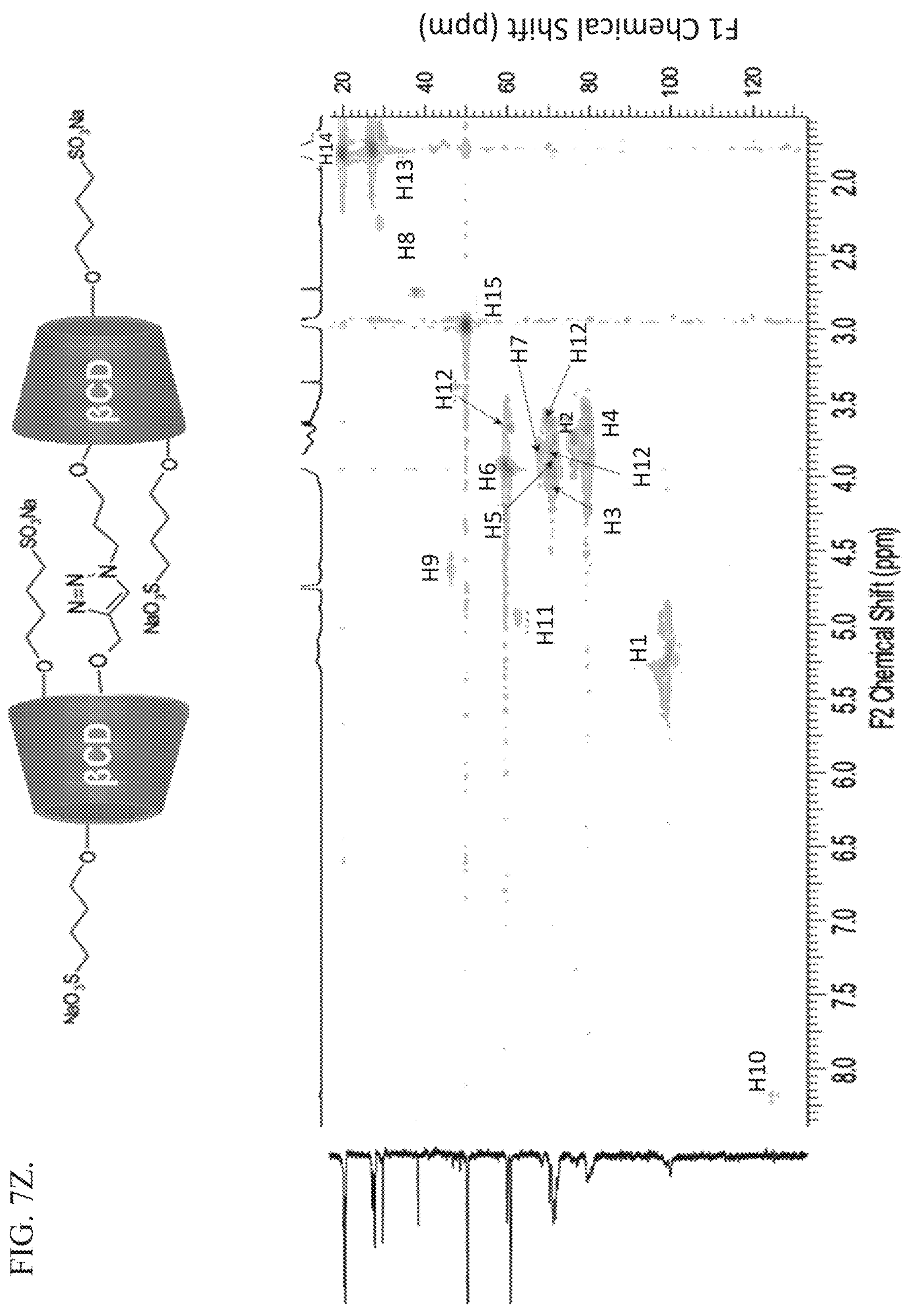
FIG. 7Z. DEPT-edited HSQC spectrum of SB(βCD-TRIAZOLE-βCD) dimer High DS with full assignment ($D_2O$, 298K). Converted to black and white.
Figure 7A:
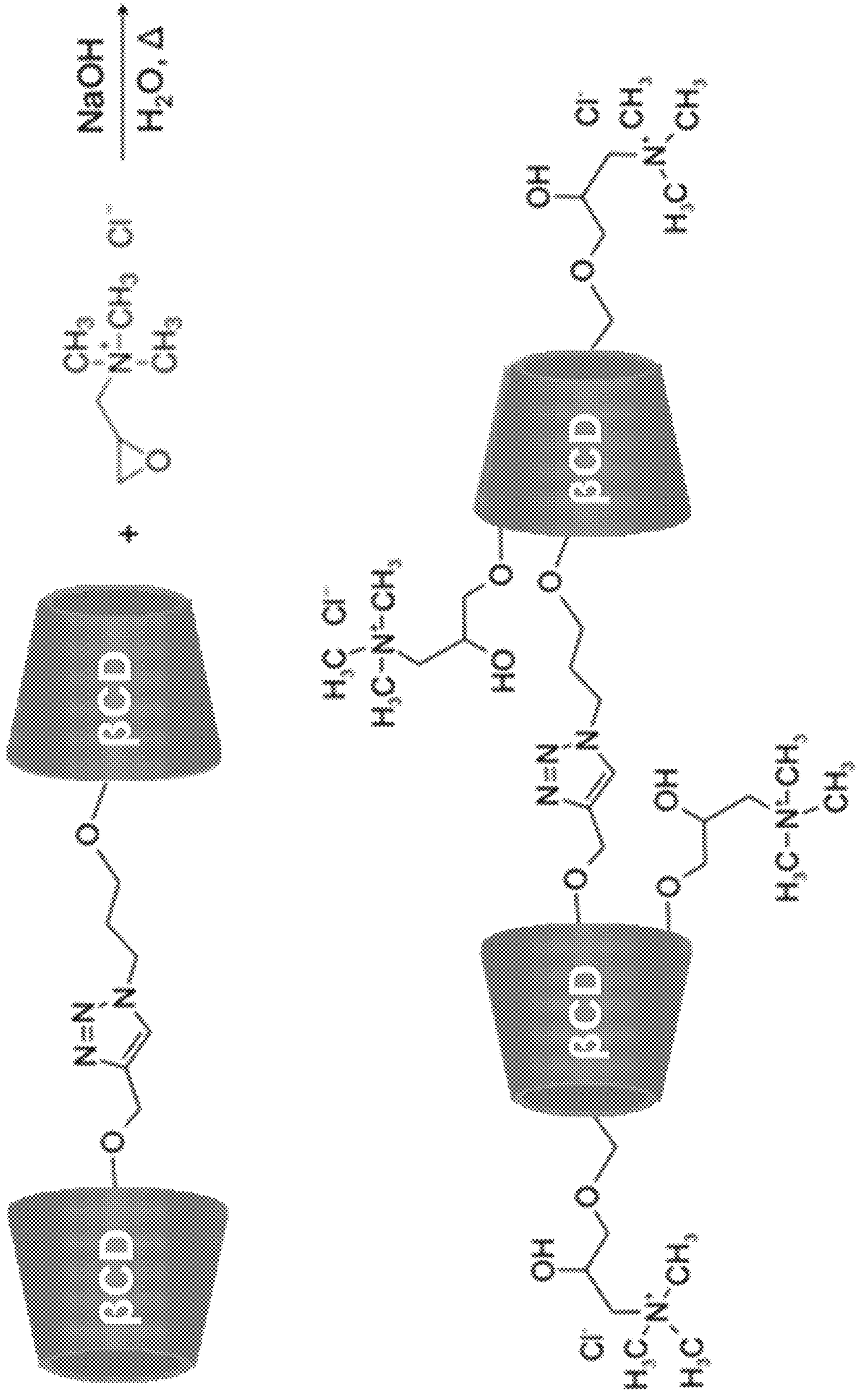
Figure 7A:
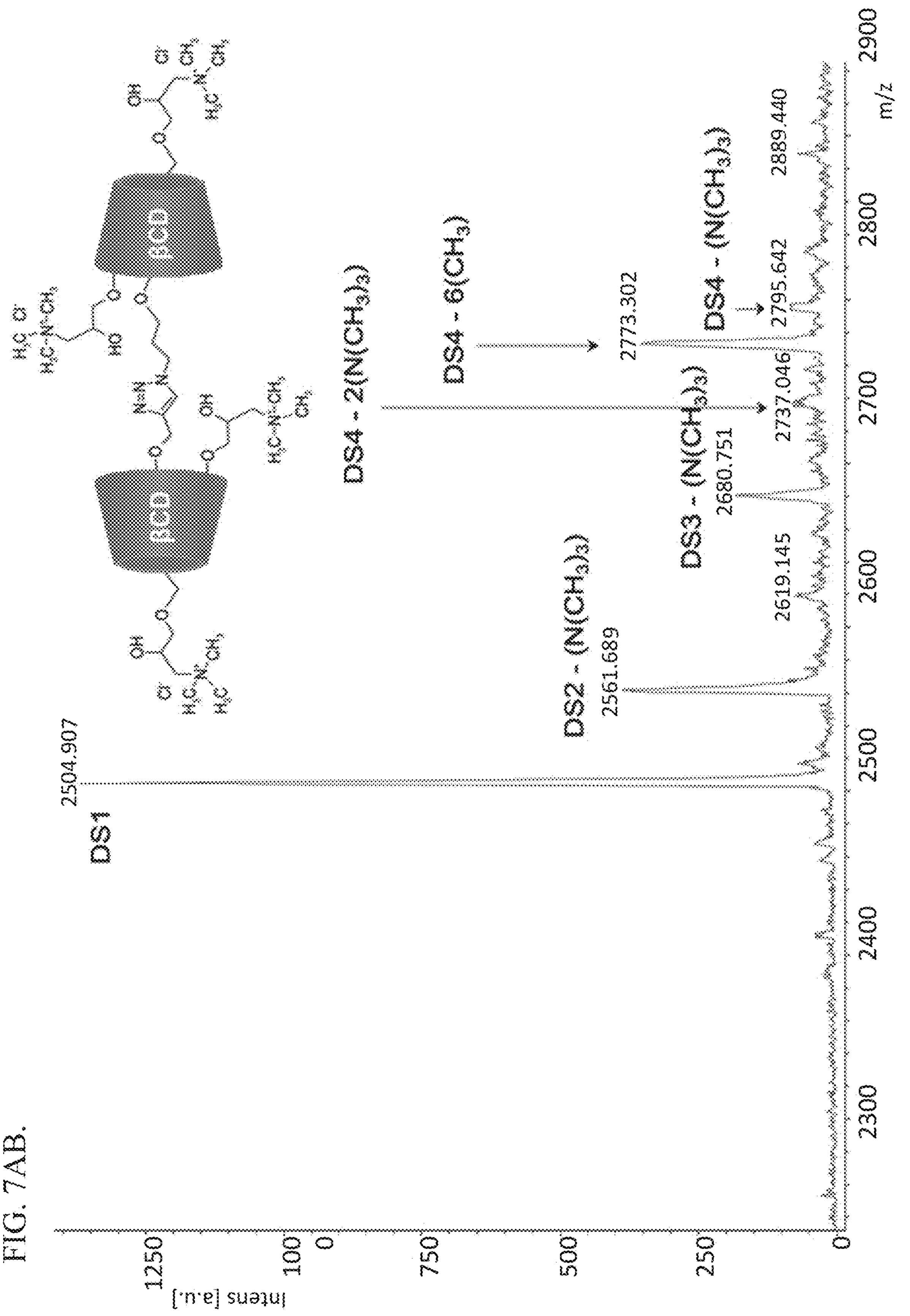
Figure 7A:
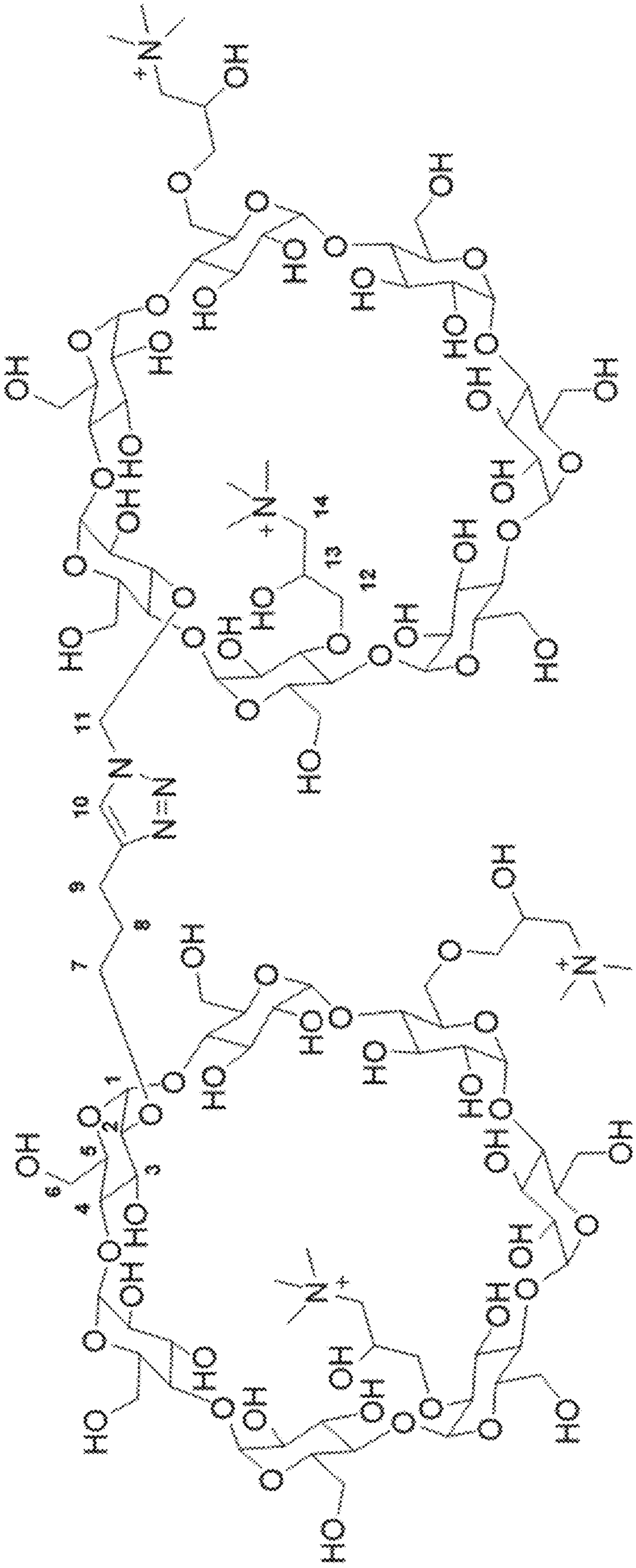
Figure 7A:
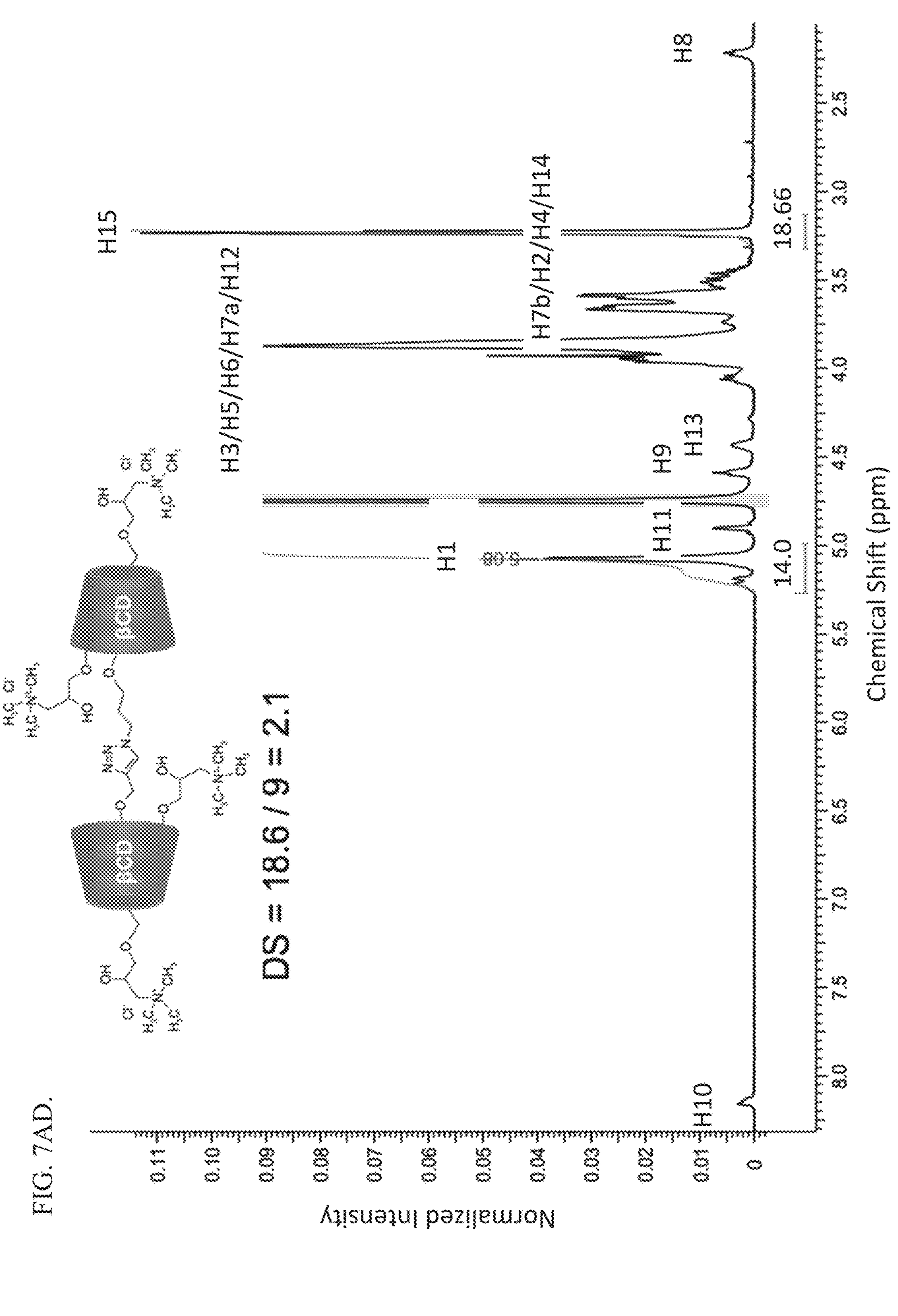
Figure 7A:
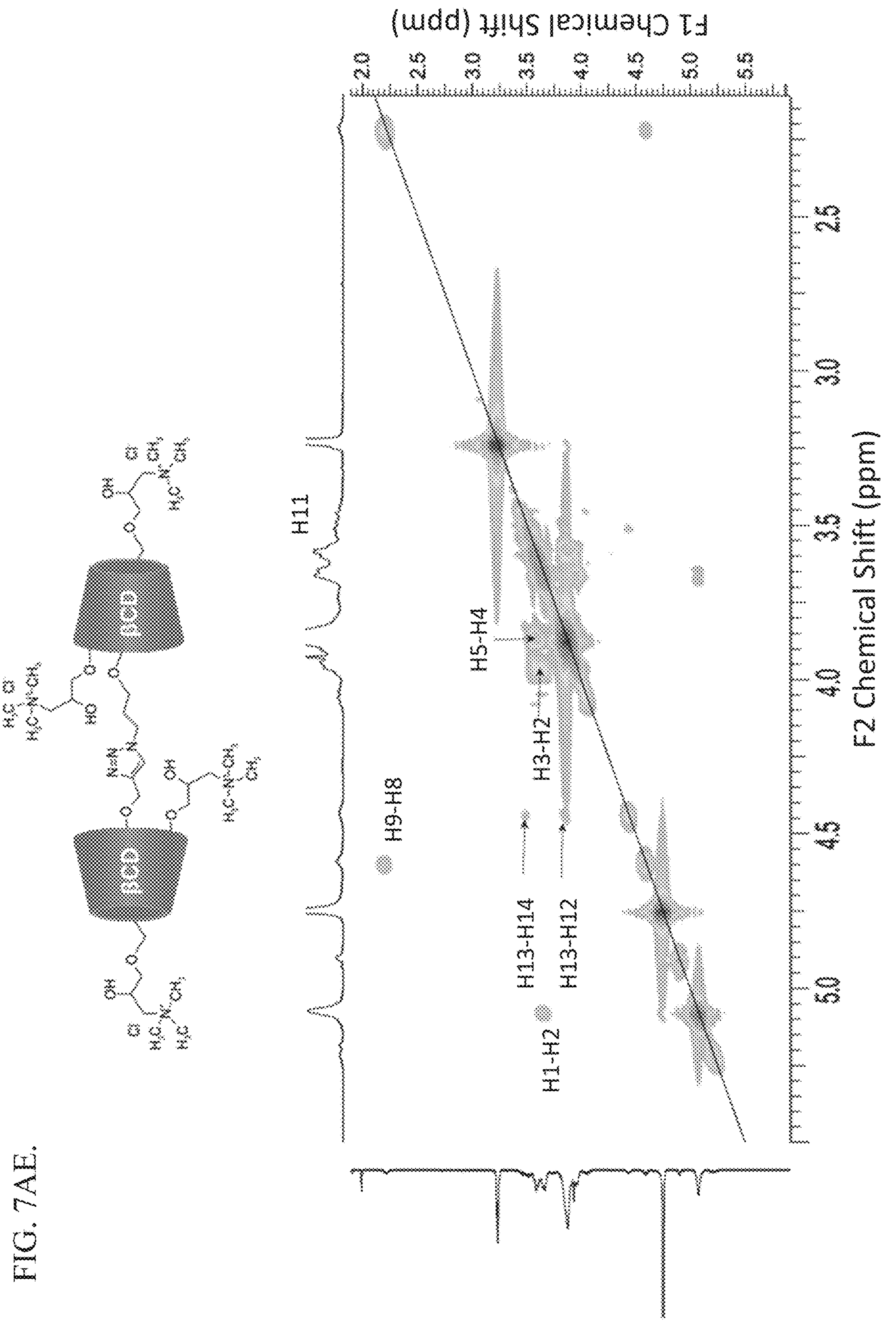
Figure 7A:
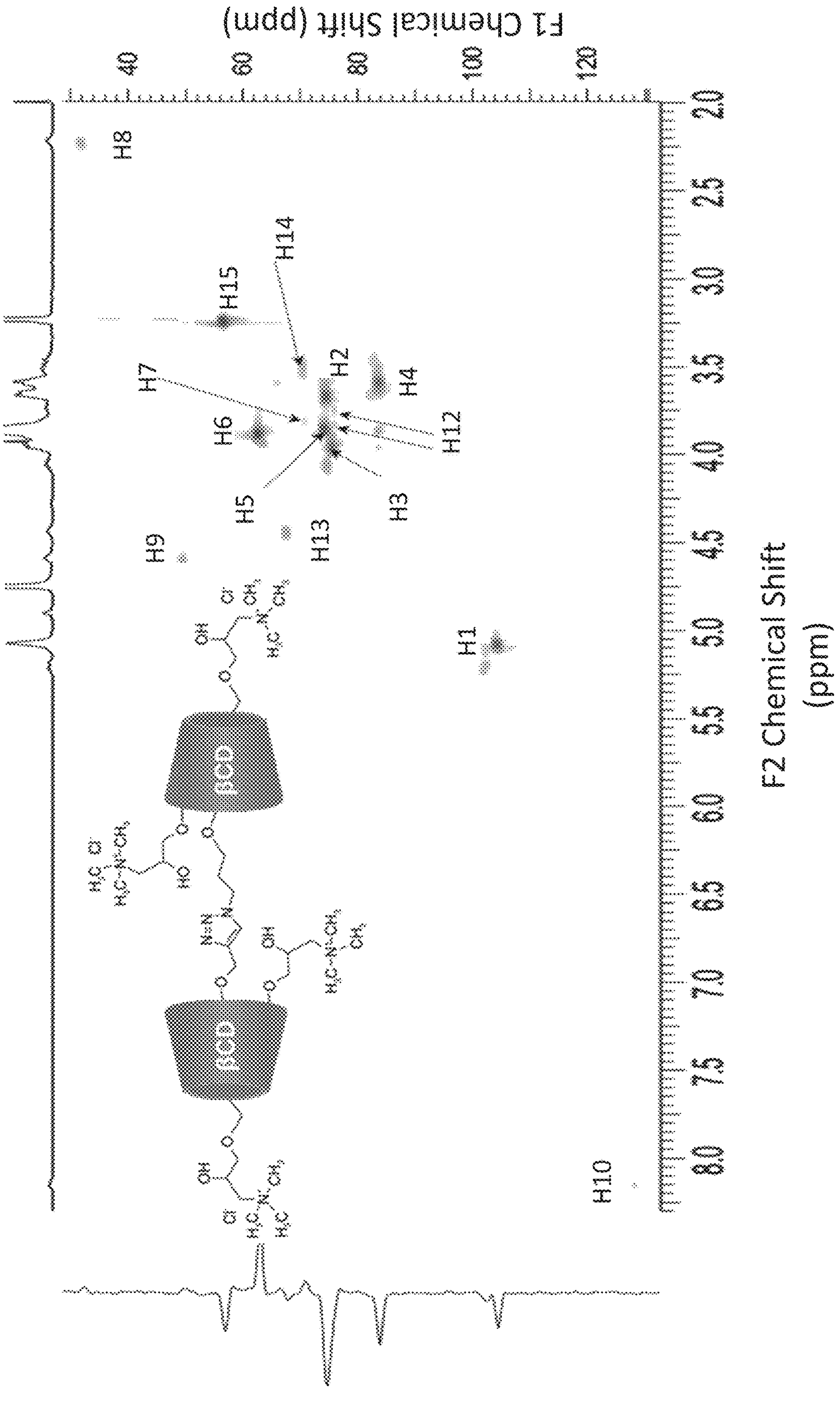
Figure 7A:
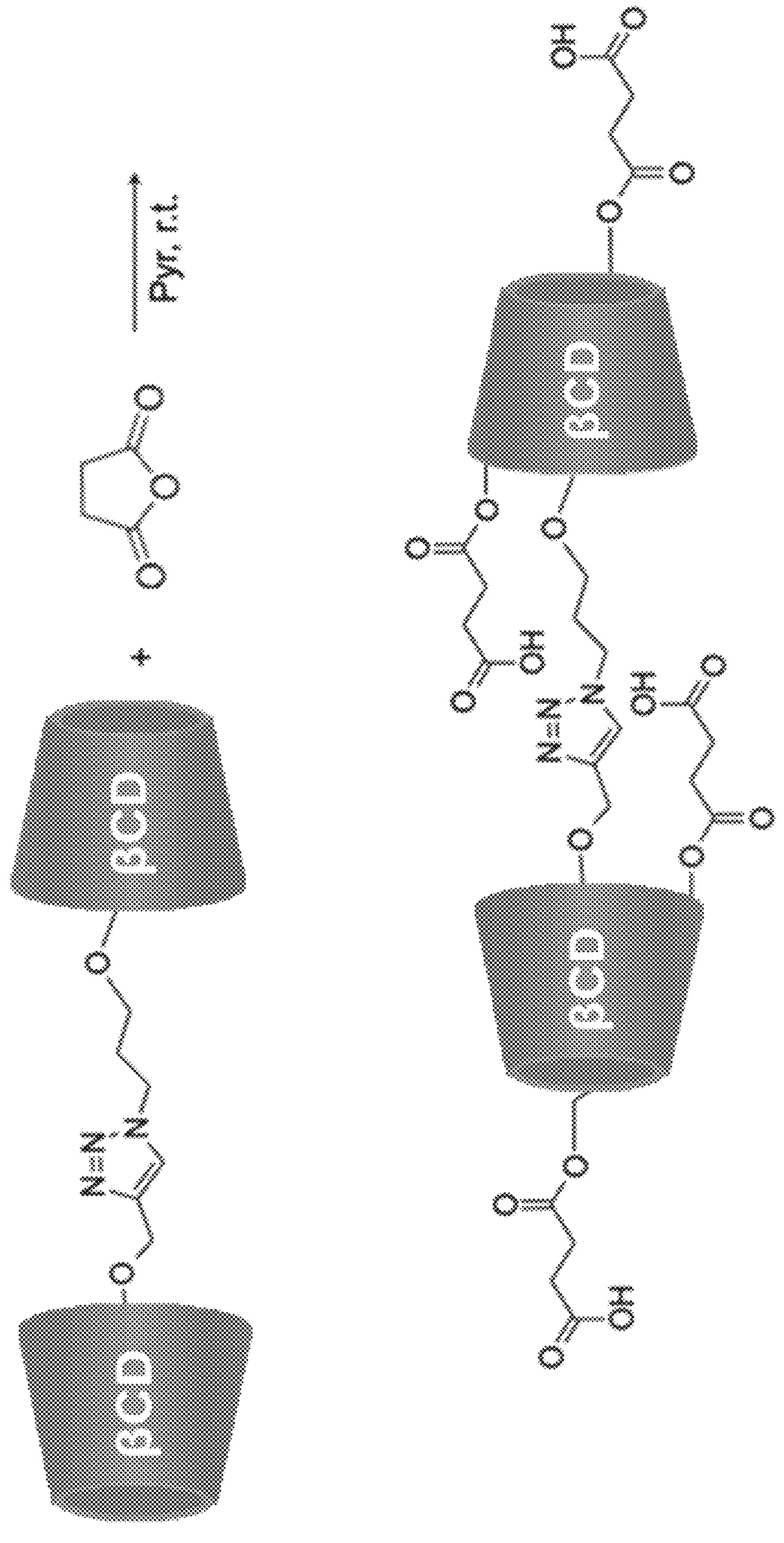
Figure 7A:
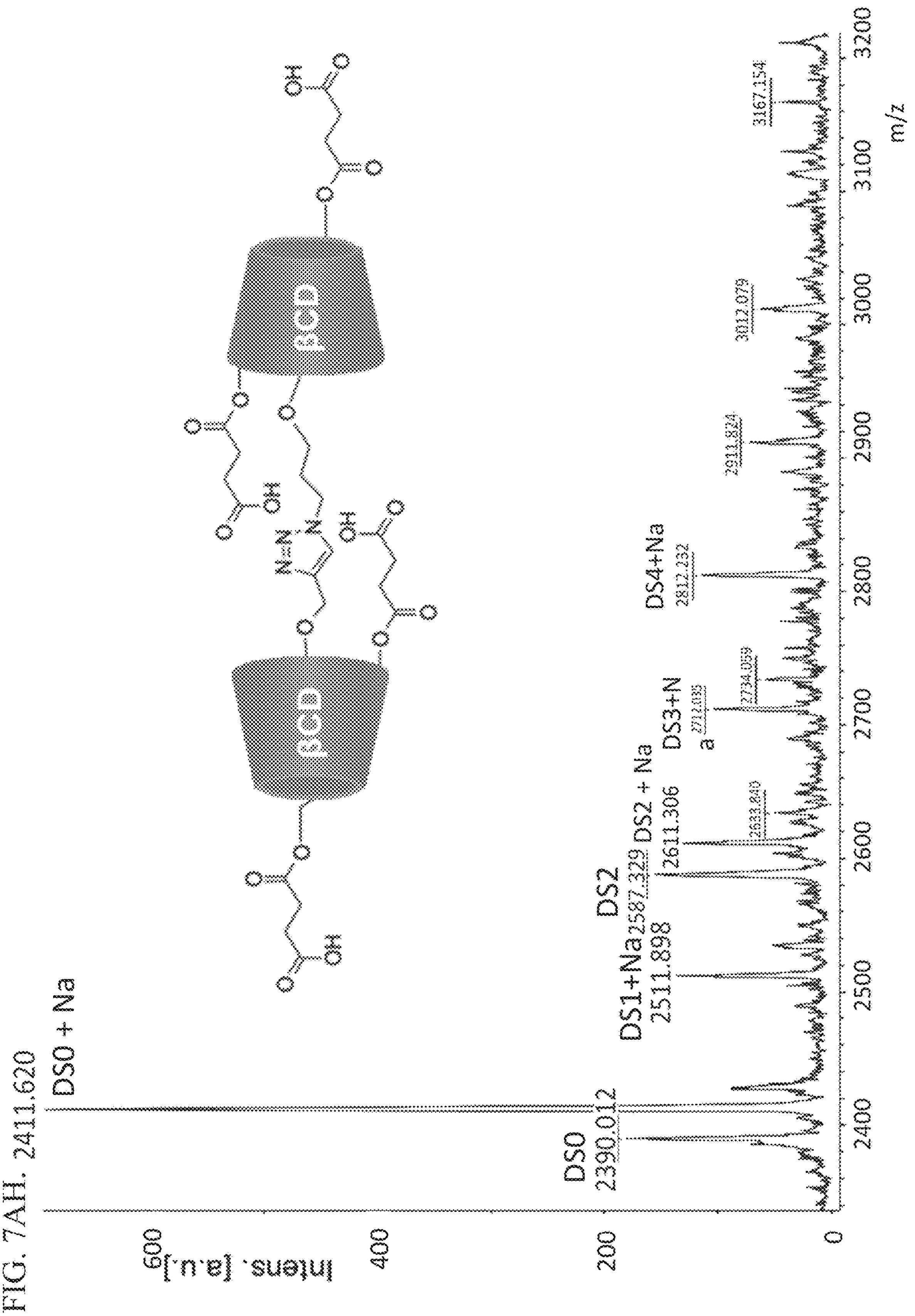
Figure 7A:
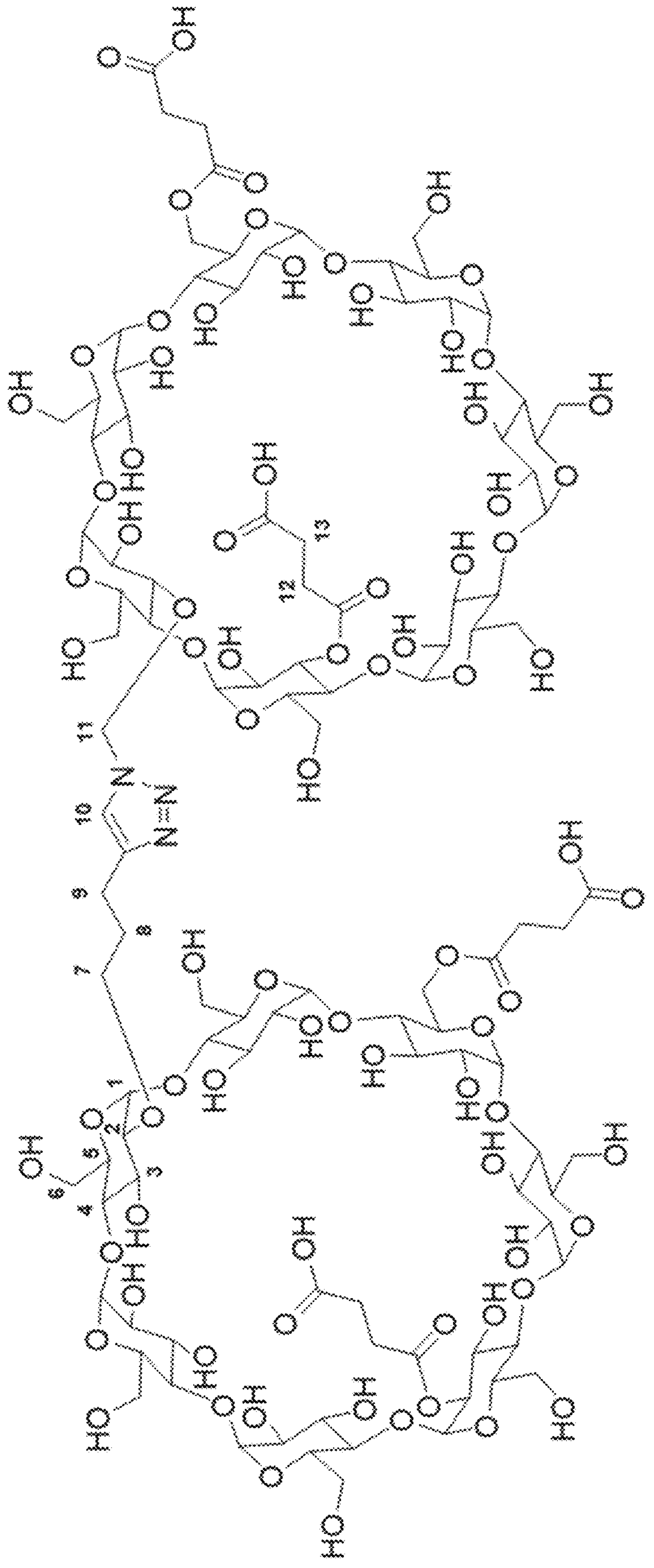
Figure 7A:
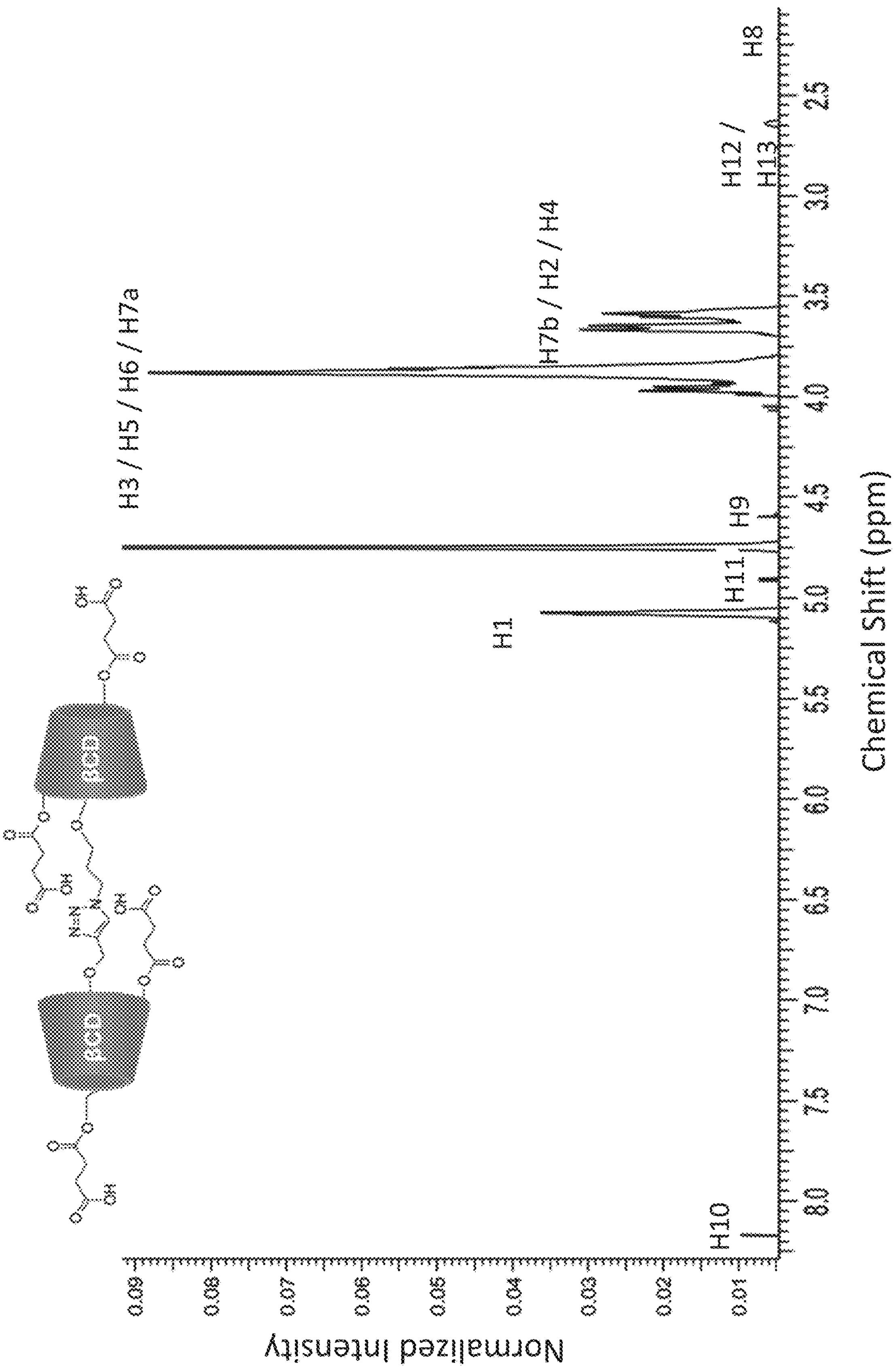
Figure 7A:
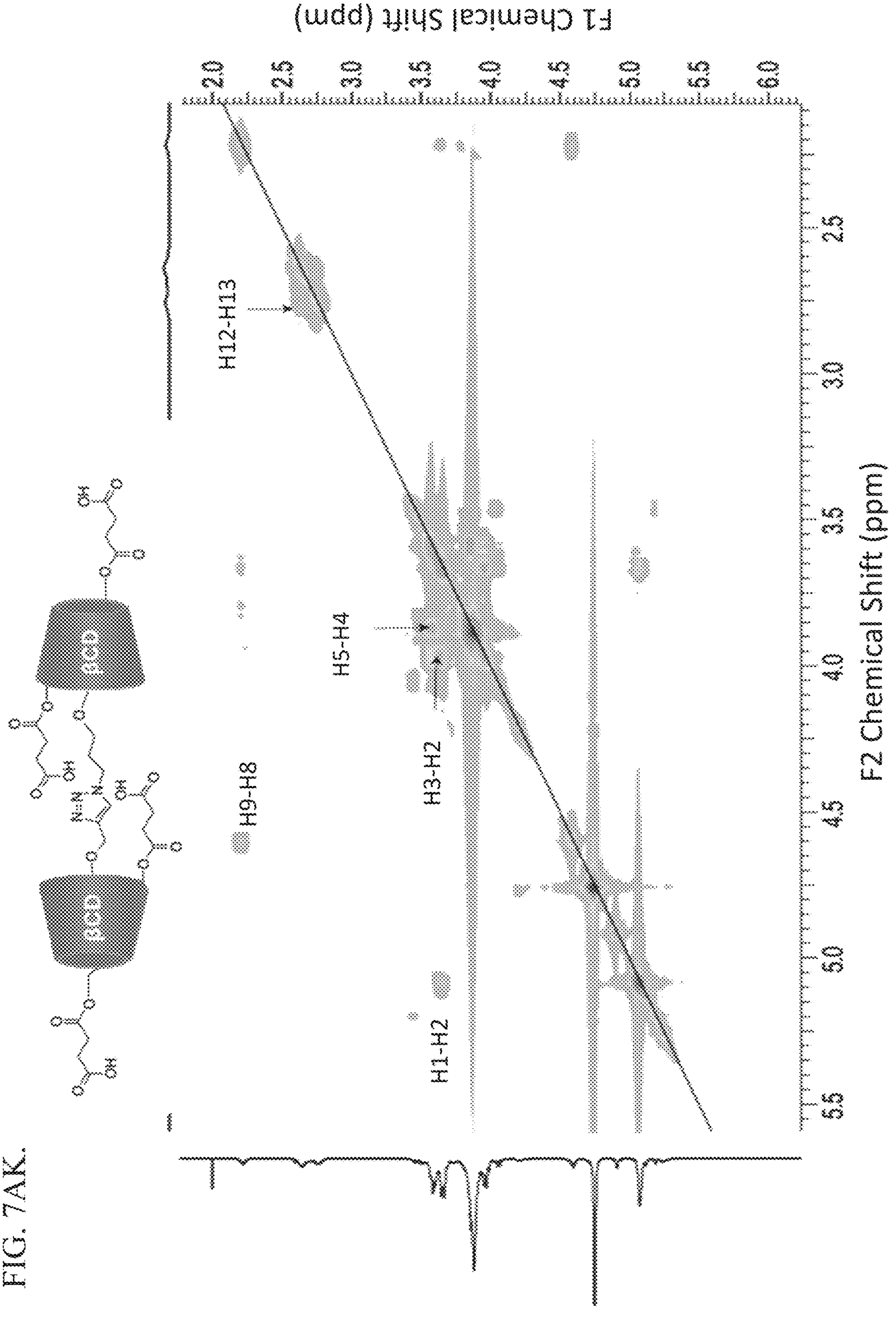
Figure 7A:
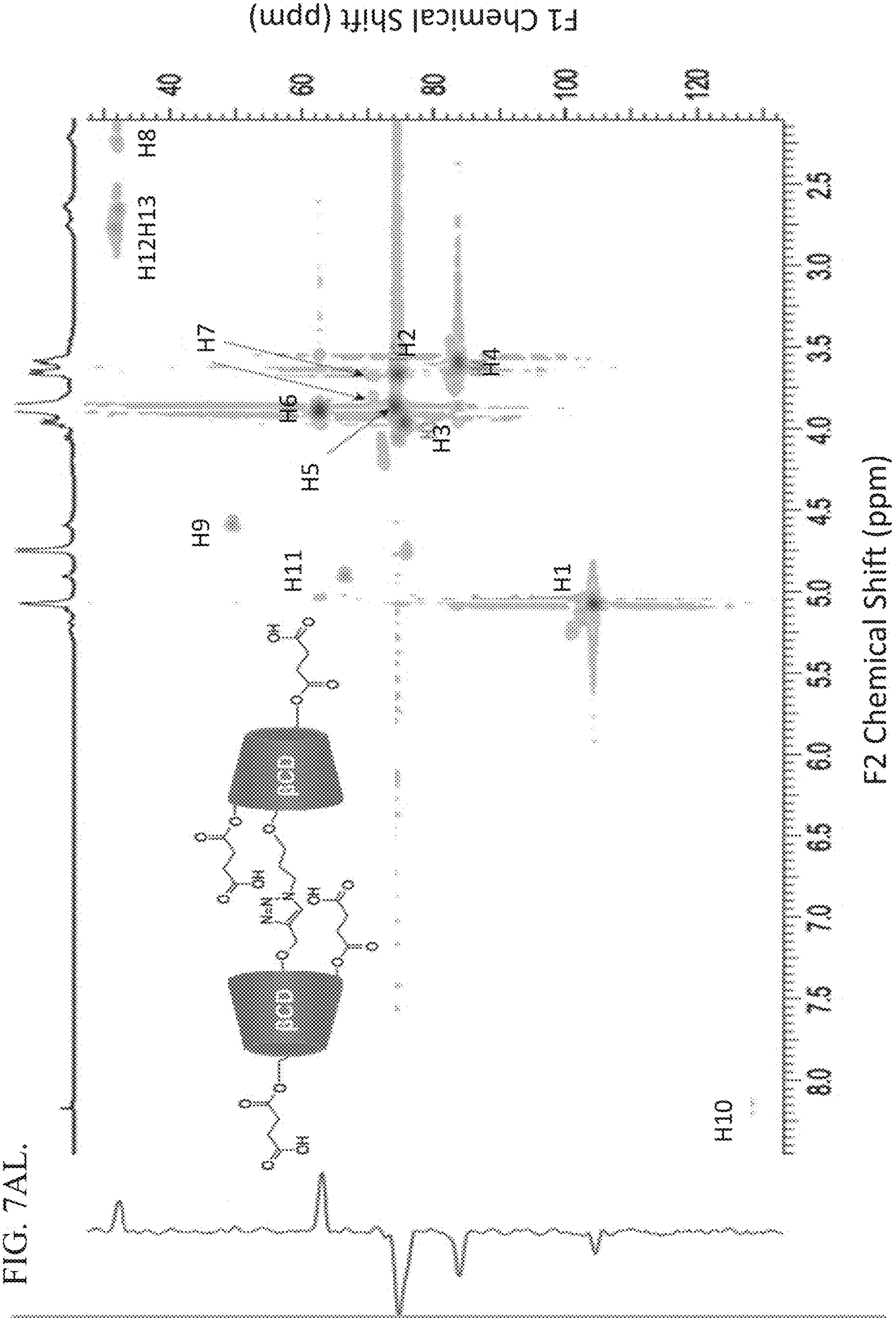
Figure 8B:
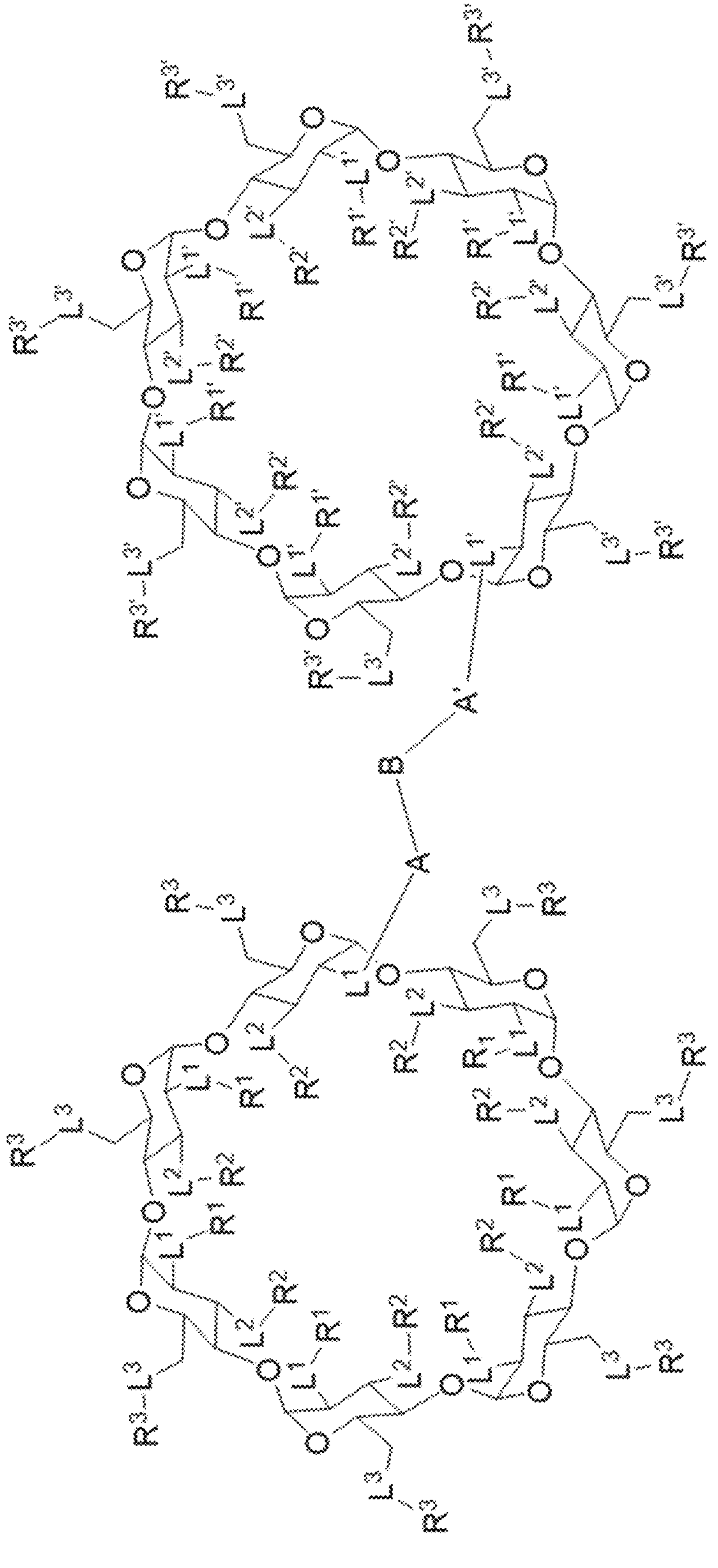
FIG. 8B depicts the chemical structure of a homodimer consisting of two βCD covalently bonded at the L1 and L1' positions on the secondary face of each CD with general linker A-B-A'.
Figure 8C:
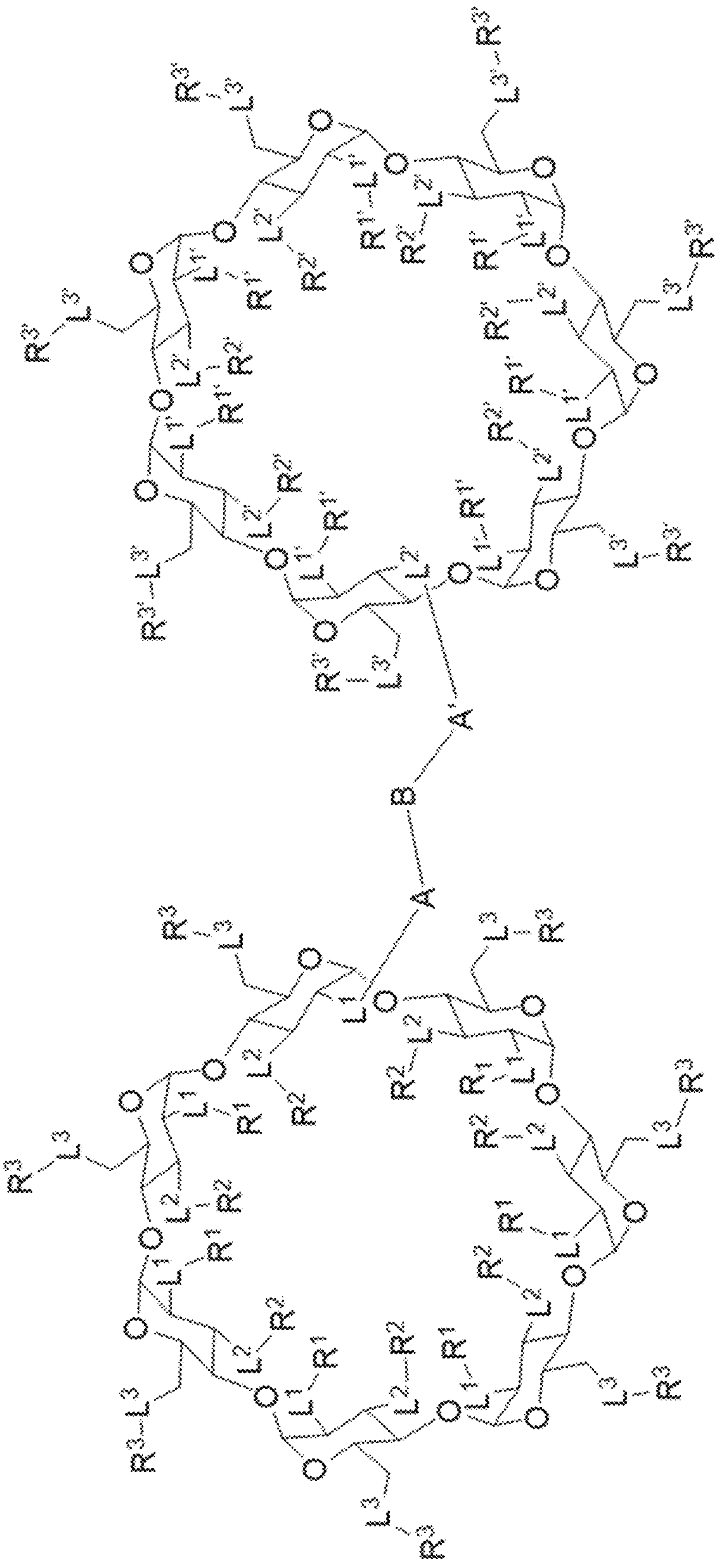
FIG. 8C depicts the chemical structure of a homodimer consisting of two βCD covalently bonded at the L1 and L2' positions on the secondary face of each CD with general linker A-B-A'.
Figure 8D:
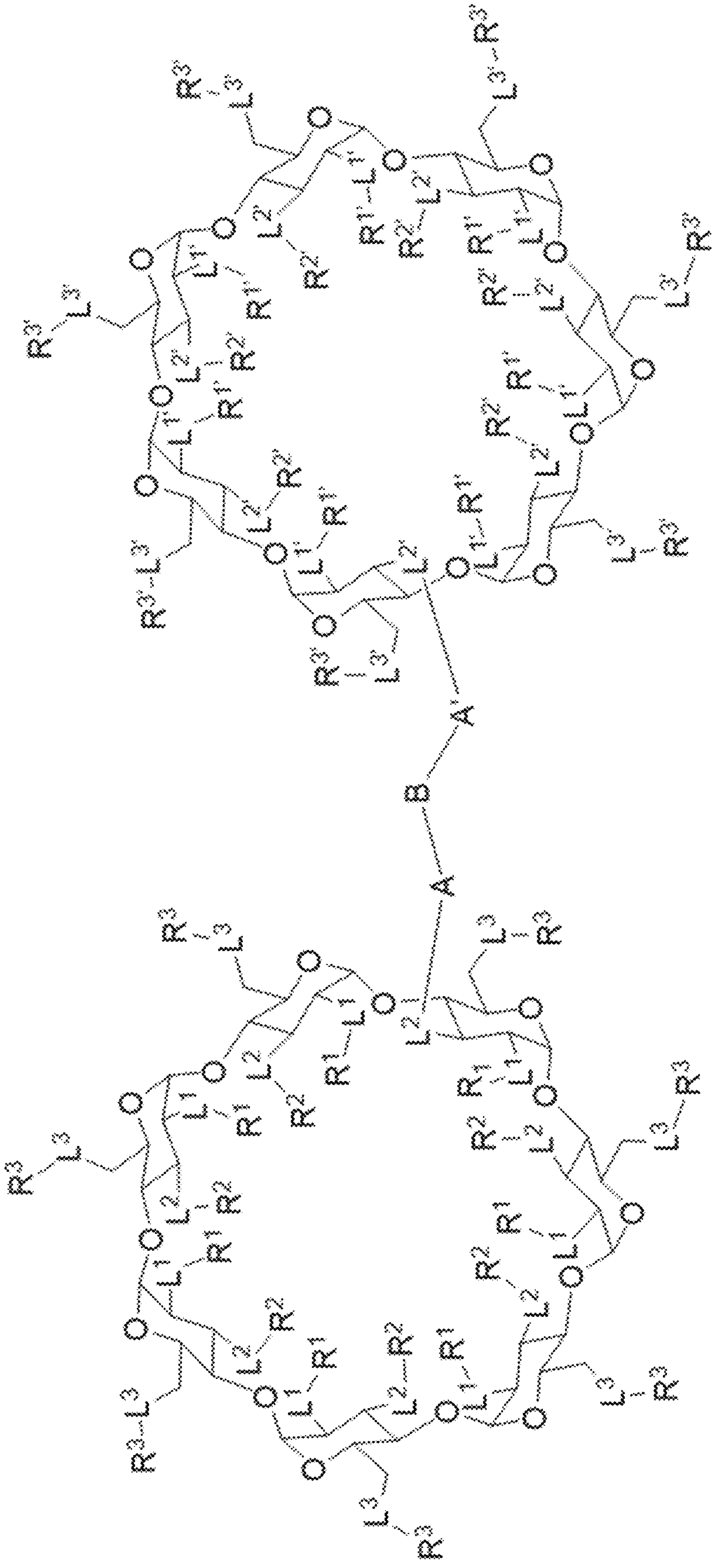
FIG. 8D depicts the chemical structure of a homodimer consisting of two βCD covalently bonded at the L2 and L2' positions on the secondary face of each CD with general linker A-B-A'.
Figure 9A:
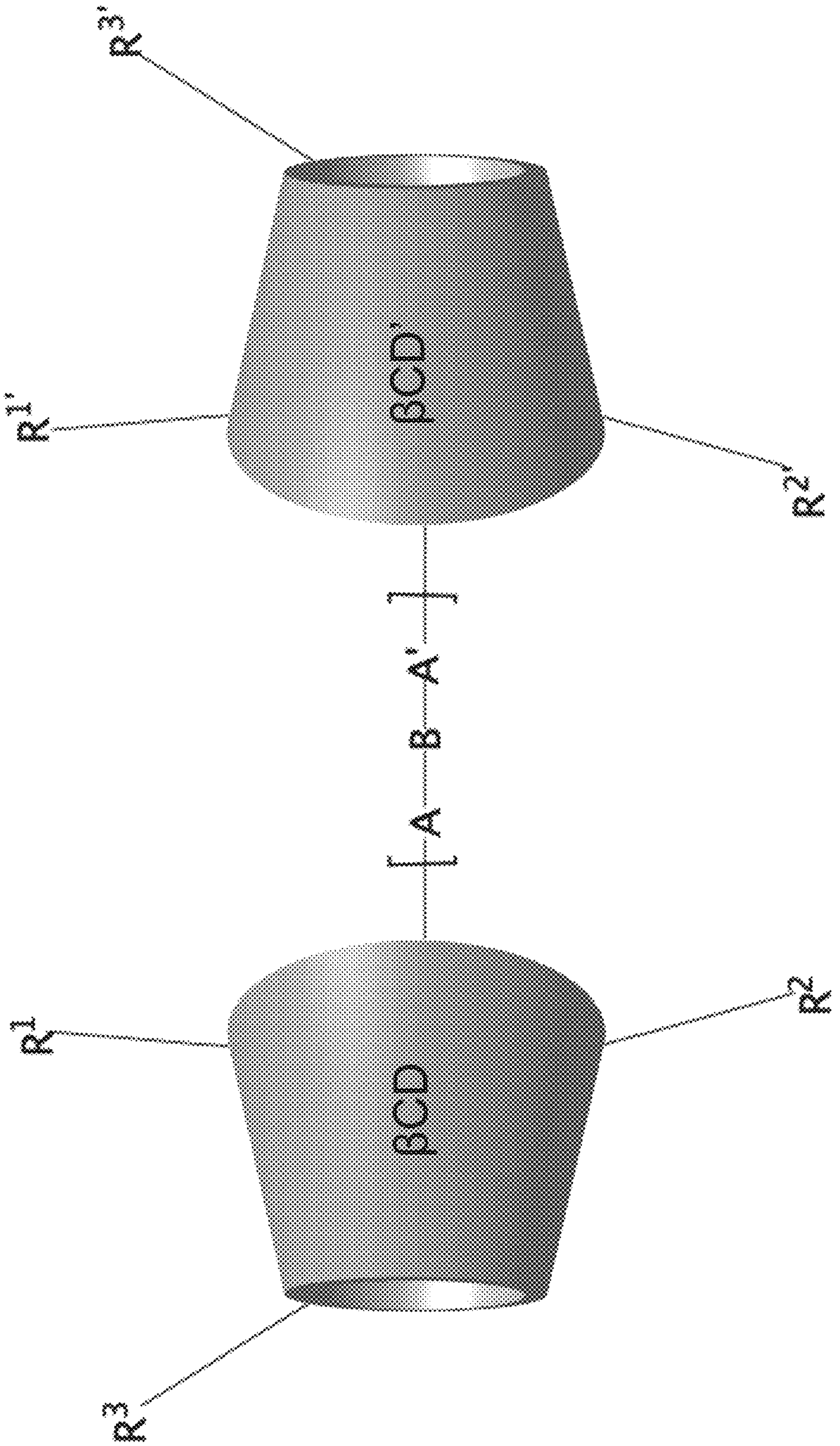
FIG. 9A depicts a schematic structure of a dimerized βCD with a general linker denoted by A-B-A', wherein said A-B-A' are as defined herein. Both monomers are randomly substituted with the same functional group at the primary and secondary faces.
Figure 9B:
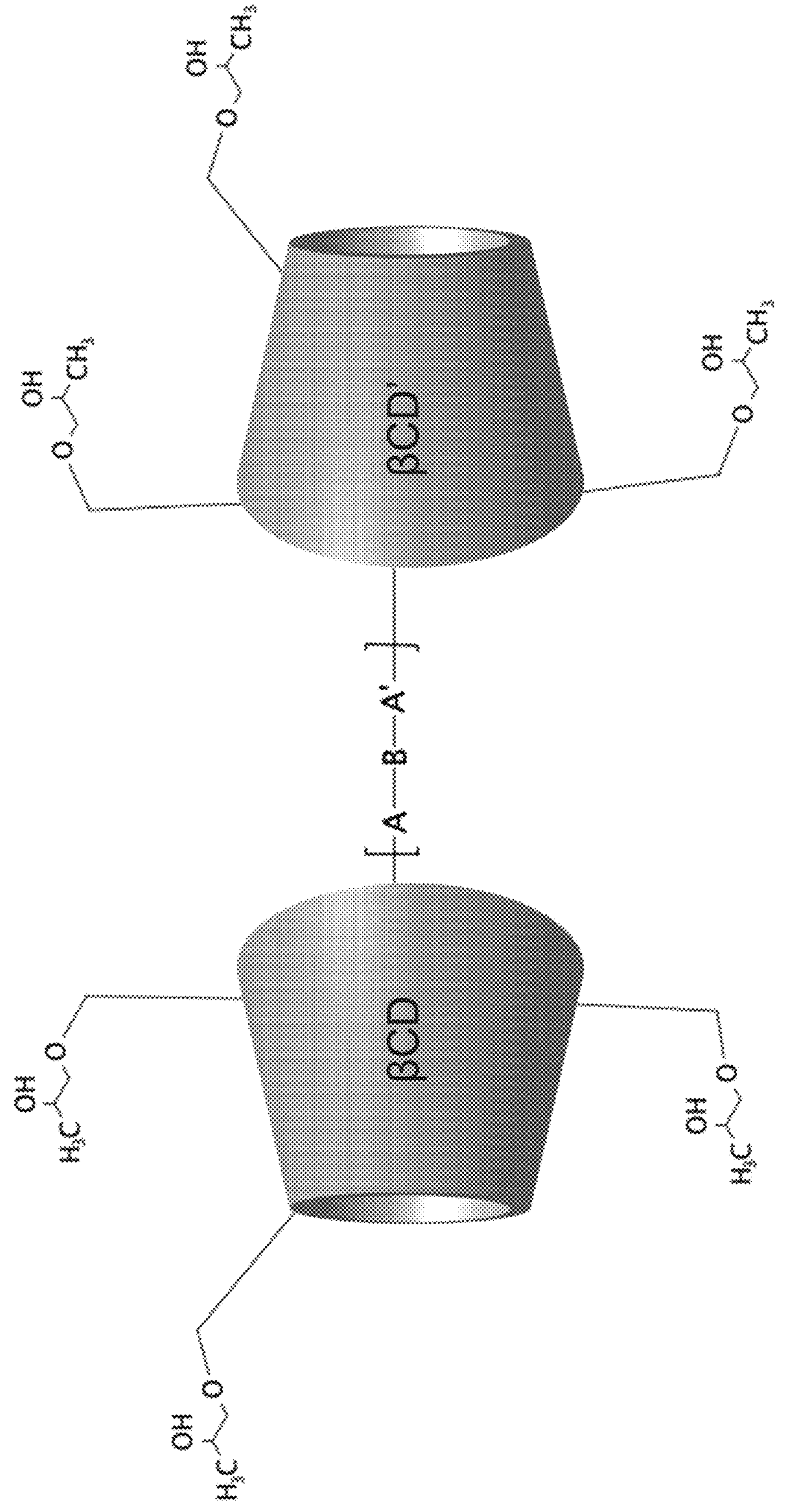
FIG. 9B depicts a schematic structure of a 2-hydroxypropyl substituted DS6 βCD homodimer with a general A-B-A' linker, wherein said A-B-A' are as defined herein.
Figure 9C:
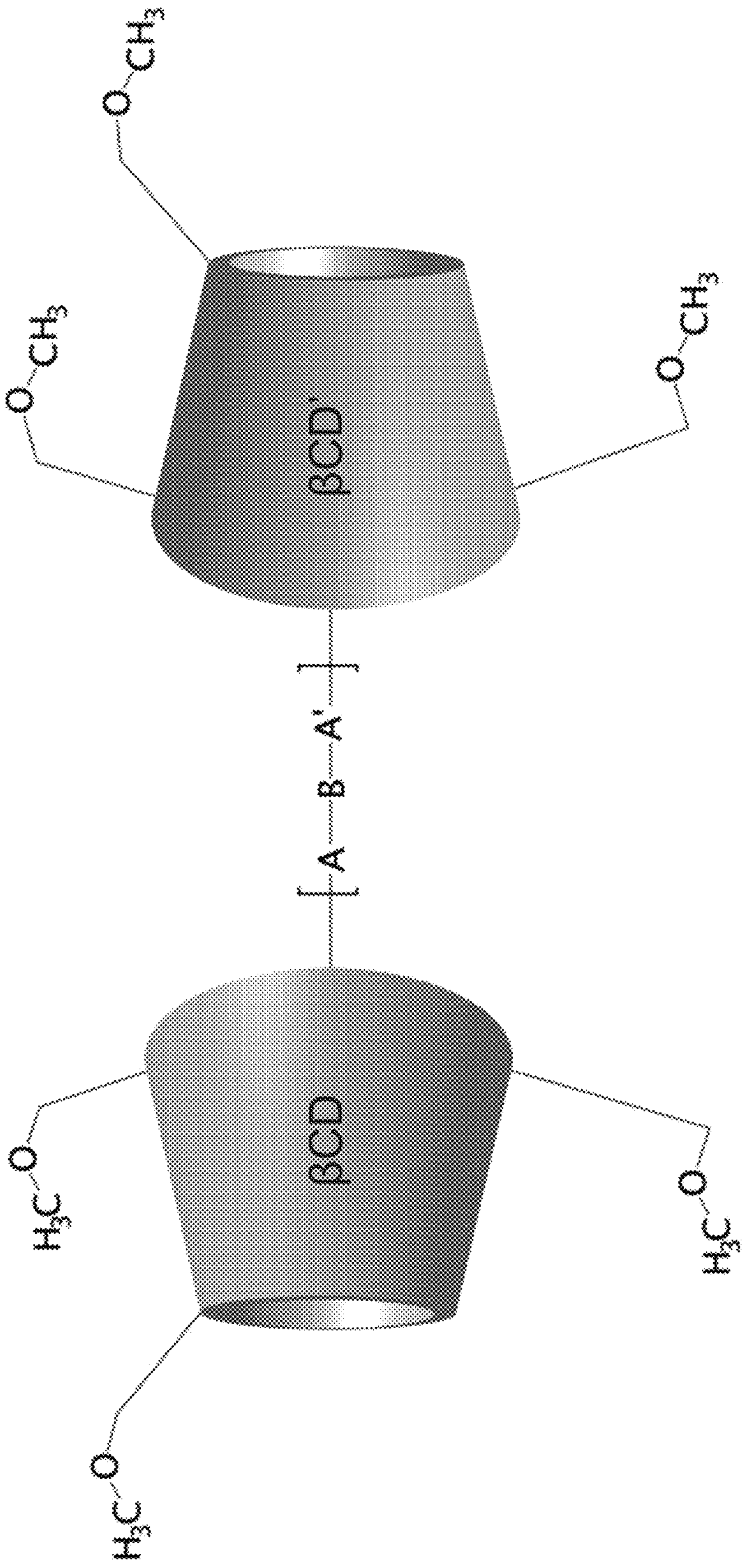
FIG. 9C depicts a schematic structure of a methyl substituted βCD homodimer with a general A-B-A' linker, wherein said A-B-A' are as defined herein.
Figure 9D:
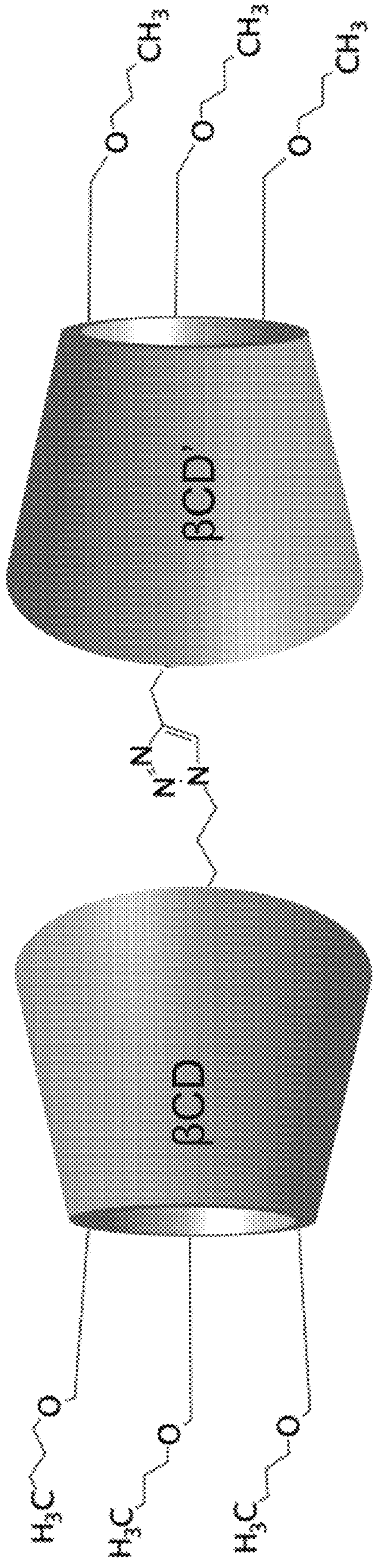
FIG. 9D depicts a schematic structure of a triazole-linked βCD homodimer substituted with butyl moieties on the primary side DS6 assessed in MD simulations.
Figure 9E:
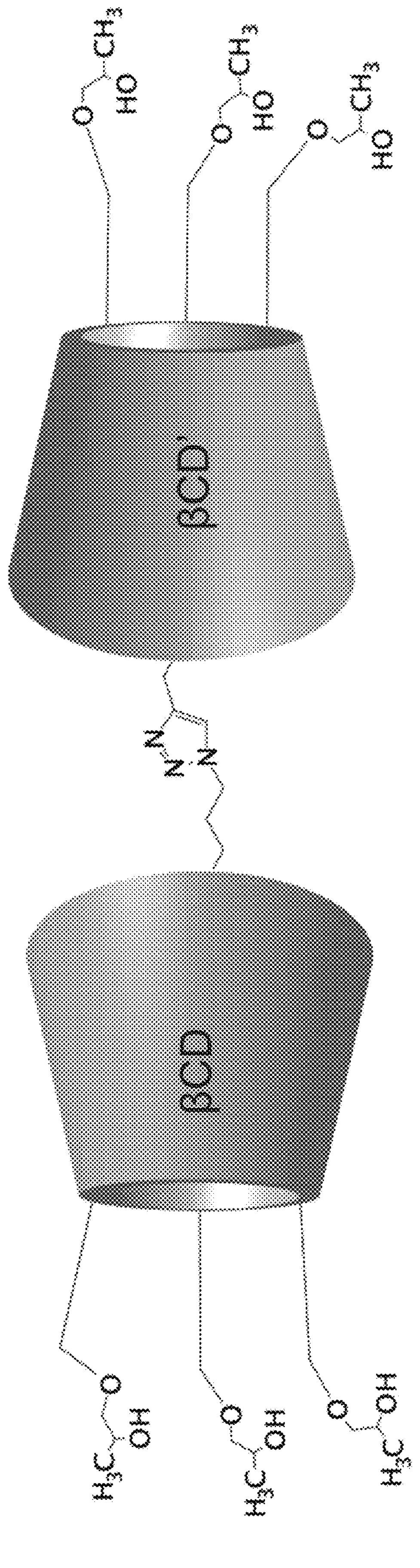
FIG. 9E depicts a schematic structure of a triazole-linked βCD homodimer substituted with (2-hydroxypropyl) moieties on the primary side DS6 assessed in MD simulations.

The resulting material was characterized by MALDI-TOF (FIG. 7W) and NMR analysis as in FIGS. 7X-7Z.

Example 8. Synthesis of Quaternary Ammonium Substituted CD Dimers

FIG. 7AC illustrates the molecule to be synthesized.

This example describes the synthesis of quaternary ammonium substituted CD dimers with a triazole-containing linker.

Quaternary Ammonium (Cd-Triazole-βCd) Dimer (Exemplary Synthesis)

The preparation of the QA dimer was accomplished in one-step reaction (see FIG. 7AA). The βCD-TRIAZOLE-βCD dimer core is prepared according to the synthetic strategy described in Example 5 above.

Qa(βCd-Triazole-βCd) Dimer (Exemplary Synthesis)

βCD-TRIAZOLE-βCD dimer core (1.2 g, 0.5 mmol) was suspended in deionized H2O (100 mL) under vigorous stirring and sodium hydroxide (0.39 g, 9.8 mmol) was added. The resulting slightly yellow suspension was stirred for 30 min until complete solubilization. The temperature of the yellowish, transparent solution stabilized at 5-10° C. and glycidyltrimethylammonium chloride (1.17 mL, 1.32 g, 8.7 mmol) was added in one portion under vigorous stirring. The reaction mixture was stirred for 24 h at room temperature, then the temperature of solution was stabilized at 5-10° C. and a second portion of glycidyltrimethylammonium chloride was added (0.4 mL, 0.45 g, 3 mmol). The reaction mixture was heated at 50° C. for 3 hours, then cooled-down and treated with ion exchange resins: $H^+$ resin (6 g) and $OH^-$ (6 g) resin were added to the solution, stirred for 15 min and filtered (the resins were washed with deionized water 3×15 mL). The resulting filtrate (final pH=7) was clarified with activated charcoal: under vigorous stirring, activated charcoal (0.2 g) was added to the solution, stirred for 30 min and filtered-off (the charcoal pad was washed with deionized water 3×15 mL). Evaporation of the colorless solution under reduced pressure (40° C.) yielded the title compound as white powder (~800 mg).

Characterization

The resulting material was characterized by MALDI-TOF (FIG. 7AB) and NMR analysis as in FIGS. 7AD-7AF.

In the case of QA-BCD derivatives the typical Gaussian distribution with regular patterns observed during the MALDI analysis for random substituted derivatives is missing, while irregular patterns of fragmentation are detectable. The identification/assignment of these irregular peaks is complicated as no simple pattern of fragmentation can be predicted. The irregular pattern observed in the MALDI spectrum is most probably due to the instability of the trimethylammonium moieties under the experimental conditions. In particular, the elimination products are the results of trimethylammonium moieties cleavage, while the desmethylation products are the results of the progressive cleavage of the methyl groups from the cationic side-chains. It is reasonable to conclude that the MALDI conditions are not suitable for the determination of the DS of QA-CD derivatives as uninformative peaks generate during the laser desorption. However, the DS of QA-CD derivatives can be determined by NMR (FIG. 7AD) and was estimated to be about 2.1.

Example 9. Synthesis of Succinyl Substituted CD Dimers

FIG. 7AI illustrates the molecule to be synthesized. The preparation of the Succinyl substituted Dimer (Succ-DIMER) was achieved in one-step reaction (FIG. 7AG).

Synthesis of Succinyl Substituted Cyclodextrin Dimers

βCD-TRIAZOLE-βCD dimer core (1.2 g, 0.5 mmol) was suspended in pyridine (23 mL) under vigorous stirring and inert atmosphere. The suspension was heated at 40° C. for 1 h in order to increase the solubility of the βCD-TRIAZOLE-βCD dimer core, however, a complete solubilization was not achieved. A second portion of pyridine (23 mL) was added to suspension, but dilution did not improve the solubility of the βCD-TRIAZOLE-βCD dimer core further. Succinic anhydride (0.1 g, 1 mmol) was added at r.t. and the reaction mixture was stirred for 24 h. The reaction crude was concentrated under reduced pressure, solubilized in water (a clear solution was not achieved) (50 mL) and treated with ion exchange resins: $H^+$ resin (2 g) and $OH^-$ (2 g) resin were added to the solution, stirred for 15 min and filtered (the resins were washed with deionized water 3×15 mL). The resulting filtrate (final pH=7) was clarified with activated charcoal: under vigorous stirring, activated charcoal (0.5 g) was added to the solution, stirred for 30 min and filtered (the charcoal pad was washed with deionized water 3×15 mL). Evaporation of the colorless solution under reduced pressure (40° C.) yielded the title compound as white powder (~900 mg).

Characterization

The resulting material was characterized by MALDI-TOF (FIG. 7AH) and NMR analysis as in FIGS. 7AJ-AL.

As in the case of the QA-DIMER, MALDI analysis proved unfavorable for the DS determination and the DS was determined by NMR (FIG. 7AD) and was estimated to be about 2.1.

Detailed Description of Synthesis of HpβCd-Triazole-βCd (Randomly Substituted) Asymmetric Dimer The preparation of the HPβCD-TRIAZOLE-βCD DS3 (randomly substituted) asymmetric dimer will be accomplished through multiple synthetic steps as shown in FIG. 20A.

Step 1: Preparation of the Azido-Linker 1,3-Dibromopropane (10 mL, 20.18 g, 0.1 mol) is solubilized in 40 mL DMSO under vigorous stirring. A solution of sodium azide (6.7 g, 0.1 mol) in DMSO (240 mL) is prepared and added dropwise (2 hours addition) to the solution of 1,3-dihalopropane. The solution is stirred at room temperature overnight. The reaction crude is then extracted with n-hexane (3×100 mL), the collected organic phases are extracted with water (3×50 mL), and the obtained organic phases are carefully evaporated under reduced pressure (at 40° C., 400 mbar strictly, otherwise the target compound may distillate out). The residue, an oil, is purified by chromatography (n-hexane-EtOAc=98:2 as eluent, isocratic elution). The appropriate fractions are collected based on TLC analysis, concentrated under reduced pressure and the target compound is obtained as a viscous oil (which may be stored under inert atmosphere in a dark, refrigerated container). The compound is visualized by dipping the TLC plate in a triphenylphosphine solution in dichloromethane (10%) for ~15 s, drying the TLC plate below 60° C., dipping the TLC in a ninhydrin ethanol solution (2%) for ~15 s and final drying of the TLC plate below 60° C. The target compound appears as a violet spot on the TLC plate.

Step 2.1: Preparation of 2-O Monopropargyl-βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h). Propargyl bromide (1.97 mL, 17.62 mmol) and a catalytic amount of lithium iodide (~20 mg) are then added and the mixture is stirred at 55° C. in the absence of light for 5 h. TLC (10:5:2 $CH_3CN$—$H_2O$-25% aqueous $NH_{3(aq)}$) is used to characterize the products and it shows spots corresponding to monopropargylated and nonpropargylated βCD, respectively. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and chromatography (10:5:2 $CH_3CN$—$H_2O$-25% $NH_{3(aq)}$) yielded, after freeze-drying, 2-O-monopropargyl-βCD as a solid. The 2-O-monopropargyl-BCD was analyzed by MALDI and NMR.

Step 2.2: Random (2-Hydroxypropyl)-2-O-Monopropargyl-βCD

2-O-Monopropargyl/CD which may be obtained according to step 2.1 (4.9 g, 4.2 mmol) was suspended in water (500 mL), sodium hydroxide (DS3=3.2 g, 80 mmol) was added to the reaction vessel and the mixture turned to a slight yellow solution. The reaction mixture was cooled by water bath (10° C.) and propylene oxide (DS3=4.9 mL, 4.2 g, 72.5 mmol) was added in one portion. The reaction vessel was flushed with argon, sealed and stirred for two days at room temperature. The solution was concentrated under reduced pressure until obtaining a viscous syrup that was precipitated with acetone (50 mL). The white solid was filtered on a sintered glass filter and extensively washed with acetone (3×15 mL). The material was solubilized with water (50 mL), treated with ion exchange resins (in order to remove the salts), clarified with charcoal, membrane filtered and dialyzed for one day against purified water. The retentate was evaporated under reduced pressure until dry. Random (2-hydroxypropyl)-2-O-monopropargyl-βCD was isolated as white solid (4.2 g) and analyzed by NMR (FIGS. 22A-D). The degree of substitution was calculated by NMR spectroscopy analysis (FIG. 22B).

Step 2.3: Synthesis of 2-O-Mono(3-Azidopropyl)/CD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h). 3-Azido-1-bromo-propane (3 mL) and a catalytic amount of lithium iodide (~20 mg) are then added and the mixture is stirred at 55° C. in the absence of light for 5 h. TLC (10:5:2 $CH_3CN$—$H_2O$-25% $NH_{3(aq)}$) is used to characterize the products and it shows spots corresponding to 2-O-mono(3-azidopropyl)-BCD and βCD. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue was obtained. This crude mixture is applied on top of a column of silica and chromatography (10:5:2 $CH_3CN$—$H_2$-25% $NH_{3(aq)}$) yielded, after drying, 2-O-mono(3-azidopropyl)-3CD as a white solid.

Step 3: Synthesis of HpβCd'-Triazole-βCd (Randomly Substituted) Asymmetric Dimer Random (2-hydroxypropyl)-2-O-monopropargyl-βCD and 2-O-mono(3-azidopropyl)-3CD are suspended in water (300 mL) under vigorous stirring (each at a concentration of between about 8-12 mM). N, N-Dimethylformamide (DMF) (approx. 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN$:$H_2O$:25% $NH_{3(aq)}$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% $NH_{3(aq)}$) yielded, after drying, HPβCD-TRIAZOLE-βCD asymmetric dimer DS3 random substituted. A preparation of the dimer will be characterized by NMR.

Detailed Description of Synthesis C6HpβCd-Triazole-βCd Ds3 Asymmetric Dimer

The preparation of the C6HPβCD-TRIAZOLE-βCD DS3 asymmetric dimer shall be accomplished through multiple synthetic steps as shown in FIGS. 20B-D.

Step 1A: Preparation of the Azido-Linker 1,3-Dibromopropane (10 mL, 20.18 g, 0.1 mol) is solubilized in 40 mL DMSO under vigorous stirring. A solution of sodium azide (6.7 g, 0.1 mol) in DMSO (240 mL) is prepared and added dropwise (2 hours addition) to the solution of 1,3-dihalopropane. The solution is stirred at room temperature overnight. The reaction crude is then extracted with n-hexane (3×100 mL), the collected organic phases are extracted with water (3×50 mL), and the obtained organic phases are carefully evaporated under reduced pressure (at 40° C., 400 mbar strictly, otherwise the target compound may distillate out). The residue, an oil, is purified by chromatography (n-hexane-EtOAc=98:2 as eluent, isocratic elution). The appropriate fractions are collected based on TLC analysis, concentrated under reduced pressure and the target compound is obtained as a viscous oil (which may be stored under inert atmosphere in a dark, refrigerated container). The compound is visualized by dipping the TLC plate in a triphenylphosphine solution in dichloromethane (10%) for ~15 s, drying the TLC plate below 60° C., dipping the TLC in a ninhydrin ethanol solution (2%) for ~15 s and final drying of the TLC plate below 60° C. The target compound appears as a violet spot on the TLC plate.

Step 1B: Preparation of Protected 2 Hydroxypropylating Agent (1 Bromo-2 Benzyloxy-Propane)

2 Benzyloxy-1 Propanol

The acid-catalized alcoholysis was conducted in a round-bottom flask, a reflux condenser, a thermometer and a graduated dropping funnel. The benzyl alcohol containing the catalyst (sulfuric acid) is heated to the reaction temperature and propylene oxide added as fast as the rate of reflux will permit. Heating is continued after the addition until the temperature of the boiling liquid becomes constant, indicating that the olefin oxide has been consumed. The catalyst is neutralized with sodium hydroxide and the product isolated by fractional distillation. In detail, during the course of four hours 63.8 g. (1.1 moles) of propylene oxide is added to 600 g (5.55 moles) of benzyl alcohol containing 1 g. of sulfuric acid, while the liquid was kept at 120-125° C. After two additional hours of heating, the temperature will become constant at 120° C. The mixture should yield approximately 77 g. of 2-benzyloxy-1-propanol.

1 Bromo-2 Benzyloxy-Propane 2-benzyloxy-1-propanol (16.6 g, 0.1 mol) is solubilized in ACN (100 mL) and slowly added (20 min addition) to a ACN suspension of $P_2O_5$ (21.3 g, 0.15 mol and KBr (17.85 g, 0.15 mol) under vigorous stirring and inert atmosphere. The reaction mixture is stirred at r.t. for 3 h then concentrated under reduced pressure (~10 mL). The suspension is solubilized in water under cooling (0-5° C.) and neutralized with sodium carbonate. The resulting mixture is extracted with DCM (3×100 mL), organic phases are combined and concentrated under reduced pressure to yield a viscous, yellowish oil. The residue is purified by silica gel chromatography (20% EtOAc/n-hexane) to give 1-bromo-2-benzyloxy-propane (17.7 g, 85%) as a colorless oil; $^1H$ NMR (500 MHz, $CDCl_3$) δ: 1.33 (3H, d, J=6.7 Hz, $CH_3$), 3.39 (1H, dd, J=4.9, 10.4 Hz, $CH_2Br$), 3.46 (1H, dd, J=4.9, 10.4 Hz, $CH_2Br$), 3.73-3.76 (1H, m, CH), 4.59 (2H, s, $PhCH_2$), 7.27-7.38 (5H, m, phenyl); 13C NMR (126 MHz, $CDCl_3$) δ: 19.2, 36.8, 71.2, 74.3, 127.9, 128.6, 138.4.

Step 2.1: Preparation of 2-O-Monopropargyl-βCD

Lithium hydride (212 mg, 26.43 mmol) is added to an anhydrous solution of βCD (20 g, 17.62 mmol) in DMSO (300 mL). The resulting suspension is stirred under $N_2$ at room temperature until it becomes clear (12-24 h). Propargyl bromide (1.97 mL, 17.62 mmol) and a catalytic amount of lithium iodide (~20 mg) are then added and the mixture is stirred at 55° C. in the absence of light for 5 h. TLC (10:5:2 $CH_3CN$—$H_2O$-25% aqueous $NH_{3(aq)}$) is used to characterize the products and it shows spots corresponding to monopropargylated and nonpropargylated βCD, respectively. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and chromatography (10:5:2 $CH_3CN$—$H_2O$-25% $NH_{3(aq)}$) yielded, after freeze-drying, 2-O-monopropargyl-BCD as a solid. The 2-O-monopropargyl-βCD was analyzed by MALDI and NMR.

Step 2.2: Per-6-O-Tert-Butyldimethylsilyl-2-O-Monopropargyl-βCD

2-O-Monopropargyl-βCD (10 g, 8.5 mmol) was suspended in dry pyridine (200 mL) under $N_2$ and stirred at room temperature until a clear solution formed (30 min). Tert-butyldimethylsilyl chloride (10.8 g, 71.4 mmol) was then added in one portion, and the resulting suspension was stirred at room temperature for 6 h. TLC (15:2:1 EtOAc-96% v/v EtOH-$H_2O$) showed formation of the title product ($R_f$=0.65), along with materials both less and more polar corresponding to under- and oversilylated species, respectively. Portions of TBDMSCl (2.7 g, 17.9 mmol) were added every 6 h until the former spots completely disappeared (FIG. 23A). The solution was then poured into a mixture of 5% aqueous HCl (3 L) and ice, stirred until the ice melted, and extracted with $CH_2Cl_2$ (2×4 L). Combined organic phases were washed with $H_2O$ (2×4 L), dried ($MgSO_4$) and concentrated. Traces of pyridine were removed by co-evaporation with toluene (2×3 L). The resulting material was mixed with silica gel (30 g), suspended in $CH_2Cl_2$, and the solvent was removed under vacuum. Chromatography was performed using first 40:40:20:4 $CH_2Cl_2$—$CH_3CN$-96% v/v EtOH-30% v/v aqueous $NH_3$ as eluent until compounds with TLC (15:2:1 EtOAc-96% v/v EtOH-$H_2O$) spots at $R_f$=0.87 and 0.80 had been eluted (2 L). Subsequently with 40:40:20:4 $CH_2Cl_2$—$CH_3CN$-96% v/v EtOH-$H_2O$ (1.5 L) as solvent yielded per-6-O-tert-butyldimethylsilyl-2-O-monopropargyl-BCD as a white, amorphous powder which was dried at 100° C. under high vacuum for 6 h (12.6 g, 6.4 mmol, 75%); the material decomposes at 232-236° C.; $[\alpha]^{25}_D$+96 (c 1.0, $CH_2Cl_2$); $R_f$=0.64 (15:2:1 EtOAc-96% v/v EtOH-$H_2O$); IR (ATR) (FIG. 23F): 3313, 2953, 2930, 2887, 2857, 1253, 1155, 1083, 1038, 833, 777, 735 $cm^{-1}$, (Trotta, F.; Martina, K.; Robaldo, B.; Barge, A.; Cravotto, G. J. Incl. Phenom. Macrocyclic Chem. 2007, 57, 3-7) (KBr) 3420, 3325, 1473, 1254, 1086, 1040, 835 $cm^{-1}$; $^1H$ NMR (FIG. 23C-D) (500 MHz, $CDCl_3$) δ 5.34 (bs, OH), 5.05 (d, 1H, $^3J_{1,2}$=3.2 Hz, H-$1^{I}$), 4.89-4.88 (m, 6H, H-$1^{III-VII}$), 4.50 (dd, 1H, $^2J$=16.7 Hz, $^4J$=2.3 Hz, CHO), 4.41 (dd, 1H, $^2J$=16.7 Hz, $^4J$=2.3 Hz, CHO), 4.11-3.82 (m, 14H, H-$3^{I-VII}$,$6a^{I-VII}$,), 3.74-3.49 (m, 28K H-$2^{I-VII}$, $4^{I-VII}$, $5^{I-VII}$, $6b^{I-VII}$), 2.40 (t, 1H, $^4J$=2.3 Hz, ≡CH), 0.88-0.86 [m, 63K $SiC(CH_3)_3$], 0.04-0.02 (m, 42H, $SiCH_3$); $^{13}C$ NMR (FIG. 23E) (125 MHz, $CDCl_3$) δ 103.1-102.0 (C-$1^{II-VII),}$ 101.3 (C-$1^{I}$), 82.1-81.7 (C-$4^{III-VII),}$ 80.5-80.4 (C-$4^{I,II}$), 79.6 (C≡), 75.2 (≡CH), 74.0-72.5 ($C2^{I-VII}3^{I-VII}$, $5^{I,VII}$), 62.3-61.6 (C-$6^{I-VII}$), 59.9 ($CH_2C$≡), 26.0 [$SiC(CH_3)_3$], 18.5-18.3 [$SiC(CH_3)_3$], −4.9-(−5.1) ($SiCH_3$); MALDI-TOF (FIG. 23B): $[M+Na]^+$ calcd for $C_{87}H_{170}O_{35}Si_7Na$, 1995.0; found: 1995.0. Anal. calcd for $C_{87}H_{170}O_{35}Si_7$: C, 52.97; H, 8.69. Found: C, 52.93; H, 8.71.

Step 2.3: Per-6-O-tert-butyldimethylsilyl-per-2,3-O-benzyl-2-O-monopropargyl-βCD Per-6-O-tert-butyldimethylsilyl-2-O-monopropargyl-βCO (12.6 g, 64 mmol) is dissolved in THE (500 mL). The solution was cooled-down with an ice-water bath to 10° C. and KOH (129 g, 1.98 mcl) was added portion-wise under vigorous stirring. The obtained white suspension at first slightly becomes viscous then easier to stir. Methyltriphenylphosphonium bromide (5.04 g, 14 mmol) was added to the reaction mixture and the white suspension was stirred for 3 h. Benzyl bromide (46.1 mL, 66.4 g, 0.39 mmol) was slowly and carefully added to the heterogeneous mixture (2 h addition), by keeping the temperature always below 25° C. After 1 h stirring the reaction mixture becomes of a pearly white colour showing a milk-like consistence. The reaction was stirred at room temperature overnight. The proceeding of the reaction was monitored by TLC (n-hexane:EtOAc=9:1), the reaction mixture was cooled-down to 10° C. and a second portion of KOH (12.96 g, 0.23 mob and BnBr (4.6 mL, 6.64 g, 0.04 mol) was added After 2 h, a third portion of KOH (6.5 g, 0.12 mol) and BnBr (2.3 mL, 3.3 g, 0.02 mmol) was added and the reaction mixture was additionally stirred for 3 h. The heterogeneous mixture was filtered on a sintered glass filter (porosity 4) and the solid was thoroughly washed with THF (3×200 mi.). The filtrate was concentrated at rotavapor (~50 mL) and poured to MeOH (500 mL) under vigorous stirring. The resulting yellowish, gel-like material was separated by decantation. The solid was extensively washed with $H_2O$ (5×600 mL) and with MeOH:$H_2O$=1.9 (3×400 mL) and finally dried until constant weight in a vacuum drying box in the presence of $P_2O_5$ and KOH as desiccants. Per-6-O-tert-butyldimethylsilyl-per-2,3-O-benzyl-2-O-monopropargyl-βCD was isolated as white powder (42 g, 80%).

Step 2.4: Per-2,3-O-benzyl-2-O-monopropargyl-βCD

Per-6-O-ter-butyidimethylsilyl-per-2,3-O-benzyl-2-O-monopropargyl-βCD (42 g) was solubilized in THF (800 mL) under inert atmosphere and tetrabutylammonium fluoride trihydrate (19.75, 0.062 mol) was added portionwise. The yellowish solution was stirred overnight at room temperature. The desilylation was followed by TLC ($CHCl_3$:MeOH=9:1) and it was completed overnight. The reaction crude was concentrated at rotavapor, methanol was added (600 mL) and the solution was once more concentrated at rotavapor The azeotropic distillation procedure was repeated three times (3×600 mL methanol) and the crude was finally concentrated until dryness. The residual yellowish material was suspended in water (1 L), filtered on a sintered glass filter (porosity 4) and extensively washed with water (5×300 mL) and with a mixture of MeOH:$H_2O$=1:4 (3×300 mL) until a white, odourless, solid was obtained. The white solid was dried until constant weight into a vacuum drying box in the presence of $P_2O_5$ and KOH as desiccants. Per-2,3-O-benzyl-2-O-monopropargyl-βCD was isolated as white solid (21 g, 8.96 mmol).

Step 2.5: Tris(6-O-(2-O-benzyloxypropyl))-per-2,3-O-benzyl-2-O-monopropargyl-βCD Per-2,3-O-benzyl-2-O-monopropargyl-βCD (21 g, 8.96 mmol) was dissolved in THF (300 mL). The solution was cooled-down with an ice-water bath to 10° C. and KOH (2.5 g, 44.8 mmol) was added portion-wise under vigorous stirring. The obtained white suspension at first slightly becomes viscous then easier to stir Methyltriphenylphosphonium bromide (0.5 g, 1.4 mmol) was added to the reaction mixture and the white suspension was stirred for 0.3 h. 1-Bromo-2-benzyloxy-propane (10.3 g, 44.8 mmol) was slowly added to the heterogeneous mixture, by keeping the temperature always below 25° C. After 1 h stirring the reaction mixture becomes of a pearly white colour showing a milk-like consistence. The reaction was stirred at room temperature overnight. The proceeding of the reaction was monitored by TLC (n-hexane:EtOAc=9:1) The heterogeneous mixture was filtered on a sintered glass filter (porosity 4) and the solid was thoroughly washed with THE (3×50 mL). The filtrate was concentrated at rotavapor (~30 mL) and poured to MeOH (200 mL) under vigorous stirring. The resulting yellowish, gel-like material was separated by decantation. The solid was extensively washed with $H_2O$ (5×100 mL) and with MeOH:$H_2O$=1:9 (3×100 mL). Tris(6-O-(2-O-benzyloxypropyl))-per-2,3-O-benzyl-2-O-monopropargyl-βCD was purified by chromatography with isocratic elution on silica gel (n-hexane:EtOAc=9:1). Fractions were combined based on TLC analysis and concentrated under reduced pressure to dryness. Tris(6-O-(2-O-benzyloxypropyl))-per-2,3-O-benzyl-2-O-monopropargyl-βCD was isolated as white powder (15 g, 5.4 mmol, 60%).

Step 2.6: Tris-6-O-(2-O-hydroxypropyl)-2-O-monopropargyl-βCD

Tris(6-O-(2-O-benzyloxypropyl))-per-2,3-O-benzyl-2-O-monopropargyl-βCD (15 g, 5.4 mmol) was solubilized in methanol (500 mL). The reaction mixture was heated at 40° C., Pd/C (3.1 g) was added under vigorous stirring and hydrazine carbonate (120 mL) was added dropwise to the vessel (1.3 h addition). The mixture was heated at gentle reflux for 3 hours and the proceeding of the reaction was monitored by TLC (1,4-dioxane:25% $NH_{3(aq)}$:1-propanol=10:7:3). The reaction mixture was cooled-down to room temperature, filtered on a sintered glass filter (porosity 3) and the Pd/C pad was thoroughly washed with MeOH (3×300 mL), $H_2O$ (3×300 mL) and MeOH:$H_2O$=50:50 (3×300 mL). The filtrate was evaporated until dryness at rotavapor (60° C.). The residual solid was solubilized in water (120 mL), treated with ion exchange resins and clarified with charcoal. The obtained solution was then filtered through a pad of celite and finally evaporated until dryness. The solid was dried until constant weight in a vacuum drying box in the presence of $P_2O_5$ and KOH as desiccating agents Tris-6-O-(2-O-hydroxypropyl)-2-O-monopropargyl-βCD was isolated as white powder (6 g, 4.45 mmol, 82%).

Step 2.7: Synthesis of 2-O-Mono(3-azidopropyl)-βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h) 3-Azido-1-bromo-propane (3 mL) and a catalytic amount of lithium iodide (~20 mg) are then added and the mixture is stirred at 55° C. in the absence of light for 5 h. TLC (10:5:2 $CH_3CN$—$H_2O$-25% $NH_{3(aq)}$) is used to characterize the products and it shows spots corresponding to 2-O-mono(3-azidopropyl)-βCD and βCD. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue was obtained. This crude mixture is applied on top of a column of silica and chromatography (10:5:2 $CH_2CN$—$H_2O$-25% $NH_{3(aq)}$) yielded, after drying, 2-O-mono(3-azidopropyl)-βCD as a white solid.

Step 3: Synthesis of C6HPβCD-Triazole-βCD DS3 Asymmetric Dimer

Tris-6-O-(2-O-hydroxypropyl)-2-O-monopropargyl-βCD and 2-O-mono(3-azidopropyl)-βCD are suspended in water (300 mL) under vigorous stirring (each at a concentration of between about: 8-12 mM) N, N-Dimethylformamide (DMF) (approx 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN$:$H_2O$:25% $NH_{3(aq)}$=10.5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% $NH_{3(aq)}$) yielded, after drying, C6HPβ CD-TRIAZOLE-βCD symmetric dimer DS3.

Detailed Description of Synthesis C6HPβCD-TRIAZOLE-βCD DS7 Asymmetric Dimer

The preparation of the C6HPβCD-TRIAZOLE-βCD DS7 asymmetric dimer was accomplished through multiple synthetic steps as shown in FIGS. 21A-21D.

Step 1A: Preparation of the Azido-Linker 1,3-Dibromopropane (10 mL, 20.18 g, 0.1 mol) is solubilized in 40 mL DMSO under vigorous stirring A solution of sodium azide (6.7 g, 0.1 mol) in DMSO (240 mL) is prepared and added dropwise (2 hours addition) to the solution of 1,3-dihalopropane. The solution is stirred at room temperature overnight. The reaction crude is then extracted with n-hexane (3×100 mL), the collected organic phases are extracted with water (3×50 mL), and the obtained organic phases are carefully evaporated under reduced pressure (at 40° C., 400 mbar strictly, otherwise the target compound may distillate out). The residue, an oil, is purified by chromatography (n-hexane-EtOAc=98:2 as eluent, isocratic elution). The appropriate fractions are collected based on TLC analysis, concentrated under reduced pressure and the target compound is obtained as a viscous oil (which may be stored under inert atmosphere in a dark, refrigerated container). The compound is visualized by dipping the TLC plate in a triphenylphosphine solution in dichloromethane (10%) for ~15 s, drying the TLC plate below 60° C., dipping the TLC in a ninhydrin ethanol solution (2%) for ~15 s and final daring of the TLC plate below 60° C. The target compound appears as a violet spot on the TLC plate.

Step 1B: Preparation of Protected 2-Hydroxypropylating Agent (1-Bromo-2-Benzyloxy-propane)

The acid-catalized alcoholysis was conducted in a round-bottom flask, a reflux condenser, a thermometer and a graduated dropping funnel. The benzyl alcohol containing the catalyst (sulfuric acid) was heated to the reaction temperature and propylene oxide was added as fast as the rate of reflux would permit. Heating was continued after the addition until the temperature of the boiling liquid had become constant, indicating that the olefin oxide had been consumed. The catalyst was neutralized with sodium hydroxide and the product was isolated by fractional distillation. In detailed, during the course of four hours 63.8 g. (1.1 moles) of propylene oxide was added to 600 g (5.55 moles) of benzyl alcohol containing 1 g. of sulfuric acid, while the liquid was kept at 120-125° C. After two additional hours of heating, the temperature had become constant at 120° C. The mixture yielded 77 g of 2-benzyloxy-1-propanol 1-Bromo-2-Benzyloxy-propane 2-benzyloxy-1-propanol (16.6 g, 0.1 mol) was solubilized in ACN (100 ml) and slowly added (20 min addition) to a ACN suspension of $P_2O_5$ (21.3 g, 0.15 mol and KBr (17.85 g, 0.15 mol) under vigorous stirring and men atmosphere. The reaction mixture was stirred at r.t. for 3 h then concentrated under reduced pressure (~10 mL). The suspension was solubilized in water under cooling (0-5° C.) and neutralized with sodium carbonate. The resulting mixture was extracted with DCM (3×100 ml.), organic phases were combined and concentrated under reduced pressure to yield a viscous, yellowish oil. The residue was purified by silica gel chromatography (20% EtOAc/n-hexane) to give 1-bromo-2-benzyloxy-propane (17.7 g, 85%) as a colorless oil; $^1$H NMR (500 MHz, $CDCl_3$) δ: 1.33 (3H, d. J=6.7 Hz, $CH_3$), 3.39 (1H, dd, J=4.9, 10.4 Hz, $CH_2Br$), 3.46 (1H, dd, J=4.9, 10.4 Hz, $CH_2Br$), 3.73-3.76 (1H, m, CH), 4.59 (2H, s, $PhCH_2$), 7.27-7.38 (5H, m, phenyl): 13C NMR. (126 MHz, $CDCl_3$) δ: 19.2, 36.8, 71.2, 74.3, 127.9, 128.6, 138.4.

Steep 2.1: Preparation of 2-O-Monopropargyl-βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h). Propargyl bromide (1.97 mL, 17.62 mmol) and a catalytic amount of lithium iodide (~20 mg) are then added and the mixture is stirred at 55° C. in the absence of light for 5 h. TLC (10:5:2 $CH_3CD$-$H_2O$-25% aqueous $NH_{3(aq)}$) is used to characterize the products and it shows spots corresponding to monopropargylated and nonpropargylated βCD, respectively. The solution is poured into acetone (3.2 L) and the precipitate is Filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica (25×6 cm), and chromatography (10:5:2 $CH_3CN$—$H_2O$-25% $NH_{3(aq)}$) yielded, after freeze-drying, 2-O-monopropargyl-βCD as a solid. The 2-O-monopropargyl-βCD was analyzed by MALDI and NMR.

Step 2.2: Per-6-O-tert-butyldimethylsilyl-2-O-monopropargyl-βCD

2-O-Monopropargyl-βCD (10 g, 8.5 mmol) was suspended in dry pyridine (200 mL) under $N_2$ and stirred at room temperature until a clear solution firmed (30 min). Tert-butyldimethylsilyl chloride (10.8 g, 71.4 mmol) was then added in one portion, and the resulting suspension was stirred at mom temperature for 6 h. TLC (15:2:1 EtOAc-96% v/v EtOH-$H_2O$) showed formation of the title product ($R_f$=0.65), along with materials both less and more polar corresponding to under- and oversilylated species, respectively. Portions of TBDMSCI (2.7 S, 17.9 mmol) were added every 6 h until the former spots completely disappeared (FIG. 23A). The solution was then poured into a mixture of 5% aqueous HCl (3 L) and ice, stirred until the ice melted, and extracted with $CH_2Cl_2$ (2×4 L). Combined organic phases were washed with $H_2O$ (2×4 L), dried ($MgSO_3$) and concentrated. Traces of pyridine were removed by co-evaporation with toluene (2×3 L). The resulting material was mixed with silica gel (30 g), suspended in $CH_2Cl_2$, and the solvent, was removed under vacuum. Chromatography was performed using first 40:40:20:4 $CH_2Cl_2$—$CH_3CN$-96% v/v EtOH-30% v/v aqueous $NH_3$ as eluent until compounds with TLC (15.2:1 EtOAc-96% v/v EtOH-$H_2O$) spots at $R_f$=0.87 and 0.80 had been eluted (2 L) Subsequently with 40:40.20:4 $CH_2Cl_2$—$CH_3CN$-96% v/v EtOH-$H_2O$ (1.5 L) as solvent yielded per-6-O-tert-butyldimethylsilyl-2-O-monopropargyl-βCD as a white, amorphous powder which was dried at 100° C. under high vacuum for 6 h (12.6 g, 6.4 mmol, 75%), the material decomposes at 232-236° C.; $[\alpha]^{25}_D$+96 (c 1.0, $CH_2Cl_2$); $R_f$=0.64 (15:2.1 EtOAc-96% v/v EtOH-$H_2O$), IR (ATR) (FIG. 23F): 3313, 2953, 2930, 2887, 2857, 1253, 1155, 1083, 1038, 833, 777, 735 $cm^{-1}$, (Trotta. F.; Martina, K.; Robaldo, B.; Barge, A.; Cravotto, G. J. Incl. Phenom. Macrocyclic Chem. 2007, 57, 3-7) (KBr) 3420, 3325, 1473, 1254, 1086, 1040, 835 $cm^{-1}$; $^1$H NMR (FIG. 23C-D) (500 MHz, $CDCl_3$) δ 5.34 (bs, OH), 5.05 (d, 1H, $^3J_{1,2}$=3.2 Hz, H-$1^{I}$), 4.89-4.88 (m, 6H, H-$1^{II-VII}$), 4.50 (dd, 1H, $^2$J=16.7 Hz, $^4$J=2.3 Hz, CHO), 4.41 (dd, 1H, $^2$J=16.7 Hz, $^4$J=2.3 Hz, CHO), 4.11-3.82 (m, 14H, H-$3^{I-VII}$, $6a^{I-VII}$), 3.74-3.49 (m, 28H, H-$2^{I-VII}$, $4^{I-VII}$, $5^{I-VII}$, $6b^{I-VII}$), 2.40 (t, 1H, $^4$J=2.3 Hz, ≡CH), 0.88-0.86 [m, 63H, $SiC(CH_3)_3$), 0.04-0.02 (m, 42H, $SiCH_3$); $^{13}$C NMR (FIG. 23E) (125 MHz, $CDCl_3$) δ 103.1-102.0 (C-$1^{II-VII}$), 101.3 (C-$1^{I}$), 82.1-81.7 (C-$4^{III-VII}$), 80.5-80.4 (C-$4^{I,II}$) 79.6 (C≡), 75.2 (≡CH), 74.0-72.5 ($C2^{I-VII}$,$3^{I-VII}$,$5^{I-VII}$), 62.3-61.6 (C-$6^{I-VII}$), 59.9 ($CH_2C$≡), 26.0 [$SiC(CH_3)_3$], 18.5-18.3 [$SiC(CH_3)_3$], −4.9-(−5.1) ($SiCH_3$); MALDI-TOF (FIG. 23B): $[M+Na]^+$ calculated for $C_{87}H_{170}O_{35}Si_7Na$, 1995.0; found: 1995.0. Anal. calculated for $C_{87}H_{170}O_{35}Si_7$: C, 52.97; H, 8.69. Found: C, 52.93; H, 8.71.

Step 2.3: Per-6-O-tert-butyldimethylsilyl-per-2,3-O-benzyl-2-O-monopropargyl-βCD Per-6-O-tert-butyidimethylsilyl-2-O-monopropargyl-βCD (12.6 g, 6.4 mmol) is dissolved in THF (500 mL) The solution is cooled-down with an ice-water bath to 10° C. and KOH (129 g, 1.98 mol) is added portion-wise under vigorous stirring. The obtained white suspension at first slightly becomes viscous then easier to stir. Methyltriphenylphosphonium bromide (5.04 g, 14 mmol) is added to the reaction mixture and the white suspension is stirred for 3 h Benzyl bromide (46.1 mL, 66.4 g, 0.39 mmol) is slowly and carefully added to the heterogeneous mixture (2 h addition), by keeping the temperature always below 25° C. After 1 h stirring the reaction mixture becomes of a pearly white colour showing a milk-like consistence. The reaction is stirred at room temperature overnight. The proceeding of the reaction is monitored by TLC (n-hexane:EtOAc=1), the reaction mixture is cooled to 10° C. and a second portion of KOH (12% g, 0.23 mol) and BnBr (4.6 mL, 6.64 g, 0.04 moo) is added. After 2 h, a third portion of KOH (6.5 g, 0.12 mol) and BnBr (2.3 ml, 3.3 g, 0.02 mmol) is added and the reaction mixture is additionally stirred for 3 h. The heterogeneous mixture is filtered on a sintered glass filter (porosity 4) and the solid is thoroughly washed with THE (3×200 mL). The filtrate is concentrated at rotavapor (~50 mL) and poured to MeOH (500 mL) under vigorous stirring. The resulting yellowish, gel-like material is separated by decantation. The solid is extensively washed with $H_2O$ (5×600 mL) and with $MeOH:H_2O$=1.9 (3×400 mL) and finally dried until constant weight in a vacuum drying box in the presence of $P_2O_5$ and KOH as desiccants. Per-6-O-tert-butyldimethylsilyl-per-2,3-O-benzyl-2-O-monopropargyl-βCD is isolated as white powder (42 g, 80%).

Step 2.4:
Per-2,3-O-benzyl-2-O-monopropargyl-βCD

Per-6-O-tert-butyldimethylsilyl-per-2,3-O-benzyl-2-O-monopropargyl-βCD (42 g) is solubilized in THF (800 mL) under inert atmosphere and tetrabutylammonium fluoride trihydrate (19.75 g, 0.062 mol) is added portionwise. The yellowish solution is stirred overnight at room temperature. The desilylation is followed by TLC ($CHCl_3$:MeOH=9:1) and it is completed overnight. The reaction crude is concentrated at rotavapor, methanol is added (600 mL) and the solution is once more concentrated at rotavapor. The azeotropic distillation procedure is repeated three times (3×600 mL methanol) and the crude is finally concentrated until dryness. The residual yellowish material is suspended in water (1 L), filtered on a sintered glass filter (porosity 4) and extensively washed with water (5×300 mL) and with a mixture of $MeOH:H_2O$=1.9(3×300 mL) until a white, odourless, solid is obtained. The white solid is dried until constant weight into a vacuum drying box in the presence of $P_2O_5$ and KOH as desiccants. Per-2,3-O-benzyl-2-O-monopropargyl-βCD is isolated as white solid (21 g, 8.96 mmol).

Step 2.5: Per-6-O-(2-O-benzyloxypropyl)-per-2,3-O-benzyl-2-O-monopropargyl-βCD

Per-2,3-O-benzyl-2-O-monopropargyl-3CD (21 g, 8.96 mmol) is dissolved in THE (300 mL). The solution is cooled-down with an ice-water bath to 10° C. and KOH (25 g, 448 mmol) is added portion-wise under vigorous stirring. The obtained white suspension at first becomes slightly viscous then easier to stir. Methyltriphenylphosphonium bromide (S g, 14 mmol) is added to the reaction mixture and the white suspension is stirred for 3 h. 1-Bromo-2-benzyloxy-propane (103 g, 448 mmol) is slowly added to the heterogeneous mixture, by keeping the temperature always below 25° C. After 0.1 h stirring the reaction mixture becomes a pearly white color of a milk-like consistency. The reaction is stirred at room temperature overnight. The proceeding of the reaction is monitored by TLC (n-hexane: EtOAc=9:1). The heterogeneous mixture is filtered on a sintered glass filter (porosity 4) and the solid is thoroughly washed with THF (3×50 mL). The filtrate is concentrated at rotavapor (~30 mL) and poured to MeOH. (200 mL) under vigorous stirring. The resulting yellowish, gel-like material is separated by decantation. The solid is extensively washed with $H_2O$ (5×100 mL) and with $MeOH:H_2O$=1.9 (3×100 ml.). Tris(6-O-(2-O-benzyloxypropyl)))-per-2,3-O-benzyl-2-O-monopropargyl-βCD is purified by chromatography with isocratic elution on silica gel (n-hexane:EtOAc=9.1). Fractions were combined based on TLC analysis and concentrated under reduced pressure to dryness, Per-6-O-benzyloxypropyl)-per-2,3-O-benzyl-2-O-monopropargyl-βCD is isolated as white powder (24 g, 7.0 mmol, 78%).

Step 2.6: Per-6-O-(2-O-hydroxypropyl)-2-O-monopropargyl-β CD

Per-6-O-(2-O-benzyloxypropyl)-per-2,3-O-benzyl-2-O-monopropargyl-βCD (24 g, 7.0 mmol) is solubilized in methanol (600 mL). The reaction mixture is heated at 40° C., Pd/C (8 g) is added under vigorous stirring and hydrazine carbonate (360 mL) is added dropwise to the vessel (3 h addition). The mixture is heated at gentle reflux for 3 hours and the proceeding of the reaction is monitored by TLC (1,4-dioxane:25% $NH_{3(aq)}$:1-propanol=10:7:3). The reaction mixture is cooled-down to room temperature, filtered on a sintered glass filter (porosity 3) and the Pd/C pad is thoroughly washed with MeOH (3×500 mL). $H_2O$ (3×500 mL) and $MeOH:H_2O$=50:50 (3×500 mL). The filtrate is evaporated until dryness at rotavapor (60° C.). The residual solid is solubilized in water (200 mL), treated with ion exchange resins and clarified with charcoal. The obtained solution is then filtered through a pad of celite and finally evaporated until dryness. The solid is dried until constant weight in a vacuum drying box in the presence of $P_2O_5$ and KOH as desiccating agents. Per-6-O-(2-O-hydroxypropyl)-2-O-monopropargyl-βCD is isolated as white powder (8 g, 5.06 mmol, 71%).

Step 2.7: Synthesis of
2-O-Mono(3-azidopropyl)βCD

Lithium hydride (212 mg, 26.432 mmol) is added to an anhydrous solution of βCD (20 g, 17.62 mmol) in DMSO (300 mL). The resulting suspension is stirred under $N_2$ at room temperature until it becomes clear (12-24 h), 3-Azido-1-bromo-propane (3 mL) and a catalytic amount of lithium iodide (~20 mg) are then added and the mixture is stirred at 55° C. in the absence of light for 5 h. TLC (10:5:2 $CH_3CN$—$H_2O$-25% $NH_{3(aq)}$) is used to characterize the products and it shows spots corresponding to 2-O-mono(3-azidopropyl)-β CD and βCD. The solution is poured into acetone (3.2 L) and the precipitate is filtered and washed thoroughly with acetone. The resulting solid is transferred into a round-bottom flask and dissolved in a minimum volume of water. Silica gel (40 g) is added and the solvent is removed under vacuum until powdered residue is obtained. This crude mixture is applied on top of a column of silica and chromatography (10:5:2 $CH_3CN$—$H_2O$-25% $NH_{3(aq)}$) yielded, after drying, 2-O-mono(3-azidopropyl)-βCD as a white solid.

Step 3: Synthesis of C6HPβCD-TRIAZOLE-βCD
DS7 Asymmetric Dimer

Per-6-O-(2-O-hydroxypropyl)-2-O-monopropargyl-βCD and 2-O-mono(3-azidopropyl)-βCD are suspended in water (300 mL) under vigorous stirring (each at a concentration of between about 8-12 mM). N,N-Dimethylformamide (DMF) (approx 300 mL) is added to the suspension in order to cause complete dissolution of the heterogeneous mixture (the addition of DMF is a slightly exothermic process). Copper bromide (2 g, 13.49 mmol) is added to the solution. The suspension is stirred for 1 hour at room temperature. The reaction is monitored with TLC and is expected to be completed after about 1 hour (eluent: $CH_3CN:H_2O$:25% $NH_{3(aq)}$=10:5:2). The reaction crude is filtered and the mother liquor concentrated under reduced pressure (60° C.). The gel-like material is diluted with water and silica (15 g) is added. The heterogeneous mixture is concentrated under reduced pressure to dryness. This crude mixture is applied on top of a column of silica and chromatography (10:5:2 $CH_3CN$—$H_2O$-25% $NH_{3(aq)) yielded, after drying. C}$6HPβCD-TRIAZOLE-βCD asymmetric dimer DS7.

Detailed Description of Synthesis of SB(αCD-TRIAZOLE-βCD) and SB(βCD-TRIAZOLE-αCD) Diners Step 4a. SB(αCD-TRIAZOLE-αCD) Dimer Low DS αCD-TRIAZOLE-βCD dimer (1.1 g, 0.5 mmol) is suspended in deionized $H_2O$ (60 mL) under vigorous stirring. Sodium hydroxide (0.39 g, 9.75 mmol) is added to the mixture and the obtained solution is heated at 60° C. 1,4-Butane sultone (0.88 mL, 1.17 g, 8.6 mmol) is added dropwise at 60° C. and the solution is heated at the same temperature for 3 h. The reaction is then heated to 90° C. for 1 additional hour in order to destroy the residual 1,4-butane sultone. The reaction mixture is cooled down and treated with ion exchange resins. Cationic exchange resin ($H^+$ resin, 2 g) and anionic exchange resin ($OH^-$ resin, 2 g) were added to the solution, stirred for 15 min and filtered-off (the resins were washed with deionized water 3×15 mL). The resulting filtrate (final pH=7) is clarified with activated charcoal: under vigorous stirring, activated charcoal (0.3 g) is added to the solution, stirred for 30 min and filtered-off (the charcoal pad is washed with deionized water 3×15 mL).

Evaporation of the colorless solution under reduced pressure (40° C.) yielded a white powder (1.3 g).

Step 4b. SB(βCD-TRIAZOLE-αCD) Dimer Low DS

βCD-TRIAZOLE-αCD dimer (1.1 g, 0.5 mmol) is suspended in deionized H2O (60 mL) under vigorous stirring. Sodium hydroxide (0.39 g. 9.75 mmol) is added to the mixture and the obtained solution is heated at 60° C. 1,4-Butane sulfone (0.88 mL, 1.17 g, 8.6 mmol) is added dropwise at 60° C. and the solution is heated at the same temperature for 3 h. The reaction is then heated to 90° C. for 1 additional hour in order to destroy the residual 1,4-butane sultone. The reaction mixture is cooled down and treated with ion exchange resins. Cationic exchange resin ($H^+$ resin, 2 g) and anionic exchange resin ($OH^-$ resin, 2 g) were added to the solution, stirred for 15 min and filtered-off (the resins were washed with deionized water 3×15 mL). The resulting filtrate (final pH=7) is clarified with activated charcoal: under vigorous stirring, activated charcoal (0.3 g) is added to the solution, stirred for 30 min and filtered-off (the charcoal pad is washed with deionized water 3×15 mL).

Evaporation of the colorless solution under reduced pressure (40° C.) yielded a white powder (1.3 g).

Example 10. Extraction of 7KC and cholesterol from blood cells with βCD dimers and monomers Methods Blood was collected from healthy volunteers by licensed phlebotomists. The test substances or PBS atone (negative control) were added to whole blood at various concentrations and incubated for 3 hours at 37 C. Blood was then spun down and serum collected. Serum was frozen and then processed for mass spectrometry.

Plasma free 7KC was determined by LC-MS/MS following protein precipitation and extraction with acetonitrile and derivatization with the novel quaternary aminooxy (QAO) mass tag reagent, Amplifex Keto Reagent (AB Sciex, Framingham, MA, USA), which has been used in the analysis of testosterone (Star-Weinstock (et al.), Analytical Chemistry, 84(21):9310-9317. (2012)).

A 50 μL sample of plasma was spiked with 0.5 ng of the internal standard, d7-7KC (Toronto Research Chemicals. North York, Ontario, CA) prepared at 0.1 ng/μL in 100% ethanol. The sample was treated with 250 μL of acetonitrile, vortex mixed, centrifuged to remove protein at 12,000×g for 10 min. The supernatant was dried under vacuum and then treated with 75 μL of QAO reagent. The working reagent was prepared by mixing 0.7 mL of Amplifex keto reagent with 0.7 mL of Amplifex keto diluent to prepare a 10 mg/mL stock. This stock was then diluted 1:4 with 5% acetic acid in methanol to a final working concentration of 2.5 mg/mL. The mixture was allowed to react at room temperature for two days before LC-MS/MS analysis.

Standards of 7KC (Toronto Research Chemicals, North York, Ontario, CA) were prepared from 1 to 100 ng/ml in charcoal stripped plasma, SP1870, (Golden West Biological, Temecula, CA, USA) and in phosphate buffered saline. There was residual 7KC detected in the stripped plasma, so the standards from PBS were used.

QAO-7KC derivatives were analyzed using a 4000 Q-TRAP hybrid/triple quadrupole linear ion trap mass spectrometer (SCIEX, Framingham. MA, USA) with electrospray ionization (ESI) in positive mode. The mass spectrometer was interfaced to a Shimadzu (Columbia, MD) SIL-20AC XR auto-sampler followed by 2 LC-20AD XR LC pumps.

The instrument was operated with the following settings: source voltage 4500 kV, GS1 50, GS2 50, CUR 20, TEM 550 and CAD gas medium. Compounds were quantified with multiple reaction monitoring (MRM) and transitions optimized by infusion of pure derivatized compounds as presented in Table 1 below. The bold transitions were used for quantification.

| Q1 mass (Da) | Q3 mass (Da) | Dwell Time (msec) | Compound | Declustering Potential | Entrance Potential | Collision Energy | Collision Cell Exit Potential |
|---|---|---|---|---|---|---|---|
| 515.5 | 58.8 | 150 | QAO-7KC | 106 V | 10 V | 99 V | 8 V |
| 515.5 | 456.3 | 150 | QAO-7KC | 106 V | 10 V | 43 V | 12 V |
| 522.5 | 463.4 | 150 | QAO-d7KC | 61 V | 10 V | 45 V | 14 V |
| 522.5 | 432.8 | 150 | QAO-d7KC | 61 V | 10 V | 31 V | 14 V |

Separation was achieved using a Gemini 3 μm C6-phenyl 110 Å, 100×2 mm column (Phenomenex, Torrance, CA, USA) kept at 35° C. using a Shimadzu (Columbia, MD) CTO-20AC column oven. The gradient mobile phase was delivered at a flow rate of 0.5 mL/min, and consisted of two solvents, A: 0.1% formic acid in water, B. 0.1% formic acid in acetonitrile. The initial concentration of solvent B was 20% followed by a linear increase to 60c B in 10 min, then to 95% B in 0.1 min. held for 3 minutes, decreased back to starting 20% B over 0.1 min, and then held for 4 min. The retention time for 7KC was 8.46 min.

Data were acquired using Analyst 1.6.2 (SCIEX. Framingham, MA, USA) and analyzed with Multiquant 3.0.1 (SCIEX, Framingham, MA, USA) software. Sample values were calculated from standard curves generated from the peak area ratio of the analyte to internal standard versus the analyte concentration that was fit to a linear equation with 1/x weighting. The lower limit of quantification was 1 ng/mL with an accuracy of 102% and precision (relative standard deviation) of 8.5%. Signal to noise (S/N) was 19:1. At a concentration of 100 ng/mL accuracy was 98% and precision was 0.5% with a S/N of 24:1.

Results

Figure 5F:
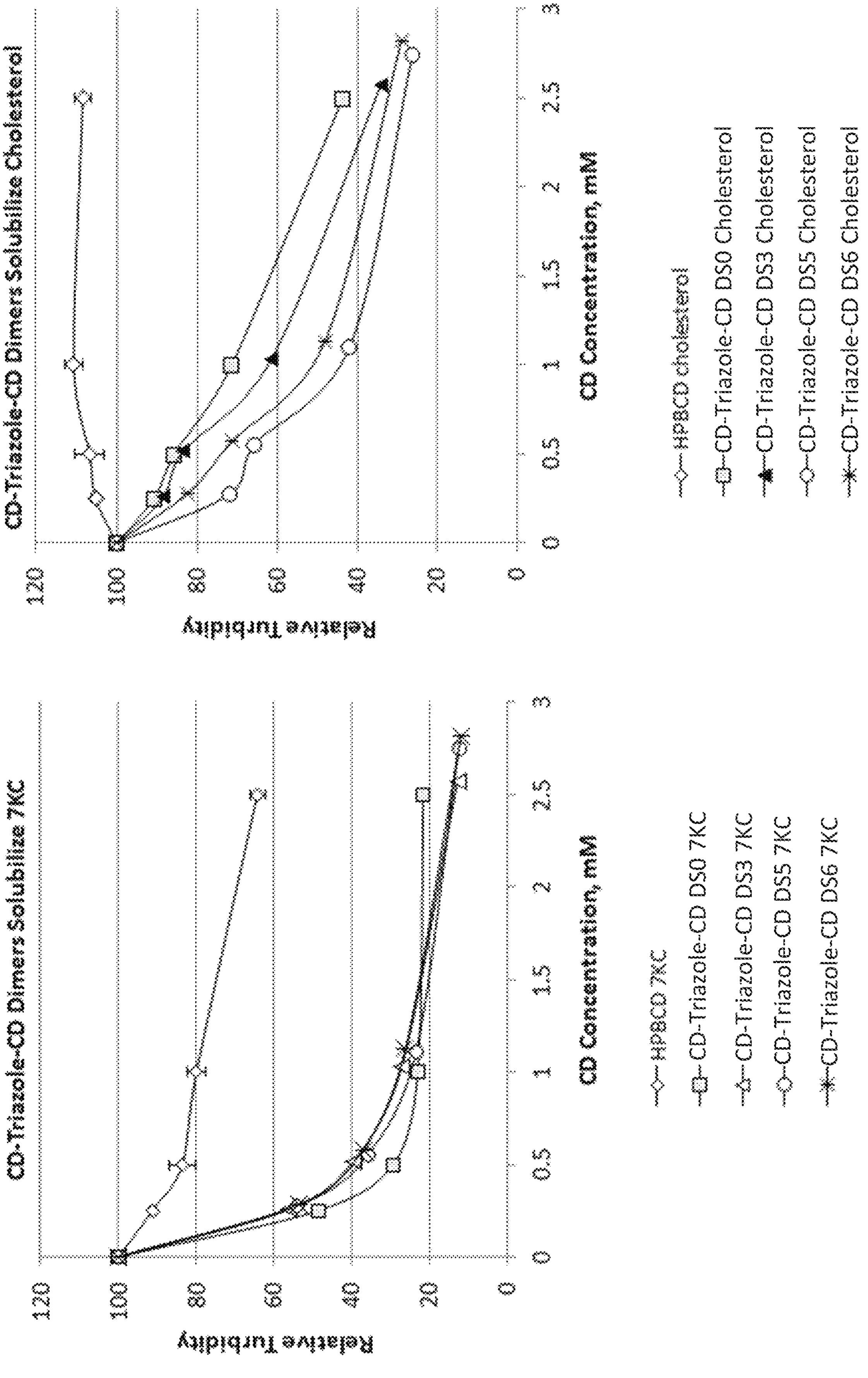
FIG. 5F. Solubilization of cholesterol and 7KC by HPβCD triazole-linked dimers of various DS compared to HPβCD monomer.
Figure 5G:
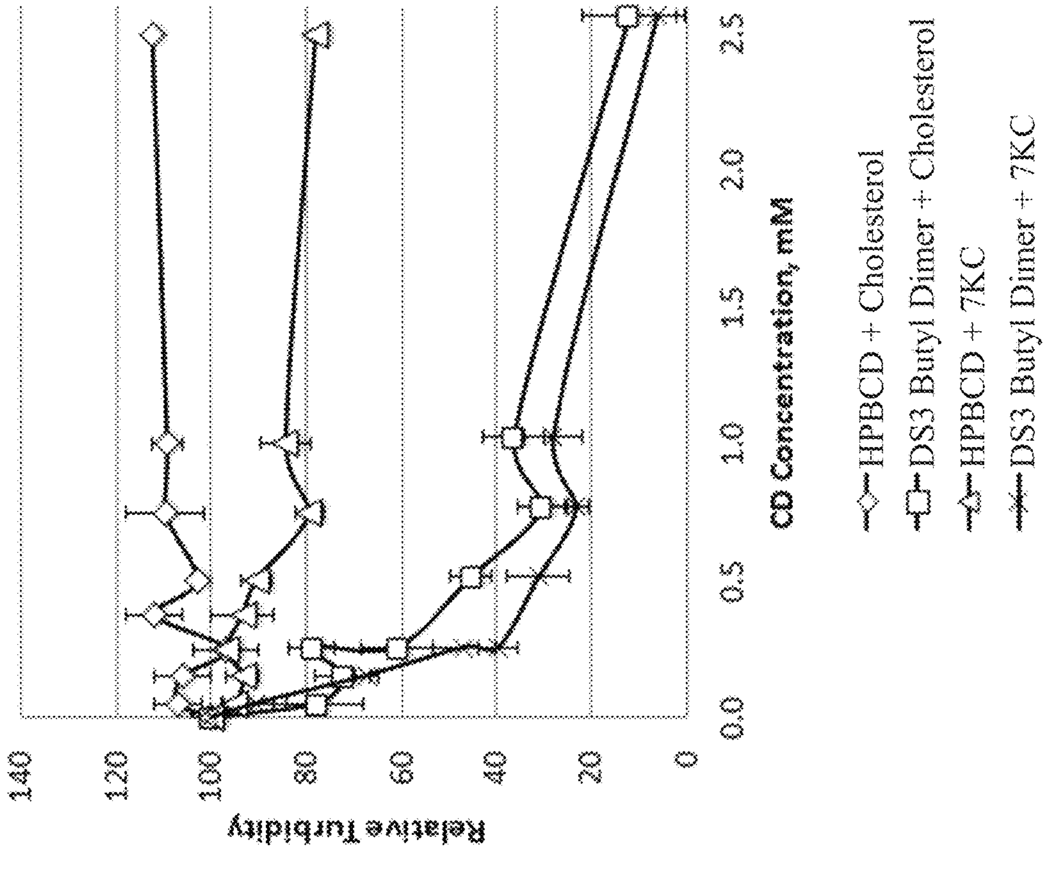
FIG. 5G. Solubilization of cholesterol and 7KC by HPβCD DS3 butyl linked dimers compared to HPβCD monomer.
Figure 5H:
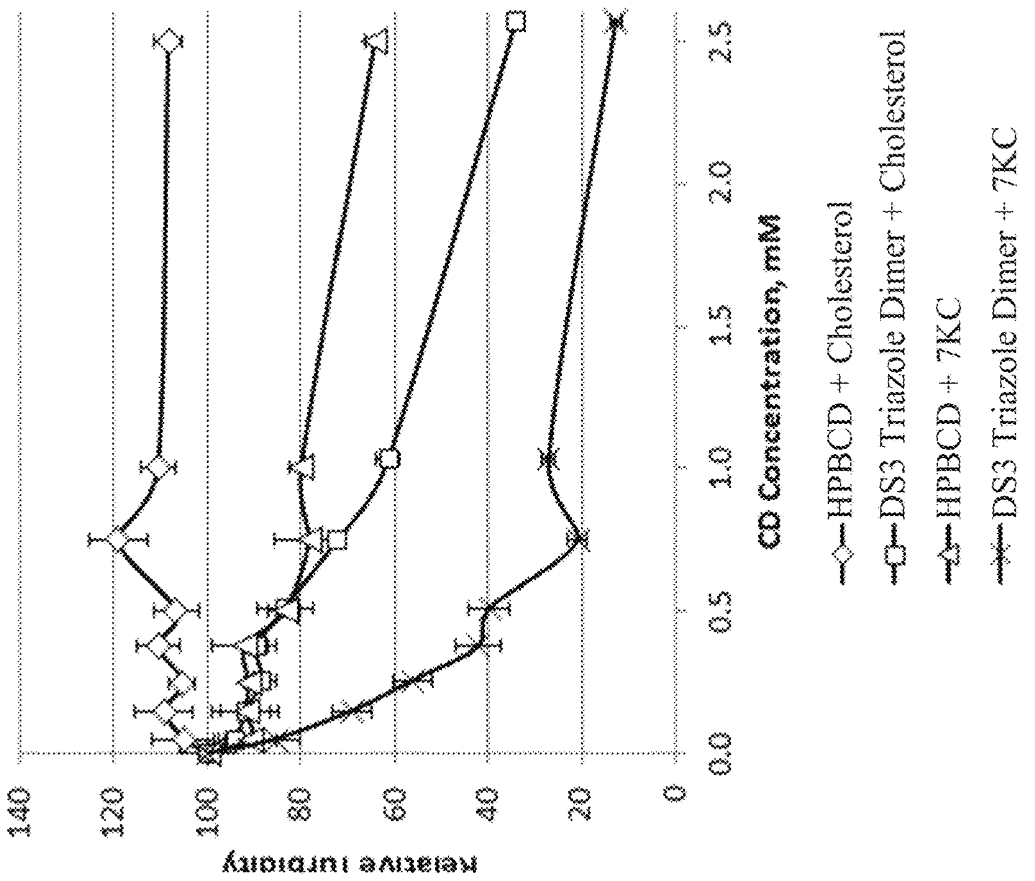
FIG. 5H. Solubilization of cholesterol and 7KC by HPβCD DS3 triazole linked dimers compared to HPβCD monomer.
Figure 5I:
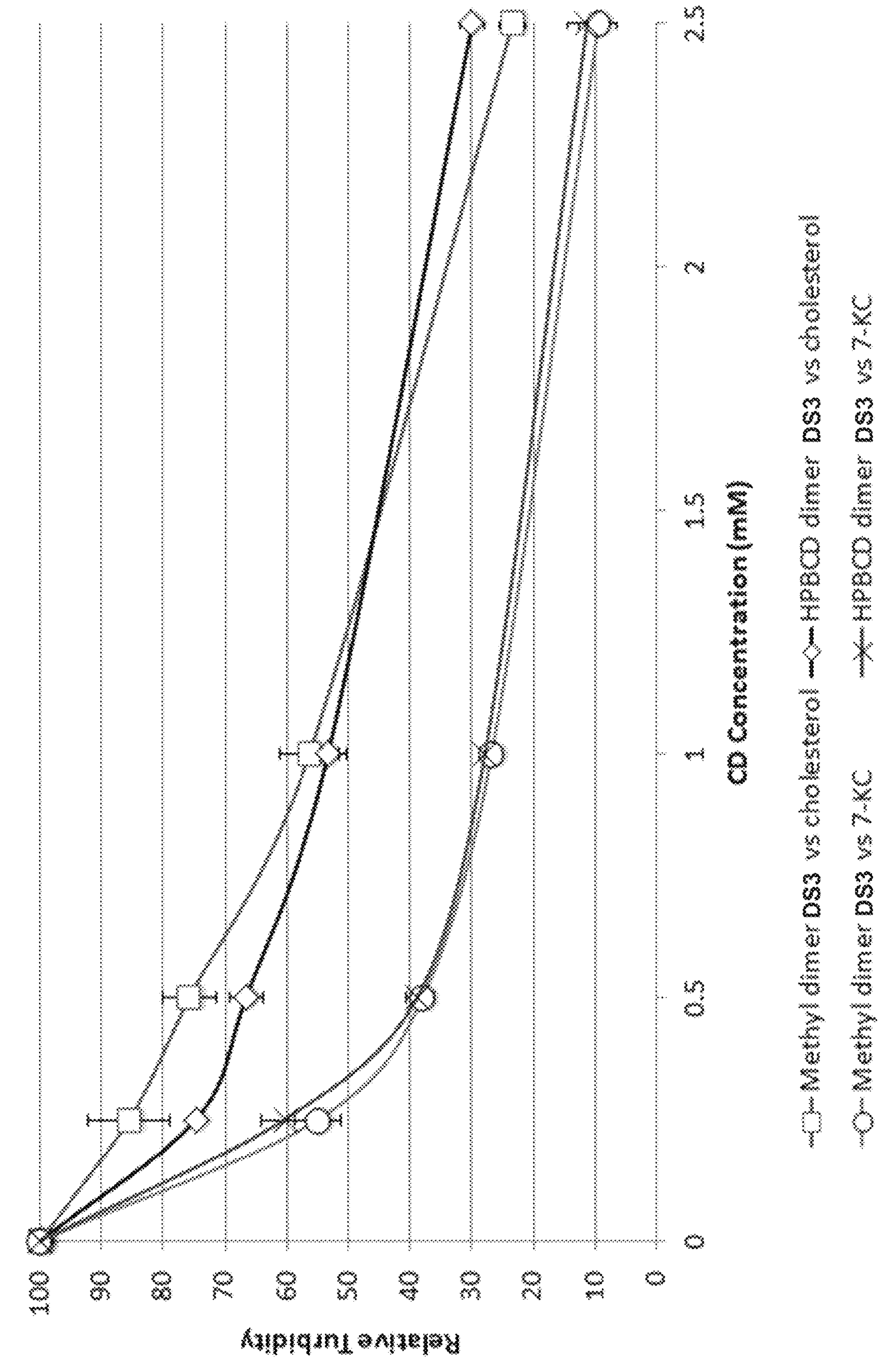
FIG. 5I. Solubilization of cholesterol and 7KC by MeβCD DS3 triazole linked and HPβCD DS3 triazole linked dimers.
Figure 5J:
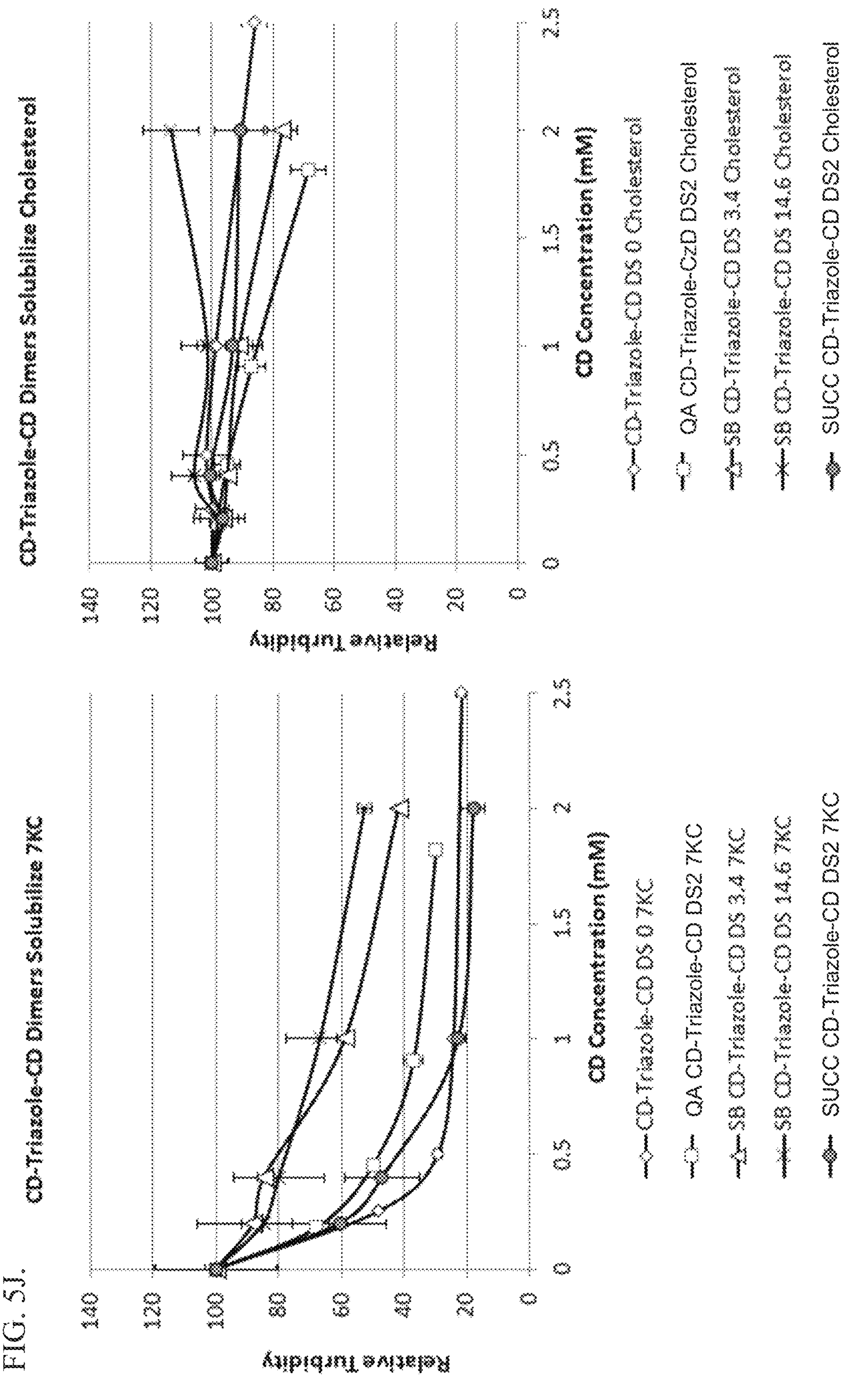
FIG. 5J. Solubilization of cholesterol and 7KC by βCD, QAβCD, SBβCD, and SUCCβCD triazole-linked dimers of various DS.
Figure 5K:
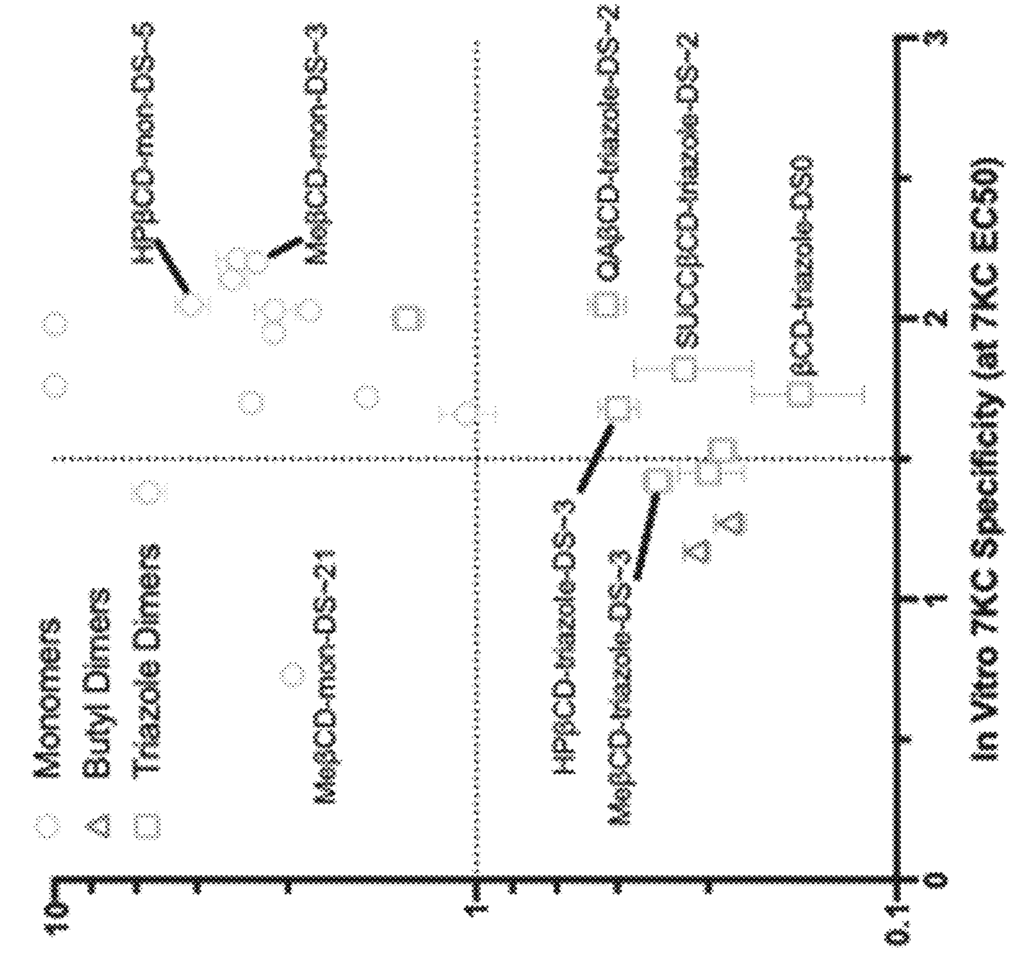
FIG. 5K. Compilation of 7KC EC50 and in-vitro 7KC specificity scores into a scatter plot, comparing in-vitro performances of βCD monomers and dimers. A low 7KC EC50 indicates that the CD has a strong affinity for 7KC. A higher 7KC specificity score indicates that 7KC was better solubilized by the CD than cholesterol. Triangles indicate the βCD butyl-linked dimers, squares indicate the triazole-linked dimers, and circles indicate the βCD monomers.
Figure 5L:
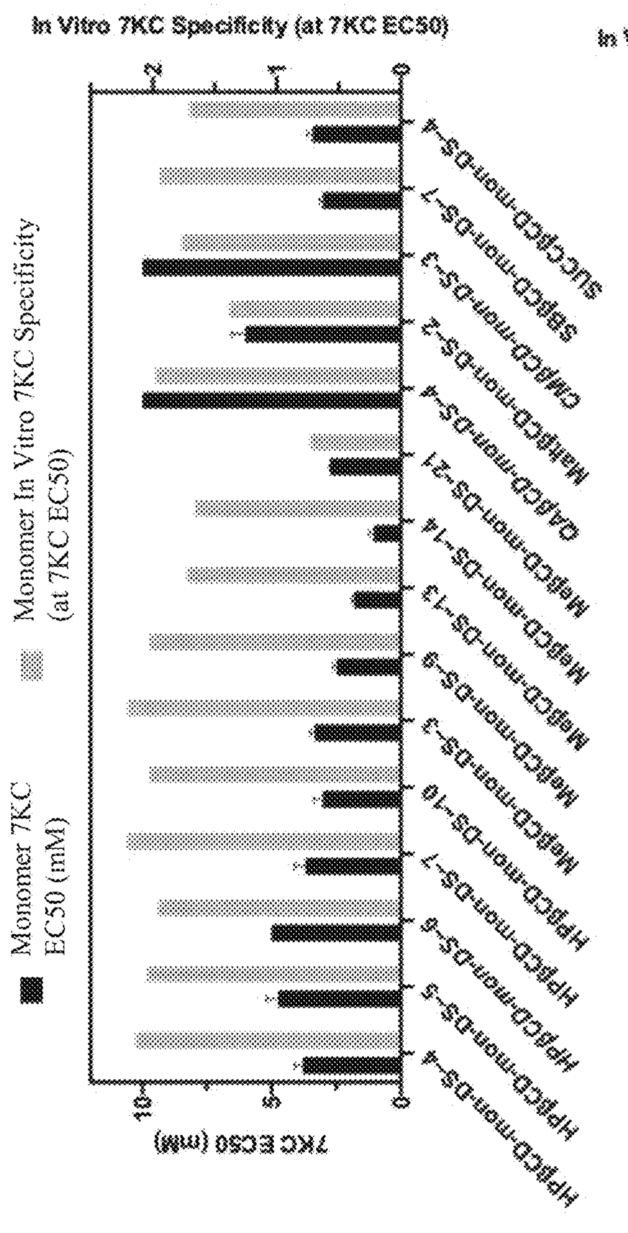
FIG. 5L. Bar graph comparison between the 7KC EC50 measured in turbidity assay and in-vitro 7KC specificity scores among the different substituted βCD monomers (solid bars) across various DS.
Figure 5M:
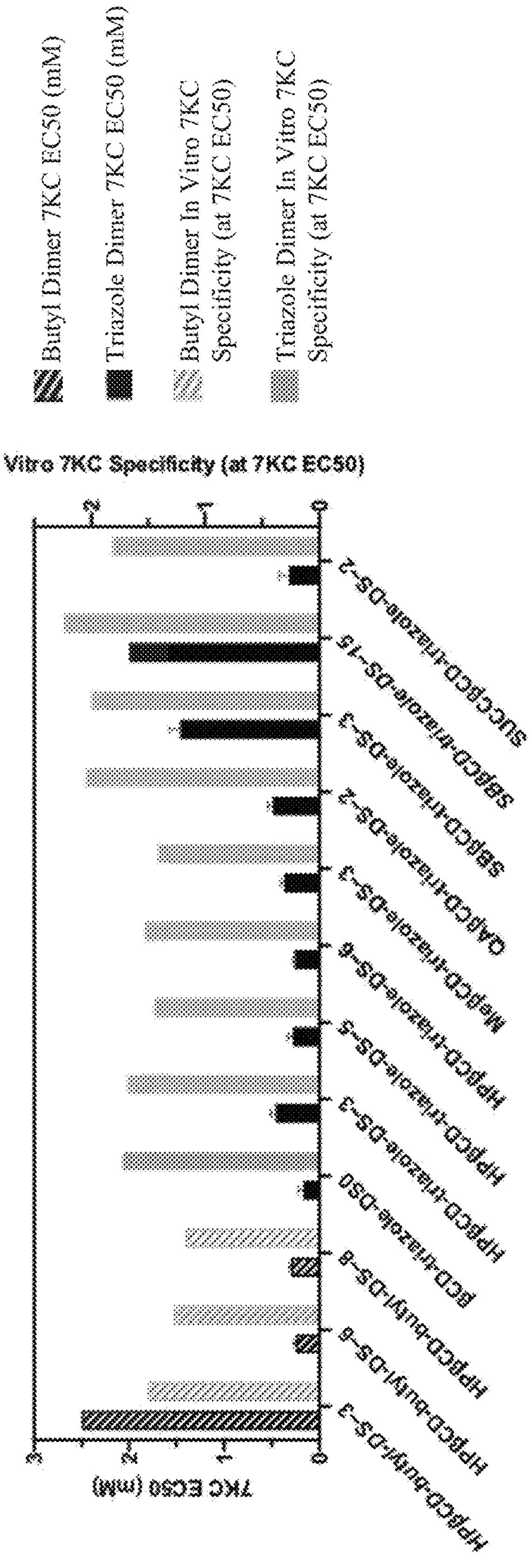
FIG. 5M. Bar graph comparison between the 7KC EC50 measured in turbidity assay and in-vitro 7KC specificity scores among butyl-linked (diagonal stripes) and triazole-linked (solid bars) substituted βCD dimers.
Figure 5N:
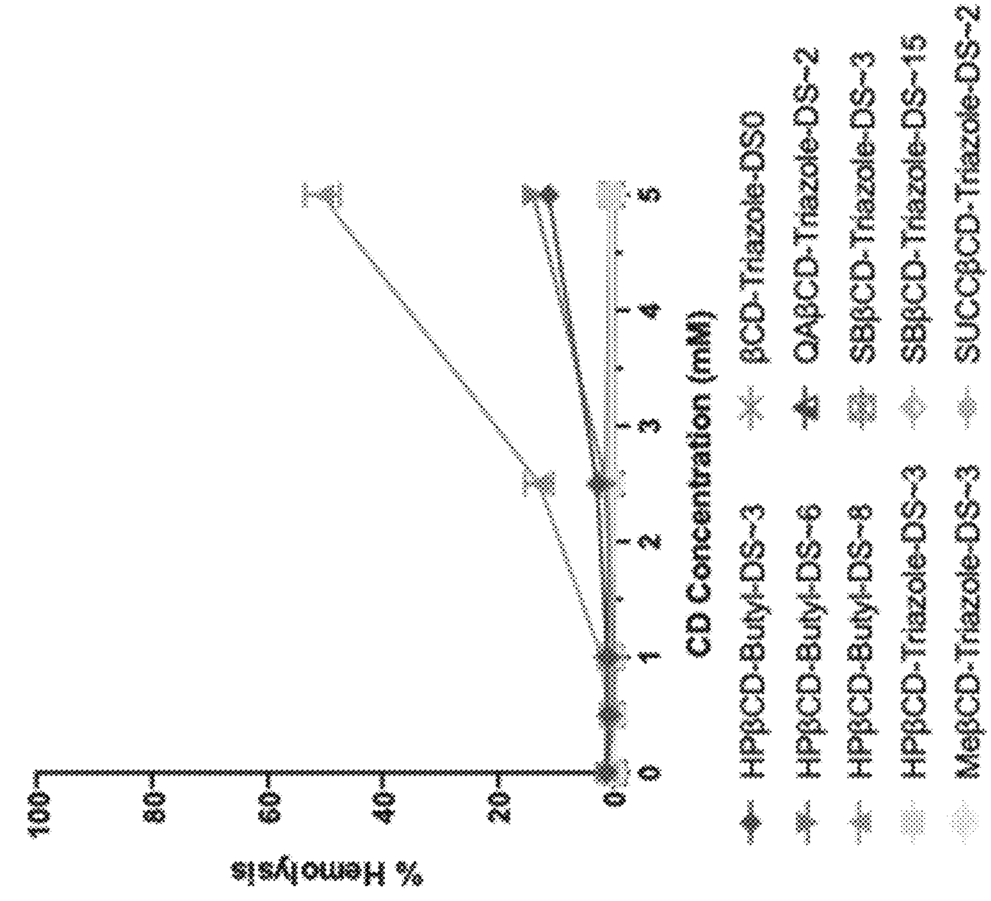
FIG. 5N. Percentage of hemolysis of red blood cells (RBCs) after treatment from different concentrations and substitutions of triazole-linked and butyl-linked βCD dimers at different DS.
Figure 5O:
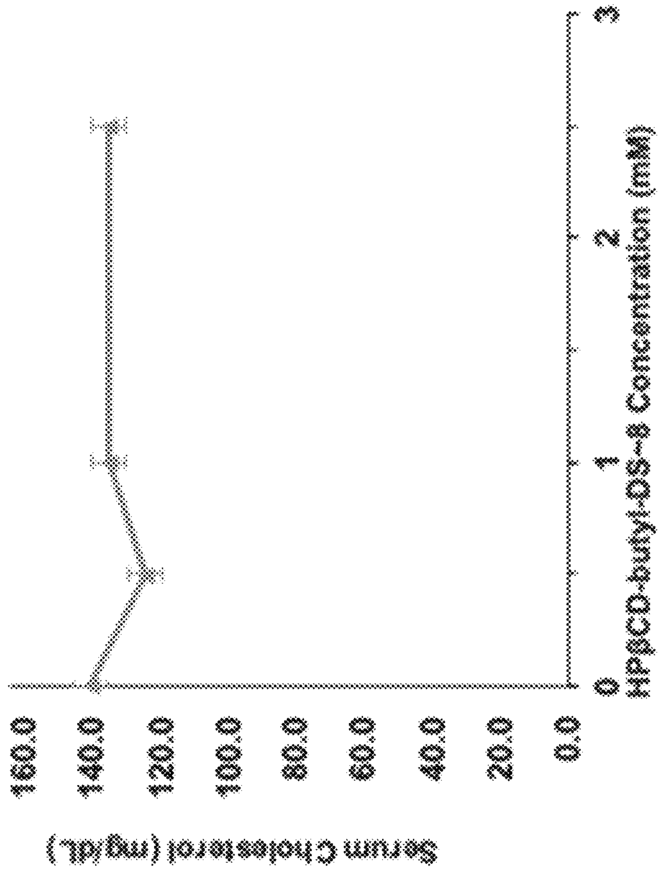
FIG. 5O. Concentration of cholesterol in serum (mg/dl) after incubation of various concentrations of HPβCD-butyl-DS~8 dimer (0-2.5 mM) with whole blood.
Figure 5P:
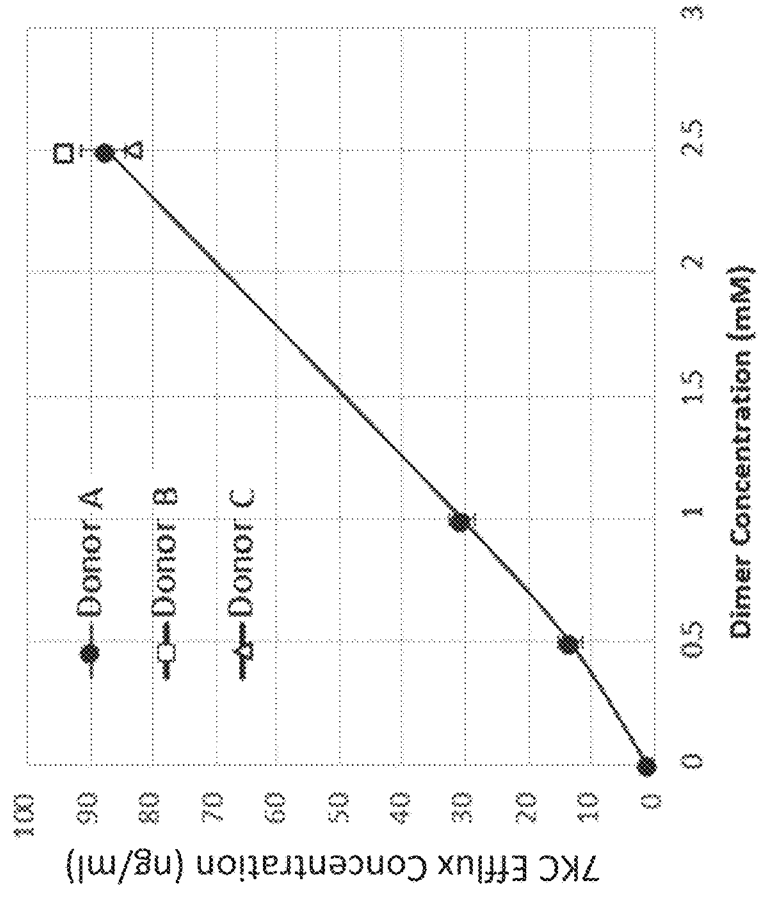
FIG. 5P. 7KC effluxed from red blood cells into plasma by treatment with HPβCD-butyl-DS~8 dimer (0-2.5 mM).
Figure 5Q:
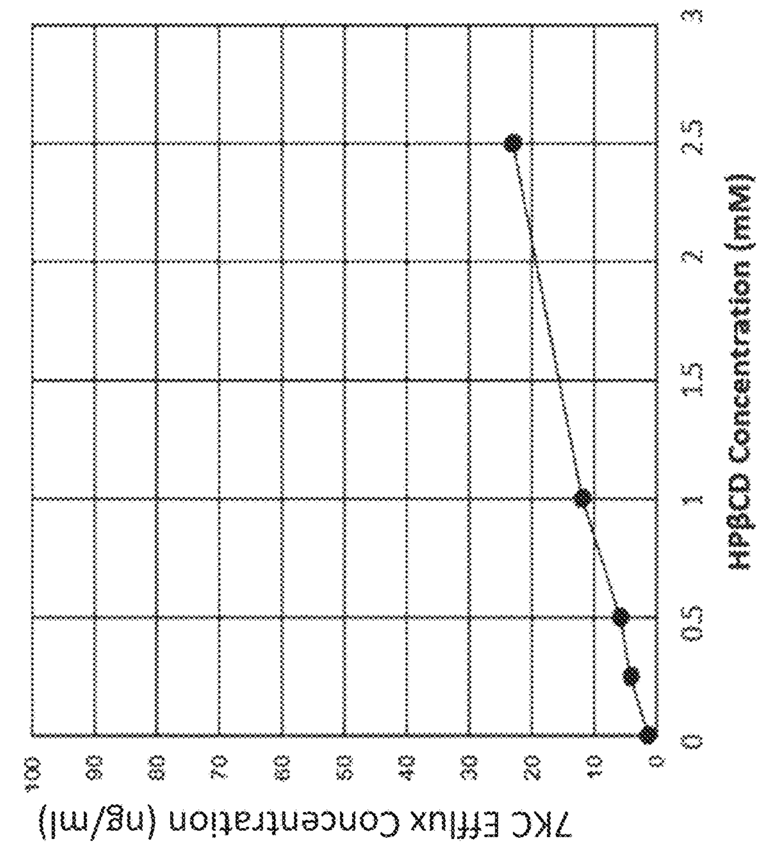
FIG. 5Q. 7KC effluxed from red blood cells into plasma by treatment with HPβCD monomer DS~5 (0-2.5 mM).
Figure 6A:
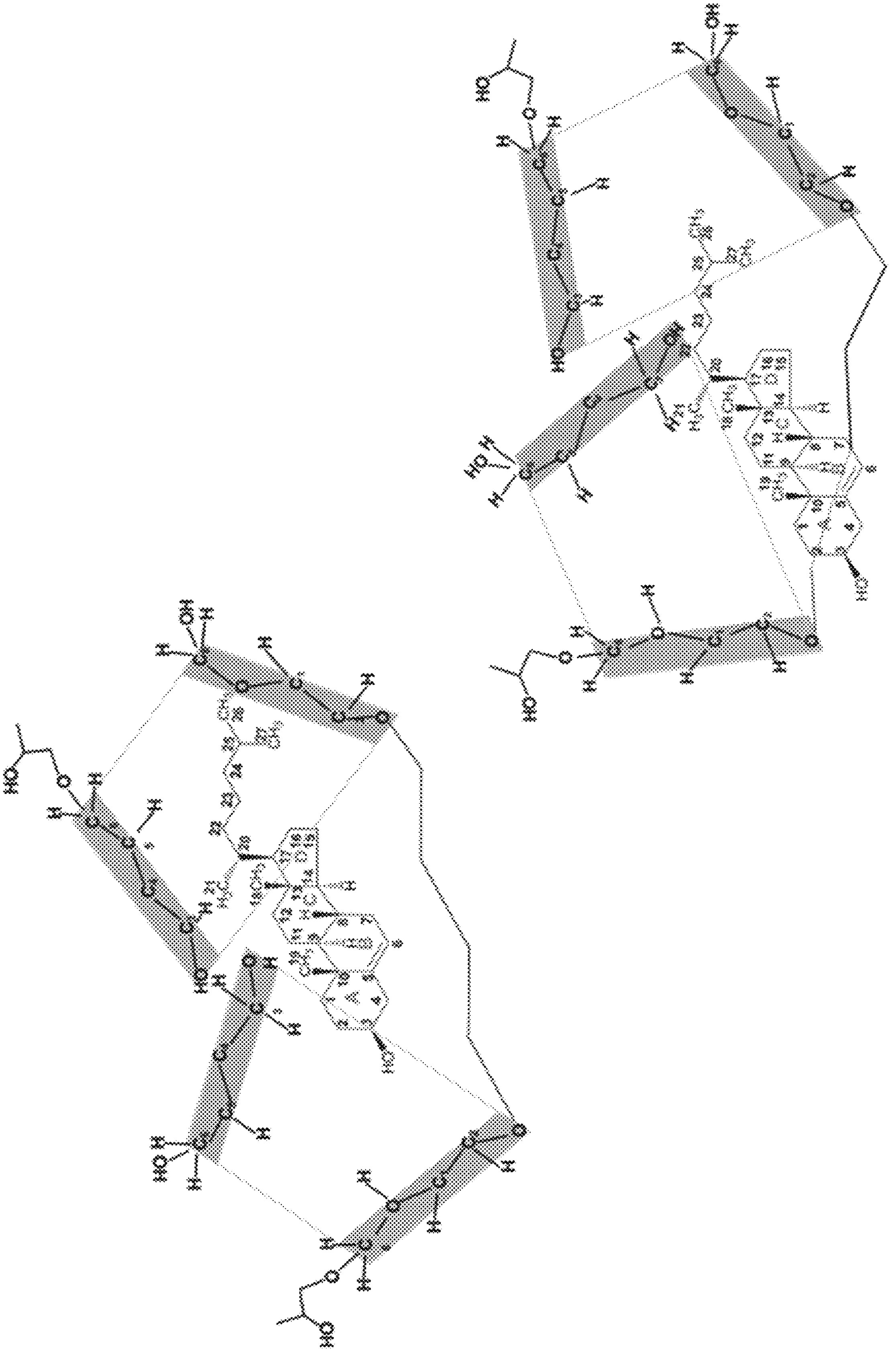
FIG. 6A. Schematic cross sections for the spatial interaction with HPβCD-butyl-DS~8 dimer and cholesterol in the CD host-guest complex determined by HSQC and ROESY NMR. The left model has the cholesterol included in the secondary face of both HPβCD units and the right model has the cholesterol tail being partially included in the secondary face of one HPβCD unit.
Figure 6B:
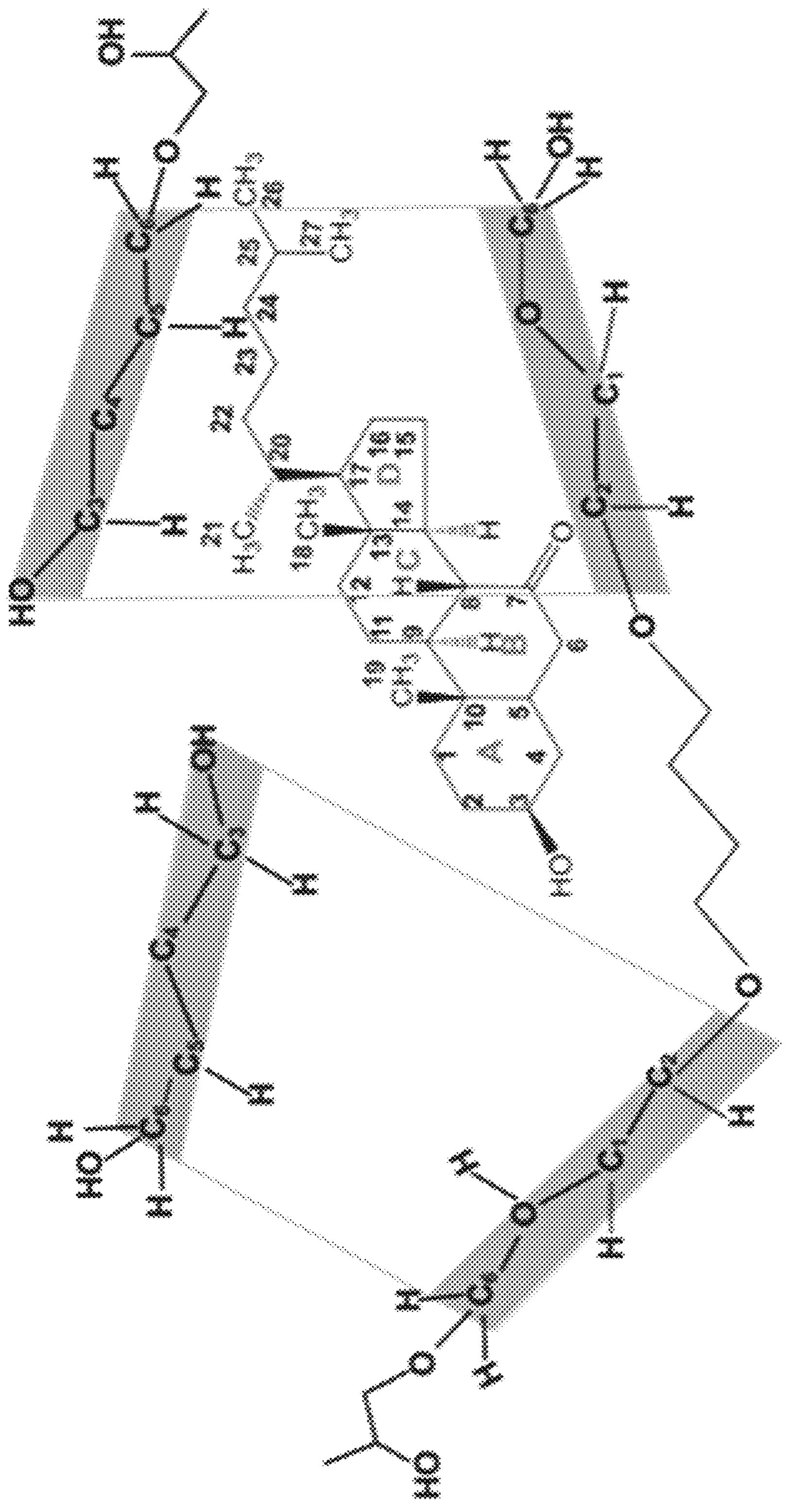
FIG. 6B. Schematic cross sections for the spatial interaction with HPβCD-butyl-DS~8 dimer and 7KC in the CD host-guest complex determined by HSQC and ROESY NMR.
Figure 6C:
FIG. 6C. Schematic cross sections for the spatial interaction with HPβCD-triazole-DS-3 dimer and cholesterol in the CD host-guest complex determined by HSQC and ROESY NMR. The left model has the cholesterol included in the secondary face of both HPβCD units and the right model has the cholesterol tail being partially included in the secondary face of one HPβCD unit.
Figure 6D:
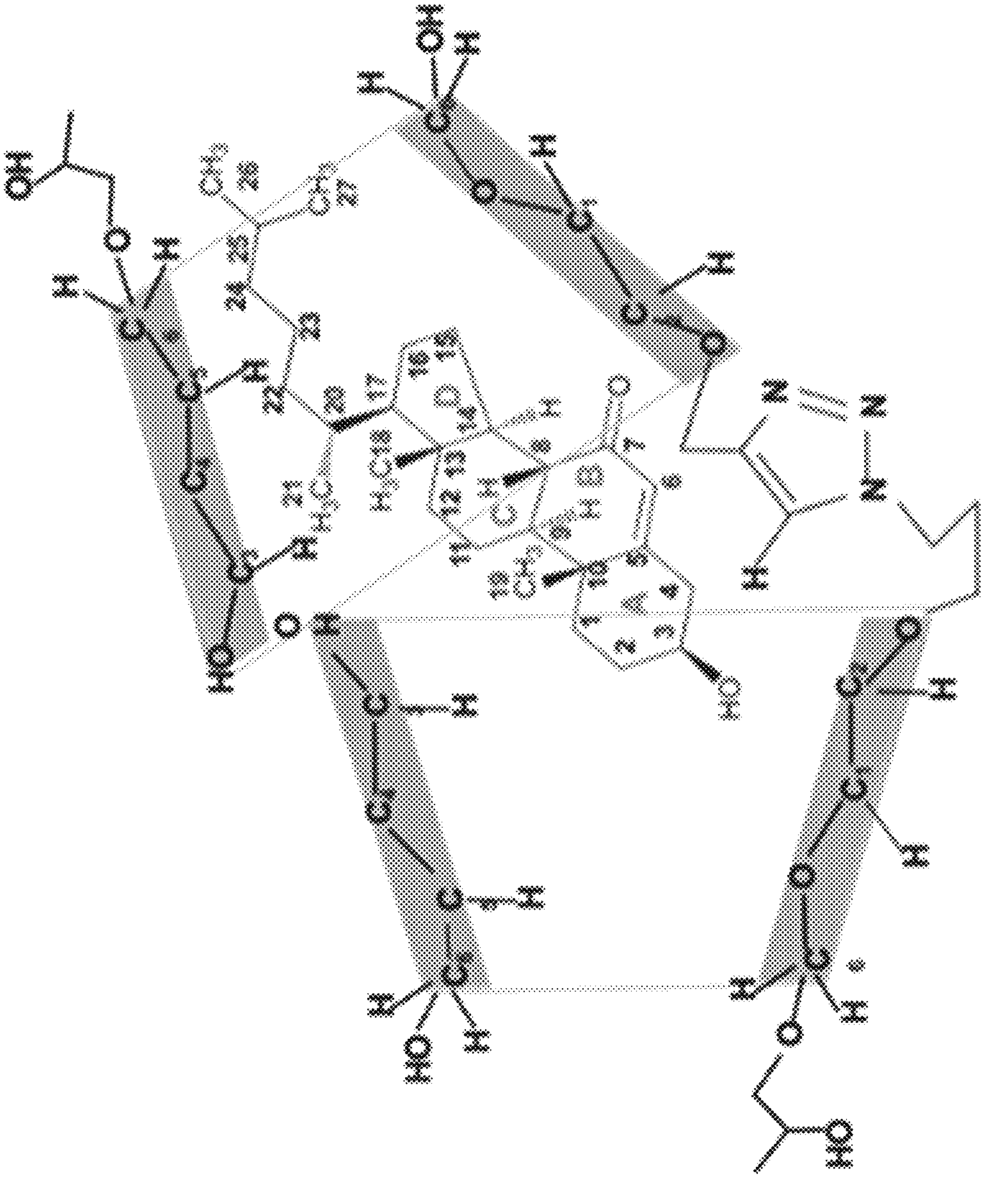
FIG. 6D. Schematic cross section for the spatial interaction with HPβCD-triazole-DS~3 dimer and 7KC in the CD host-guest complex determined by HSQC and ROESY NMR.

FIGS. 5P and 5Q demonstrate that HPβCD dimers (DS~8 as determined by both MALDI and NMR) can remove 7KC from blood cells (whole blood) much more efficiently than HPβCD monomers. This is an ex vivo assay on human subjects which allows us to achieve results that could predict the effects on human patients with even more accuracy than experiments on non-human animals. FIG. 5O demonstrates that this does not appreciably impact plasma cholesterol levels. This implies that the HPβCD dimers are not removing large quantities of cholesterol from blood cells. Removal of too much cholesterol from cells could potentially lead to rupturing of cell and organelle membranes and cause cell death. We wished to investigate this directly and therefore performed hemolysis assays.

Example 11. Hemolysis Induced Only by High Concentrations of CD Dimers

Methods

For the test solutions, the amount of PBS varied depending on the concentration of CD being tested, Samples were tested in triplicate. 50 μL of blood was added to each sample with PBS and CD solution (stocks also made in PBS) to achieve the appropriate concentration in a final volume of 200 μL. 5% Triton X-100 was used as the positive control and PBS was the negative control. Once all the samples were mixed the samples were placed into a 37 C incubator for three hours with agitation. The positive control was 100% hemolyzed by Triton X-100 detergent Once the samples were out of incubation, they were diluted by the same factor in a 96 hydrograde plate and normalized to the positive control absorbance, which Is around 1.1. The absorbance is read at 540 nm. The average of the samples was then corrected by subtracting the negative control. The experiment was run three times, and the error bars are the standard error of the mean (Malanga [et al.]. Journal of Pharmaceutical Sciences, 105(9):2921-31. (2016)). (Kiss let al.), European Journal of Pharmaceutical Sciences, 40(4):376-80. (2010)).

FIG. 5N demonstrates that butyl and triazole-linked dimer toxicity to blood cells remains quite low and have no appreciable toxicity in the pharmacological range of less than 1 mM. FIG. 5N shows hemolysis by butyl-linked HP-dimers of three different DS (DS~3, DS~6, DS~8), a DS~3 triazole-linked HP dimer, and a DS~3 triazole-linked Me dimer. At higher concentrations only the three butyl-linked dimers demonstrated measurable hemolysis. In FIG. 5N we further tested for hemolysis in various other substitutions of triazole-linked βCD dimers We tested unsubstituted: DS~2 quaternary ammonium, DS~2 succinyl, and DS~3 and DS~15 sulfobutyl. DS of each of the dimers was determined by MALDI and confirmed by NMR. Only unsubstituted dimers were tested up to 7.5 mM, at which concentration we can detect ~5% hemolysis. The other dimers were only tested up to 5 mM and no significant hemolysis was detected at any of the concentrations tested.

It would appear that the triazole dimerized forms of βCD are less hemolytic at high concentrations than the HPβCD butyl dimers tested, but both linkers and all substitution types show very low lysis, suggesting low toxicity.

Example 12. Solubilization of Sterols and Sterol-Like Compounds by CD Dimers

Cholesterol and 7KC were tested for solubilization by the dimers described in Examples 5-9.

Methods for In Vitro Solubility Assay (Turbidity Assay)

Sterol stock solutions (including cholesterol and 7KC) were suspended in 100% ethanol. Final concentration of suspensions: 3% ethanol, 300 μM sterol, in PBS with various concentrations of CDs. Samples were incubated for 30 mins at 37 C, and then absorbance was measured in a spectrophotometer plate reader at 350 nm. Samples were prepared in quadruplicate using a Beckman Biomek 2000 liquid handler, and plates with a hydrophilic coating were used to minimize sterol binding to the surfaces of the well. All experiments were run 3 or more times, and error bars are the standard error of the mean.

Turbidity values were normalized to the percentage of the turbidity measured in the absence of CDs.

Results

We tested our new dieters against cholesterol and 7KC in an in vitro spectrometry assay. In FIG. 5E-5F, DS3 is the butyl-linked dimer with an average of ~3 hydroxypropyl groups, DSβ is the butyl-linked dimer with an average of ~6 substitutions, and DS8 is the butyl-linked dimer with an average of ~8 hydroxypropyl substitutions. DS of each of the dimers was determined by MALDI and confirmed by NMR. The sterol concentration was always held constant at 300 μM, tested against various concentrations of HPβCD dimers. HP(CD-triazole-CD) are the triazole-linked CD dinners of the noted average number of substitutions as determined by MALDI while HP(CD-but-CD) denotes the butyl-linked dimers of noted DS.

FIGS. 5E-5F show that all HPβCD dimers that we synthesized solubilize both 7KC and cholesterol much more efficiently than HPβCD monomers. This is consistent with our computational models and predictions illustrating how two linked monomers can completely surround the sterol, protect it from water, maintain binding for long periods of time, and recover it if it is lost. At some low concentrations of dimer it is possible to compare the solubilization achieved to that achieved by high concentrations of monomers and approximate that the same solubilization is achieved with approximately 1/10th of the molar concentration. This implies that the affinity for cholesterol and 7KC might be in the range of approximately 10 times higher than that of the monomers, though we must await the results of other experiments to rigorously determine the affinity constants. We then further sought to determine whether these dimerized HPβCDs could bind 7KC with favorable affinity.

We found that several different HPβCD dimers could indeed bind 7KC favorably (FIGS. 5E-5F). FIG. 5F shows that triazole dimers labeled DS 3 bind 7KC with greater specificity than DS 6 or DS 7 dimers. These DS values were determined by MALDI. We further discovered that these HPβCDs could bind 7KC more favorably than cholesterol.

As described above in FIGS. 5O and 5P we found that, in human blood. DS8 HPβCD dimers removed substantial quantities of 7KC from the cells of donors while serum cholesterol levels seem to be unperturbed. This implies that, while the affinity for cholesterol may result in the removal of cholesterol from cells at the concentrations tested, it was not sufficient to perturb plasma cholesterol levels from the normal range.

We observed that the dimers with the lowest DS had the highest specificity for 7KC over cholesterol, so we performed a more detailed analysis of the least substituted molecules of each linked dimer. FIGS. 5G, 5H, and 5I go into more detail for the HP and methyl dimers that showed the best specificity for 7KC. We confirmed, in greater detail, that both head-to-head linked CD dimers with ~3 HP or methyl substitutions preferentially solubilized 7KC over cholesterol. These dimers show substantial affinity and specificity for 7KC at concentrations below 0.5 mM.

Based on the prediction that dimerized βCDs with other substitution groups with similar degrees of substitution would also bind 7KC and cholesterol with similar affinity and specificity, new substituted triazole-linked dimers were synthesized (Examples 6-9 above). We utilized a set of charged functional groups (quaternary ammonium (QA), sulfobutyl (SB), and succinyl (SUCC)) typically used as substitutions on CDs. These low-substitution compounds resulted in comparable or improved affinity and specificity for 7KC (FIG. 5J) as compared to unsubstituted, hydroxypropyl, or methyl substituted triazole-linked dimers (FIGS. 5G-5I). Conversely, highly substituted SB dimers did not bind either cholesterol or 7KC well. This is likely caused by the many bulky SB groups limiting access to the binding cavity of the CD dimer.

Turbidity data for a variety of monomers and dinners of varying substitution degree and identity are summarized in FIGS. 5K-5M. Taking the monomer and dimer turbidity data together with the computational data we can make two generalized conclusions: that low substitutions (likely most important on the secondary face) promote specificity for certain interactions, particularly with 7KG. The modeling data show that hydrogen bonding between secondary face hydroxyl groups and the 7-keto group may promote this specificity. Further, in general, the modeling data show that bulky substitutions can block access to the cavity of any potential guest molecules indiscriminately if present in sufficiently high DS levels. Thus non-bulky groups such as methyl groups added to a CD dimer at high substitution levels are predicted to bind sterol molecules such as cholesterol and 7KC with high affinity, but not particularly high selectivity for 7KG as compared to cholesterol, while a low substitution methyl beta CD dimer is predicted to bind 7KC with high specificity as compared to cholesterol. Conversely, CD dimers containing bulky substitutions such as SB are predicted to bind 7KC with specificity over cholesterol at low substitution levels, but at high substitution levels not to bind either cholesterol or 7KC, and likely no other sterols either, due to blocking access to the binding cavity. A somewhat less bulky group such as HP is predicted to behave similarly to SB, but in general a higher number of HP groups than SB groups would be required to block access to the cavity.

Based on the foregoing results, we predict that randomly methyl-substituted BCD dimers preferentially bind 7KC over cholesterol up to a substitution level of at least DS 10. Beyond this DS level, the specificity for 7KC over cholesterol may gradually decrease owing to the decreasing number of hydroxyl groups on the secondary face that are available for hydrogen bonding to 7KC as the degree of methyl substitution increases; however, binding to both 7KC and cholesterol are still expected to occur.

By contrast, randomly SB-substituted βCD dimers are predicted to preferentially bind 7KC over cholesterol up to a substitution level of at least DS 4 to DS 5, with the hydroxyl groups in the secondary face again contributing hydrogen bonds to 7KC and promoting stronger binding relative to cholesterol. However, beyond this DS level, specificity for 7KC may gradually decrease and additionally binding to both 7KC and cholesterol as well as other similar guest molecules is expected to decrease due to steric interference with guest access to the βCD cavity. In our data DS over 14 seems to nearly abolish binding to either cholesterol or 7KC.

For similar reasons, HP-substituted dimers are predicted to preferentially bind 7KC over cholesterol up to a substitution level of at least DS 4 or DS 5, while from above this level up to about DS 20 binding specificity for 7KC over cholesterol is expected to gradually decrease with both being bound, and above DS 20 binding to both 7KC and cholesterol is expected to decrease due to steric interference with guest access to the βCD cavity.

SUCC-substituted and QA-substituted βCD dimers are also predicted to preferentially bind 7KC over cholesterol up to a substitution level of at least DS 4 or DS 5, with the hydroxyl groups in the secondary face again contributing hydrogen bonds to 7KC and promoting stronger binding relative to cholesterol. However, beyond this DS level, specificity for 7KC may decrease and additionally binding to both 7KC and cholesterol is expected to gradually decrease due to steric interference with guest access to the βCD cavity over a certain DS level, perhaps over DS 15.

Our wet lab data validate these models as follows: all commonly used substitutions that we placed on our variously synthetic. βCD dieters in low quantities (~DS 3-4) demonstrated specificity for 7KC over cholesterol. Increasing the DS of HP groups over 4 and up to 8 reduced affinity for 7KC, but not for cholesterol. Increasing the DS of SB dimers to ~15 severely reduced binding to both cholesterol and 7KC.

Figure 14A:
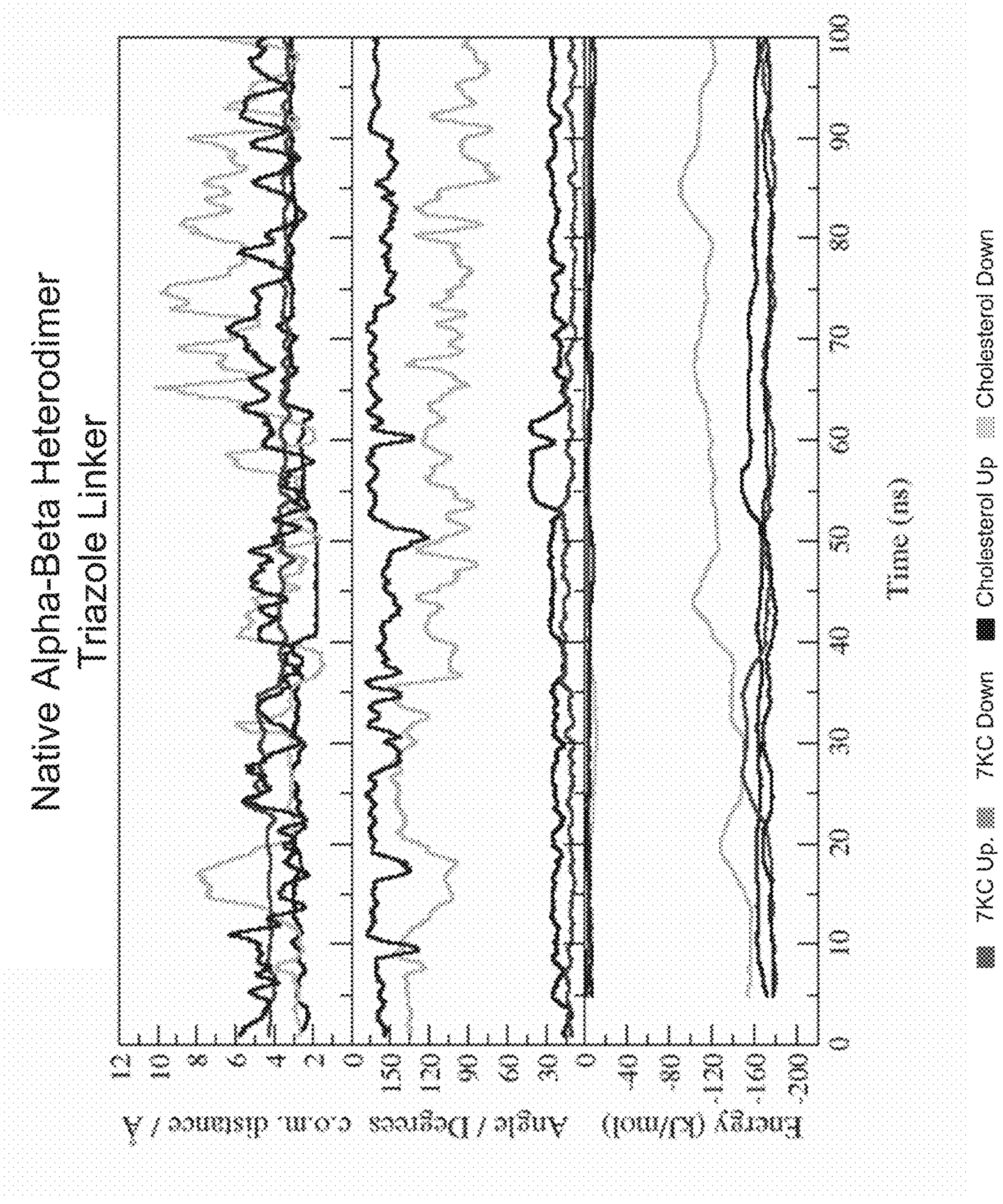
FIG. 14A depicts results from MD simulations of a native αCD-native βCD heterodimer complexed with 7KC or cholesterol in both orientations.

Example 13. MD Simulations for Native αCD-TZL-Native βCD Heterodimer-Sterol Complexation FIG. 14A shows trajectory results from MD simulations of a native αCD-TZL-native βCD heterodimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns.

The data shows that the heterodimer forms comparatively stable host-guest interactions with cholesterol and 7KC, but the least stable complex is the one with cholesterol in the down orientation. This indicates that, while 7KC can form a strong complex in both directions, cholesterol cannot. This suggests that these heterodimers may show specificity for 7KC in vitro.

Figures 14B, 14C:
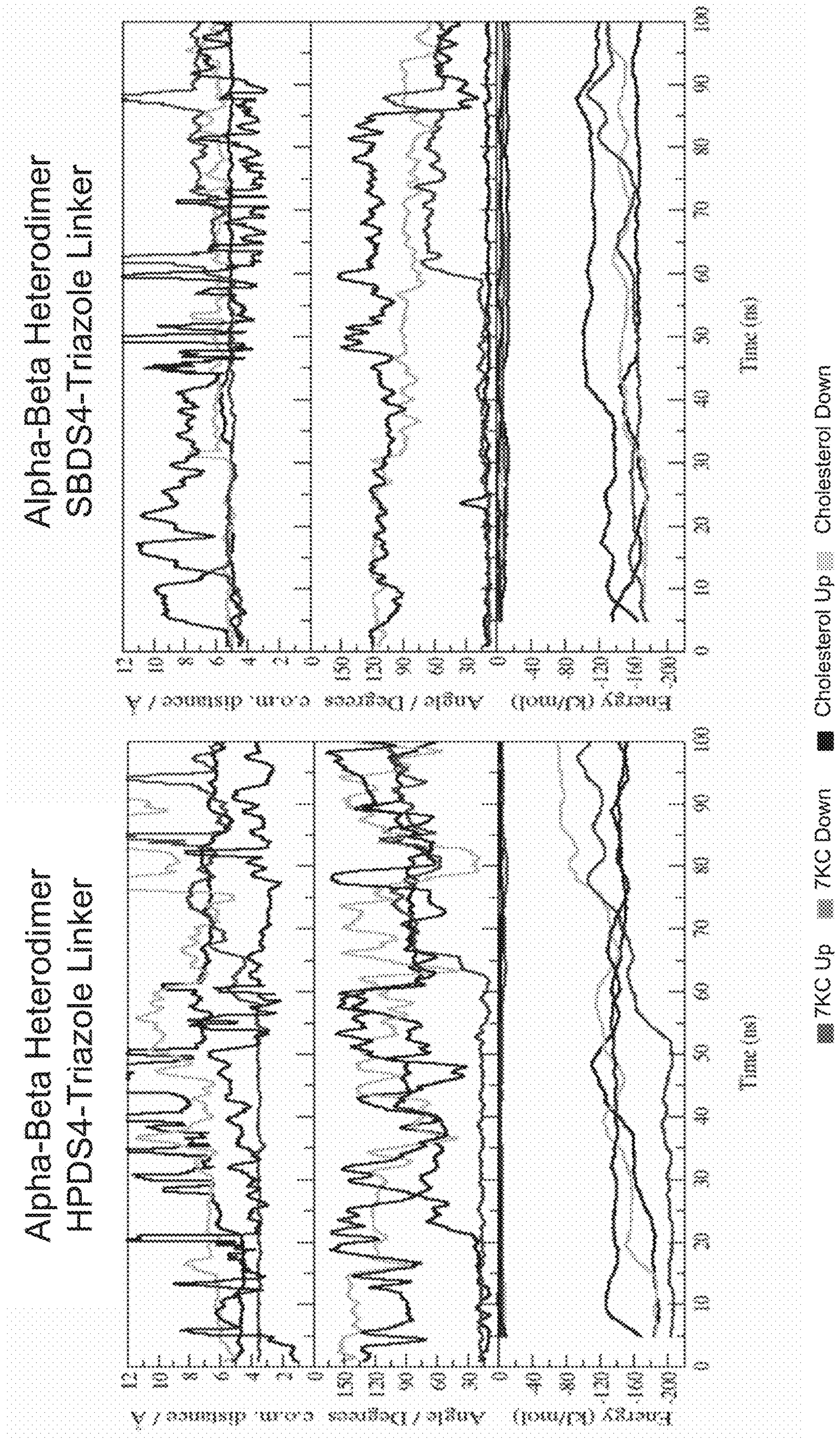
FIG. 14B depicts results from MD simulations of a HPDS2αCD-HPDS2βCD heterodimer complexed with 7KC or cholesterol in both orientations.
FIG. 14C depicts results from MD simulations of a SBDS2αCD-SBDS2βCD heterodimer complexed with 7KC or cholesterol in both orientations.

Example 14. MD Simulations for HPαCD DS2-TZL-HPβCD DS2 Heterodimer-Sterol Complexation FIG. 14B shows trajectory results from MD simulations of a HPαCD DS2-TZL-HPβCD DS2 heterodimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD direr and the sterol (i.e. the host and guest, respectively, in their host-guest complexing) over a period of 100 ns.

The data shows specificity for 7KC in the up orientation (this is expected; as the smaller cavity encases the tailgroup and the larger cavity encases the bulkier headgroup). All other complexes break by −40 ns. 7KC In the up orientation has the best interaction energy (~200 kJ/mol) while cholesterol in the down orientation has the worst (−80 kJ/mol to −150 kJ/mot), This suggests specificity for 7KC by this molecule, though further studies are necessary to fully understand why.

Example 15. MD Simulations for SBαCD DS2-TZL-SBβCD DS2 Heterodimer-Sterol Complexation FIG. 14C shows trajectory results from MD simulations of a SBαCD DS2-TZL-SBβCD DS2 heterodimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns.

The data shows again that 7KC in the up orientation has a favorable interaction, but in this case cholesterol had a stronger energy of interaction. Presumably, the steric hindrance of the SB groups affects complexation with 7KC more than the hydroxypropyl groups, All of the complexes except for cholesterol in the up orientation break before the end of 100 ns. More research is necessary to fully understand the specificity of this type of molecule, but it is clear that the sterols are still effectively encapsulated by this dimer.

Figure 15A:
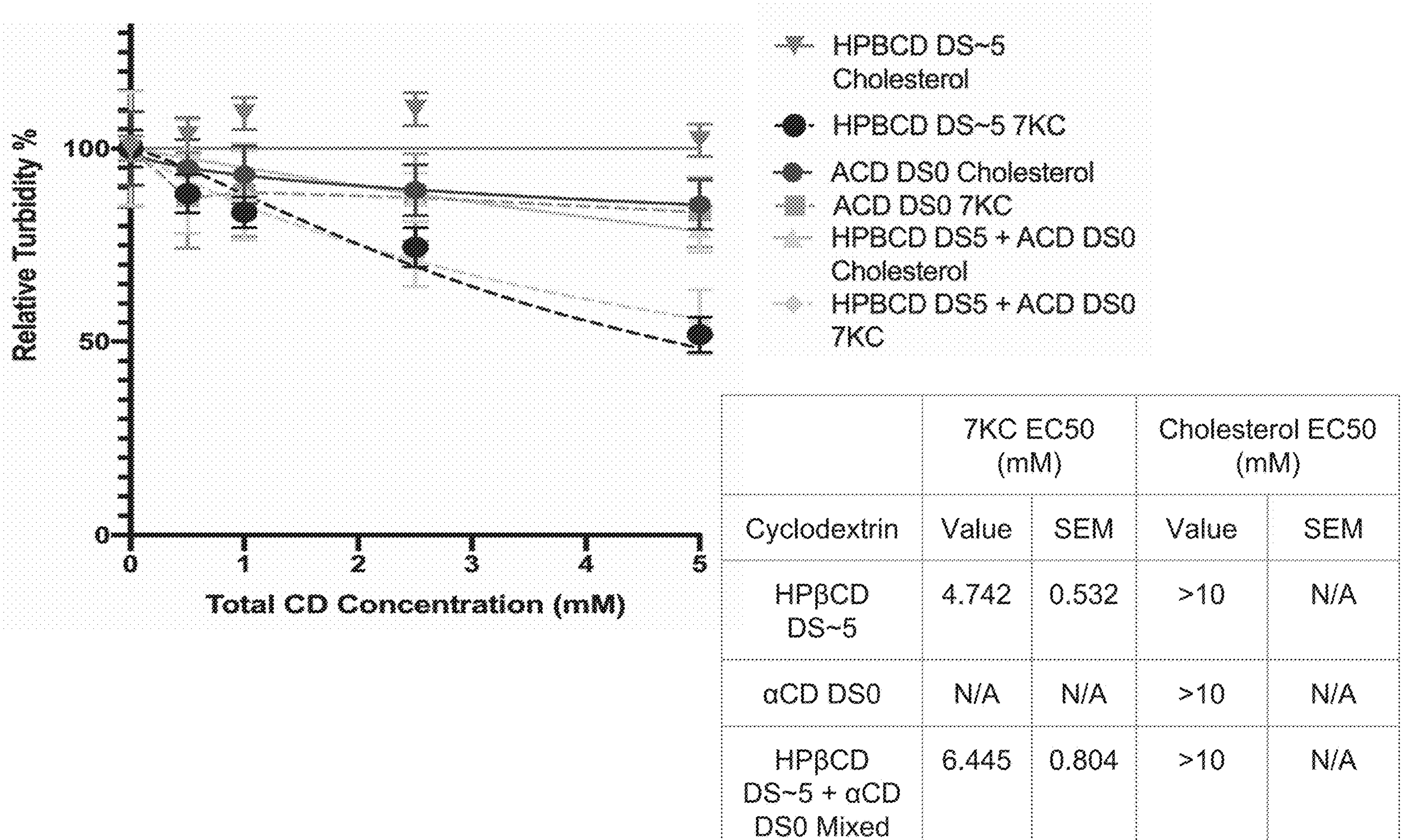
FIG. 15A depicts in-vitro % turbidity results of the solubilization of 7KC or cholesterol by native αCD, HPβCD DS~5, and a 1:1 molar mixed monomer solution of native αCD and HPβCD DS~5 at 350 nm from a turbidity assay.

Example 16. Solubilization of 7KC and Cholesterol by HPβCD, Native αCD, and Mixed Monomer Solution of HPβCD and Native αCD FIG. 15A shows the ability of HPβCD (DS~5) monomer and native αCD monomer to solubilize 7KC and cholesterol assessed by percent turbidity. Lower turbidity indicates greater ability to solubilize a given sterol.

We also combined HPβCD (DS~5) and native αCD in a 1:1 molar ratio and assessed the turbidity of the monomer mixture. The mixed monomer concentration is given as the total monomer concentration. The native αCD showed no specificity and low affinity for 7KC and cholesterol. The ability of the mixed monomers to solubilize 7KG was similar to that of the HPβCD (DS~5) (FIG. 15A, top). The mixed monomer solution resulted in an more effective encapsulation of both sterols and increased specificity for 7KC, relative to the native αCD on it's own (FIG. 15A, bottom). The similar turbidity profiles between native αCD and the mixed monomer solution for 7KC suggest that there may be complexations of the CD with 7KC at a ratio greater than 1:1 between the CD and 7KC. Presumably, the CD sterol complexes may include single monomers encapsulating 7KC, multiple distinct monomers with 7KC, or a combination of HPβCD and native αCD both encapsulating different regions of 7KC in the mixed monomer solution. More research is needed to identify a ratio between the HPβCD and the native αCD for the mixed monomer to show a synergistic effect. These results suggest a hetero dimer between native αCD and HPβCD could be a promising encapsulator of 7KC and other sterols.

Figure 10A:
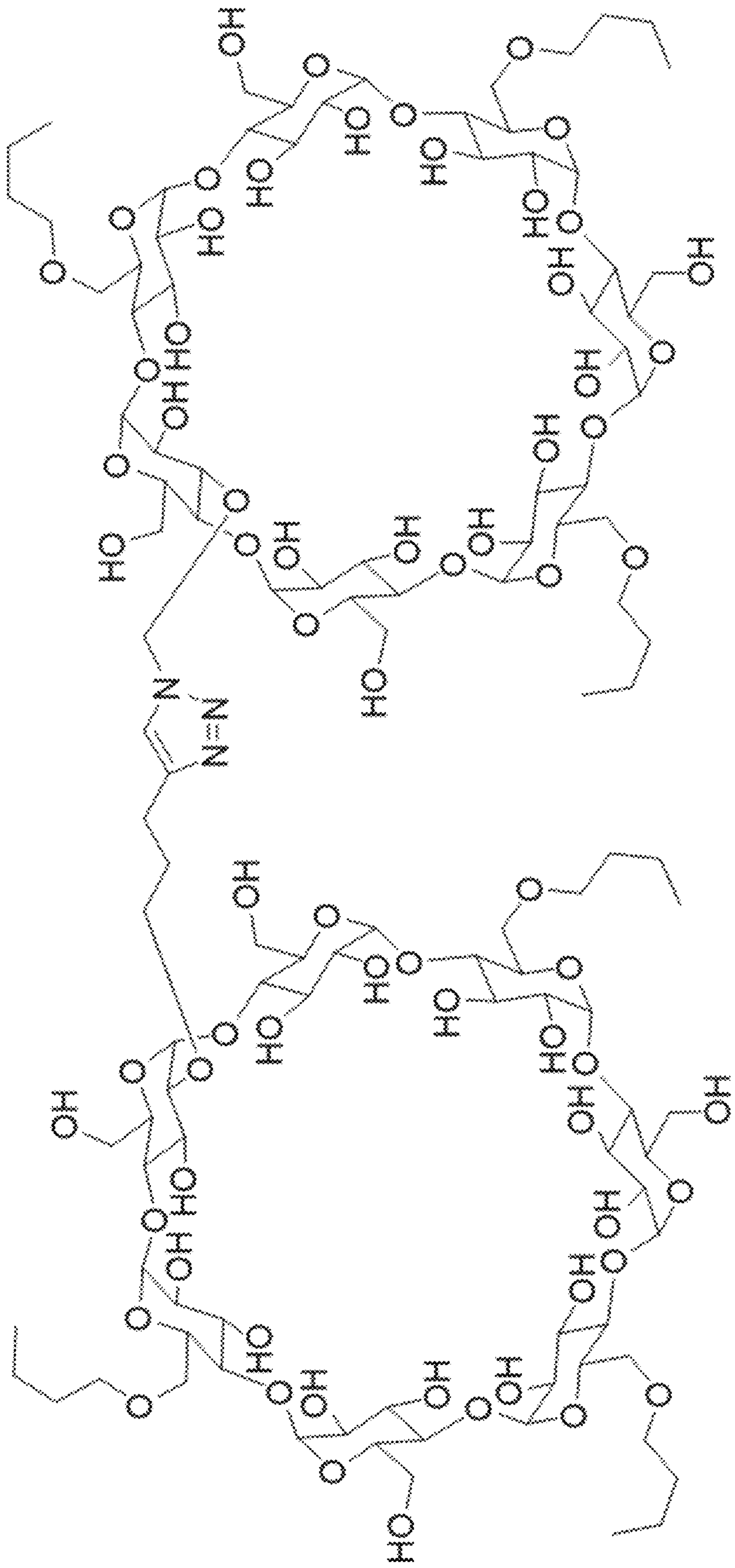
FIG. 10A depicts the full chemical structure of one possible isomer of a triazole-linked βCD homodimer substituted with butyl moieties on the primary side DS6 assessed in MD simulations.
Figure 10B:
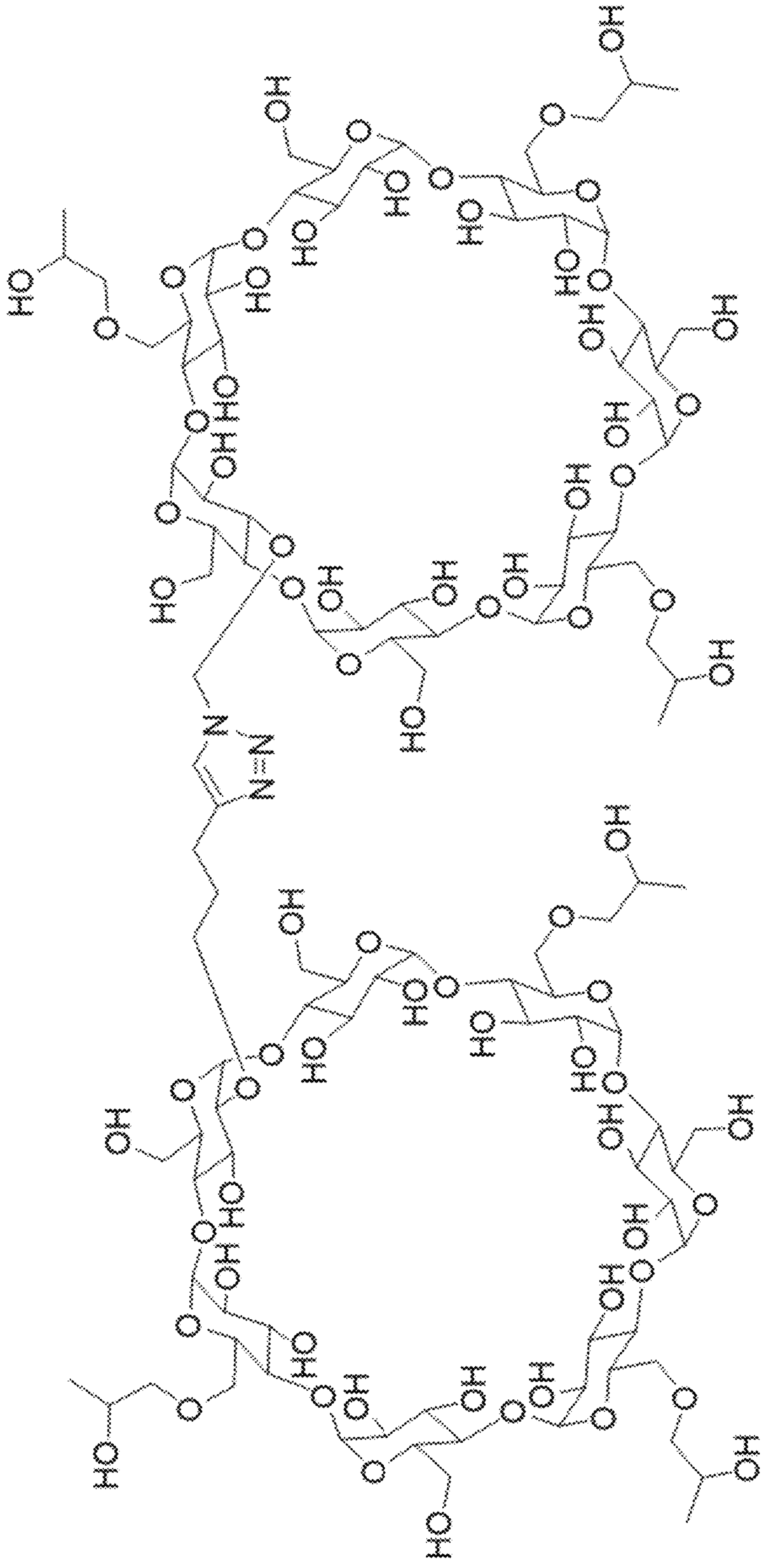
FIG. 10B depicts the full chemical structure of one possible isomer of a triazole-linked βCD homodimer substituted with (2-hydroxypropyl) moieties on the primary side DS6 assessed in MD simulations.
Figure 15B:
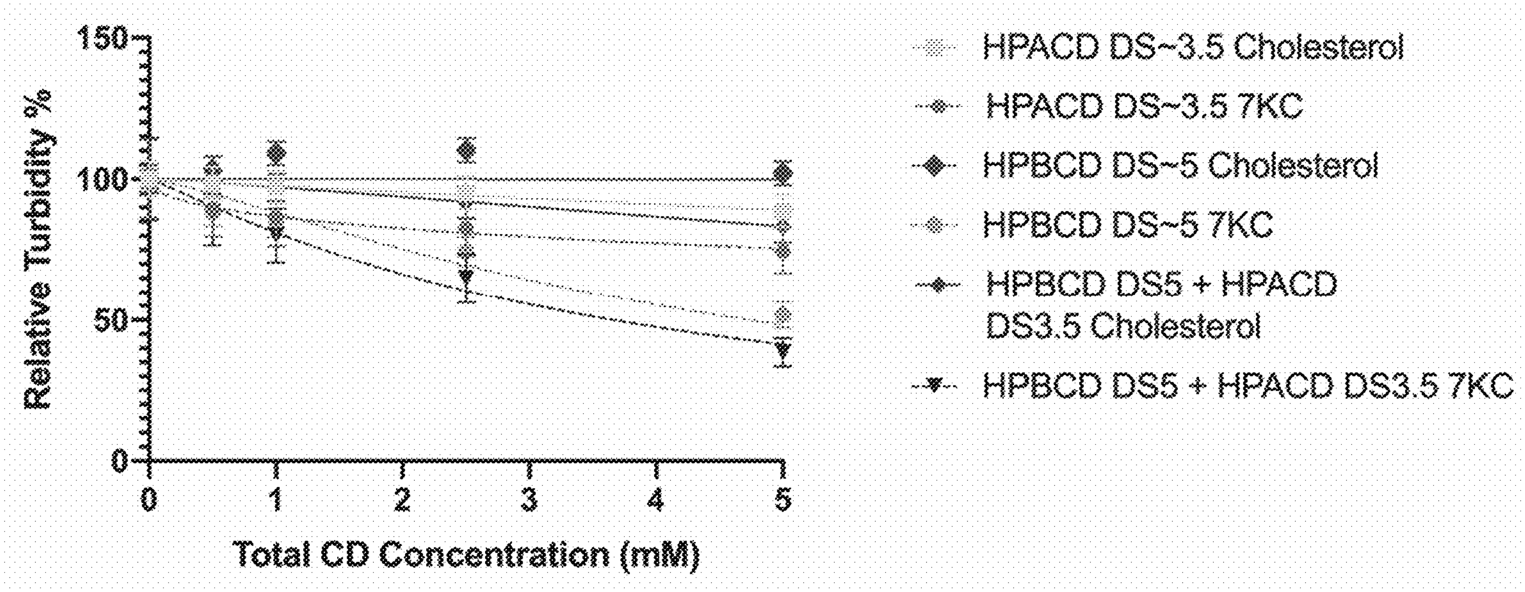
FIG. 15B depicts in-vitro % turbidity results of the solubilization of 7KC or cholesterol by HP-αCD, HPβCD DS~5, and a 1:1 molar mixed monomer solution of HP-αCD and HPβCD DS~5 at 350 nm from a turbidity assay.
Figure 17B:
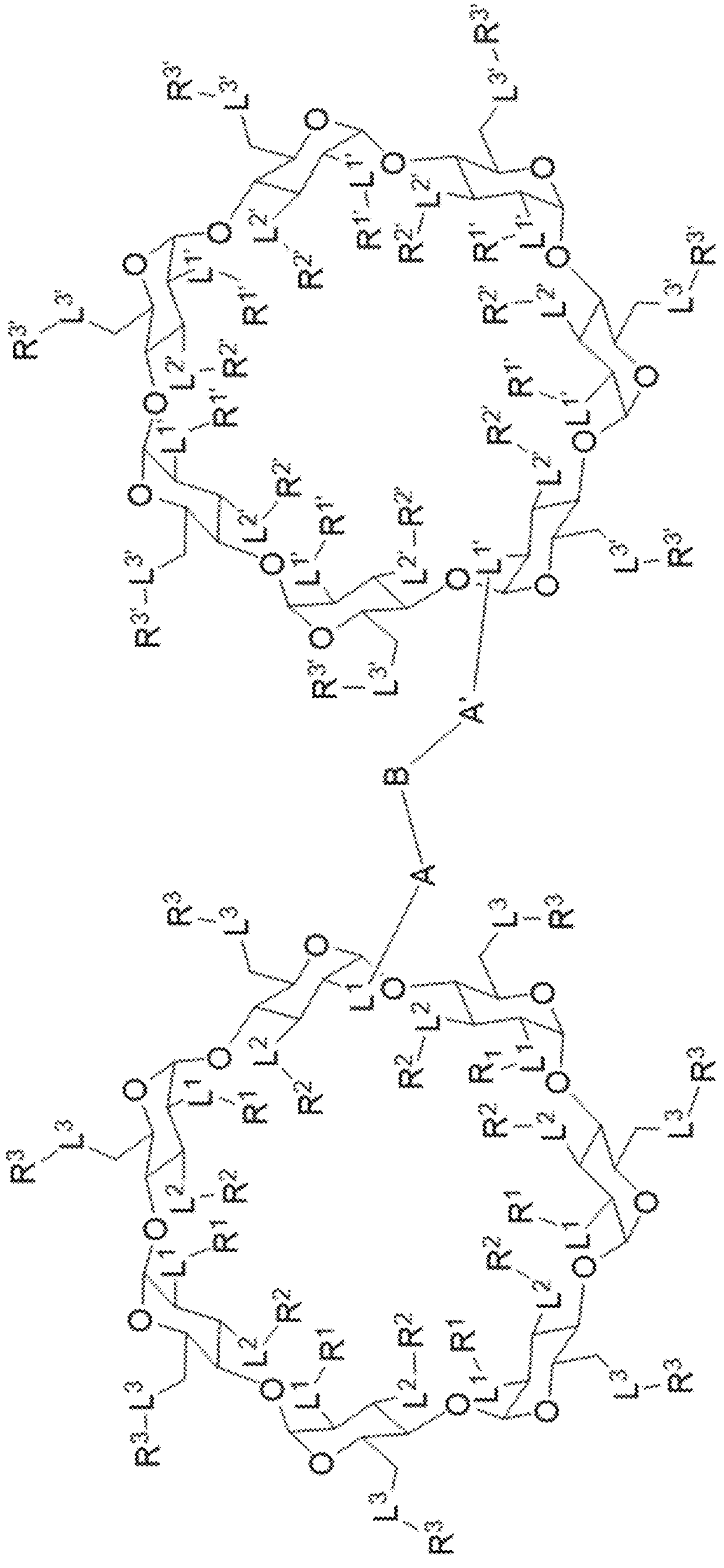
FIG. 17A depicts chemical structures of two βCDs, C-Xa and C-Xb, that are combined to form an asymmetric dimer covalently linking at the L1, L2, L1', and L2' positions of the CD secondary face.
Figure 17C:
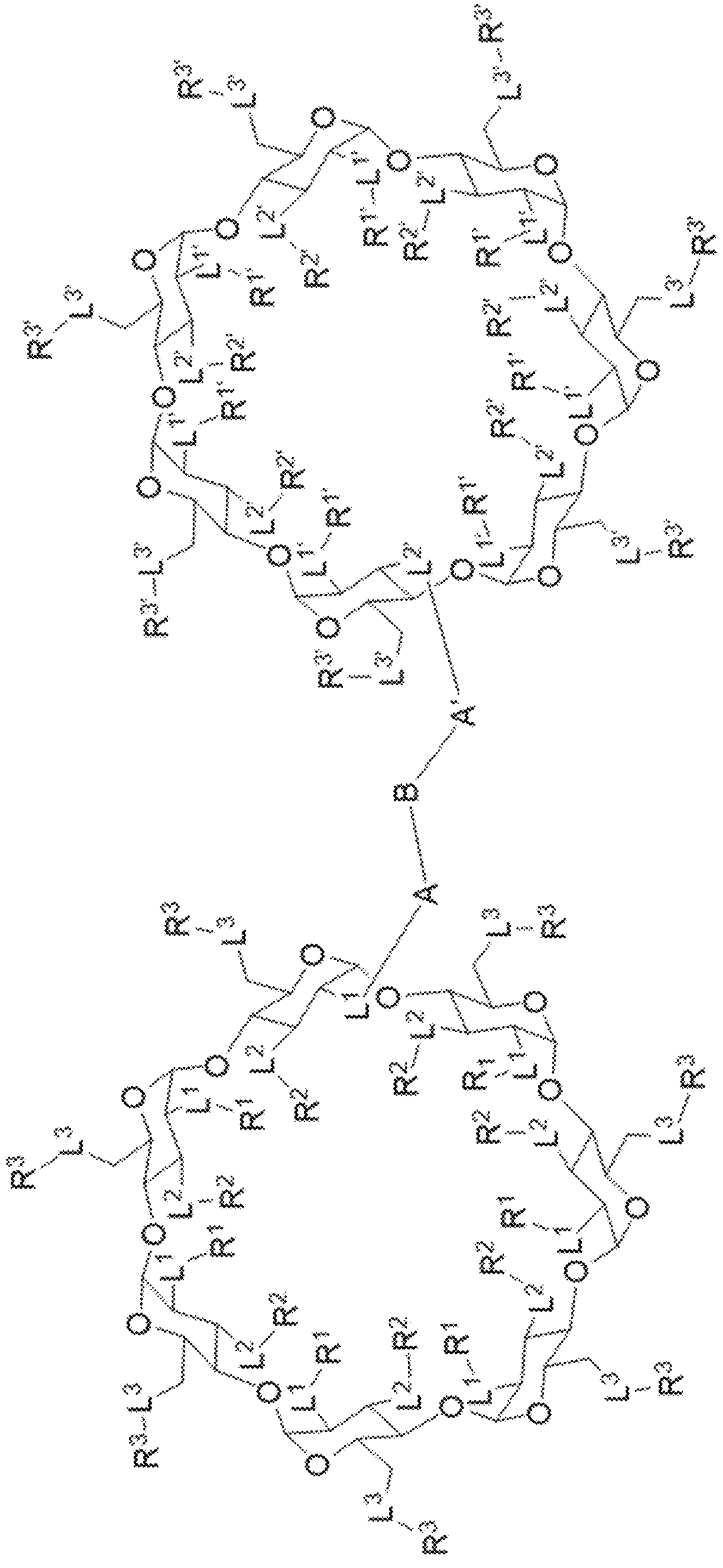
Figure 17D:
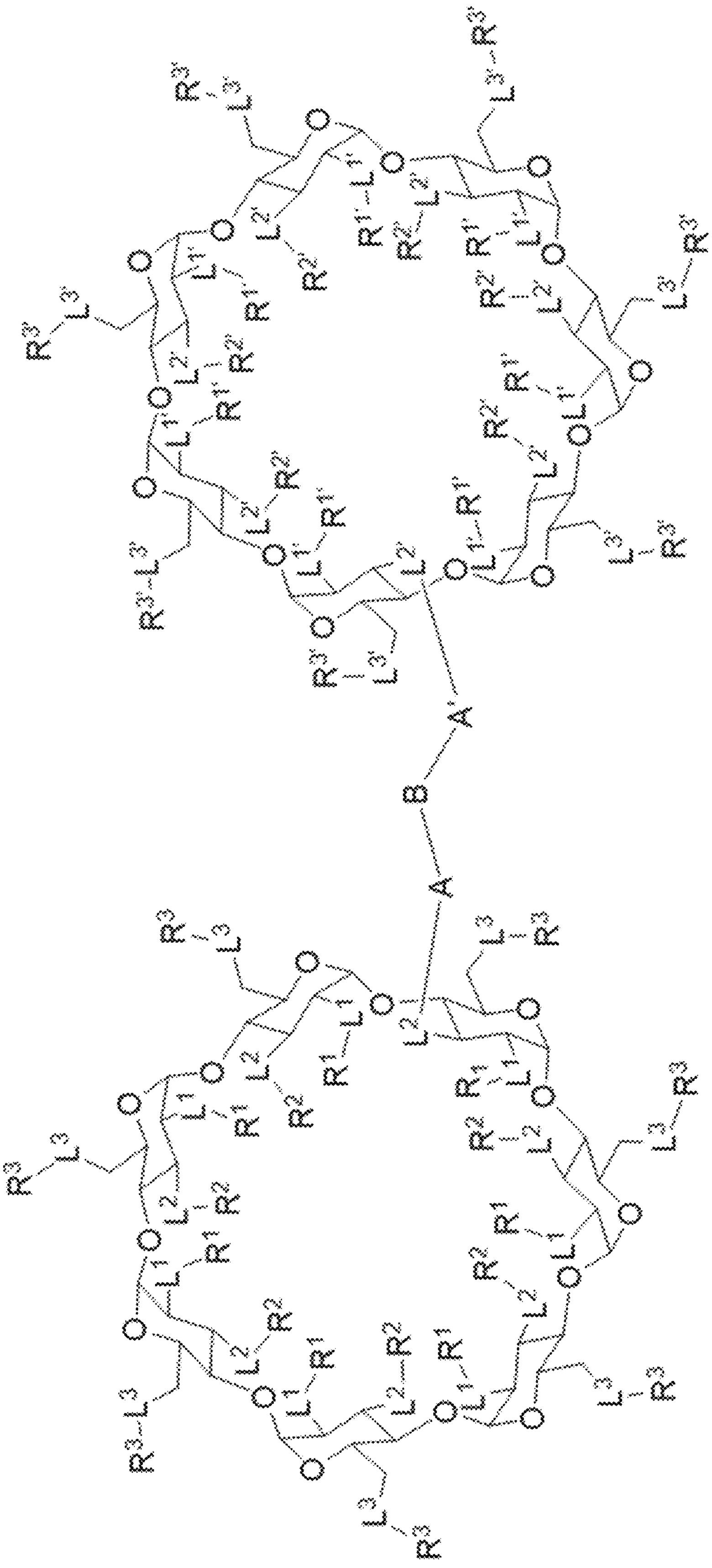
Figure 18A:
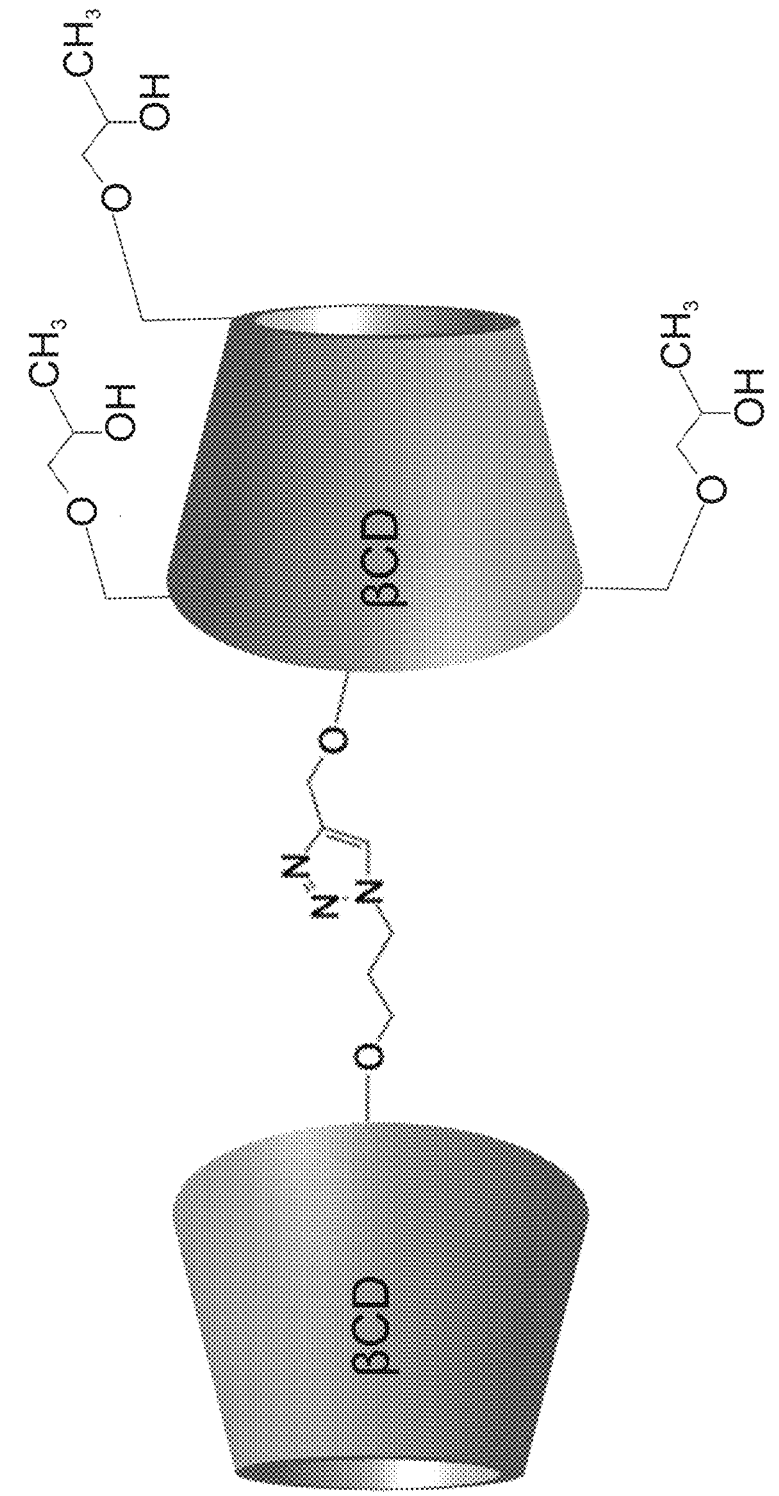
Figure 18B:
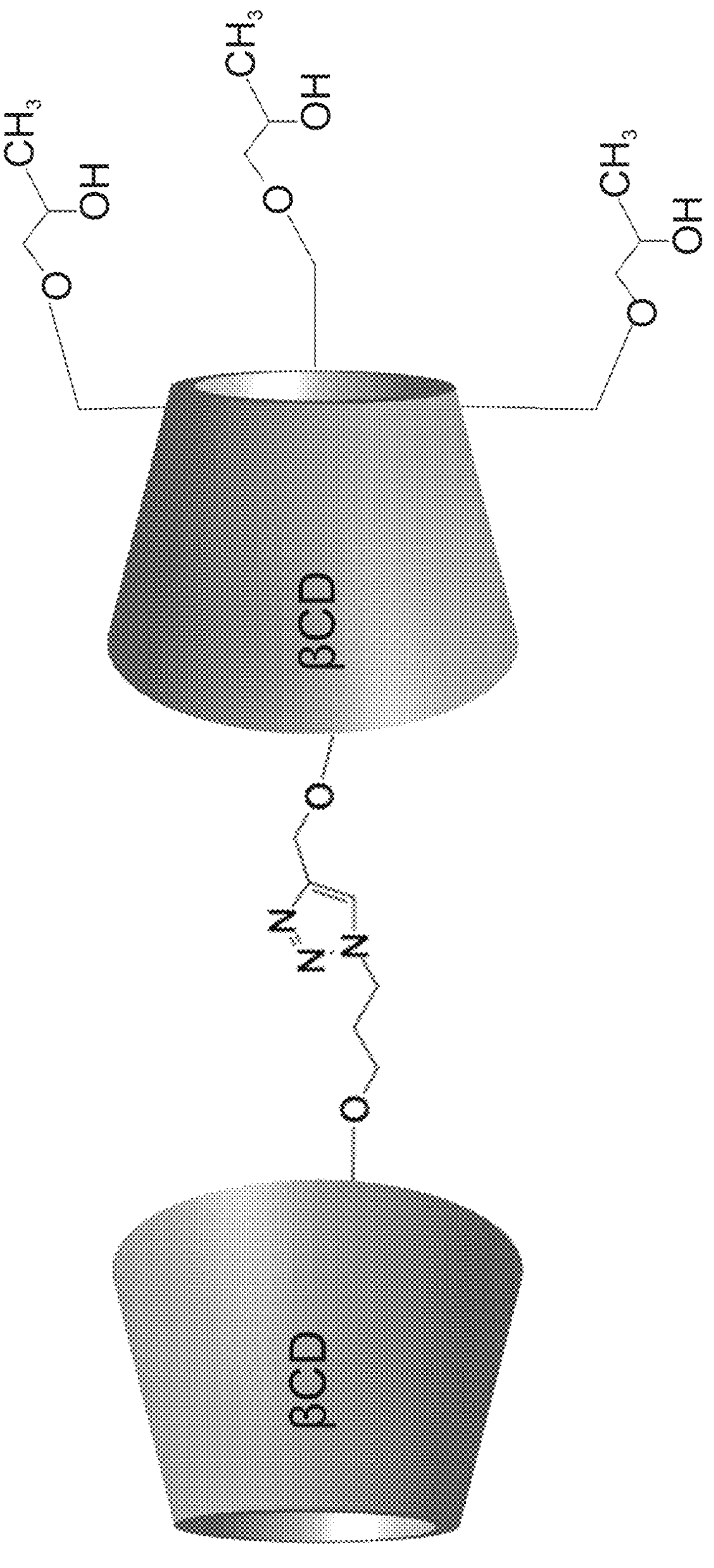
Figure 18C:
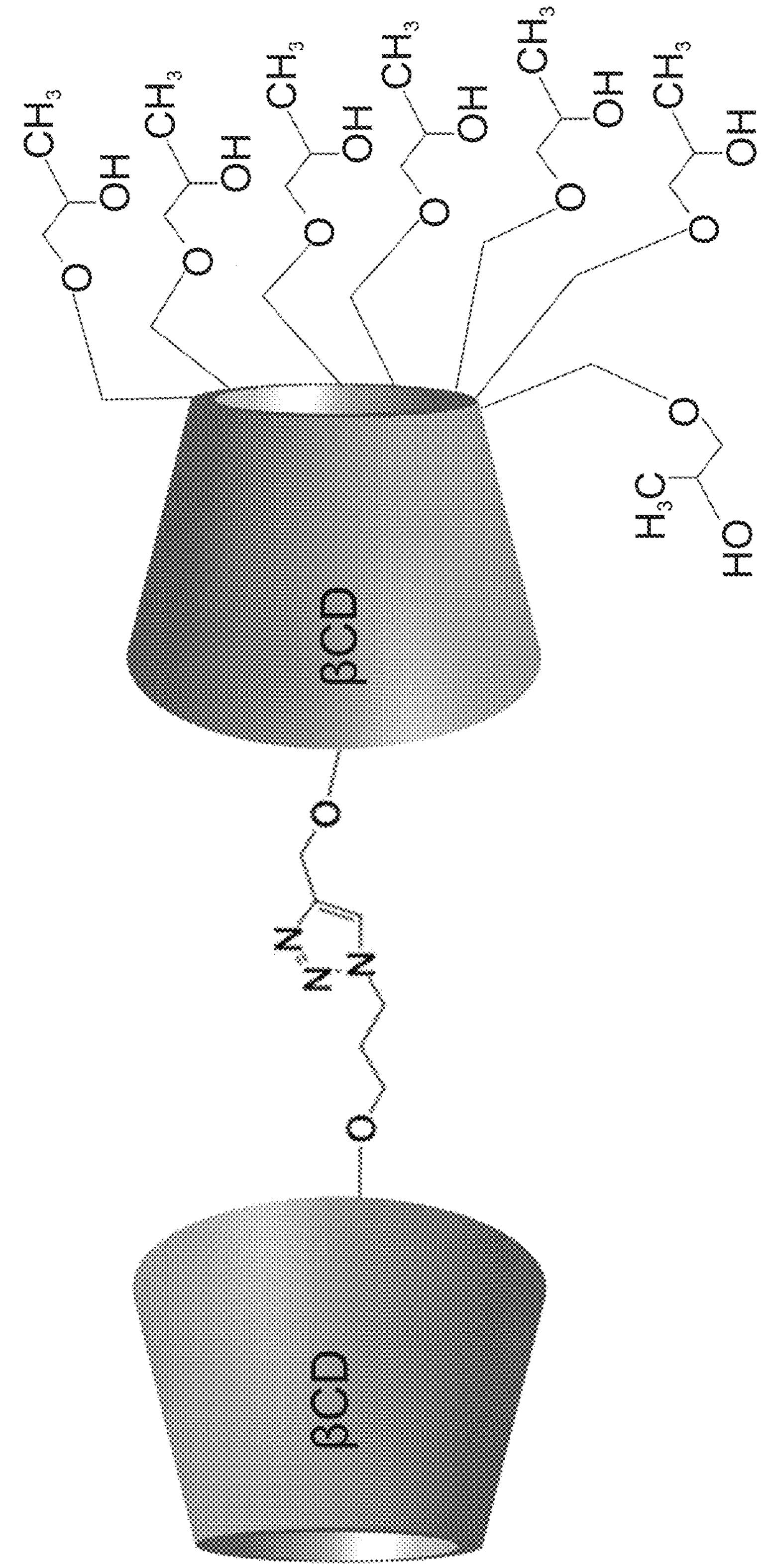

Example 17, Solubilization of 7KC and Cholesterol by HPβCD, HPαCD; and Mixed Monomer Solution of HPβCD and HPαCD FIG. 15B shows the ability of HPβCD (DS~5) monomers and HPαCD (DS~3.5) monomers to solubilize 7KC and cholesterol assessed by percent turbidity. Lower turbidity indicates greater ability to solubilize a given sterol. We also combined HP(CD (DS~5) and HPαCD (DS~3.5) by adding a 1:1 ratio of and HPβCD (DS~5) and HPαCD (DS~3.5) in a 1:1 molar ratio and assessed the turbidity of the monomer mixture. The mixed monomer concentration is given as the total monomer concentration HPαCD (DS~3.5) showed minor specificity and affinity for 7KC and low affinity for cholesterol. The ability of the mixed monomers to solubilize 7KC was similar to that of the HPβCD (DS~5) (FIG. 10B, top). The mixed monomer solution resulted in an more effective encapsulation of both sterols and increased specificity for 7KG, relative to the native αCD on its own (FIG. 10B, bottom). The similar turbidity profiles between HPαCD (DS~3.5) and the mixed monomer solution for 7KC suggest that there may be complexations of the CD with 7KC at a ratio greater than 1:1 between the CD and 7KC. Presumably, the CD-sterol complexes may include single monomers encapsulating 7KC, multiple distinct monomers with 7KC, or a combination of HPβCD and native αCD both encapsulating different regions of 7KC in the mixed monomer solution. More research is needed to identify a ratio between the HP(CD and the native αCD for the mixed monomer to show a synergistic effect. These results suggest a hetero dimer between HPαCD and HPβCD could be a promising encapsulator of 7KC and other sterols.

Figure 19A:
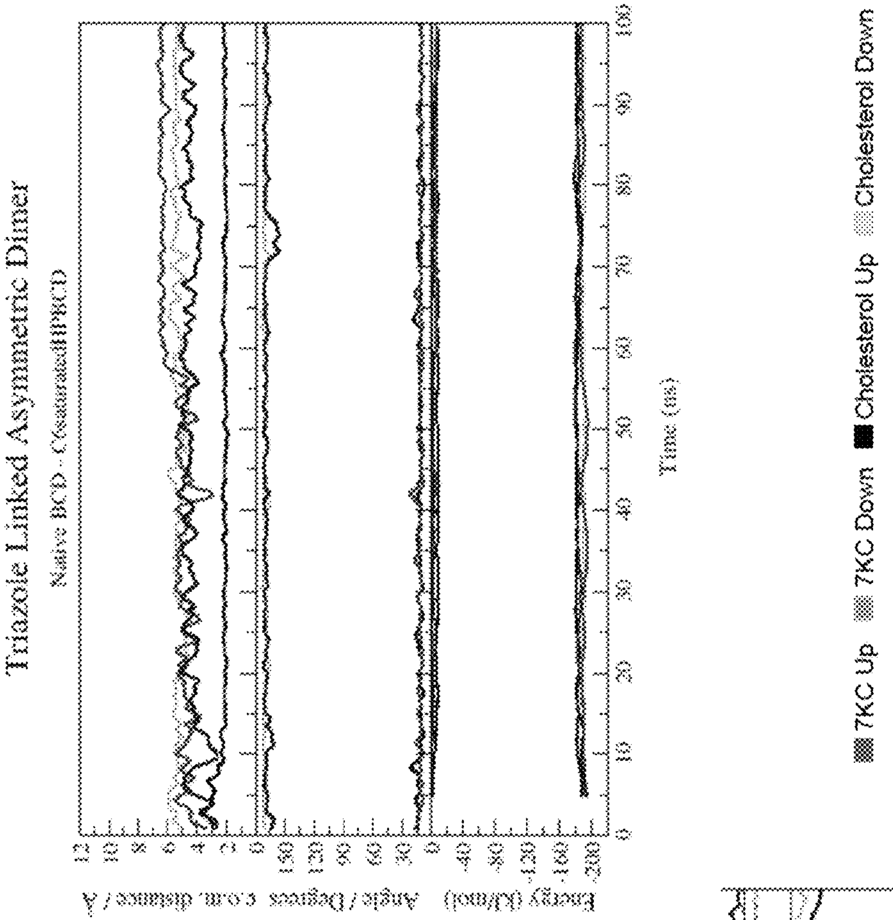

Example 18. MD Simulations for Native βCD-TZL-C6 HPβCD DS7 Asymmetric Dimer-Sterol Complexation FIG. 19A shows trajectory results from MD simulations of a native βCD-TZL C6 HPβCD DS7 asymmetric dimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 as.

The data shows that all of the sterols have strong affinity for complexation with this dimer—no complex breaks after 100 ns. Extension of this simulation may be performed to obtain further detail. From these results, it is clear that this dimer effectively encapsulates sterols.

Figure 19B:
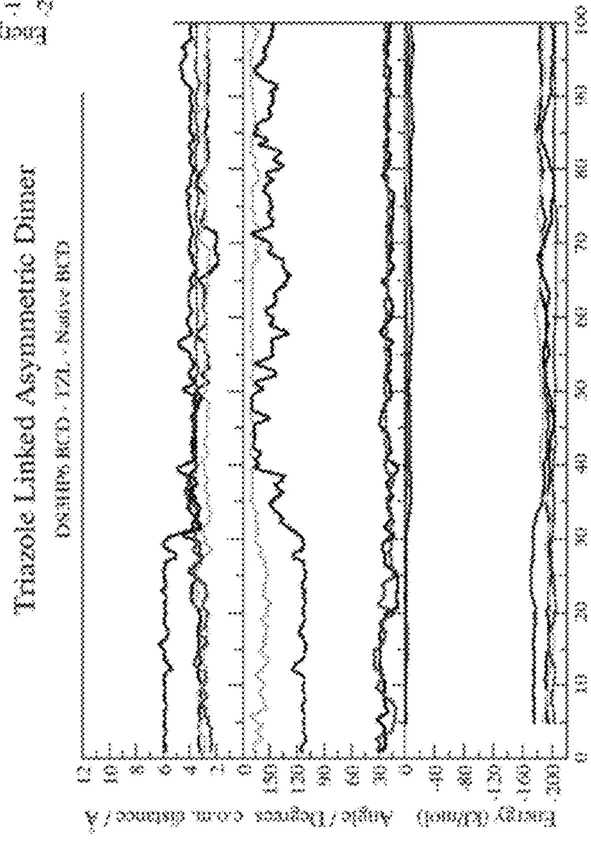

Example 19. MD Simulations for Native βCD-TZL-C6 HPβCD DS3 Asymmetric Dimer-Sterol Complexation FIG. 19B shows trajectory results from MD simulations of a native βCD-TZL C6 HPβCD DS3 asymmetric dimer independently complexing with 7KC and cholesterol in both up and down orientations. The top chart displays the distance between the center of mass between the ring of O4 atoms of one of the CD monomers of the dimer and the center of mass of the sterol over a period of 100 ns. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns.

The data shows that all of the sterols have strong affinity for complexation with this dimer—no complex breaks after 100 ns. Extension of this simulation may be performed for more detailed information. From these results it is clear that this dimer effectively encapsulates sterols. Without intent to be limited to theory, this data coupled with the previous example suggests that the DS at the small face does not greatly affect the complexation of these dimers with sterols, so long as the large face interface is free of substitutions.

Figure 19C:
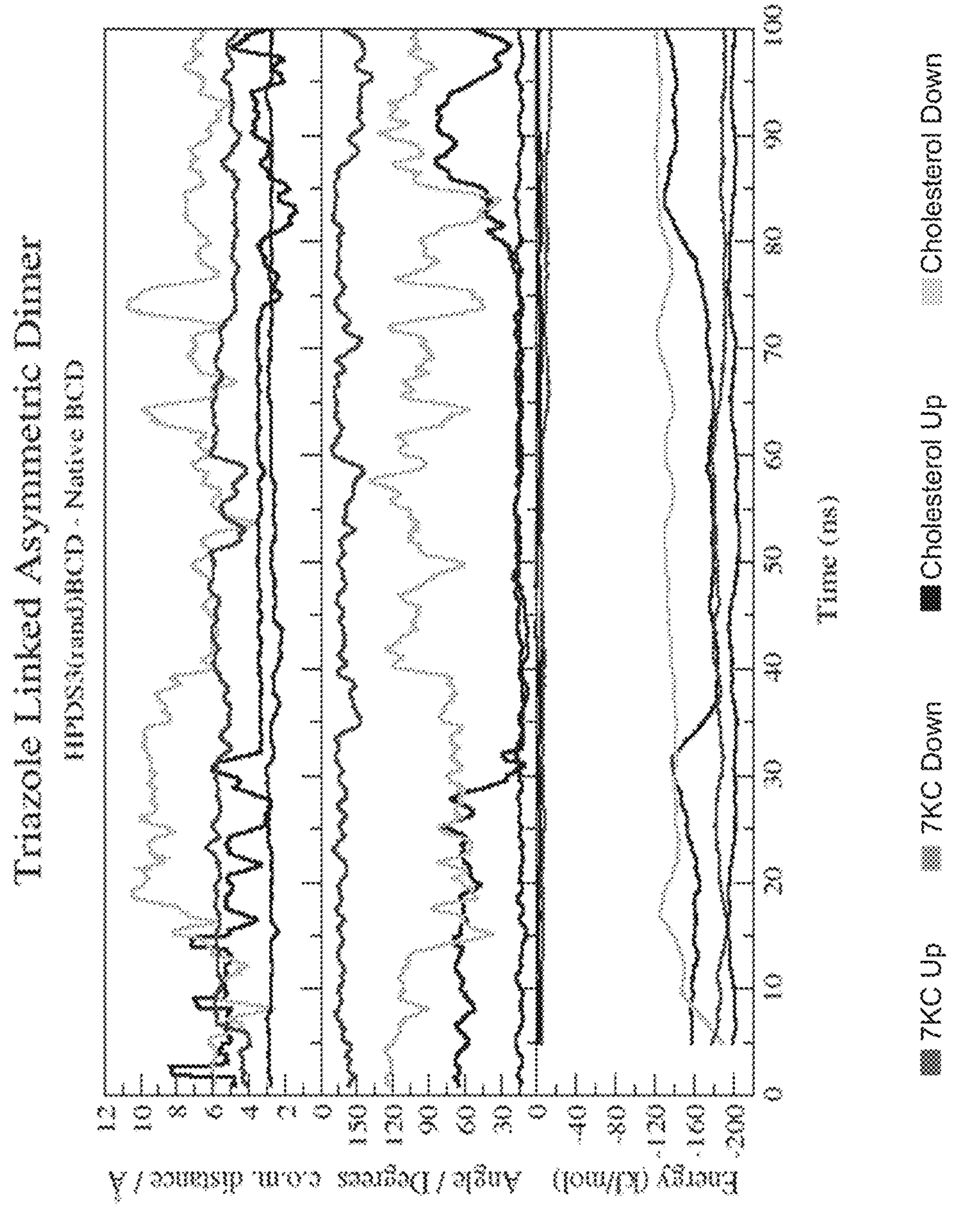

Example 20. MD Simulations for Native βCD-TZL-HPβCD DS3 (Random) Asymmetric Dimer-Sterol Complexation FIG. 19C shows trajectory results from MD simulations of a native βCD-TZL-HPβCD DS3 (random) asymmetric dimer independently complexing with 7KC and cholesterol in both up and down orientations. The top chart displays the distance between the center of mass between the ring of O4 atoms of one of the CD monomers of the dimer and the center of mass of the sterol over a period of 100 as. The middle chart displays the angle formed between the major axis of the sterol and an axis perpendicular to the ring of O4 atoms (as displayed in FIG. 3C) over a period of 100 ns. The bottom chart displays the interaction energy between the CD dimer and the sterol (i.e. the host and guest, respectively, in their host-guest complexing) over a period of 100 ns.

This data shows specificity shown for 7KC in both orientations—both of the cholesterol complexes break (more so in the up orientation) while 7KC complexes remain stable throughout. The complexes show similar energies of interaction, but 7KC complexes are somewhat stronger (7KC complexes are about −200 kJ/mol while cholesterol stays at about −150 to 180 kJ/mol). This simulation, in combination with the previous two, provides further support for the proposed mechanism wherein substitutions at the interface of the dimer are important for 7KC specificity.

Molecular dynamics simulations in examples 13-20 were conducted essentially as described in Example 3.

Exemplary Embodiments of the Invention

A1. A CD dimer having the general formula Structure A-X:

CD-[A-B-A']-CD' (Structure A-X)

wherein

CD has the Structure A-Xa:

(Structure A-Xa)

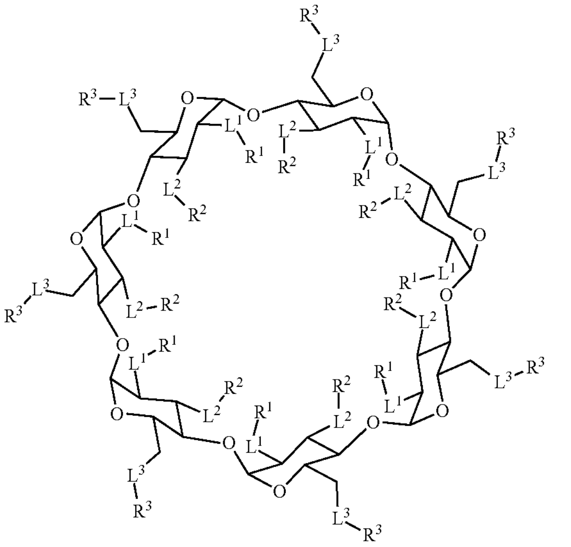

CD' has the Structure A-Xb:

(Structure A-Xb)

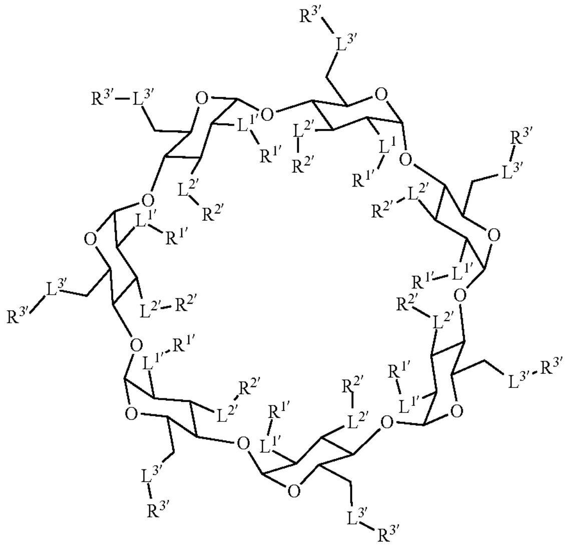

wherein:

L1, L2, L3, L1', L2', and L3' can be the same or different in each instance, and each are independently selected from the group consisting of a bond, —O—, —NH—, —NR4- or —S—, or wherein at least one L1, L2, L3, L1', L2', and L3' is a bond and the corresponding R1, R2. R3, R1', R2', or R3' group is N3, SH, or a halogen such as F, Cl, Br, or I;

R1, R2, R3, R4, R1', R2', and R3' can be the same or different in each instance, and each are independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclyalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide: palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl; sulfonamido; thioalkyl; trialkylammonium,

[A-B-A'] are together defined as a linking group,

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A. and A' of each linking group is connected to at least one L1' or L2' and the corresponding R1' or R2' is omitted and replaced in this manner by A'; and at least one of A, B, and A of each linking group cannot be a bond wherein at least one L1, L2, L3, L1', L2', and/or L3' is not O.

A2. A cyclodextrin dimer having the general formula Structure A-X:

CD-[A-B-A']-CD' (Structure A-X)

wherein

DD has the Structure A-Xa:

(Structure A-Xa)

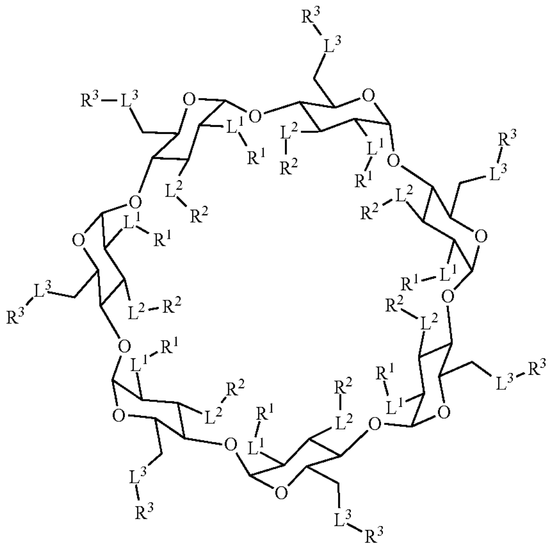

CD' has the Structure A-Xb:

(Structure A-Xb)

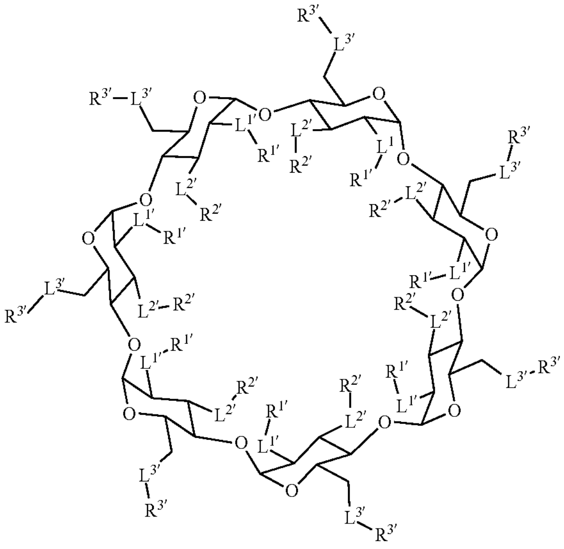

L1; L2, L3, L1', L2', and L3' can be the same or different in each instance, and each are independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R1, R2, R3. R4, R1', R2', and R3' can be the same or different in each instance, and each are independently selected from the group consisting of hydrogen, alkyl, heteroalkyl, haloalkyl, carbocylyl, heterocycyl cycloalkyl, heterocyloalkyl, alkenyl, cycloalkenyl, heterocyloalkyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkysulfonyl, alkylsulfonylalkyl, alkylsulfonamido, alkylamino: dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido: carbamoyl, ureido, halogen, haloalkyl, haloalkoxy, cyano, cyanoalkyl, cyanoalkoxy, azido, nitro, nitrite, phosphate, phosphoryl, phosphene oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid.

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene, B is selected from the group consisting of a bond, —O—, —NH—, —NR4—, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B. and A' of each linking group cannot be a bond;

wherein at least one L1, L2, L3, L1', L2', and/or L3' is not O.

A3. A CD dimer having the general formula Structure A-X:

CD-(A-B-A')-CD' (Structure A-X)

wherein

CD has the Structure A-Xa:

(Structure A-Xa)

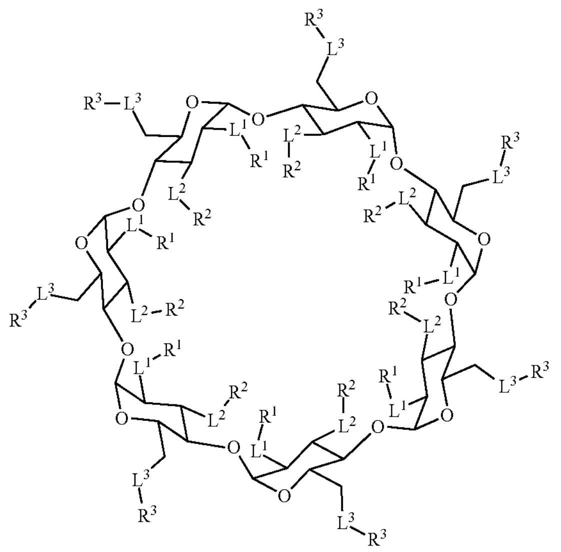

CD' has the Structure A-Xb:

(Structure A-Xb)

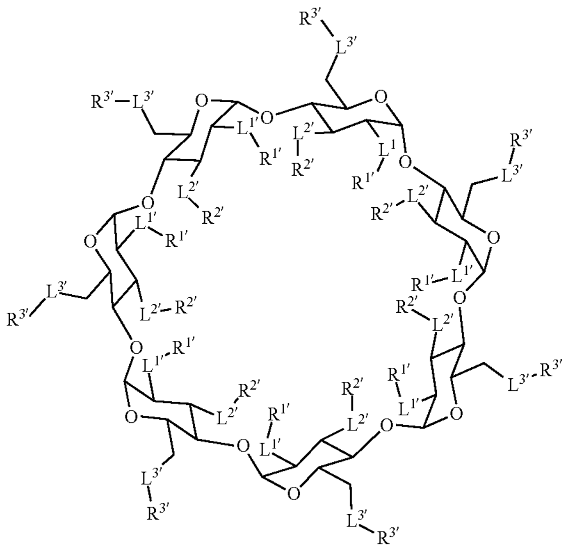

wherein:

L1, L2, L3, L9', L2', and L3 can be the same or different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R1, R1', R2, and R2' are each hydrogen;

R3, R4, and R3' can be the same or different in each instance, and each is independently selected from the group consisting of hydrogen, methyl, hydroxypropyl, sulfobutyl, succinyl, quaternary ammonium such as —CH2CH(OH)CH2N(CH3) 3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkysulfonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

A4. A cyclodextrin dimer having the general formula Structure A-X:

CD-[A-B-A']-CD' (Structure A-X)

wherein

CD has the Structure A-Xa:

(Structure A-Xa)

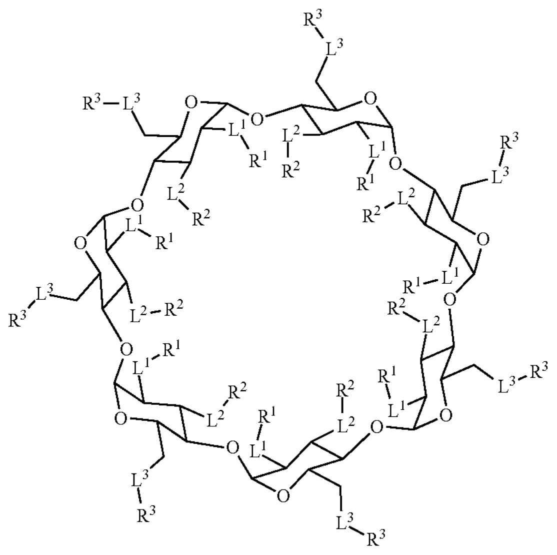

CD' has the Structure A-Xb:

(Structure A-Xb)

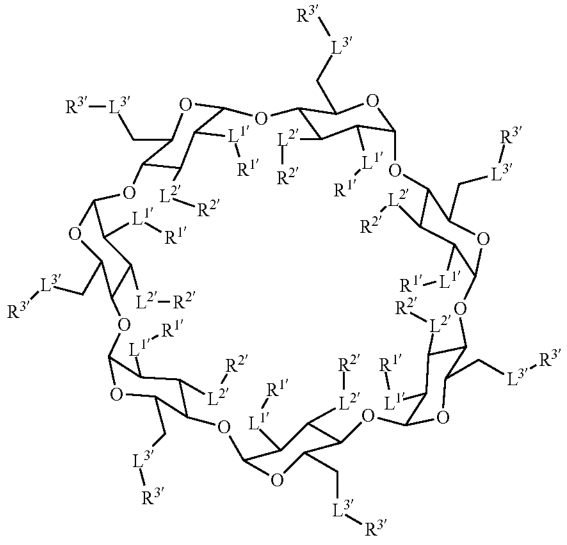

L1, L2, L3, L1', L2', and L3' can be the same or different in each instance, and each is independently selected from the group consisting of a bond, —O—, —NH—, —NR4- or —S—, or wherein at least one L1, L2, L3, L1', L2 and L3' is a bond and the corresponding R1, R2, R3, R1', R2, or R3' group is N3, SH, or a halogen such as F, Cl, Br, or I;

R1, R1', R2, and R2' are each hydrogen;

R3, R4, and R3' can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4—, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

A5. The dimer of any one of clauses A1-A4, wherein at least two of R3 and R3' are not hydrogen.

A6. The dimer of clause A5, wherein at least two and no more than four of R3 and R3' are not hydrogen, A7. A CD dimer having the general formula Structure A-X:

CD-[A-B-A']-CD' (Structure A-X)

wherein

CD has the Structure A-Xa:

(Structure A-Xa)

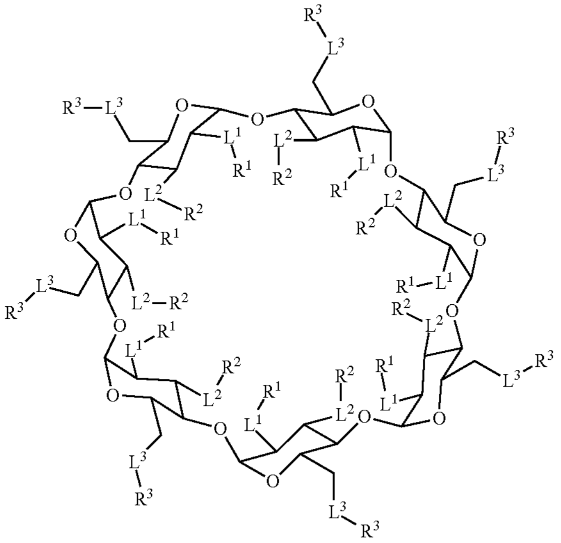

CD' has the Structure A-Xb:

(Structure A-Xb)

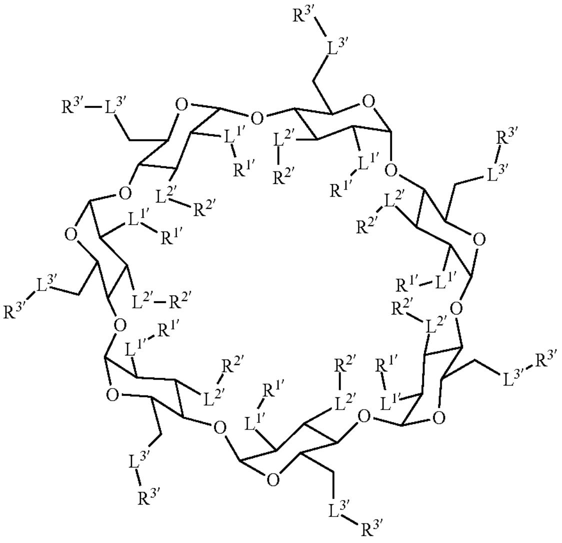

wherein:

L1, L2, L3, L1, L2', and L3' can be the same or different in each instance, and each is independently selected from the group consisting of a bond, —O—, —NH—, —NR4- or —S—, or wherein at least one L1, L2. L3, L1', L2', and L3' is a bond and the corresponding R1, R2, R3, R1', R2', or R3' group is N3, SH, or a halogen such as F, Cl, Br, or I;

R3 and R3' are each hydrogen;

R1, R1', R2, R2', and R4 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom: a substituted or unsubstituted alkylene, a substituted or unsubstituted heteroalkylene;

B is selected from the group consisting of a bond, —O—, —NH—, —NR4, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

A8. A cyclodextrin dimer having the general formula Structure A-X:

CD-[A-B-A']-CD' (Structure A-X)

wherein

CD has the Structure A-Xa:

(Structure A-Xa)

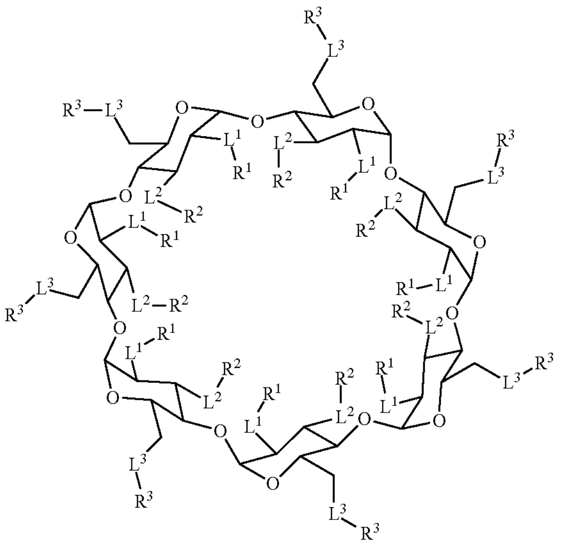

CD' has the Structure A-Xb:

(Structure A-Xb)

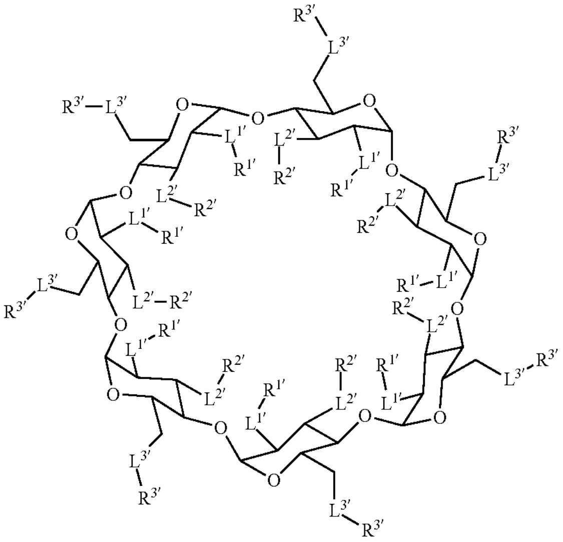

L1, L2, L3, L1', L2', and L3' can be the same or different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each hydrogen

R1, R1', R2, R2', and R4 can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy; alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

A9, A CD dimer having the general formula Structure A-X.

CD-[A-B-A']-CD' (Structure A-X)

wherein

CD has the Structure A-Xa:

(Structure A-Xa)

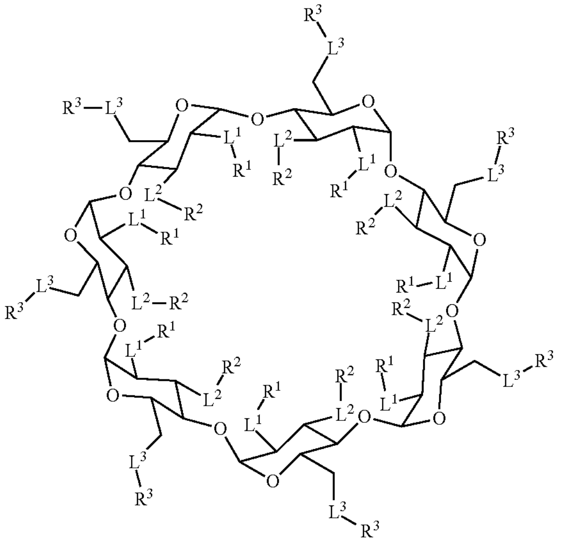

CD' has the Structure A-Xb:

(Structure A-Xb)

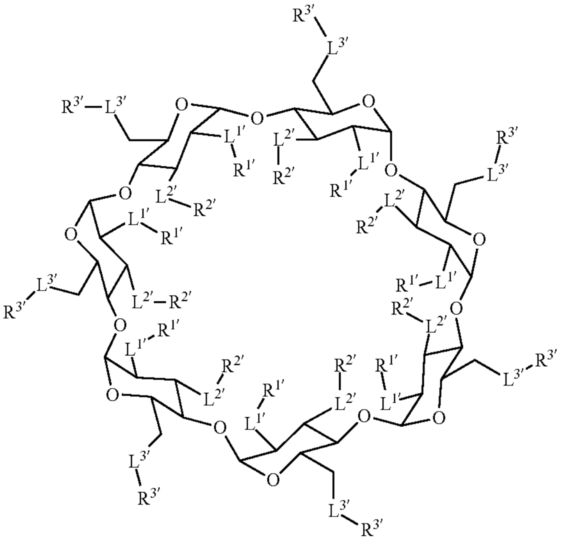

wherein:

L1, L2, L3, L1', L2', and L3 can be the same or different in each instance, and each is independently selected from the group consisting of a bond, —O—, —NH—, —NR4-, or —S—, or wherein at least one L1, L2, L3, L1', L2' and L3' is a bond and the corresponding R1, R2, R3, R1', R2', or R3' group is N3, SH, or a halogen such as F, Cl, Br, or I;

R3 and R3' are each an identical group selected from the group consisting of hydrogen, methyl, hydroxypropyl, sulfobutyl, succinyl, quaternary ammonium such as —CH2CH(OH)CH2N(CH3)3+, alkyl, tower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

R1, R1', R2, R2', and R4 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocyclization, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group,

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

A10. A cyclodextrin dimer having, the general formula Structure A-X:

CD-[A-B-A']-CD' (Structure A-X)

wherein

CD has the Structure A-Xa:

(Structure A-Xa)

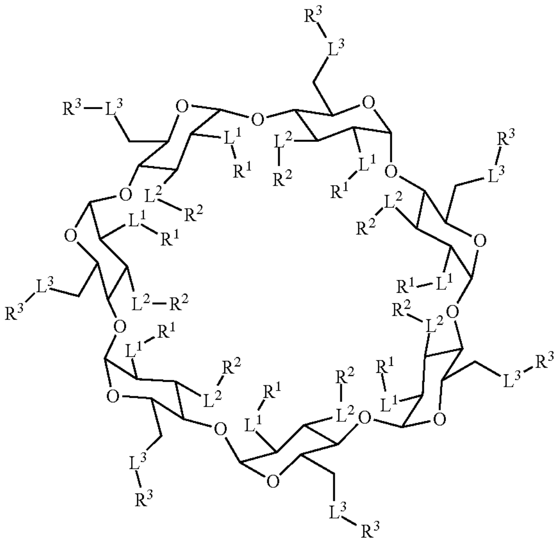

CD' has the Structure A-Xb:

(Structure A-Xb)

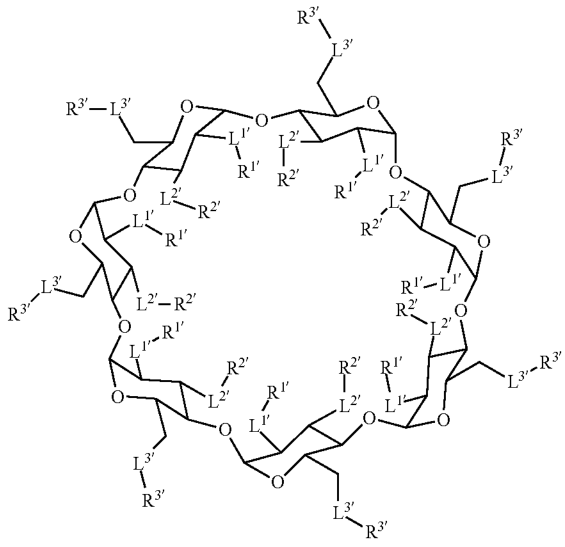

L1, L2, L3, L1', L2', and L3' can be the same or different in each instance, and each is independently selected from the group consisting of a bond, —O—, —NH—, —NR4-, or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each an identical group selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphene oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

R1, R1', R2, R2', and R4 can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2 and the corresponding R1' or R2' is omitted and replaced in this manner by A'; and at least one of A, B, and A' of each linking group is not a bond.

A11. The dimer of clause A6 wherein R3 and R3' is hydroxypropyl or, alternatively, an alkyl group, such as a butyl group.

A12. The dimer of any one of clauses A3-A11, wherein at least one L from L1, L2, L1' or L2' is not O.

A13. The dimer of any one of clauses A1-A12, wherein L1, L2, L3, L1', L2', and L3' that are not linked to the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro, bromo, and iodo.

A14. The dimer of clause A13, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, methyl, 2-hydroxypropyl, sulfobutyl, succinyl, maltosyl, carboxymethyl, trimethylammonium propyl, 2-hydroxytrimethylammonium propyl.

A15. The dimer of any one of clauses A1-A12, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' are independently selected from the group consisting of hydrogen, hydroxyl, and 2-hydroxypropyl, and wherein at least one of R1, R2, R3, R1', R2', and R3' is 2-hydroxypropyl.

A16. The dimer of any one of clauses A1-A12, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, and methyl, and wherein at least one of R1, R2, R3, R1', R2', and R3' is methyl.

A17. The dimes of any one of clauses A1-A12, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, and sulfobutyl, and wherein at least one of R1, R2, R3, R1', R2', and R3' is sulfobutyl.

A18. The dimer of any one of clauses A1-A12, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, and succinyl, and wherein at least one of R1, R2, R3, R1', R2', and R3' is succinyl.

A19. The dimer of any one of clauses A1-A12, wherein L1, L2, L3, L1', L2', and L3' that are not a part of the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, and 2-hydroxytrimethylammonium propyl, and wherein at least one of R1, R2, R3, R1', R2', and R3' is 2-hydroxytrimethylammonium propyl.

A20. The dimer of any one of clauses A1-A12, wherein L1, L2, L3, L1', L2', and L3' that are not a part of the linking group can be the same or different in each instance, and each is independently selected from the group consisting of a bond, and —O—, and wherein at least one of R1, R2, R3, R1', R2', and R3' is maltosyl, and wherein at least one of R1, R2, R3, R1', R2', and R3' is maltosyl.

A21. The dimer of any one of clauses A1-A12, wherein L1, L2, L3, L1', L2', and L3' that are not a part of the linking group can be the same or different in each instance, and each is independently selected from the group consisting of a bond, and —O—, and wherein at least one of R1, R2, R3, R1', R2', and R3' is carboxymethyl, and wherein at least one of R1, R2, R3, R1', R2', and R3' is carboxymethyl.

A22. The dimer of clause A1 or A2, wherein said dieter has a DS with methyl substituents of between 10 and 40.

A23. The dimer of clause A22, wherein said dimer has a DS with methyl substituents of between 10 and 20.

A24. The dimer of clause A22, wherein said dimer is fully saturated with methyl substituents at the C2 position (desponding to R1) and C6 position (corresponding to R3) on CD A25. The dimer of any one of clauses A22-A24, wherein said dimer is fully saturated with methyl substituents at the C2 position (corresponding to R1') and C6 position (corresponding to R3') on CD'.

A26. The dimer of any one of clauses A1-A25, wherein the length of the linking group is between 2 and 8.

A27. The dimer of any one of clauses A1-A25, wherein the length of the linking group is between 4 and 7 or is between 6 and 8.

A28. The dieter of any one of clauses A1-A25, wherein the length of the linking group is 4.

A29. The dimer of any one of clauses A1-A25, wherein the length of the linking group is 7.

A30. The dither of any one of clauses A1-A29, wherein A and A are each a bond and B is substituted or unsubstituted alkylene.

A31. The dimer of clause A30, wherein B is substituted or unsubstituted butyl.

A32. The dimer of any one of clauses A1-A29, wherein B is substituted or unsubstituted heteroaryl.

A33. The dimer of clause A32, wherein B is substituted or unsubstituted triazole.

A34. The dimer of clause A33, wherein B is unsubstituted triazole having connectivity to A and A' as shown in Structure Y:

(Structure Y)

Figure 2B:
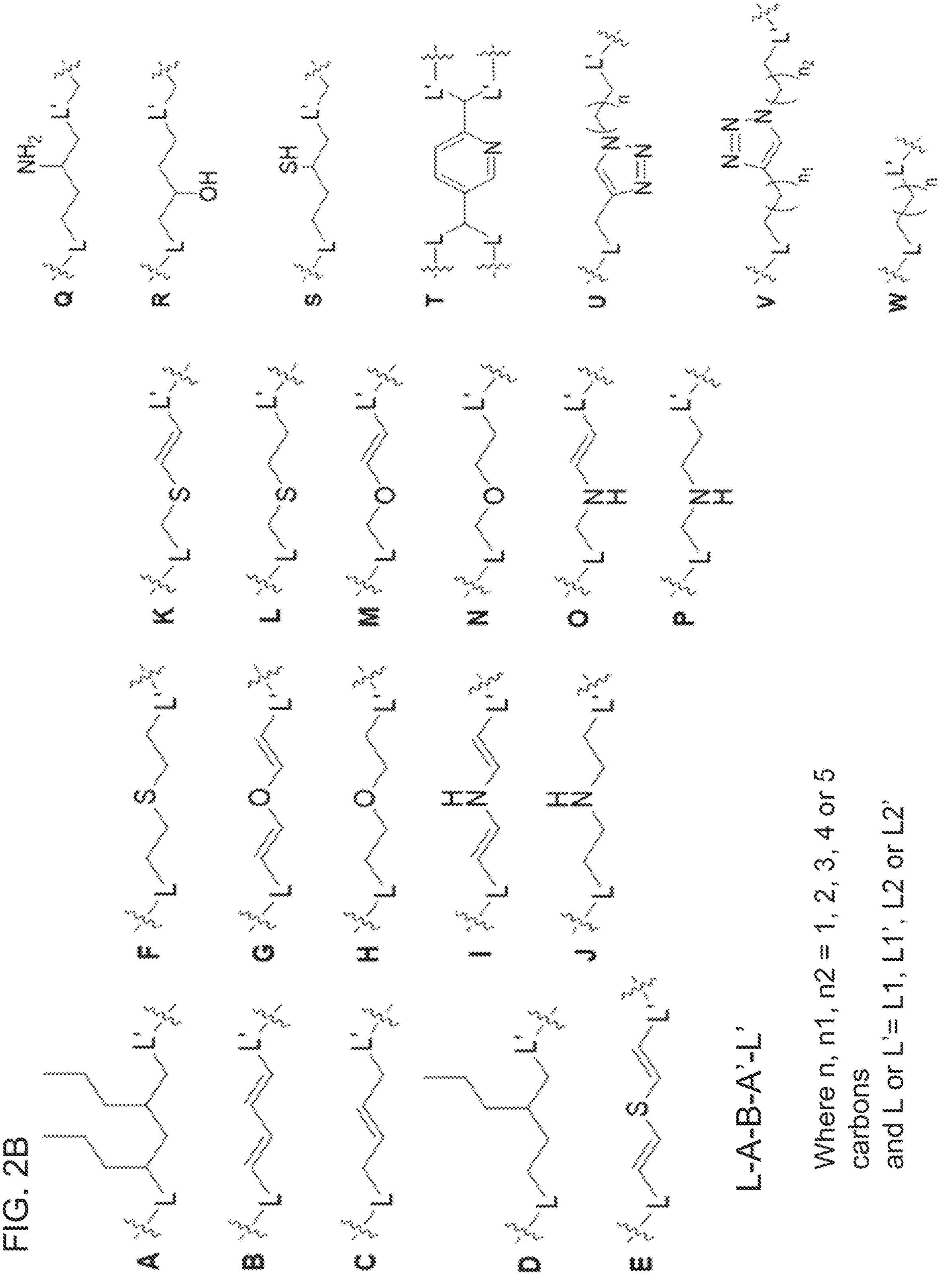
FIG. 2B depicts examples of possible linkers with the following notation: L-A-B-A'-L', where n, n1, n2=1, 2, 3, 4 or 5 carbons and L or L'=L1, L1', L2 or L2'.

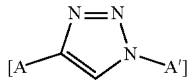

or wherein said linking group has any of the structures shown in FIG. 2B.

A35. The dimer of clause A34, wherein A and A' are independently substituted or unsubstituted alkylene each having a length of 1 to 8 carbons.

A36. The dimer of clause A35, wherein A and A' independently each have a length of four or fewer carbons.

A37. The dimer of clause A36, wherein A is unsubstituted methyl and A' is unsubstituted propyl.

A38. The dimer of any one of clauses A1-A37, wherein CD and CD are connected by only one linking group, or by two or more linking groups.

A39. The dimer of clause A38, wherein CD and CD' are connected by two linking groups which are the same as or different than each other.

A40. The dimer of any one of clauses A1-A39, wherein at least one of A and A' independently connect to two or more of L1 or L2, or L1' or L2', respectively.

A41. The CD dimer of any one of clauses A1-A40, which has the structure shown in any one of FIGS. 9B-9E.

A42. The CD dimer of any one of clauses A1-A41, wherein said CD dimer exhibits greater affinity for 7KC than cholesterol, wherein optionally said greater affinity is determined by a turbidity test.

A43. The CD dimer of clause A42, wherein said CD dinner exhibits at least 1.1-fold, 1.5-fold, 2-fold, 3-fold, 4-fold, 5-fold, or 10-fold, greater affinity for 7KC than cholesterol.

A44. The dimer of any one of clauses A1-A43, wherein each R4 is independently selected from the group consisting of group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphoryl, amino, azido, sulfate, sulfuryl, fluoro, chloro, bromo, and iodo.

A45. The dimer of any one of clauses A1-A44, wherein said L1, L1', L2, and L2' that is connected to said linking group is each independently selected from the group consisting of —O— and bond, and/or wherein when L1, L2, L3, L1', L2', or L3' is a bond the corresponding R1, R2, R3, R1', R2', or R3', respectively, is not hydroxyl.

A46. The dimer of any one of clauses A1-A45, wherein for each R1, R2, R3, R1', R2', or R3' that is alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphene oxide, sulfate alkyl, sulfonamido, thioalkyl, or trialkylammonium, the corresponding L1, L2, L3, L1', L2', or L3', respectively, is a bond.

A47. A composition comprising a mixture of two or more CD dimers according to clauses A1-A46, wherein optionally said composition is substantially free of other CD dimers.

A48. A pharmaceutical composition comprising a CD dimer according to any one of clauses A1-A48 or a composition according to clause A47 and a pharmaceutically acceptable carrier.

A49. The pharmaceutical composition of clause A48, wherein said CD dimer is the only active ingredient in said composition.

A50. The pharmaceutical composition of clause A48, which consists of or consists essentially of said CD dimer and said pharmaceutically acceptable carrier.

A51 The pharmaceutical composition of clause A48, further comprising at least one hydrophobic drug, optionally wherein said pharmaceutical composition comprises an amount of said CD dimer or CD dimers that is effective to solubilize said hydrophobic drug.

A52. A method of improving the solubility of a hydrophobic drug, comprising admixing said hydrophobic drug and a CD dimer according to any one of clauses A1-A46 or a composition according to clause A47 or A48.

A53. A therapeutic method comprising administration of an effective amount of a CD dinner according to any one of clauses A1-A46 or a composition according to any one of clauses A47-A50 to a subject in need thereof.

A54. The method of clause A53, wherein the subject in need thereof is suffering from harmful or toxic effects of 7KC.

A55. A method for reducing the amount of 7KC in a subject in need thereof comprising administration of an effective amount of a CD dimer according to any one of clauses A1-A46 or a composition according to any one of clauses A47-A50 to a subject in need thereof.

A58. The method of any one of clauses A53-A55, wherein said CD dimer is administered to said subject via parenteral (e.g., subcutaneous, intramuscular, or intravenous), topical, transdermal, oral, sublingual, or buccal administration.

A57. The method of clause A56, wherein said CD dimer is administered intravenously.

A58. The method of any one of clauses A53-A57, which comprises administering to said subject (a) between about 1 mg and 20 g, such as between 10 mg and 1 g. between 50 mg and 200 mg, or 100 mg of said CD dimer to said subject, or (b) between 1 and 10 g of said CD dimer, such as about 29, about 3 g, about 4 g, or about 5 g. or (c) between 50 mg and 5 g of said CD dimer, such as between 100 mg and 2.5 g, between 100 mg and 2 g, between 250 mg and 2.5 g.

A59. The method of any one of clauses A53-A58, which prevents, treats, ameliorates the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis. Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X linked adrenoleukodystrophy, sickle cell disease, Niemann-Pick Type A disease, Nieman-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome. Crohn's disease, ulcerative colitis, and/or hypercholesterolemia; wherein optionally said treatment is administered in combination with another therapy.

A60. The method of any one of clauses A53-A58, which prevents, treats, ameliorates the symptoms of atherosclerosis.

A61. The method of clause A60, further comprising administering a second therapy to said subject, wherein said second therapy is administered concurrently or sequentially in either order.

A62. The method of clause A61, wherein said second therapy comprises one or more of an anti-cholesterol drug, such as a fibrate or statin, anti-platelet drug, anti-hypertension drug, or dietary supplement.

A63. The method of clause A62, wherein said statin comprises ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin). MEVACOR® (lovastatin), PRAVACHOL® (pravastatin), SIMCOR® (niacin extended-release/simvastatin), VYTORIN® (ezetimibe/simvastatin), or ZOCOR® (simvastatin).

A64. The method of clause A62, wherein said second therapy comprises an anti-cholesterol drug and an anti-hypertension drug.

A65. A method of purification of oxysterols, comprising: contacting a composition comprising oxysterols with a CD dimer according to any one of clauses A1-A46, thereby solubilizing said oxysterols in said CD dimer; and recovering said CD dimer and solubilized oxysterols.

A66. The method of cause A65, wherein said oxysterols comprise or consist of 7KC.

A67. The method of clause A66, further comprising measuring the amount or concentration of 7KC in said solubilized oxysterols, thereby determining the relative concentration of 7KC in the composition.

A68. The method of clause A67, wherein said composition comprises a patient sample.

A89. An in vitro method of removing oxysterols from a sample, comprising: contacting a sample comprising oxysterols with a CD dimer according to any one of clauses A1-A46, thereby solubilizing said oxysterols in said CD dimes; and separating said sample from said CD dimer and solubilized sterols, and optionally reintroducing said sample into a subject from which said sample is obtained.

A70. A method of producing a reduced cholesterol product, comprising: contacting a product comprising cholesterol with a CD dimer according to any one of clauses A1-A46, thereby solubilizing said cholesterols in said CD dimes; and removing said CD dimer and solubilized cholesterol from said product.

A71. The method of clause A70, wherein said product is a food product.

A72. The method of clause A71, wherein said food product comprises meat an l/or dairy.

A73. A method of making a CD dimer according to any one of clauses A1-A46 comprising:

(a) reacting β-CD molecules that are protected on the primary face with a dialkylating agent, thereby producing a primary face-protected βCD dimer linked through the secondary face; and optionally purifying said primary protected CD dimer, (b) deprotecting said primary face protected CD dimer, thereby producing a deprotected CD dimer, and optionally purifying said deprotected CD dimer; and (c) functionalizing said deprotected CD to said R1, R2, R3, R1', R2', and/or R3' groups, thereby producing said CD dimer, and optionally purifying said CD dimer.

A74. The method of clause A73, wherein said CD that is protected on the primary face comprises a trityl, benzoyl, test-butyidimethylsilyl (TBDMS), tert-butyidiphenylsilyl (TBDPS), triisopropylsilyl (TIPS) and the like, preferably TBDMS as in heptakis(7-O-tert-butyldimethylsilyl)-β-CD.

A75. The method of clause A73 or A74, wherein said dialkylating agent comprises a dihaloalkane, ditosylalkane, dimesylalkane, ditriflatealkane and the like, preferably 1,4 dibromobutane.

A76. The method of any one of clauses A73-A75, wherein step (a) is performed in anhydrous conditions using a base like imidazole, pyridine, DMAP, sodium hydroxide, sodium hydride, lithium hydride and the like, preferably sodium hydride.

A77. The method of any one of clauses A73-A78, wherein said purification in step (a) composes direct or reverse phase chromatography with isocratic elution and/or a crystallization/precipitation.

A78. The method of any one of clauses A73-A77, wherein step (b) is performed in tetrahydrofuran (THF) or methanol (MeOH) with HF-pyridine, tetrabutylammonium fluoride (TBAF), acetic acid, sulfuric acid, triflic acid and the like, preferably in THE with TBAF.

A79. The method of any one of clauses A73-A78, wherein said purification in step (b) comprises direct or reverse phase chromatography with isocratic elution and/or crystallization/precipitation.

A80. The method of any one of clauses A73-A78, wherein step (a) comprises reacting said deprotected CD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium reagent such as glycidyltrimethylammonium chloride.

A81. The method of any one of clauses A73-A80, wherein step (c) is performed in aqueous conditions using a base like sodium hydroxide, lithium hydroxide, preferably sodium hydroxide.

A82. The method of any one of clauses A73-A81, wherein said purification in step (c) comprises one or more of ion exchange resin treatment, charcoal clarification and dialysis.

A83. A method of making a βCD dimer comprising (a) reacting a 2-O-(n-azidoalkyl)-βCD or a 3-O-(n-azidoalkyl)-βCD or a mixture thereof and a 2-O-(n-alkyne)-βCD or a 3-O-(n-alkyne)-βCD or a mixture thereof, thereby forming a βCD-triazole-βCD dimer having the structure βCD-alk1-triazole-alk2-OCD, and optionally (b) purifying said βCD-triazole-βCD dimer.

A84. The method of clause A83, wherein step (a) is performed with a copper (I), silver (I) or ruthenium catalyst, preferably 15 mM copper (1) like copper bromide (CuBr) or copper tris(triphenylphosphine) bromide [(PPh3)3CuBr].

A85. The method of clause A83 or A84, wherein step (a) is carried out in an aqueous solution.

A86. The method of clause A85, wherein the aqueous solution comprises dimethylformamide (DMF), optionally about 50% DMF (v/v).

A87. The method of any one of clauses A84-A86, wherein step (b) comprises silica gel chromatography or crystallization/precipitation.

A88. The method of any one of clauses A84-A87, further comprising, prior to step (a) producing said 2-O-(n-azidoalkyl)-CD or 3-O-(n-azidoalkyl)-CD or mixture thereof by a method comprising: (1) reacting n-azido-1-bromo-alkane with β-CD, optionally with a catalytic amount of lithium iodide, thereby producing said 2-O-(n-azidoalkyl)-OCD or 3-O-(n-azidoalkyl)-CD or mixture thereof; and (2) optionally purifying said 2-O-(n-azidoalkyl)-βCD or 3-O-(n-azidoalkyl)-CD or mixture thereof.

A89. The method of clause A88, wherein step (2) comprises silica gel chromatography or crystallization/precipitation.

A90. The method of any one of clauses A84-A89, further comprising, prior to step (a) producing 2-O-(n-alkyne)-βCD or 3-O-(n-alkyne)-βCD or mixture thereof by a method comprising: (i) reacting n-bromo-1-alkyne with a β-CD, optionally with a catalytic amount of lithium iodide, thereby producing said 2-O-(n-alkyne)-βCD or 3-O-(n-alkyne)-βCD or mixture thereof and (ii) optionally purifying said 2-O-(n-alkyne)-βCD or 3-O-(n-alkyne)-βCD or mixture thereof.

A91. The method of clause A80, wherein step (ii) comprises silica gel chromatography or crystallization/precipitation.

A92. The method of clause A90 or A91, wherein step (i) is carried out in dry DMSO.

A93. The method of any one of clauses A88-A90, wherein the reaction in step (i) or (1) comprises lithium hydride, sodium hydride, n-butyl lithium and the like.

A94. The method of anyone of clauses A90-A93, further comprising (c) hydroxypropylation, methylation, succinylation, sulfobutylation and/or quaternary ammonium functionalization said CD-triazole-CD dimer, thereby producing a CD dimer, and optionally purifying said CD dimer.

A95. The method of clause A94, wherein step (c) comprises reacting said deprotected CD dimer with a hydroxypropylation agent such as propylene oxide, a methylation reagent such as methyl iodide, a succinylation reagent such as succinic anhydride, a sulfobutyrate reagent such as 1,4 butane sultone, and/or a quaternary ammonium functionalization reagent such as glycidyltrimethylammonium chloride.

A96. The method of clause A94 or A95, wherein step (c) is performed in aqueous conditions, optionally comprising sodium hydroxide as a base.

A97 The method of any one of clauses A90-A95, wherein said purification in step (c) comprises one or more of ion exchange resin treatment, charcoal clarification, membrane nitration, and dialysis.

A98. The method of any one of clauses A73-A97, wherein the length of the linking group is between 2 and 8.

A99. The method of any one of clauses A73-A97, wherein the length of the linking group is between 4 and 7 or is between 6 and 8.

A100. The method of any one of clauses A73-A97, wherein the length of the linking group is 4.

A101. The method of any one of clauses A73-A97, wherein the length of the linking group is 7.

A102. The method of any one of clauses A73-A101, wherein A and A' are each a bond and B is substituted or unsubstituted alkylene.

A103. The method of clause A102, wherein B is substituted or unsubstituted butyl.

A104. The method of any one of clauses A73-A101, wherein B is substituted or unsubstituted heteroaryl.

A105. The method of clause A104, wherein B is substituted or unsubstituted triazole.

A106. The method of clause A105, wherein B is unsubstituted triazole having connectivity to A and A' as shown in Structure Y:

(Structure Y)

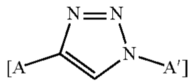

or A' to A as shown in Structure Y':

(Structure Y')

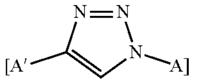

or wherein said linking group has any of the structures shown in FIG. 2B.

A107. The method of clause A106, wherein A and A' are independently substituted or unsubstituted alkylene each having a length of 1 to 8 carbons.

A108. The method of clause A107, wherein A and A' independently each have a length of four or fewer carbons.

A109. The method of clause A108, wherein A is unsubstituted methyl and A' is unsubstituted propyl.

A110. The method of any one of clauses A73-A109, wherein CD and CD' are connected by only one linking group, or by two or more linking groups.

A111. The method of clause A110, wherein CD and CD' are connected by two linking groups which are the same as or different than each other.

A112. The method of any one of clauses A73-A111, wherein at least one of A and A' independently connect to two or more of L1 or L2, or L1' or L2', respectively.

A113. The method of any one of clauses A73-A112, wherein said CD dimer has the structure shown in any one of FIGS. 9B-9E.

A114. The method of any one of clauses A73-A112, which is adapted to produce the CD dimer of any one of clauses A1-A46.

B1. A CD dimer having the general formula Structure B-X or Structure B-X':

CD-[A-B-A']-CD' (Structure B-X)

CD'-[A-B-A']-CD (Structure B-X')

wherein

CD comprises an αCD having the Structure B-Xa:

(Structure B-Xa)

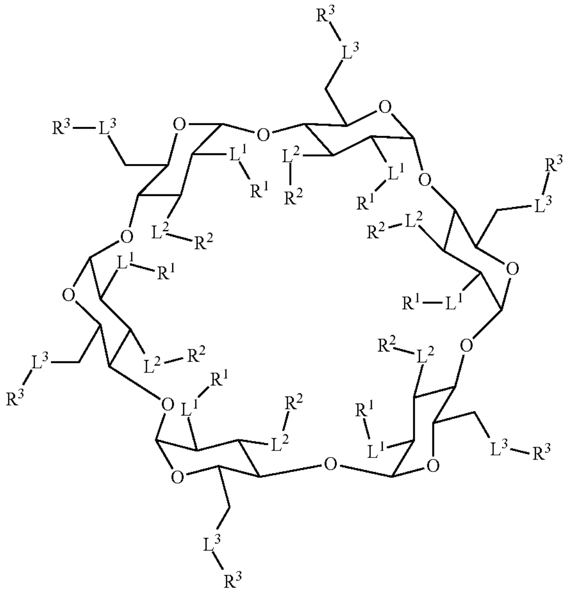

CD' comprises a βCD having the Structure B-Xb:

(Structure B-Xb)

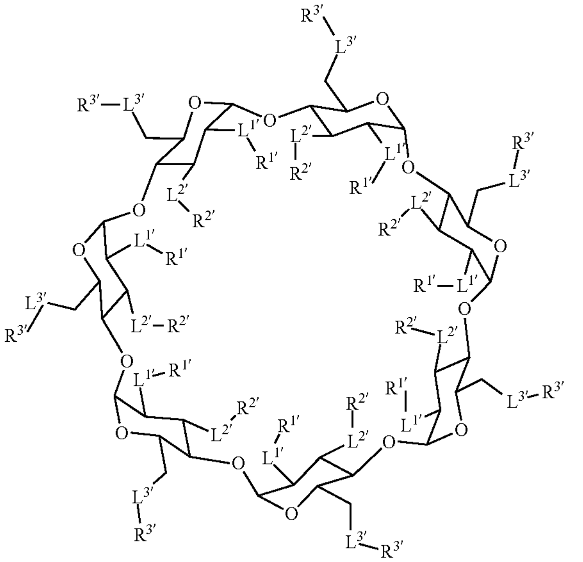

wherein:

L1, L2, L3, L1', L2', and L3 can be the same or different in each instance, and each are independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R1, R2, R3, R4, R1', R2', and R3' can be the same or different in each instance, and each are independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocycyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group cannot be a bond:

B2. A cyclodextrin direr having the general formula Structure B-X or Structure B-X':

CD-[A-B-A']-CD' (Structure B-X)

CD'-[A-B-A']-CD (Structure B-X')

wherein

CD composes an αCD having the Structure B-Xa:

(Structure B-Xa)

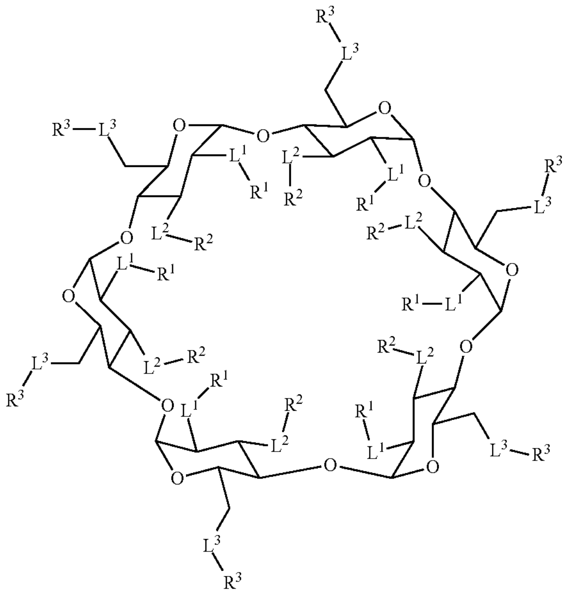

CD' comprises a αCD having the Structure B-Xb:

(Structure B-Xb)

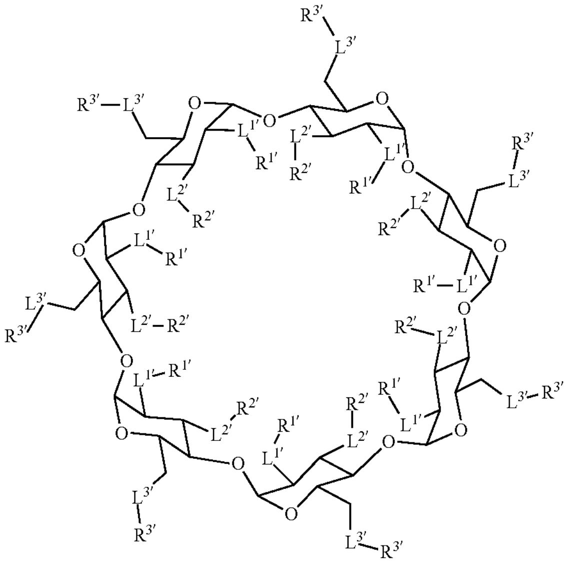

L1, L2, L3, L1', L2', and L3' can be the same or different in each instance, and each are independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R1, R2, R3, R4, R1', R2', and R3' can be the same or different in each instance, and each are independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, akylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphene oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid:

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group cannot be a bond.

B3. A CD dimer having the general formula Structure B-X or Structure B-X':

CD-[A-B-A']-CD' (Structure B-X)

CD'-[A-B-A']-CD (Structure B-X')

wherein

CD comprises an αCD having the Structure B-Xa:

(Structure B-Xa)

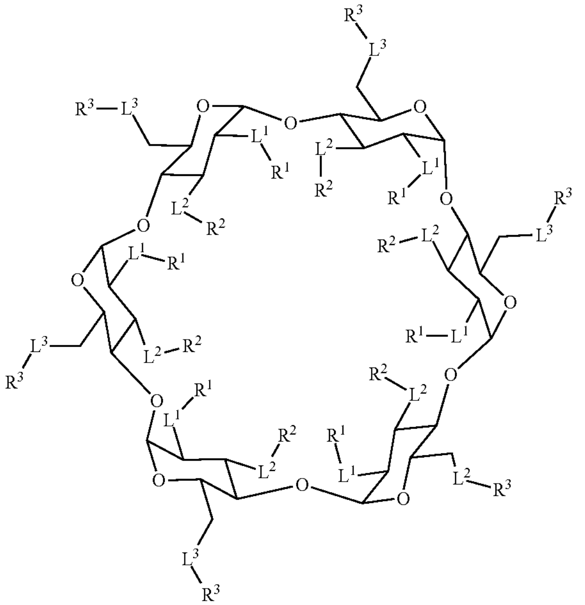

CD' comprises a βCD having the Structure B-Xb:

(Structure B-Xb)

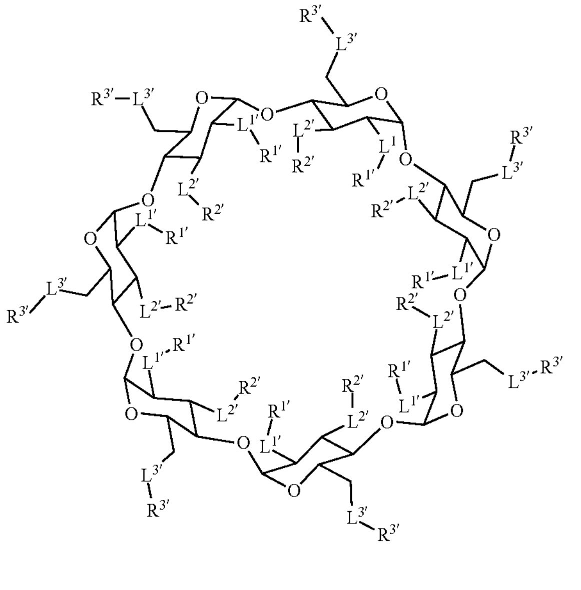

wherein:

- L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3 group is N3, SH, or a halogen such as F, Cl, Br, or I;

R1, R1', R2, and R2' are each hydrogen.

R3 and R3' can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl; aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl: phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocycyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

- [A-B-A'] are together defined as a linking group;
- A and A' are independently selected from the group consisting of a bond, —O—, —NH—, —NR4-, —S—, a heteroatom, a substituted or unsubstituted alkylene, a substituted or unsubstituted heteroalkylene;
- B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;
- CD and CD' are connected by at least one linking group;
- A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each finking group is not a bond.

B4. A cyclodextrin dimer having the general formula Structure. B-X or Structure B-X':

CD-[A-B-A']-CD' (Structure B-X)

CD'-[(A-B-A']-CD (Structure B-X')

wherein

CD comprises an αCD having the Structure B-Xa:

(Structure B-Xa)

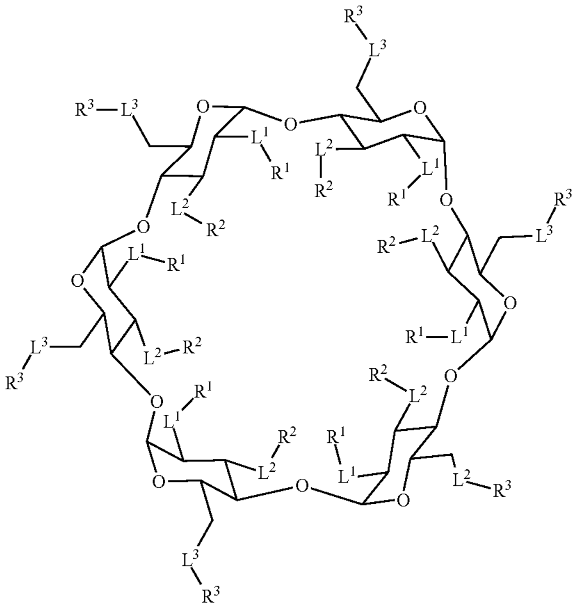

CD comprises a βCD having the Structure B-Xb:

(Structure B-Xb)

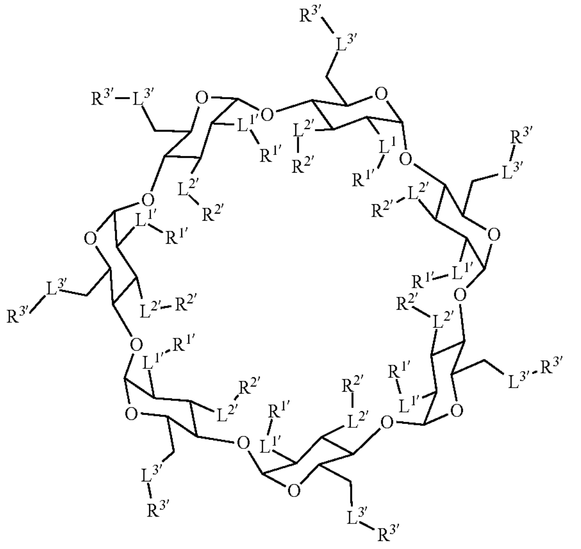

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2, and L3' is a bond and the corresponding R1, R2, R3, R1', R2', or R3' group is N3, SH, or a halogen such as F, Cl, Br, or I;

R1, R1', R2, and R2' are each hydrogen;

R3 and R3' can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsufonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroaryalkyl, aryloxyl, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thin, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

B5. The dimer of any one of clauses B1-B4, wherein at least two or R3 and R3' are not hydrogen.

B6 The dimer of clause B5, wherein at least two and no more than four of R3 and R3' are not hydrogen.

B7. A CD dimer having the general formula Structure B-X or Structure B-X,

CD-[A-B-A']-CD' (Structure B-X)

CD'-[A-B-A']-CD (Structure B-X')

wherein

CD comprises an αCD having the Structure B-Xa:

(Structure B-Xa)

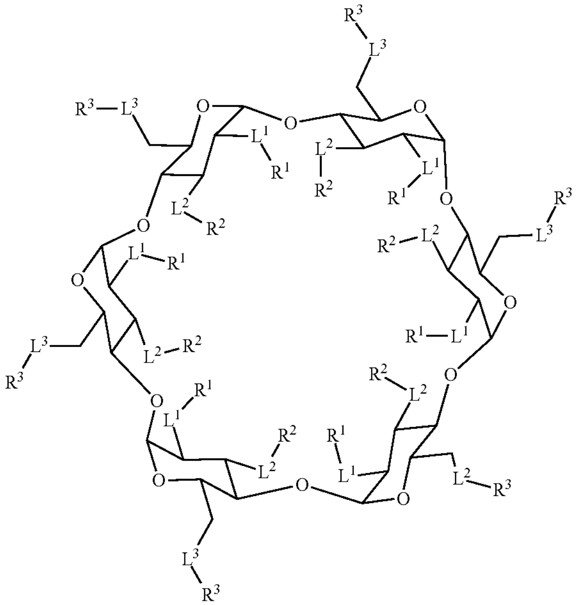

CD' comprises a ICD having the Structure B-Xb:

(Structure B-Xb)

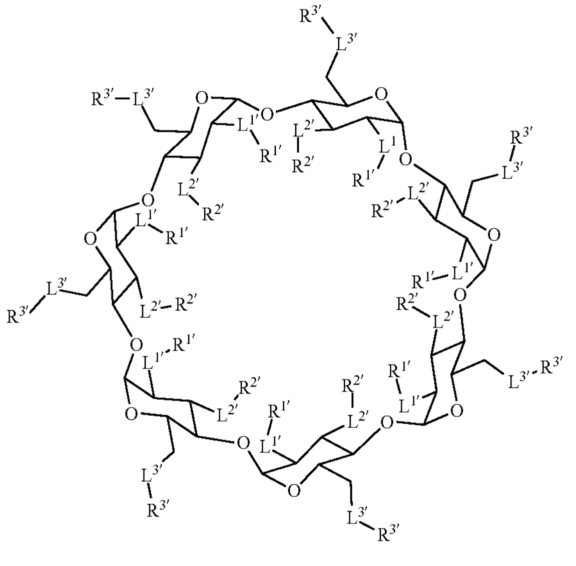

wherein:

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each hydrogen;

R1, R1', R2, and R2' can be the same or different in each instance, and each is independently selected from the group consisting of hydrogen, methyl, hydroxypropyl, sulfobutyl, succinyl, quaternary ammonium such as —CH2CH(OH) CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkytalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl; hydroxycarbonyl alkyl, hydroxyalkylamino, hydroxyalkyl, hydroxycycloalkyl, ureido, carboxy, sulfuryl, phosphoryl, phenoxy: acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl: carboxamido, cyano, cycloamino, heterocycyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium,

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group,

A of each linking group is connected to at least one L1 or L2 and the corresponding R1 or R2 is omitted and replaced in this manner by A, and A' of each linking group is connected to at least one L1' or L2' and the corresponding R1 or R2' is omitted and replaced in this manner by A'; and at least one of A, B, and A' of each linking group is not a bond.

B8. A cyclodextrin dimer having the general formula Structure B-X or Structure B-X':

CD-[A-B-A']-CD' (Structure B-X)

CD'-[A-B-A']-CD (Structure B-X')

wherein

CD comprises an αCD having the Structure B-Xa:

(Structure B-Xa)

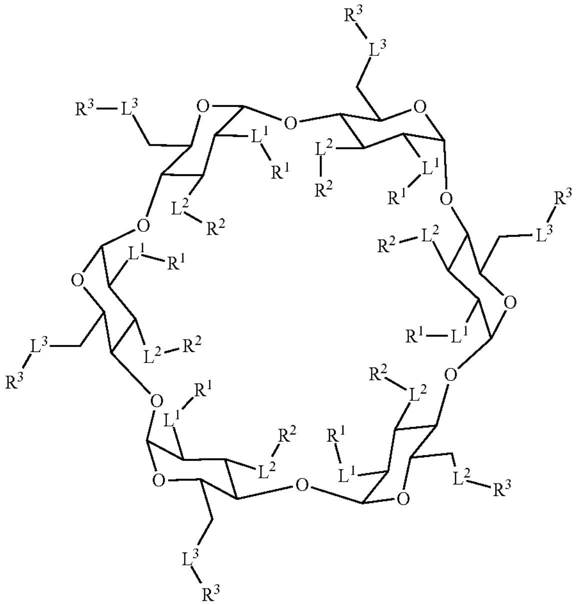

CD' comprises a βCD having the Structure B-Xb:

(Structure B-Xb)

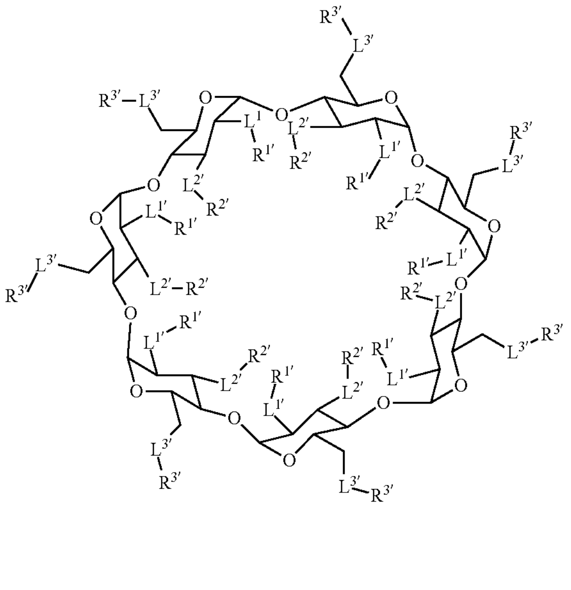

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each hydrogen

R1, R1', R2, and R2' can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl; sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl; hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A of each linking group is connected to at least one L1' or L2' and the corresponding R1' or R2' is omitted and replaced in this manner by A'; and at least one of A. B, and A' of each linking group is not a bond.

B9. A CD dimer having the general formula Structure B-X or Structure B-X':

CD-[A-B-A']-CD' (Structure B-X)

CD'-[A-B-A']-CD (Structure B-X')

wherein

CD comprises an αCD having the Structure B-Xa:

(Structure B-Xa)

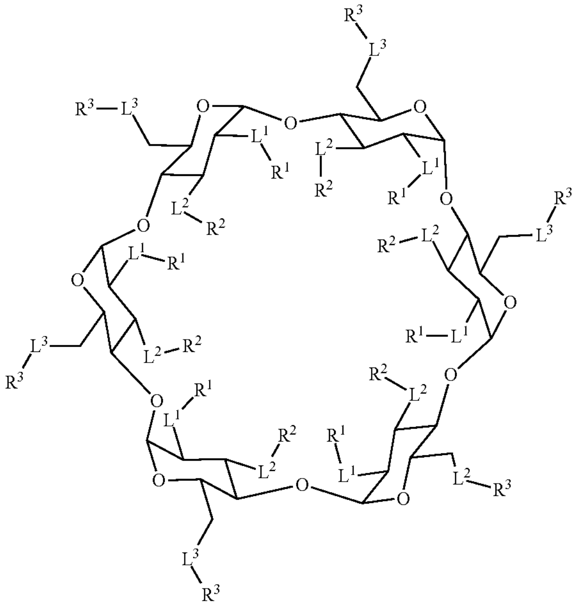

(Structure B-Xb)

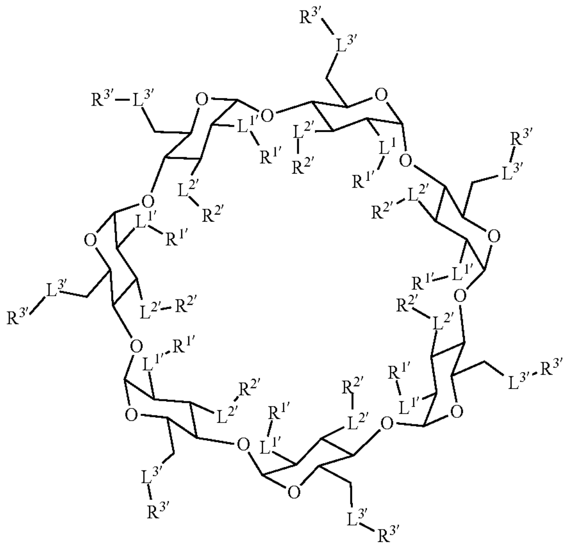

wherein:

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each an identical group selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl alkylsulfonyl, alkylsulfonylalkyl, akylamino, dialkylamino, alkylaminoalkyl, dialkylaminoalkyl, aminoalkyl, alkylsulfonamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocycylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite; nitro, phosphate, phosphine oxide, sulfate alkyl, sulfonamido, thioalkyl, trialkylammonium;

R1, R1', R2, and R2' can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocylyloxy, haloalkyl, haloalkoxy, heterocycloamino, carbocyclyl, heterocyclyl, heterocycylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl; heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene, B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

B10. A cyclodextrin dinner having the general formula Structure B-X or Structure B-X':

CD-[A-B-A']-CD' (Structure B-X)

CD'-[A-B-A']-CD'(Structure B-X')

wherein

CD comprises an αCD having the Structure B-Xa:

(Structure B-Xa)

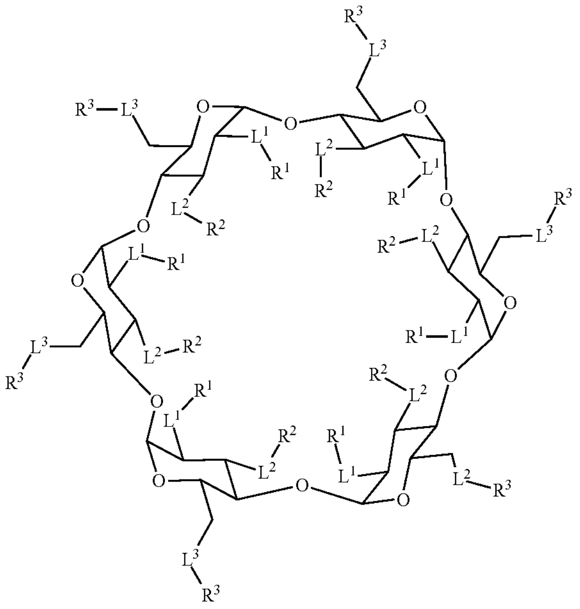

CD' has the Structure B-Xb:

(Structure B-Xb)

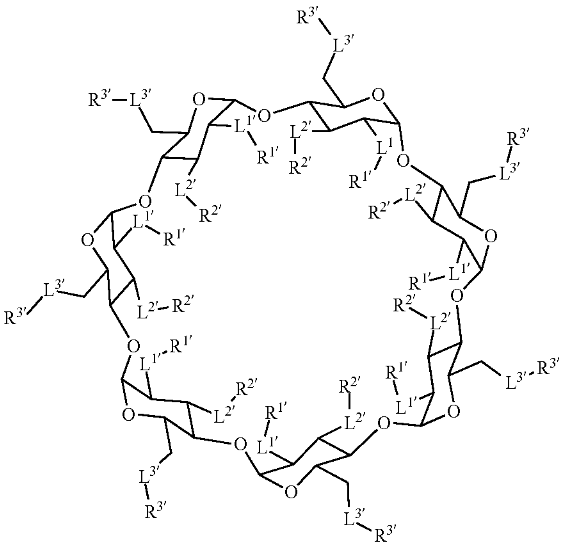

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each an identical group selected from the group consisting of hydrogen, alkyl; heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkysulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxy trialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphene oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

R1, R1', R2, and R2' can be the same or different in each instance, and each is independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino; trialkylammonium, alkylaminoalkyl, dialkylaminoalkyl, trialkylammonium alkyl, n-hydroxytrialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, aryalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbonyl, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl: carboxy, carbalkoxy, carboxamido, carbamoyl, ureido, halogen, haloalkyl, haloalkoxy, cyan, cyanoalkyl: cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—. —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or 1.2 and the corresponding R1 or R2 is omitted and replaced in this manner by A, and A' of each linking group is connected to at least one L1' or L2' and the corresponding R1' or R2' is omitted and replaced in this manner by A'; and at least one of A, B, and A' of each linking group is not a bond.

B11. The dimer of clause B9 or B10, wherein R3 and R3' is hydroxypropyl or, alternatively, an alkyl group, such as a butyl group.

B12. The dimer of any one of clauses B3-B11, wherein at least one of L1, L2, L1' or L2' is not O.

B13. The dimer of any one of clauses B1-B12, wherein L1, L2. L3, L1', L2', and L3' that are not linked to the linking group can be the same or different in each instance, and each is independently selected from the group consisting of a bond, and —O—, and wherein R1, R2, R3, R1', R2', and R3' can be the same or different in each instance, and each is independently selected from the group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro, bromo, and iodo.

B14. The dimer of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, methyl, 2-hydroxypropyl, sulfobutyl, succinyl, maltosyl, carboxymethyl, trimethylammonium propyl and 2-hydroxytrimethylammonium propyl.

B15. The dimer of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and 2-hydroxypropyl and wherein at least one of R1, R2, R3, R1', R2', and R3' is 2-hydroxypropyl.

B16. The dimer of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and methyl and wherein at least one of R1, R2, R3, R1', R2', and R3' is methyl.

B17. The dimer of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and sulfobutyl and wherein at least one of R1, R2, R3, R1', R2', and R3' is sulfobutyl.

B18. The dimer of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and succinyl and wherein at least one of R1, R2, R3, R1', R2', and R3' is succinyl.

B19. The dieter of any one of clauses B1-B12, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3 can be the same or a different in each instance, and each is independently selected from the group consisting of hydrogen, hydroxyl, and a quaternary ammonium such as 2-hydroxytrimethylammonium propyl and wherein at least one of R1, R2, R3, R1', R2', and R3' is a quaternary ammonium such as 2-hydroxytrimethylammonium propyl.

B20. The dimer of any one of clauses B1-B12, wherein L1. L2, L3, L1', L2', and L3' that are not linked to the linking group can be the same or a different in each instance, and each is independently selected from the group consisting of a bond, and —O—, and wherein at least one of R1, R2, R3, R1', R2', and R3 can be the same or a different in each instance, and each is independently selected from the group consisting of hydrogen, hydroxyl, and maltosyl, and wherein at least one of R1, R2, R3, R1', R2', and R3' is maltosyl.

B21. The dimer of any one of clauses B1-B12, wherein L1, L2, L3, L1', L2', and L3' that are not linked to the linking group be the same or a different in each instance, and each is independently selected from the group consisting of a bond, and —O—, and wherein at least one of R1, R2, R3, R1', R2', and R3 can be the same or a different in each instance, and each is independently selected from the group consisting of hydrogen, hydroxyl, and carboxymethyl, and wherein at least one of R1, R2, R3, R1', R2', and R3' is carboxymethyl.

B22. The dimer of clause B1 or B2, wherein CD has a DS at the C6 position (corresponding to L3/R3) of between 3 and 6.

B23, The dimer of clause B22, wherein each R3 that is not hydrogen is independently selected from butyl, hydroxypropyl, sulfobutyl, ethyl, propyl, quaternary ammonium, succinyl, maltosyl, carboxymethyl, trimethylammonium propyl, 2-hydroxytrimethylammonium propyl, or 2-(carboxyethyl)sulfanyl, preferably 2-hydroxypropyl, butyl, 2-(carboxyethyl)sulfanyl, or sulfobutyl.

B24. The dimer of clause B23, wherein each R3 that is not hydrogen is the same.

B25. The dimer of any one of clauses B22-B24, wherein CD' has a DS at the C6 position (corresponding to L3'/R3') of 0, 1, or 2.

B26. The dimer of clause B25, wherein CD' has a DS of 1 or 2 at the C6 position (corresponding to L3'/R3'), wherein each R3' that is not hydrogen is independently selected from butyl, hydroxypropyl, sulfobutyl, ethyl, propyl, quaternary ammonium, succinyl, maltosyl, carboxymethyl, trimethylammonium propyl, 2-hydroxytrimethylammonium propyl, or 2-(carboxyethyl)sulfanyl, preferably 2-hydroxypropyl, butyl, 2-(carboxyethyl)sulfanyl, or sulfobutyl.

B27. The dimer of clause B26, wherein each R3' that is not hydrogen is the same.

B28. The dimer of any one of clauses B22-B27, wherein the combined total DS of C2 positions (corresponding to L1/R1 and L1'/R1') and C3 positions (corresponding to L2/R2 and L2'/R2') on CD and CD' together is 0, 1, 2, 3, or 4.

B29. The dim r of clause B28, wherein each R1, R1', R2, and R2' that is not hydrogen is independently selected from hydroxypropyl, sulfobutyl, methyl, ethyl, quaternary ammonium, succinyl, maltosyl, carboxymethyl, trimethylammonium propyl, thiol, alkoxyamine, amine, 2-hydroxytrimethylammonium propyl, or 2-(carboxyethyl)sulfanyl, preferably 2-hydroxypropyl, methyl, quaternary ammonium, or sulfobutyl.

B30. The dimer of clause B29, wherein each R1 and R2 that is not hydrogen is the same.

B31. The dimer of clause B29 or B30, wherein each R1' and R2' that is not hydrogen is the same.

B32. The dimer of clause B29, wherein each R1, R1', R2, and R2' that is not hydrogen is the same.

B33. The dimer of any one of clauses B28-B32, wherein the combined total DS at positions C2 (corresponding to R1) and C3 (corresponding to R2) on CD is 2 or 3.

B34, The dimer of clause B1 or B2, wherein said dimer has a DS with methyl substituents of between 10 and 40.

B35. The dimer of clause B34, wherein said dimer has a DS with methyl substituents of between 10 and 20.

B36. The dimer of clause B34, wherein said dimer is fully saturated with methyl substituents at the C2 position (corresponding to R1) and C6 position (corresponding to R3) on CD.

B37. The dimer of any one of clauses B34-B36, wherein said dimer is fully saturated with methyl substituents at the C2 position (corresponding to R1') and C6 position (corresponding to R3') on CD'.

B38. The dimes of any one of clauses B1-B37, wherein the length of the linking group is between 2 to 8 atoms.

B39. The dimer of any one of clauses B1-B37, wherein the length of the linking group is between 4 and 7 or is between 8 and 8.

B40. The dimer of any one of clauses B1-B37, wherein the length of the linking group is 4.

B41. The dimer of any one of clauses B1-B37, wherein the length of the linking group is 7.

B42. The dimer of any one of clauses B1-B41, wherein A and A' are each a bond and B is substituted or unsubstituted alkylene.

B43. The dimer of clause B42, wherein B is substituted or unsubstituted butyl.

B44. The dimer of any one of clauses B1-B41, wherein B is substituted or unsubstituted heteroaryl.

B45. The dimer of clause B44, wherein B is substituted or unsubstituted triazole.

B46. The dimer of clause B45, wherein B is unsubstituted triazole having connectivity to A and A' as shown in Structure Y:

(Structure Y)

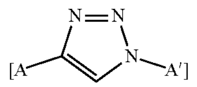

or A' to A as shown in Structure Y':

(Structure Y')

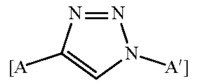

or wherein said finking group has any of the structures shown in FIG. 2B.

B47. The dimer of clause B46, wherein A and A' are independently substituted or unsubstituted alkylene having a length of 1 to 8 carbons.

B48. The dimer of clause B47, wherein A and A' independently each have a length of four or fewer carbons.

B49. The dimer of clause B48, wherein A is unsubstituted methyl and A is unsubstituted propyl.

B50. The dieter of any one of clauses B1-B49, wherein CD and CD' are connected by only one linking group, or by two or more linking groups.

B51, The dimer of clause B50, wherein CD and CD' are connected by two linking groups which are the same as or different than each other.

B52. The dimer of any one of clauses B1-B51, wherein at least one of A and A' independently connect to two or more of L1 or L2, or L1' or L2', respectively.

B53. The CD dimer of any one of clauses B1-B52, which has the structure depicted in FIG. 2B.

B54. The CD dimer of any one of clauses B1-B53, wherein said CD dimer exhibits greater affinity for 7KC than cholesterol, wherein optionally said greater affinity is determined by a turbidity test.

B55. The CD dimer of clause B54, wherein said CD dimer exhibits at least 1.1-fold, 1.5-fold, 2-fold, 3-fold, 4-fold, 5-fold, or 10-fold, greater affinity for 7KC than cholesterol.

B56. A dimer of any one of clauses B1-B53 that has a higher affinity for cholesterol than for the CD monomers depicted herein as determined by turbidity test such as in FIGS. 5A-5J.

B57. The dimer of any one of clauses B1-B56, Wherein each R4 is independently selected from the group consisting of group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro: bromo, and iodo.

B58. The dimer of any one of clauses B1-B57, wherein said L1, L1'; L2, and L2' that is connected to said linking group is each independently selected from the group consisting of —O— and bond.

B59. The dinner of any one of clauses B1-B58, wherein when L1, L2, L3, L1', L2', or L3' is a bond the corresponding R1, R2, R3, R1', R2, or R3', respectively, is not hydroxyl.

B60. The dimer of any one of clauses B1-B58, wherein for each R1, R2, R3, R1', R2, or R3' that is alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, or trialkylammonium, the corresponding L1, L2, L3, L1', L2', or L3' respectively, is a bond.

B61. A composition comprising a mixture of two or more CD dimers according to clauses B1-B60.

B62. The composition of clause B61, wherein said composition is substantially free of other CD dimers.

B63. A pharmaceutical composition comprising a CD dimer according to any one of clauses B1-B60 or a composition according to clause B61 or B62 and a pharmaceutically acceptable carrier.

B64. The pharmaceutical composition of clause B63, wherein said CD dimer is the only active ingredient in said composition.

B65. The pharmaceutical composition of clause B63, which consists of or consists essentially of said CD dimer and said pharmaceutically acceptable carrier.

B66. The pharmaceutical composition of clause B63, further comprising at least one hydrophobic drug, optionally wherein said pharmaceutical composition comprises an amount of said CD dimer or CD dimers that is effective to solubilize said hydrophobic drug.

B67. A method of improving the solubility of a hydrophobic drug, comprising admixing said hydrophobic drug and a CD dimer according to any one of clauses B1-B60 or a composition according to clause B61 or B62.

B68. A CD composition comprising an αCD having the Structure B-Xa:

(Structure B-Xa)

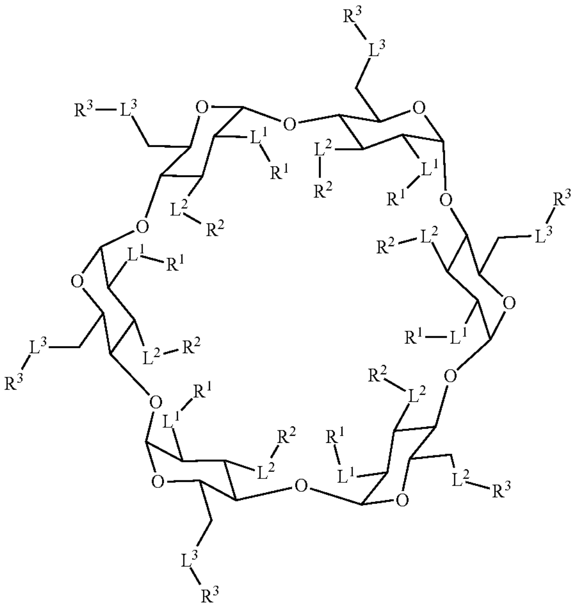

and a βCD having the Structure B-XD:

(Structure B-Xb)

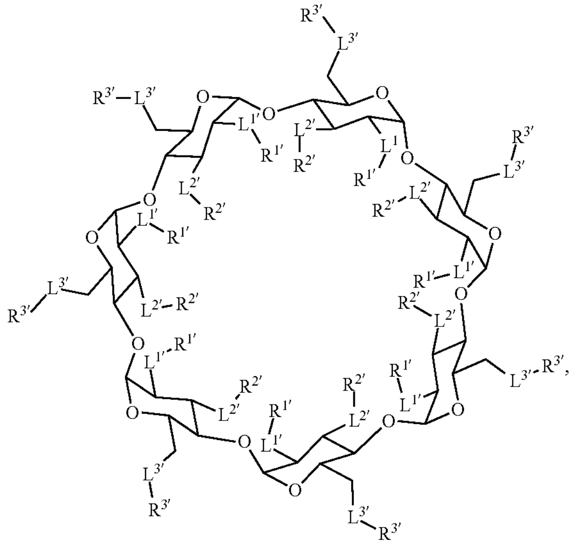

wherein,

L1, L2, L3, L1', L2', and L3 can be the same or different in each instance, and each are independently selected from the group consisting of a bond, —O—, —NH—, —NR4- or —S—, or wherein at least one L1, L2, L3, L1', L2', and L3' is a bond and the corresponding R1, R2, R3, R1', R2', or R3 group is N3, SH, or a halogen such as F, Cl, Br, or I;

R1, R2, R3, R4, R1', R2', and R3' can be the same or different in each instance, and each are independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thin, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium.

B69. A CD composition comprising an αCD having the Structure B-Xa:

(Structure B-Xa)

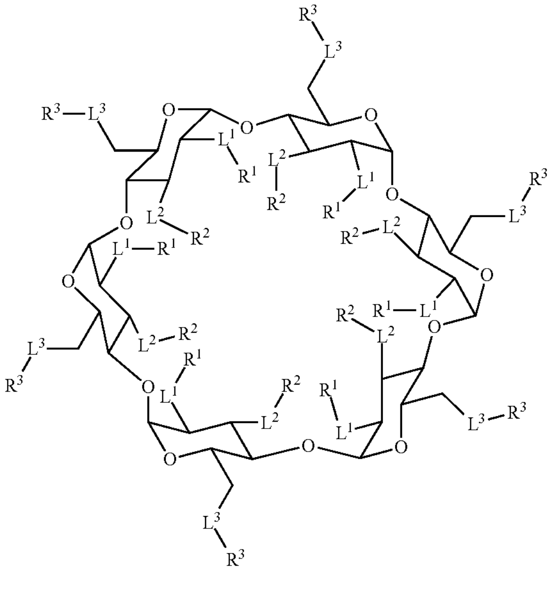

and a βCD having the Structure B-Xb:

(Structure B-Xb)

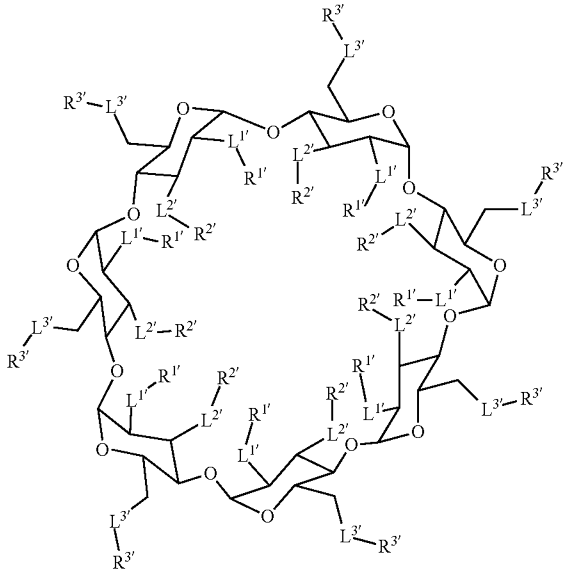

wherein.

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3 is a bond and the corresponding R1, R2, R3, R1', R2', or R3' group is N3, SH, or a halogen such as F, Cl, Br, or I;

R1, R1', R2, and R2' are each hydrogen-,

R3 and R3' can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, akylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkyene, deoxy, glucosyl, heteroalkyl, heteroaryl, heteroarylalkyl, heteroaryloxy, heteroaralkyloxy, cycloalkoxy, heterocylyloxy, haloalkyl, haloalkoxy, heterocycloamino, carbocyclyl, heterocyclyl, heterocycylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy; acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl: ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium.

B70. The CD composition of any one of clauses B68-B69, wherein at least two of R3 and R3' are not hydrogen.

B71. The CD composition of clause B70, wherein at least two and no more than four of R3 and R3' are not hydrogen.

B72. A CD composition comprising an αCD having the Structure B-Xa;

(Structure B-Xa)

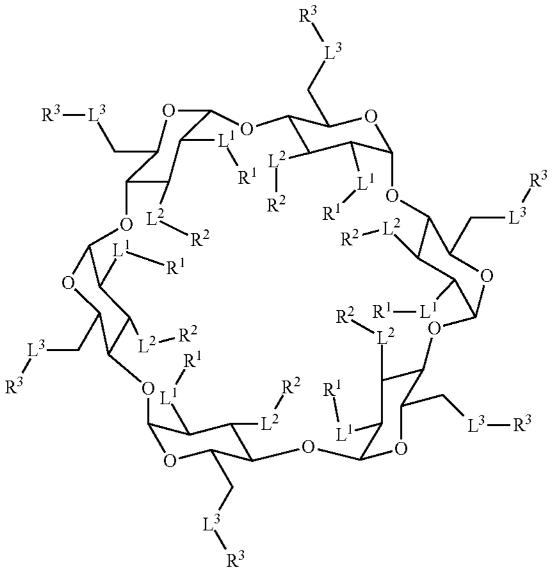

and a βCD having the Structure B-Xb:

(Structure B-Xb)

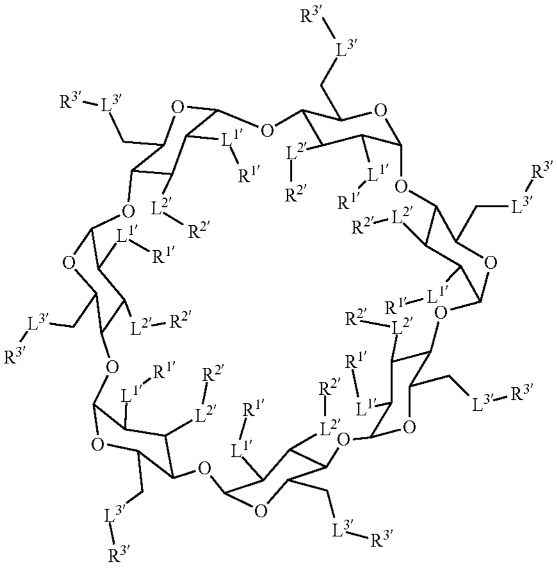

wherein:

L1, L2, L3, L1', L2, and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each hydrogen;

R1, R1', R2, and R2 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy; cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl: alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, TN alkylammonium.

B73. A CD composition comprising an αCD having the Structure B-Xa:

(Structure B-Xa)

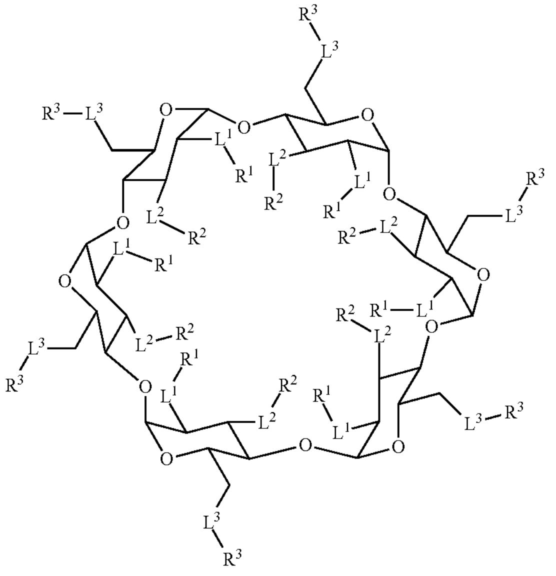

and a βCD having the Structure B-Xb:

(Structure B-Xb)

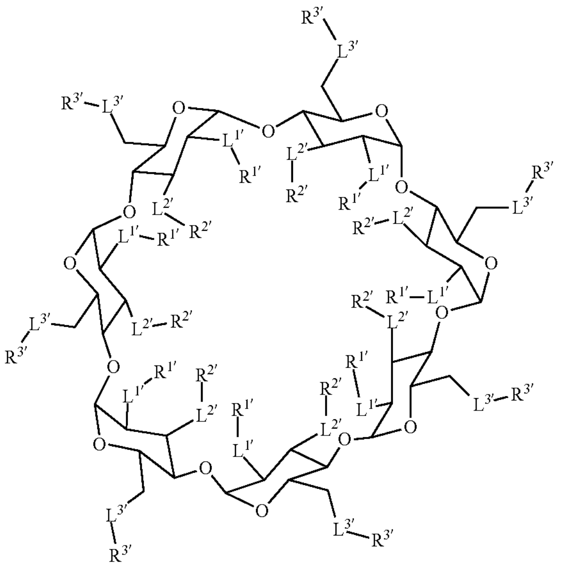

wherein:

L1, L2, L3, L1', L2', and L3' can be the same or a different in each instance, and each is independently selected from the group consisting of a bond, —O—, —NH—, —NR4- or —S—, or wherein at least one L1, L2, L3, L1', L2', and L3' is a bond and the corresponding R1, R2, R3, R1', R2', or R3' group is N3, SH, or a halogen such as F, Cl, Br, or I;

R3 and R3' are each an identical group selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

R1, R1', R2, and R2' can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocylyl, heterocyclyl, heterocycylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium.

B74. The CD composition of any one of clauses B61-B66, wherein for each R1, R2, R3, R1', R2, or R3' that is alkoxyamino, alkoxycarbonylamino, alkoxycarbonyloxy, alkylaminocarbonyl, alkylaminocarbonylalkyl, alkylsulfanyl, alkylsutfonamido, alkylureido; amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, or trialkylammonium, the corresponding L1, L2, L3, L1', L2', or L3', respectively, is a bond.

B75. The CD composition according to any one of clauses B68-B74, wherein the molar ratio of said αCD to said βCD is between 3:1 and 1.3, between 2.5.1 and 1:2.5, between 2.1 and 1:2, between 1.5:1 and 1:1.5, between 1.2:1 and 1:1.2, or about 1:1, preferably about 1:1.

B76. A pharmaceutical composition comprising a CD composition according to any one of clauses B88-B75 and a pharmaceutically acceptable carrier.

B77. The pharmaceutical composition of clause B76, wherein said CD composition is the only active ingredient in said composition.

B78. The pharmaceutical composition of clauses B76, which consists of or consists essentially of said CD composition and said pharmaceutically acceptable carrier.

B79. The pharmaceutical composition of clause B76, further comprising at least one hydrophobic drug, optionally wherein said pharmaceutical composition comprises an amount of said CD composition that is effective to solubilize said hydrophobic drug.

B80. A method of improving the solubility of a hydrophobic drug, comprising admixing said hydrophobic drug and a CD composition according to any one of clauses B68-B75 or a composition according to clause B76.

B81. A therapeutic method comprising administration of an effective amount of a CD composition according to any one of clauses B68-B75 or pharmaceutical composition according to any one of clauses B76-B78 to a subject in need thereof.

B82. A method for reducing the amount of 7KC and/or cholesterol in a subject in need thereof comprising administration of an effective amount of a CD composition according to any one of clauses B68-B75 or pharmaceutical composition according to any one of clauses B76-B78 to a subject in need thereof.

B83. The method of any one of clauses B81-B82, which prevents, treats, ameliorates the symptoms of one or more of atherosclerosis coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lamb-Opitz Syndrome, infantile neuronal ceroid lipofuscinosis, lysosomal acid lipase deficiency, cerebrotendinous xanthomatosis. X-linked adrenoleukodystrophy, sickle cell disease, Niemann-Pick Type A disease, Niemann-Pick Type B disease. Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy.

B84. A therapeutic method comprising administration of an effective amount of a CD dimer according to any one of clauses B1-B60 or a composition according to any one of clauses B61-B65 to a subject in need thereof.

B85. The method of clause B84, wherein the subject in need thereof is suffering from harmful or toxic effects of 7KC.

B86. A method for reducing the amount of 7KC in a subject in need thereof comprising administration of an effective amount of a CD dimer according to any one of clauses BB-860 or a composition according to any one of clauses B61-B65 to a subject in need thereof.

B87. The method of any one of clauses B84-B86, wherein said CD dimer is administered to said subject via parenteral (e.g., subcutaneous, intramuscular, or intravenous), topical, transdermal, oral, sublingual, or buccal administration.

B88. The method of clause B87, wherein said CD dimer is administered intravenously.

B89. The method of any one of clauses B84-B88, which comprises administering to said subject (a) between about 1 mg and 20 g, such as between 10 mg and 1 g, between 50 mg and 200 mg, or 100 mg of said CD dimer to said subject, or (b) between 1 and 10 g of said CD dimer, such as about 2 g, about 3 g, about 4 g, or about 5 g, or (c) between 50 mg and 5 g of said CD dimer, such as between 100 mg and 2.5 g, between 100 mg and 2 g, between 250 mg and 2.8 g.

B90. The method of any one of clauses B84-B88, which prevents, treats, ameliorates the symptoms of one or more of atherosclerosis/coronary artery disease, arteriosclerosis, coronary atherosclerosis due to calcified coronary lesion, heart failure (all stages). Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy.

B91. The method of any one of clauses B84-B89, which prevents, treats, ameliorates the symptoms of atherosclerosis.

B92. The method of clause B91, further comprising administering a second therapy to said subject; wherein said second therapy is administered concurrently or sequentially in either order.

B93. The method of clause B92, wherein said second therapy comprises one or more of an anti-cholesterol drug, such as a fibrate or statin, anti-platelet drug, anti-hypertension drug, or dietary supplement.

B94. The method of clause B93, wherein said statin comprises ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), or ZOCOR® (simvastatin).

B95. The method of clause B93, wherein said second therapy comprises an anti-cholesterol drug and an anti-hypertension drug.

B96, A method of purification of oxysterols, comprising: contacting a composition comprising oxysterols with a CD dimer according to any one of clauses B1-B60, thereby solubilizing said oxysterols in said CD dimer, and recovering said CD dimer and solubilized oxysterols.

B97, The method of clause 896, wherein said oxysterols comprise or consist of 7KC.

B98. The method of clause B97, further comprising measuring the amount or concentration of 7KC in said solubilized oxysterols, thereby determining the relative concentration of 7KC in the composition.

B99. The method of clause B98, wherein said composition comprises a patient sample.

B100. An in vitro method of removing oxysterols from a sample, comprising: contacting a sample comprising oxysterols with a CD dimer according to any one of clauses B1-B60, thereby solubilizing said oxysterols in said CD dimer; and separating said sample from said CD dimer and solubilized sterols, and optionally reintroducing said sample into a subject from which said sample is obtained.

B101. A method of producing a reduced cholesterol product, comprising: contacting a product comprising cholesterol with a CD dimer according to any one of clauses B1-B80, thereby solarizing said cholesterols in said CD dimer; and removing said CD dimer and solubilized cholesterol from said product.

B102. The method of clause B101, wherein said product is a food product.

B103. The method of clause B102, wherein said food product comprises meat and/or dairy.

B104. A method of making a CD dimer according to any one of clauses B1-B60, comprising:

(a) reacting α- or β-CD molecules that are protected on the primary face with a dialkylating agent and with native β- or α-CD respectively, thereby producing a primary face-protected α-βCD dimer linked through the secondary face, and optionally purifying said primary protected α-βCD dimes;

(b) deprotecting said primary face protected α-βCD dieter, thereby producing a deprotected CD dimer, and optionally purifying said deprotected CD dimer, and (c) functionalizing said deprotected α-βCD to said R1, R2, R3, R1', R2', and/or R3' groups, thereby producing said α-βCD dimer, and optionally purifying said α-βCD dimer.

B105. The method of clause B104, wherein said α- or βCD that is protected on the primary face comprises a trityl, benzoyl, tert-butyldimethylsilyl (TBDMS), tert-butyldiphenylsilyl (TBDPS), triisopropylsilyl (TIPS) and the like, preferably TBDMS as in heptakis(7-O-tert-butyldimethylsilyl)-β-CD.

B106. The method of clause B104 or B105, wherein said dialkylating agent comprises a dihaloalkane, ditosylalkane, dimesylalkane, ditriflatealkane and the like, preferably 1,4 dibromobutane.

B107. The method of any one of clauses B104-B106, wherein step (a) is performed in anhydrous conditions using a base like imidazole, pyridine, DMAP, sodium hydroxide, sodium hydride, lithium hydride and the like: preferably sodium hydride.

B108. The method of any one of clauses B104-B107, wherein said purification in step (a) comprises direct phase chromatography with isocratic elution and/or a crystallization/precipitation B109. The method of any one of clauses B104-B108, wherein step (b) is performed in tetrahydrofuran (THF) or methanol (MeOH) with HF-pyridine, tetrabutylammonium fluoride (TBAF), acetic acid, sulfuric acid, triflic acid and the like, preferably in THF with TBAF.

B110. The method of any one of clauses B104-B109, wherein said purification in step (b) comprises direct phase chromatography with isocratic elution and/or crystallization/precipitation.

B111. The method of any one of clauses B104-B110, wherein step (c) comprises reacting said deprotected α-βCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium reagent such as glycidyltrimethylammonium chloride.

B112. The method of any one of clauses B104-B111, wherein step (c) is performed in aqueous conditions using a base like sodium hydroxide, lithium hydroxide, preferably sodium hydroxide.

B113. The method of any one of clauses B104-B112, wherein said purification in step (c) comprises one or more ion exchange resin treatment, charcoal clarification and dialysis.

B114. A method of making a CD dimer having the structure CD-L-CD', wherein CD comprises an αCD, CD' comprises a βCD', and L comprises a linking group, the method comprising (a) reacting either a 2-O-(n-azidoalkyl)-CD or a 3-O-(n-azidoalkyl)-CD or a 2-O-(n-azidoalkyl)-CD' or a 3-O-(n-azidoalkyl)-CD' or a mixture thereof of 2- and 3-substituted CD, with either a 2-O-(n-alkyne)-CD or a 3-O-(n-alkyne)-CD or 2-O-(n-alkyne)-CD' or a 3—O-(n-alkyne)-CD' or a mixture thereof of 2- and 3-substituted CD respectively, thereby forming a CD-triazole-CD' dimer having the structure αCD-alk1-triazole-alk2-βCD', and optionally (b) purifying said CD-triazole-CD' dimer.

B115. A method of making a CD dimer having the structure CD L CD', wherein CD comprises an αCD, CD' comprises a βCD', and L comprises a linking group that comprises a triazole, the method comprising (a)(1) reacting a 2-O-(n-azidoalkyl)-CD or a 3-O-(n-azidoalkyl)-CD or mixture thereof with a 2-O-(n-alkyne)-CD' or a 3-O-(n-alkyne)-CD or a mixture thereof, thereby forming a CD-triazole-CD' dimer having the structure αCD-alk1-triazole-alk2-βCD';

or (2) reacting a 2-O-(n-azidoalkyl)-CD' or a 3-O-(n-azidoalkyl)-CD' or mixture thereof with a 2-O-(n-alkyne)-CD or a 3-O-(n-alkyne)-CD' or a mixture thereof, thereby forming a CD-triazole-CD' dieter having the structure αCD-alk1-triazole-alk2-βCD'; and optionally (b) purifying said CD dither.

B116. The method of clause B114 or B115, wherein step (a) is performed with a copper (I), silver (I) or ruthenium catalyst, preferably 15 mM copper (I) like copper bromide (CuBr) or copper tris(triphenylphosphine) bromide [(PPh3) 3CuBr].

B117. The method of any one of clauses B114-B116, wherein step (a) is carried out in an aqueous solution.

B118. The method of clause B117, wherein the aqueous solution comprises dimethylformamide (DMF), optionally about 50% DMF (v/v)

B119. The method of any one of clauses B114-B118, wherein step (b) comprises silica gel chromatography or crystallization/precipitation.

B120. The method of anyone of clauses B114-B119, further comprising, prior to step (a) producing said 2-O-(n-azidoalkyl)-CD or 3-O-(n-azidoalkyl)-CD or mixture thereof by a method comprising: (1) reacting n-azido-1-bromo-alkane with an α or β-CD, optionally with a catalytic amount of lithium iodide, thereby producing said 2-β-(n-azidoalkyl)-βCD or 3-O-(n-azidoalkyl)-CD or mixture thereof, and (2) optionally purifying said 2-O-(n-azidoalkyl)-βCD or 3-O-(n-azidoalkyl)-CD or mixture thereof.

B121. The method of clause B120, wherein step (i) comprises silica gel chromatography or crystallization/precipitation.

B122. The method of any one of clauses B114-B121, further comprising, prior to step (a) producing 2-O-(n-alkyne)-CD or 3-O-(n-alkyne)-CD or mixture thereof by a method comprising: (i) reacting n-bromo-1-alkyne with a CD comprising an α-CD or β-CD, optionally with a catalytic amount of lithium iodide, thereby producing said 2-O-(n-alkyne)-CD or 3-O-(n-alkyne)-CD or mixture thereof and (ii) optionally purifying said 2-O-(n-alkyne)-CD or 3-O-(n-alkyne)-CD or mixture thereof.

B123. The method of clause B122, wherein step (ii) comprises silica gel chromatography or crystallization/precipitation.

B124. The method of clause B122 or B123, wherein step (i) is carried out in dry DMSO.

B125. The method of any one of clauses B120 or B122, wherein the reaction in step (i) or (1) comprises lithium hydride, sodium hydride, n-butyl lithium and the like, preferably lithium hydride.

B126. The method of any one of clauses B114-B125, further comprising (c) hydroxypropylation, methylation, succinylation, sulfobutylation and/or quaternary ammonium functionalization said CD dimer, thereby producing a functionalized CD dimer, and optionally purifying said functionalized CD dimer.

B127. The method of clause B126, wherein step (c) comprises reacting said deprotected CD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium functionalization reagent such as glycidyltrimethylammonium chloride.

B128. The method of clause B126 or B127, wherein step (c) is performed in aqueous conditions, optionally comprising sodium hydroxide as a base.

B129. The method of anyone of clauses B126-B128, wherein said purification in step (c) comprises one or more ion exchange resin treatments, charcoal clarification, membrane filtration, and dialysis.

B130. The method of any one of clauses B104-B129, wherein the length of the (inking group is between 2 and 8.

B131. The method of any one of clauses B104-B129, wherein the length of the linking group is between 4 and 7 or is between 6 and 8.

B132. The method of any one of clauses B104-B129, wherein the length of the linking group is 4.

B133. The method of any one of clauses B104-B129, wherein the length of the linking group is 7.

B134. The method of any one of clauses B104-B133, wherein A and A are each a bond and B is substituted or unsubstituted alkylene B135. The method of douse B134, wherein B is substituted or unsubstituted butyl.

B136. The method of any one of clauses B104-B133, wherein B is substituted or unsubstituted heteroaryl.

B137. The method of clause B136, wherein B is substituted or unsubstituted triazole.

B138. The method of clause B137, wherein B is unsubstituted triazole having connectivity to A and A' as shown in Structure Y:

(Structure Y)

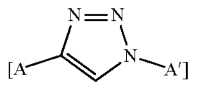

or A' to A as shown in Structure Y':

(Structure Y')

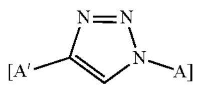

or wherein said linking group has any of the structures shown in FIG. 28.

B139. The method of clause B138, wherein A and A' are independently substituted or unsubstituted alkylene each having a length of 1 to 8 carbons. B140. The method of clause B139, wherein A and A' independently each have a length of four or fewer carbons.

B141. The method of clause B140, wherein A is unsubstituted methyl and A' is unsubstituted propyl.

B142. The method of any one of clauses B104-B141, wherein CD and CD' are connected by only one linking group, or by two or more linking groups.

B143. The method of clause B142, wherein CD and CD' are connected by two linking groups which are the same as or different than each other.

B144. The method of anyone of clauses B104-B143, wherein at least one of A and A' independently connect to two or more of L1 or L2, or L1' or L2', respectively.

B145. The method of any one of clauses B104-B144, wherein said CD dimer has the structure depicted in FIG. 28.

B146. The method of any one of clauses B104-B144, which is adapted to produce the CD dimer of any one of clauses B1-B60.

P C1. A CD dimer having the general formula Structure C—X:

CD-[A-B-A']-CD' (Structure C—X)

wherein

CD has the structure C-Xa:

(Structure C-Xa)

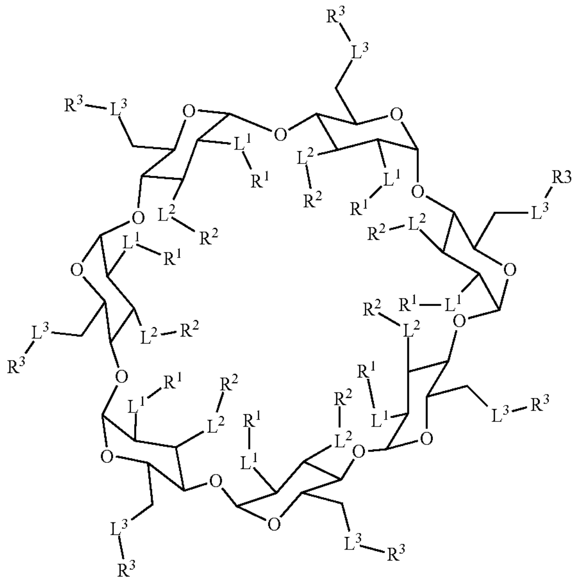

CD' has the structure C-Xb:

(Structure C-Xb)

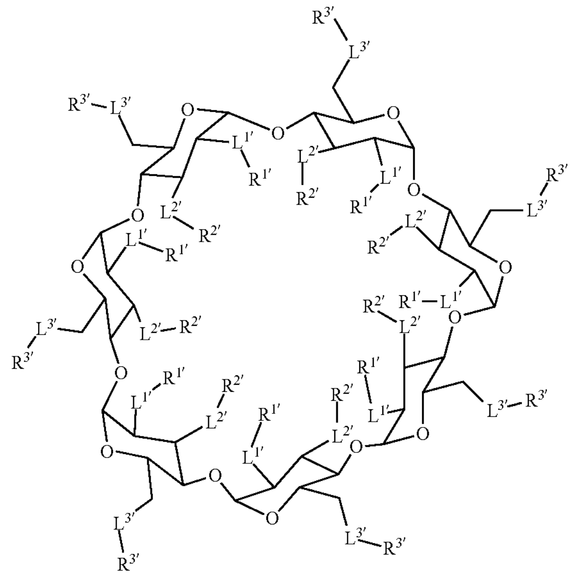

wherein:

L1. L2, L3, L1', L2', and L3' can be the same or a different in each instance, and each are independently selected from the group consisting of a bond, —O—, —NH—, —NR4- or —S— or wherein at least one L1, L2, L3, L1', L2', and L3' is a bond and the corresponding R1, R2, R3, R1', R2', or R3' group is N3, SH, or a halogen such as F, Cl, Br, or I;

R1, R2, R3, R4, R1', R2', and R3' can be the same or a different in each instance, and each are independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy; alkylaminocarbonyl, alkylaminocarbonylalkyl; alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl: sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1 or L2' and the corresponding R1' or R2' is omitted and replaced in this manner by A'; and at least one of:

(a) the DS at position C2 in CD (corresponding to L1/R1) does not equal the DS at position C2 in CD' (corresponding to L1'/R1'); or (b) the DS at position C3 in CD (corresponding to L2/R2) does not equal the DS at position C3 in CD' (corresponding to R2'/R2'), or (c) the DS at position C6 in CD (corresponding to L3/R3) does not equal the DS at position C6 in CD' (corresponding to L3'/R3'); or (d) at least one L1/R1, L2/R2, or L3/R3 pair differs from each L1'/R1', L2'/R2', and L3'/R3' pair, (e) at least one L1'/R1', L2'/R2', or R3'/R3' pair differs from each L1/R1, L2/R2, and L3/R3 pair.

C2. A cyclodextrin dimer having the general formula Structure C—X:

CD-[A-B-A']-CD' (Structure C—X)

wherein

CD has the structure C-Xa:

(Structure C-Xa)

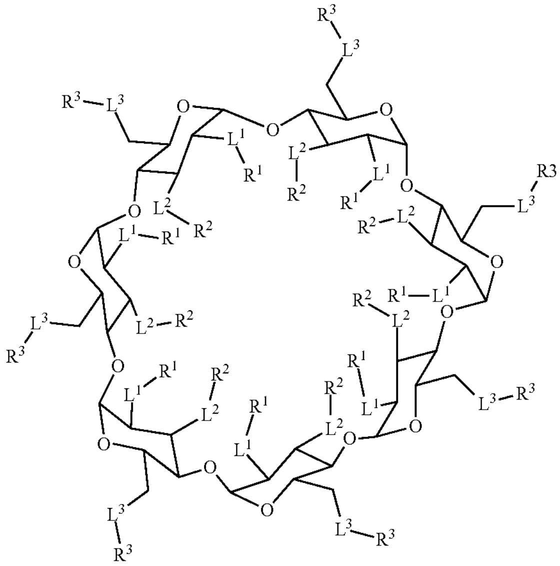

CD' has the structure C-Xb:

(Structure C-Xb)

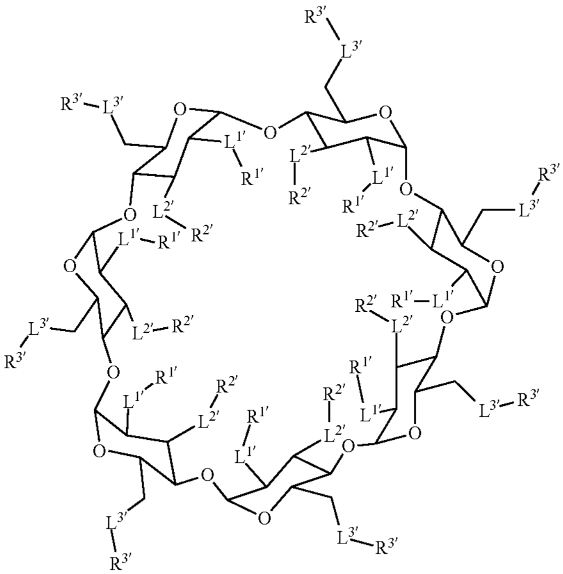

L1, L2, L3, L1', L2', and L3' can be the same or a different in each instance, and each are dependently selected from the group consisting of a bond, —O—, —NH—, —NR4- or —S— or wherein at least one L1, L2, L3, L1', L2', and L3' is a bond and the corresponding R1, R2, R3, R1', R2', or R3' group is N3, SH, or a halogen such as F, Cl, Br, or I;

R1, R2, R3, R4, R1', R2', and R3' can be the same or a different in each instance, and each are independently selected from the group consisting of hydrogen, alkyl, heteroalkyl, haloalkyl, carbocyclyl, heterocyclyl cycloalkyl, heterocycloalkyl, alkenyl, cycloalkenyl, heterocycloalkenyl, alkynyl, alkoxy, alkoxyalkyl, alkoxyalkoxyalkyl, heteroalkoxy, haloalkoxy, alkynylalkoxy, cycloalkoxy, heterocycloalkoxy, alkylcarbonyl, alkylcarbonyloxy, alkylcarbonyloxyalkyl, alkylsulfanyl, alkylsulfonyl, alkylsulfonylalkyl, alkylsulfonamido, alkylamino, dialkylamino, trialkylammonium, alkylaminoalkyl, dialkylaminoalkyl, trialkylammonium alkyl, n-hydroxy trialkylammonium alkyl, alkoxyamino, alkoxycarbonylamino, alkylaminocarbonyl, alkoxycarbonyloxy, alkylcarbonylaminoalkyl, alkylaminocarbonylalkyl, alkylureido, aryl, heteroaryl, haloaryl, arylalkyl, heteroarylalkyl, aryloxy, heteroaryloxy, arylcarbonyl, arylsulfanyl, arylsulfonyl, heteroarylsulfonyl, arylsulfonamido, arylamino, arylureido, amino, ammonium, aminoalkyl, aminoalkoxy, aminocarbony, aminocarbonyloxyalkyl, cycloamino, heterocycloamino thio, sulfatyl, sulfuryl, sulfonamido, thioalkyl, sulfate alkyl, aminosulfonyl, alkylaminosulfonyl, dialkylaminosulfonyl, carboxy, carbalkoxy, carboxamido, carbamoyl, ureido, halogen, haloalkyl, haloalkoxy, cyano, cyanoalkyl, cyanoalkoxy, azido, nitro, nitrite, phosphate, phosphoryl, phosphine oxide, hydroxyl, hydroxyalkyl, hydroxycycloalkyl, hydroxyalkoxy, hydroxyalkoxyalkyl, hydroxyalkylamino, hydroxyalkylaminoalkyl, hydoxycarbonyl, hydroxycarbonylalkyl, monosaccharide, disaccharide, palmitoyl, fatty acid:

[A —B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene, CD and CD' are connected by at least one linking group, A of each linking group is connected to at least one L1 or L2 and the corresponding R1 or R2 is omitted and replaced in this manner by A, and A' of each linking group is connected to at least one L1' or L2' and the corresponding R1 or R2' is omitted and replaced in this manner by A'; and at least one of:

(a) the degree of substitution at position C2 in CD (corresponding to L1/R1) does not equal the degree of substitution at position C2 in CD' (corresponding to L1'/R1'); or (b) the degree of substitution at position C3 in CD (corresponding to L2/R2) does not equal the degree of substitution at position C3 in CD' (corresponding to L2'/R2'); or (c) the degree of substitution at position C6 in CD (corresponding to L3/R3) does not equal the degree of substitution at position C6 in CD' (corresponding to L3'/R3'); or (d) at least one L1/R1, L2/R2, or L3/R3 pair differs from each L1'/R1', L2'/R2', and L3'/R3' pair; or (e) at least one L1'/R1', L2'/R2', or L3'/R3' pair differs from each L1/R1, L2/R2, and L3/R3 pair.

C3. The dimer of clause C1 or C2, wherein each R3 is not hydrogen, or wherein each R3' is not hydrogen.

C4. The dimer of clause C1 or C2, wherein at feast one L1/R1 pair differs from each L2/R2, L3/R3, L1'/L1', L2'/R2', and L3'/R3' pair.

C5. The dimer of clause C1 or C2, wherein at least one L2/R2 pair differs from each L1/R1, L3/R3, L1'/R1', L2'/R2', and L3'/R3' pair.

C6. The dimer of clause C1 or C2, Wherein at least one L3/R3 pair differs from each L1/R1, L2/R2, L1'/R1', L2'/R2', and L3'/R3' pair.

C7. The dimer of clause C1 or C2, wherein at least one L1'/R1' pair differs from each L1/R1, L2/R2, L3/R3, L2'/R2', and L3/R3' pair.

C8. The dimer of clause C1 or C2, wherein at least one L2'/R2' pair differs from each L1/R1, L2/R2, L3/R3, L1'/R1', and L3'/R3' pair.

C9. The dimer of clause C1 or C2, wherein at least one L3'/R3' pair differs from each L1/R1, L2/R2, L3/R3, L1'/R'1, and L2'/R2' pair.

C10. The dimer of clause C1, C2, C6, or C9, wherein R1, R1', R2, and R2' are each hydrogen.

C11. The dimer of any one of clauses C1-C10, wherein at least two of R3 and R3' are not hydrogen.

C12. The dimer of clause C11, wherein at least two and no more than four of R3 and R3' are not hydrogen.

C13. The CD of clause C1 or C2, wherein R3 and R3' are each hydrogen.

C14. The dimer of clause C1 or C2, wherein R3 and R3' are each identical.

C15, The dimer of clause C14 wherein R3 and R3' is hydroxypropyl or, alternatively, an alkyl group, such as a butyl group.

C16. The dimer of any one of clauses C1-C15, wherein at least one of L1, L2, L1', L2', L3, or L3' is not O.

C17 The dimer of any one of clauses C1-C16, wherein L1, L2, L3, L1', L2', and L3' that are not finked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro, bromo, and iodo.

C18. The dinner of clause C17, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, methyl, 2-hydroxypropyl, sulfobutyl, succinyl, maltosyl, carboxymethyl, trimethylammonium propyl, 2-hydroxytrimethylammonium propyl.

C19. The dimer of clause C17, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' are independently selected from the group consisting of hydrogen, hydroxyl, and 2-hydroxypropyl, and wherein at least one of R1, R2, R3, R1', R2', and R3' is 2-hydroxypropyl.

C20. The dimer of clause C17, wherein L1, L2, L3, L1', L2', and L3' that are not linked to the finking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and methyl, and wherein at least one of R1, R2, R3, R1', R2', and R3' is methyl.

C21. The dimer of clause C17, wherein L1, L2, L3, L1', L2', and L3 that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and sulfobutyl, and wherein at least one of R1, R2, R3, R1', R2', and R3' is sulfobutyl.

C22. The dimer of clause C17, wherein L1, L2, L3, L1', L2', and L3' that are not linked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and succinyl, and wherein at least one of R1, R2, R3, R1', R2', and R3' is succinyl.

C23. The dimer of clause C17, wherein L1, L2, L3, L1', L2', and L3' that are not finked to the linking group can be the same or a different in each instance, and each is independently selected from the group consisting of a bond, and —O—, and wherein R1, R2, R3, R1', R2', and R3' can be the same or a different in each instance, and each is independently selected from the group consisting of hydrogen, hydroxyl, and 2-hydroxytrimethylammonium propyl, and wherein at least one of R1, R2, R3, R1', R2', and R3' is 2-hydroxytrimethylammonium propyl.

C24. The dimer of clause C17, wherein L1, L2, L3, L1', L2', and L3' that are not linked to the linking group can be the same or a different in each instance, and each is independently selected from the group consisting of a bond, and —O—, and wherein at least one of R1, R2, R3, R1', R2', and R3' can be the same or different in each instance, and each is independently selected from the group consisting of hydrogen, hydroxyl and maltosyl, and wherein at least one of R1, R2, R3, R1', R2', and R3' is maltosyl.

C25. The dimer of clause C17, wherein L1, L2, L3, L1', L2', and L3' that are not linked to the linking group can be the same or a different in each instance, and each is independently selected from the group consisting of a bond, and —O—, and wherein at least one of R1, R2, R3, R1', R2', and R3' can be the same or different in each instance, and each is independently selected from the group consisting of hydrogen, hydroxyl and carboxymethyl, and wherein at least one of R1, R2, R3, R1', R2', and R3' is carboxymethyl.

C26. The dimer of clause C1 or C2, wherein CD has a DS at the C6 position (corresponding to L3/R3) of between 3 and 7.

C27. The dimer of clause C26, wherein each R3 that is not hydrogen is independently selected from butyl, hydroxypropyl, sulfobutyl, ethyl, propyl, quaternary ammonium, succinyl, maltosyl, carboxymethyl, dimethylammonium propyl, 2-hydroxytrimethylammonium propyl, or 2-(carboxyethyl) sulfanyl.

C28. The dimer of clause C27, wherein each R3 that is not hydrogen is the same.

C29. The dimer of clause C1 or C2 or any one of clauses C26-C28, wherein CD' has a DS at the C6 position (corresponding to L3'/R3') of between 3 and 7.

C30. The dimer of clause C28, wherein each R3' that is not hydrogen is independently selected from butyl, hydroxypropyl, sulfobutyl, ethyl, propyl, quaternary ammonium, succinyl, maltosyl, carboxymethyl, trimethylammonium propyl, 2-hydroxytrimethylammonium propyl, or 2-(carboxyethyl)sulfanyl.

C31. The dimer of clause C30, wherein each R3' that is not hydrogen is the same.

C32. The dimer of clause C1 or C2, wherein CD has a DS at the C6 position (corresponding to L3/R3) of between 3 and 7 and CD' has a DS at the C6 position (corresponding to L3'/R3') of between 3 and 7.

C33. The dimer of clause C32, wherein each R3 and R3' that is not hydrogen is independently selected from butyl, hydroxypropyl, sulfobutyl, ethyl, propyl, quaternary ammonium, succinyl, maltosyl, carboxymethyl, trimethylammonium propyl, 2-hydroxytrimethylammonium propyl, or 2-(carboxyethyl)sulfanyl.

C34. The dimer of clause C33, wherein each R3 that is not hydrogen is different than each R3' that is not hydrogen.

C35. The dimer of clause C33 or C34, wherein each R3 that is not hydrogen is the same as each other R3 that is not hydrogen, and/or each R3' that is not hydrogen is the same as each other R3' that is not hydrogen.

C36. The dimer of any one of clauses C26-C35, wherein the combined total DS of C2 positions (corresponding to L1/R1 and L1'/R1') and C3 positions (corresponding to L2/R2 and L2'/R2') on CD and CD' together is 4, 1, 2, 3, or 4.

C37. The dimer of clause C36, wherein each R1, R1', R2, and R2' that is not hydrogen is independently selected from hydroxypropyl, sulfobutyl, methyl, ethyl, quaternary ammonium, succinyl, maltosyl, carboxymethyl, trimethylammonium propyl, thiol, alkoxyamine, amine, 2-hydroxytrimethylammonium propyl, or 2-(carboxyethyl)sulfanyl, preferably 2-hydroxypropyl, methyl, quaternary ammonium, or sulfobutyl.

C38. The dimer of clause C37, wherein each R1 and R2 that is not hydrogen is the same as each other, and/or each R1' and R2' that is not hydrogen is the same as each other, and/or each R1, R1', R2, and R2' that is not hydrogen is the same as each other.

C39. The dimer of any one of clauses C1-C38, wherein the length of the linking group is between 2 and 8.

C40. The dimer of any one of clauses C1-C39, wherein the length of the linking group is between 4 and 7 or is between 6 and 8.

C41. The dimer of any one of clauses C1-C40, wherein the length of the linking group is 4.

C42. The dimer of any one of clauses C1-C41, wherein the length of the linking group is 7.

C43. The dimer of any one of clauses C1-C42, wherein A and A' are each a bond and B is substituted or unsubstituted alkylene.

C44. The dimer of clause C43, wherein B is substituted or unsubstituted butyl.

C45. The dimer of any one of clauses C1-C42, wherein B is substituted or unsubstituted heteroaryl.

C46. The dimer of clause C45, wherein B is substituted or unsubstituted triazole.

C47. The dimer of clause C46, wherein B is an unsubstituted triazole having connectivity to A and A' as shown in Structure Y:

(Structure Y)

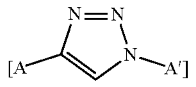

or A' to A as shown in Structure Y':

(Structure Y')

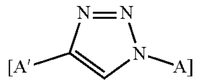

or wherein said linking group has any of the structures shown in FIG. 2B.

C48. The dimer of clause C47, wherein A and A' are independently substituted or unsubstituted alkylene each having a length of 1 to 8 carbons.

C49. The dimer of clause C48, wherein A and A' independently each have a length of four or fewer carbons.

C50. The dimer of clause C49, wherein A is unsubstituted methyl and A' is unsubstituted propyl.

C51. The dimer of any one of clauses C1-C50, wherein CD and CD' are connected by only one linking group, or by two or more linking groups.

C52. The dimer of clause C59, wherein CD and CD' are connected by two linking groups which are the same as or different than each other.

C53. The dimer of any one of clauses C1-C52, wherein at least one of A and A' independently connect to two or more of L1 or L2, or L1' or L2', respectively.

C54. The dimer of any one of clauses C1-C53, which has the structure depicted in any one of FIGS. 17A-17D.

C55. The dinner of any one of clauses C1-C54, wherein said CD dimer exhibits greater affinity for 7KC than cholesterol, wherein optionally said greater affinity is determined by a turbidity test.

C56. The dimer of clause C55, wherein said CD dimes exhibits at least 1.1 fold, 1.5-fold, 2-fold, 3-fold, 4-fold, 5-fold, or 10-fold, greater affinity for 7KC than cholesterol.

C57. A dimes of clauses C1-C56 that has a higher affinity for cholesterol than for the CD monomers depicted herein as determined by turbidity test such as in FIGS. 5A-5J.

C58. The dieter of any one of clauses C1-C57, wherein each R4 is independently selected from the group consisting of group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphoryl, amino, azido, sulfate, sulfuryl, fluoro, chloro, bromo, and iodo.

C59. The dimer of any one of clauses C1-C58, wherein said L1, L1', L2, and L2' that is connected to said linking group is each independently selected from the group consisting of —O— and bond.

C60. The dimer of any of clauses C1-C59, wherein for any R1, R2, R3, R1', R2', or R3' that is a hydroxyl, the corresponding L1, L2. L3, L1', L2', L3', respectively, is not a bond.

C61. The dimer of any of clauses C1-C60, wherein when L1, L2, L3, L1', L2', or L3' is a bond the corresponding R1, R2, R3, R1', R2, or R3', respectively, is not hydroxyl.

C62. The dimer of any one of clauses C1-C61, wherein for each R1, R2, R3, R1', R2, or R3' that is alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, or trialkylammonium, the corresponding L1, L2, L3, L1', L2', or L3', respectively, is a bond.

C63. A composition comprising a mixture of two or more CD dimers according to clauses C1-C62.

C64. The composition of clause C63, wherein said composition is substantially free of other CD dimers.

C65. A pharmaceutical composition comprising a CD dieter according to any one of clauses C1-C62 or a composition according to any one of clauses C63-C64 and a pharmaceutically acceptable carrier.

C66. The pharmaceutical composition of clause C65, wherein said CD dimer is the only active ingredient in said composition.

C67. The pharmaceutical composition of clause C65, which consists of or consists essentially of said CD dimer and said pharmaceutically acceptable carrier.

C68. The pharmaceutical composition of clause C65, further comprising at least one hydrophobic drug, optionally wherein said pharmaceutical composition comprises an amount of said CD dimer or CD dimers that is effective to solubilize said hydrophobic drug.

D69. A method of improving the solubility of a hydrophobic drug, comprising admixing said hydrophobic drug and a CD dimer according to any one of clauses C1-C62 or a composition according to clause C63.

C70. A therapeutic method comprising administration of an effective amount of a CD dimer according to any one of clauses C1-C62 or a composition according to any one of clauses C63-C67 to a subject in need thereof.

C71. The method of clause C70, wherein the subject in need thereof is suffering from harmful or toxic effects of 7KC.

C72. A method for reducing the amount of 7KC in a subject in need thereof comprising administration of an effective amount of a CD dimer according to any one of clauses C1-C62 or a composition according to any one of clauses C63-C67 to a subject in need thereof.

C73. The method of any one of clauses C70-C72, wherein said CD dimer is administered to said subject via parenteral (e.g., subcutaneous, intramuscular, or intravenous), topical, transdermal, oral, sublingual, or buccal administration.

C74. The method of clause C73, wherein said CD dimer is administered intravenously.

C75. The method of any one of clauses C70-C74, which comprises administering to said subject (a) between about 1 mg and 20 g, such as between 10 mg and 1 g, between 50 mg and 200 mg, or 100 mg of said CD dinner to said subject, or (b) between 1 and 10 g of said CD dimer, such as about 2 g, about 3 g, about 4 g, or about 5 g, or (c) between 50 mg and 5 g of said CD timer, such as between 100 mg and 2.5 g, between 100 mg and 2 g, between 250 mg and 2.5 g.

C76. The method of any one of clauses C70-C75, which prevents, treats, ameliorates the symptoms of one or more of atherosclerosis/coronary artery disease, arteriosclerosis, coronary atherosclerosis due to calcified coronary lesion, heart failure (all stages), Alzheimer s disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X-linked adrenoleukodystrophy, sickle cell disease. Niemann-Pick Type A disease, Niemann-Pick Type B disease, Niemann-Pick Type C disease. Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome. Crohn's disease, ulcerative colitis, and/or hypercholesterolemia: wherein optionally said treatment is administered in combination with another therapy.

C77. The method of any one of clauses C70-C75, which prevents, treats, ameliorates the symptoms of atherosclerosis.

C78. The method of clause C77, further comprising administering a second therapy to said subject, wherein said second therapy is administered concurrently or sequentially in either order.

C79. The method of clause C78, wherein said second therapy comprises one or more of an anti-cholesterol drug, such as a fibrate or statin, anti-platelet drug, anti-hypertension drug, or dietary supplement.

C80. The method of clause C79, wherein said statin comprises ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin). SIMCOR® (niacin extended-release/simvastatin), VYTORIN® (ezetimibe/simvastatin), or ZOCOR® (simvastatin).

C81. The method of clause C79, wherein said second therapy comprises an anti-cholesterol drug and an anti-hypertension drug.

C82. A method of purification of oxysterols, comprising: contacting a composition comprising oxysterols with a CD dimer according to any one of clauses C1-C62, thereby solubilizing said oxysterols in said CD dimer, and recovering said CD dimer and solubilized oxysterols.

C83. The method of clause C82, wherein said oxysterols comprise or consist of 7KC.

C84. The method of clause C83, further comprising measuring the amount or concentration of 7KC in said solubilized oxysterols, thereby determining the relative concentration of 7KC in the composition.

C85. The method of clause C84, wherein said composition comprises a patient sample.

C86. An in vitro method of removing oxysterols from a sample, comprising: contacting a sample comprising oxysterols with a CD dimer according to any one of clauses C1-C62, thereby solubilizing said oxysterols in said CD dimer; and separating said sample from said CD dimer and solubilized sterols, and optionally reintroducing said sample into a subject from which said sample is obtained.

C87. A method of producing a reduced cholesterol product, comprising: contacting a product comprising cholesterol with a CD dimer according to any one of clauses C1-C62, thereby solubilizing said cholesterols in said CD dimer, and removing said CD dimer and solubilized cholesterol from said product.

C88. The method of clause C87, wherein said product is a food product.

C89. The method of clause C88, wherein said food product comprises meat and/or dairy.

C90. A method of making a CD dimer according to any one of clauses C1-C62 comprising:

(a) reacting β-CD molecules that are protected on the primary face with a dialkylating agent, thereby producing a primary face-protected βCD dimer linked through the secondary face, and optionally purifying said primary protected CD dimer;

(b) deprotecting said primary face protected CD dimer, thereby producing a deprotected CD dimer, and optionally purifying said deprotected CD dimes; and (c) functionalizing said deprotected CD to said R1, R2, R3, R1', R2', and/or R3' groups, thereby producing said CD dimer, and optionally purifying said CD dimer.

C91. The method of clause C90, wherein said CD that is protected on the primary face comprises a trityl, benzoyl, tert-butyldimethylsilyl (TBDMS), tart-butyidiphenylsilyl (TBDPS), triisopropylsilyl (TIPS) and the like, preferably TBDMS as in heptakis(6-O-tert-butyidimethylsilyl)-β-CD.

C92. The method of clause C90 or C91, wherein said dialkylating agent comprises a dihaloalkane, ditosylalkane, dimesylalkane, ditriflatealkane and the like, preferably 1,4 dibromobutane.

C93. The method of any one of clauses C90-C92, wherein step (a) is performed in anhydrous conditions using a base tike imidazole, pyridine. DMAP, sodium hydroxide, sodium hydride, lithium hydride and the like, preferably sodium hydride.

C94 The method of any one of clauses C90-C93, wherein said purification in step (a) comprises direct or reverse phase chromatography with isocratic elution and/or a crystallization/precipitation.

C95. The method of any one of clauses C90-C94, wherein step (b) is performed in tetrahydrofuran (THF) or methanol (MeOH) with HF-pyridine, tetrabutylammonium fluoride (TBAF), acetic acid, sulfuric acid, triflic acid and the like, preferably in THF with TBAF.

C96. The method of any one of clauses C90-C95, wherein said purification in step (b) comprises direct or reverse phase chromatography with isocratic elution and/or crystallization/precipitation.

C97. The method of any one of clauses C90-C96, wherein step (c) comprises reacting said deprotected CD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium reagent such as glycidyltrimethylammonium chloride.

C98. The method of any one of clauses C90-C97, wherein step (c) is performed in aqueous conditions using a base tike sodium hydroxide, lithium hydroxide, preferably sodium hydroxide.

C99. The method of any one of clauses C90-C98, wherein said purification in step (c) comprises one or more ion exchange resin treatment, charcoal clarification and dialysis.

C100. A method of making a βCD dimer comprising (a) reacting a 2-C-mono(n-azidoalkyl)-βCD or a 3-O-mono(n-azidoalkyl)-βCD or a mixture thereof and a 2-O-mono(n-alkyne)-βCD or a 3-O-mono(n-alkyne)-βCD or a mixture thereof, thereby forming a βCD-triazole-βCD dimer having the structure βCD-alk1-triazole-alk2-βCD, and optionally (b) purifying said βCD-triazole-βCD dimer.

C101, The method of clause C100, wherein step (a) is performed with a copper (I), silver (I) or ruthenium catalyst, preferably 15 Mm copper (I) like copper bromide (CuBr) or copper tris(triphenylphosphine) bromide [$(PPh_3)_3CuBr$].

C102. The method of clause C100 or C101, wherein step (a) is carried out in an aqueous solution.

C103. The method of clause C102, wherein the aqueous solution comprises dimethylformamide (DMF), optionally about 50% DMF (v/v).

C104. The method of any one of clauses C100-C103, wherein step (b) comprises silica gel chromatography or crystallization/precipitation.

C105. The method of any one of clauses C100-C104, further comprising, prior to step (a) producing said 2-O-mono(n-azidoalkyl)-CD or 3-O-mono(n-azidoalkyl)-CD or mixture thereof by a method comprising. (1) reacting n-azido-1-bromo-alkane with β-CD, optionally with a catalytic amount of lithium iodide, thereby producing said 2-O-mono(n-azidoalkyl)-CD or 3-O-mono(n-azidoalkyl)-CD or mixture thereof; and (2) optionally purifying said 2-O-(n-azidoalkyl)-CD or 3-O-mono(n-azidoalkyl)-CD or mixture thereof.

C108. The method of clause C105, wherein step (2) comprises silica gel chromatography or crystallization/precipitation.

C107. The method of any one of clauses C100-C108, further comprising, prior to step (a) producing 2-O-mono(n-azidoalkyl)-CD or 3-O-mono(n-azidoalkyl)-CD or mixture thereof by a method comprising: (i) reacting n-bromo-1-alkyne with a β-CD, optionally with a catalytic amount of lithium iodide, thereby producing said 2-O-mono(n-azidoalkyl)-CD or 3-O-mono(n-azidoalkyl)-CD or mixture thereof and (ii) optionally purifying said 2-O-mono(n-azidoalkyl)-CD or 3-O-mono(n-azidoalkyl)-CD or mixture thereof C108. The method of clause C107, wherein step (ii) comprises silica gel chromatography or crystallization/precipitation.

C108. The method of clause C107 or C108, wherein step (I) is carried out in dry DMSO.

C110. The method of any one of clauses C105 or C107, wherein the reaction in step (i) or (1) comprises lithium hydride, sodium hydride, n-butyl lithium and the like, preferably lithium hydride.

C111. The method of any one of clauses C100-C110, further comprising (c) hydroxypropylation, methylation, succinylation, sulfobutylation and/or quaternary ammonium functionalization said CD-triazole-CD' dimes, thereby producing a CD dimmer, and optionally purifying said CD dimer.

C112. The method of clause C111, wherein step (c) comprises reacting said deprotected CD dimer with a hydroxypropylation agent such as propylene oxide, a methylation reagent such as methyl iodide, a succinylation reagent such as succinic anhydride, a sulfobutylation reagent such as 1,4 butane sulfone, and/or a quaternary ammonium functionalization reagent such as glycidyltrimethylammonium chloride C113. The method of clause C111 or C112, wherein step (c) is performed in aqueous conditions, optionally comprising sodium hydroxide as a base.

C114. The method of any one of clauses C111-C113, wherein said purification in step (c) comprises one or more ion exchange resin treatment, charcoal clarification, membrane filtration, and dialysis.

C115. The method of any one of clauses C90-C114, wherein the length of the linking group is between 2 and 8.

C116. The method of any one of clauses C90-C114, wherein the length of the linking group is between 4 and 7 or is between 6 and 8.

C117. The method of any one of clauses C90-C114, wherein the length of the linking group is 4.

C118. The method of any one of clauses C90-C114, wherein the length of the linking group is 7.

C119. The method of any one of clauses C90-C118, wherein A and A' are each a bond and B is substituted or unsubstituted alkylene.

C120. The method of clause C119, wherein B is substituted or unsubstituted butyl.

C121. The method of any one of clauses C90-C118, wherein B is substituted or unsubstituted heteroaryl.

C122. The method of clause C121, wherein S is substituted or unsubstituted triazole.

C123. The method of clause C122, wherein B is unsubstituted triazole having connectivity to A and A' as shown in Structure Y:

(Structure Y)

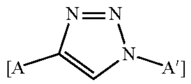

or A' to A as shown in Structure Y':

(Structure Y')

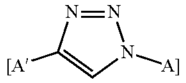

or wherein said linking group has any of the structures shown in FIG. 2B.

C124. The method of clause C123, wherein A and A' are independently substituted or unsubstituted alkylene each having a length of 1 to 8 carbons.

C125. The method of clause C123, wherein A and A' independently each have a length of four or fewer carbons.

C126, The method of clause C123, wherein A is unsubstituted methyl and A' is unsubstituted propyl.

C127. The method of any one of clauses C90-C126, wherein CD and CD' are connected by only one linking group, or by two or more linking groups.

C128. The method of clause C127, wherein CD and CD' are connected by two linking groups which are the same as or different than each other.

C129. The method of any one of clauses C90-C128, wherein at least one of A and A' independently connect to two or more of L1 or L2, or L1' or L2', respectively.

C130. The method of any one of clauses C90-C129, wherein said CD dieter has the structure depicted in any one of FIGS. 17A-17D.

C131. The method of any one of clauses C90-C129; which is adapted to produce the CD dimer of any one of clauses C1-C82.

D1. A CD dieter having the general formula Structure B-X or Structure B-X:

CD-[A-B-A']-CD' (Structure B-X)

CD'-[A-B-A']-CD (Structure B-X')

wherein

CD and CD' each comprise an αCD having the Structure B-Xa:

(Structure B-Xa)

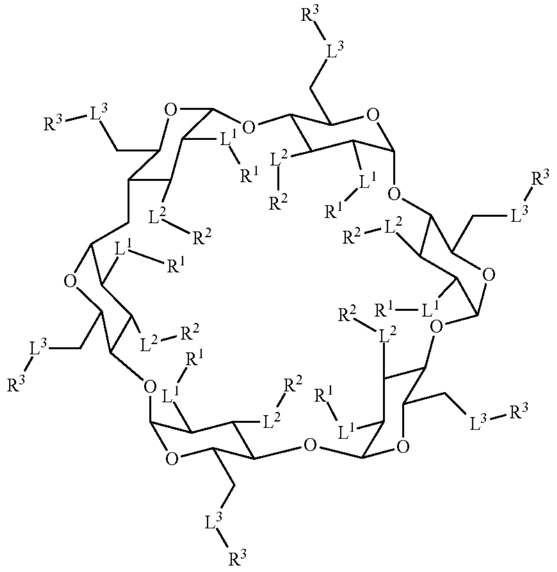

wherein:

L1, L2, and L3 can be the same or different in each instance, and each are independently selected from the group consisting of a bond, —O—, —NH—, —NR4- or —S—, or wherein at least one L1, L2, and L3 is a bond and the corresponding R1, R2, or R3 group is N3, SH, or a halogen such as F, Cl, Br, or I;

R1, R2, R3; and R4 can be the same or different in each instance, and each are independently selected from the group consisting of hydrogen, methyl, hydroxypropyl, sulfobutyl, succinyl, quaternary ammonium such as —CH2CH(OH) CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsufonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkytalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each sinking group is connected to at least one L1 or L2 of CD and the corresponding R1 or R2 is omitted and replaced in this manner by A, and A' of each linking group is connected to at least one L1 or L2 of CD' and the corresponding R1 or R2 is omitted and replaced in this manner by A'; and at least one of A, B, and A' of each linking group cannot be a bond;

D2. A CD dimer having the general formula Structure B-X or Structure B-X':

CD-[A-B-A']-CD' (Structure B-X)

CD'-[A-B-A']-CD (Structure B-X')

wherein

CD and CD' each comprise an αCD having the Structure B-Xa:

(Structure B-Xa)

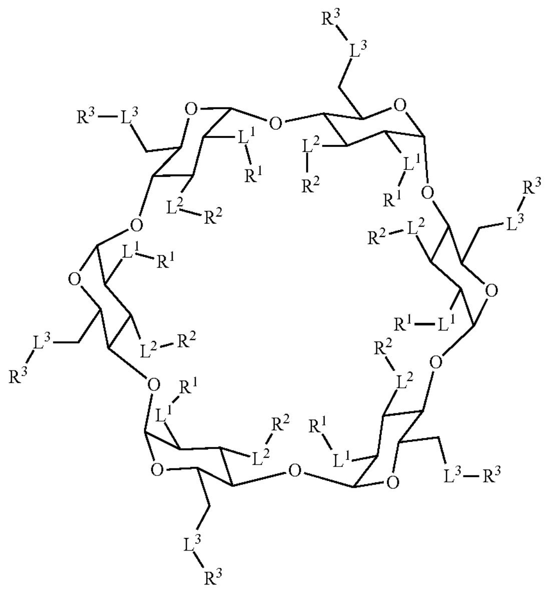

wherein,

L1, L2, and L3 can be the same or a different in each instance, and each is independently selected from the group consisting of a bond, —O—, —NH—, —NR4- or —S—, or wherein at least one L1, L2, and L3 is a bond and the corresponding R1, R2, or R3 group is N3, SH, or a halogen such as F, Cl, Br, or I;

R1 and R2 are each hydrogen;

R3 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonamido, aminocarbonyloxyalkyl, alkylaminosulfonyl, dialkylaminosulfonyl, aryl, aryalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclyalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphene oxide, sulfate alkyl, sulfonamido, thioalkyl, trialkylammonium;

[A-B-A'] are together defined as a linking group;

A and A' are independently selected from the group consisting of a bond, —O—, —NH—, —NR4, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 of CD and the corresponding R1 or R2 is omitted and replaced in this manner by A, and A' of each linking group is connected to at least one L1 or L2 of CD and the corresponding R1 or R2 of CD' is omitted and replaced in this manner by A'; and at least one of A, B, and A' of each linking group is not a bond.

D3. The dimer of any one of clauses D1-D2, wherein at least two of R3 are not hydrogen.

D4. The dimer of clause D3, wherein at least two and no more than four of R3 are not hydrogen.

D5. A CD dimer having the general formula Structure B-X or Structure B-X':

CD-[A-B-A']-CD' (Structure B-X)

CD'-[A-B-A']-CD (Structure B-X')

wherein

CD and CD' each comprise an αCD having the Structure B-Xa:

(Structure B-Xa)

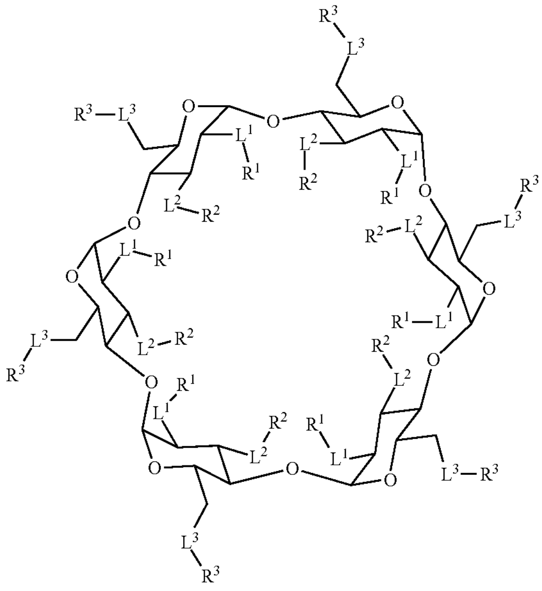

wherein:

L1, L2, and L3 can be the same or a different in each instance, and each is independently selected from the group consisting of a bond, —O—, —NH—, —NR4- or —S—, or wherein at least one L1, L2, and L3 is a bond and the corresponding R1, R2, or R3 group is N3, SH, or a halogen such as F, Cl, Br, or I;

R3 are each hydrogen;

R1 and R2 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkysulfonyl, alkylsulfonylalkyl, alkylamino, dialkylamino, alkylaminoalkyl, dialkylaminoalkyl, aminoalkyl, alkylsulfonylamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkyene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclyalkyl, heterocylyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocycyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

[A-B-A'] are together defined as a linking group;

A and A' are independently selected from the group consisting of a bond, —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 of CD and the corresponding R1 or R2 of CD is omitted and replaced in this manner by A, and A' of each linking group is connected to at least one L1 or L2 of CD' and the corresponding R1 or R2 of CD' is omitted and replaced in this manner by A'; and at least one of A, B, and A' of each linking group is not a bond.

D6. A CD dimer having the general formula Structure B-X or Structure B-X':

CD-[A-B-A']-CD' (Structure B-X)

CD'-[A-B-A']-CD (Structure B-X')

wherein

CD and CD' each comprise an αCD having the Structure B-Xa:

(Structure B-Xa)

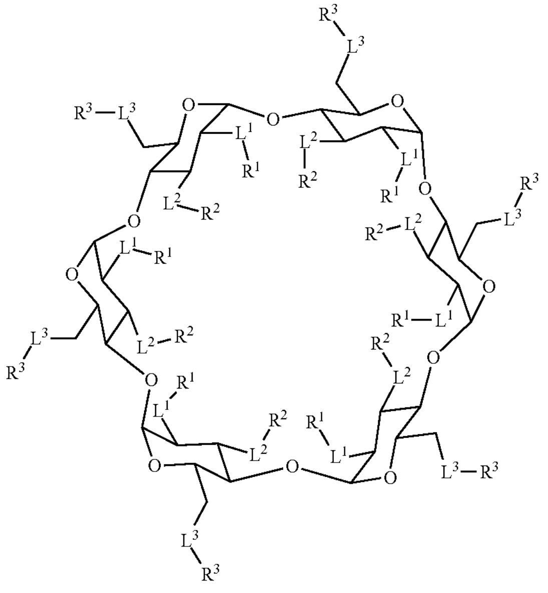

wherein:

L1, L2, and L3 can be the same or a different in each instance, and each is independently selected from the group consisting of a bond, —O—, —NH—, —NR4- or —S—, or wherein at least one L1, L2, and L3 is a bond and the corresponding R1, R2, or R3 group is N3, SH, or a halogen such as F, Cl, Br, or I;

R3 are each an identical group selected from the group consisting of hydrogen, methyl, hydroxypropyl, sulfobutyl, succinyl, quaternary ammonium such as —CH2CH(OH) CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonamido, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy: cycloalkoxy, heterocyclyalkoxy, haloalkyl, haloalkoxy, heterocycloamino, carbocyclyl, heterocycyl, heterocyclylalkyl, heterocyclyloxy, hydroxyalkoxy, hydroxyalkylamino, hydroxyalkylaminoalkyl, hydroxyalkyl; hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, trialkylammonium;

R1 and R2 can be the same or different in each instance, and each is independently selected from the group consisting of hydrogen, methyl, hydroxypropyl, sulfobutyl, succinyl, quaternary ammonium such as —CH2CH(OH)CH2N(CH3)3+, alkyl, lower alkyl, alkenyl, alkynyl, alkoxy, alkoxyalkyl, alkoxyalkoxyalkyl, heteroalkoxy: alkylcarbonyloxyalkyl, alkylcarbonyl, alkylsulfonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, deoxy, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocycyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl; sulfonamido, thioalkyl; trialkylammonium;

[A-B-A'] are together defined as a linking group;

A and A' are independently selected from the group consisting of a bond, —O—, —NH—. —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L7 or L2 of CD and the corresponding R1 or R2 of CD is omitted and replaced in this manner by A, and A' of each linking group is connected to at least one L1 or L2 of CD' and the corresponding R1 or R2 of CD' is omitted and replaced in this manner by A; and at least one of A, B, and A' of each linking group is not a bond.

D7. The dimer of clause D6, wherein R3 is hydroxypropyl or, alternatively, an alkyl group, such as a butyl group.

D8. The dimer of any one of clauses D2-D7, wherein at least one of L1 or L2 is not O.

D9. The dimer of any one of clauses D1-D8, wherein L1, L2, and L3 that are not linked to the linking group can be the same or different in each instance, and each is independently selected from the group consisting of a bond, and —O—, and wherein R1; R2, and R3 can be the same or different in each instance, and each is independently selected from the group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro, bromo, and iodo.

D10. The dimer of any one of clauses D1-D8, wherein L1, L2, and L3 that are not linked to the linking group can be the same or a different in each instance, and each is independently selected from the group consisting of a bond, and —O—, and wherein R1. R2, and R3 can be the same or a different in each instance, and each is independently selected from the group consisting of hydrogen, hydroxyl, methyl, 2-hydroxypropyl, sulfobutyl, succinyl, maltosyl, carboxymethyl trimethylammonium propyl and 2-hydroxytrimethylammonium propyl.

D11. The dimer of any one of clauses D1-D8, wherein L1, L2, and L3 that are not linked to the linking group can be the same or a different in each instance, and each is independently selected from the group consisting of a bond, and —O—, and wherein R1. R2, and R3 can be the same or a different in each instance, and each is independently selected from the group consisting of hydrogen; hydroxyl, and 2-hydroxypropyl and wherein at least one of R1, R2, and R3 is 2-hydroxypropyl.

D12. The dimer of any one of clauses D1-D8, wherein L1, L2, and L3 that are not linked to the linking group can be the same or a different in each instance, and each is independently selected from the group consisting of a bond, and —O—, and wherein R1, R2, and R3 can be the same or a different in each instance, and each is independently selected from the group consisting of hydrogen, hydroxyl, and methyl and wherein at least one of R1, R2, and R3 is methyl.

D13. The dimer of any one of clauses D1-D8, wherein L1, L2, and L3 that are not linked to the linking group can be the same or a different in each instance, and each is independently selected from the group consisting of a bond, and —O—, and wherein R1, R2, and R3 can be the same or a different in each instance, and each is independently selected from the group consisting of hydrogen, hydroxyl, and sulfobutyl and wherein at least one of R1. R2, and R3 is sulfobutyl.

D14. The dimer of any one of clauses D1-D8, wherein L1, L2, and L3 that are not linked to the linking group can be the same or a different in each instance, and each is independently selected from the group consisting of a bond, and —O—, and wherein R1, R2, and R3 can be the same or a different in each instance, and each is independently selected from the group consisting of hydrogen, hydroxyl, and succinyl and wherein at least one of R1, R2, and R3 is succinyl.

D15. The dimer of any one of clauses D1-D8, wherein L1, L2, and L3 that are not linked to the risking group can be the same or a different in each instance, and each is independently selected from the group consisting of a bond, and —O—, and wherein R1, R2, and R3 can be the same or a different in each instance, and each is independently selected from the group consisting of hydrogen, hydroxyl, and a quaternary ammonium such as 2-hydroxytrimethylammonium propyl and wherein at least one of R1, R2, and R3 is a quaternary ammonium such as 2-hydroxytrimethylammonium propyl.

D16. The dimer of any one of clauses D1-D8, wherein L1, L2, and L3 that are not linked to the linking group can be the same or a different in each instance, and each is independently selected from the group consisting of a bond, and —O—, and wherein at least one of R1, R2, and R3 can be the same or a different in each instance, and each is independently selected from the group consisting of hydrogen, hydroxyl, and maltosyl, and wherein at least one of R1, R2, and R3 is maltosyl.

D17. The dimer of any one of clauses D1-D8, wherein L1, L2, and L3 that are not linked to the linking group be the same or a different in each instance, and each is independently selected from the group consisting of a bond, and —O—, and wherein at least one of R1. R2, and R3 can be the same or a different in each instance, and each is independently selected from the group consisting of hydrogen, hydroxyl, and carboxymethyl, and wherein at least one of R1, R2, and R3 is carboxymethyl.

D18. The dimer of clause D1, wherein CD has a DS at the C6 position (corresponding to L3/R3) of between 3 and 6.

D19 The dieter of clause D18, wherein each R3 that is not hydrogen is independently selected from butyl, hydroxypropyl, sulfobutyl, ethyl, propyl, quaternary ammonium, succinyl, maltosyl, carboxymethyl, trimethylammonium propyl, 2-hydroxytrimethylammonium propyl, or 2-(carboxyethyl)sulfanyl, preferably 2-hydroxypropyl, butyl, 2-(carboxyethyl)sulfanyl, or sulfobutyl.

D20 The dimer of clause D19, wherein each R3 that is not hydrogen is the same.

D21. The dimer of any one of clauses D18-D20, wherein CD has a DS at the C6 position (corresponding to L3/R3) of 0, 1, or 2.

D22. The dimer of clause D21, wherein CD' has a DS of 1 or 2 at the C6 position (corresponding to L3/R3): wherein each R3 that is not hydrogen is independently selected from butyl, hydroxypropyl, sulfobutyl: ethyl, propyl, quaternary ammonium, succinyl, maltosyl, carboxymethyl, trimethylammonium propyl, 2-hydroxytrimethylammonium propyl, or 2-(carboxyethyl)sulfanyl, preferably 2-hydroxypropyl, butyl, 2-(carboxyethyl)sulfanyl, or sulfobutyl.

D23. The dimer of clause D22, wherein each R3 of CD' that is not hydrogen is the same.

D24. The dimer of any one of clauses D18-D23, wherein the combined total DS of C2 positions (corresponding to L1/R1) and C3 positions (corresponding to L2/R2) on CD and CD together is 0, 1, 2, 3, or 4.

D25. The dimer of clause D24, wherein each R1 and R2 that is not hydrogen is independently selected from hydroxypropyl, sulfobutyl, methyl, ethyl, quaternary ammonium, succinyl, maltosyl, carboxymethyl, trimethylammonium propyl, thiol, alkoxyamine, amine, 2-hydroxytrimethylammonium propyl, or 2-(carboxyethyl) sulfanyl, preferably 2-hydroxypropyl, methyl, quaternary ammonium, or sulfobutyl.

D26. The dimer of clause D25, wherein each R1 and R2 that is not hydrogen is the same.

D27. The dimer of clause D25 or D26, wherein each R1 and R2, of CD that is not hydrogen is the same.

D28. The dimer of clause D25, wherein each R1 and R2 that is not hydrogen is the same.

D29. The dimer of any one of clauses D24-D28, wherein the combined total DS at positions C2 (corresponding to R1) and C3 (corresponding to R2) on CD is 2 or 3.

D30. The dimer of clause D1, wherein said dimer has a DS with methyl substituents of between 10 and 34.

D31. The dinner of clause D30, wherein said dimer has a DS with methyl substituents of between 10 and 20.

D32. The dimer of clause D30, wherein said dimer is fully saturated with methyl substituents at the C2 position (corresponding to R1) and C6 position (corresponding to R3) on CD.

D33. The dieter of any one of clauses D30-D32, wherein said dimer is fully saturated with methyl substituents at the C2 position (corresponding to R1) and C6 position (corresponding to R3) on CD'.

D34. The dimer of any one of clauses D1-D33, wherein the length of the linking group is between 2 to 8 atoms.

D35. The dimer of any one of clauses D1-D33, wherein the length of the linking group is between 4 and 7 or is between 6 and 8.

D36. The dimer of any one of clauses D1-D33, wherein the length of the linking group is 4.

D37. The dimer of any one of clauses D1-D33, wherein the length of the linking group is 7.

D38. The dimer of any one of clauses D1-D37, wherein A and A' are each a bond and B is substituted or unsubstituted alkylene.

D39. The timer of clause D38, wherein B is substituted or unsubstituted butyl.

D40. The dimer of any one of clauses D1-D37, wherein B is substituted or unsubstituted heteroaryl.

D41. The dimer of clause D40, wherein 8 is substituted or unsubstituted triazole.

D42. The dimer of clause D41, wherein B is unsubstituted triazole having connectivity to A and A' as shown in Structure Y:

(Structure Y)

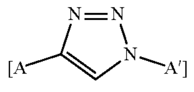

or A' to A as shown in Structure Y':

(Structure Y')

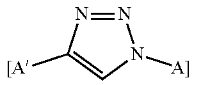

or wherein said linking group has any of the structures shown in FIG. 2B.

D43. The dimer of clause D42, wherein A and A' are independently substituted or unsubstituted alkylene having a length of 1 to 8 carbons.

D44. The dimer of clause D43, wherein A and A' independently each have a length of four or fewer carbons.

D45. The dimer of clause D44, wherein A is unsubstituted methyl and A' is unsubstituted propyl.

D46. The dimer of any one of clauses D1-D45, wherein CD and CD' are connected by only one linking group, or by two or more linking groups.

D47. The dimer of clause D46, wherein CD and CD' are connected by two linking groups which are the same as or different than each other.

D48. The dieter of any one of clauses D1-D47, wherein at least one of A and A' independently connect to two or more of L1 or L2 of CD and/or CD'.

D49 The CD dimer of any one of clauses D1-D48, which has the structure depicted in FIG. 2B.

D50. The CD rimer of any one of clauses D1-D49, wherein said CD dimer exhibits greater affinity for 7KC than cholesterol, wherein optionally said greater affinity is determined by a turbidity test.

D51. The CD dimer of clause D50, wherein said CD direr exhibits at least 1.1-fold, 1.5-fold, 2-fold, 3-fold, 4-fold, 5-fold, or 10-fold, greater affinity for 7KC than cholesterol.

D52. A dimer of any one of clauses D1-D49 that has a higher affinity for cholesterol than for the CD monomers depicted herein as determined by turbidity test such as in FIGS. 5A-5J.

D53. The dimer of any one of clauses D1-D51, wherein each R4 is independently selected from the group consisting of group consisting of hydrogen, hydroxyl, substituted or unsubstituted alkyl, methyl, ethyl, propyl, isopropyl, butyl, isobutyl, 2-hydroxypropyl, trimethylammonium propyl, and 2-hydroxytrimethylammonium propyl, 1,2-ethylenediamine, sulfobutyl, acetyl, succinyl, carboxymethyl, phenoxy, maltosyl, glucosyl, palmitoyl, phosphate, phosphoryl, amino, azido, sulfate, sulfuryl, fluoro, chloro, bromo, and iodo.

D54. The dimer of any one of clauses D1-D52, wherein said L1 or L2 that is connected to said linking group is each independently selected from the group consisting of —O— and bond.

D55. The dimer of any one of clauses D1-D54, wherein when L1, L2, or L3 is a bond the corresponding R1, R2, or R3, respectively, is not hydroxyl;

D56. The dimer of any one of clauses D1-D55, wherein for each R1, R2, or R3, that is alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloakyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro; phosphate, phosphine oxide, sulfate alkyl, sulfonamido, thioalkyl, or trialkylammonium, the corresponding L1, L2, or L3, respectively, is a bond.

D57. A composition comprising a mixture of two or more CD dimers according to clauses D1-D56.

D58, The composition of clause D57, wherein said composition is substantially free of other CD dimers.

D59. A pharmaceutical composition comprising a CD dimer according to any one of clauses D1-D56 or a composition according to any one of clauses D57-D58 and a pharmaceutically acceptable carrier.

D60. The pharmaceutical composition of clause D58, wherein said CD dieter is the only active ingredient in said composition.

D61. The pharmaceutical composition of clause D59, further comprising at least one hydrophobic drug, optionally wherein said pharmaceutical composition comprises an amount of said CD dimer or CD dimers that is effective to solubilize said hydrophobic drug.

D62. A method of improving the solubility of a hydrophobic drug, comprising admixing said hydrophobic drug and a CD dimer according to any one of clauses D1-D61 or a composition according to any one of clauses D57-D59.

D63. The pharmaceutical composition of any one of clauses D59-D60, which consists of or consists essentially of said CD dimer and said pharmaceutically acceptable carrier.

D64. A therapeutic method comprising administration of an effective amount of a CD dimer according to any one of clauses D1-D56 or a composition according to any one of clauses D57-D60 or D61 to a subject in need thereof.

D65. A method of administering iodine to a subject in need thereof, comprising administering an effective amount of a complex of iodine and a CD dimer according to any one of clauses D1-D56 or composition according to any one of clauses D57-D59 or D61 and comprising said iodine in complex with said CD dimer to a subject in need thereof.

D66. The method of clause D65, wherein said iodine is non-radioactive, wherein said method treats, prevents, or ameliorates harm due to poisoning with radioactive iodine, optionally due to accidental or intentional exposure or due to a medical procedure involving the administration of radioactive iodine.

D67. The method of clause D65, wherein said iodine comprises a radioisotope such as I-131.

D68. A method of removing iodine isotopes from a subject, comprising administering an effective amount a CD dimer according to any one of clauses D1-D56 or composition according to any one of clauses D57-D60 to a subject in need thereof.

D69. A method of solubilizing lipid deposits in a subject, comprising administering an effective amount a CD dieter according to any one of clauses D1-D56 or composition according to any one of clauses D57-D60 to a subject in need thereof.

D70. The method of clause D69, wherein said method treats or prevents atherosclerosis, removes of triglycerides, removes fatty streaks, removes fatty deposits in vessel walls, and/or removes excess lipids from cell membranes; and/or promotes beneficial changes in gene expression resulting from alpha cyclodextrin dimers binding to phospholipids on cell membrane surfaces.

D71. The method of any one of clauses D69-D70, wherein said CD dimer comprises a linker comprising an aliphatic chain carbon linker, such as a butyl linker.

D72. The method of any one of clauses D64-D71, wherein said CD dimer is administered to said subject via parenteral (e.g., subcutaneous, intramuscular, or intravenous), topical, transdermal, oral, sublingual, or buccal administration.

D73. The method of clause D72, wherein said CD dimer is administered intravenously.

D74. The method of any one of clauses D64-D73, which comprises administering to said subject (a) between about 1 mg and 20 g, such as between 10 mg and 1 g, between 50 mg and 200 mg, or 100 mg of said CD dimer to said subject, or (b) between 1 and 10 g of said CD dimer, such as about 2 g, about 3 g, about 4 g, or about 5 g, or (a) between 50 mg and 5 g of said CD dimer, such as between 100 mg and 2.5 g, between 100 mg and 2 g. between 250 mg and 2.5 g.

D75. The method of any one of clauses D64-D74, which prevents, treats, ameliorates the symptoms of one or more of atherosclerosis/coronary artery disease, arteriosclerosis, coronary atherosclerosis due to calcified coronary lesion, heart failure (all stages), Alzheimer's disease, Parkinson's disease, vascular dementia, liver damage, liver failure, non-alcoholic steatohepatitis, non-alcoholic fatty liver disease, irritable bowel syndrome, Crohn's disease, and/or ulcerative colitis; wherein optionally said treatment is administered in combination with another therapy.

D76. The method of any one of clauses D64-D74, which prevents, treats, ameliorates the symptoms of atherosclerosis.

D77. The method of clause D76, further comprising administering a second, therapy to said subject, wherein said second therapy is administered concurrently or sequentially in either order.

D78. A method of making a CD dimer according to any one of clauses D1-D66, comprising:

(a) reacting α-CD molecules that are protected on the primary face with a dialkylating agent and with native α-CD respectively, thereby producing a primary face-protected α-αCD dimer linked through the secondary face, and optionally purifying said primary protected α-αCD dimer, (b) deprotecting said primary face protected α-αCD dimer, thereby producing a deprotected CD dimer, and optionally purifying said deprotected CD dimer; and (c) functionalizing said deprotected α-αCD to said R1, R2, and/or R3 groups, thereby producing said α-αCD dimer, and optionally purifying said α-αCD dimer.

D79. The method of clause D91, wherein said αCD that is protected on the primary face comprises a trityl, benzoyl, tert-butyldimethylsilyl (TBDMS), tert-butyldiphenylsilyl (TBDPS), triisopropylsilyl (TIPS) and the like, preferably TBDMS as in heptakis(7-O-tert-butyldimethylsilyl)-α-CD.

D80. The method of clause D78 or D79, wherein said dialkylating agent comprises a dihaloalkane, ditosylalkane, dimesylalkane, ditriflatealkane and the like, preferably 1,4 dibromobutane.

D81. The method of any one of clauses D78-D80, wherein step (a) is performed in anhydrous conditions using a base like imidazole, pyridine, DMAP, sodium hydroxide, sodium hydride, lithium hydride and the like; preferably sodium hydride.

D82. The method of any one of clauses D78-D81, wherein said purification in step (a) comprises direct phase chromatography with isocratic elution and/or a crystallization/precipitation D83. The method of any one of clauses D78-D82, wherein step (b) is performed in tetrahydrofuran (THF) or methanol (MeOH) with HF-pyridine, tetrabutylammonium fluoride (TBAF), acetic acid, sulfuric acid, triflic acid and the like, preferably in THF with TBAF.

D84. The method of any one of clauses D78-D83, wherein said purification in step (b) comprises direct phase chromatography with isocratic elution and/or crystallization/precipitation.

D85. The method of any one of clauses D78-D84, wherein step (c) comprises reacting said deprotected α-αCD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium reagent such as glycidyltrimethylammonium chloride.

D88. The method of any one of clauses D78-D85, wherein step (c) is performed in aqueous conditions using a base like sodium hydroxide, lithium hydroxide, preferably sodium hydroxide.

D87. The method of any one of clauses D78-D86, wherein said purification in step (c) comprises one or more ion exchange resin treatment, charcoal clarification and dialysis.

D88. A method of making a CD dimer having the structure CD-L-CD', wherein CD comprises an αCD, CD' comprises a αCD, and L comprises a linking group, the method comprising (a) reacting either a 2-O-(n-azidoalkyl)-CD or a 3-O-(n-azidoalkyl)-CD or a 2-O-(n-azidoalkyl)-CD' or a 3-O-(n-azidoalkyl)-CD' or a mixture thereof of 2- and 3-substituted CD, with either a 2-O-(n-alkyne)-CD or a 3-O-(n-alkyne)-CD or 2-O-(n-alkyne)-CD' or a 3-O-(n-alkyne)-CD' or a mixture thereof of 2- and 3-substituted CD respectively, thereby forming a CD-triazole-CD' dimer having the structure αCD-alk1-triazole-alk2-αCD', and optionally (b) purifying said CD-triazole-CD' dimer.

D89. A method of making a CD dimer having the structure CD L CD', wherein CD comprises an αCD, CD' comprises a αCD, and L comprises a linking group that comprises a triazole, the method comprising (a) (1) reacting a 2-O-(n-azidoalkyl)-CD or a 3-O-(n-azidoalkyl)-CD or mixture thereof with a 2-O-(n-alkyne)-CD' or a 3-O-(n-alkyne)-CD' or a mixture thereof, thereby forming a CD-triazole-CD' dimer having the structure αCD-alk1-triazole-alk2-αCD';

or (2) reacting a 2-O-(n-azidoalkyl)-CD' or a 3-O-(n-azidoalkyl)-CD' or mixture thereof with a 2-O-(n-alkyne)-CD or a 3-O-(n-alkyne)-CD' or a mixture thereof, thereby forming a CD-triazole-CD' dimer having the structure αCD-alk1-triazole-alk2-αCD'; and optionally (b) purifying said CD dimer.

D90. The method of clause D88 or D89, wherein step (a) is performed with a copper (I), silver (I) or ruthenium catalyst, preferably 15 mM copper (I) like copper bromide (CuBr) or copper tris(triphenylphosphine) bromide [$(PPh_3)_3CuBr$].

D91. The method of any one of clauses D88-D90, wherein step (a) is carried out in an aqueous solution.

D92. The method of clause D91, wherein the aqueous solution comprises dimethylformamide (DMF), optionally about 50% DMF (v/v).

D93. The method of any one of clauses D88-D92, wherein step (b) comprises silica gel chromatography or crystallization/precipitation.

D94. The method of any one of clauses D88-D93, further comprising, prior to step (a) producing said 2-O-(n-azidoalkyl)-CD or 3-O-(n-azidoalkyl)-CD or mixture thereof by a method comprising: (1) reacting n-azido-1-bromo-alkane with an α-CD, optionally with a catalytic amount of lithium iodide, thereby producing said 2-O-(n-azidoalkyl)-αCD or 3-O-(n-azidoalkyl)-CD or mixture thereof; and (2) optionally purifying said 2-O-(n-azidoalkyl)-αCD or 3-O-(n-azidoalkyl)-CD or mixture thereof.

D95. The method of clause D94, wherein step (i) comprises silica gel chromatography or crystallization/precipitation.

D96. The method of any one of clauses D88-D95, further comprising, prior to step (a) producing 2-O-(n-alkyne)-CD or 3-O-(n-alkyne)-CD or mixture thereof by a method comprising: (1) reacting n-bromo-1-alkyne with a CD comprising an α-CD or α-CD, optionally with a catalytic amount of lithium iodide, thereby producing said 2-O-(n-alkyne)-CD or 3-O-(n-alkyne)-CD or mixture thereof and (ii) optionally purifying said 2-O-(n-alkyne)-CD or 3-O-(n-alkyne)-CD or mixture thereof.

D97. The method of clause D96, wherein step (ii) comprises silica get chromatography or crystallization/precipitation.

D98. The method of clause D96 or D97, wherein step (I) is carried out in dry DMSO.

D99. The method of any one of clauses D94 or D96, wherein the reaction in step (i) or (1) comprises lithium hydride, sodium hydride, n-butyl lithium and the like, preferably lithium hydride.

D100. The method of any one of clauses D88-D99, further comprising (c) hydroxypropylation, methylation, succinylation, sulfobutylation and/or quaternary ammonium functionalization said CD dimer, thereby producing a functionalized CD dimer, and optionally purifying said functionalized CD dimer.

D101. The method of clause D100, wherein step (c) comprises reacting said deprotected CD dimer with a hydroxypropylation agent such as propylene oxide, a methylation reagent such as methyl iodide, a succinylation reagent such as succinic anhydride, a sulfobutylation reagent such as 1,4 butane sultone, and/or a quaternary ammonium functionalization reagent such as glycidyltrimethylammonium chloride.

D102. The method of clause D100 or D101, wherein step (C) is performed in aqueous conditions, optionally comprising sodium hydroxide as a base.

D103. The method of any one of clauses D100-D102, wherein said purification in step (c) comprises one or more ion exchange resin treatments, charcoal clarification, membrane filtration, and dialysis.

D104. The method of any one of clauses D78-D103, wherein the length of the linking group is between 2 and 8.

D105. The method of any one of clauses D78-D103, wherein the length of the linking group is between 4 and 7 or is between 6 and 8.

D106. The method of any one of clauses D78-D103, wherein the length of the linking group is 4.

D107. The method of any one of clauses D78-D103, wherein the length of the linking group is 7

D108. The method of any one of clauses D78-D107, wherein A and A' are each a bond and B is substituted or unsubstituted alkylene.

D109. The method of clause D108, wherein 8 is substituted or unsubstituted butyl.

D110. The method of any one of clauses D78-D107, wherein B is substituted or unsubstituted heteroaryl.

D111. The method of clause D110, wherein B is substituted or unsubstituted triazole.

D112. The method of clause D111, wherein S is unsubstituted triazole having connectivity to A and A' as shown in Structure Y:

(Structure Y)

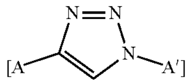

or A' to A as shown in Structure Y':

(Structure Y')

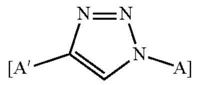

or wherein said linking group has any of the structures shown in FIG. 2B.

D113. The method of clause D112, wherein A and A are independently substituted or unsubstituted alkylene each having a length of 1 to 8 carbons.

D114, The method of clause D113, wherein A and A independently each have a length of four or fewer carbons.

D115. The method of clause D114, wherein A is unsubstituted methyl and A' is unsubstituted propyl.

D116. The method of any one of clauses D78-D115, wherein CD and CD' are connected by only one linking group, or by two or more linking groups.

D117. The method of clause D116, wherein CD and CD' are connected by two linking groups which are the same as or different than each other.

D118. The method of any one of clauses D78-D117, wherein at least one of A and A' independently connect to two or more of L1 or L2 of CD and/or CD'.

D119. The method of any one of clauses D78-D118, wherein said CD dimer has the structure depicted in FIG. 2B.

D120. The method of any one of clauses D78-D118, wherein said method is adapted to produce a CD dimer according to any one of clauses D1-D56.

What is claimed is:

1. A cyclodextrin (CD) dimer having the general formula Structure A-X:

CD-[A-B-A']-CD' (Structure A-X)

wherein

CD has the Structure A-Xa:

(Structure A-Xa)

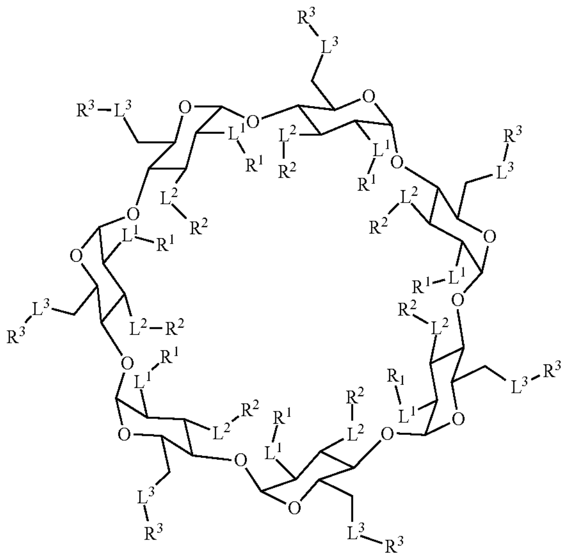

CD' has the Structure A-Xb:

(Structure A-Xb)

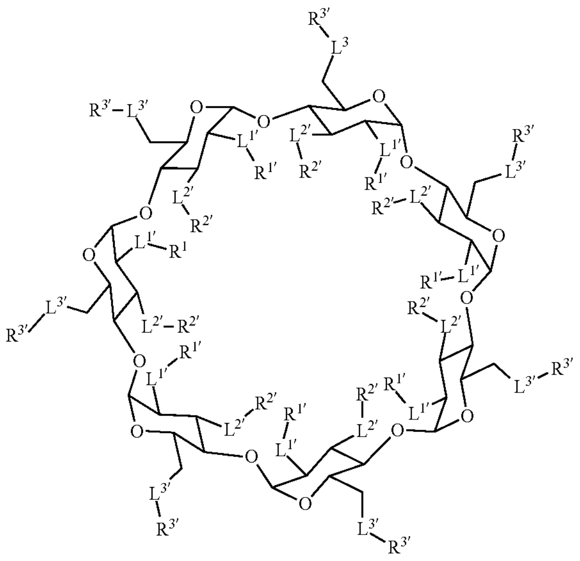

wherein:

L1, L2, L3, L1', L2', and L3' can be the same or different in each instance, and each is independently selected from the group consisting of a bond, —O—, —NH—, —NR4- or —S—, or wherein at least one L1, L2, L3, L1', L2, and L3' is a bond and the corresponding R1, R2, R3, R1', R2', or R3' group is N3, SH, or a halogen comprising F, Cl, Br, or I;

R1, R2, R3, R4, R1', R2', and R3' can be the same or different in each instance, and each is independently selected from the group consisting of hydrogen, and Group (I) consisting of methyl, hydroxypropyl, sulfobutyl, succinyl, a quaternary ammonium group, —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsufonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thin, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, and trialkylammonium;

[A-B-A'] are together defined as a linking group;

A and A' are independently selected from the group consisting of —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene, a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and wherein optionally at least one L1, L2, L3, L1', L2', and/or L3' is not O;

wherein either or both of CD and CD' have at least one substitution, wherein at least one of R1, R2, R3, R4, R1', R2', or R3 is not hydrogen and is selected from said Group (I), and further wherein CD and CD' each comprise different substituents and/or different numbers of the same substituent; and wherein the CD dimer comprises no more than 20 methyl groups.

2. The CD dimer of claim 1, wherein

R1, R1', R2, and R2' are each hydrogen;

at least two of R3 and R3' are not hydrogen;

at least two and no more than four of R3 and R3' are not hydrogen;

R3 and R3' are each hydrogen; or

R3 and R3' are each an identical group.

3. A CD dimer having the general formula Structure C—X:

CD-[A-B-A']-CD' (Structure C—X)

wherein

CD has the structure C-Xa:

(Structure C-Xa)

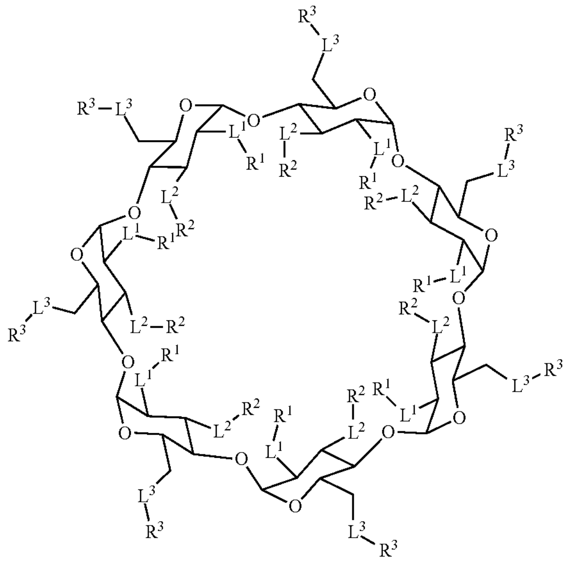

CD' has the structure C-Xb:

(Structure C-Xb)

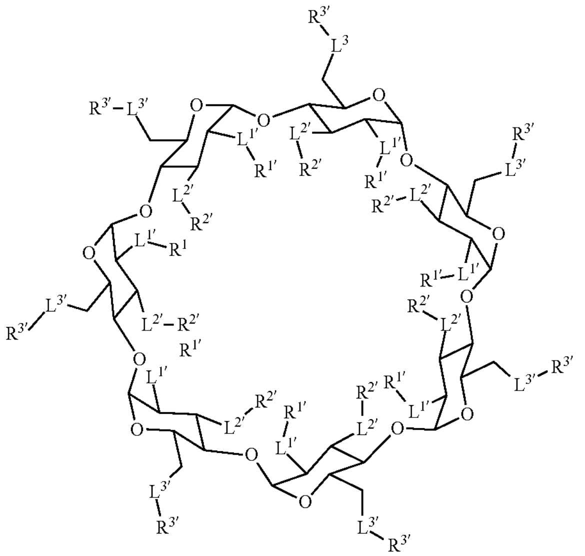

wherein:

L1, L2, L3, L1', L2', and L3' can be the same or a different in each instance, and each is independently selected from the group consisting of a bond, —O—, —NH—, —NR4- or —S— or wherein at least one L1, L2, L3, L1', L2, and L3' is a bond and the corresponding R1, R2, R3, R1', R2', or R3' group is N3, SH, or a halogen comprising F, Cl, Br, or I;

R1, R2, R3, R4, R1', R2', and R3' can be the same or a different in each instance, and each is independently selected from the group consisting of hydrogen, and Group (I) consisting of methyl, hydroxypropyl, sulfobutyl, succinyl, a quaternary ammonium group comprising —CH2CH(OH)CH2N(CH3)$^{3+}$, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsufonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thin, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, and trialkylammonium;

[A-B-A'] are together defined as a linking group;

A and A' are independently selected from the group consisting of —O—, —NH—, —NR4-, —S—, a heteroatom, a substituted or unsubstituted alkylene, a substituted or unsubstituted heteroalkylene;

B is selected from the group consisting of a bond, —O—, —NH—, —NR4-, —S—, a heteroatom, a substituted or unsubstituted alkylene, a substituted or unsubstituted heteroalkylene, a substituted or unsubstituted and saturated or unsaturated cycloalkylene, a substituted or unsubstituted and saturated or unsaturated heterocycloalkylene, a substituted or unsubstituted arylene, and a substituted or unsubstituted heteroarylene;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A';

wherein either or both of CD and CD' have at least one substitution, wherein at least one of R1, R2, R3, R4, R1', R2', or R3 is not hydrogen and is selected from said Group (I) and further wherein CD and CD' are asymmetrically substituted, wherein at least one:

(a) the DS at position C2 in CD (corresponding to L1/R1) does not equal the DS at position C2 in CD' (corresponding to L1'/R1'); or (b) the DS at position C3 in CD (corresponding to L2/R2) does not equal the DS at position C3 in CD' (corresponding to L2'/R2'); or (c) the DS at position C6 in CD (corresponding to L3/R3) does not equal the DS at position C6 in CD' (corresponding to L3'/R3'); or (d) at least one L1/R1, L2/R2, or L3/R3 pair differs from each L1'/R1', L2'/R2', and L3'/R3' pair; or (e) at least one L1'/R1', L2'/R2', or L3'/R3' pair differs from each L1/R1, L2/R2, and L3/R3 pair.

4. The CD dimer of claim 1, wherein for each R1, R2, R3, R1', R2, or R3' that is alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thio, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, or trialkylammonium, the corresponding L1, L2, L3, L1', L2', or L3', respectively, is a bond.

5. A method of improving the solubility of a hydrophobic drug, comprising admixing said hydrophobic drug and a CD dimer according claim 1.

6. A therapeutic method comprising administration of an effective amount of a CD dimer according to claim 1 to a subject in need thereof, wherein optionally said method reduces the amount of 7KC in said subject and/or said method prevents, treats, ameliorates the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy.

7. A method of making a CD dimer according to claim 1, comprising:

(a) reacting CD molecules that are protected on the primary face with a dialkylating agent, thereby producing a primary face-protected CD dimer linked through the secondary face, and optionally purifying said primary protected CD dimer;

(b) deprotecting said primary face protected CD dimer, thereby producing a deprotected CD dimer, and optionally purifying said deprotected CD dimer; and (c) functionalizing said deprotected CD dimer to said R1, R2, R3, R1', R2', and/or R3' groups, thereby producing said CD dimer, and optionally purifying said CD dimer.

8. A method of making a CD dimer according to claim 1, comprising (a) reacting a 2-O-(n-azidoalkyl)-CD or a 3-O-(n-azidoalkyl)-CD or a mixture thereof and a 2-O-(n-alkyne)-CD or a 3-O-(n-alkyne)-CD or a mixture thereof, thereby forming a CD-triazole-βCD dimer having the structure CD-alk1-triazole-alk2-CD, and optionally (b) purifying said CD-triazole-CD dimer.

9. A method of improving the solubility of a hydrophobia drug, comprising admixing said hydrophobic drug and a CD dimer according to claim 3.

10. A therapeutic method comprising administration of an effective amount of a CD dimer according to claim 3 to a subject in need thereof, which optionally reduces the amount of 7KC in said subject and/or which prevents, treats, ameliorates the symptoms of one or more of atherosclerosis/coronary artery disease, arteriosclerosis, coronary atherosclerosis due to calcified coronary lesion, heart failure (all stages), Alzheimer's disease, amyotrophic lateral sclerosis, Parkinson's disease, Huntington's disease, vascular dementia, multiple sclerosis, Smith-Lemli-Opitz Syndrome, infantile neuronal ceroid lipofuscinosis, lysosomal acid lipase deficiency, cerebrotendinous xanthomatosis, X-linked adrenoleukodystrophy, sickle cell disease, Niemann-Pick Type A disease, Niemann-Pick Type B disease, Niemann-Pick Type C disease, Gaucher's disease, Stargardt's disease, age-related macular degeneration (dry form), idiopathic pulmonary fibrosis, chronic obstructive pulmonary disease, cystic fibrosis, liver damage, liver failure, non-alcoholic steatohepatitis, non-alcoholic fatty liver disease, irritable bowel syndrome, Crohn's disease, ulcerative colitis, and/or hypercholesterolemia; wherein optionally said treatment is administered in combination with another therapy.

11. A method of making a CD dimer according to claim 3, comprising:

(a) reacting CD molecules that are protected on the primary face with a dialkylating agent, thereby producing a primary face-protected CD dimer linked through the secondary face, and optionally purifying said primary protected CD dimer;

(b) deprotecting said primary face protected CD dimer, thereby producing a deprotected CD dimer, and optionally purifying said deprotected CD dimer; and (c) functionalizing said deprotected CD dimer to said R1, R2, R3, R1', R2', and/or R3' groups, thereby producing said CD dimer, and optionally purifying said CD dimer;

or comprising:

(a) reacting a 2-O-(n-azidoalkyl)-CD or a 3-O-(n-azidoalkyl)-CD or a mixture thereof and a 2-O-(n-alkyne)-CD or a 3-O-(n-alkyne)-CD or a mixture thereof, thereby forming a CD-triazole-CD dimer having the structure CD-alk1-triazole-alk2-CD, and optionally (b) purifying said CD-triazole-CD dimer.

12. The CD dimer of claim 1, wherein B is an unsubstituted triazole having connectivity to A and A' as shown in Structure Y:

(Structure Y)

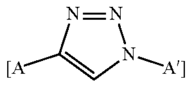

or A to A as shown in Structure Y':

(Structure Y')

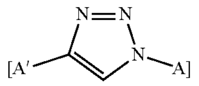

and wherein A and A' are independently substituted or unsubstituted alkylene each having a length of 1 to 8 carbons.

13. The CD dimer of claim 3, wherein B is an unsubstituted triazole having connectivity to A and A' as shown in Structure Y:

(Structure Y)

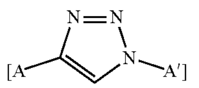

or A' to A as shown in Structure Y':

(Structure Y')

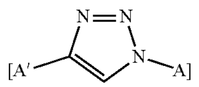

and wherein A and A' are independently substituted or unsubstituted alkylene each having a length of 1 to 8 carbons.

14. A cyclodextrin (CD) dimer having the general formula Structure A-X:

CD-[A-B-A']-CD' (Structure A-X)

wherein

CD has the Structure A-Xa:

(Structure A-Xa)

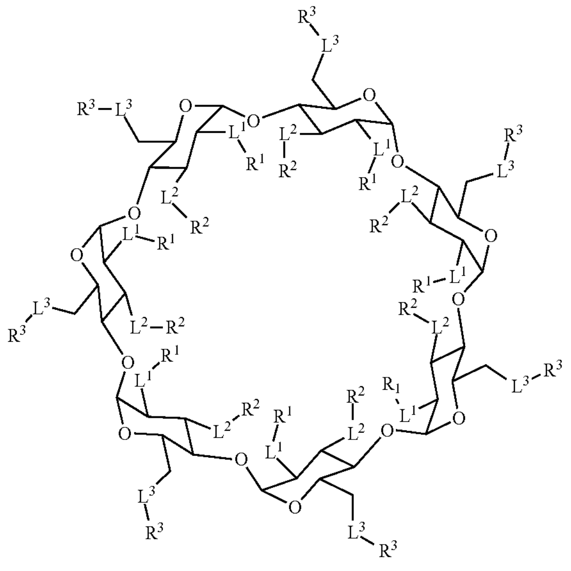

CD' has the Structure A-Xb:

(Structure A-Xb)

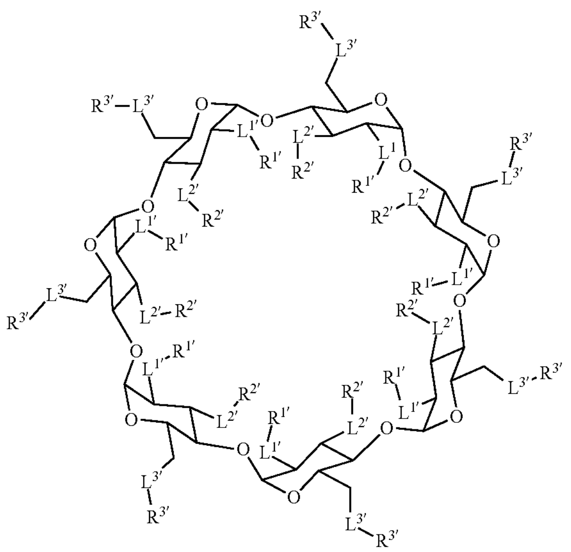

wherein:

L1, L2, L3, L1', L2', and L3' can be the same or different in each instance, and each is independently selected from the group consisting of a bond, —O—, —NH—, —NR4- or —S—, or wherein at least one L1, L2, L3, L1', L2, and L3' is a bond and the corresponding R1, R2, R3, R1', R2', or R3' group is N3, SH, or a halogen comprising F, Cl, Br, or I;

R1, R2, R3, R4, R1', R2', and R3' can be the same or different in each instance, and each is independently selected from the group consisting of hydrogen, and Group (I) consisting of methyl, hydroxypropyl, sulfobutyl, succinyl, a quaternary ammonium group, —CH2CH(OH)CH2N(CH3)3+, alkyl, lower alkyl, alkenyl, alkynyl, alkoxy, alkoxyalkyl, alkoxyalkoxyalkyl, heteroalkoxy, alkylcarbonyloxyalkyl, alkylcarbonyl, alkylsufonyl, alkylsulfonylalkyl, alkylamino, dialkylamino, alkylaminoalkyl, dialkylaminoalkyl, aminoalkyl, alkylsulfonylamino, aminocarbonyloxyalkyl, alkylaminosulfonyl, dialkylaminosulfonyl, aryl, arylalkyl, aryloxy, haloaryl, arylcarbonyl, arylsulfanyl, cyanoalkyl, cycloalkyl, heterocycloalkyl, cycloalkenyl, heterocycloalkenyl, cycloalkylalkyl, cycloalkylene, cycloalkylalkylene, glucosyl, heteroalkyl, heteroaryl, heteroarylalkyl, heteroaryloxy, heteroaralkyloxy, cycloalkoxy, heterocyclyalkoxy, haloalkyl, haloalkoxy, heterocycloamino, carbocyclyl, heterocyclyl, heterocyclylalkyl, heterocyclyloxy, hydroxyalkoxy, hydroxyalkylamino, hydroxyalkylaminoalkyl, hydroxyalkyl, hydroxycarbonyl alkyl, hydroxyalkylamino, hydroxyalkyl, hydroxycycloalkyl, ureido, carboxy, sulfuryl, phosphoryl, phenoxy, acetyl group, monosaccharide, disaccharide, palmitoyl, fatty acid, alkoxyamino, alkoxycarbonylamino, alkoxycarbonyloxy, alkylaminocarbonyl, alkylaminocarbonylalkyl, alkylsulfanyl, alkylsulfonamido, alkylureido, amino, aminosulfonyl, ammonium, arylamino, arylsulfonamido, arylsulfonyl, arylureido, carbalkoxy, carbamoyl, carboxamido, cyano, cycloamino, heterocyclyl cycloalkyl, heteroarylsulfonyl, heterocycloalkoxy, heterocycloamino thin, hydoxycarbonyl, hydroxyalkoxyalkyl, hydroxycarbonylalkyl, hydroxyl, nitrite, nitro, phosphate, phosphine oxide, sulfate alkyl, sulfonamido, thioalkyl, and trialkylammonium;

[A-B-A'] are together defined as a linking group having a length of 5-10 atoms;

CD and CD' are connected by at least one linking group;

A of each linking group is connected to at least one L1 or L2 and the corresponding R1 or R2 is omitted and replaced in this manner by A, and A' of each linking group is connected to at least one L1' or L2' and the corresponding R1' or R2' is omitted and replaced in this manner by A'; and wherein optionally at least one L1, L2, L3, L1', L2', and/or L3' is not O;

wherein B is an unsubstituted triazole having connectivity to A and A' as shown in Structure Y:

(Structure Y)

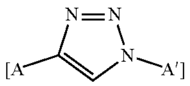

or A' to A as shown in Structure Y':

(Structure Y')

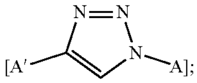

wherein A and A' are independently substituted or unsubstituted alkylene; and wherein either or both of CD and CD' have at least one substitution, wherein at least one of R1, R2, R3, R4, R1', R2', or R3' is not hydrogen and is selected from said Group (I).

15. The cyclodextrin (CD) dimer of claim 14, wherein A is a methylene and A' is an unsubstituted alkylene comprising a length of 3 carbons.

* * * * *